(12) United States Patent
Zhao et al.

(10) Patent No.: US 11,390,609 B2
(45) Date of Patent: Jul. 19, 2022

(54) RHO-ASSOCIATED PROTEIN KINASE INHIBITOR, PHARMACEUTICAL COMPOSITION COMPRISING SAME, AND PREPARATION METHOD AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Gong Li, Beijing (CN); Yuanyuan Jiang, Beijing (CN); Xiang Li, Beijing (CN); Bin Liu, Beijing (CN); Weiting Zhong, Beijing (CN); Kai Liu, Beijing (CN); Fajie Li, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 114 days.

(21) Appl. No.: 16/344,965

(22) PCT Filed: Jun. 29, 2018

(86) PCT No.: PCT/CN2018/093713
§ 371 (c)(1),
(2) Date: Apr. 25, 2019

(87) PCT Pub. No.: WO2019/001572
PCT Pub. Date: Jan. 3, 2019

(65) Prior Publication Data
US 2019/0276440 A1    Sep. 12, 2019

(30) Foreign Application Priority Data

Jun. 30, 2017 (CN) ................ PCT/CN2017/091085
Sep. 29, 2017 (CN) ................ PCT/CN2017/104290
Nov. 8, 2017 (CN) ........................ 201711089580.6

(51) Int. Cl.
| | |
|---|---|
| *C07D 403/14* | (2006.01) |
| *C07D 409/14* | (2006.01) |
| *C07D 413/14* | (2006.01) |
| *C07D 487/04* | (2006.01) |
| *C07D 495/04* | (2006.01) |
| *C07D 471/04* | (2006.01) |
| *C07D 401/14* | (2006.01) |
| *C07D 405/14* | (2006.01) |
| *C07D 471/10* | (2006.01) |

(Continued)

(52) U.S. Cl.
CPC .......... *C07D 403/14* (2013.01); *A61K 31/416* (2013.01); *A61K 31/506* (2013.01); *A61P 29/00* (2018.01); *A61P 37/00* (2018.01); *C07D 401/14* (2013.01); *C07D 405/14* (2013.01); *C07D 409/14* (2013.01); *C07D 413/14* (2013.01); *C07D 417/14* (2013.01); *C07D 453/02* (2013.01); *C07D 471/04* (2013.01); *C07D 471/10* (2013.01); *C07D 487/04* (2013.01); *C07D 491/048* (2013.01); *C07D 495/04* (2013.01); *C07D 513/04* (2013.01); *C07D 519/00* (2013.01); *C07F 9/65583* (2013.01)

(58) Field of Classification Search
CPC .. C07D 403/14; C07D 413/14; C07D 487/04; C07D 495/04; C07D 471/04; C07D 401/14; C07D 405/14; C07D 471/10; C07D 519/00; C07D 491/048; C07D 513/04; C07D 417/14; C07D 4553/02; C07D 409/14; C07F 9/65583
USPC ........................................................... 514/80
See application file for complete search history.

(56) References Cited

U.S. PATENT DOCUMENTS

| | | | |
|---|---|---|---|
| 9,783,536 B2 | 10/2017 | Furuyama et al. | |
| 10,323,023 B2 * | 6/2019 | Zhao ................... | C07D 487/04 |

(Continued)

FOREIGN PATENT DOCUMENTS

| | | |
|---|---|---|
| CA | 2689117 | 12/2008 |
| CA | 2441492 C | 8/2011 |

(Continued)

OTHER PUBLICATIONS

John D. Potter, Carcinogenesis vol. 35, No. 5, pp. 974-982, 2014.*
(Continued)

*Primary Examiner* — Tracy Vivlemore
*Assistant Examiner* — Ebenezer O Sackey
(74) *Attorney, Agent, or Firm* — Robin L. Teskin; Baker, Donelson, Bearman, Caldwell & Berkowitz PC

(57) ABSTRACT

The present invention relates to a Rho-associated protein kinase inhibitor of formula (I), a pharmaceutical composition comprising the same, a preparation method thereof, and a use of the same in preventing or treating a disease mediated by Rho-associated protein kinase (ROCK).

Formula (I)

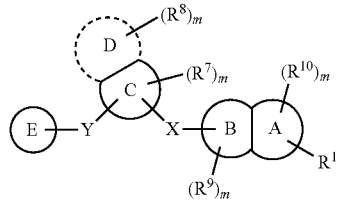

28 Claims, No Drawings

(51) Int. Cl.

| | |
|---|---|
| C07D 519/00 | (2006.01) |
| C07D 491/048 | (2006.01) |
| C07D 513/04 | (2006.01) |
| C07D 417/14 | (2006.01) |
| C07D 453/02 | (2006.01) |
| C07F 9/6558 | (2006.01) |
| A61P 37/00 | (2006.01) |
| A61K 31/416 | (2006.01) |
| A61K 31/506 | (2006.01) |
| A61P 29/00 | (2006.01) |

(56) References Cited

U.S. PATENT DOCUMENTS

| | | | |
|---|---|---|---|
| 10,329,282 B2 * | 6/2019 | Zhao | C07D 417/14 |
| 2012/0202793 A1 | 8/2012 | Sweetnam et al. | |

FOREIGN PATENT DOCUMENTS

| | | |
|---|---|---|
| CN | 1486310 | 3/2004 |
| CN | 101208094 A | 6/2008 |
| CN | 101228161 | 7/2008 |
| CN | 104334553 | 2/2015 |
| CN | 104903312 | 9/2015 |
| CN | 104903320 | 9/2015 |
| CN | 106478651 | 3/2017 |
| EP | 2433636 | 3/2012 |
| EP | 3055301 A1 | 8/2016 |
| JP | 2010529137 | 8/2010 |
| JP | 2020525522 | 8/2020 |
| JP | 2020525525 | 8/2020 |
| WO | 2001/040215 | 6/2001 |
| WO | 02/22607 | 3/2002 |
| WO | 02/057259 | 7/2002 |
| WO | 02/076976 | 10/2002 |
| WO | 03/030909 | 4/2003 |
| WO | 03/059913 | 7/2003 |
| WO | 2004/046118 | 6/2004 |
| WO | 2004/048365 | 6/2004 |
| WO | 2006/105081 | 10/2006 |
| WO | 2006127587 | 11/2006 |
| WO | 2006/135383 | 12/2006 |
| WO | 2007/076161 | 7/2007 |
| WO | 2008/054599 | 5/2008 |
| WO | 2010/056758 | 5/2010 |
| WO | 2012/040499 | 3/2012 |
| WO | 2012135631 | 10/2012 |
| WO | 2013/025628 * | 2/2013 |
| WO | 2013156608 | 10/2013 |
| WO | 2014/052699 | 4/2014 |
| WO | 2014/055996 | 4/2014 |
| WO | 2014109414 | 7/2014 |
| WO | 2015/054317 | 4/2015 |
| WO | 2015/157556 | 10/2015 |
| WO | 2016010950 | 1/2016 |
| WO | 2016138335 A1 * | 1/2016 |
| WO | 2016/057834 | 4/2016 |
| WO | 2016/138335 | 9/2016 |
| WO | 2016/160833 | 10/2016 |
| WO | 2016/210330 | 12/2016 |
| WO | 2016/210331 | 12/2016 |
| WO | 2017/048675 | 3/2017 |
| WO | 2019000683 | 9/2017 |
| WO | 2017205536 * | 10/2017 |
| WO | 2017205536 | 11/2017 |
| WO | 2018/039539 | 3/2018 |

OTHER PUBLICATIONS

Wolff, Manfred E., Burger's Medicinal Chemistry and Drug Discovery, Fifth Ed., vol. 1: Principles and Practice, John Wiley & Sons, 1996; Fifth Edition, vol. 1: 975-977.

Banker, Gilbert S. et al., Modern Pharmaceutics, Marcel Dekker, New York, 1996; Third Edition: 596-597.

West, Anthony R., Solid State Chemistry and Its Applications, Wiley, New York, 1988; pp. 358 & 365.

Zhao et al.,"Rho-Associated Protein Kinase Inhibitor, Pharmaceutical Composition Comprising the Same, as Well as Preparation Method and Use Thereof." Int'l Application No. PCT/CN2017/091085 filed Jun. 30, 2017.

Zhao et al.,"Rho-Associated Protein Kinase Inhibitor, Pharmaceutical Composition Comprising the Same, as Well as Preparation Method and Use Thereof." Int'l Application No. PCT/CN2017/091086 filed Jun. 30, 2017.

Duan et al. "Advances in the study of Rho kinase and its inhibitors." Yao xue xue bao / Acta pharmaceutica Sinica. Oct. 2007;42(10):1013. (English abstract).

Gamo et al. "Thousand of chemical starting points for antimalarial lead identification." Nature. May 2010;465 (7296):305-10.

Oduor Ret al. "Trypanosoma brucei glycogen synthase kinase-3, a target fo anti-trypanosomal drug development: a public-private partnership to identify novel leads." neglected tropical diseases. Apr. 5, 2011;5(4):e1017.

* cited by examiner

RHO-ASSOCIATED PROTEIN KINASE INHIBITOR, PHARMACEUTICAL COMPOSITION COMPRISING SAME, AND PREPARATION METHOD AND USE THEREOF

CROSS-REFERENCE TO RELATED APPLICATIONS

This application is a U.S. National Phase under 35 U.S.C. § 371 of International Appl. No. PCT/CN2018/093713, filed Jun. 29, 2018, which claims priority to Chinese Appl. No. 201711089580.6, filed Nov. 8, 2017, International Appl. No. PCT/CN2017/104290, filed Sep. 29, 2017, and International Appl. No. PCT/CN2017/091085, filed Jun. 30, 2017, the disclosures of each of which are hereby incorporated by reference in their entireties.

FIELD OF THE INVENTION

The present invention relates to a Rho-associated protein kinase inhibitor, a pharmaceutical composition comprising the same, a preparation method thereof, and use thereof for the prevention or treatment of a disease mediated by the Rho-associated protein kinase (ROCK).

BACKGROUND OF THE INVENTION

Rho-associated protein kinase (ROCK) is a serine/threonine kinase from the AGC kinase family, and comprises two isoforms, ROCK1 and ROCK2. ROCK1 and ROCK2 are expressed and regulated differently in specific tissues. For example, ROCK1 is ubiquitously expressed at a relatively high level, while ROCK2 is preferentially expressed in heart, brain and skeletal muscle. ROCK is the first downstream effector of the Rho protein discovered, and its biological function is achieved by phosphorylating the downstream effector proteins (MLC, Lin-11, Isl-1, LIMK, ERM, MARCKS, CRMP-2, etc.). Studies have shown that various diseases (e.g., pulmonary fibrosis, cardiac-cerebral vascular disease, neurological disease and cancer etc.) are related to the pathways mediated by ROCK. As such, ROCK is considered as an important target in the development of novel drugs.

However, at present, only Fasudil is approved as a ROCK inhibitor for the treatment of cerebral vasospasm and ischemia in Japan. Although various small molecule ROCK inhibitors have been reported by now, most of them are for topical ophthalmic application, and no small molecule ROCK inhibitor suitable for systemic administration is available.

SUMMARY OF THE INVENTION

The present invention provides a compound for use as a ROCK (preferably ROCK2) inhibitor, it has superior properties, such as excellent inhibitory activity on ROCK (preferably ROCk2), good selectivity (higher selectivity towards ROCK2 as compared with ROCK1), better physicochemical properties (e.g., solubility, physical and/or chemical stability), improved pharmacokinetic properties (e.g., improved bioavailability, proper half-life and duration of action), improved safety (low toxicity and/or less side effects, wide therapeutic window), and the like.

According to an aspect of the present invention, a compound or a pharmaceutically acceptable salt, ester, stereoisomer, polymorph, solvate, N-oxide, isotopically labeled compound, metabolite or prodrug thereof is provided, wherein the compound has the structure of Formula (I):

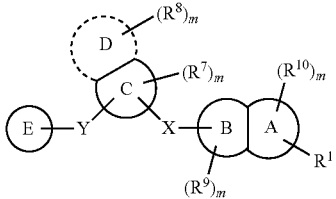

Formula (I)

wherein:
X and Y are each independently selected from the group consisting of a direct bond, C(=O), O, S(=O), and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O); provided that when ring B is a heterocycle containing a nitrogen atom, ring B is not attached to X via the nitrogen atom;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring E is selected from the group consisting of

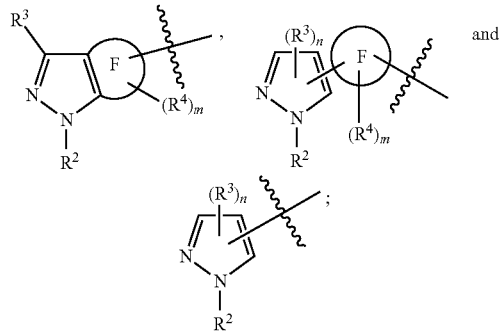

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

$R^1$ is selected from the group consisting of H, —NH$_2$, C$_{1-6}$ alkyl, C$_{6-10}$ aryl, 5- to 14-membered heteroaryl, N-methylpyrrolidinyl, N-methylpiperidinyl,

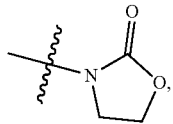 [SMILES: *N1CCOC1=O]

acetyl,

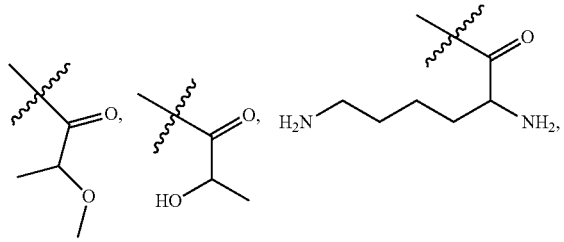

—C(=O)—(C$_{1-6}$ alkylene)$_n$-CF$_3$, —C(=O)—(C$_{1-6}$ alkylene)$_n$-CN, —C(=O)-(saturated or partially unsaturated C$_{3-10}$ cyclic hydrocarbyl), —NHC(=O)-(saturated or partially unsaturated C$_{3-10}$ cyclic hydrocarbyl), —C(=O)-(saturated or partially unsaturated 3- to 10-membered heterocyclyl), —C(=O)—C$_{1-6}$ alkylene-(saturated or partially unsaturated 3- to 10-membered heterocyclyl), —C(=O)-(5- to 14-membered heteroaryl), —C(=O)—C$_{1-6}$ alkylene-NH(C$_{1-6}$ alkyl), —C(=O)—C$_{3-6}$ alkylene-N(C$_{1-6}$ alkyl)$_2$, N-methylpiperazine substituted acetyl, —S(=O)$_2$R$^{1a}$, —P(=O)R$^{1a}$R$^{1b}$,

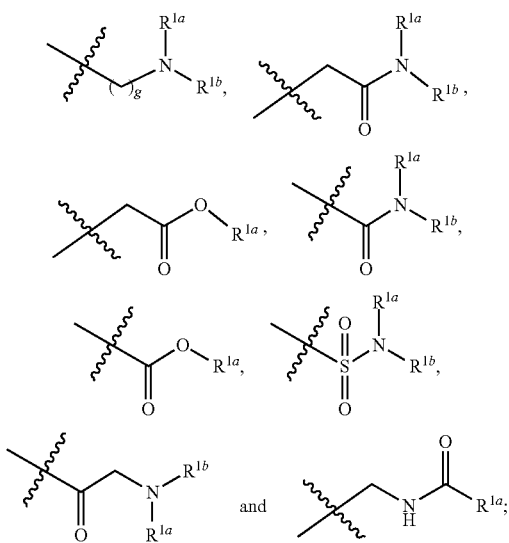

provided that when one of $R^1$ and $R^{10}$ is C$_{1-6}$ alkyl, and the other is H or C$_{3-10}$ cyclic hydrocarbyl, at least one of X and Y is a direct bond, and ring C is not a 5-membered heteroaromatic ring; when one of $R^1$ and $R^{10}$ is H, and the other is

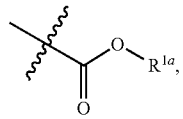

ring C is not a 5-membered heteroaromatic ring; when both $R^1$ and $R^{10}$ are H, ring A contains at least one nitrogen atom, and is not a 5- or 6-membered ring; when one of $R^1$ and $R^{10}$ is H, and the other is

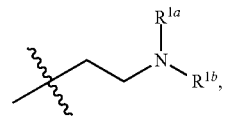

ring C is not a 5-membered heteroaromatic ring; and when one of $R^1$ and $R^{10}$ is H, and the other is H or acetyl, ring D is absent;

$R^{1a}$ and $R^{1b}$ are each independently selected from the group consisting of H, halogen, amino, cyano, nitro, C$_{1-6}$ alkyl, C$_{2-6}$ alkenyl, C$_{2-6}$ alkynyl, C$_{3-10}$ cyclic hydrocarbyl, 3- to 10-membered heterocyclyl, C$_{6-10}$ aryl, 5- to 14-membered heteroaryl, C$_{6-12}$ aralkyl, —C(=O)R$^5$, —OC(=O)R$^5$, —C(=O)OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$, —C$_{1-6}$ alkylene-OR$^5$ and —O—C$_{1-6}$ alkylene-NR$^5$R$^6$, provided that when one of $R^{1a}$ and $R^{1b}$ is n-propyl, the other is not H; or $R^{1a}$ and $R^{1b}$ together with the atom to which they are attached form a 3- to 12-membered heterocycle or heteroaromatic ring;

$R^2$, $R^3$, $R^4$, $R^8$, $R^9$ and $R^{10}$, at each occurrence, are each independently selected from the group consisting of H, halogen, amino, cyano, nitro, C$_{1-6}$ alkyl, C$_{2-6}$ alkenyl, C$_{2-6}$ alkynyl, C$_{3-10}$ cyclic hydrocarbyl, 3- to 10-membered heterocyclyl, C$_{6-10}$ aryl, 5- to 14-membered heteroaryl, C$_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$, —C$_1$0.6 alkylene-O(P=O)(OH)$_2$ and —O—C$_{1-6}$ alkylene-NR$^5$R$^6$;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of halogen, hydroxyl, oxo, amino, cyano, nitro, C$_{1-6}$ alkyl, C$_{2-6}$ alkenyl, C$_{2-6}$ alkynyl, C$_{3-6}$ cyclic hydrocarbyl, 3- to 10-membered heterocyclyl, C$_{6-10}$ aryl, 5- to 14-membered heteroaryl, C$_{6-12}$ aralkyl, =N—OR$^5$, —C(=NH)NH$_2$, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C(=O)R$^6$, —NR$^5$—C(=O)OR$^6$, —NR$^5$—S(=O)$_2$—R$^6$, —NR$^5$—C(=O)—NR$^5$R$^6$, —C$_{1-6}$ alkylene-NR$^5$R$^6$ and —O—C$_{1-6}$ alkylene-NR$^5$R$^6$, and the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, C$_{1-6}$ alkyl, C$_{3-6}$ cyclic hydrocarbyl, 3- to 10-membered heterocyclyl, $C_{6-10}$ aryl, 5- to 14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_60.12$ aralkyl;

m, at each occurrence, is each independently an integer of 0, 1, 2 or 3;

n is an integer of 0, 1 or 2;

i is an integer of 0, 1 or 2; and g is an integer of 0, 1, 2, 3 or 4.

According to another aspect of the invention, a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers is provided, and the pharmaceutical composition is preferably in the form of a solid, semi-solid, liquid, or gas preparation.

According to another aspect of the invention, use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor, is provided.

According to another aspect of the invention, the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor, is provided.

According to another aspect of the invention, a method for the prevention or treatment of a disease mediated by the Rho-associated protein kinase (ROCK) is provided, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

According to another aspect of the invention, a method for the preparation of the compound of the present invention is provided.

DETAILED DESCRIPTION OF THE INVENTION

Definition

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2C_1$ or $—CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or ten-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g. 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —$NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C=O, S, S=O and S(=O)2. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^2H$, $^3H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^3H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term" stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (-), a solid wedge ( ━━━ ) or a dotted wedge ( ......ııııı ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free from, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Hand book of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, Comprehensive Organic Synthesis, vol. 7, pp 748-750; A. R. Katritzky and A. J. Boulton, Eds., Academic Press; and G. W. H. Cheeseman and E. S. G. Werstiuk, Advances in Heterocyclic Chemistry, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems, Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

Compound

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

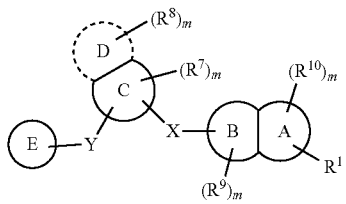

Formula (I)

wherein:

X and Y are each independently selected from the group consisting of a direct bond, C(=O), O, S(=O), and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O); provided that when ring B is a heterocycle containing a nitrogen atom, ring B is not attached to X via the nitrogen atom;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

ring E is selected from the group consisting of

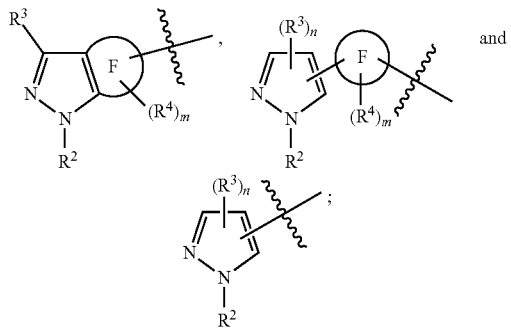

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(=O);

$R^1$ is selected from the group consisting of H, —$NH_2$, $C_{1-6}$ alkyl, $C_{6-10}$ aryl, 5- to 14-membered heteroaryl, N-methylpyrrolidinyl, N-methylpiperidinyl,

acetyl,

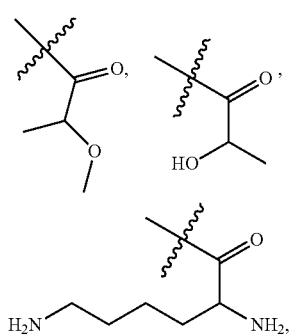

—C(=O)—($C_{1-6}$ alkylene)$_N$-CF$_3$, —C(=O)—($C_{1-6}$ alkylene) CN, —C(=O)-(saturated or partially unsaturated $C_{3-10}$ cyclic hydrocarbyl), —NHC(=O)-(saturated or partially unsaturated $C_{3-10}$ cyclic hydrocarbyl), —C(=O)-(saturated or partially unsaturated 3- to 10-membered heterocyclyl), —C(=O)—$C_{1-6}$ alkylene-(saturated or partially unsaturated 3- to 10-membered heterocyclyl), —C(=O)-(5- to 14-membered heteroaryl), —C(=O)—$C_{1-6}$ alkylene-NH ($C_{1-6}$ alkyl), —C(=O)—$C_{1-6}$ alkylene-N($C_{1-6}$ alkyl)$_2$, N-methylpiperazine substituted acetyl, —S(=O)$_2$R$^{1a}$, —P(=O)R$^{1a}$R$^{1b}$,

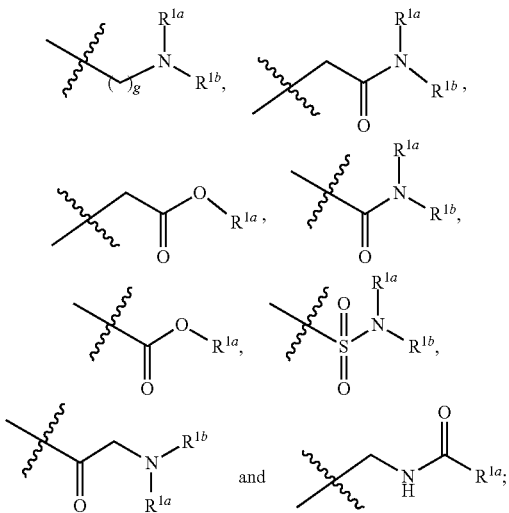

provided that when one of R$^1$ and R$^{10}$ is $C_{1-6}$ alkyl, and the other is H or $C_{3-10}$ cyclic hydrocarbyl, at least one of X and Y is a direct bond, and ring C is not a 5-membered heteroaromatic ring; when one of R$^1$ and R$^{10}$ is H, and the other is

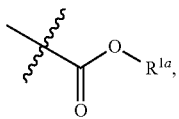

ring C is not a 5-membered heteroaromatic ring; when both R$^1$ and R$^{10}$ are H, ring A contains at least one nitrogen atom, and is not a 5- or 6-membered ring; when one of R$^1$ and R$^{10}$ is H, and the other is

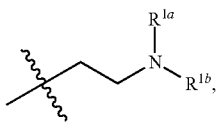

ring C is not a 5-membered heteroaromatic ring; and when one of R$^1$ and R$^{10}$ is H, and the other is H or acetyl, ring D is absent;

R$^{1a}$ and R$^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C (=O)R$^6$, —NR$^5$—C(=O)OR$^6$, —NR$^5$—S(=O)$_2$—R$^6$, —NR$^5$—C(=O)—NR$^5$R$^6$, —$C_{1-6}$ alkylene-NR$^5$R$^6$, —$C_{1-6}$ alkylene-OR$^5$ and —O—$C_{1-6}$ alkylene-NR$^5$R$^6$, provided that when one of R$^{1a}$ and R$^{1b}$ is n-propyl, the other is not H; or R$^{1a}$ and R$^{1b}$ together with the atom to which they are attached form a 3- to 12-membered heterocycle or heteroaromatic ring;

R$^2$, R$^3$, R$^4$, R$^7$, R$^8$, R$^9$ and R$^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$, —OC(=O)R$^5$, —C(=O)OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C (=O)R$^6$, —NR$^5$—C(=O)OR$^6$, —NR$^5$—S(=O)$_2$—R$^6$, —NR$^5$—C(=O)—NR$^5$R$^6$, —$C_{1-6}$ alkylene-NR$^5$R$^6$, —$C_{1-6}$ alkylene- O(P=O)(OH)$_2$ and —O—$C_{1-6}$ alkylene-NR$^5$R$^6$;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of halogen, hydroxyl, oxo, amino, cyano, nitro, $C_{1-6}$ alkyl, $C_{2-6}$ alkenyl, $C_2$0.6 alkynyl, $C_{3-6}$ cyclic hydrocarbyl, 3- to 10-membered heterocyclyl, $C_{6-10}$ aryl, 5- to 14-membered heteroaryl, $C_{6-12}$ aralkyl, =N—OR$^5$, —C(=NH)NH$_2$, —C(=O)R$^5$, —OC(=O)R$^5$, —C(=O) OR$^5$, —OR$^5$, —SR$^5$, —S(=O)R$^5$, —S(=O)$_2$R$^5$, —S(=O)$_2$NR$^5$R$^6$, —NR$^5$R$^6$, —C(=O)NR$^5$R$^6$, —NR$^5$—C (=O)R$^6$, —NR$^5$—C(=O)OR$^6$, —NR$^5$—S(=O)$_2$—R$^6$, —NR$^5$—C(=O)—NR$^5$R$^6$, —$C_1$-6 alkylene-NR$^5$R$^6$ and —O—$C_{1-6}$ alkylene-NR$^5$R$^6$, and the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl and $C_{6-12}$ aralkyl;

R$^5$ and R$^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2;

i is an integer of 0, 1 or 2; and g is an integer of 0, 1, 2, 3 or 4.

In some embodiments, the present invention provides a compound or a pharmaceutically acceptable salt, ester, stereoisomer, polymorph, solvate, N-oxide, isotopically labeled compound, metabolite or prodrug thereof, wherein X and Y are each independently selected from the group consisting of a direct bond, C(=O), 0, S, S(=O), S(=O)$_2$, NH and NCH$_3$, and preferably, at least one of X and Y is a direct bond.

In some embodiments, the present invention provides a compound or a pharmaceutically acceptable salt, ester, stereoisomer, polymorph, solvate, N-oxide, isotopically labeled compound, metabolite or prodrug thereof, wherein at least one of ring A and ring B is selected from the group consisting of saturated or partially unsaturated 3- to 10-membered heterocycle and 5- to 14-membered heteroaromatic ring, and at most 2 ring members in the heterocycle are C(=O).

In some embodiments,

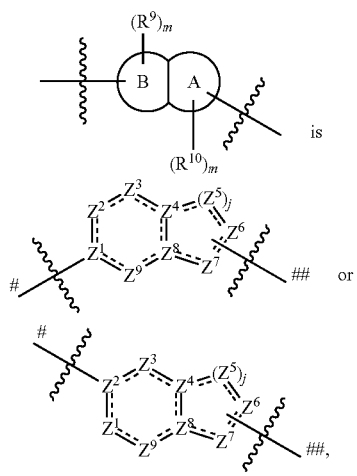

is preferably

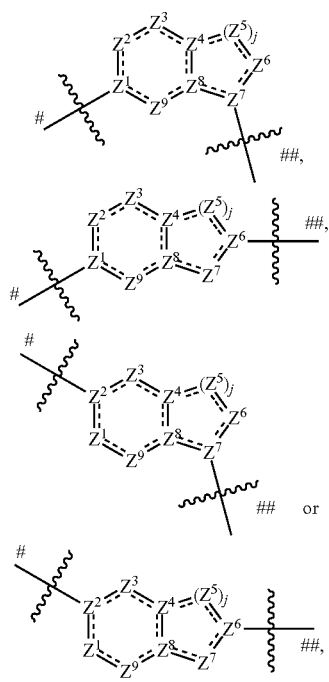

the above group is attached to X at either of the two positions labeled # or ##, and is attached to R¹ at the other position, wherein:

--- represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, C(=O), N, $NR^9$, Ne, O and S; preferably, $Z^1$, $Z^2$, $Z^3$, $Z^4$, $Z^5$, $Z^6$, $Z^7$, $Z^8$ and $Z^9$, at each occurrence, are each independently selected from the group consisting of C, CH, CF, CCl, $CCH_3$, $CH_2$, $C(CH_3)_2$, C—$OCH_3$, C(=O), N, NH, $NCH_3$, $NCH_2CH_3$, $NCH(CH_3)_2$, NCH=$CH_2$, $NCH_2F$, $NCHF_2$, $NCH_2CHF_2$, NC(=O)$CH_3$, $NCH_2OH$, $NCH_2OMe$, $NCH_2CH_2OMe$, $NCH_2$—O(P=O)(OH)$_2$, $NCH_2CH_2$—N(CH$_3$)$_2$, O and S; and j is 0, 1, 2, 3 or 4;

provided that at most two groups among $Z^1$-$Z^9$ are simultaneously C(=O), and the atom attached to X is not a nitrogen atom.

In more preferred embodiments, wherein ring A' and ring B' are each independently selected from the group consisting of saturated or partially unsaturated 3- to 10-membered heterocycle and 5- to 14-membered heteroaromatic ring, and at most 2 ring members in the heterocycle are C(=O); provided that when ring B' is a heterocycle containing a nitrogen atom, ring B' is not attached to X via the nitrogen atom.

In some embodiments, is preferably

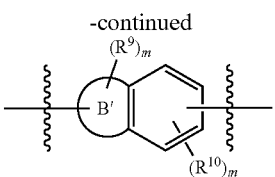

is preferably

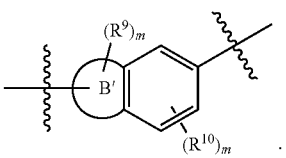

In preferred embodiments, $R^9$ and $R^{10}$, at each occurrence, are each independently selected from the group consisting of halogen (e.g., F, Cl, or Br), methyl, ethyl, propyl (e.g., n-propyl or isopropyl), vinyl, cyclopropyl, cyclobutyl, cyclopentyl, oxetanyl, monofluoromethyl, difluoromethyl, trifluoromethyl, —CH$_2$CHF$_2$, acetyl, —OCH$_3$, —CH$_2$OH, —CH$_2$OCH$_3$, —CH$_2$CH$_2$OCH$_3$, —CH$_2$—O(P=O)(OH)$_2$,

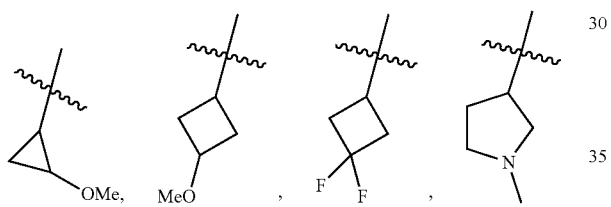

and —CH$_2$CH$_2$—N(CH$_3$)$_2$.

In the most preferred embodiments,

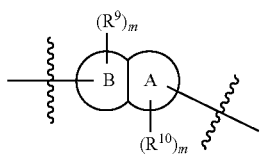

is selected from the group consisting of

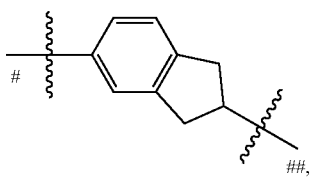

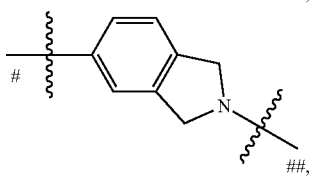

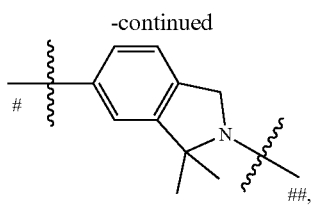

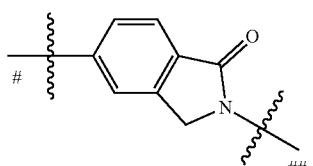

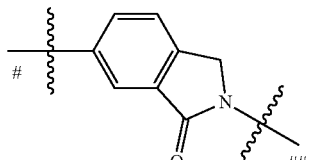

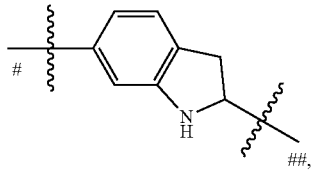

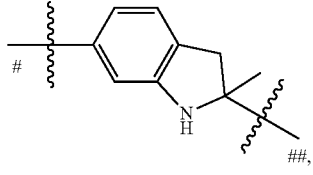

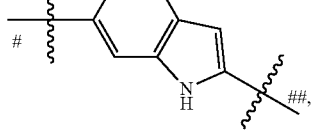

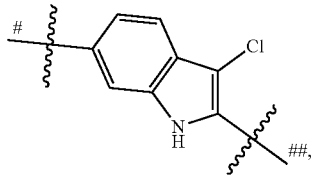

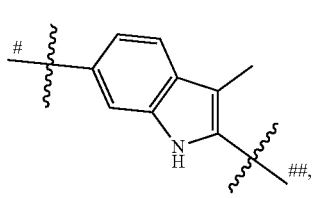

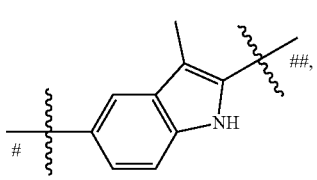

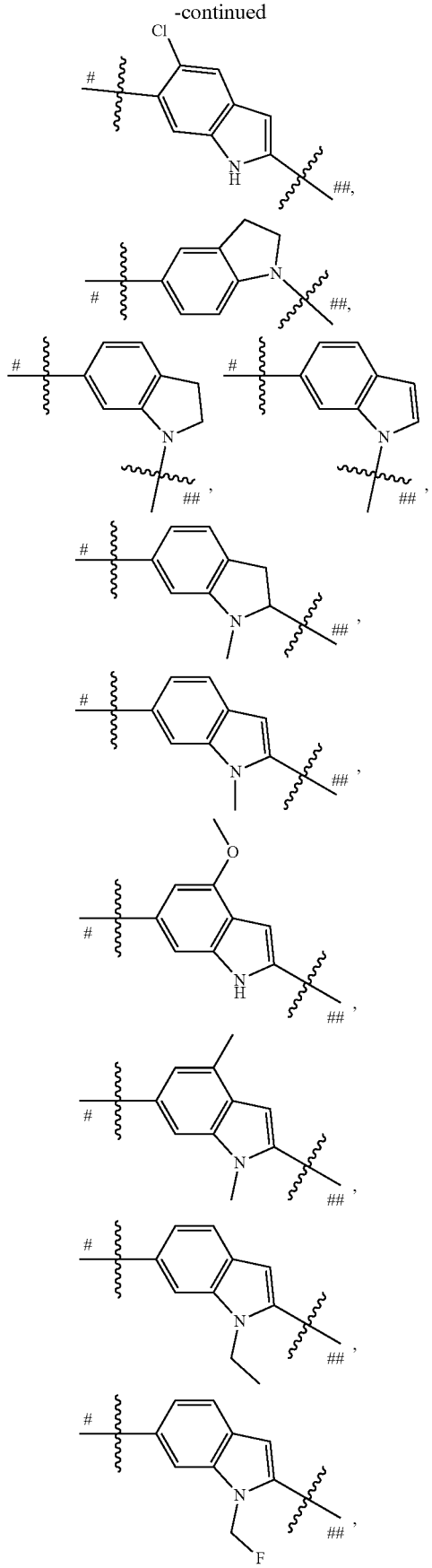
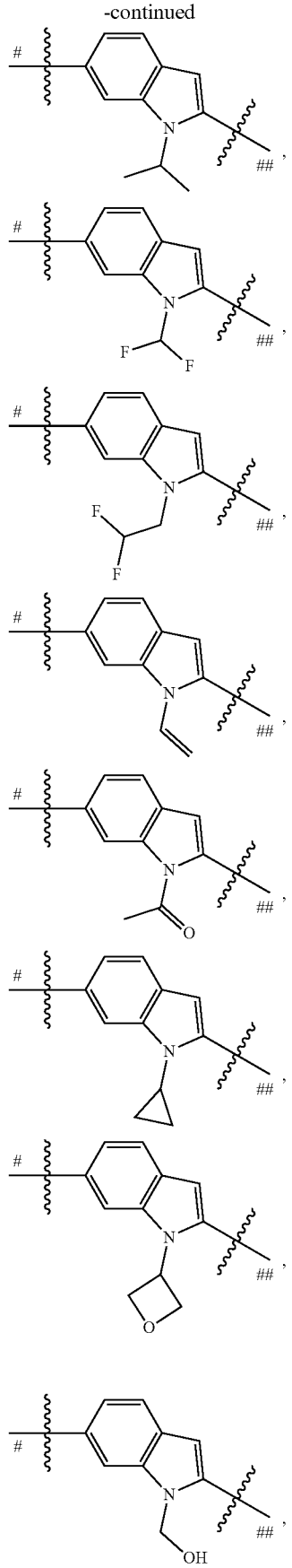

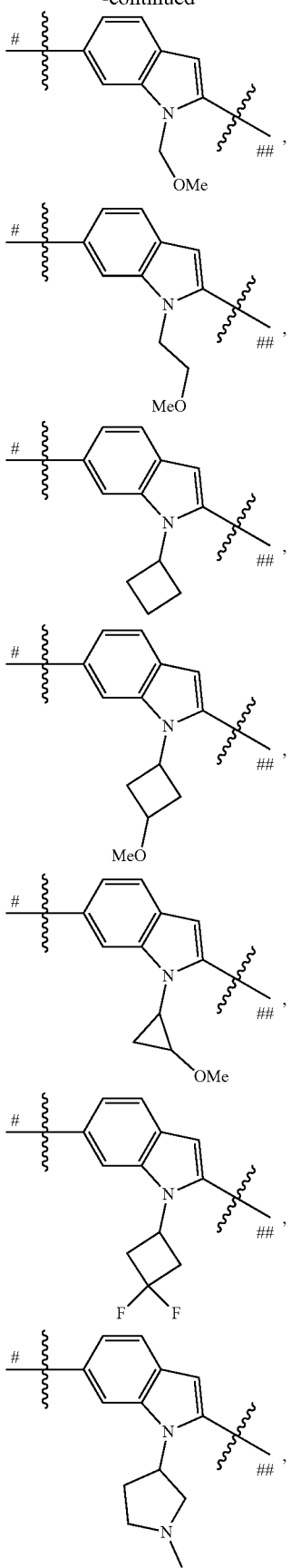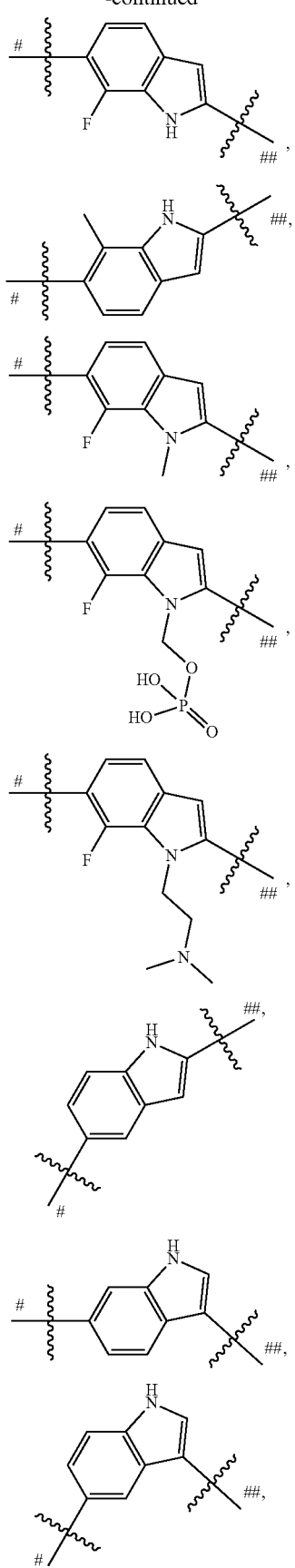

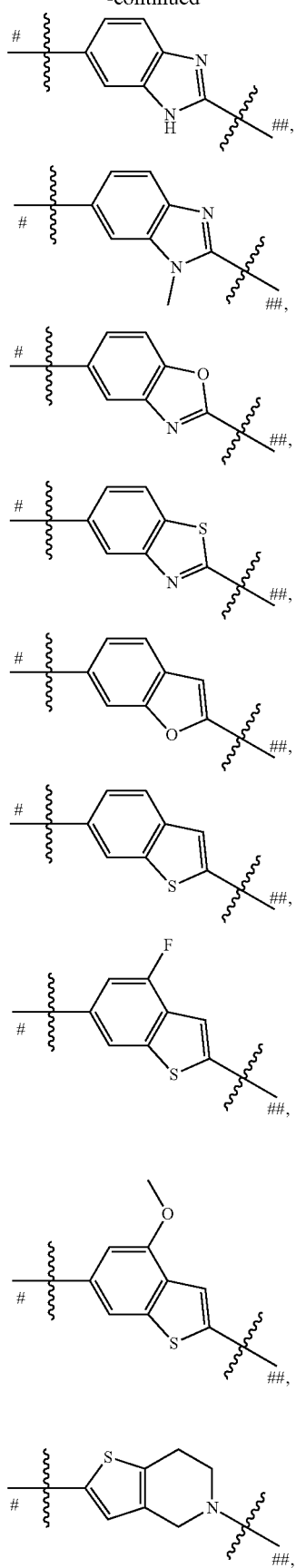
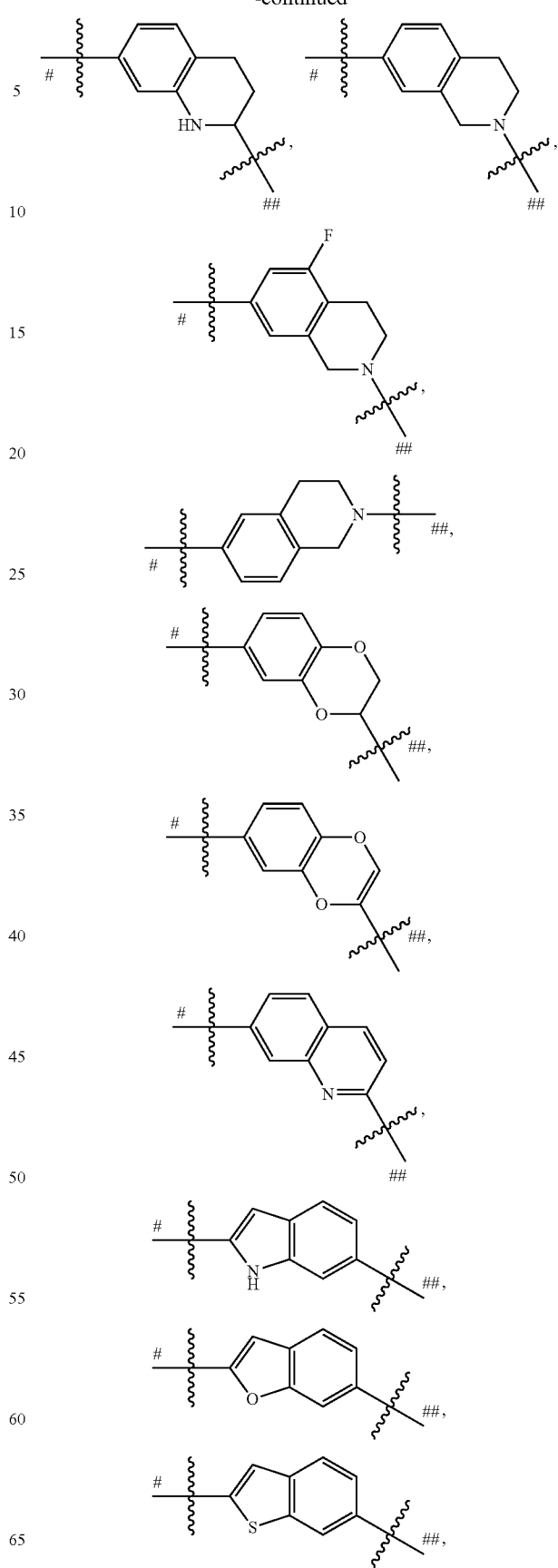

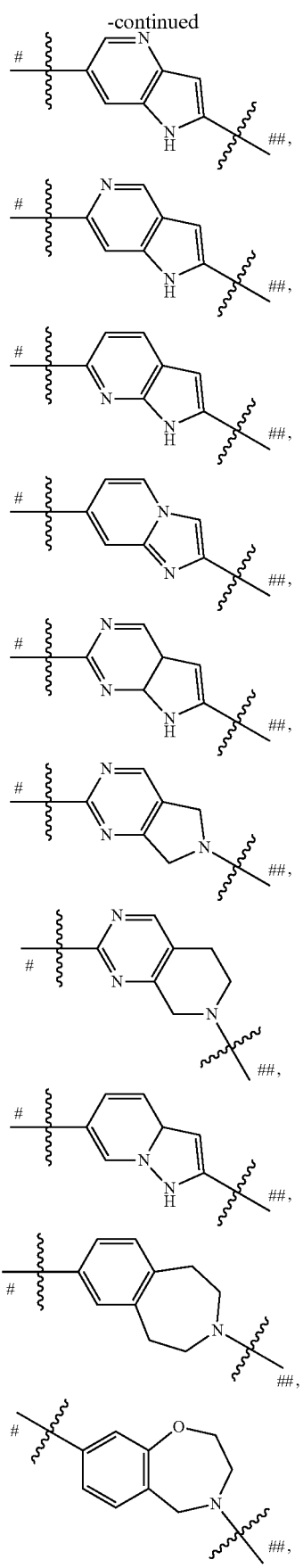

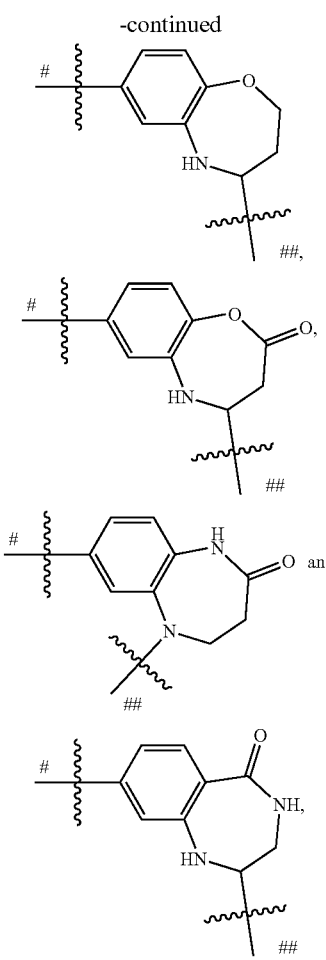

the above group is attached to X at either of the two positions labeled # or ##, and is attached to $R^1$ at the other position, provided that the atom attached to X is not a nitrogen atom.

In some embodiments, the present invention provides a compound or a pharmaceutically acceptable salt, ester, stereoisomer, polymorph, solvate, N-oxide, isotopically labeled compound, metabolite or

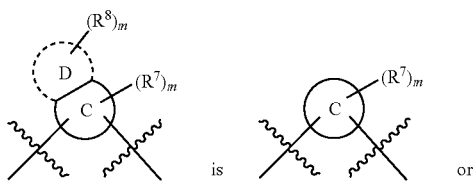

is or

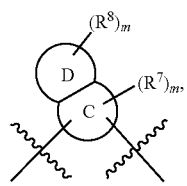

prodrug thereof, wherein more preferably

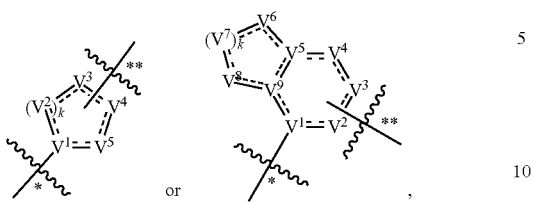

or , and more preferably

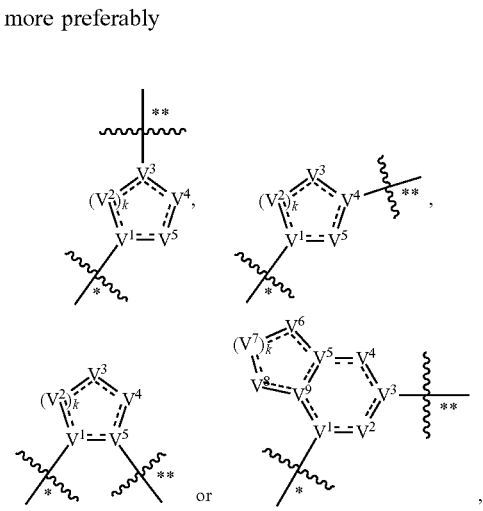

or , the above group is attached to Y at either of the two positions labeled * or **, and is attached to X at the other position, wherein:

---- represents either a single or a double bond, and the adjacent bonds are not double bonds simultaneously;

$V^1$, $V^2$, $V^3$, $V^4$, $V^5$, $V^6$, $V^7$, $V^8$ and $V^9$, at each occurrence, are each independently selected from the group consisting of C, $CR^7$, $C(R^7)_2$, $CR^8$, $C(R^8)_2$, C(=O), N, $NR^7$, $NR^8$, O and S; preferably, $V^1$, $V^2$, $V^3$, $V^4$, $V^5$, $V^6$, $V^7$, $V^8$ and $V^9$, at each occurrence, are each independently selected from the group consisting of C, CH, CF, CCl, CCN, $CCH_3$, C—$OCH_3$, $CCF_3$, C—$CH_2$-Ph, C—NH-Ph, C—O-Ph, C—$CH_2OCH_3$, C—$CH_2$—$NHCH_3$, C—$N(CH_3)_2$, C—$CH_2NH_2$, C—C(=O)OH, C—C(=O)$OCH_2CH_3$, C—C(=O)$NH_2$, —C—O—$CH_2CH_2$—$N(CH_3)_2$, $CH_2$, C(=O), N, NH, $NCH_3$, N—C(=O)$CH_3$, N-Ph, —N—$CH_2CH_2$—$N(CH_3)_2$, O and S; and k is 0, 1, 2, 3 or 4;

provided that at most two groups among $V^1$-$V^9$ are simultaneously C(=O).

In preferred embodiments,

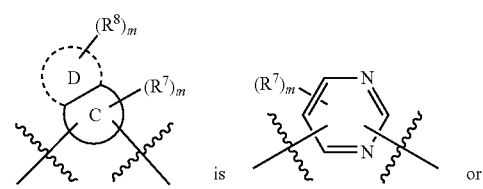

is

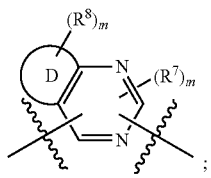

or more preferably

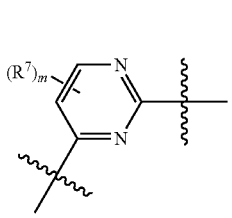

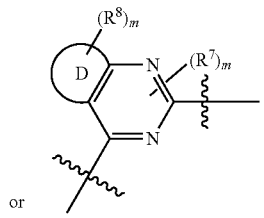

or

In preferred embodiments, $R^7$ and $R^8$, at each occurrence, are each independently selected from the group consisting of F, Cl, Br, I, cyano, —$N(CH_3)_2$, methyl, ethyl, propyl, methoxy, trifluoromethyl, phenyl, —$CH_2$-Ph, —NH-Ph, —O-Ph, —$CH_2OCH_3$, —$CH_2NH_2$, —$CH_2$—$NHCH_3$, —C(=O)$CH_3$, —C(=O)OH, —C(=O)$OCH_2CH_3$, —C(=O)$NH_2$, —O—$CH_2CH_2$—$N(CH_3)_2$ and —$CH_2CH_2$—$N(CH_3)_2$.

In the most preferred embodiments,

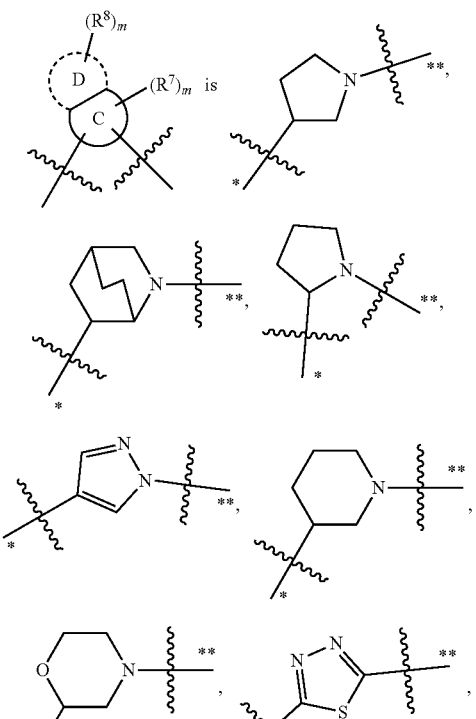

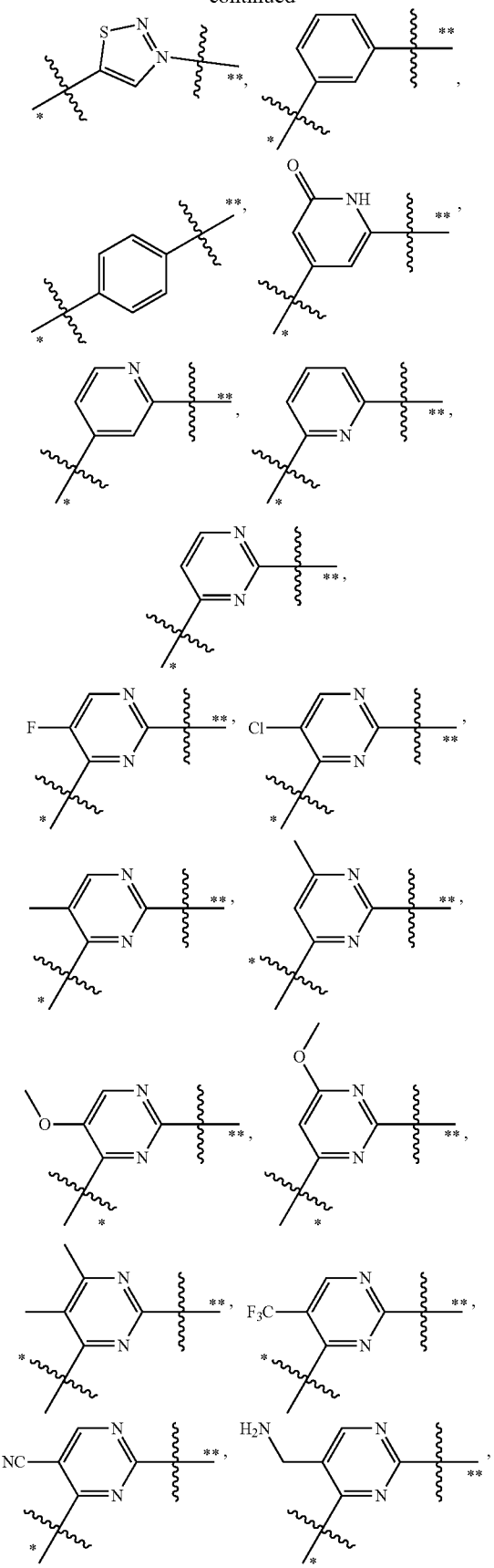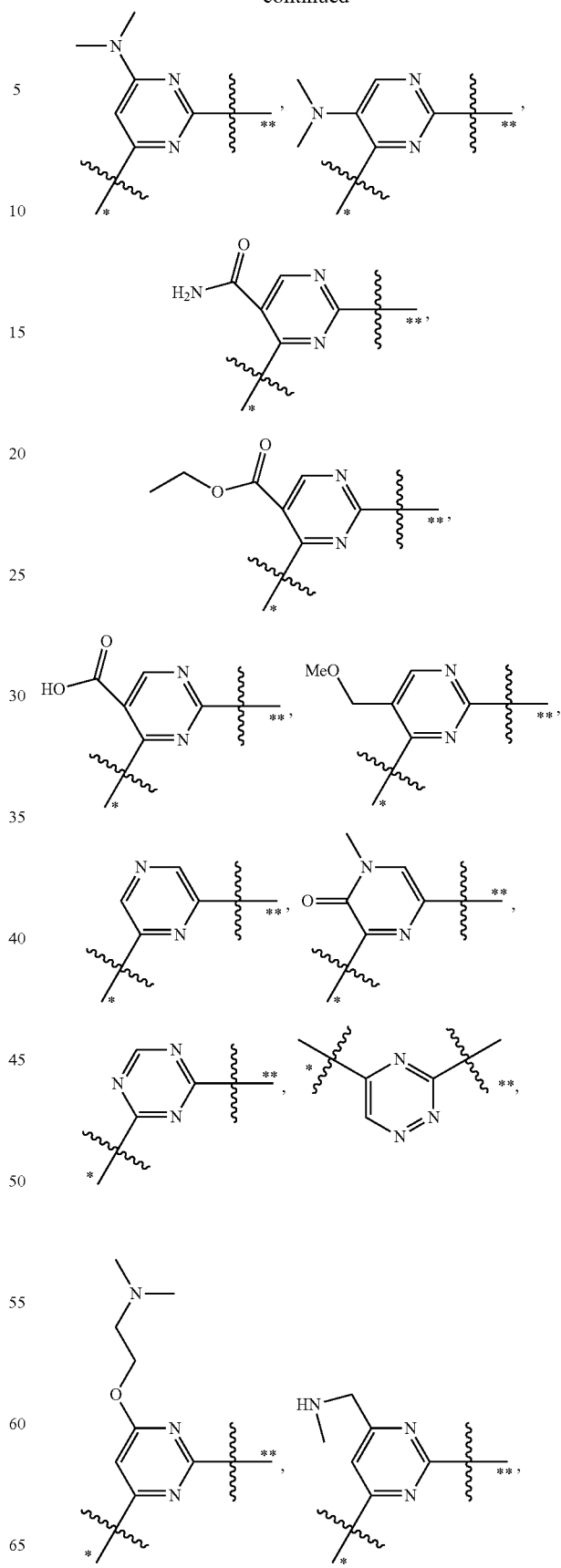

-continued
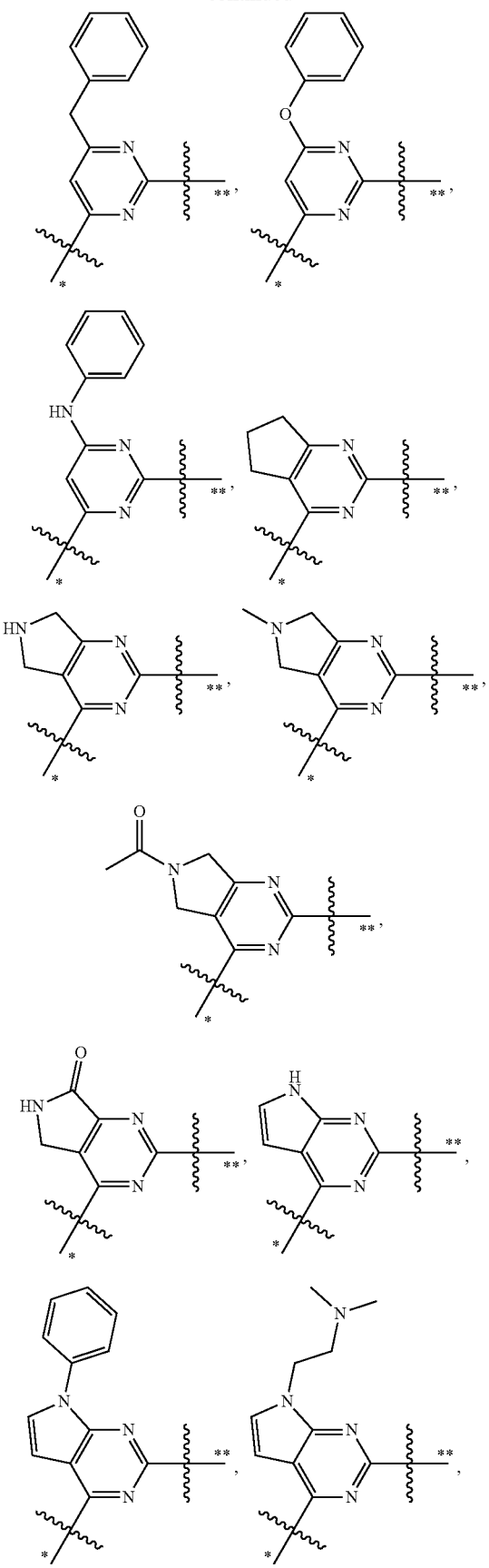
-continued
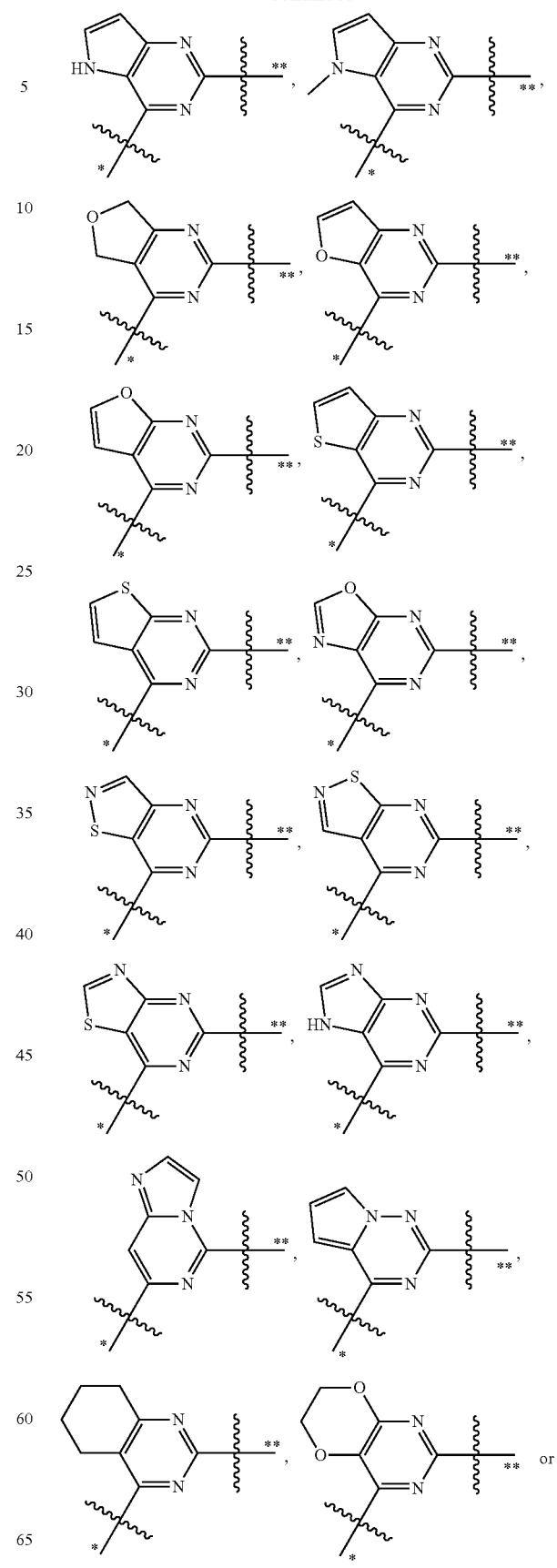

-continued

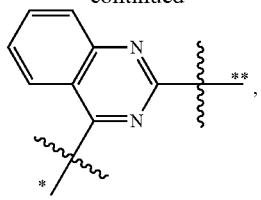

the above group is attached to Y at either of the two positions labeled * or **, and is attached to X at the other position.

In some embodiments, the present invention provides a compound or a pharmaceutically acceptable salt, ester, stereoisomer, polymorph, solvate, N-oxide, isotopically labeled compound, metabolite or prodrug thereof, wherein ring E is

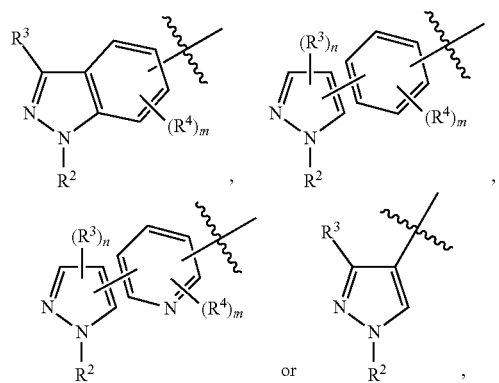

preferably

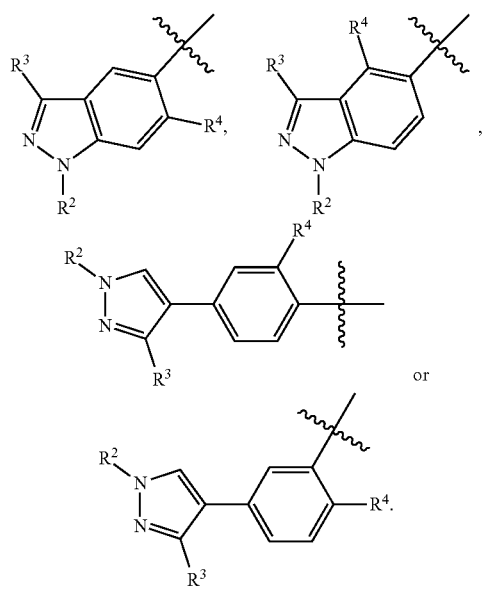

In some embodiments, $R^3$ and $R^4$, at each occurrence, are each independently selected from the group consisting of H, F, Cl, Br, I, —OH, methyl, ethyl, propyl, methoxy, —NH$_2$, —N(CH$_3$)$_2$, —O-ethylene-N(CH$_3$)$_2$.

In preferred embodiments, ring E is

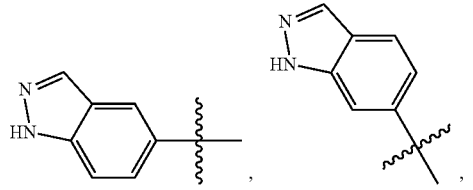

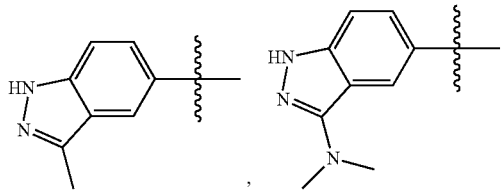

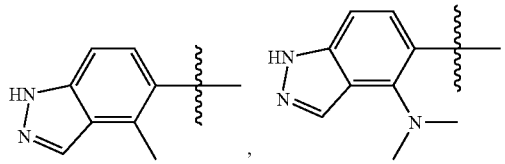

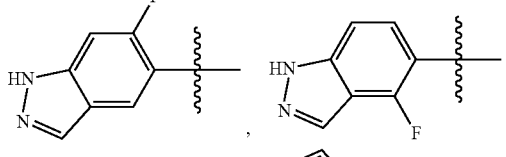

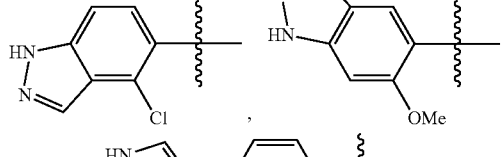

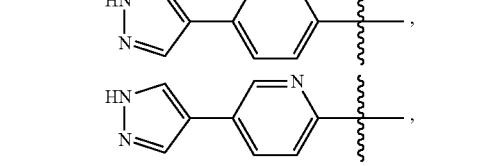

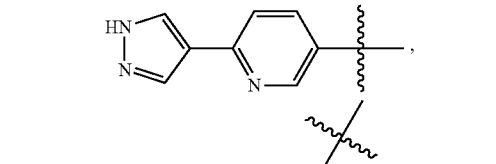

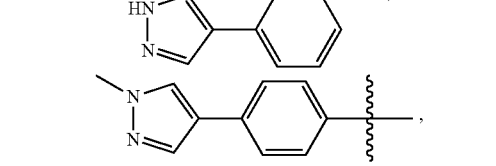

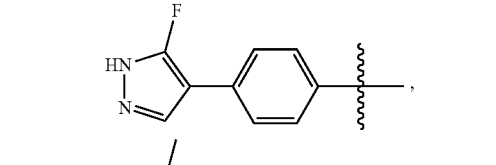

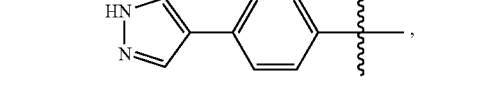

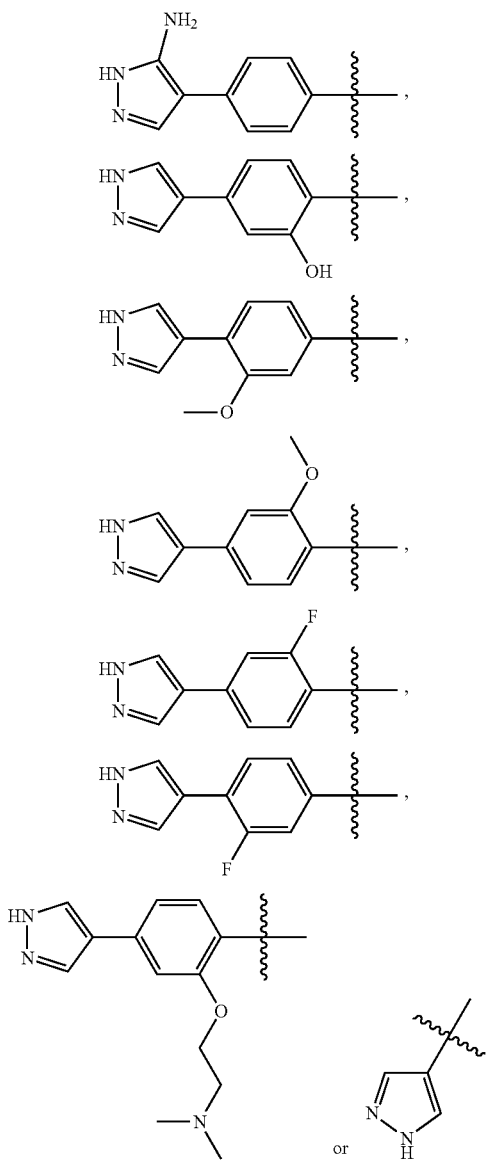
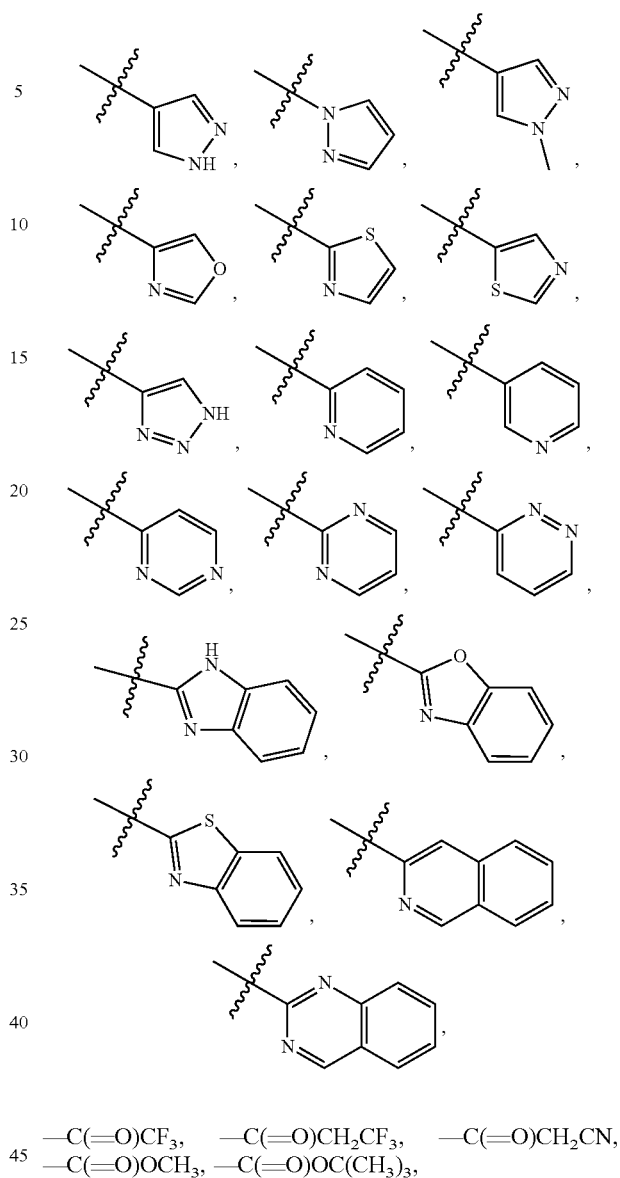
In some embodiments, the present invention provides a compound or a pharmaceutically acceptable salt, ester, stereoisomer, polymorph, solvate, N-oxide, isotopically labeled compound, metabolite or
prodrug thereof, wherein R[1] is methyl, —CH$_2$OH,
—C(═O)CF$_3$, —C(═O)CH$_2$CF$_3$, —C(═O)CH$_2$CN, —C(═O)OCH$_3$, —C(═O)OC(CH$_3$)$_3$,
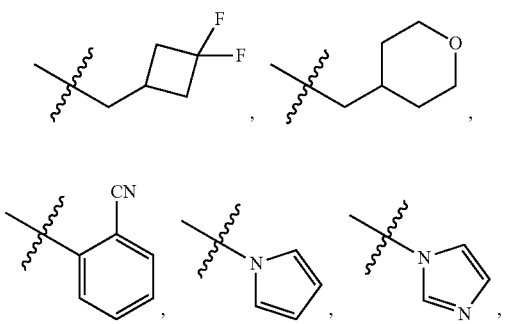
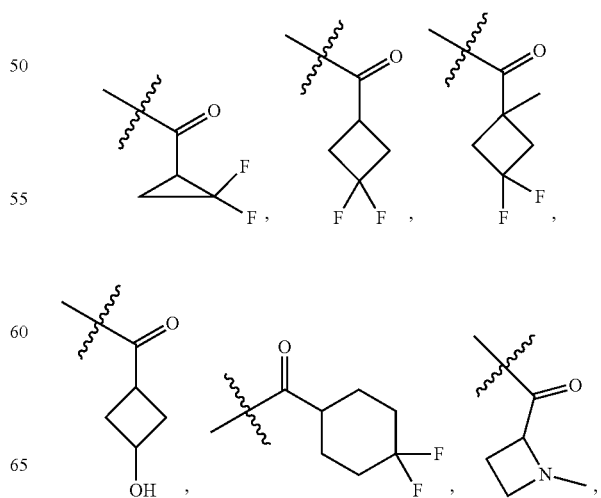

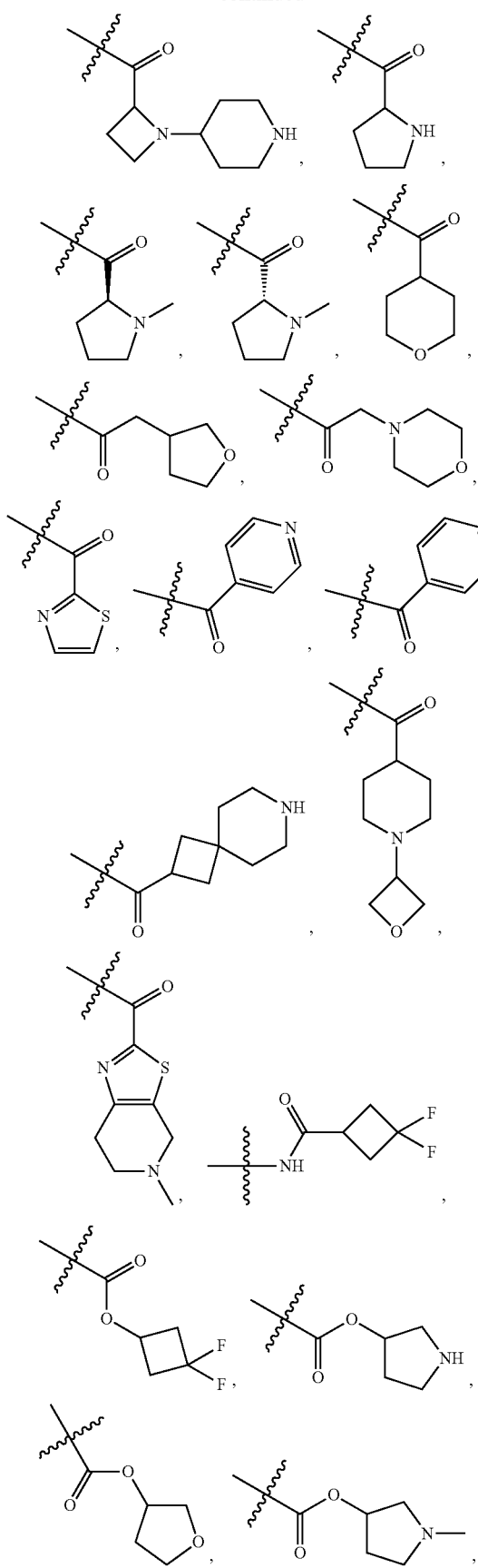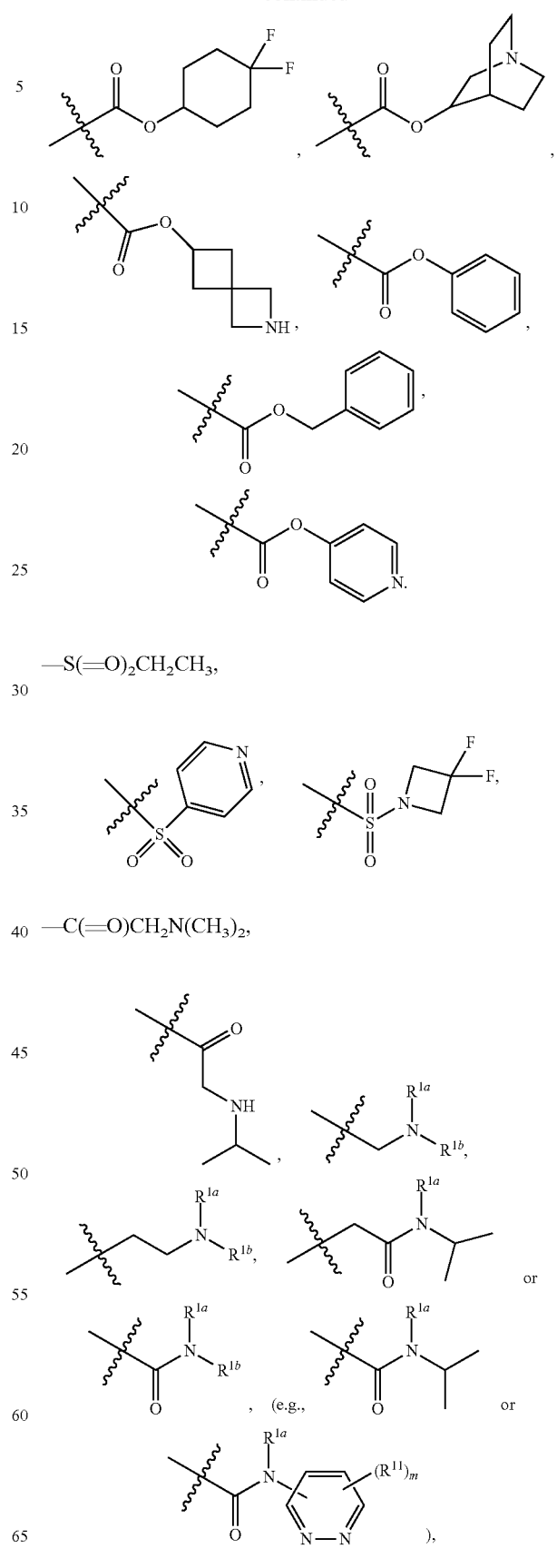
—S(=O)$_2$CH$_2$CH$_3$,
—C(=O)CH$_2$N(CH$_3$)$_2$, more preferably

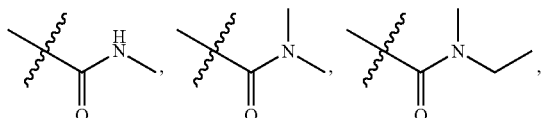

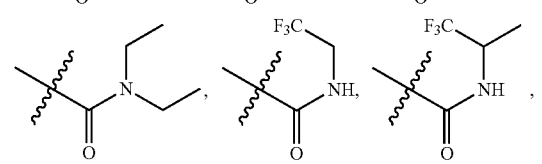

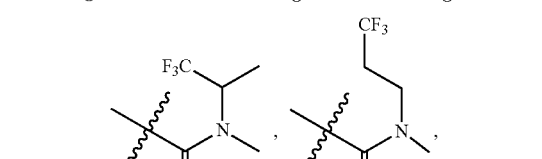

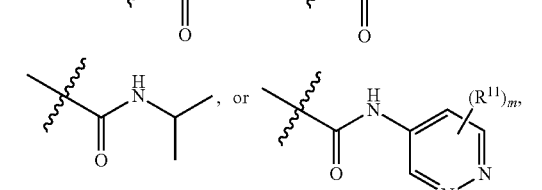

wherein $R^{11}$ is H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)$R^5$, —OC(=O)$R^5$, —C(=O)O$R^5$, —O$R^5$, —S$R^5$, —S(=O)$R^5$, —S(=O)$_2$$R^5$, —S(=O)$_2$N$R^5$$R^6$, —N$R^5$$R^6$, —C(=O)N$R^5$$R^6$, —N$R^5$—C(=O)$R^6$, —N$R^5$—C(=O)O$R^6$, —N$R^5$—S(=O)$_2$—$R^6$, —N$R^5$—C(=O)—N$R^5$$R^6$, —C$_{1-6}$ alkylene-N$R^5$$R^6$ or —O—C$_{1-6}$ alkylene-N$R^5$$R^6$.

In some embodiments, the present invention provides a compound or a pharmaceutically acceptable salt, ester, stereoisomer, polymorph, solvate, N-oxide, isotopically labeled compound, metabolite or prodrug thereof, wherein $R^{1a}$ and $R^{1b}$ are each independently selected from the group consisting of H, methyl, —CF$_3$, ethyl, —CH$_2$CF$_3$, —CH$_2$CH$_2$CF$_3$, —CH(CH$_3$)CF$_3$, n-propyl, isopropyl, cyclopropyl, cyclobutyl, cyclopentyl, cyclohexyl, -ethylene-O-methyl, —CH$_2$CN, —CH$_2$CH$_2$CN, —CH$_2$CH$_2$OH,

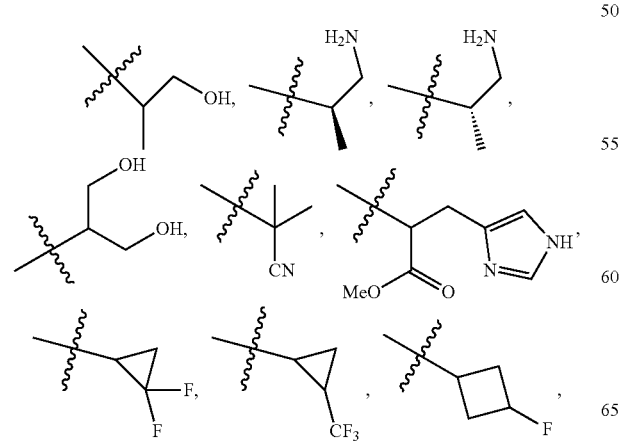

-continued

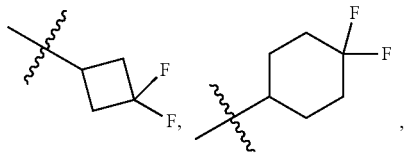

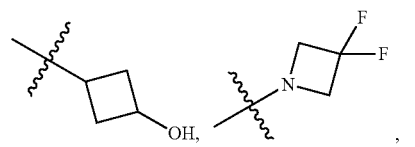

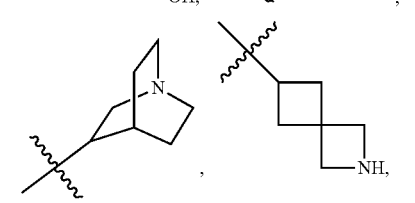

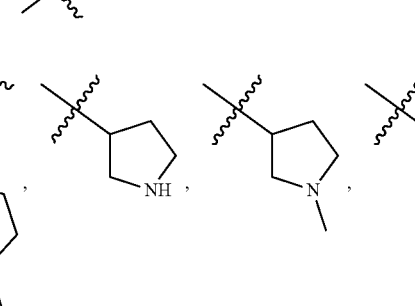

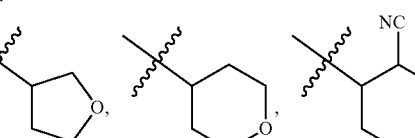

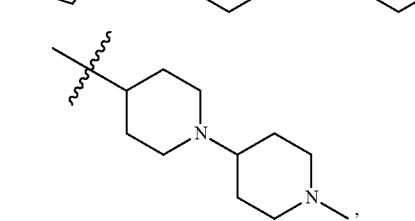

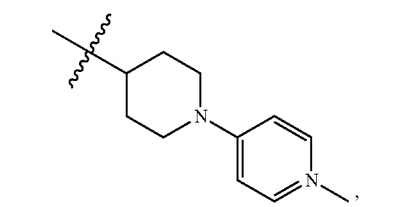

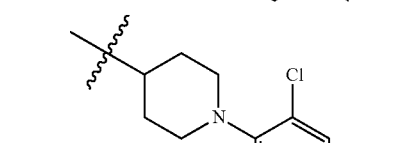

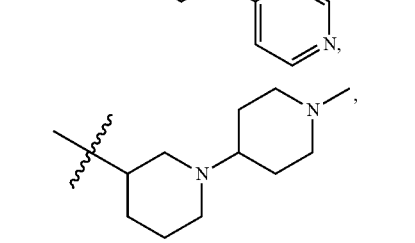

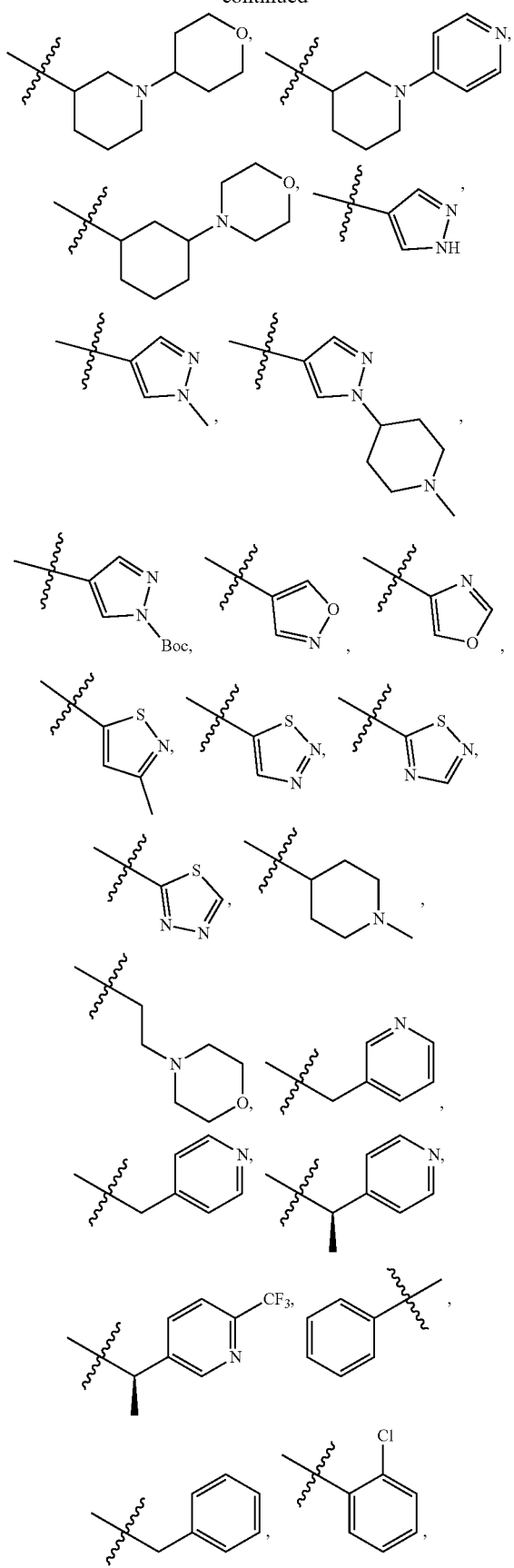
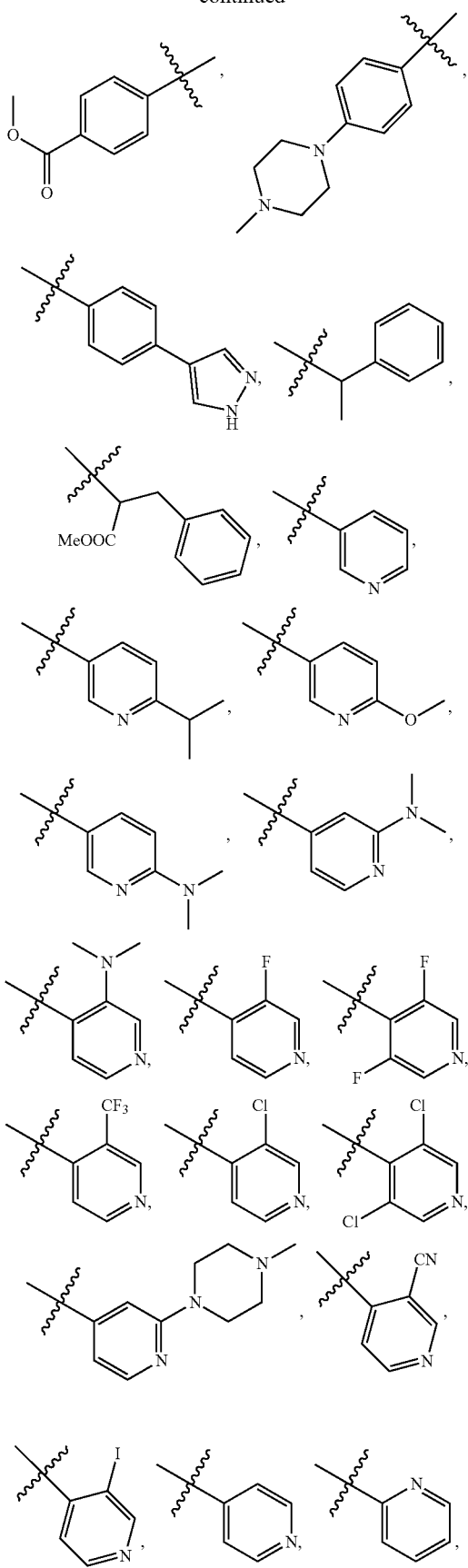

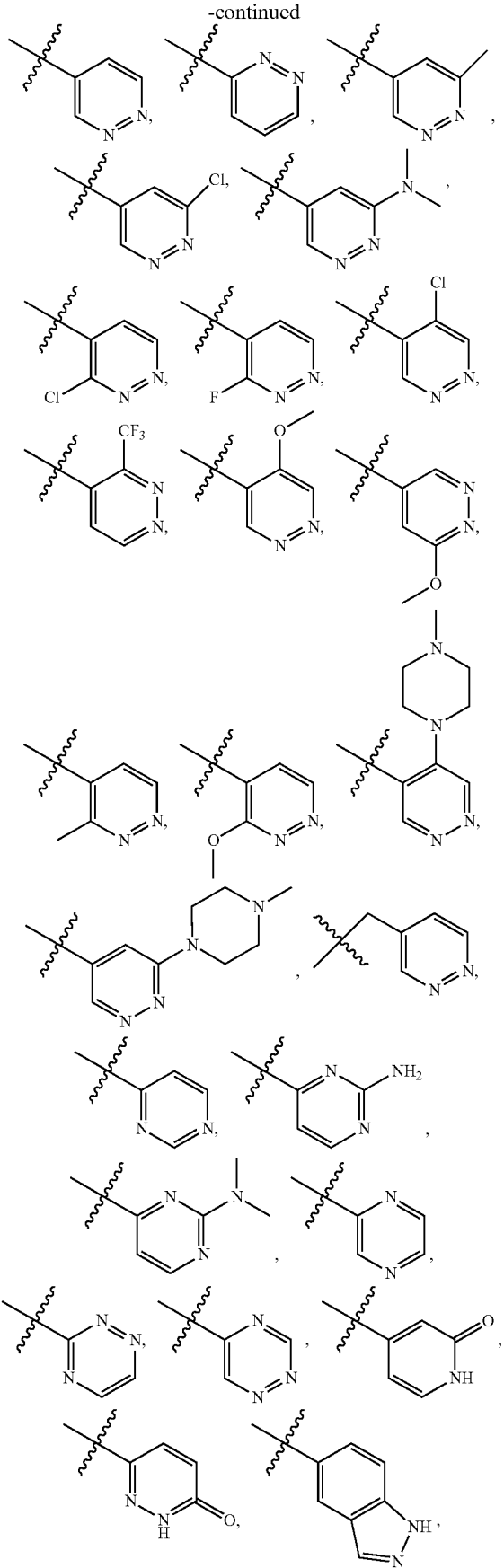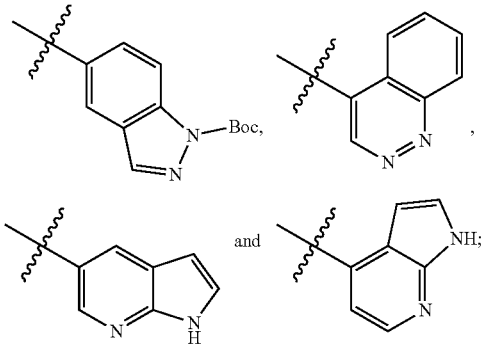
or $R^{1a}$ and $R^{1b}$ together with the atom to which they are attached form the following group:
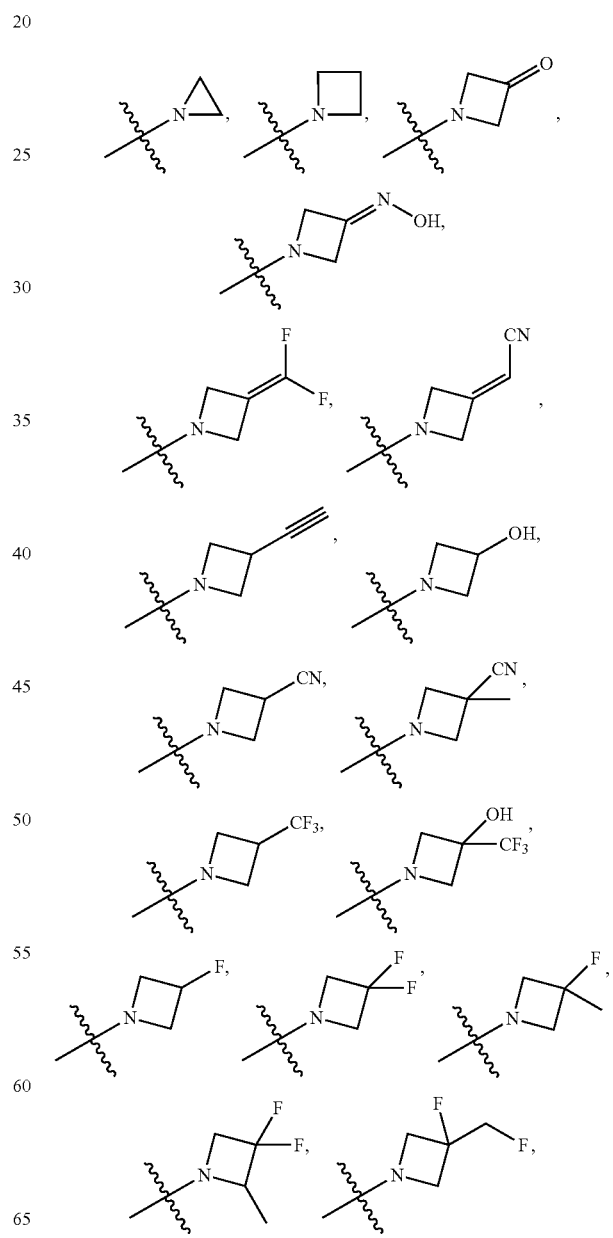

-continued
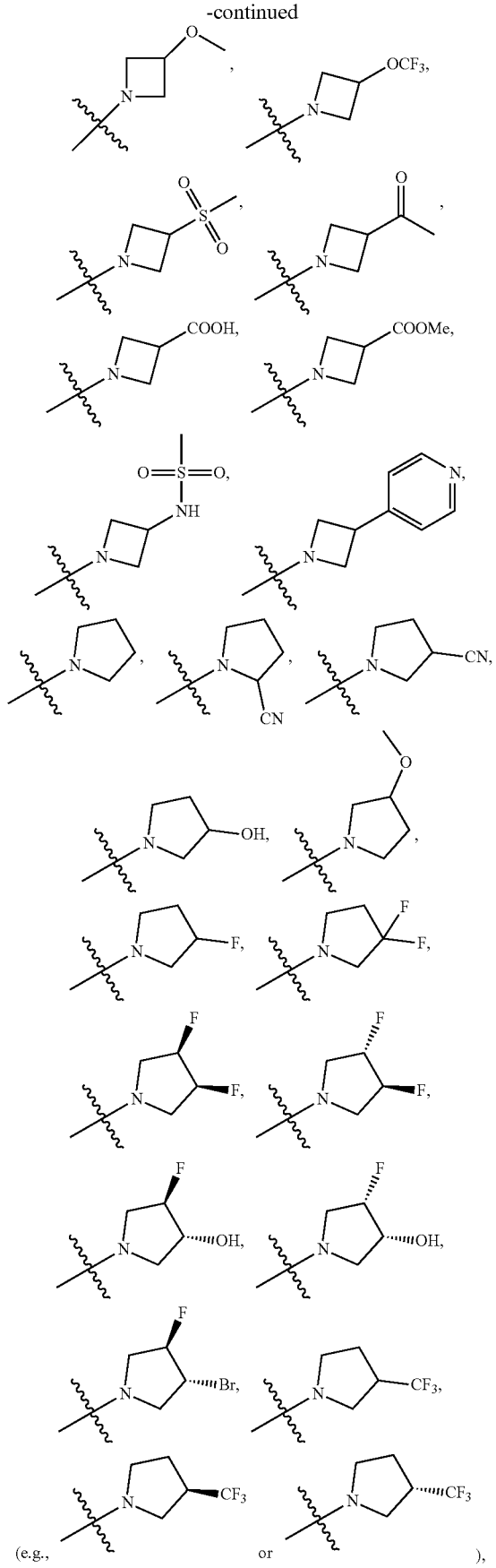
(e.g., or ),
-continued

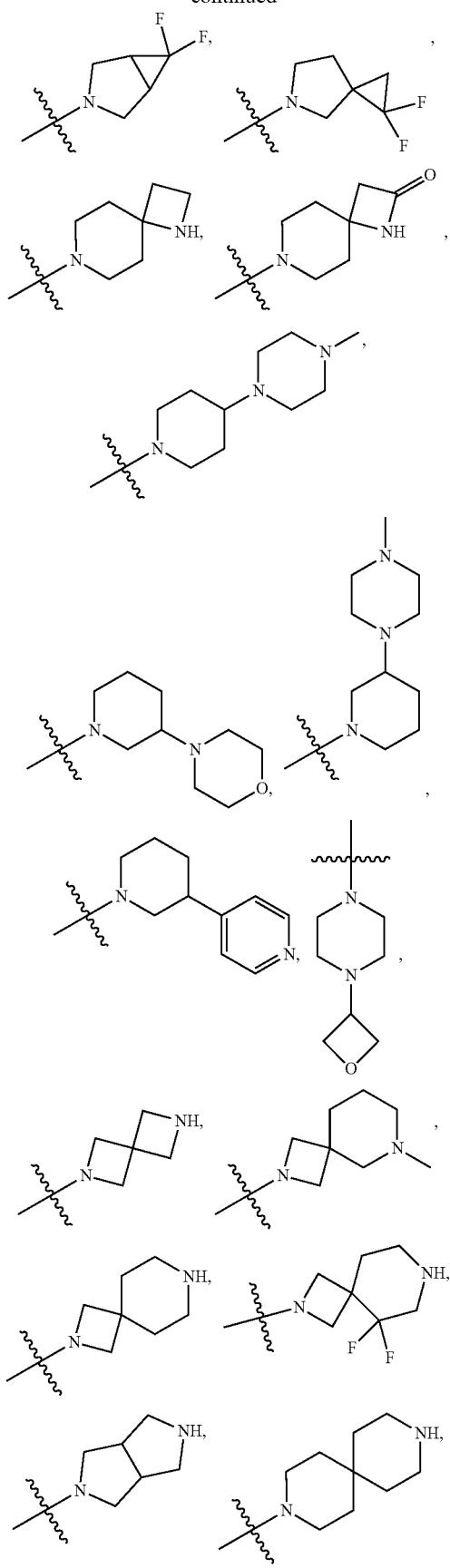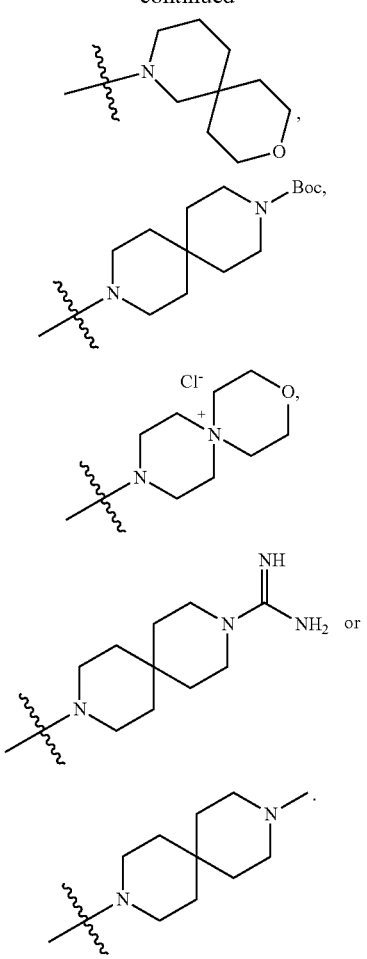
In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of any of the following formulae:
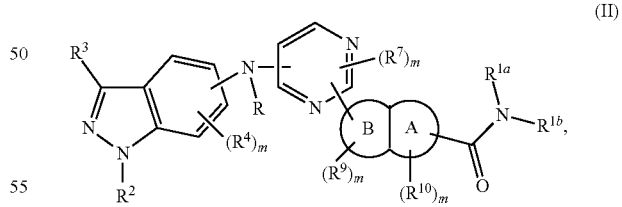
(II)
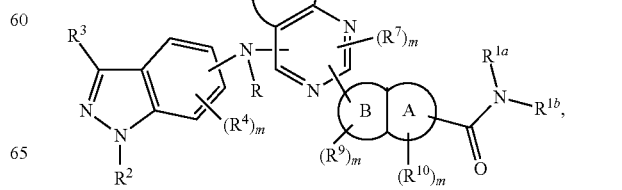
(II')

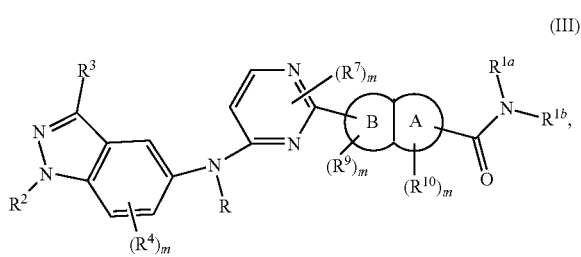
(III)
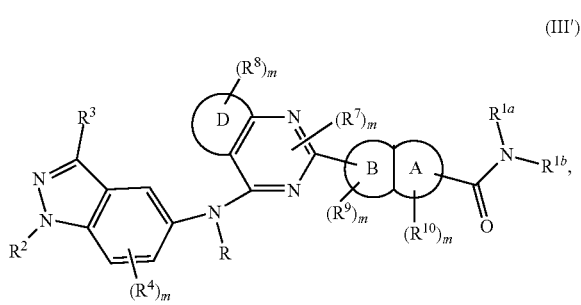
(III')
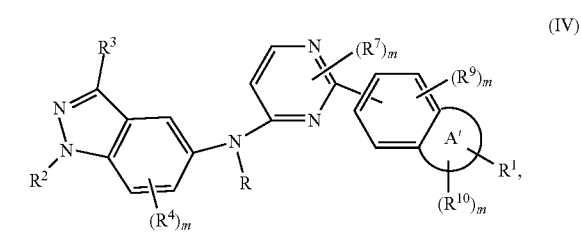
(IV)
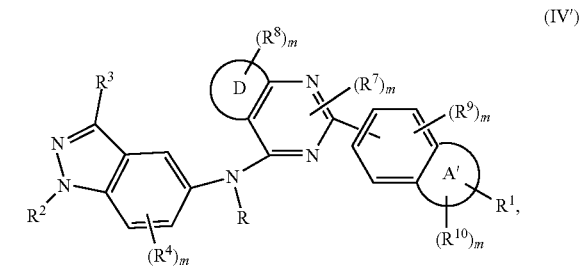
(IV')
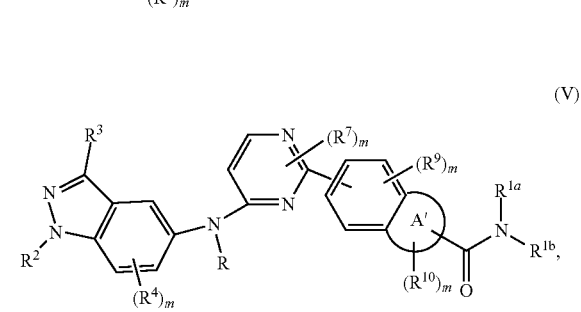
(V)
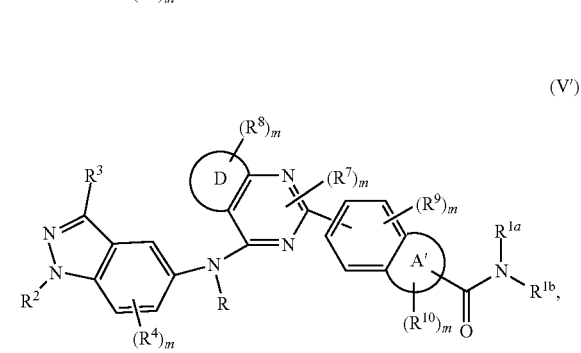
(V')
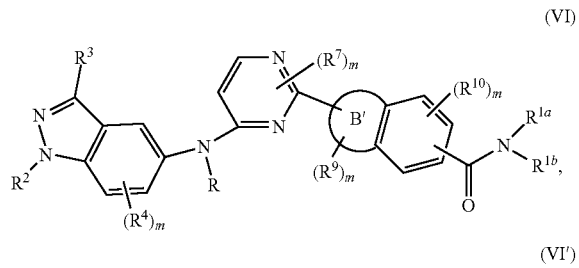
(VI)
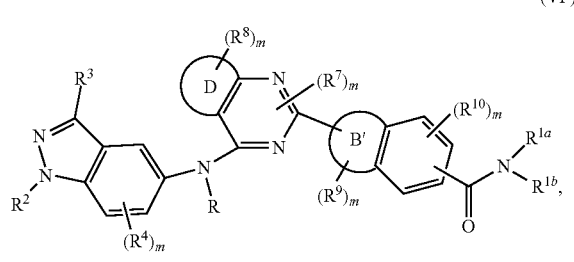
(VI')
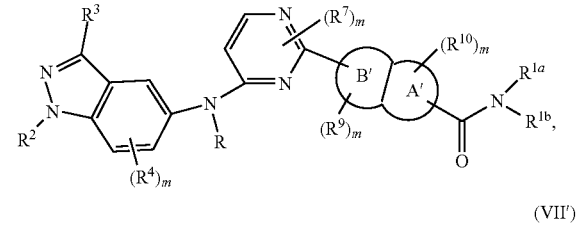
(VII)
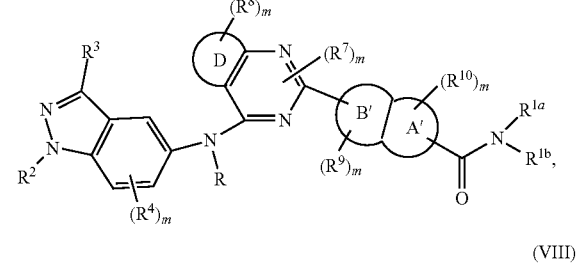
(VII')
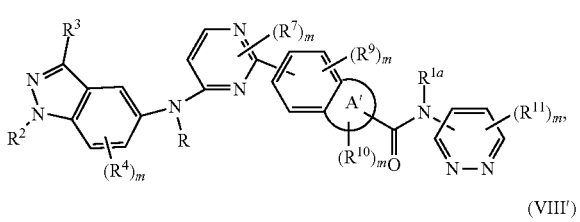
(VIII)
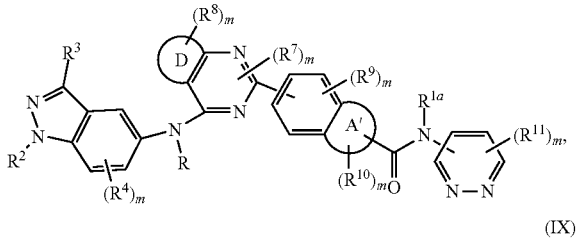
(VIII')
(IX)

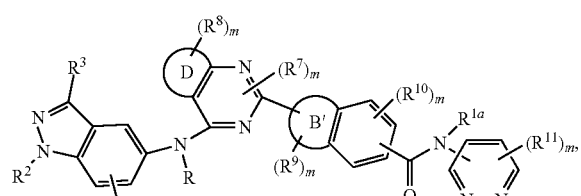
(IX')
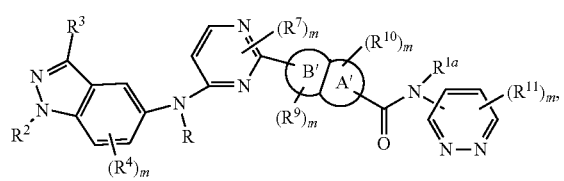
(X)
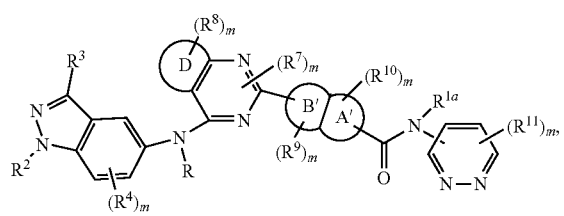
(X')
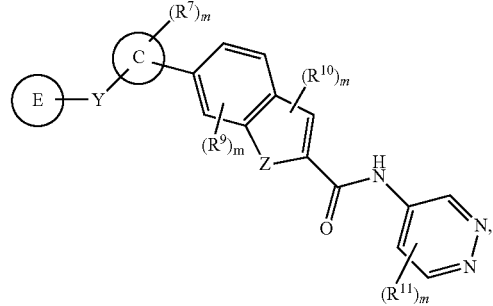
(XI)
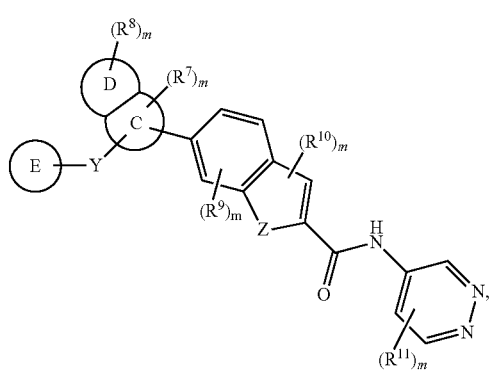
(XI')
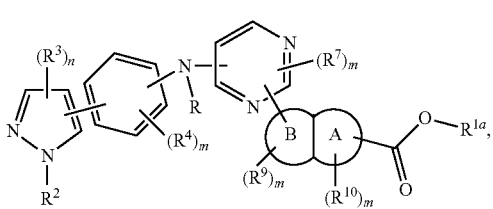
(XII)
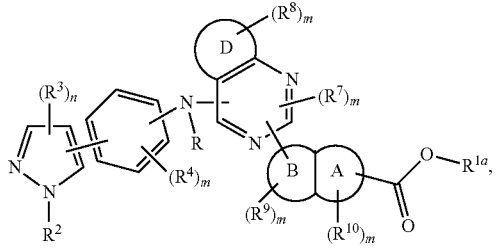
(XII')
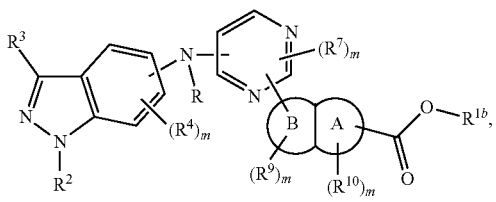
(XIII)
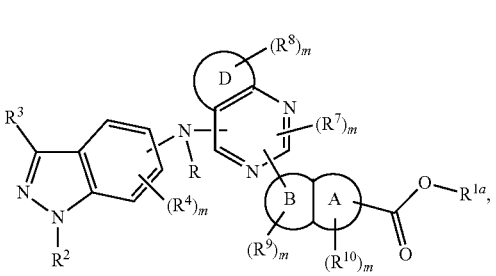
(XIII')
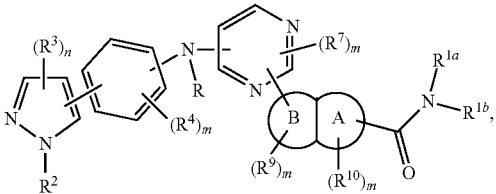
(XIV)
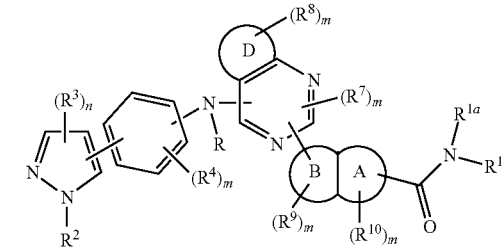
(XIV')
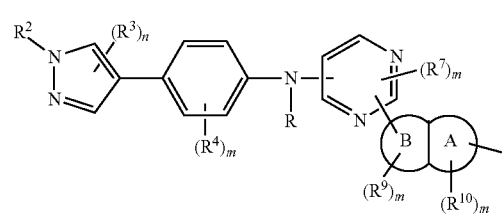
(XV)

(XV')

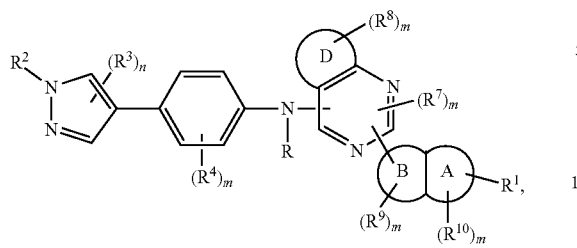

(XV')-1

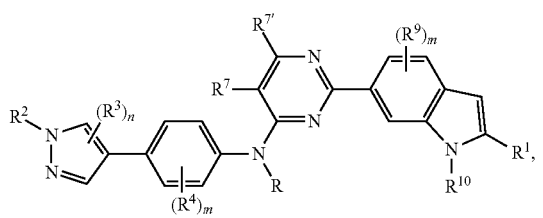

(XV')-2

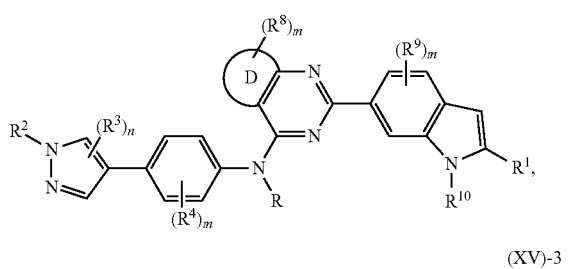

(XV')-3

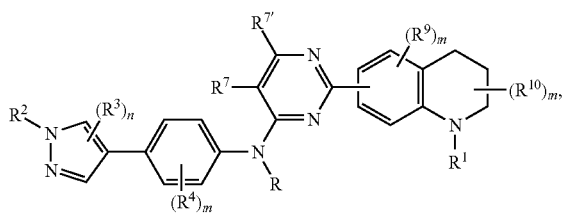

(XV')-4

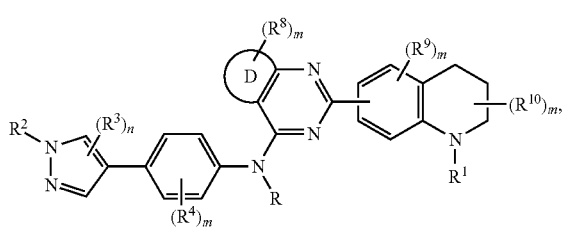

(XVI)

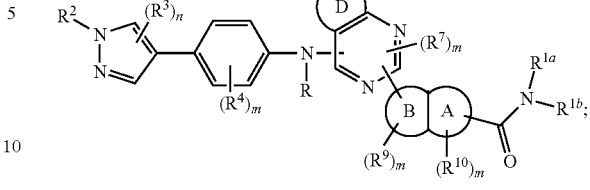

(XVI')

wherein:

Z is selected from the group consisting of O, S(=O), and NR;

each of the remaining groups is as defined above.

In preferred embodiments, the present invention provides a compound or a pharmaceutically acceptable salt, ester, stereoisomer, polymorph, solvate, N-oxide, isotopically labeled compound, metabolite or prodrug thereof, wherein the compound has the structure of formula (XVII) or formula (XVII'):

(XVII)

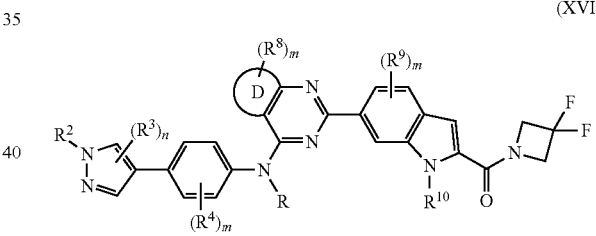

or (XVII')

wherein:

R is selected from the group consisting of H and $C_{1-6}$ alkyl;

ring D is saturated or partially unsaturated 3- to 10-membered heterocycle, $C_{6-10}$ aryl or 5- to 10-membered heteroaromatic ring, preferably

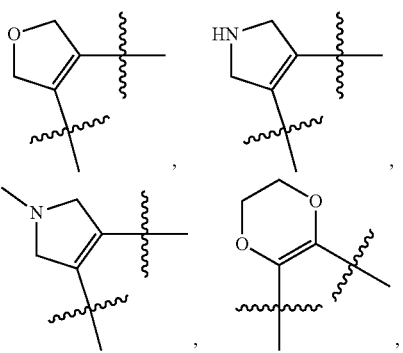

phenyl ring, N-methylpyrrole ring, furan ring or thiophene ring;

$R^2$ is selected from the group consisting of H and $C_{1-6}$ alkyl;

$R^3$, $R^4$, $R^7$, $R^{7'}$ and $R^8$, at each occurrence, are each independently selected from the group consisting of H, halogen, —NH$_2$, —OH, $C_{1-6}$ alkyl and —OR$^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R$^5$ and —$C_{1-6}$ alkylene-O(P=O)(OH)$_2$;

the above alkyl, alkenyl, cyclic hydrocarbyl, heterocyclyl, aryl, heteroaryl, heteroaromatic ring and aralkyl, at each occurrence, are each optionally substituted with one or more substituents independently selected from the group consisting of halogen, $C_{1-6}$ alkyl and —OR$^5$;

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3; and n is an integer of 0, 1 or 2.

In preferred embodiments, $R^5$ and $R^6$, at each occurrence, are each independently selected from the group consisting of H, methyl and ethyl.

In preferred embodiments, $R^3$, $R^4$, $R^7$, $R^{7'}$ and $R^8$, at each occurrence, are each independently selected from the group consisting of H, F, Cl, Br, —NH$_2$, —OH, methyl, trifluoromethyl, —CH$_2$-Ph, methoxy, ethoxy and —CH$_2$OCH$_3$.

In preferred embodiments, $R^9$ and $R^{10}$, at each occurrence, are each independently selected from the group consisting of H, F, Cl, Br, methyl, ethyl, n-propyl, isopropyl, vinyl, cyclopropyl, cyclobutyl, cyclopentyl, oxetanyl, monofluoromethyl, difluoromethyl, trifluoromethyl, acetyl, —CH$_2$CHF$_2$, —CH$_2$OH, —CH$_2$OCH$_3$, —CH$_2$CH$_2$OCH$_3$, —CH$_2$—O(P=O)(OH)$_2$,

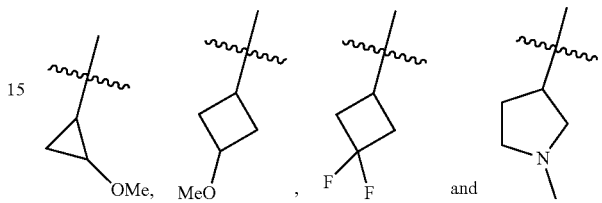

The compound obtained by any combination of the various embodiments is encompassed by the invention.

In some embodiments, the present invention provides a compound or a pharmaceutically acceptable salt, ester, stereoisomer, polymorph, solvate, N-oxide, isotopically labeled compound, metabolite or prodrug thereof, wherein the structure and characterization data of the compound is as follows:

| No. | Structural Formula | MS m/z (ESI): [M + H] |
|---|---|---|
| TDI01102 | | 413.2 |
| TDI01103 | | 431.2 |
| TDI01104 | | 429.3 |
| TDI01105 | | 413.2 |

-continued

| No. | Structural Formula | MS m/z (ESI): [M + H] |
|---|---|---|
| TDI01106 | | 429.2 |
| TDI01107 | | 429.3 |
| TDI01108 | | 412.2 |
| TDI01109 | | 401.1 |
| TDI01110 | | 415.1 |
| TDI01111 | | 427.2 |
| TDI01112 | | 469.1 |
| TDI01113 | | 457.0 |

-continued

| No. | Structural Formula | MS m/z (ESI): [M + H] |
|---|---|---|
| TDI01114 | | 484.3 |
| TDI01115 | | 464.2 |
| TDI01116 | | 465.1 |
| TDI01117 | | 428.2 |
| TDI01118 | | 444.1 |
| TDI01119 | | 469.1 |
| TDI01120 | | 485.1 |

-continued

| No. | Structural Formula | MS m/z (ESI): [M + H] |
|---|---|---|
| TDI01121 | | 516.2 |
| TDI01122 | | 539.1 |
| TDI01127 | | 412.1 |
| TDI01128 | | 462.2 |
| TDI01129 | | 410.2 |
| TDI01130 | | 504.1 |

-continued
| No. | Structural Formula | MS m/z (ESI): [M + H] |
|---|---|---|
| TDI01131 | 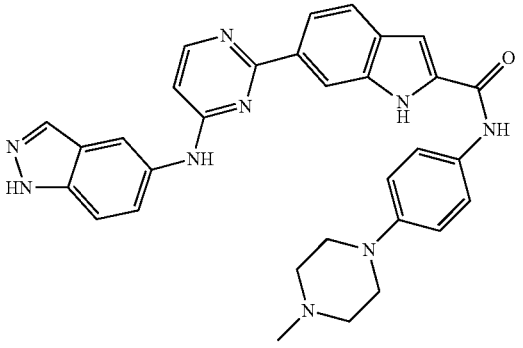 [SMILES: CN1CCN(c2ccc(NC(=O)c3cc4ccc(-c5nccc(Nc6ccc7[nH]ncc7c6)n5)cc4[nH]3)cc2)CC1] | 544.2 |
| TDI01132 | 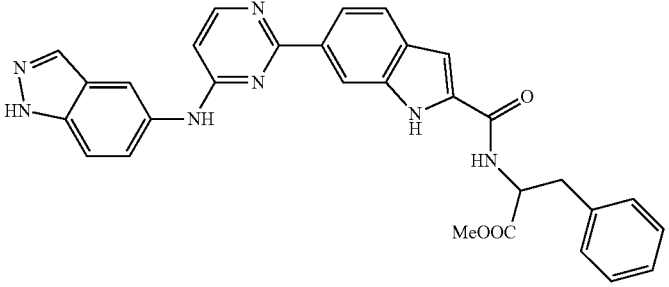 [SMILES: COC(=O)C(Cc1ccccc1)NC(=O)c1cc2ccc(-c3nccc(Nc4ccc5[nH]ncc5c4)n3)cc2[nH]1] | 532.2 |
| TDI01133 | 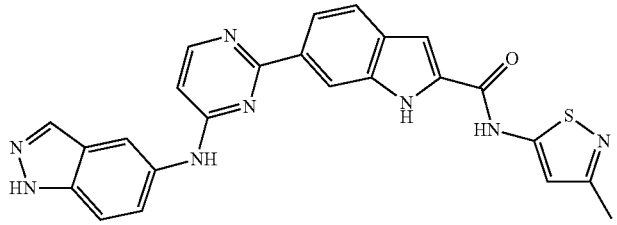 [SMILES: Cc1cc(NC(=O)c2cc3ccc(-c4nccc(Nc5ccc6[nH]ncc6c5)n4)cc3[nH]2)sn1] | 467.1 |
| TDI01134 | 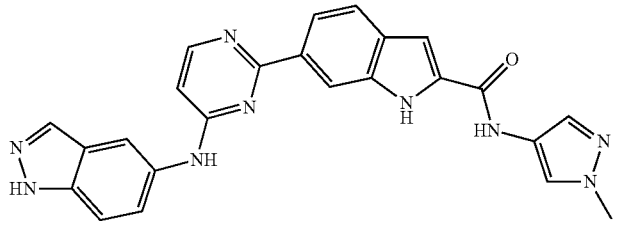 [SMILES: Cn1cc(NC(=O)c2cc3ccc(-c4nccc(Nc5ccc6[nH]ncc6c5)n4)cc3[nH]2)cn1] | 450.2 |
| TDI01135 | 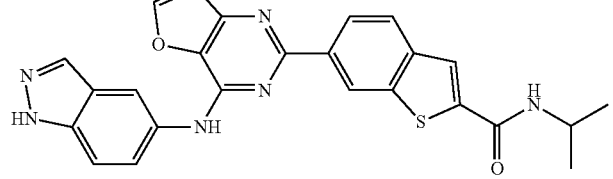 | 469.1 |
| TDI01136 | 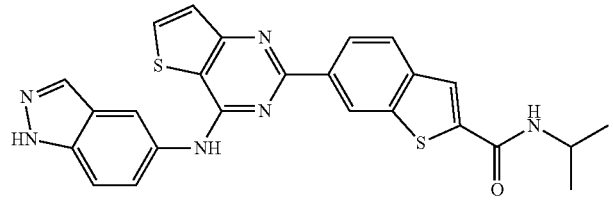 [SMILES: CC(C)NC(=O)c1cc2ccc(-c3nc(Nc4ccc5[nH]ncc5c4)c4sccc4n3)cc2s1] | 485.1 |

| No. | Structural Formula | MS m/z (ESI): [M + H] |
|---|---|---|
| TDI01139 | | 435.1 |
| TDI01140 | | 474.1 |
| TDI01141 | | 468.2 |
| TDI01142 | | 468.1 |
| TDI01143 | | 451.1 |
| TDI01144 | | 451.2 |

| No. | Structural Formula | MS m/z (ESI): [M + H] |
|---|---|---|
| TDI01145 | | 453.2 |
| TDI01146 | | 453.2 |
| TDI01147 | | 418.1 |
| TDI01148 | | 469.1 |
| TDI01149 | | 469.1 |
| TDI01150 | | 469.1 |

| No. | Structural Formula | MS m/z (ESI): [M + H] |
|---|---|---|
| TDI01151 | | 410.2 |
| TDI01152 | | 448.2 |
| TDI01153 | | 447.1 |
| TDI01154 | | 454.1 |
| TDI01155 | | 398.1 |
| TDI01156 | | 437.1 |
| TDI01157 | | 437.1 |

-continued

| No. | Structural Formula | MS m/z (ESI): [M + H] |
|---|---|---|
| TDI01158 | | 454.1 |
| TDI01159 | | 454.1 |
| TDI01160 | | 448.2 |
| TDI01161 | | 448.1 |
| TDI01162 | | 448.2 |
| TDI01163 | | 449.2 |
| TDI01164 | | 487.1 |

-continued

| No. | Structural Formula | MS m/z (ESI): [M + H] |
|---|---|---|
| TDI01165 | | 502.2 |
| TDI01166 | | 488.2 |
| TDI01167 | | 449.3 |
| TDI01168 | | 473.2 |
| TDI01169 | | 498.1 |
| TDI01171 | | 447.1 |
| TDI01172 | | 462.2 |

-continued

| No. | Structural Formula | MS m/z (ESI): [M + H] |
|---|---|---|
| TDI01173 | | 448.2 |
| TDI01174 | | 474.1 |
| TDI01175 | | 504.1 |
| TDI01176 | | 428.2 |
| TDI01177 | | 385.2 |
| TDI01178 | | 462.1 |
| TDI01179 | | 482.1 |

| No. | Structural Formula | MS m/z (ESI): [M + H] |
|---|---|---|
| TDI01180 | | 482.1 |
| TDI01181 | | 482.2 |
| TDI01182 | | 486.1 |
| TDI01183 | | 463.2 |
| TDI01184 | | 463.2 |
| TDI01185 | | 498.2 |
| TDI01186 | | 464.2 |

-continued

| No. | Structural Formula | MS m/z (ESI): [M + H] |
|---|---|---|
| TDI01187 | | 448.2 |
| TDI01188 | | 448.2 |
| TDI01189 | | 449.1 |
| TDI01190 | | 449.2 |
| TDI01191 | | 448.2 |
| TDI01192 | | 449.2 |

-continued

| No. | Structural Formula | MS m/z (ESI): [M + H] |
|---|---|---|
| TDI01193 | | 449.0 |
| TDI01194 | | 466.1 |
| TDI01195 | | 450.1 |
| TDI01196 | | 449.2 |
| TDI01197 | | 450.1 |
| TDI01198 | | 451.2 |
| TDI01199 | | 436.1 |

-continued

| No. | Structural Formula | MS m/z (ESI): [M + H] |
|---|---|---|
| TDI01200 | | 536.1 |
| TDI01201 | | 462.2 |
| TDI01209 | | 439.1 |
| TDI01211 | | 448.2 |
| TDI01212 | | 449.1 |
| TDI01213 | | 466.1 |
| TDI01214 | | 466.1 |

| No. | Structural Formula | MS m/z (ESI): [M + H] |
|---|---|---|
| TDI01215 | | 446.1 |
| TDI01216 | | 516.1 |
| TDI01217 | | 546.2 |
| TDI01218 | | 544.2 |
| TDI01219 | | 403.2 |
| TDI01220 | | 399.2 |

| No. | Structural Formula | MS m/z (ESI): [M + H] |
|---|---|---|
| TDI01221 | | 490.1 |
| TDI01222 | | 489.2 |
| TDI01223 | | 478.2 |
| TDI01224 | | 478.2 |
| TDI01225 | | 478.2 |
| TDI01226 | | 462.2 |

-continued

| No. | Structural Formula | MS m/z (ESI): [M + H] |
|---|---|---|
| TDI01227 | | 546.2 |
| TDI01228 | | 466.1 |
| TDI01229 | | 369.3 |
| TDI01230 | | 467.3 |
| TDI01231 | | 516.2 |
| TDI01232 | | 476.3 |
| TDI01233 | | 538.1 |

| No. | Structural Formula | MS m/z (ESI): [M + H] |
|---|---|---|
| TDI01234 | | 451.3 |
| TDI01235 | | 519.2 |
| TDI01236 | | 460.3 |
| TDI01237 | | 450.2 |
| TDI01238 | | 464.3 |
| TDI01239 | | 478.2 |
| TDI01240 | | 478.2 |

| No. | Structural Formula | MS m/z (ESI): [M + H] |
|---|---|---|
| TDI01241 | | 474.2 |
| TDI01242 | | 482.1 |
| TDI01243 | | 396.1 |
| TDI01244 | | 494.2 |
| TDI01245 | | 396.2 |

| No. | Structural Formula | MS m/z (ESI): [M + H] |
|---|---|---|
| TDI01246 | | 434.2 |
| TDI01247 | | 454.1 |
| TDI01248 | | 586.2 |
| TDI01249 | | 448.0 |
| TDI01250 | | 462.3 |
| TDI01251 | | 462.1 |
| TDI01253 | | 444.2 |

-continued

| No. | Structural Formula | MS m/z (ESI): [M + H] |
|---|---|---|
| TDI01254 | | 456.2 |
| TDI01255 | | 456.2 |
| TDI01256 | | 483.1 |
| TDI01257 | | 508.2 |
| TDI01258 | | 486.2 |
| TDI01259 | | 485.2 |

-continued

| No. | Structural Formula | MS m/z (ESI): [M + H] |
|---|---|---|
| TDI01260 | | 400.2 |
| TDI01261 | | 462.1 |
| TDI01262 | | 507.3 |
| TDI01263 | | 403.2 |
| TDI01264 | | 359.2 |
| TDI01265 | | 372.1 |

| No. | Structural Formula | MS m/z (ESI): [M + H] |
|---|---|---|
| TDI01266 | | 442.1 |
| TDI01267 | | 416.2 |
| TDI01268 | | 428.2 |
| TDI01271 | | 484.2 |
| TDI01272 | | 460.2 |
| TDI01273 | | 412.2 |

| No. | Structural Formula | MS m/z (ESI): [M + H] |
|---|---|---|
| TDI01274 | | 508.2 |
| TDI01275 | | 462.2 |
| TDI01276 | | 462.2 |
| TDI01277 | | 466.1 |
| TDI01278 | | 516.2 |
| TDI01280 | | 438.3 |
| TDI01281 | | 460.2 |

-continued

| No. | Structural Formula | MS m/z (ESI): [M + H] |
|---|---|---|
| TDI01282 | | 476.3 |
| TDI01283 | | 436.2 |
| TDI01285 | | 412.3 |
| TDI01286 | | 426.2 |
| TDI01287 | | 398.2 |
| TDI01288 | | 343.2 |

| No. | Structural Formula | MS m/z (ESI): [M + H] |
|---|---|---|
| TDI01289 | | 490.2 |
| TDI01290 | | 481.1 |
| TDI01291 | | 454.3 |
| TDI01292 | | 414.2 |
| TDI01294 | | 424.2 |
| TDI01295 | | 416.2 |
| TDI01296 | | 410.2 |

-continued

| No. | Structural Formula | MS m/z (ESI): [M + H] |
|---|---|---|
| TDI01297 | | 545.2 |
| TDI01298 | | 444.2 |
| TDI01299 | | 439.2 |
| TDI01300 | | 462.2 |
| TDI01310 | | 398.2 |
| TDI01311 | | 447.2 |
| TDI01312 | | 414.2 |

| No. | Structural Formula | MS m/z (ESI): [M + H] |
|---|---|---|
| TDI01314 | | 467.2 |
| TDI01315 | | 477.2 |
| TDI01316 | | 533.2 |
| TDI01317 | | 550.3 |
| TDI01318 | | 550.3 |
| TDI01319 | | 536.3 |

-continued

| No. | Structural Formula | MS m/z (ESI): [M + H] |
|---|---|---|
| TDI01320 | | 521.3 |
| TDI01321 | | 521.3 |
| TDI01322 | | 333.1 |
| TDI01323 | | 412.2 |
| TDI01324 | | 436.2 |
| TDI01325 | | 497.2 |

| No. | Structural Formula | MS m/z (ESI): [M + H] |
|---|---|---|
| TDI01326 | | 469.2 |
| TDI01327 | | 424.2 |
| TDI01328 | | 410.1 |
| TDI01329 | | 438.2 |
| TDI01330 | | 436.2 |
| TDI01331 | | 466.2 |
| TDI01332 | | 452.2 |

-continued

| No. | Structural Formula | MS m/z (ESI): [M + H] |
|---|---|---|
| TDI01333 | | 441.1 |
| TDI01334 | | 480.2 |
| TDI01335 | | 466.2 |
| TDI01336 | | 512.2 |
| TDI01337 | | 466.2 |
| TDI01338 | | 480.2 |
| TDI01339 | | 479.2 |

| No. | Structural Formula | MS m/z (ESI): [M + H] |
|---|---|---|
| TDI01340 | | 454.2 |
| TDI01341 | | 442.2 |
| TDI01342 | | 468.2 |
| TDI01343 | | 479.2 |
| TDI01344 | | 466.2 |
| TDI01345 | | 479.2 |
| TDI01346 | | 482.2 |

| No. | Structural Formula | MS m/z (ESI): [M + H] |
|---|---|---|
| TDI01347 | | 462.2 |
| TDI01348 | | 458.1 |
| TDI01348P-2 | | 445.1 |
| TDI01350 | | 438.4 |
| TDI01351 | | 452.2 |
| TDI01353 | | 398.1 |
| TDI01354 | | 507.3 |
| TDI01355 | | 492.1 |

-continued

| No. | Structural Formula | MS m/z (ESI): [M + H] |
|---|---|---|
| TDI01356 | | 449.1 |
| TDI01357 | | 412.3 |
| TDI01358 | | 471.3 |
| TDI01360 | | 507.3 |
| TDI01360P-1 | | 607.5 |
| TDI01361 | | 480.1 |

-continued

| No. | Structural Formula | MS m/z (ESI): [M + H] |
|---|---|---|
| TDI01362 | | 426.2 |
| TDI01363 | | 473.2 |
| TDI01364 | | 414.2 |
| TDI01365 | | 428.1 |
| TDI01366 | | 426.1 |
| TDI01367 | | 509.2 |
| TDI01368 | | 480.3 |

| No. | Structural Formula | MS m/z (ESI): [M + H] |
|---|---|---|
| TDI01369 | | 477.1 |
| TDI01370 | | 494.2 |
| TDI01371 | | 422.1 |
| TDI01372 | | 498.1 |
| TDI01373 | | 497.1 |
| TDI01374 | | 483.1 |
| TDI01375 | | 455.2 |

-continued

| No. | Structural Formula | MS m/z (ESI): [M + H] |
|---|---|---|
| TDI01376 | | 483.1 |
| TDI01379 | | 466.1 |
| TDI01380 | | 536.3 |
| TDI01381 | | 494.2 |
| TDI01382 | | 470.1 |
| TDI01383 | | 457.2 |

| No. | Structural Formula | MS m/z (ESI): [M + H] |
|---|---|---|
| TDI01384 | | 447.1 |
| TDI01385 | | 522.4 |
| TDI01386 | | 461.1 |
| TDI01387 | | 461.1 |
| TDI01388 | | 475.2 |
| TDI01389 | | 357.1 |
| TDI01390 | | 537.3 |

| No. | Structural Formula | MS m/z (ESI): [M + H] |
|---|---|---|
| TDI01391 | | 455.1 |
| TDI01392 | | 471.1 |
| TDI01393 | | 490.2 |
| TDI01394 | | 465.2 |
| TDI01395 | | 515.0 |
| TDI01396 | | 483.1 |
| TDI01397 | | 473.1 |

-continued

| No. | Structural Formula | MS m/z (ESI): [M + H] |
|---|---|---|
| TDI01398 | | 461.2 |
| TDI01399 | | 455.1 |
| TDI01400 | | 529.3 |
| TDI01402 | | 438.2 |
| TDI01344-2A | | 484.2 |
| TDI01403 | | 449.1 |

-continued

| No. | Structural Formula | MS m/z (ESI): [M + H] |
|---|---|---|
| TDI01404 | | 563.2 |
| TDI01405 | | 440.3 |
| TDI01406 | | 454.1 |
| TDI01407 | | 468.1 |
| TDI01408 | | 424.2 |
| TDI01410 | | 492.0 |

-continued

| No. | Structural Formula | MS m/z (ESI): [M + H] |
|---|---|---|
| TDI01411 | | 426.5 |
| TDI01415 | | 468.1 |
| TDI01416 | | 454.2 |
| TDI01417 | | 443.2 |
| TDI01418 | | 480.3 |
| TDI01419 | | 480.2 |
| TDI01420 | | 464.2 |

-continued

| No. | Structural Formula | MS m/z (ESI): [M + H] |
|---|---|---|
| TDI01421 | | 487.2 |
| TDI01422 | | 480.3 |
| TDI01423 | | 522.2 |
| TDI01424 | | 506.3 |
| TDI01425 | | 533.3 |
| TDI01426 | | 510.2 |
| TDI01427 | | 492.2 |

| No. | Structural Formula | MS m/z (ESI): [M + H] |
|---|---|---|
| TDI01428 | | 509.2 |
| TDI01429 | | 492.2 |
| TDI01430 | | 449.2 |
| TDI01431 | | 480.3 |
| TDI01432 | | 506.2 |
| TDI01433 | | 504.2 |
| TDI01434 | | 472.0 |

-continued

| No. | Structural Formula | MS m/z (ESI): [M + H] |
|---|---|---|
| TDI01435 | | 486.2 |
| TDI01436 | | 520.2 |
| TDI01437 | | 452.2 |
| TDI01438 | | 466.1 |
| TDI01439 | | 511.1 |
| TDI01440 | | 560.2 |
| TDI01441 | | 468.2 |
| TDI01442 | | 463.2 |

-continued

| No. | Structural Formula | MS m/z (ESI): [M + H] |
|---|---|---|
| TDI01443 | | 506.2 |
| TDI01444 | | 518.3 |
| TDI01445 | | 489.2 |
| TDI01446 | | 442.1 |
| TDI01447 | | 562.4 |
| TDI01448 | | 475.2 |
| TDI01449 | | 468.1 |

| No. | Structural Formula | MS m/z (ESI): [M + H] |
|---|---|---|
| TDI01450 | | 522.2 |
| TDI01451 | | 508.3 |
| TDI01452 | | 506.1 |
| TDI01453 | | 442.1 |
| TDI01454 | | 513.1 |
| TDI01455 | | 454.2 |
| TDI01456 | | 495.1 |

| No. | Structural Formula | MS m/z (ESI): [M + H] |
|---|---|---|
| TDI01457 | | 506.2 |
| TDI01458 | | 480.2 |
| TDI01459 | | 480.1 |
| TDI01460 | | 450.1 |
| TDI01461 | | 475.3 |
| TDI01462 | | 466.3 |
| TDI01463 | | 486.1 |
| TDI01464 | | 505.3 |

-continued

| No. | Structural Formula | MS m/z (ESI): [M + H] |
|---|---|---|
| TDI01465 | | 514.3 |
| TDI01466 | | 480.2 |
| TDI01467 | | 474.3 |
| TDI01468 | | 519.3 |
| TDI01469 | | 562.2 |
| TDI01470 | | 486.2 |
| TDI01471 | | 489.1 |

| No. | Structural Formula | MS m/z (ESI): [M + H] |
|---|---|---|
| TDI01472 | | 528.1 |
| TDI01473 | | 468.2 |
| TDI01474 | | 446.1 |
| TDI01475 | | 481.1 |
| TDI01476 | | 481.1 |
| TDI01477 | | 486.3 |
| TDI01478 | | 486.2 |
| TDI01479 | | 516.1 |

-continued
| No. | Structural Formula | MS m/z (ESI): [M + H] |
|---|---|---|
| TDI01480 | 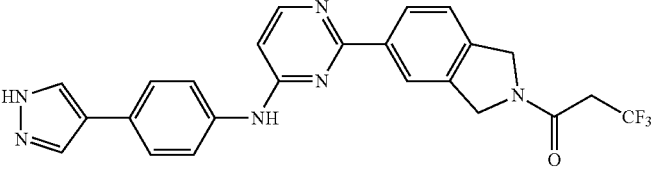 [SMILES: O=C(CC(F)(F)F)N1Cc2ccc(-c3nccc(Nc4ccc(-c5cn[nH]c5)cc4)n3)cc2C1] | 465.1 |
| TDI01481 | 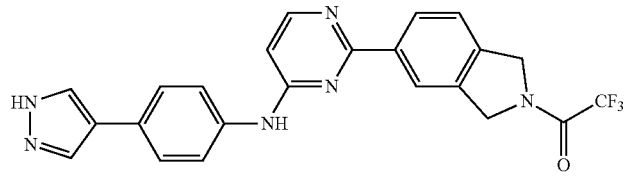 [SMILES: O=C(N1Cc2ccc(-c3nccc(Nc4ccc(-c5cn[nH]c5)cc4)n3)cc2C1)C(F)(F)F] | 451.0 |
| TDI01482 | 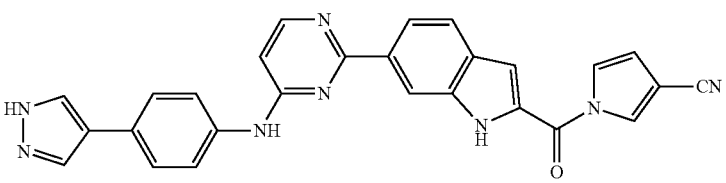 [SMILES: N#Cc1ccn(C(=O)c2cc3ccc(-c4nccc(Nc5ccc(-c6cn[nH]c6)cc5)n4)cc3[nH]2)c1] | 471.1 |
| TDI01483 | 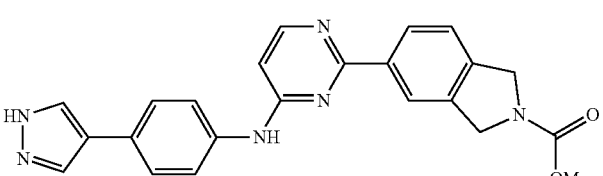 | 413.1 |
| TDI01484 | 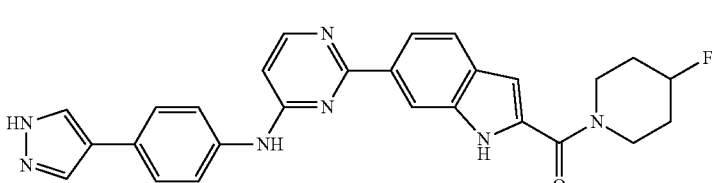 | 482.1 |
| TDI01485 | 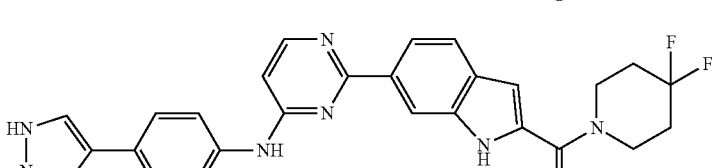 | 500.2 |
| TDI01486 | 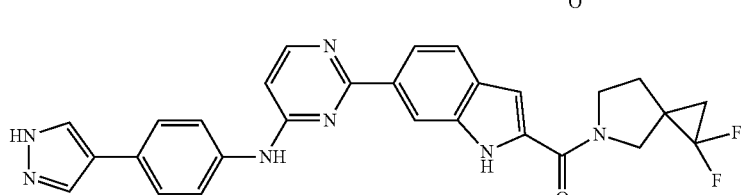 | 512.2 |
| TDI01487 | 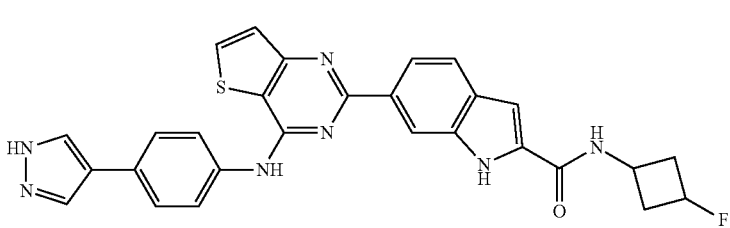 [SMILES: O=C(NC1CC(F)C1)c1cc2ccc(-c3nc(Nc4ccc(-c5cn[nH]c5)cc4)c4sccc4n3)cc2[nH]1] | 524.2 |

| No. | Structural Formula | MS m/z (ESI): [M + H] |
|---|---|---|
| TDI01488 | | 542.1 |
| TDI01489 | | 529.3 |
| TDI01490 | | 498.2 |
| TDI01491 | | 482.1 |
| TDI01492 | | 500.1 |
| TDI01493 | | 502.1 |
| TDI01494 | | 484.1 |

-continued

| No. | Structural Formula | MS m/z (ESI): [M + H] |
|---|---|---|
| TDI01495 | | 448.2 |
| TDI01496 | | 468.1 |
| TDI01497 | | 514.2 |
| TDI01498 | | 465.2 |
| TDI01499 | | 494.1 |
| TDI01500 | | 478.1 |
| TDI01501 | | 517.0 |
| TDI01502 | | 463.1 |

| No. | Structural Formula | MS m/z (ESI): [M + H] |
|---|---|---|
| TDI01503 | | 500.1 |
| TDI01504 | | 532.3 |
| TDI01505 | | 548.2 |
| TDI01506 | | 532.2 |
| TDI01507 | | 500.3 |
| TDI01508 | | 542.2 |
| TDI01509 | | 506.1 |
| TDI01510 | | 477.1 |

| No. | Structural Formula | MS m/z (ESI): [M + H] |
|---|---|---|
| TDI01511 | | 498.1 |
| TDI01512 | | 512.2 |
| TDI01513 | | 526.2 |
| TDI01514 | | 500.2 |
| TDI01515 | | 487.2 |
| TDI01516 | | 471.4 |
| TDI01517 | | 492.3 |
| TDI01518 | | 498.2 |

-continued
| No. | Structural Formula | MS m/z (ESI): [M + H] |
|---|---|---|
| TDI01519 | 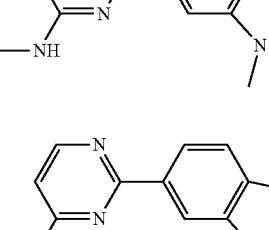 | 560.2 |
| TDI01520 | 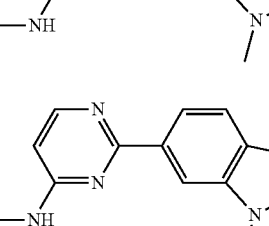 | 498.2 |
| TDI01521 |  | 532.1 |
| TDI01522 |  | 532.1 |
| TDI01523 | 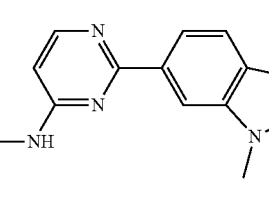 | 534.3 |
| TDI01524 | 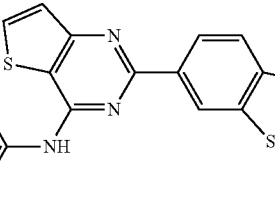 | 500.3 |
| TDI01525 | 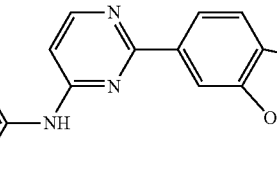 | 545.1 |
| TDI01526 |  | 473.1 |

-continued

| No. | Structural Formula | MS m/z (ESI): [M + H] |
|---|---|---|
| TDI01529 | | 516.1 |
| TDI01530 | | 504.1 |
| TDI01531 | | 452.3 |
| TDI01532 | | 487.2 |
| TDI01533 | | 525.3 |
| TDI01534 | | 475.2 |
| TDI01535 | | 475.2 |

-continued

| No. | Structural Formula | MS m/z (ESI): [M + H] |
|---|---|---|
| TDI01536 | | 473.8 |
| TDI01537 | | 514.0 |
| TDI01538 | | 518.3 |
| TDI01543 | | 449.6 |
| TDI01544 | | 434.2 |
| TDI01545 | | 434.2 |
| TDI01546 | | 505.8 |

-continued

| No. | Structural Formula | MS m/z (ESI): [M + H] |
|---|---|---|
| TDI01547 | | 541.1 |
| TDI01550 | | 502.6 |
| TDI01551 | | 467.8 |
| TDI01552 | | 482.0 |
| TDI01553 | | 451.7 |
| TDI01554 | | 482.8 |

| No. | Structural Formula | MS m/z (ESI): [M + H] |
|---|---|---|
| TDI01555 | | 522.8 |
| TDI01556 | | 521.1 |
| TDI01557 | | 354.7 |
| TDI01557B | | 455.0 |
| TDI01558 | | 447.1 |
| TDI01559 | | 489.0 |

| No. | Structural Formula | MS m/z (ESI): [M + H] |
|---|---|---|
| TDI01560 | | 466.8 |
| TDI01561 | | 452.8 |
| TDI01562 | | 489.0 |
| TDI01563 | | 521.8 |
| TDI01564 | | 511.6 |

| No. | Structural Formula | MS m/z (ESI): [M + H] |
|---|---|---|
| TDI01565 | | 512.1 |
| TDI01566 | | 467.7 |
| TDI01567 | | 515.8 |
| TDI01567B | | 545.0 |
| TDI01567C | | 516.7 |

-continued

| No. | Structural Formula | MS m/z (ESI): [M + H] |
|---|---|---|
| TDI01569 | | 559.5 |
| TDI01570 | | 486.6 |
| TDI01571 | | 501.1 |
| TDI01571B | | 482.8 |
| TDI01572 | | 502.1 |

-continued

| No. | Structural Formula | MS m/z (ESI): [M + H] |
|---|---|---|
| TDI01573 | | 501.1 |
| TDI01574 | | 472.1 |
| TDI01575 | | 460.7 |
| TDI01578 | | 502.5 |
| TDI01579 | | 500.1 |
| TDI01580 | | 462.6 |

-continued

| No. | Structural Formula | MS m/z (ESI): [M + H] |
|---|---|---|
| TDI01581 | | 472.7 |
| TDI01582 | | 489.6 |
| TDI01583 | | 471.1 |
| TDI01584 | | 528.5 |
| TDI01585 | | 504.5 |
| TDI01586 | | 484.6 |

| No. | Structural Formula | MS m/z (ESI): [M + H] |
|---|---|---|
| TDI01587 | | 556.2 |
| TDI01588 | | 422.1 |
| TDI01589 | | 464.7 |
| TDI01590 | | 491.1 |
| TDI01591 | | 485.1 |
| TDI01592 | | 516.1 |

-continued

| No. | Structural Formula | MS m/z (ESI): [M + H] |
|---|---|---|
| TDI01593 | | 491.1 |
| TDI01594 | | 458.7 |
| TDI01594B | | 544.5 |
| TDI01596 | | 504.7 |
| TDI01596B | | 486.6 |
| TDI01597 | | 485.1 |

-continued

| No. | Structural Formula | MS m/z (ESI): [M + H] |
|---|---|---|
| TDI01597B | | 466.8 |
| TDI01598 | | 509.1 |
| TDI01609 | | 506.5 |
| TDI01611 | | 504.6 |
| TDI01613 | | 480.7 |
| TDI01615 | | 504.1 |

| No. | Structural Formula | MS m/z (ESI): [M + H] |
|---|---|---|
| TDI01617 | | 533.6 |
| TDI01618A | | 491.1 |
| TDI01620 | | 521.8 |
| TDI01621 | | 503.1 |
| TDI01622 | | 477.1 |

| No. | Structural Formula | MS m/z (ESI): [M + H] |
|---|---|---|
| TDI01623 | | 544.1 |
| TDI01628 | | 505.0 |
| TDI01633 | | 556.5 |
| TDI01634 | | 493.9 |
| TDI01653 | | 474.1 |

| No. | Structural Formula | MS m/z (ESI): [M + H] |
|---|---|---|
| TDI01654 | | 488.1 |
| TDI01655 | | 518.6 |
| TDI01656 | | 531.1 |
| TDI01657 | | 533.1 |

-continued

| No. | Structural Formula | MS m/z (ESI): [M + H] |
|---|---|---|
| TDI01658 | | 532.6 |
| TDI01659 | | 505.1 |
| TDI01662 | | 519.1 |
| TDI01665 | | 520.6 |
| TDI01666 | | 544.1 |

-continued

| No. | Structural Formula | MS m/z (ESI): [M + H] |
|---|---|---|
| TDI01667 | | 524.7 |
| TDI01668 | | 530.1 |
| TDI01670 | | 509.1 |
| TDI01672 | | 506.5 |
| TDI01673 | | 483.1 |
| TDI01674 | | 440.8 |

-continued

| No. | Structural Formula | MS m/z (ESI): [M + H] |
|---|---|---|
| TDI01675 | | 507.0 |
| TDI01676 | | 500.8 |
| TDI01678 | | 535.5 |
| TDI01681 | | 553.7 |
| TDI01682 | | 460.7 |
| TDI01683 | | 460.7 |

| No. | Structural Formula | MS m/z (ESI): [M + H] |
|---|---|---|
| TDI01684 | | 451.1 |
| TDI01689 | | 501.1 |
| TDI01690 | | 516.6 |
| TDI01691 | | 506.2 |
| TDI01692 | | 492.0 |
| TDI01693 | | 493.1 |

-continued

| No. | Structural Formula | MS m/z (ESI): [M + H] |
|---|---|---|
| TDI01694 | | 479.1 |
| TDI01695 | | 457.1 |
| TDI01698 | | 500.1 |
| TDI01706 | | 500.7 |
| TDI01708 | | 487.1 |
| TDI01709 | | 502.1 |
| TDI01710 | | 419.1 |

| No. | Structural Formula | MS m/z (ESI): [M + H] |
|---|---|---|
| TDI01712 | | 473.1 |
| TDI01714 | | 487.1 |
| TDI01715 | | 484.1 |
| TDI01721 | | 493.1 |
| TDI01801 | | 478.2 |
| TDI01802 | | 478.1 |

-continued

| No. | Structural Formula | MS m/z (ESI): [M + H] |
|---|---|---|
| TDI01803 | | 494.9 |
| TDI01804 | | 482.8 |
| TDI01806 | | 456.0 |
| TDI01807 | | 411.9 |
| TDI01808 | | 552.3 |

-continued

| No. | Structural Formula | MS m/z (ESI): [M + H] |
|---|---|---|
| TDI01809 | | 491.1 |
| TDI01810 | | 491.1 |
| TDI01811 | | 490.7 |
| TDI01812 | | 491.1 |
| TDI01813 | | 477.9 |

-continued

| No. | Structural Formula | MS m/z (ESI): [M + H] |
|---|---|---|
| TDI01814 | | 529.9 |
| TDI01815 | | 515.9 |
| TDI01816 | (TFA) | 443.7 |
| TDI01816B | | 470.2 |
| TDI01818 | | 396.0 |
| TDI01819 | | 444.0 |

| No. | Structural Formula | MS m/z (ESI): [M + H] |
|---|---|---|
| TDI01820 | | 457.8 |
| TDI01821 | | 443.8 |
| TDI01822 | | 457.7 |
| TDI01823 | | 482.0 |
| TDI01824 | | 481.9 |
| TDI01825 | | 462.1 |

-continued

| No. | Structural Formula | MS m/z (ESI): [M + H] |
|---|---|---|
| TDI01825B | | 440.0 |
| TDI01825C | | 466.0 |
| TDI01826 | | 436.2 |
| TDI01827 | | 420.1 |
| TDI01829 | | 472.1 |
| TDI01829B | | 498.0 |

| No. | Structural Formula | MS m/z (ESI): [M + H] |
|---|---|---|
| TDI01829C | | 598.8 |
| TDI01830 | | 428.1 |
| TDI01831 | | 428.1 |
| TDI01832 | | 454.2 |
| TDI01833 | | 430.9 |
| TDI01834 | | 479.1 |

-continued

| No. | Structural Formula | MS m/z (ESI): [M + H] |
|---|---|---|
| TDI01835 | | 495.1 |
| TDI01836 | | 467.2 |
| TDI01837 | | 425.2 |
| TDI01838 | | 425.2 |
| TDI01839 | | 515.1 |
| TDI01840 | | 530.0 |
| TDI01841 | | 494.8 |

| No. | Structural Formula | MS m/z (ESI): [M + H] |
|---|---|---|
| TDI01842 | | 442.2 |
| TDI01842B | | 489.9 |
| TDI01843 | | 342.1 |
| TDI01844 | | 481.9 |
| TDI01845 | | 522.7 |
| TDI01846 | | 429.2 |
| TDI01847 | | 563.6 |

-continued

| No. | Structural Formula | MS m/z (ESI): [M + H] |
|---|---|---|
| TDI01847B | | 589.8 |
| TDI01848 | | 442.9 |
| TDI01849 | | 475.0 |
| TDI01849B | | 500.9 |
| TDI01850 | | 508.1 |
| TDI01851 | | 543.9 |

-continued

| No. | Structural Formula | MS m/z (ESI): [M + H] |
|---|---|---|
| TDI01852 | | 496.0 |
| TDI01853 | | 495.7 |
| TDI01854 | | 463.2 |
| TDI01855 | | 453.0 |
| TDI01856 | | 452.8 |
| TDI01861 | | 479.9 |
| TDI01862 | | 488.0 |

-continued

| No. | Structural Formula | MS m/z (ESI): [M + H] |
|---|---|---|
| TDI01863 | | 438.1 |
| TDI01864 | | 478.0 |
| TDI01865 | | 524.8 |
| TDI01867 | | 468.2 |
| TDI01868 | | 522.2 |
| TDI01869 | | 429.9 |
| TDI01870 | | 430.7 |

-continued

| No. | Structural Formula | MS m/z (ESI): [M + H] |
|---|---|---|
| TDI01871 | | 466.0 |
| TDI01872 | | 479.2 |
| TDI01873 | | 418.9 |
| TDI01874 | | 432.9 |
| TDI01875 | | 417.9 |
| TDI01876 | | 419.1 |
| TDI01876B | | 433.1 |

| No. | Structural Formula | MS m/z (ESI): [M + H] |
|---|---|---|
| TDI01877 | 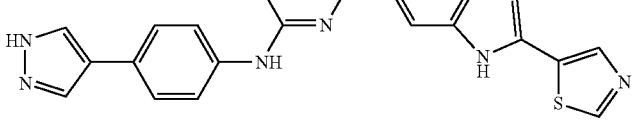 | 435.9 |
| TDI01878 | 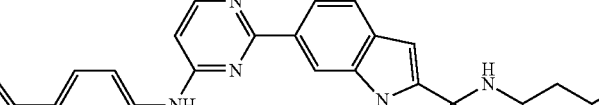 | 562.9 |
| TDI01879 | 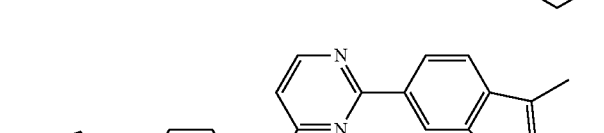 | 466.0 |
| TDI01880 |  | 548.6 |
| TDI01881 | 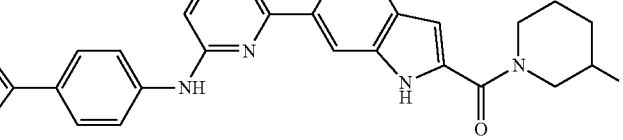 | 460.0 |
| TDI01882 | 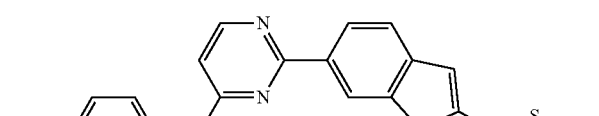 | 556.0 |
| TDI01883 |  | 541.2 |

| No. | Structural Formula | MS m/z (ESI): [M + H] |
|---|---|---|
| TDI01884 | | 606.9 |
| TDI01885 | | 575.8 |
| TDI01886 | | 453.9 |
| TDI01887 | | 442.9 |
| TDI01888 | | 393.9 |
| TDI01890 | | 429.9 |
| TDI01891 | | 430.9 |

| No. | Structural Formula | MS m/z (ESI): [M + H] |
|---|---|---|
| TDI01892 | | 453.9 |
| TDI01893 | | 430.9 |
| TDI01894 | | 493.9 |
| TDI01898 | | 501.6 |
| TDI01898B | | 575.8 |

| No. | Structural Formula | MS m/z (ESI): [M + H] |
|---|---|---|
| TDI01899 | | 504.0 |
| TDI01900 | | 503.0 |
| TDI01901 | | 341.1 |
| TDI01902 | | 454.9 |
| TDI01903 | | 499.2 |
| TDI01904 | | 504.1 |

-continued

| No. | Structural Formula | MS m/z (ESI): [M + H] |
|---|---|---|
| TDI01905 | | 503.5 |
| TDI01906 | | 460.0 |
| TDI01907 | | 514.2 |
| TDI01908 | | 453.9 |
| TDI01909 | | 484.0 |
| TDI01910 | | 516.2 |
| TDI01911 | | 604.0 |

-continued

| No. | Structural Formula | MS m/z (ESI): [M + H] |
|---|---|---|
| TDI01912 | | 465.6 |
| TDI01913 | | 507.9 |
| TDI01914 | | 501.6 |
| TDI01915 | | 516.0 |
| TDI01916 | | 525.6 |
| TDI01917 | | 521.1 |
| TDI01918 | | 535.9 |

-continued

| No. | Structural Formula | MS m/z (ESI): [M + H] |
|---|---|---|
| TDI01919 | | 449.9 |
| TDI01920 | | 516.6 |
| TDI01921 | | 529.6 |
| TDI01923 | | 498.0 |
| TDI01924 | | 514.1 |
| TDI01925 | | 512.2 |
| TDI01926 | | 528.2 |

| No. | Structural Formula | MS m/z (ESI): [M + H] |
|---|---|---|
| TDI01927 | | 526.2 |
| TDI01928 | | 556.2 |
| TDI01929 | | 542.2 |
| TDI01930 | | 562.2 |
| TDI01931 | | 555.2 |
| TDI01932 | | 504.0 |

| No. | Structural Formula | MS m/z (ESI): [M + H] |
|---|---|---|
| TDI01933 | | 490.2 |
| TDI01934 | | 504.2 |
| TDI01935 | | 582.1 |
| TDI01936 | | 486.6 |
| TDI01937B | | 486.6 |
| TDI01938 | | 501.9 |
| TDI01939 | | 437.0 |

| No. | Structural Formula | MS m/z (ESI): [M + H] |
|---|---|---|
| TDI01940 | | 437.0 |
| TDI01941 | | 475.6 |
| TDI01942 | | 472.9 |
| TDI01943 | | 501.6 |
| TDI01944 | | 472.5 |
| TDI01945 | | 538.5 |
| TDI01946 | | 525.9 |

| No. | Structural Formula | MS m/z (ESI): [M + H] |
|---|---|---|
| TDI01947 | | 541.9 |
| TDI01948 | | 524.9 |
| TDI01949 | | 519.9 |
| TDI01950 | | 499.2 |
| TDI01951 | | 487.8 |
| TDI01952 | | 527.6 |
| TDI01953 | | 526.6 |

-continued

| No. | Structural Formula | MS m/z (ESI): [M + H] |
|---|---|---|
| TDI01954 | | 540.5 |
| TDI01955 | | 500.0 |
| TDI01956 | | 503.9 |
| TDI01957 | | 487.6 |
| TDI01958 | | 486.6 |
| TDI01959 | | 488.1 |

-continued

| No. | Structural Formula | MS m/z (ESI): [M + H] |
|---|---|---|
| TDI01960 | | 526.0 |
| TDI01962 | | 527.6 |
| TDI01965 | | 459.6 |
| TDI01966 | | 459.6 |
| TDI01967 | | 447.0 |
| TDI01968A | | 466.1 |

| No. | Structural Formula | MS m/z (ESI): [M + H] |
|---|---|---|
| TDI01968B | | 465.7 |
| TDI01969 | | 452.0 |
| TDI01972 | | 465.9 |
| TDI01973 | | 535.1 |
| TDI01974 | | 466.0 |
| TDI01975 | | 472.0 |

-continued

| No. | Structural Formula | MS m/z (ESI): [M + H] |
|---|---|---|
| TDI01976 | | 512.6 |
| TDI01978 | | 490.9 |
| TDI01979 | | 474.0 |
| TDI01989 | | 426.9 |
| TDI01990 | | 472.0 |

| No. | Structural Formula | MS m/z (ESI): [M + H] |
|---|---|---|
| TDI01991 | | 472.6 |
| TDI01995 | | 521.0 |
| TDI01996 | | 507.1 |
| TDI01998 | | 535.0 |
| TDI01999 | | 513.6 |
In some embodiments, the present invention provides a method for the preparation of a compound of Formula (II), wherein the method comprises the following steps:
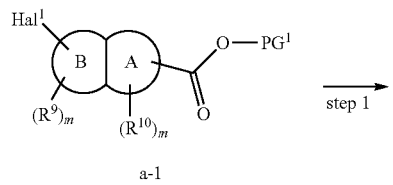
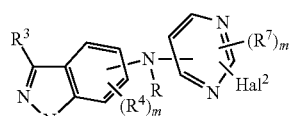
-continued
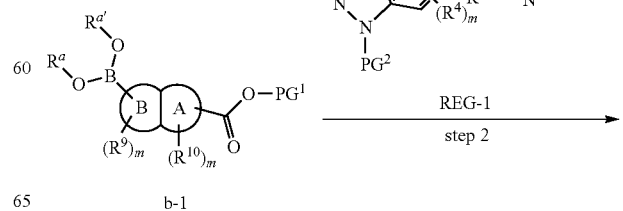

-continued

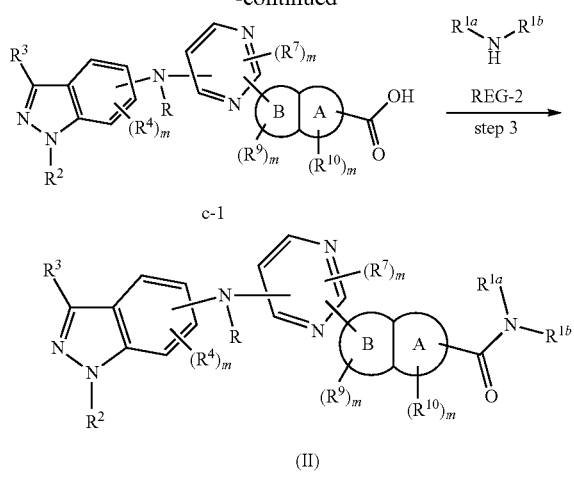

c-1

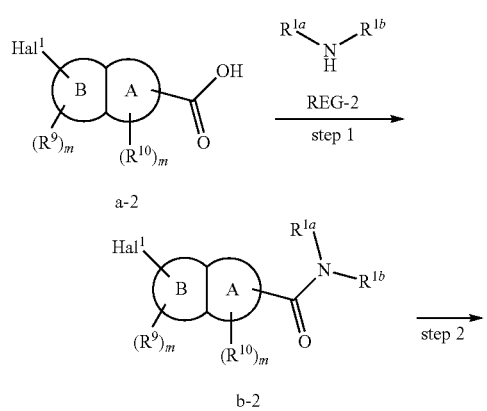

(II)

wherein:

$R^2$ is H;

$Hal^1$ and $Hal^2$ are same or different halogens, e.g., F, Cl, Br or I;

$PG^1$ is a carboxy protecting group, preferably $C_{1-6}$ alkyl;

$PG^2$ is H or an amino protecting group, preferably tert-butyloxycarbonyl (Boc);

$R^a$ and $R^{a'}$ at each occurrence, are each independently selected from the group consisting of H and $C_{1-6}$ alkyl; or $R^a$ and $R^{a'}$ together with the group to which they are attached form a 5- to 10-membered ring system;

the remaining groups are as defined above;

the reaction conditions for each step are as follows:

step 1: reacting compound a-1 with a boric acid or borate under the catalysis of a palladium catalyst (preferably in the presence of a base), to obtain compound b-1;

step 2: reacting compound b-1 with compound REG-1 under the catalysis of a palladium catalyst (preferably in the presence of a base), to obtain compound c-1; and step 3: reacting compound c-1 with compound REG-2 (preferably in the presence of an appropriate condensation agent and an appropriate base), to obtain the compound of Formula (II);

alternatively, the method comprises the following steps:

-continued

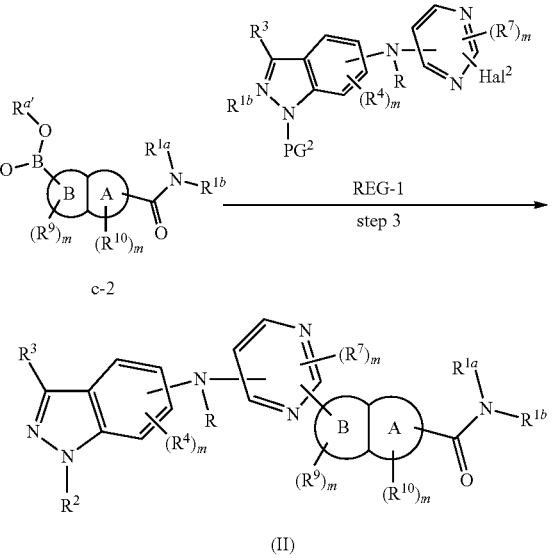

c-2

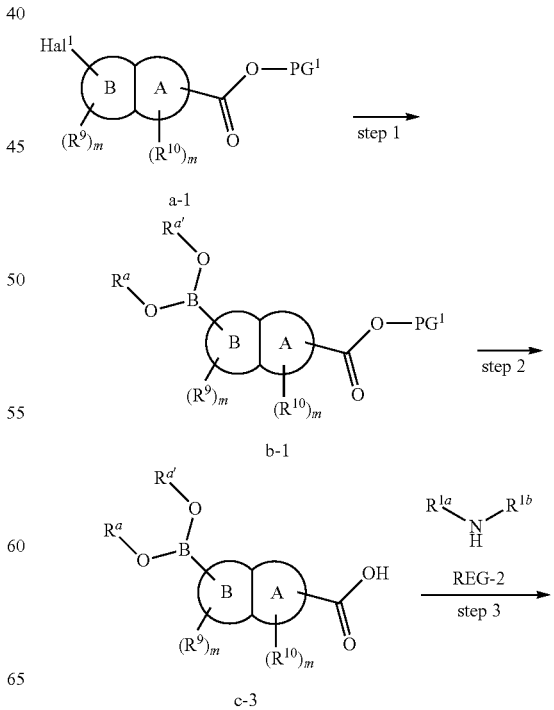

(II)

wherein each of the groups is as defined above;

the reaction conditions for each step are as follows:

step 1: reacting compound a-2 with compound REG-2 (preferably in the presence of an appropriate condensation agent and an appropriate base), to obtain compound b-2;

step 2: reacting compound b-2 with a boric acid or borate under the catalysis of a palladium catalyst (preferably in the presence of a base), to obtain compound c-2; and step 3: reacting compound c-2 with compound REG-1 under the catalysis of a palladium catalyst (preferably in the presence of a base), to obtain the compound of Formula (II);

alternatively, the method comprises the following steps:

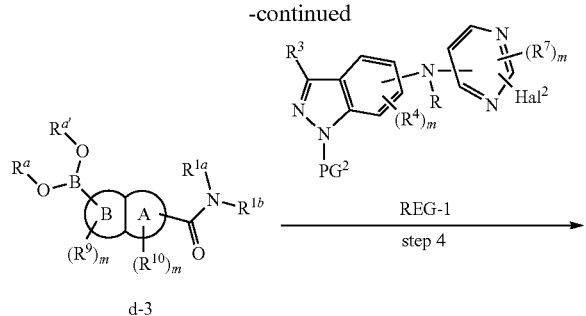

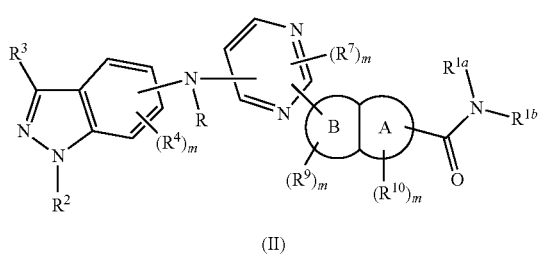

wherein each of the groups is as defined above;
the reaction conditions for each step are as follows:

step 1: reacting compound a-1 with a boric acid or borate under the catalysis of a palladium catalyst (preferably in the presence of a base), to obtain compound b-1;

step 2: deprotecting compound b-1 under a condition corresponding to $PG^1$, to obtain compound c-3;

step 3: reacting compound c-3 with compound REG-2 (preferably in the presence of an appropriate condensation agent and an appropriate base), to obtain compound d-3; and step 4: reacting compound d-3 with compound REG-1 under the catalysis of a palladium catalyst (preferably in the presence of a base), to obtain the compound of Formula (II);

In some embodiments, the present invention provides a method for the preparation of a compound of Formula (XII), wherein the method comprises the following steps:

wherein:

$R^2$ is H;

$Hal^1$ and $Hal^2$ are same or different halogens, e.g., F, Cl, Br or I;

$PG^1$ is a carboxy protecting group, preferably $C_{1-6}$ alkyl;

$PG^2$ is H or an amino protecting group, preferably tert-butyloxycarbonyl (Boc);

$R^a$ and $R^{a'}$, at each occurrence, are each independently selected from the group consisting of H and $C_{1-6}$ alkyl; or $R^a$ and $R^{a'}$ together with the group to which they are attached form a 5- to 10-membered ring system;

the remaining groups are as defined above;

the reaction conditions for each step are as follows:

step 1: reacting compound a-1 with a boric acid or borate under the catalysis of a palladium catalyst (preferably in the presence of a base), to obtain compound b-1;

step 2: reacting compound b-1 with compound REG-1' under the catalysis of a palladium catalyst (preferably in the presence of a base), to obtain compound c-1'; and step 3: reacting compound c-1' with compound REG-2' (preferably in the presence of an appropriate condensation agent and an appropriate base), to obtain the compound of Formula (XII).

In some embodiments, the present invention provides a method for the preparation of a compound of Formula (XIII), wherein the method comprises the following steps:

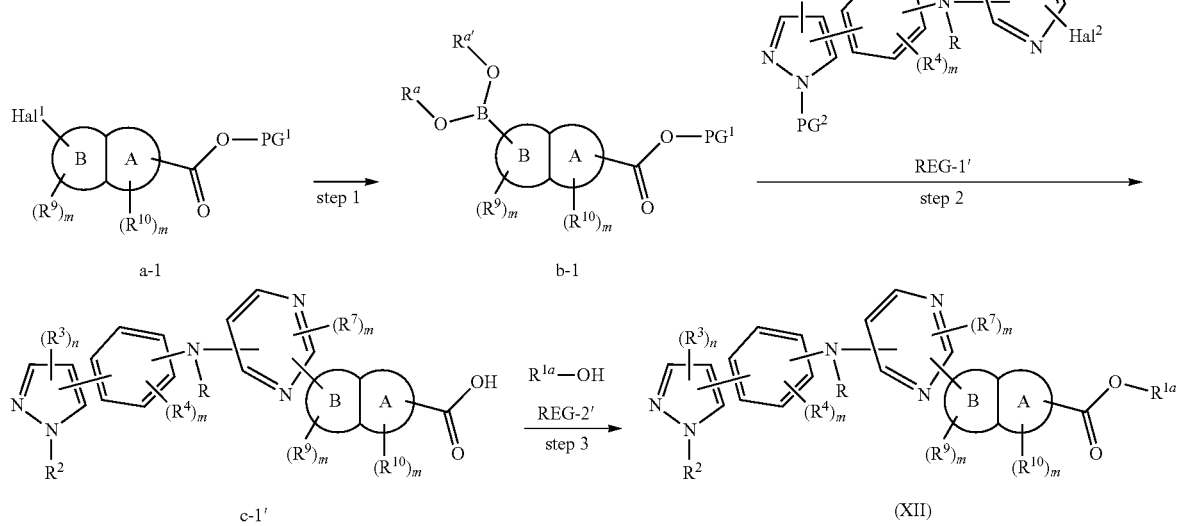

-continued

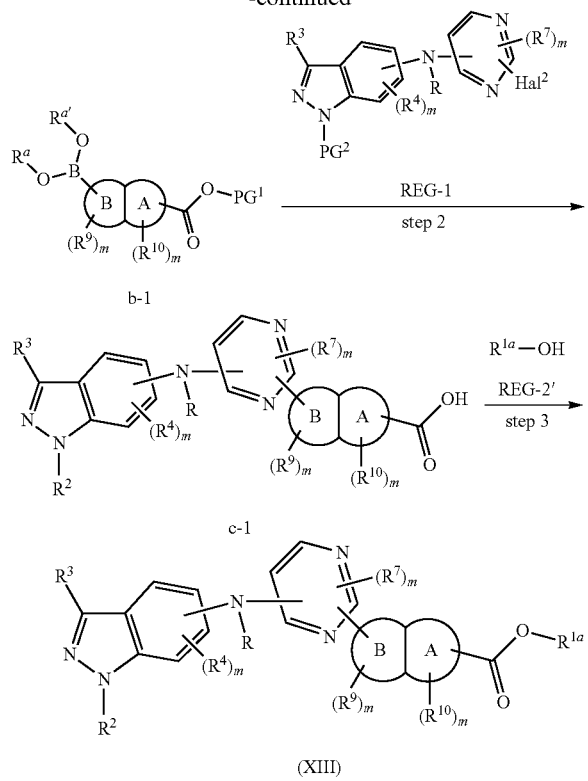

wherein:

R² is H;

Hal¹ and Hal² are same or different halogens, e.g., F, Cl, Br or I;

PG¹ is a carboxy protecting group, preferably $C_{1-6}$ alkyl;

PG² is H or an amino protecting group, preferably tert-butyloxycarbonyl (Boc);

$R^a$ and Re', at each occurrence, are each independently selected from the group consisting of H and $C_{1-6}$ alkyl; or $R^a$ and $R^{a'}$ together with the group to which they are attached form a 5- to 10-membered ring system;

the remaining groups are as defined above;

the reaction conditions for each step are as follows:

step 1: reacting compound a-1 with a boric acid or borate under the catalysis of a palladium catalyst (preferably in the presence of a base), to obtain compound b-1;

step 2: reacting compound b-1 with compound REG-1 under the catalysis of a palladium catalyst (preferably in the presence of a base), to obtain compound c-1; and step 3: reacting compound c-1 with compound REG-2' (preferably in the presence of an appropriate condensation agent and an appropriate base), to obtain the compound of Formula (XIII).

In some embodiments, the present invention provides a method for the preparation of a compound of Formula (XIV), wherein the method comprises the following steps:

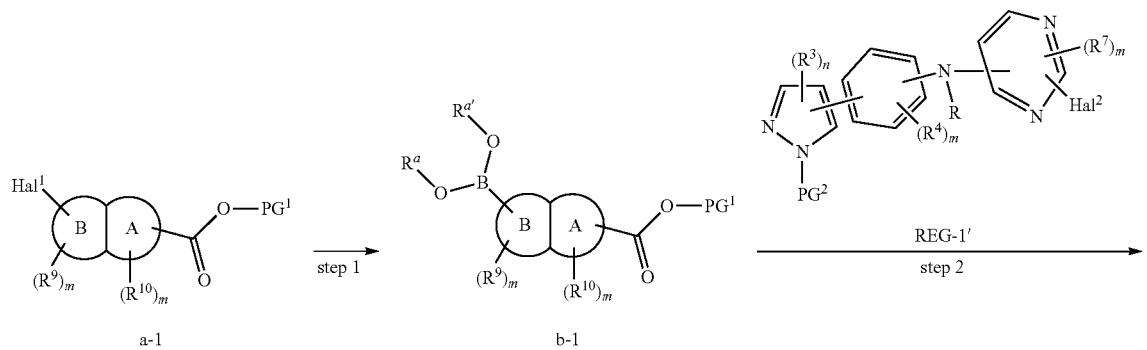

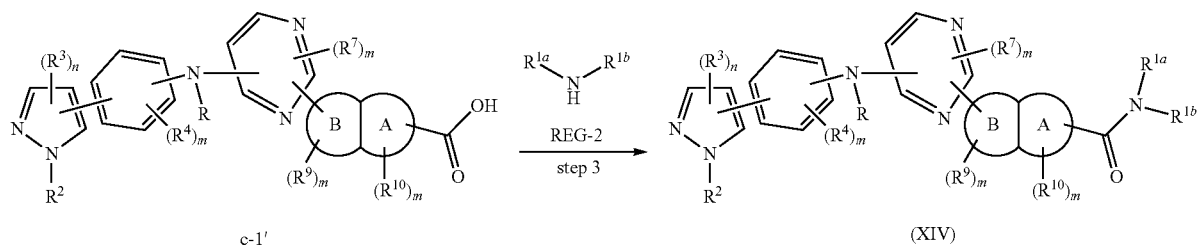

wherein:

R² is H;

Hal¹ and Hal² are same or different halogens, e.g., F, Cl, Br or I;

PG¹ is a carboxy protecting group, preferably $C_{1-6}$ alkyl;

PG² is H or an amino protecting group, preferably tert-butyloxycarbonyl (Boc);

$R^a$ and $R^{a'}$, at each occurrence, are each independently selected from the group consisting of H and $C_1$. 6 alkyl; or $R^a$ and $R^{a'}$ together with the group to which they are attached form a 5- to 10-membered ring system;

the remaining groups are as defined above;
the reaction conditions for each step are as follows:

step 1: reacting compound a-1 with a boric acid or borate under the catalysis of a palladium catalyst (preferably in the presence of a base), to obtain compound b-1;

step 2: reacting compound b-1 with compound REG-1' under the catalysis of a palladium catalyst (preferably in the presence of a base), to obtain compound c-1'; and step 3: reacting compound c-1' with compound REG-2 (preferably in the presence of an appropriate condensation agent and an appropriate base), to obtain the compound of Formula (XIV);

alternatively, the method comprises the following steps:

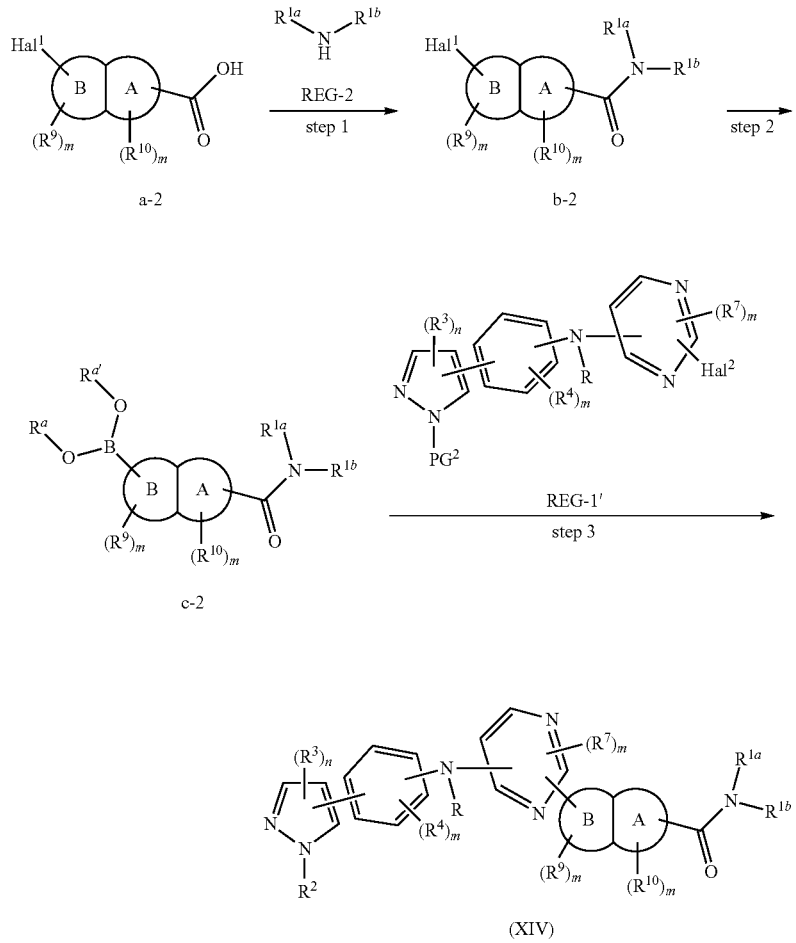

wherein each of the groups is as defined above;
the reaction conditions for each step are as follows:

step 1: reacting compound a-2 with compound REG-2 (preferably in the presence of an appropriate condensation agent and an appropriate base), to obtain compound b-2;

step 2: reacting compound b-2 with a boric acid or borate under the catalysis of a palladium catalyst (preferably in the presence of a base), to obtain compound c-2; and step 3: reacting compound c-2 with compound REG-1' under the catalysis of a palladium catalyst (preferably in the presence of a base), to obtain the compound of Formula (XIV);

alternatively, the method comprises the following steps:

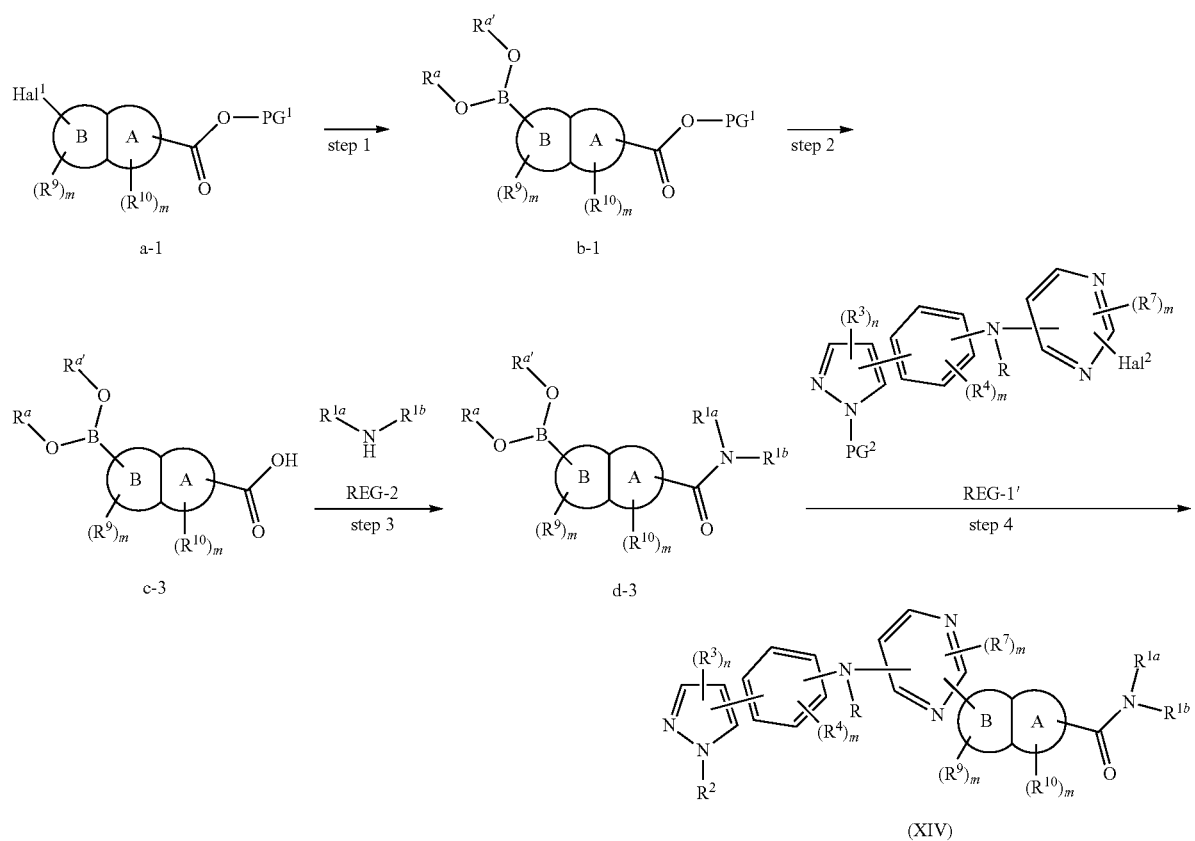

wherein each of the groups is as defined above;
the reaction conditions for each step are as follows:

step 1: reacting compound a-1 with a boric acid or borate under the catalysis of a palladium catalyst (preferably in the presence of a base), to obtain compound b-1;

step 2: deprotecting compound b-1 under a condition corresponding to PG', to obtain compound c-3;

step 3: reacting compound c-3 with compound REG-2 (preferably in the presence of an appropriate condensation agent and an appropriate base), to obtain compound d-3; and step 4: reacting compound d-3 with compound REG-1' under the catalysis of a palladium catalyst (preferably in the presence of a base), to obtain the compound of Formula (XIV).

In preferred embodiments, the boric acid or borate is e.g., bis(pinacolato)diboron.

In preferred embodiments, the palladium catalyst is e.g., $Pd(dppf)Cl_2$, $Pd(PPh_3)_4$, $Pd(OAc)_2$ or $Pd(PPh_3)_2Cl_2$.

In preferred embodiments, the condensation agent is e.g., DCC, EDCI, HATU, PyBOP.

In preferred embodiments, the appropriate base is e.g., diisopropylethylamine, triethylamine, pyridine, sodium carbonate, potassium acetate, potassium carbonate, potassium hydroxide, cesium carbonate.

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the preparation of a medicament for use as a Rho-associated protein kinase (ROCK) inhibitor, preferably a selective ROCK2 inhibitor.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use as a Rho-associated protein kinase (ROCK) inhibitor, preferably a selective ROCK2 inhibitor.

In some embodiments, the present invention provides a method for the prevention or treatment of a disease mediated by the Rho-associated protein kinase (ROCK), wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

In some embodiments, the disease mediated by the Rho-associated protein kinase (ROCK) includes an autoimmune disorder (comprising rheumatoid arthritis, systemic lupus erythematosus (SLE; lupus), psoriasis, Crohn's disease, atopic dermatitis, eczema, or graft-versus-host disease (GVHD)); a cardiovascular disorder (comprising hypertension, atherosclerosis, restenosis, cardiac hypertrophy, cerebral ischemia, cerebral vasospasm, or erectile dysfunction); inflammation (comprising asthma, cardiovascular inflammation, ulcerative colitis, or renal inflammation); a central nervous system disorder (comprising neuronal degeneration or spinal cord injury; and the central nervous system disorder is preferably Huntington's disease, Parkinson's disease, Alzheimer's disease, Amyotrophic lateral sclerosis (ALS), or multiple sclerosis); an arterial thrombotic disorder (comprising platelet aggregation, or leukocyte aggregation); a fibrotic disorder (comprising liver fibrosis, lung fibrosis, or kidney fibrosis); a neoplastic disease (comprising a lymphoma, carcinoma (e.g., squamous cell cancer, small-cell lung cancer, pituitary cancer, esophageal cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, bladder cancer, liver cancer, breast cancer, colon cancer, colorectal cancer, endometrial or uterine carcinoma, salivary gland carcinoma, kidney cancer, prostate cancer, vulval cancer, thyroid cancer, brain cancer, endometrial cancer, testis cancer, cholangiocarcinoma, gallbladder carcinoma, gastric cancer, melanoma, or head and neck cancer), leukemia, astrocytoma, soft tissue sarcoma, sarcoma, or blastoma); a metabolic syndrome; insulin resistance; hyperinsulinemia; type 2 diabetes; glucose intolerance; osteoporosis; an ocular disorder (comprising ocular hypertension, age related macular degeneration (AMD), choroidal neovascularization (CNV), diabetic macular edema (DME), iris neovascularization, uveitis, glaucoma (comprising primary open-angle glaucoma, acute angle-closure glaucoma, pigmentary glaucoma, congenital glaucoma, normal tension glaucoma, secondary glaucoma or neo vascular glaucoma), or retinitis of prematurity (ROP)).

In some embodiments, the disease mediated by the Rho-associated protein kinase (ROCK) includes lupus nephritis, atherosclerosis, rheumatoid arthritis (RA), hemangioma, angiofibroma, lung fibrosis, psoriasis, corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis, delayed hypersensitivity, inflammatory bowel disease, septic shock, osteoporosis, osteoarthritis, neuronal inflammation, Osier-Weber syndrome, restenosis, fungal infection, parasitic infection, and viral infection.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation.

For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

Examples

The present invention is further described with reference to the following examples, which are not provided to limit the scope of the present invention.

The structure of the compound was confirmed by nuclear magnetic resonance spectrum ($^1$H NMR) or mass spectrum (MS).

Chemical shifts (δ) are expressed in parts per million (ppm). $^1$HNMR was recorded on a Bruker BioSpin GmbH 400 spectrometer, the test solvent was deuterated methanol ($CD_3OD$), deuterated chloroform ($CDCl_3$) or hexadeuterated dimethyl sulfoxide (DMSO-$d_6$), and the internal standard was tetramethylsilane (TMS).

The LC-MS assay was conducted on Shimadzu LC-MS-2020 liquid chromatography-mass spectrometer (Manufacturer: Shimadzu, Model: Shimadzu LC-MS-2020).

Preparative high-performance liquid chromatography was conducted on Waters 2767 (waters sunfire, C18, 19×250 mm 10 um chromatographic column).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, hexane and ethyl acetate system, as well as petroleum ether and ethyl acetate system, and was adjusted (by adjusting the volume ratio the solvents, or by adding triethylamine, etc.) according to the polarity of the compound to be separated.

The microwave reaction was conducted by Biotagelnitiator+(400 W, RT 300° C.) microwave reactor.

Silica gel (200~300 mesh) produced by Yucheng Chemical Co., Ltd was normally employed as a stationary phase in column chromatography. The eluent system included dichloromethane and methanol system, as well as hexane and ethyl acetate system, and was adjusted (by adjusting the volume ratio the solvents, or by adding triethylamine, etc.) according to the polarity of the compound to be separated.

In the following examples, unless otherwise specified, the reaction temperature was room temperature (20° C.~0.30° C.).

The reagents employed in the Examples were purchased from companies such as Acros Organics, Aldrich Chemical Company, or Bide Pharmatech Ltd. etc.

The abbreviations as used in the present invention have the following meanings:

| Abbreviation | Meaning |
|---|---|
| ACN | acetonitrile |
| AcOH | acetic acid |
| AcOK/KOAc | potassium acetate |
| aq. | aqueous solution |
| BINAP | (±)-2,2'-Bis(diphenylphosphino)-1,1'-binaphthalene |
| $Boc_2O$ | Di-tert-butyl dicarbonate |
| $Cs_2CO_3$ | cesium carbonate |
| $Cu(AcO)_2$ | copper acetate |
| CuCN | cuprous cyanide |
| DCC | Dicyclohexylcarbodiimide |
| DCE | 1,2-dichloroethane |
| DCM | dichloromethane |
| DIAD | diisopropyl azodiformate |
| DIEA/DIPEA | N,N-diisopropylethylamine |
| DMAP | dimethylaminopyridine |
| DMF | N,N-dimethylformamide |
| DMSO | dimethyl sulfoxide |
| DNPC | bis(4-nitrophenyl)carbonate |
| EA | ethyl acetate |
| EDCI | 1-ethyl-(3-dimethylaminopropyl)carbodiimide hydrochloride |
| $Et_3N$ | triethylamine |
| EtOH | ethanol |
| HATU | O-(7-azabenzotriazol-1-yl)-N,N,N',N'-tetramethyluronium hexafluorophosphate |
| HCl | hydrochloric acid |
| $H_2O$ | water |
| IPA | isopropanol |
| $K_2CO_3$ | potassium carbonate |
| $KMnO_4$ | potassium permanganate |
| KOH | potassium hydroxide |
| KTB | potassium tert-butoxide |
| $LiAlH_4$ | lithium aluminium hydride |
| $LiOH \cdot H_2O$ | lithium hydroxide monohydrate |
| m-CPBA | metachloroperbenzoic acid |
| MeCN | acetonitrile |
| MeOH | methanol |
| $MgCl_2$ | magnesium chloride |
| $Mg_2SO_4$ | magnesium sulfate |
| $MnO_2$ | manganese dioxide |
| MsCl | methylsulfonyl chloride |
| MTBE | methyl tert-butyl ether |
| $NaBH_4$ | sodium borohydride |
| $NaBH(OAc)_3$ | sodium triacetoxyborohyride |
| $Na_2CO_3$ | sodium carbonate |
| NaH | sodium hydride |
| NaOH | sodium hydroxide |
| NBS | N-bromosuccinimide |
| $NH_4Cl$ | ammonium chloride |
| $N_2H_4 \cdot H_2O$ | hydrazine hydrate |
| NMP | N-methylpyrrolidone |
| $O_2$ | oxygen |
| Pd/C | palladium/carbon |
| $Pd_2(dba)_3$ | tris(dibenzylideneacetone)dipalladium |
| $Pd(dppf)Cl_2$ | [1,1'-bis(diphenylphosphino)ferrocene]dichloropalladium |
| $Pd(OAc)_2$ | palladium acetate |
| $Pd(PPh_3)_4$ | tetrakis(triphenylphosphine)palladium |
| $Pd(PPh_3)_2Cl_2$ | dichlorobis(triphenylphosphine)palladium |
| PE | petroleum ether |
| $Pin_2B_2$ | bis(pinacolato)diboron |
| $POCl_3$ | phosphorus oxychloride |
| $PPh_3$ | triphenylphosphine |
| PyBOP | Benzotriazol-1-yl-oxytripyrrolidinophosphonium hexafluorophosphate |
| $SOCl_2$ | thionyl chloride |
| t-BuXPhos | 2-di-tert-butylphosphino-2',4',6'-triisopropylbiphenyl |
| TEA | triethylamine |
| TFA | trifluoroacetic acid |
| THF | tetrahydrofuran |
| TsCl | 4-toluenesulfonyl chloride |
| Xantphos | 4,5-bis(diphenylphosphino)-9,9-dimethylxanthene |
| Zn | zinc |

Preparation of Intermediates
Intermediate Example 1

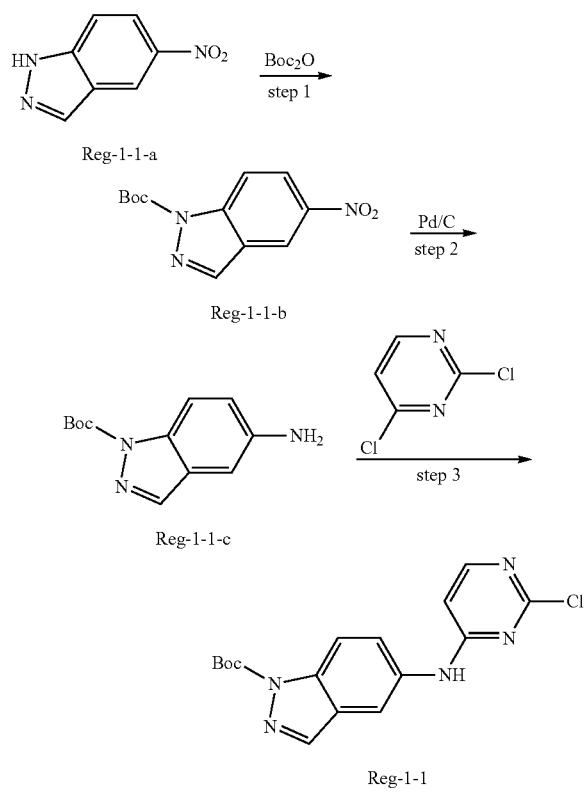

Step 1:

Compound Reg-1-1-a (26 g, 159.38 mmol) and tetrahydrofuran (400 mL) were added to a 1 L flask, and ethylamine (45 mL, 324.6 mmol) and 4-dimethylaminopyridine (2.92 g, 23.91 mmol) were added, followed by slowly dropwise addition of Boc$_2$O (41.74 g, 191.25 mmol). The reaction was performed overnight at room temperature. Thin layer chromatography (petroleum ether:ethyl acetate=3:1) indicated the reaction was complete. The reaction mixture was concentrated to obtain a crude product, which was dissolved in dichloromethane (400 mL), and the organic phase was washed three times with 0.5M dilute hydrochloric acid. The organic phase was then washed with saturated brine, dried over anhydrous sodium sulfate, filtered and concentrated to afford compound Reg-1-1-b (39 g, brown solid, yield: 92.95%).

$^1$H NMR (400 MHz, CDCl$_3$) δ 8.70 (d, J=2.1 Hz, 1H), 8.42 (dd, J=9.1, 2.1 Hz, 1H), 8.34 (d, J=9.6 Hz, 2H), 1.75 (s, 9H). MS m/z (ESI): 164.2 [M-Boc+H].

Step 2:

Compound Reg-1-1-b (38 g, 144.35 mmol) was dissolved in methanol (700 mL), Pd/C (3.8 g, 10% water) was added, purge with hydrogen was performed for three times, and the reaction was performed under a hydrogen atmosphere overnight. Thin layer chromatography (petroleum ether:ethyl acetate=3:1) indicated the reaction was complete. The reaction solution was filtered through Celite to afford compound Reg-1-1-c (33.2 g, brown solid, yield: 98.6%).

$^1$H NMR (400 MHz, CDCl$_3$) δ 7.97 (d, J=10.8 Hz, 2H), 7.00-6.87 (m, 2H), 3.74 (s, 2H), 1.71 (s, 9H).

Step 3:

Compound Reg-1-1-c (4 g, 17.14 mmol) and 2,4-dichloropyrimidine (5.1 g, 34.28 mmol) were dissolved in N,N-dimethylformamide (60 mL), diisopropylethylamine (11.08 g, 85.8 mmol) was added, and the reaction was placed in an oil bath at 80° C., and allowed to proceed overnight. Thin layer chromatography (petroleum ether:ethyl acetate=2:1) indicated the reaction was complete. The reaction solution was cooled to room temperature, concentrated under reduced pressure to give a crude product, which was separated through preparative chromatography (petroleum ether:ethyl acetate=100:1~1.5:1) to afford compound Reg-1-1 (3 g, yellow solid, yield: 50.60%).

$^1$H NMR (400 MHz, CDCl$_3$) δ 9.50-9.23 (m, 1H), 8.52-7.91 (m, 4H), 7.89-7.45 (m, 1H), 7.28-6.51 (m, 1H), 1.73 (s, 9H). MS m/z (ESI): 346.1 [M+H].

The following intermediates were prepared according to methods similar to that described in Intermediate Example 1:

| No. | Structure of Intermediate | Characterization Data |
| --- | --- | --- |
| Reg-1-2 | | $^1$H NMR (400 MHz, CDCl$_3$) δ 8.41 (s, 1H), 8.24-8.22 (m, 2H), 7.91-7.87 (m, 2H), 7.86-7.82 (m, 1H), 7.74 (s, 1H), 7.67 (d, J = 8.8 Hz, 1H), 7.59 (t, J = 7.6 Hz, 1H), 1.75 (s, 9H). |
| Reg-1-3 | | $^1$H NMR (400 MHz, CDCl$_3$) δ 8.28 (s, 1H), 8.21 (d, J = 8.0 Hz, 2H), 7.79 (d, J = 2.0 Hz, 1H), 7.60 (d, J = 8.8 Hz, 1H), 7.27 (s, 1H), 6.87 (d, J = 2.0 Hz, 1H), 1.74 (s, 9H). |

| No. | Structure of Intermediate | Characterization Data |
|---|---|---|
| Reg-1-4 | (structure) | $^1$H NMR (400 MHz, DMSO-d$_6$) δ 10.35 (s, 1H), 8.48 (s, 1H), 8.28 (d, J = 5.2 Hz, 1H), 8.22 (s, 1H), 8.11 (d, J = 9.2 Hz, 1H), 7.83 (d, J = 9.2 Hz, 1H), 7.43 (d, J = 5.2 Hz, 1H), 1.67 (s, 9H). MS m/z (ESI): 402.1 [M + H]. |
| Reg-1-5 | (structure) | MS m/z (ESI): 402.1 [M + H]. |
| Reg-1-6 | (structure) | $^1$H NMR (400 MHz, DMSO-d$_6$) δ 11.99 (s, 1H), 10.06 (s, 1H), 8.46-8.41 (m, 2H), 8.06 (d, J = 8.0 Hz, 1H), 7.93 (d, J = 8.0 Hz, 1H), 7.24 (s, 1H), 6.86 (s, 1H). MS m/z (ESI): 385.2 [M + H]. |
| Reg-1-7 | (structure) | $^1$H NMR (400 MHz, DMSO-d$_6$) δ 10.84 (s, 1H), 9.42 (s, 1H), 8.49 (s, 1H), 8.33 (d, J = 1.2 Hz, 1H), 8.07 (d, J = 8.8 Hz, 1H), 7.97 (dd, J = 8.8, 1.6 Hz, 1H), 1.67 (s, 9H). |
| Reg-1-8 | (structure) | $^1$H NMR (400 MHz, DMSO-d$_6$) δ 10.08 (s, 1H), 8.49 (s, 1H), 8.34 (s, 1H), 8.24 (d, J = 1.5 Hz, 1H), 8.14-8.11 (m, 1H), 7.87 (dd, J = 9.0, 1.9 Hz, 1H), 7.64 (d, J = 0.9 Hz, 1H), 7.14 (s, 1H), 1.67 (s, 10H). MS m/z (ESI): 385.0 [M + H]. |
| Reg-1-9 | (structure) | $^1$H NMR (400 MHz, CDCl$_3$) δ 8.21 (s, 1H), 8.19 (s, 1H), 8.04 (s, 1H), 7.56 (dd, J = 8.9, 1.8 Hz, 1H), 7.26 (s, 2H), 7.21 (s, 1H), 6.97 (d, J = 3.6 Hz, 1H), 5.81 (d, J = 2.9 Hz, 1H), 4.30 (t, J = 6.4 Hz, 2H), 2.33 (s, 6H), 1.73 (d, J = 13.8 Hz, 9H). MS m/z (ESI): 454.1 [M − H]. |

| No. | Structure of Intermediate | Characterization Data |
| --- | --- | --- |
| Reg-1-10* | | $^1$H NMR (400 MHz, CD$_3$OD) δ 8.13 (d, J = 3.7 Hz, 1H), 8.05 (s, 1H), 7.86 (d, J = 8.9 Hz, 1H), 7.51 (m, 6H), 7.04 (m, 3H), 6.65 (d, J = 9.0 Hz, 1H). MS m/z (ESI): 361.1 [M + H]. |
| Reg-1-11 | | $^1$H NMR (400 MHz, CDCl$_3$) δ 8.49 (d, J = 24.0 Hz, 1H), 8.21-8.03 (m, 3H), 7.69 (d, J = 40.0 Hz, 1H), 7.46 (dd, J = 8.8, 4.0 Hz, 1H), 1.66 (s, 9H). MS m/z (ESI): 347.1 [M + H]. |
| Reg-1-12 | | $^1$H NMR (400 MHz, DMSO-d$_6$) δ 10.20 (s, 1H), 8.47 (s, 1H), 8.35 (d, J = 3.6 Hz, 1H), 8.21 (d, J = 1.2 Hz, 1H), 8.07 (d, J = 8.8 Hz, 1H), 7.82 (dd, J = 8.8, 2.0 Hz, 1H), 1.66 (s, 9H). |
| Reg-1-15 | | $^1$H NMR (400 MHz, DMSO-d$_6$) δ 10.07 (s, 1H), 8.44 (s, 1H), 8.16 (s, 1H), 8.05 (d, J = 9.2 Hz, 1H), 7.63 (d, J = 8.8 Hz, 1H), 6.61 (s, 1H), 2.29 (s, 3H), 1.66 (s, 9H). MS m/z (ESI): 360.0 [M + H]. |
| Reg-1-30 | | $^1$H NMR (400 MHz, CDCl$_3$) δ 8.25 (d, J = 8.8 Hz, 1H), 8.20 (s, 1H), 7.76 (s, 1H), 7.54 (s, 1H), 7.43 (d, J = 8.8 Hz, 1H), 6.48 (s, 1H), 1.73 (s, 9H). |
| Reg-1-53 | | $^1$H NMR (400 MHz, DMSO-d$_6$) δ 10.12 (s, 1H), 8.45 (d, J = 11.3 Hz, 1H), 8.18 (s, 1H), 8.03 (d, J = 9.1 Hz, 1H), 7.63 (t, J = 8.9 Hz, 1H), 7.33 (dt, J = 17.3, 8.3 Hz, 4H), 6.53 (d, J = 12.4 Hz, 1H), 3.94 (s, 2H), 1.66 (s, 9H). MS m/z (ESI): 436.0 [M + H]. |

| No. | Structure of Intermediate | Characterization Data |
|---|---|---|
| Reg-1-55 | | ¹H NMR (400 MHz, DMSO-d₆) δ 7.49 (s, 1H), 7.35 (s, 1H), 7.20 (d, J = 8.9 Hz, 1H), 6.89 (d, J = 8.9 Hz, 1H), 6.77 (d, J = 7.6 Hz, 2H), 6.51 (s, 2H), 6.30 (m, 1H), 5.40 (s, 1H), 0.92 (s, 9H). MS m/z (ESI): 436.6, 438.7 [M + H]. |
| Reg-1-80 | | ¹H NMR (400 MHz, DMSO-d₆) δ 9.52 (s, 1H), 8.44 (s, 1H), 8.25 (s, 1H), 8.02 (d, J = 9.0 Hz, 1H), 7.96 (s, 1H), 7.85 (d, J = 9.0 Hz, 1H), 3.96 (s, 3H), 1.66 (s, 9H). MS m/z (ESI): 375.9 [M + H]. |
| Reg-1-81 | | MS m/z (ESI): 379.9, 381.8 [M + H]. |
| Reg-1-83 | | ¹H NMR (400 MHz, DMSO-d₆) δ 12.85 (s, 1H), 9.40 (s, 1H), 8.16 (s, 1H), 7.97 (s, 1H), 7.56 (dd, J = 9.0, 1.4 Hz, 1H), 7.44 (d, J = 8.9 Hz, 1H), 6.14 (s, 1H), 2.70 (s, 6H). MS m/z (ESI): 289.1 [M + H]. |

The reagent employed in step 3 for the preparation of Reg-1-10 was prepared according to the following reaction:

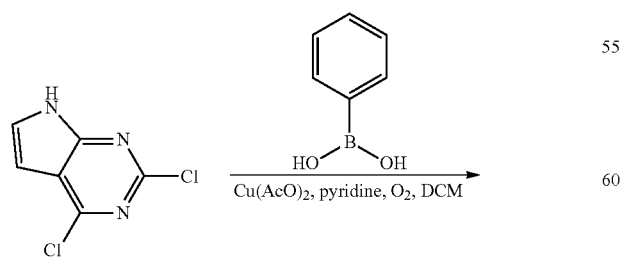

Reg-1-10-1

-continued

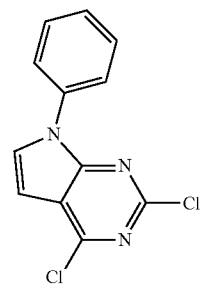

Reg-1-10-2

Compound Reg-1-10-1 (1.0 g, 5.32 mmol), phenylboronic acid (972.79 mg, 7.98 mmol) and pyridine (2.52 g, 31.86 mmol) were dissolved in dichloromethane (30 mL), followed by addition of copper acetate (0.966 g, 4.99 mmol) and molecular sieve (0.5 g), and then the reaction was performed under an oxygen atmosphere for 12 h. LC-MS indicated the reaction was complete. The reaction solution was filtered, and the filtrate was concentrated under reduced pressure to give a crude product, which was separated and purified through a medium pressure preparative column (petroleum ether:ethyl acetate=100:1~3:1) to afford compound Reg-1-10-2 (0.9 g, white solid, yield: 64.07%). MS m/z (ESI): 264.0 [M+H].

Intermediate Example 2

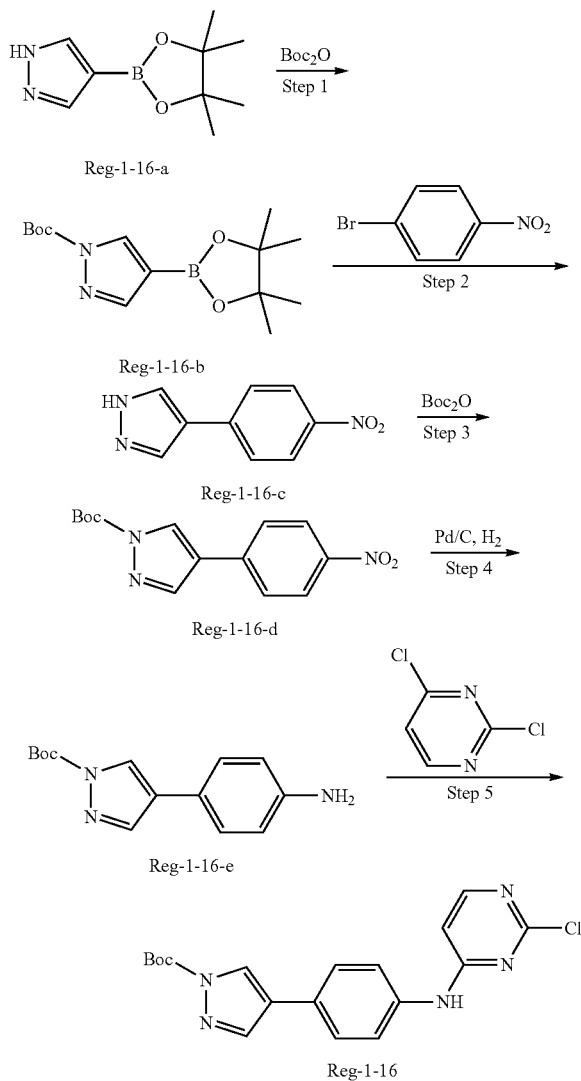

Step 1:

Compound Reg-1-16-a (4.5 g, 2.58 mmol) and dichloromethane (200 mL) were added to a 100 mL flask, diisopropylethylamine (5.99 g, 46.38 mmol) and 4-dimethylaminopyridine (424 mg, 3.48 mmol) were added, followed by slow dropwise addition of Boc$_2$O (7.59 g, 34.79 mmol). The reaction was performed overnight at room temperature. Thin layer chromatography (petroleum ether:ethyl acetate=3:1) indicated the reaction was complete. The reaction solution was concentrated to give a crude product, which was dissolved in dichloromethane (100 mL), and the organic phase was then washed three times with 0.5M dilute hydrochloric acid. The organic phase was further washed with saturated brine, dried over anhydrous sodium sulfate, filtered, and concentrated to obtain Reg-1-16-b (6.8 g, colorless oil, yield: 99.68%). MS m/z (ESI): 195.2 [M-Boc+H].

Step 2:

Compound Reg-1-16-b (6.8 g, 23.12 mmol) and 1-bromo-4-nitrobenzene (7.0 g, 34.68 mmol) were dissolved in a mixture of 1,4-dioxane/water (4:1) (200 mL), followed by addition of potassium carbonate (9.58 g, 69.35 mmol) and Pd(dppf)Cl$_2$ (0.9 g, 1.16 mmol). Purge with argon was performed for 3 times, and the reaction was placed in an oil bath at 80° C. overnight. LC-MS indicated the reaction was complete. The reaction solution was cooled to room temperature, filtered, and concentrated under reduced pressure to afford compound Reg-1-16-c (12 g, brown solid). The crude was used directly in the next reaction. MS m/z (ESI): 190.1 [M+H].

Step 3:

Compound Reg-1-16-c (4.5 g, 2.58 mmol) and dichloromethane (200 mL) were added to a 250 mL flask, and diisopropylethylamine (8.54 mL, 52.86 mmol) and 4-dimethylaminopyridine (484 mg, 3.96 mmol) were added, followed by slow dropwise addition of BOC$_2$O (8.65 g, 39.65 mmol). The reaction was performed overnight at room temperature. Thin layer chromatography (petroleum ether:ethyl acetate=3:1) indicated the reaction was complete. The reaction solution was concentrated to give a crude product, which was purified through flash column chromatography (petroleum ether:ethyl acetate=100:1 to 1.5:1) to afford compound Reg-1-16-d (6 g, light yellow oil, yield: 78.47%).

$^1$H NMR (400 MHz, CDCl$_3$) δ 8.44 (s, 1H), 8.27 (d, J=8.8 Hz, 2H), 8.06 (s, 1H), 7.69 (d, J=8.8 Hz, 2H), 1.34-1.12 (m, 9H). MS m/z (ESI): 190.2 [M-Boc+H].

Step 4:

Compound Reg-1-16-d (6 g, 20 mmol) was dissolved in methanol (100 mL), Pd/C (10% water) was added, and purge with hydrogen was performed for 3 times. The reaction was performed under a hydrogen atmosphere overnight. LC-MS indicated the reaction was complete. The reaction solution was filtered through Celite, and concentrated to afford compound Reg-1-16-e (5 g, white solid, yield: 92.97%).

$^1$H NMR (400 MHz, CDCl$_3$) δ 7.74 (s, 1H), 7.49 (s, 1H), 6.89-6.82 (m, 2H), 6.25 (d, J=8.8 Hz, 2H), 1.43-1.08 (m, 9H). MS m/z (ESI): 260.2 [M+H].

Step 5:

Compound Reg-1-16-e (3.8 g, 14.65 mmol) and 2,4-dichloropyrimidine (4.37 g, 29.31 mmol) were dissolved in N,N-dimethylformamide (30 mL), diisopropylethylamine (7.22 mL, 43.98 mmol) was added, and the reaction was performed in an oil bath at 80° C. for 8 h. LC-MS indicated the reaction was complete. The reaction solution was cooled to room temperature, and concentrated under reduced pressure to afford a crude product, which was separated through preparative chromatography (dichloromethane/methanol =100:1~100:5) to afford compound Reg-1-16 (2.2 g, yellow solid, yield: 54.80%).

$^1$H NMR (400 MHz, CDCl$_3$) δ 8.31 (s, 1H), 8.16 (d, J=5.9 Hz, 1H), 7.99 (s, 1H), 7.57 (d, J=8.4 Hz, 2H), 7.38 (d, J=8.4 Hz, 2H), 6.98 (s, 1H), 6.62 (d, J=5.9 Hz, 1H), 1.69 (s, 9H). MS m/z (ESI): 372.1 [M+H].

The following intermediates were prepared according to methods similar to that described in Intermediate Example 2:

| No. | Structure of Intermediate | Characterization Data |
|---|---|---|
| Reg-1-33 | 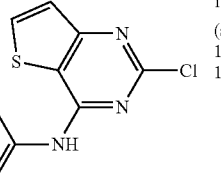 | $^1$H NMR (400 MHz, DMSO-d$_6$) δ 10.22 (s, 1H), 8.73 (s, 1H), 8.32 (s, 1H), 8.30 (d, J = 5.6 Hz, 1H), 7.80 (s, 1H), 7.76 (s, 1H), 7.66 (s, 1H), 7.43 (d, J = 5.6 Hz, 1H), 1.62 (s, 9H). MS m/z (ESI): 428.3 [M + H]. |
| Reg-1-34 | 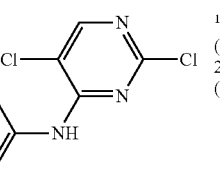 | $^1$H NMR (400 MHz, DMSO-d$_6$) δ 9.56 (s, 1H), 8.72 (s, 1H), 8.39 (s, 1H), 8.31 (s, 1H), 7.78 (d, J = 8.8 Hz, 2H), 7.65 (d, J = 8.8 Hz, 2H), 1.61 (s, 9H). MS m/z (ESI): 404.1 [M − H]. |
| Reg-1-36 | 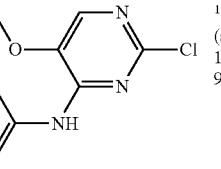 | $^1$H NMR (400 MHz, DMSO-d$_6$) δ 9.52 (s, 1H), 8.44 (s, 1H), 8.25 (s, 1H), 8.02 (d, J = 8.0 Hz, 1H), 7.96 (s, 1H), 7.85 (d, J = 8.0 Hz, 1H), 3.96 (s, 3H), 1.66 (s, 9H). MS m/z (ESI): 375.9 [M − H]. |
| Reg-1-70 | 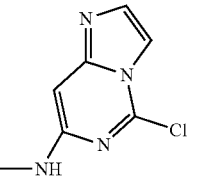 | MS m/z (ESI): 311.1 [M + H]. |

Intermediate Example 3

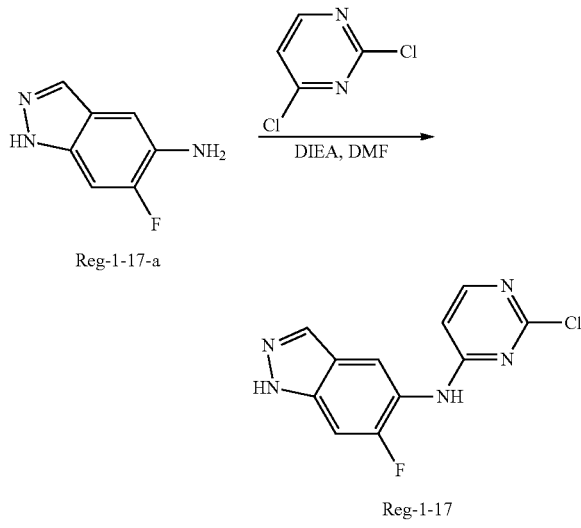

Compound Reg-1-17-a (650 mg, 4.30 mmol) and 2,4-dichloropyrimidine (1.28 g, 8.60 mmol) were dissolved in N,N-dimethylformamide (20 mL), diisopropylethylamine (2.22 g, 17.2 mmol) was added, and the reaction was performed in an oil bath at 80° C. overnight. Thin layer chromatography (petroleum ether:ethyl acetate=1:1) indicated the reaction was complete. The reaction solution was cooled to room temperature, diluted with ethyl acetate (80 mL), and was successively washed with a saturated aqueous solution of ammonium chloride (80 mL×2) and saturated brine (100 mL×2). The organic phase was dried over anhydrous sodium sulfate, filtered, concentrated under reduced pressure, and the crude was separated and purified by column chromatography (petroleum ether:ethyl acetate=10:1, 4:1 to 2:1) to afford compound Reg-1-17 (480 mg, yellow solid, yield: 42.5%).

$^1$H NMR (400 MHz, DMSO-d$_6$) δ 13.20 (s, 1H), 9.75 (s, 1H), 8.21-8.06 (m, 2H), 7.98 (d, J=7.6 Hz, 1H), 7.50 (d, J=12.0 Hz, 1H), 6.67 (s, 1H).

The following intermediates were prepared according to methods similar to that described in Intermediate Example 3:

| No. | Structure of Intermediate | Characterization Data |
|---|---|---|
| Reg-1-13 | | $^1$H NMR (400 MHz, DMSO-d$_6$) δ 8.81 (s, 1H), 8.06 (s, 1H), 7.85 (s, 1H), 7.53 (d, J = 8.8 Hz, 1H), 7.43 (d, J = 8.8 Hz, 1H), 2.32 (s, 3H), 2.16 (s, 3H). MS m/z (ESI): 274.0 [M + H]. |
| Reg-1-14 | | $^1$H NMR (400 MHz, DMSO-d$_6$) δ 13.07 (s, 1H), 8.92 (s, 1H), 8.08 (s, 1H), 8.00 (s, 1H), 7.93 (s, 1H), 7.56 (d, J = 8.8 Hz, 1H), 7.49 (dd, J = 8.9, 1.4 Hz, 1H), 2.18 (s, 3H). MS m/z (ESI): 260.1 [M + H]. |
| Reg-1-19 | | $^1$H NMR (400 MHz, DMSO-d$_6$) δ 13.20 (s, 1H), 9.75 (s, 1H), 8.21-8.06 (m, 2H), 7.98 (d, J = 7.6 Hz, 1H), 7.50 (d, J = 12.0 Hz, 1H), 6.67 (s, 1H). |
| Reg-1-20 | | $^1$H NMR (400 MHz, DMSO-d$_6$) δ 12.72 (s, 1H), 10.14 (s, 1H), 8.14 (d, J = 5.9 Hz, 1H), 8.00 (s, 1H), 7.93 (s, 1H), 7.52 (d, J = 8.8 Hz, 1H), 7.45 (d, J = 8.5 Hz, 1H), 2.51 (s, 3H). MS m/z (ESI): 260.1 [M + H]. |
| Reg-1-21 | | $^1$H NMR (400 MHz, DMSO-d$_6$) δ 13.10 (s, 1H), 9.99 (s, 1H), 8.13-8.06 (m, 2H), 7.99 (s, 1H), 7.57 (d, J = 8.8 Hz, 1H), 7.40 (d, J = 8.5 Hz, 1H), 6.70 (d, J = 5.8 Hz, 1H). |
| Reg-1-22 | | $^1$H NMR (400 MHz, DMSO-d$_6$) δ 12.98 (s, 1H), 9.69 (s, 1H), 8.20 (s, 1H), 8.01 (s, 1H), 7.50 (d, J = 15.6 Hz, 2H), 2.42 (s, 3H), 2.19 (s, 3H). MS m/z (ESI): 274.0 [M + H]. |
| Reg-1-26 | | $^1$H NMR (400 MHz, DMSO-d$_6$) δ 13.11 (s, 1H), 9.59 (s, 1H), 8.17 (s, 1H), 8.03 (d, J = 5.5 Hz, 1H), 7.41 (d, J = 8.6 Hz, 1H), 7.20 (d, J = 8.6 Hz, 1H), 2.40 (s, 3H). MS m/z (ESI): 260.1 [M + H]. |

| No. | Structure of Intermediate | Characterization Data |
|---|---|---|
| Reg-1-28 | 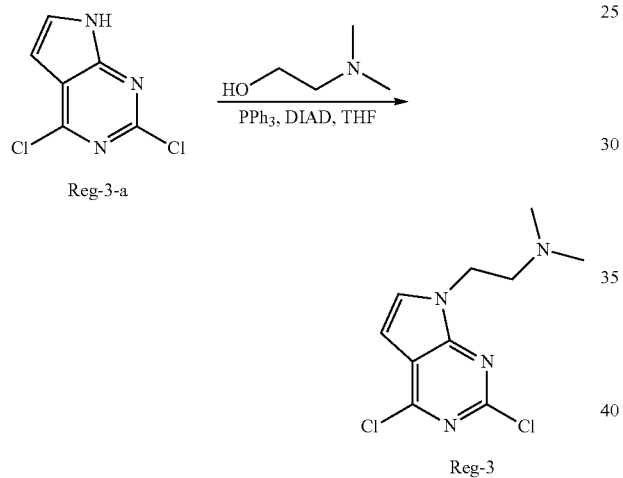 | MS m/z (ESI): 302.1 [M + H]. |
| Reg-1-88 | | $^1$H NMR (400 MHz, DMSO-d$_6$) δ 12.95 (s, 1H), 9.43 (s, 1H), 8.22 (t, J = 13.4 Hz, 1H), 7.99 (s, 1H), 7.77 (s, 1H), 7.07 (s, 1H), 3.84 (s, 3H). MS m/z (ESI): 293.8 [M + H]. |

Intermediate Example 4

Compound Reg-3-a (3 g, 15.63 mmol), 2-(dimethylamino)ethanol (1.7 g, 19.11 mmol) and triphenylphosphine (5.01 g 19.11 mmol) were dissolved in tetrahydrofuran (200 mL), diisopropyl azodiformate (4.83 g, 23.89 mmol) was added at 0° C., purge with argon was performed for 3 times, and the reaction was performed at room temperature for 6 hours. LC-MS indicated the reaction was complete. 200 mL ethyl acetate was added to the reaction solution; the organic phase was washed with water (100 mL×3), dried, concentrated under reduced pressure, and the residue was purified by column chromatography (dichloromethane:methanol=100:1~20:1) to afford compound Reg-3 (3 g, brown solid, yield: 72.55%). MS m/z (ESI): 259.0 [M+H].

Intermediate Example 5

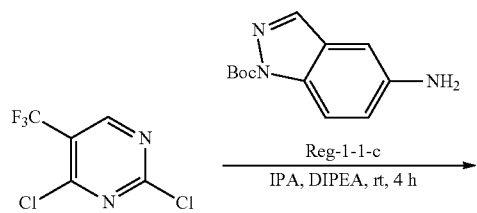

Compound 2,4-dichloro-5-(trifluoromethyl)pyrimidine (3 g, 13.825 mmol) and N,N-diisopropylethylamine (2.14 g, 16.59 mmol) were dissolved in isopropanol (100 mL), compound Reg-1-1-c (3.2 g, 13.825 mmol) was then added to the aforementioned solution in portions. The reaction was performed at room temperature for 16 hours. LC-MS indicated the reaction was complete. The reaction solution was filtered, and the filter cake was rinsed once with isopropanol to afford compound Reg-1-24 (2.3 g, pink solid, yield: 40.19%); the filtrate was washed with saturated brine, dried over anhydrous sodium sulfate, and then concentrated to dryness, to afford compound Reg-1-23 (1.84 g, dark red solid, yield: 32.15%). Characterization data of the compound are as follows:

| No. | Structure of Intermediate | Characterization Data |
|---|---|---|
| Reg-1-23 | 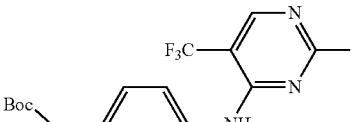 | ¹H NMR (400 MHz, CDCl₃): δ 8.46 (s, 1H), 8.21 (m, 2H), 8.08 (d, 1H), 7.53 (dd, 1H), 7.20 (s, 1H), 1.74 (s, 9H). MS m/z (ESI): 414.1 [M + H]. |
| Reg-1-24 |  | ¹H NMR (400 MHz, CDCl₃) δ 8.59 (s, 1H), 8.20 (m, 3H), 7.71 (s, 1H), 7.53 (dd, 1H), 1.73 (s, 9H). MS m/z (ESI): 414.1 [M + H]. |

Intermediate Example 6

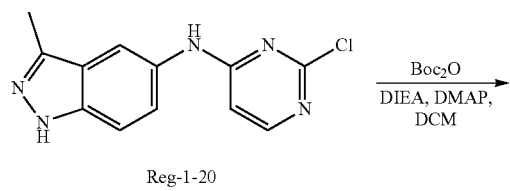

Reg-1-20

Compound Reg-1-20 (0.8 g, 3.09 mmol) was dissolved in dichloromethane (100 mL), DIEA (1.59 g, 12.36 mmol) and DMAP (188 mg, 1.55 mmol) were added, and Boc₂O (2.02 g, 9.27 mmol) was added after stir at room temperature for 10 minutes, the reaction was performed at room temperature for 3 hours. Thin layer chromatography (petroleum ether:ethyl acetate=2:1) indicated the reaction was complete. The reaction solution was dissolved in dichloromethane (400 mL), and successively washed with water (250 mL×3) and saturated brine (250 mL), the organic phase was dried over anhydrous sodium sulfate, concentrated under reduced pressure, and the residue was separated and purified by column chromatography (petroleum ether:ethyl acetate=1:0 to 5:1), to afford compound Reg-1-25 (2.01 g, white solid).

¹H NMR (400 MHz, CDCl₃) δ 8.45 (d, J=5.6 Hz, 1H), 8.15 (d, J=8.8 Hz, 1H), 7.96 (d, J=5.6 Hz, 1H), 7.41 (d, J=1.6 Hz, 1H), 7.29 (d, J=1.6 Hz, 1H), 2.59 (s, 3H), 1.74 (s, 9H), 1.41 (s, 9H). MS m/z (ESI): 460.3 [M+H].

The following intermediate was prepared according to a method similar to that described in Intermediate Example 6:

| No. | Structure of Intermediate | Characterization Data |
|---|---|---|
| Reg-1-27 | 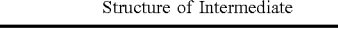 | ¹H NMR (400 MHz, DMSO-d₆) δ 8.63 (d, J = 6.0 Hz, 1H), 8.45 (s, 1H), 8.13 (d, J = 8.8 Hz, 1H), 8.02 (d, J = 6.0 Hz, 1H), 7.82 (d, J = 2.0 Hz, 1H), 7.50 (dd, J = 8.8, 2.0 Hz, 1H), 1.67 (s, 9H), 1.36 (s, 9H). |

-continued

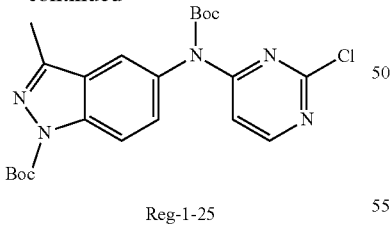

Reg-1-25

Intermediate Example 7

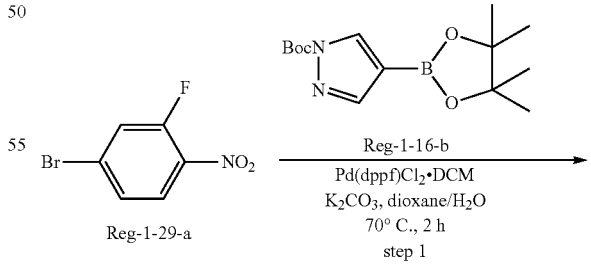

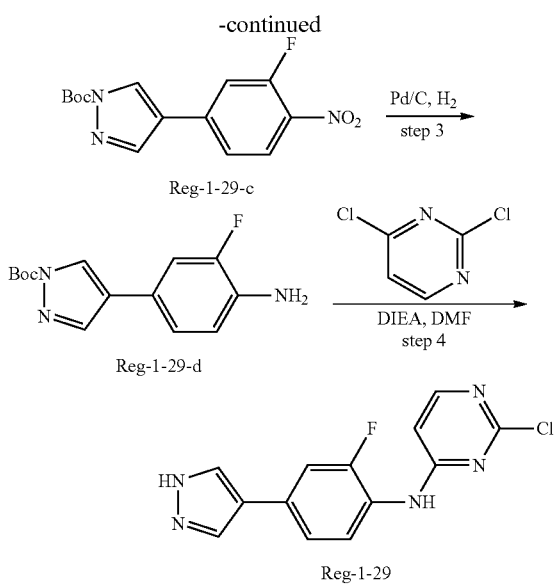

Step 1:

A solution of Reg-1-29-a (6.7 g, 30.612 mmol) and Reg-1-16-b (6.0 g, 20.408 mmol) dissolved in a mixture of dioxane and water (4:1) (84 mL) was added to a 250 mL single neck flask, potassium carbonate (11.28 g, 81.59 mmol) and [1,1'-bis(diphenylphosphino)ferrocene]dichloropalladium dichloromethane complex (833 mg, 1.020 mmol) were added, purge with argon was performed for 3 times, and the reaction was placed in an oil bath at 70° C. for 3 hours. The reaction was cooled to room temperature, water (50 mL) was added, and the solution was extracted three times with ethyl acetate (150 mL). The organic phase was dried over sodium sulfate, filtered, dried by rotary evaporation, and the residue was directly used in the next reaction. MS m/z (ESI): 208.2 [M+H].

Step 2:

Reg-1-29-b (4.58 g, 22.126 mmol) was dissolved in dichloromethane (50 mL), DMAP (270 mg, 2.213 mmol) and DIEA (5.7 g, 44.251 mmol) were added, followed by slow dropwise addition of Boc$_2$O (5.79 g, 26.551 mmol). The reaction was performed overnight at room temperature. After the reaction was complete, the reaction solution was concentrated under reduced pressure to afford a crude product, which was separated by medium pressure preparative chromatography to afford Reg-1-29-c (3.6 g, yellow solid, yield: 53.04%).

$^1$H NMR (400 MHz, CDCl$_3$) δ 8.44 (s, 1H), 8.17-8.10 (m, 1H), 8.03 (s, 1H), 7.43 (dt, J=6.5, 2.1 Hz, 2H), 1.69 (s, 9H). MS m/z (ESI): 206.1 [M-Boc-H].

Step 3:

Reg-1-29-c (3.6 g, 11.726 mmol) and methanol (100 mL) were added to a 250 mL single neck flask, and then Pd/C (10 wt %, 360 mg) was added. The reaction was performed under a hydrogen atmosphere overnight. After thin layer chromatography indicated completion of the reaction, the reaction solution was filtered through Celite to afford Reg-1-29-d (3.0 g, brown oil, yield: 92.36%).

$^1$H NMR (400 MHz, CDCl$_3$) δ 8.17 (s, 1H), 7.89 (s, 1H), 7.18-7.08 (m, 2H), 6.82-6.75 (m, 1H), 1.67 (s, 9H). MS m/z (ESI): 178.3 [M-Boc+H].

Step 4:

Reg-1-29-d (3.3 g, 12.74 mmol) and 2,4-dichloropyrimidine (3.8 g, 25.48 mmol) were dissolved in DMF (60 mL), DIEA (4.93 g, 38.22 mmol) was added, and the reaction was performed in an oil bath at 120° C. overnight. Thin layer chromatography indicated the reaction was complete. The reaction solution was cooled to room temperature, followed by addition of water (30 mL), and extraction with ethyl acetate (150 mL). The organic phase was dried over sodium sulfate, filtered, and dried by rotary evaporation to afford a crude product, which was separated by column chromatography to afford Reg-1-29 (1 g, yellow solid, yield: 29.52%).

$^1$H NMR (400 MHz, DMSO-d$_6$) δ 13.04 (s, 1H), 9.78 (s, 1H), 8.33-7.96 (m, 3H), 7.79-7.57 (m, 2H), 7.48 (dd, J=8.3, 1.5 Hz, 1H), 6.75 (d, J=5.3 Hz, 1H). MS m/z (ESI): 290.0 [M+H].

The following intermediates were prepared according to methods similar to that described in Intermediate Example 7:

| No. | Structure of Intermediate | Characterization Data |
|---|---|---|
| Reg-1-32 | | $^1$H NMR (400 MHz, DMSO-d$_6$) δ 12.99 (s, 1H), 9.48 (s, 1H), 9.23 (s, 1H), 8.53 (s, 1H), 8.17 (d, J = 5.9 Hz, 1H), 7.73 (d, J = 5.2 Hz, 1H), 7.61 (d, J = 5.2 Hz, 1H), 7.49 (dd, J = 8.2, 1.7 Hz, 1H), 7.28 (dd, J = 8.2, 1.7 Hz, 1H), 3.94 (s, 3H). MS m/z (ESI): 302.3 [M + H]. |
| Reg-1-37 | | $^1$H NMR (400 MHz, DMSO-d$_6$) δ 12.89 (s, 1H), 9.30 (s, 1H), 8.02 (s, 1H), 7.94 (s, 1H), 7.73 (d, J = 8.0 Hz, 2H), 7.58 (d, J = 8.0 Hz, 2H), 3.95 (s, 3H). MS m/z (ESI): 302.0 [M + H]. |

Intermediate Example 8

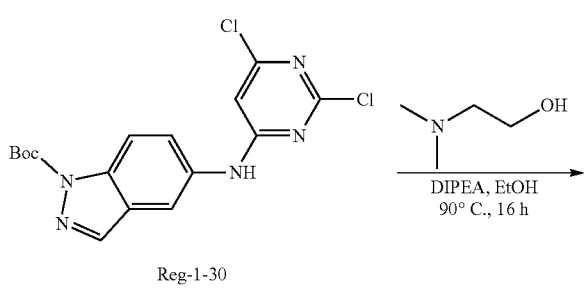

Reg-1-30

Intermediate Example 9

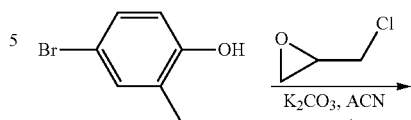

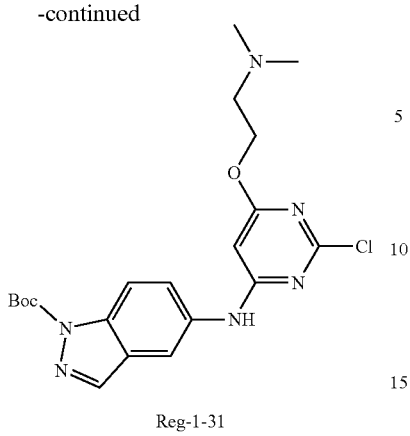

Reg-1-31

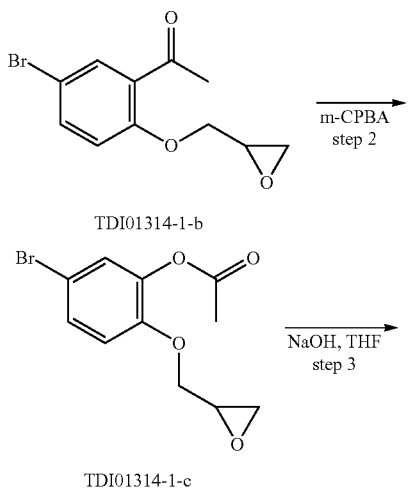

Compound Reg-1-30 (2.0 g, 5.26 mmol) was dissolved in anhydrous ethanol (20 mL), and dimethylaminoethanol (468 mg, 5.26 mmol) and DIPEA (905 mg, 5.26 mmol) were added. The obtained mixture was heated to 90° C., at which temperature the reaction was performed overnight. LC-MS indicated the starting material underwent complete reaction. The reaction solution was concentrated under reduced pressure, and ethyl acetate (40 mL) and water (40 mL) were added to the residue. The organic layer was separated, and Reg-1-31 was obtained after evaporation under reduced pressure to remove solvents. MS m/z (ESI): 432.9 [M+H].

The following intermediates were prepared according to methods similar to that described in Intermediate Example 8:

| No. | Structure of Intermediate | Characterization Data |
|---|---|---|
| Reg-1-54 | 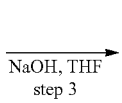 | MS m/z (ESI): 437.7 [M + H]. |
| Reg-1-82 | | $^1$H NMR (400 MHz, DMSO-d$_6$) δ 13.06 (s, 1H), 9.93 (s, 1H), 8.14-8.01 (m, 2H), 7.53 (d, J = 8.8 Hz, 1H), 7.42 (d, J = 8.8 Hz, 1H), 3.86 (s, 3H). |

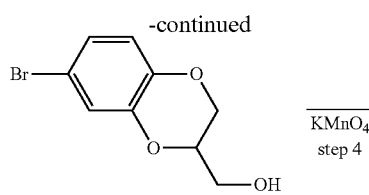

TDI01314-1-d

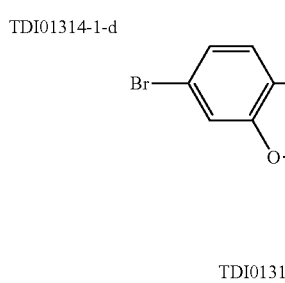

TDI01314-1

Step 1:

TDI01314-1-a (8.00 g, 37.20 mmol) and 2-(chloromethyl)oxirane (6.88 g, 74.40 mmol) were dissolved in acetonitrile (200 mL), potassium carbonate (15.42 g, 111.60 mmol) was added, and the reaction was performed at 80° C. overnight. Thin layer chromatography indicated the reaction was complete. The reaction solution was concentrated under reduced pressure, and the crude product was separated and purified by flash column chromatography to afford TDI01314-1-b (6 g, white solid, yield: 59.49%). MS m/z (ESI): 271.1; 273.1 [M+H].

Step 2:

TDI01314-1-b (6 g, 22.13 mmol) was dissolved in dichloromethane (100 mL), m-chloroperbenzoic acid (7.64 g, 44.26 mmol) was added, and the reaction was performed at 40° C. for 8 hours. Thin layer chromatography indicated the reaction was complete. The reaction solution was cooled to room temperature, and stirred for half an hour after addition of a saturated solution of sodium sulfite. The precipitated white solid was filtered, the organic phase was concentrated, and the crude product was separated and purified by column chromatography to afford TDI01314-1-c (3 g, white solid, yield: 47.21%). MS m/z (ESI): 287.1; 289.1 [M+H].

Step 3:

TDI01314-1-c (3 g, 10.45 mmol) was dissolved in tetrahydrofuran (100 mL) and water (10 mL), sodium hydroxide (835.85 mg, 20.90 mmol) was added, and the reaction was performed at ambient temperature overnight. Thin layer chromatography indicated the reaction was complete. The reaction solution was extracted with ethyl acetate, concentrated under reduced pressure, and the residue was separated and purified by column chromatography to afford TDI01314-1-d (2 g, colorless oil, yield: 78.1%).

$^1$H NMR (400 MHz, CDCl$_3$) δ 7.06 (dd, J=11.2, 2.3 Hz, 1H), 6.95 (dd, J=8.6, 2.3 Hz, 1H), 6.75 (d, J=8.6 Hz, 1H), 4.33-4.22 (m, 2H), 4.14-4.05 (m, 1H), 3.95-3.79 (m, 2H).

Step 4:

TDI01314-1-d (2 g, 8.16 mmol) was added to water (100 mL), followed by addition of potassium carbonate (2.26 g, 16.32 mmol) and potassium permanganate (2.58 g, 16.32 mmol), and the reaction was performed at ambient temperature for 12 hours. LC-MS assay indicated the reaction was complete. The reaction solution was filtered, and the filtrate was concentrated to give a crude product, which was then separated and purified by column chromatography to afford TDI01314-1 (1 g, white solid, yield: 47.3%).

$^1$H NMR (400 MHz, CDCl$_3$) δ 7.16 (d, J=2.3 Hz, 1H), 6.99 (dd, J=8.7, 2.3 Hz, 1H), 6.76 (d, J=8.6 Hz, 1H), 4.88 (dd, J=4.3, 3.0 Hz, 1H), 4.44 (dd, J=11.5, 4.4 Hz, 1H), 4.36 (dd, J=11.5, 2.9 Hz, 1H).

Intermediate Example 10

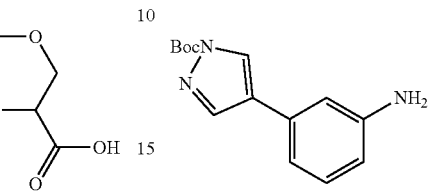

Reg-1-38-a

Reg-1-38

Compound Reg-1-38-a (320 mg, 1.24 mmol) and 2,4-dichloropyrimidine (221 mg, 1.48 mmol) were dissolved in N,N-dimethylformamide (20 mL), diisopropylethylamine (638 mg, 4.94 mmol) was added, and the reaction solution was slowly warmed to 80° C., and kept at this temperature for 16 hours. Thin layer chromatography (petroleum ether/ethyl acetate=2:1) indicated the reaction was complete. The reaction solution was dissolved in ethyl acetate (250 mL), and successively washed with water (250 mL×2) and saturated brine (250 mL). The organic phase was dried over anhydrous sodium sulfate, concentrated, and the crude product was directly used in the next reaction.

The crude product obtained from the last step was dissolved in dichloromethane (20 mL), diisopropylethylamine (417 mg, 3.24 mmol) and 4-dimethylaminopyridine (99 mg, 0.81 mmol) were added, and the reaction was stirred at room temperature for 10 minutes. Di-tert-butyl dicarbonate (705 mg, 3.24 mmol) was then added, and the reaction was performed at room temperature for 3 hours. Thin layer chromatography (petroleum ether/ethyl acetate=2:1) indicated the reaction was complete. The reaction solution was dissolved in dichloromethane (400 mL), and successively washed with water (250 mL×32) and saturated brine (250 mL). The organic phase was dried over anhydrous sodium sulfate, concentrated under reduced pressure, and the residue was separated and purified by column chromatography (petroleum ether:dichloromethane =100:1 to 0:1) to afford compound Reg-1-38 (400 mg, light yellow oil).

$^1$H NMR (400 MHz, CDCl$_3$) δ 8.44 (d, J=5.6 Hz, 1H), 8.31 (s, 1H), 7.99 (s, 1H), 7.90 (d, J=5.6 Hz, 1H), 7.73 (dd, J=5.6, 3.2 Hz, 1H), 7.53 (dd, J=5.6, 3.2 Hz, 3H), 7.08 (d, J=7.6 Hz, 1H), 1.68 (s, 9H), 1.43 (s, 9H). MS m/z (ESI): 472.3 [M+H].

Intermediate Example 11

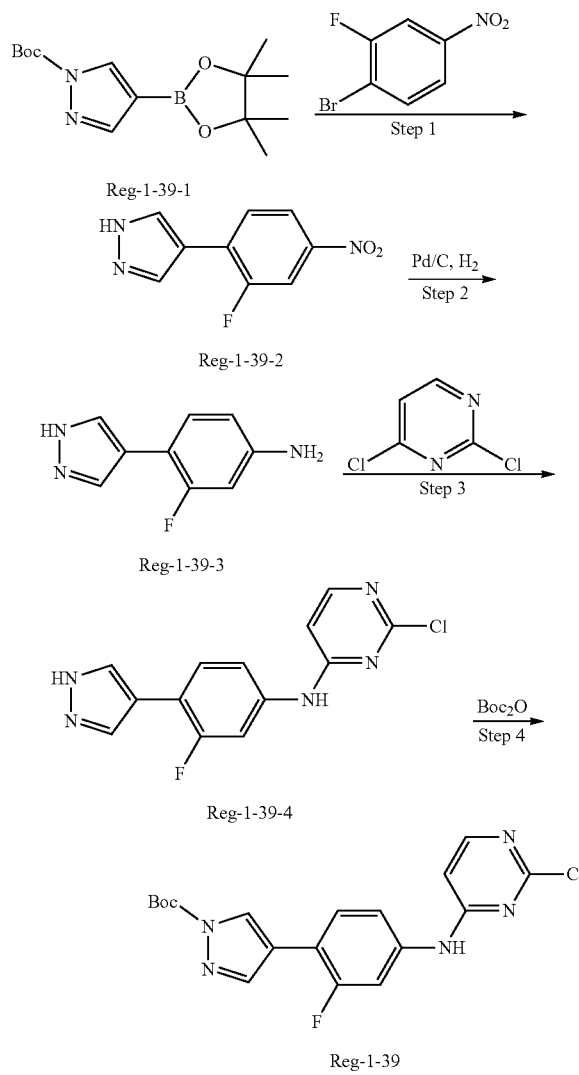

Step 1:

Compound Reg-1-39-1 (15 g, 68 mmol), 3-fluoro-4-bromonitrobenzene (24.2 g, 82 mmol) and potassium carbonate (28 g, 204 mmol) were mixed in mixed solvents of 1,4-dioxane (500 mL) and water (50 mL), the flask was purged with $N_2$ 3 times, followed by addition of Pd(dppf)Cl$_2$ (10 g, 13.6 mmol). The flask was purged with $N_2$ 3 times again, and then the reaction solution was heated to reflux for 16 hours. LC-MS indicated the reaction was complete. The reaction solution was cooled to room temperature, filtered to remove salt impurities, the filtrate was concentrated under reduced pressure, and the crude product was separated through column chromatography on silica gel (petroleum ether:ethyl acetate=3:1-1:3) to afford compound Reg-1-39-2 (10 g, brown solid, yield: 71.7%).

$^1$H NMR (300 MHz, DMSO-d$_6$) δ 13.40 (s, 1H), 8.42 (s, 1H), 8.29-7.95 (m, 4H). MS m/z (ESI): 207.8 [M+H].

Step 2:

Compound Reg-1-39-2 (10 g, 48 mmol) and Pd/C (10 g, 10%) were mixed in isopropanol (50 mL) and tetrahydrofuran (50 mL), the flask was purged with hydrogen 3 times, and the reaction was placed at room temperature under an atmosphere of hydrogen overnight. LC-MS indicated the reaction was complete. The reaction was filtered, the filter cake was washed repeatedly with tetrahydrofuran (200 mL), and the filtrates were combined and concentrated under reduced pressure to afford compound Reg-1-39-3 (8 g, brown solid, yield: 94%).

$^1$H NMR (301 MHz, DMSO-d$_6$) δ 12.84 (s, 1H), 7.89 (s, 1H), 7.73 (s, 1H), 7.32 (t, J=8.8 Hz, 1H), 6.38 (t, J=9.2 Hz, 2H), 5.35 (s, 2H). MS m/z (ESI): 178.0 [M+H].

Step 3:

Compound Reg-1-39-3 (8 g, 45 mmol), 2,4-dichloropyrimidine (6.69 g, 45 mmol) and DIPEA (17.42 g, 135 mmol) were dissolved in DMF (160 mL) and heated to 80° C. overnight. LC-MS indicated the reaction was complete. The reaction solution was cooled to room temperature, concentrated under reduced pressure, and the crude product was separated through column chromatography on silica gel (petroleum ether:ethyl acetate=3:1-1:3) to afford compound Reg-1-39-4 (4.8 g, yellow solid, yield: 36.9%).

$^1$H NMR (301 MHz, DMSO-d$_6$) δ 10.22 (s, 1H), 8.20 (d, J=5.9 Hz, 1H), 8.01 (s, 2H), 7.73-7.66 (m, 2H), 7.36 (dd, J=8.5, 2.1 Hz, 1H), 6.80 (d, J=5.9 Hz, 1H). MS m/z (ESI): 289.8, 291.7 [M+H, Cl].

Step 4:

Compound Reg-1-39-4 (4.8 g, 16.6 mmol) and Boc20 (5.07 g, 23 mmol) were dissolved in DMF (50 mL), DIPEA (6.4 g, 49.8 mmol) and DMAP (0.203 g, 1.66 mmol) were added, and the reaction was stirred at room temperature overnight. LC-MS indicated the reaction was complete. The reaction was concentrated under reduced pressure, and the crude product was separated by flash chromatography (petroleum ether:ethyl acetate=3:1-1:3) to afford compound Reg-1-39 (4.6 g, yellow solid, yield: 71.3%).

$^1$H NMR (400 MHz, DMSO-d$_6$) δ 10.30 (s, 1H), 8.54 (d, J=1.1 Hz, 1H), 8.27-8.22 (m, 2H), 7.85 (t, J=8.7 Hz, 1H), 7.75 (dd, J=13.7, 1.9 Hz, 1H), 7.41 (dd, J=8.6, 2.0 Hz, 1H), 6.82 (d, J=5.9 Hz, 1H), 1.61 (s, 9H). MS m/z (ESI): 389.6, 391.6 [M+H, Cl].

The following intermediates were prepared according to methods similar to that described in Intermediate Example 11:

| No. | Structure of Intermediate | Characterization Data |
|---|---|---|
| Reg-1-40 | ![structure] | $^1$H NMR (300 MHz, DMSO-d$_6$) δ 10.03 (s, 1H), 8.68 (d, J = 3.6 Hz, 1H), 8.30 (m, 2H), 7.72 (m, 4H), 1.60 (d, J = 3.5 Hz, 9H). MS m/z (ESI): 390.0, 391.9 [M + H]. |

| No. | Structure of Intermediate | Characterization Data |
|---|---|---|
| Reg-1-41 | 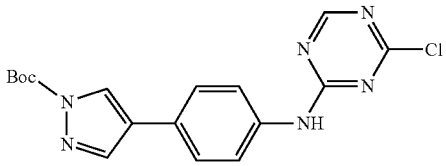 | MS m/z (ESI): 372.8 [M + H]. |
| Reg-1-42 | 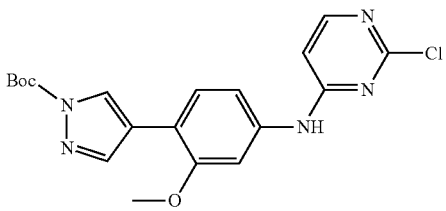 [SMILES: COc1cc(Nc2ccnc(Cl)n2)ccc1-c1cnn(C(=O)OC(C)(C)C)c1] | MS m/z (ESI): 401.9 [M + H]. |
| Reg-1-43 | 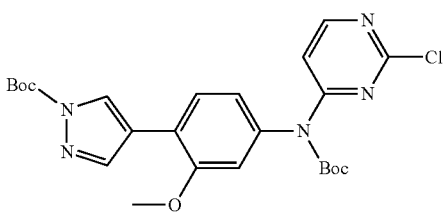 [SMILES: COc1cc(N(C(=O)OC(C)(C)C)c2ccnc(Cl)n2)ccc1-c1cnn(C(=O)OC(C)(C)C)c1] | $^1$H NMR (400 MHz, DMSO-d$_6$) δ 8.62 (t, J = 2.9 Hz, 2H), 8.35 (s, 1H), 7.88 (d, J = 5.9 Hz, 1H), 7.79 (d, J = 8.2 Hz, 1H), 7.07 (s, 1H), 6.90 (d, J = 8.2 Hz, 1H), 3.87 (s, 3H), 1.61 (s, 9H). 1.41 (s, 9H), MS m/z (ESI): 501.5 [M + H]. |
| Reg-1-44 | 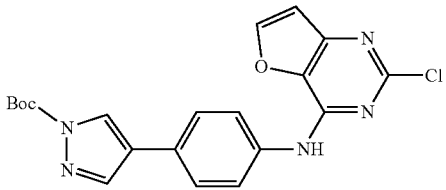 [SMILES: CC(C)(C)OC(=O)n1cc(-c2ccc(Nc3nc(Cl)nc4ccoc34)cc2)cn1] | $^1$H NMR (400 MHz, DMSO-d$_6$) δ 10.43 (s, 1H), 8.71 (s, 1H), 8.43 (d, J = 2.0 Hz, 1H), 8.31 (s, 1H), 7.80 (q, J = 8.8 Hz, 4H), 7.08 (d, J = 2.0 Hz, 1H), 1.61 (s, 9H). MS m/z (ESI): 411.7 [M + H]. |
| Reg-1-45 | 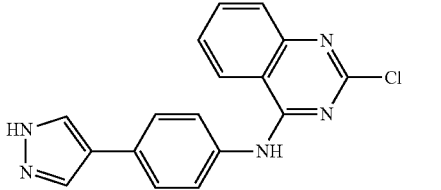 [SMILES: Clc1nc(Nc2ccc(-c3cn[nH]c3)cc2)c2ccccc2n1] | $^1$H NMR (400 MHz, DMSO-d$_6$) δ 12.95 (s, 1H), 10.21 (s, 1H), 8.58 (d, J = 8.5 Hz, 1H), 8.21 (s, 1H), 7.77 (m, 8H). MS m/z (ESI): 321.9, 323.9 [M + H]. |
| Reg-1-46 | 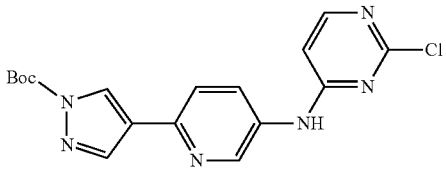 [SMILES: CC(C)(C)OC(=O)n1cc(-c2ccc(Nc3ccnc(Cl)n3)cn2)cn1] | $^1$H NMR (400 MHz, DMSO-d$_6$) δ 10.33 (s, 1H), 8.81-8.74 (m, 2H), 8.34 (s, 1H), 8.23 (d, J = 8.6 Hz, 1H), 8.13 (dd, J = 8.6, 2.4 Hz, 1H), 7.91 (d, J = 8.6 Hz, 1H), 6.82 (d, J = 5.9 Hz, 1H), 1.61 (s, 9H). |
| Reg-1-56 | 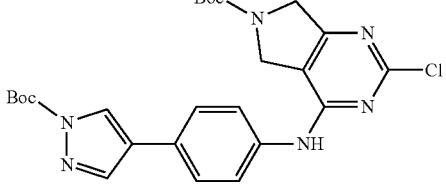 | $^1$H NMR (400 MHz, DMSO-d$_6$) δ 9.61 (d, J = 3.1 Hz, 1H), 8.70 (s, 1H), 8.30 (s, 1H), 7.73 (dt, J = 8.8, 6.4 Hz, 4H), 4.49 (dd, J = 28.5, 11.4 Hz, 4H), 1.61 (s, 9H), 1.47 (d, J = 8.0 Hz, 9H). MS m/z (ESI): 512.6, 514.6 [M + H]. |
| Reg-1-57 | 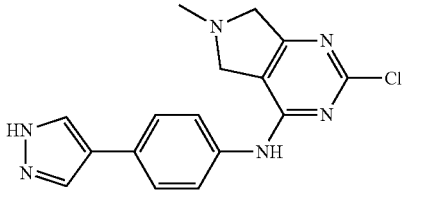 [SMILES: CN1Cc2nc(Cl)nc(Nc3ccc(-c4cn[nH]c4)cc3)c2C1] | $^1$H NMR (400 MHz, DMSO-d$_6$) δ 12.92 (s, 1H), 9.33 (s, 1H), 8.16 (s, 1H), 7.90 (s, 1H), 7.60 (s, 4, 3.80 (s, 2H), 3.75 (s, 2H), 3.17 (d, J = 5.2 Hz, 3H). MS m/z (ESI): 327.0, 329.0 [M + H]. |

| No. | Structure of Intermediate | Characterization Data |
|---|---|---|
| Reg-1-58 | 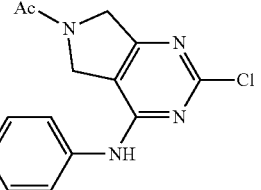 | $^1$H NMR (400 MHz, DMSO-d$_6$) δ 9.74 (d, J = 52.9 Hz, 1H), 9.47 (s, 1H), 8.84 (s, 1H), 8.39 (s, 1H), 7.79 (dd, J = 9.9, 7.0 Hz, 3H), 4.76 (d, J = 20.6 Hz, 2H), 4.51 (d, J = 33.7 Hz, 2H), 2.66 (s, 3H), 2.07 (d, J = 9.7 Hz, 3H). MS m/z (ESI): 396.6, 398.6 [M + H]. |
| Reg-1-64 | 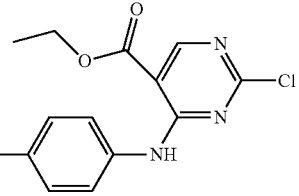 | MS m/z (ESI): 343.9 [M + H]. |
| Reg-1-65 | 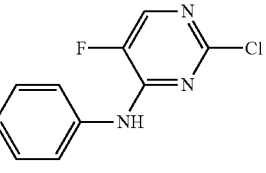 | $^1$H NMR (300 MHz, DMSO-d$_6$) δ 10.10 (s, 1H), 8.44 (s, 1H), 8.35 (d, J = 3.1 Hz, 1H), 7.78 (d, J = 8.2 Hz, 2H), 7.57 (d, J = 8.4 Hz, 2H), 2.39 (s, 3H), 1.59 (s, 9H). MS m/z (ESI): 348.0, 350.0 [M + H]. |
| Reg-1-70 | 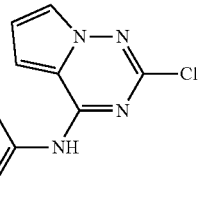 | $^1$H NMR (400 MHz, DMSO-d$_6$) δ 10.35 (s, 1H), 8.74 (s, 1H), 8.32 (s, 1H), 7.82 (d, J = 10.7 Hz, 5H), 7.25 (s, 1H), 6.77 (dd, J = 4.0, 2.7 Hz, 1H), 1.61 (s, 9H). MS m/z (ESI): 410.8 [M + H]. |
| Reg-1-71 | 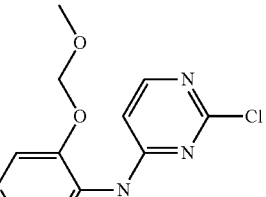 | $^1$H NMR (300 MHz, DMSO-d$_6$) δ 8.77 (s, 1H), 8.56 (d, J = 5.9 Hz, 1H), 8.31 (s, 1H), 7.92 (d, J = 5.8 Hz, 1H), 7.49 (s, 1H), 7.40 (d, J = 8.2 Hz, 1H), 7.24 (d, J = 8.1 Hz, 1H), 5.24 (s, 2H), 3.18 (s, 3H), 1.60 (s, 9H), 1.36 (s, 9H). MS m/z (ESI): 532.0 [M + H]. |
| Reg-1-72 | 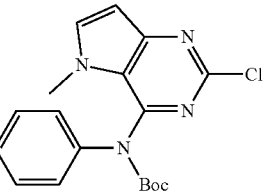 | MS m/z (ESI): 524.5 [M + H]. |
| Reg-1-73 | 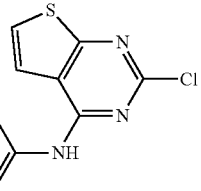 | $^1$H NMR (400 MHz, DMSO-d$_6$) δ 10.11 (s, 1H), 8.73 (s, 1H), 8.32 (s, 1H), 7.88 (d, J = 6.0 Hz, 1H), 7.82 (s, 4H), 7.76 (d, J = 5.9 Hz, 1H), 1.61 (s, 9H). MS m/z (ESI): 427.9, 429.9 [M + H]. |

-continued

| No. | Structure of Intermediate | Characterization Data |
|---|---|---|
| Reg-1-74 | | $^1$H NMR (300 MHz, DMSO-d$_6$) δ 8.89 (s, 1H), 8.68 (s, 1H), 8.28 (s, 1H), 8.04 (s, 1H), 7.76-7.66 (m, 4H), 2.18 (s, 3H), 1.61 (s, 9H). MS m/z (ESI): 386.0 [M + H]. |
| Reg-1-75 | | $^1$H NMR (400 MHz, DMSO-d$_6$) δ 9.63 (s, 1H), 8.70 (s, 1H), 8.30 (s, 1H), 7.95 (s, 1H), 7.77 (d, J = 8.4 Hz, 1H), 7.65 (dd, J = 18.4, 8.4 Hz, 2H), 4.98 (s, 2H), 4.85 (s, 2H), 1.61 (s, 9H). MS m/z (ESI): 413.6, 415.6 [M + H]. |
| Reg-1-76 | | MS m z (ESI): 386.0 [M + H]. |
| Reg-1-77 | | $^1$H NMR (400 MHz, DMSO-d$_6$) δ 9.17 (s, 1H), 8.69 (d, J = 0.6 Hz, 1H), 8.29 (d, J = 0.6 Hz, 1H), 7.73 (q, J = 9.0 Hz, 4H), 3.33 (s, 4H), 2.81 (s, 2H), 1.61 (s, 9H). MS m/z (ESI): 411.7, 413.7 [M + H]. |
| Reg-1-78 | | MS m/z (ESI): 522.0 [M + Na]. |
| Reg-1-84 | | MS m/z (ESI): 461.6 [M + H]. |
| Reg-1-87 | | MS m/z (ESI): 415.8 [M + H]. |

Intermediate Example 12

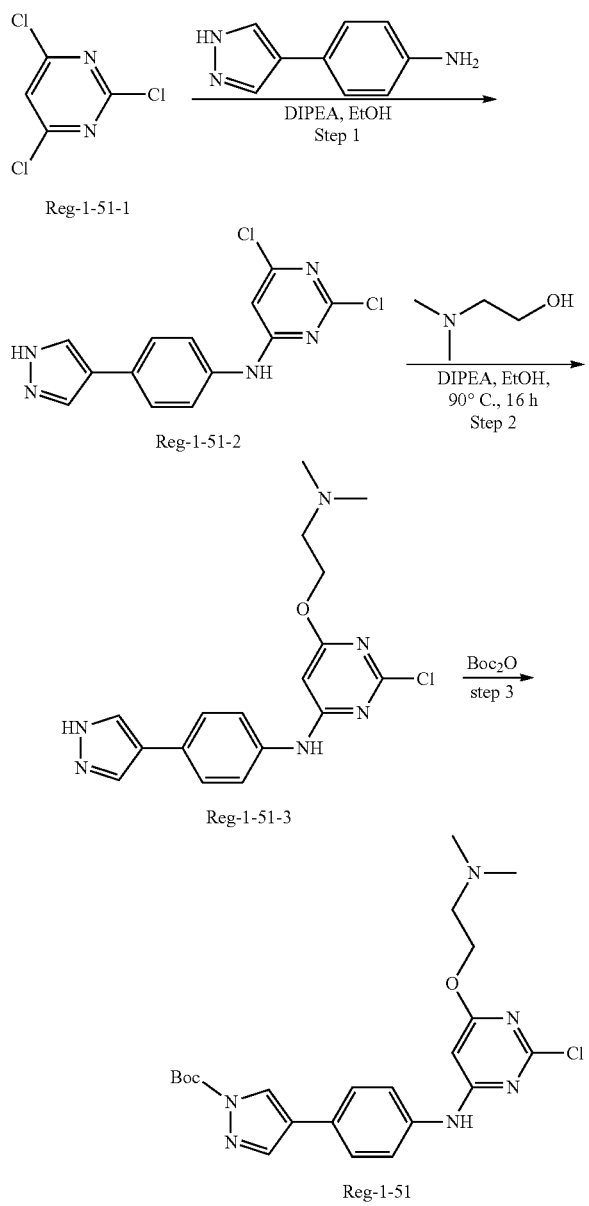

Reg-1-51

Intermediate Example 13

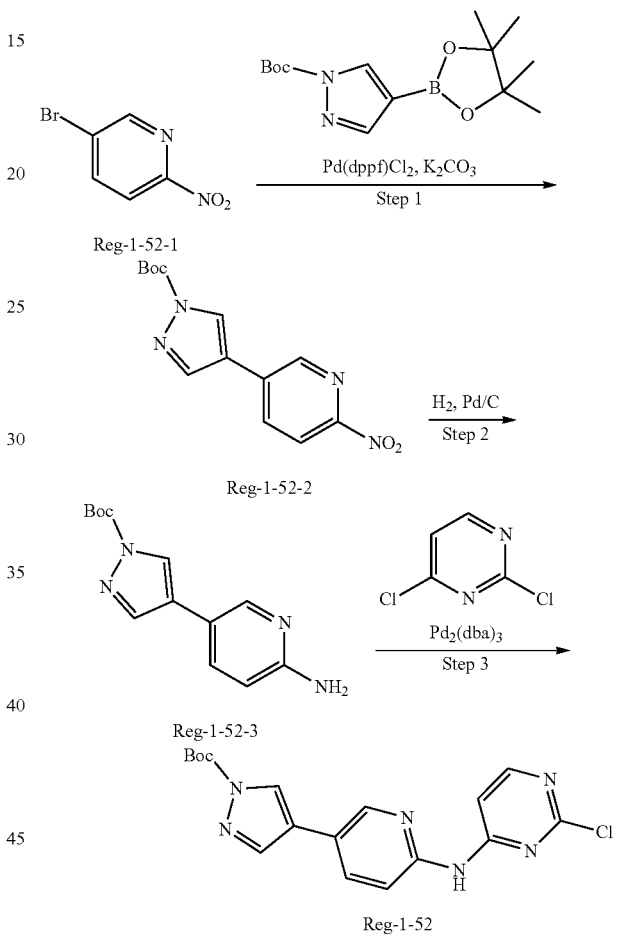

Reg-1-52

Step 1:

Compound Reg-1-51-1 (50 mg, 0.27 mmol) and 4-(1H-pyrazol-4-yl)aniline (43.4 mg, 0.27 mmol) were dissolved in ethanol (3 mL), N,N-diisopropylethylamine (0.07 mL, 0.4 mmol) was added, and the reaction solution was heated to 90° C. for 16 hours. LC-MS indicated the reaction was complete, the reaction solution was cooled to room temperature, the reaction solvent was removed through rotary evaporation under vacuum to afford the crude compound Reg-1-51-2 (100 mg).

MS m/z (ESI): 305.8 [M+H].

Step 2:

Compound Reg-1-51-2 (100 mg, 0.27 mmol) was dissolved in ethanol (50 mL), 2-(dimethylamino)ethanol (24 mg, 0.27 mmol) was added, and the reaction solution was heated to 90° C. and stirred overnight. LC-MS indicated the reaction was complete, and the reaction solvent was removed through rotary evaporation under vacuum to afford compound Reg-1-51-3 (150 mg, crude product).

MS m/z (ESI): 358.8 [M+H].

Step 3:

Compound Reg-1-51-3 (150 mg, 0.418 mmol) was dissolved in dichloromethane (5 mL), BOC anhydride (228 mg, 1.045 mmol), triethylamine (0.2 mL, 1.254 mmol) and 4-dimethylaminopyridine (5 mg, 0.042 mmol) were respectively added, and the reaction solution was stirred at room temperature for 16 hours. LC-MS indicated the reaction was complete, and the reaction solvent was removed through rotary evaporation under vacuum. The residue was purified on a preparative silica gel plate (petroleum ether:ethyl acetate=1:1) to afford compound Reg-1-51 (80 mg, 41.7% yield).

MS m/z (ESI): 458.7 [M+H].

Intermediate Example 13

Step 1:

Compound Reg-1-52-1 (1.02 g, 5 mmol) and 1-Boc-pyrazol-4-boronic acid pinacol ester (1.47 g, 5 mmol) were dissolved in 1,4-dioxane:water (40:4 mL), potassium carbonate (2.07 g, 15 mmol) was added, and the flask was purged with nitrogen three times. Pd(dppf)Cl$_2$ (0.366 g, 0.5 mmol) was added, the flask was purged with nitrogen three times, and the reaction solution was stirred at 85° C. for 6 hours. LC-MS indicated the reaction was complete, the reaction solution was cooled to room temperature, filtered, and the filtrate was rotary evaporated under vacuum to remove solvents. The residue was purified by column chromatography (petroleum ether:ethyl acetate=1:2 to ethyl acetate) to afford compound Reg-1-52-2 (0.5 g, 34.5% yield). $^1$H NMR (400 MHz, DMSO-d$_6$) δ 9.16 (s, 1H), 9.13 (d, J=2.1 Hz, 1H), 8.61 (dd, J=8.5, 2.3 Hz, 1H), 8.56 (s, 1H), 8.38 (d,J=8.5 Hz, 1H), 1.62 (s, 9H).

Step 2:

Compound Reg-1-52-2 (0.5 g, 1.71 mmol) was suspended in isopropanol (20 mL), Pd/C (0.5 g) was added, the flask was purged with hydrogen three times, and the reaction was performed overnight under normal pressure at room temperature under hydrogen atmosphere. LC-MS assay indicated the reaction was complete, the reaction solution was filtered, and the filtrate was rotary evaporated under vacuum to remove solvents, to afford compound Reg-1-52-3 (0.4 g, 89% yield). $^1$H NMR (400 MHz, DMSO-$d_6$) δ 8.54 (s, 1H), 8.32 (d, J=2.1 Hz, 1H), 8.19 (s, 1H), 7.79-7.66 (m, 1H), 6.47 (d, J=8.4 Hz, 1H), 6.05 (s, 2H), 1.59 (s, 9H).

Step 3:

Compound Reg-1-52-3 (52 mg, 0.2 mmol), 2,4-dichloropyrimidine (29.8 mg, 0.2 mmol), cesium carbonate (130 mg, 0.4 mmol), Pd2(dba)$_3$ (18.3 mg, 0.02 mmol) and Xantphos (11.6 mg, 0.02 mmol) were mixed in dioxane (2 mL), the reaction was purged with nitrogen three times, and heated to 110° C. for 1 hour. LC-MS indicated the reaction was complete. The reaction solution was cooled to room temperature, filtered to remove insoluble salt impurities, the filtrate was concentrated under reduced pressure, and the crude product was separated through column chromatography on silica gel (dichloromethane/methanol=20/1) to afford compound Reg-1-52 (20 mg, yellow solid, yield: 26.8%). $^1$H NMR (400 MHz, DMSO-$d_6$) δ 10.78 (s, 1H), 8.80 (s, 1H), 8.77 (d, J=2.1 Hz, 1H), 8.36 (d, J=5.9 Hz, 1H), 8.35 (s, 1H), 8.18 (dd, J=8.6, 2.4 Hz, 1H), 7.78 (s, 1H), 7.63 (d, J=8.5 Hz, 1H), 1.61 (s, 9H).

The following intermediates were prepared according to methods similar to that described in Intermediate Example 13:

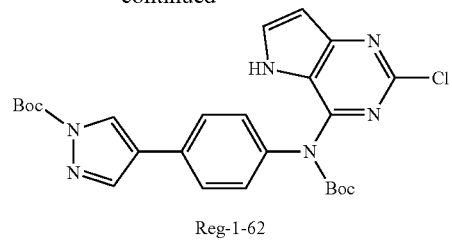

Reg-1-62

Step 1:

A mixture of compound Reg-1-62-1 (200 mg, 1.26 mmol) and tert-butanol (12 mL) was added with 2,4-dichloro-5H-pyrrolo[3,2-d]pyrimidine (236 mg, 1.26 mmol) and trifluoroacetic acid (716 mg, 5 mmol), and the reaction was heated to 100° C. for 2 hours. LC-MS indicated the reaction was complete. The reaction solution was cooled to room temperature, concentrated under reduced pressure, to afford crude product Reg-1-62-2 (800 mg, yellow solid), which was used directly in the next reaction step. $^1$H NMR (400 MHz, DMSO-$d_6$) δ 12.05 (s, 1H), 10.39 (s, 1H), 8.11 (s, 2H), 7.87 (d, J=8.7 Hz, 2H), 7.74 (t, J=2.9 Hz, 1H), 7.66 (d, J=8.7 Hz, 2H), 6.45 (dd, J=2.9, 2.0 Hz, 1H).

MS m/z (ESI): 310.7 [M+H, Cl].

| No. | Structure of Intermediate | Characterization Data |
|---|---|---|
| Reg-1-60 | Boc-pyrazole-phenyl-NH-pyridine-Br | $^1$H NMR (400 MHz, DMSO-$d_6$) δ 9.47 (s, 1H), 8.63 (s, 1H), 8.26 (s, 1H), 7.69 (d, J = 8.0 Hz, 2H), 7.64 (d, J = 8.0 Hz, 2H), 7.50 (t, J = 8.0 Hz, 1H), 6.94 (d, J = 8.0 Hz, 1H), 6.83 (d, J = 8.0 Hz, 1H), 1.60 (s, 9H). |
| Reg-1-61 | Boc-pyrazole-phenyl-NH-pyrazine-I | $^1$H NMR (400 MHz, DMSO-$d_6$) δ 9.83 (s, 1H), 8.65 (s, 1H), 8.27 (s, 1H), 8.18 (d, J = 6.0 Hz, 2H), 7.74 (d, J = 8.6 Hz, 2H), 7.66 (d, J = 8.6 Hz, 2H), 1.60 (s, 9H). |

Intermediate Example 14

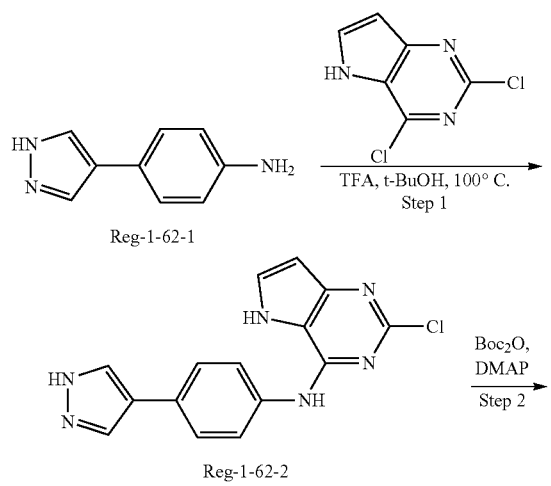

Step 2:

Compound Reg-1-62-2 (0.8 g, crude product, 1.26 mmol) and BOC anhydride (1.37 g, 6.28 mmol) were dissolved in DCM (20 mL), TEA (0.95 g, 9.42 mmol) and DMAP (0.019 g, 0.157 mmol) were added, and the reaction was stirred at room temperature overnight. LC-MS indicated the reaction was complete. The reaction was concentrated under reduced pressure, and the crude product was separated by flash column chromatography (petroleum ether:ethyl acetate=3: 1-1:3) to afford compound Reg-1-62 (0.63 g, yellow solid, yield: 78%).

$^1$H NMR (400 MHz, DMSO-$d_6$) δ 10.80 (s, 1H), 8.72 (s, 1H), 8.31 (s, 1H), 8.07 (d, J=3.8 Hz, 1H), 7.82 (d, J=8.7 Hz, 2H), 7.74 (d, J=8.8 Hz, 2H), 6.73 (d, J=3.8 Hz, 1H), 1.67 (s, 9H), 1.62 (s, 9H). MS m/z (ESI): 510.9 [M+H, Cl].

The following intermediates were prepared according to methods similar to that described in Intermediate Example 14:

| No. | Structure of Intermediate | Characterization Data |
|---|---|---|
| Reg-1-63 | | $^1$H NMR (400 MHz, DMSO-$d_6$) δ 11.91 (s, 1H), 9.69 (s, 1H), 8.03 (s, 2H), 7.76 (d, J = 8.6 Hz, 2H), 7.63 (t, J = 8.2 Hz, 2H), 7.23 (s, 1H), 6.74 (s, 1H). MS m/z (ESI): 310.7 [M + H]. |
| Reg-1-68 | | MS m/z (ESI): 407.8 [M + H]. |

Intermediate Example 15

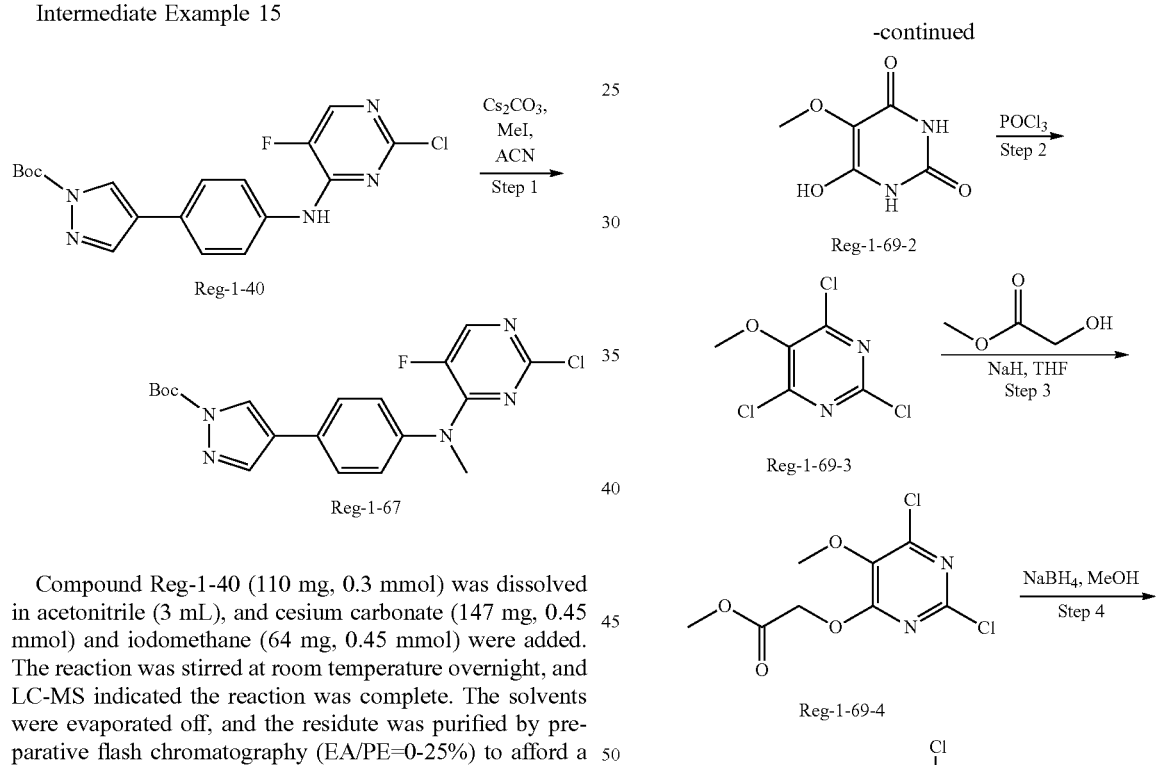

Compound Reg-1-40 (110 mg, 0.3 mmol) was dissolved in acetonitrile (3 mL), and cesium carbonate (147 mg, 0.45 mmol) and iodomethane (64 mg, 0.45 mmol) were added. The reaction was stirred at room temperature overnight, and LC-MS indicated the reaction was complete. The solvents were evaporated off, and the residue was purified by preparative flash chromatography (EA/PE=0-25%) to afford a light yellow solid Reg-1-67 (110 mg, yield: 90.9%).

1H NMR (400 MHz, DMSO-$d_6$) δ 8.78 (s, 1H), 8.33 (s, 1H), 8.19 (d, J=5.3 Hz, 1H), 7.80 (d, J=8.2 Hz, 2H), 7.41 (d, J=8.2 Hz, 2H), 3.44 (s, 3H), 1.61 (s, 9H).

Intermediate Example 16

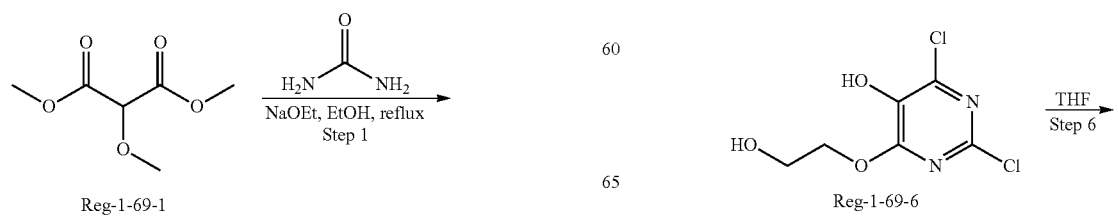

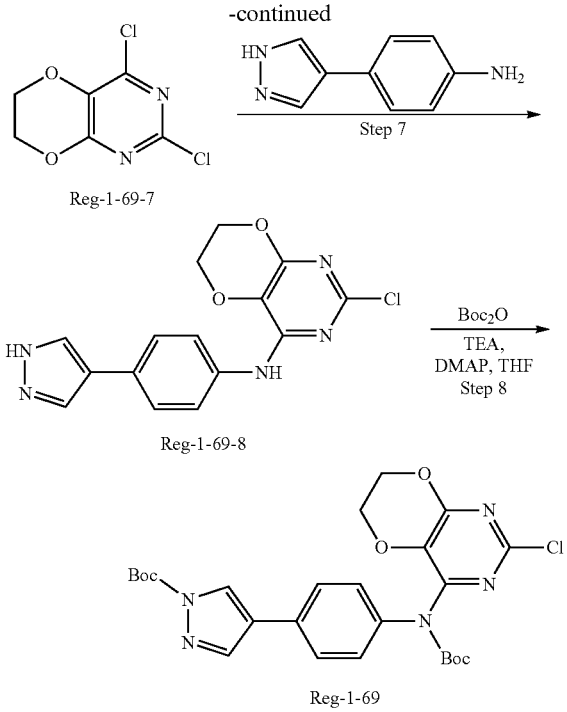

Reg-1-69-7

Reg-1-69-8

Reg-1-69

Step 1:

Metallic sodium (3.9 g, 170 mmol) was added portionwise to ethanol (250 mL) under stirring, and the reaction was continually stirred until a clear solution was obtained. Urea (10.2 g, 170 mmol) was added in one portion, the mixture was heated to reflux for 15 minutes, and then slowly cooled to room temperature. Dimethyl 2-methoxymalonate (25 g, 154 mmol) was added to result in a pink precipitate, and the reaction solution was heated to 100° C. for 48 hours. LC-MS indicated the reaction was complete, the reaction solvent was removed through rotary evaporation under vacuum. The residue was added with water (200 mL), and the pH value was adjusted with concentrated hydrochloric acid to 3-4. The reaction was extracted with ethyl acetate (300 mL×2), the organic phases were combined, dried over anhydrous sodium sulfate, filtered, and the filtrate was rotary evaporated under vacuum to remove solvents, to afford a brown oil (23 g, crude product). MS m/z (ESI): 159.0 [M+H].

Step 2:

Compound Reg-1-69-2 (23 g, crude product, 145 mmol) and phosphorus oxychloride (50 mL) were mixed. The reaction was heated to 100° C., and allowed to proceed overnight. LC-MS assay indicated that the starting materials had disappeared, and the new product had no signal in MS assay. The reaction solution was cooled to room temperature, and phosphorus oxychloride was removed by rotary evaporation under vacuum. The residue was slowly added to a mixture of ice and water (200 mL), extracted with ethyl acetate (200 mL×2), the organic phases were combined, washed with saturated sodium bicarbonate (100 mL). The mixture was dried over anhydrous sodium sulfate, filtered, and the filtrate was rotary evaporated under vacuum to remove solvents. The residue was purified by column chromatography (petroleum ether:ethyl acetate=10:1), to afford compound Reg-1-69-3 (13 g, white solid, 42% yield).

Step 3:

Compound Reg-1-69-3 (13.7 g, 64 mol) and methyl 2-hydroxyacetate (6.93 g, 77 mmol) were dissolved in tetrahydrofuran (300 mL), and cooled to −5° C.–0° C. under protection of nitrogen. NaH (3.08 g, 77 mmol) was added portionwise, and the reaction solution was allowed to warm to room temperature, and stirred 16 hours. LC-MS indicated the reaction was complete, the reaction solution was added with water (300 mL), and extracted with ethyl acetate (300 mL×2). The organic phases were combined, dried over anhydrous sodium sulfate, filtered, and the filtrate was rotary evaporated under vacuum to remove solvents. The residue was purified by column chromatography (petroleum ether: ethyl acetate=8:1), to afford compound Reg-1-69-4 (15.6 g, colourless oil, 91.3% yield).

$^1$H NMR (400 MHz, DMSO-$d_6$) δ 5.15 (s, 2H), 3.90 (s, 3H), 3.73 (s, 2H). MS m/z (ESI): 266.8 [M+H].

Step 4:

Compound Reg-1-69-4 (14.6 g, 54.7 mmol) were dissolved in methanol (146 mL), sodium borohydride (6.2 g, 164 mmol) was added portionwise, and the reaction solution was stirred at room temperature for 16 hours. LC-MS indicated the reaction was complete, and the reaction was quenched by addition of water (10 mL). The reaction solvent was removed through rotary evaporation under vacuum to afford the crude compound Reg-1-69-5 (41 g, crude product). MS m/z (ESI): 238.7 [M+H].

Step 5:

Compound Reg-1-69-5 (41 g, crude product, 54.7 mmol) was dissolved in dichloromethane (300 mL), and cooled to −50° C. under protection of nitrogen. Boron tribromide (54.7 mL, 109.4 mmol) was slowly dropwise added, and the reaction solution was allowed to warm to room temperature, and stirred for 16 hours. LC-MS assay indicated that the reaction was substantially complete, the reaction solution was added with water (500 mL), and extracted with ethyl acetate (300 mL×2). The organic phases were combined, dried over anhydrous sodium sulfate, filtered, and the filtrate was rotary evaporated under vacuum to remove solvents. The residue was purified by column chromatography (ethyl acetate), to afford compound Reg-1-69-6 (5.6 g).

$^1$H NMR (400 MHz, DMSO-$d_6$) δ 10.73 (s, 1H), 4.85 (s, 1H), 4.41 (t, J=4.9 Hz, 2H), 3.75 (t, J=4.9 Hz, 2H). MS m/z (ESI): 224.8 [M+H].

Step 6:

Compound Reg-1-69-6 (5.45 g, 24.2 mmol) and triphenylphosphine (7.63 g, 29.1 mmol) were dissolved in tetrahydrofuran (270 mL), diisopropyl azodiformate (5.88 g, 29.1 mmol) was added at room temperature under protection of nitrogen, and the reaction solution was stirred at room temperature for 16 h. LC-MS indicated the reaction was complete, and the reaction solvent was removed through rotary evaporation under vacuum. The residue was purified by column chromatography (petroleum ether:ethyl acetate=4:1 to 1:1), to afford compound Reg-1-69-7 (6.7 g, 53% purity).

$^1$H NMR (400 MHz, DMSO-$d_6$) δ 4.64-4.60 (m, 2H), 4.48-4.43 (m, 2H). MS m/z (ESI): 206.8 [M+H].

Step 7:

Compound Reg-1-69-7 (960 mg, 53% purity, 2.46 mmol) and 4-(1H-pyrazol-4-yl)aniline (390 mg, 2.46 mmol) were dissolved in N-methylpyrrolidinone (10 mL), N,N-diisopropylethylamine (1.3 mL, 7.38 mmol) was added, and the reaction solution was performed at 200° C. in the microwave for 2 hours. LC-MS assay indicated that the reaction was substantially complete, the reaction solution was added with water (80 mL), extracted with ethyl acetate (50 mL×2), and the organic phases were combined, and rotary evaporated under vacuum to remove solvents. The residue was purified by column chromatography (dichloromethane:methanol=30:1) to afford compound Reg-1-69-8 (600 mg, 74% yield).

$^1$H NMR (400 MHz, DMSO-$d_6$) δ 12.89 (s, 1H), 9.22 (s, 1H), 8.02 (d, J=28.9 Hz, 2H), 7.66 (d, J=8.5 Hz, 2H), 7.56 (d, J=8.6 Hz, 2H), 4.52 (s, 2H), 4.38 (s, 2H). MS m/z (ESI): 329.8 [M+H].

Step 8:

Compound Reg-1-69-8 (600 mg, 1.82 mmol) was dissolved in tetrahydrofuran (15 mL), BOC anhydride (834 mg, 3.82 mmol), triethylamine (0.76 mL, 5.46 mmol) and 4-dimethylaminopyridine (22 mg, 0.182 mmol) were respectively added, and the reaction solution was stirred at room temperature for 16 hours. LC-MS indicated the reaction was complete, the reaction solvent was removed through rotary evaporation under vacuum. The residue was purified by column chromatography (petroleum ether:ethyl acetate=4:1 to 1:1) to afford compound Reg-1-69 (350 mg, 36.3% yield).

$^1$H NMR (400 MHz, DMSO-$d_6$) δ 8.74 (s, 1H), 8.30 (s, 1H), 7.73 (d, J=8.5 Hz, 2H), 7.21 (d, J=8.5 Hz, 2H), 4.63 (s, 2H), 4.44 (s, 2H), 1.60 (s, 9H), 1.42 (s, 9H). MS m/z (ESI): 552.0 [M+Na].

Intermediate Example 17

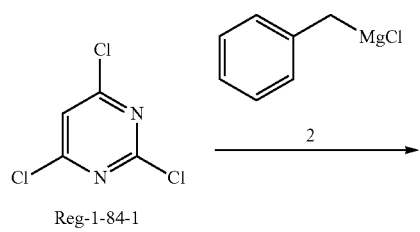

Compound Reg-1-84-1 (1.1 g, 6.0 mmol) was dissolved in tetrahydrofuran (20 mL), and cooled to −78° C. under protection of nitrogen. Benzylmagnesium chloride (6.0 mL, 6.0 mmol) was dropwise added, after which the reaction was allowed to warm to room temperature and proceed overnight. LC-MS indicated the reaction was complete. The reaction solution was concentrated under reduced pressure, the residue was added with dichloromethane (30 mL) and water (30 mL), and extracted. The organic phase was washed with a concentrated salt solution (30 mL), dried over anhydrous sodium sulfate, and rotary evaporated under reduced pressure to afford the crude compound Reg-1-84-2 (1.5 g, oil).

$^1$H NMR (400 MHz, DMSO-$d_6$) δ 7.35 (d, J=8.0 Hz, 1H), 7.29-7.15 (m, 5H), 4.12 (s, 2H). MS m/z (ESI): 238.8 [M+H].

Intermediate Example 18

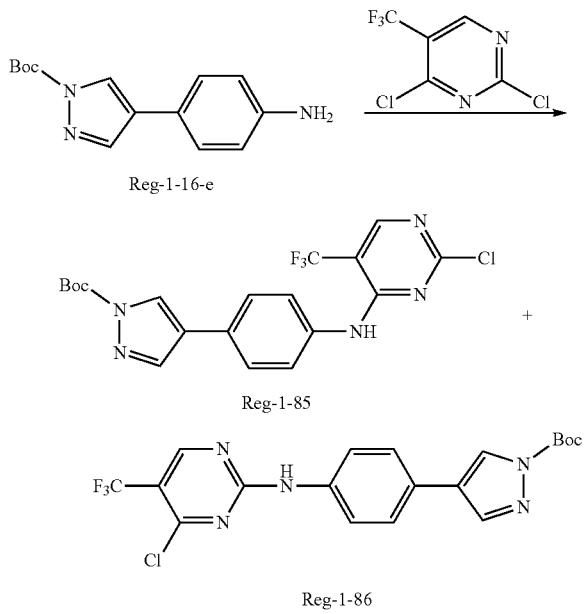

Compound Reg-1-16-e (0.3 g, 1.158 mmol) and 2,4-dichloro-5-(trifluoromethyl)pyrimidine (0.25 g, 1.158 mmol) were dissolved in N,N-dimethylformamide (20 mL), diisopropylethylamine (449 mg, 3.47 mmol) was added, and the reaction was performed in an ice-salt bath. LC-MS indicated the reaction was complete. The reaction solution was diluted with water (20 mL), and extracted with dichloromethane (30 mL×3). The organic phase was combined, dried over sodium sulfate, filtered, and concentrated under reduced pressure to afford a residue, which was separated by flash column chromatography (petroleum ether/ethyl acetate=5:1~1:5) to afford a mixture of compound Reg-1-85 and Reg-1-86 (396 mg, colourless oil, yield: 78%).

MS m/z (ESI): 439.9 [M+H]($t_R$=1.701 min), 439.9 [M+H] ($t_R$=1.784 min).

Preparation of Final Products

Example 1: preparation of 6-(4-(((1H-indazol-5-yl)amino)pyrimidin-2-yl)-N-(tetrahydrofuran-3-yl)benzo[b]thiophene-2-carboxamide (TDI01113)

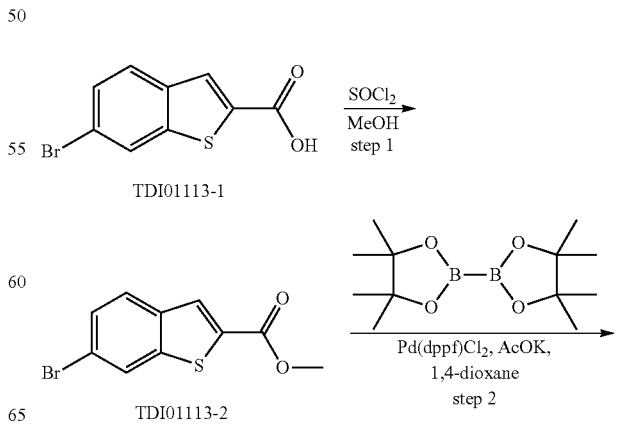

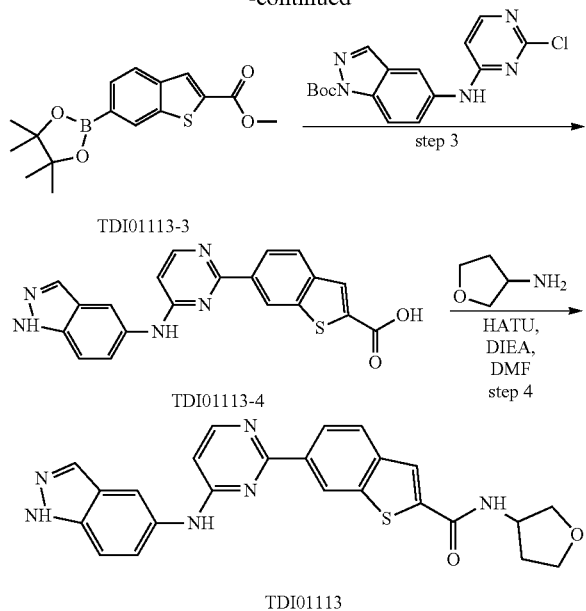

Step 1:

Compound TDI01113-1 (500 mg, 1.95 mmol) was dissolved in anhydrous methanol (20 mL), thionyl chloride (4 mL) was slowly added, and the reaction was performed at 70° C. for 2 hours. Thin layer chromatography (petroleum ether:ethyl acetate=5:1) indicated the reaction was complete. The reaction solution was cooled to room temperature, and concentrated under reduced pressure. The crude product was dissolved in dichloromethane (40 mL), and successively washed with saturated aqueous sodium carbonate (50 mL×2) and saturated brine (50 mL×2). The organic phase was dried over anhydrous sodium sulfate, filtered, and concentrated to afford compound TDI01113-2 (550 mg, yellow solid, crude product).

$^1$H NMR (400 MHz, CDCl$_3$) δ 8.01 (s, 2H), 7.73 (d, J=8.4 Hz, 1H), 7.51 (d, J=8.4 Hz, 1H), 3.95 (s, 3H).

Step 2:

Compound TDI01113-2 (550 mg, 2.04 mmol) and bis(pinacolato)diboron (621 mg, 2.44 mmol) were dissolved in 1,4-dioxane (20 mL), potassium acetate (600 mg, 6.12 mmol) and Pd(dppf)Cl$_2$ (140 mg, 0.20 mmol) were added, purge with argon was performed for 3 times, and the reaction was placed in an oil bath at 80° C. overnight. Thin layer chromatography (petroleum ether:ethyl acetate=10:1) indicated the reaction was complete. The reaction solution was cooled to room temperature, and concentrated under reduced pressure. The residue was separated and purified by column chromatography (petroleum ether:ethyl acetate=20:1) to afford compound TDI01113-3 (600 mg, white solid, yield: 92.3%).

$^1$H NMR (400 MHz, CDCl$_3$) δ 8.35 (s, 1H), 8.06 (s, 1H), 7.87 (d, J=8.0 Hz, 1H), 7.80 (d, J=8.0 Hz, 1H), 3.95 (s, 3H), 1.38 (s, 12H).

Step 3:

Compound TDI01113-3 (600 mg, 1.90 mmol) and Reg-1-1 (546 mg, 1.58 mmol) were dissolved in a mixture of ethanol/water (10:1) (55 mL), sodium carbonate (335 mg, 3.16 mmol) and Pd(PPh$_3$)$_2$Cl$_2$ (112 mg, 0.16 mmol) were added, purge with argon was performed for 3 times, and the reaction mixture was placed in an oil bath at 110° C. overnight. Thin layer chromatography (ethyl acetate) indicated the reaction was complete. The reaction solution was cooled to room temperature, filtered, and concentrated under reduced pressure. The residue was dissolved in water (40 mL), extracted with ethyl acetate (50 mL×2). The pH of the aqueous phase was adjusted to 2 with 4N HCl, the precipitated solid was filtered, dissolved in methanol, and then concentrated to afford compound TDI01113-4 (700 mg, yellow solid, crude product).

$^1$H NMR (400 MHz, DMSO-d$_6$) δ 11.90 (s, 1H), 9.06 (s, 1H), 8.37 (d, J=6.4 Hz, 2H), 8.25-8.18 (m, 4H), 7.68 (d, J=8.0 Hz, 2H), 7.51 (d, J=7.6 Hz, 1H), 7.20 (s, 1H). MS m/z (ESI): 388.1 [M+H].

Step 4:

Compound TDI01113-4 (200 mg, 0.52 mmol) and tetrahydrofuran-3-amine (54.6 mg, 0.62 mmol) were dissolved in N,N-dimethylformamide (10 mL), HATU (236 mg, 0.62 mmol) and diisopropylethylamine (268 mg, 2.08 mmol) were added, and the reaction was performed at room temperature overnight. Thin layer chromatography (dichloromethane/methanol=10:1) indicated the reaction was complete. Water (60 mL) was slowly added to the reaction solution, a large amount of solid precipitated and was filtered after being stirred for 30 minutes. The solid was purified by high-performance liquid chromatography to afford compound TDI01113 (56.2 mg, yellow solid, yield: 23.7%).

$^1$H NMR (400 MHz, DMSO-d$_6$) δ 13.05 (s, 1H), 9.67 (s, 1H), 8.93 (s, 1H), 8.90 (d, J=6.4 Hz, 1H), 8.42 (dd, J=8.4, 1.2 Hz, 1H), 8.39 (d, J=6.0 Hz, 1H), 8.23 (s, 1H), 8.18 (s, 1H), 8.10 (s, 1H), 8.06 (d, J=8.4 Hz, 1H), 7.59 (s, 2H), 6.71 (d, J=6.0 Hz, 1H), 4.51-4.45 (m, 1H), 3.91-3.85 (m, 2H), 3.77-3.71 (m, 1H), 3.66-3.63 (m, 1H), 2.24-2.15 (m, 1H), 1.99-1.92 (m, 1H). MS m/z (ESI): 457.0 [M+H].

The compounds in Table 1 were prepared according to methods similar to that described in Example 1.

TABLE 1

| No. | Compound Structure | Compound Name | Starting material or regent different from that in Example 1 | Characterization Data |
|---|---|---|---|---|
| TDI01116 | (structure) | 6-(4-((1H-indazol-5-yl)amino)-pyrimidin-2-yl)-N-(pyridazin-4-yl)benzo[b]-thiophene-2-carboxamide | -NH₂ in step 4 of Example 1 was replaced with (tetrahydrofuran-3-amine structure) and (pyridazin-4-amine structure) | ¹H NMR (400 MHz, DMSO-d₆) δ 13.16 (s, 1H), 11.28 (s, 1H), 10.18 (s, 1H), 9.56 (s, 1H), 9.18 (d, J = 4.0 Hz, 1H), 8.98 (s, 1H), 8.53 (s, 1H), 8.41 (d, J = 4.0 Hz, 2H), 8.24 (d, J = 8.0 Hz, 1H), 8.17 (s, 2H), 8.14 (s, 1H), 7.63 (d, J = 8.0 Hz, 1H), 7.60 (s, 1H), 6.80 (d, J = 8.0 Hz, 1H). MS m/z (ESI): 465.1 [M + H]. |
| TDI01121 | (structure) | 6-(4-((1H-indazol-5-yl)amino)-6-(2-(dimethyl-amino)ethoxy)-pyrimidin-2-yl)-N-isopropyl-benzo[b]thiophene-2-carboxamide | in step 3 of Example 1 was replaced with (Boc-indazole-pyrimidine-Cl structure) and (Reg-1-31 structure); and -NH₂ in step 4 was replaced with (tetrahydrofuran-3-amine structure) | ¹H NMR (400 MHz, DMSO-d₆) δ 9.82 (s, 1H), 9.65 (s, 1H), 8.71 (s, 1H), 8.61 (d, J = 8.0 Hz, 1H), 8.18 (s, 1H), 8.14 (s, 1H), 8.05 (d, J = 6.0 Hz, 2H), 8.01 (d, J = 8.0 Hz, 1H), 7.56 (d, J = 8.0 Hz, 1H), 7.49 (d, J = 8.0 Hz, 1H), 7.05 (s, 1H), 4.76-4.73 (m, 2H), 4.14-4.05 (m, 1H), 3.60 (s, 2H), 2.90 (s, 3H), 2.89 (s, 3H), 1.20 (d, J = 6.0 Hz, 6H). MS m/z (ESI): 516.2 [M + H]. |

TABLE 1-continued

| No. | Compound Structure | Compound Name | Starting material or regent different from that in Example 1 | Characterization Data |
|---|---|---|---|---|
| TDI01127 | 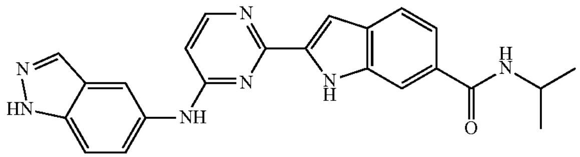 [SMILES: CC(C)NC(=O)c1ccc2cc(-c3nccc(Nc4ccc5[nH]ncc5c4)n3)[nH]c2c1] | 2-(4-((1H-indazol-5-yl)amino)pyrimidin-2-yl)-N-isopropyl-1H-indole-6-carboxamide | [boronate ester] in step 3 of Example 1 was replaced with [methyl indole-2-carboxylate boronate with Boc]; and [tetrahydrofuran-3-amine] NH₂ in step 4 was replaced with isopropylamine | ¹H NMR (400 MHz, DMSO-d₆) δ 11.88 (s, 1H), 10.22 (s, 1H), 8.34 (d, J = 6.3 Hz, 1H), 8.27 (s, 1H), 8.20 (d, J = 7.9 Hz, 1H), 8.16 (s, 1H), 8.05 (s, 1H), 7.72 (d, J = 8.5 Hz, 1H), 7.67-7.54 (m, 2H), 7.41 (s, 1H), 6.74 (d, J = 6.4 Hz, 1H), 4.17-4.11 (m, 1H), 1.19 (d, J = 6.6 Hz, 6H). MS m/z (ESI): 412.1 [M + H]. |
| TDI01130 | 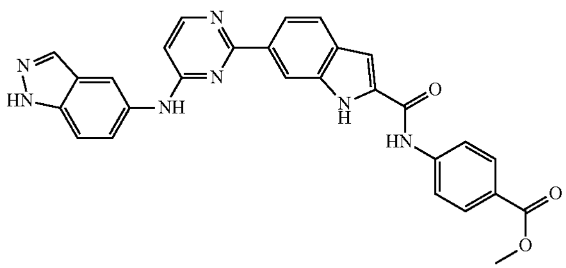 [SMILES: COC(=O)c1ccc(NC(=O)c2cc3ccc(-c4nccc(Nc5ccc6[nH]ncc6c5)n4)cc3[nH]2)cc1] | methyl 4-(6-(4-((1H-indazol-5-yl)amino)pyrimidin-2-yl)-1H-indole-2-carboxamido)benzoate | [bromo-benzothiophene-2-carboxylic acid] OH in step 1 of Example 1 was replaced with [6-bromo-1H-indole-2-carboxylic acid] OH; and [tetrahydrofuran-3-amine] in step 4 was replaced with [methyl 4-aminobenzoate] | ¹H NMR (400 MHz, DMSO-d₆) δ 13.05 (s, 1H), 12.17 (s, 1H), 10.61 (s, 1H), 9.62 (s, 1H), 8.58 (s, 1H), 8.37 (d, J = 5.9 Hz, 1H), 8.30 (s, 1H), 8.24-8.11 (m, 2H), 8.01 (s, 4H), 7.80 (d, J = 8.6 Hz, 1H), 7.58 (d, J = 20.9 Hz, 3H), 6.68 (d, J = 5.9 Hz, 1H), 3.86 (s, 3H). MS m/z (ESI): 504.1 [M + H]. |

TABLE 1-continued

| No. | Compound Name | Starting material or regent different from that in Example 1 | Characterization Data |
|---|---|---|---|
| TDI01131 | 6-(4-((1H-indazol-5-yl)amino)pyrimidin-2-yl)-N-(4-(4-methylpiperazin-1-yl)phenyl)-1H-indole-2-carboxamide | (6-bromobenzothiophene-2-carboxylic acid) in step 1 of Example 1 was replaced with (6-bromo-1H-indole-2-carboxylic acid); and (3-aminotetrahydrofuran) in step 4 was replaced with (4-(4-methylpiperazin-1-yl)aniline) | ¹H NMR (400 MHz, DMSO-d₆) δ 13.03 (s, 1H), 12.03 (s, 1H), 10.11 (s, 1H), 9.60 (s, 1H), 8.55 (s, 1H), 8.35 (d, J = 4.0 Hz, 1H), 8.30 (s, 1H), 8.16 (d, J = 8.0 Hz, 2H), 7.75 (d, J = 8.0 Hz, 1H), 7.66 (d, J = 8.0 Hz, 2H), 7.59 (s, 2H), 7.42 (s, 1H), 6.96 (d, J = 8.0 Hz, 2H), 6.66 (d, J = 16.0 Hz, 2H), 3.12 (s, 4H), 2.46 (s, 4H), 2.23 (s, 3H). MS m/z (ESI): 544.2 [M + H]. |
| TDI01132 | methyl (6-(4-((1H-indazol-5-yl)amino)pyrimidin-2-yl)-1H-indole-2-carbonyl)-phenylalaninate | (6-bromobenzothiophene-2-carboxylic acid) in step 1 of Example 1 was replaced with (6-bromo-1H-indole-2-carboxylic acid); and (3-aminotetrahydrofuran) in step 4 was replaced with (methyl phenylalaninate) | ¹H NMR (400 MHz, DMSO-d₆) δ 13.23 (s, 1H), 12.27 (s, 1H), 11.08 (s, 1H), 9.09 (d, J = 8.0 Hz, 1H), 8.35 (s, 1H), 8.30 (d, J = 4.0 Hz, 1H), 8.20 (s, 1H), 7.90 (s, 2H), 7.69-7.62 (m, 2H), 7.33 (d, J = 8.0 Hz, 3H), 7.27 (t, J = 8.0 Hz, 2H), 7.19 (t, J = 8.0 Hz, 1H), 6.87 (s, 1H), 4.78-4.72 (m, 1H), 3.67 (s, 3H), 3.24-3.20 (m, 1H), 3.15-3.09 (m, 1H). MS m/z (ESI): 532.2 [M + H]. |

TABLE 1-continued

| No. | Compound Structure | Compound Name | Starting material or regent different from that in Example 1 | Characterization Data |
|---|---|---|---|---|
| TDI01134 | 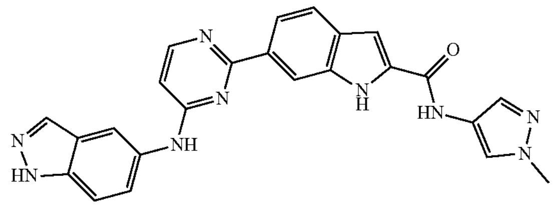 [SMILES: Cn1cc(NC(=O)c2cc3ccc(-c4nccc(Nc5ccc6[nH]ncc6c5)n4)cc3[nH]2)cn1] | 6-(4-((1H-indazol-5-yl)amino)pyrimidin-2-yl)-N-(1-methyl-1H-pyrazol-4-yl)-1H-indole-2-carboxamide | 6-bromobenzothiophene-2-carboxylic acid in step 1 of Example 1 was replaced with 6-bromoindole-2-carboxylic acid; and 3-aminotetrahydrofuran in step 4 was replaced with 4-amino-1-methyl-1H-pyrazole | $^1$H NMR (400 MHz, DMSO-$d_6$) δ 13.23 (s, 1H), 12.41 (s, 1H), 10.83 (s, 1H), 8.50 (s, 1H), 8.32 (d, J = 6.7 Hz, 1H), 8.21 (s, 1H), 8.15-8.03 (m, 2H), 7.86 (d, J = 8.5 Hz, 1H), 7.66 (d, J = 7.6 Hz, 2H), 7.43 (d, J = 2.5 Hz, 1H), 7.32 (s, 1H), 7.19 (s, 1H), 6.97 (s, 1H), 3.86 (s, 3H). MS m/z (ESI): 450.2 [M + H]. |
| TDI01140 | 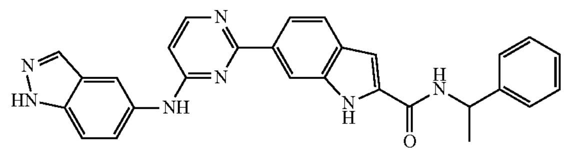 [SMILES: CC(NC(=O)c1cc2ccc(-c3nccc(Nc4ccc5[nH]ncc5c4)n3)cc2[nH]1)c1ccccc1] | 6-(4-((1H-indazol-5-yl)amino)pyrimidin-2-yl)-N-(1-phenylethyl)-1H-indole-2-carboxamide | 6-bromobenzothiophene-2-carboxylic acid in step 1 of Example 1 was replaced with 6-bromoindole-2-carboxylic acid; and 3-aminotetrahydrofuran in step 4 was replaced with 1-phenylethylamine | $^1$H NMR (400 MHz, DMSO-$d_6$) δ 13.17 (s, 1H), 12.18 (s, 1H), 10.77 (s, 1H), 8.98 (d, J = 8.0 Hz, 1H), 8.40 (s, 1H), 8.31 (d, J = 4.0 Hz, 1H), 8.19 (s, 2H), 7.94 (d, J = 8.0 Hz, 1H), 7.85 (d, J = 8.0 Hz, 1H), 7.67-7.62 (m, 2H), 7.44-7.33 (m, 5H), 7.24 (t, J = 8.0 Hz, 1H), 6.83 (d, J = 4.0 Hz, 1H), 5.26-5.22 (m, 1H), 1.53 (d, J = 8.0 Hz, 3H). MS m/z (ESI): 474.1 [M + H]. |
| TDI01151 | 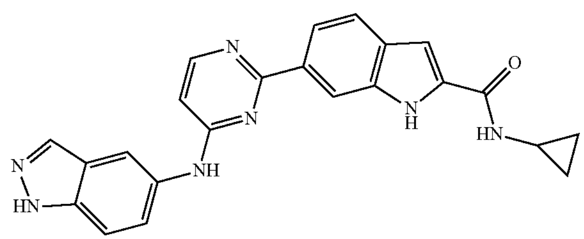 [SMILES: O=C(NC1CC1)c1cc2ccc(-c3nccc(Nc4ccc5[nH]ncc5c4)n3)cc2[nH]1] | 6-(4-((1H-indazol-5-yl)amino)pyrimidin-2-yl)-N-cyclopropyl-1H-indole-2-carboxamide | 6-bromobenzothiophene-2-carboxylic acid in step 1 of Example 1 was replaced with 6-bromoindole-2-carboxylic acid; and 3-aminotetrahydrofuran in step 4 was replaced with cyclopropylamine | $^1$H NMR (400 MHz, CD$_3$OD) δ 8.36-8.16 (m, 4H), 7.83 (s, 2H), 7.70 (s, 2H), 7.15 (s, 1H), 6.88 (br, 1H), 2.88 (s, 1H), 0.85-0.84 (d, J = 4.0 Hz, 2H), 0.68 (s, 2H). MS m/z (ESI): 410.2 [M + H]. |

TABLE 1-continued

| No. | Compound Structure | Compound Name | Starting material or regent different from that in Example 1 | Characterization Data |
|---|---|---|---|---|
| TDI01152 | 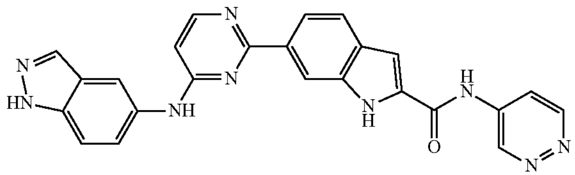 [SMILES: O=C(Nc1ccnnc1)c1cc2ccc(-c3nccc(Nc4ccc5[nH]ncc5c4)n3)cc2[nH]1] | 6-(4-((1H-indazol-5-yl)amino)-pyrimidin-2-yl)-N-(pyridazin-4-yl)-1H-indole-2-carboxamide | 6-bromobenzothiophene-2-carboxylic acid in step 1 of Example 1 was replaced with 6-bromo-1H-indole-2-carboxylic acid; and NH₂ in step 4 was replaced with 4-aminopyridazine | ¹H NMR (400 MHz, DMSO-d₆) δ 9.60 (s, 1H), 9.27 (s, 1H), 8.83 (s, 1H), 8.54 (s, 1H), 8.35 (d, J = 5.6 Hz, 1H), 8.30 (s, 1H), 8.19-8.09 (m, 2H), 8.05-8.04 (m, 1H), 7.71 (d, J = 8.8 Hz, 1H), 7.64-7.58 (m, 2H), 7.21 (s, 1H), 6.65 (d, J = 5.6 Hz, 1H). MS m/z (ESI): 448.2 [M + H]. |
| TDI01153 | 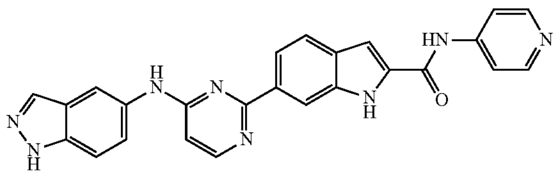 [SMILES: O=C(Nc1ccncc1)c1cc2ccc(-c3nccc(Nc4ccc5[nH]ncc5c4)n3)cc2[nH]1] | 6-(4-((1H-indazol-5-yl)amino)-pyrimidin-2-yl)-N-(pyridin-4-yl)-1H-indole-2-carboxamide | 6-bromobenzothiophene-2-carboxylic acid in step 1 of Example 1 was replaced with 6-bromo-1H-indole-2-carboxylic acid; and NH₂ in step 4 was replaced with 4-aminopyridine | ¹H NMR (400 MHz, CD₃OD) δ 8.66 (d, J = 6.1 Hz, 2H), 8.47-8.34 (m, 3H), 8.27-8.12 (t, 3H), 7.94 (q, J = 8.8 Hz, 2H), 7.73-7.56 (m, 3H), 6.89 (d, J = 6.9 Hz, 1H). MS m/z (ESI): 447.1 [M + H]. |
| TDI01156 | 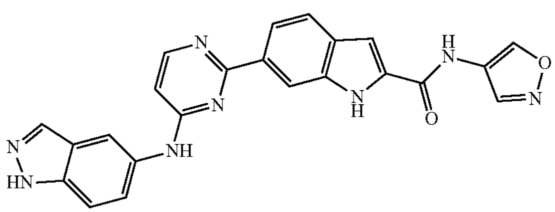 [SMILES: O=C(Nc1cnoc1)c1cc2ccc(-c3nccc(Nc4ccc5[nH]ncc5c4)n3)cc2[nH]1] | 6-(4-((1H-indazol-5-yl)amino)-pyrimidin-2-yl)-N-(isoxazol-4-yl)-1H-indole-2-carboxamide | 6-bromobenzothiophene-2-carboxylic acid in step 1 of Example 1 was replaced with 6-bromo-1H-indole-2-carboxylic acid; and NH₂ in step 4 was replaced with 4-aminoisoxazole | ¹H NMR (400 MHz, DMSO-d₆) δ 13.21 (s, 1H), 12.44 (s, 1H), 10.99 (s, 1H), 10.76 (s, 1H), 9.30 (s, 1H), 8.81 (s, 1H), 8.41 (d, J = 43.7 Hz, 2H), 8.20 (s, 2H), 7.96 (d, J = 28.6 Hz, 2H), 7.66 (s, 2H), 7.42 (s, 1H), 6.85 (s, 1H). MS m/z (ESI): 437.1 [M + H]. |

TABLE 1-continued

| No. | Compound Structure | Compound Name | Starting material or regent different from that in Example 1 | Characterization Data |
|---|---|---|---|---|
| TDI01161 | (structure) | 6-(4-((1H-indazol-5-yl)amino)pyrimidin-2-yl)-N-(pyridin-4-yl)-1H-indole-2-carboxamide | (structure) OH in step 1 of Example 1 was replaced with (structure); and —NH$_2$ in step 4 was replaced with H$_2$N-(pyridine) | $^1$H NMR (400 MHz, DMSO-d$_6$) δ 13.12 (s, 1H), 12.28 (s, 1H), 11.39 (s, 1H), 9.98 (s, 1H), 9.01 (s, 1H), 8.79 (s, 1H), 8.53 (s, 1H), 8.36 (d, J = 6.0 Hz, 1H), 8.29 (d, J = 5.2 Hz, 2H), 8.17 (s, 1H), 8.13 (d, J = 8.4 Hz, 1H), 7.81 (d, J = 9.2 Hz, 2H), 7.62 (s, 2H), 6.74 (d, J = 6.0 Hz, 1H). MS m/z (ESI): 448.1 [M + H]. |
| TDI01164 | (structure) | 6-(7-((1H-indazol-5-yl)amino)-imidazo[1,2-c]pyrimidin-5-yl)-N-(pyridazin-4-yl)-1H-indole-2-carboxamide | (structure) OH in step 1 of Example 1 was replaced with (structure); (Reg-1-1) in step 3 was replaced with (Reg-1-8); and (structure) —NH$_2$ in step 4 was replaced with H$_2$N-(pyridazine) | $^1$H NMR (400 MHz, DMSO-d$_6$) δ 13.24 (s, 1H), 12.33 (s, 1H), 10.97 (s, 1H), 10.31 (s, 1H), 9.59 (s, 1H), 9.14 (d, J = 5.8 Hz, 1H), 8.54 (s, 1H), 8.26 (s, 1H), 8.23 (s, 1H), 8.20-8.16 (m, 2H), 8.10 (s, 1H), 7.87 (s, 2H), 7.81 (d, J = 8.9 Hz, 1H), 7.77-7.71 (m, 2H), 7.59 (s, 1H). MS m/z (ESI): 487.1 [M + H]. |

TABLE 1-continued

| No. | Compound Name | Starting material or regent different from that in Example 1 | Characterization Data |
|---|---|---|---|
| TDI01167 | 6-(4-((1H-indazol-5-yl)amino)-1,3,5-triazin-2-yl)-N-(pyridazin-4-yl)-1H-indole-2-carboxamide | OH in step 1 of Example 1 was replaced with (Reg-1-1) and (Reg-1-11); in step 3 was replaced with and —NH₂ in step 4 was replaced with H₂N— | ¹H NMR (400 MHz, DMSO-d₆) δ 13.26-12.93 (m, 1H), 12.41 (s, 1H), 11.03 (s, 1H), 10.30 (s, 1H), 9.60 (s, 1H), 9.16 (d, J = 5.2 Hz, 1H), 8.81 (s, 1H), 8.64 (s, 1H), 8.21 (s, 4H), 7.89 (d, J = 8.4 Hz, 1H), 7.63 (s, 3H). MS m/z (ESI): 449.3 [M + H]. |
| TDI01169 | 6-(4-((1H-indazol-5-yl)amino)quinazolin-2-yl)-N-(pyridazin-4-yl)-1H-indole-2-carboxamide | OH in step 1 of Example 1 was replaced with (Reg-1-1) and (Reg-1-2); in step 3 was replaced with and —NH₂ in step 4 was replaced with H₂N— | ¹H NMR (400 MHz, DMSO-d₆) δ 12.54 (s, 1H), 11.15-11.07 (m, 2H), 9.60 (s, 1H), 9.16 (d, J = 4.8 Hz, 1H), 8.73 (s, 1H), 8.48 (s, 1H), 8.24-8.22 (m, 3H), 8.06 (brs, 3H), 7.86-7.73 (m, 4H), 7.64 (s, 1H). MS m/z (ESI): 498.1 [M + H]. |

TABLE 1-continued

| No. | Compound Name | Compound Structure | Starting material or regent different from that in Example 1 | Characterization Data |
|---|---|---|---|---|
| TDI01171 | 6-(4-((1H-indazol-5-yl)amino)-pyrimidin-2-yl)-N-(pyridin-3-yl)-1H-indole-2-carboxamide | 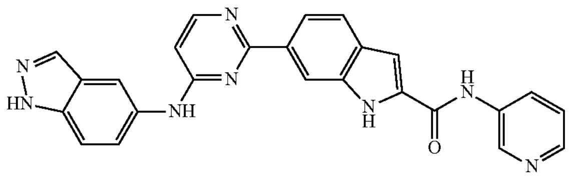 [SMILES: O=C(Nc1cccnc1)c1cc2ccc(-c3nccc(Nc4ccc5[nH]ncc5c4)n3)cc2[nH]1] | Br-(benzothiophene-2-carboxylic acid) OH in step 1 of Example 1 was replaced with Br-(6-bromo-1H-indole-2-carboxylic acid) OH; and H₂N-(pyridin-3-yl) was used to replace H₂N-(tetrahydrofuran-3-yl)NH₂ in step 4 | ¹H NMR (400 MHz, DMSO-d₆) δ 12.52 (s, 1H), 10.90 (s, 1H), 10.85 (s, 1H), 9.17 (s, 1H), 8.52-8.49 (m, 2H), 8.45-8.39 (m, 2H), 8.26 (s, 2H), 8.05-7.98 (m, 2H), 7.74-7.64 (m, 4H), 6.92 (d, J = 6.4 Hz, 1H). MS m/z (ESI): 447.1 [M + H]. |
| TDI01174 | 6-(4-(4-(1H-pyrazol-4-yl)phenyl)-amino)-pyrimidin-2-yl)-N-(pyridazin-4-yl)-1H-indole-2-carboxamide | 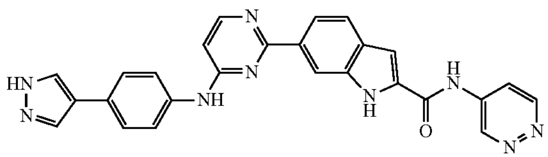 [SMILES: O=C(Nc1ccnnc1)c1cc2ccc(-c3nccc(Nc4ccc(-c5cn[nH]c5)cc4)n3)cc2[nH]1] | Br-(benzothiophene-2-carboxylic acid) OH in step 1 of Example 1 was replaced with Br-(6-bromo-1H-indole-2-carboxylic acid) OH; BocN-pyrazole-phenyl-pyrimidine-NH (Reg-1-16) was used to replace Cl-pyrimidine-NH-phenyl-pyrrolidine-NBoc (Reg-1-1) in step 3; and H₂N-pyridazine was used to replace H₂N-(tetrahydrofuran-3-yl) NH₂ in step 4 | ¹H NMR (400 MHz, DMSO-d₆) δ 12.52 (s, 1H), 11.14 (s, 1H), 10.60 (s, 1H), 9.61 (s, 1H), 9.19 (d, J = 5.9 Hz, 1H), 8.52 (s, 1H), 8.39 (d, J = 5.9 Hz, 1H), 8.26 (dd, J = 5.9, 2.5 Hz, 1H), 8.09 (s, 2H), 8.05 (d, J = 8.4 Hz, 1H), 7.96 (d, J = 8.5 Hz, 1H), 7.81 (d, J = 7.6 Hz, 2H), 7.72 (d, J = 8.5 Hz, 2H), 7.66 (s, 1H), 6.86 (d, J = 6.5 Hz, 1H). MS m/z (ESI): 474.1 [M + H]. |

| No. | Compound Structure | Compound Name | Starting material or regent different from that in Example 1 | Characterization Data |
|---|---|---|---|---|
| TDI01175 | (structure shown) | 6-(4-((1H-indazol-5-yl)amino)thieno[3,2-d]pyrimidin-2-yl)-N-(pyridazin-4-yl)-1H-indole-2-carboxamide | OH in step 1 of Example 1 was replaced with (Reg-1-1); (Reg-1-4) in step 3 was replaced with (BocN-indazole structure); and $H_2N$-tetrahydrofuran-3-yl in step 4 was replaced with $H_2N$-pyridazin-4-yl | $^1$H NMR (400 MHz, DMSO-$d_6$) δ 12.39 (s, 1H), 11.15 (s, 1H), 10.32 (s, 1H), 9.62 (s, 1H), 9.20 (d, J = 5.6 Hz, 1H), 8.56 (s, 1H), 8.30-8.26 (m, 2H), 8.19-9.17 (m, 3H), 7.88 (d, J = 8.4 Hz, 1H), 7.74 (d, J = 8.8 Hz, 1H), 7.38-7.64 (m, 2H), 7.56 (d, J = 5.4 Hz, 1H). MS m/z (ESI): 504.1 [M + H]. |
| TDI01176 | (structure shown) | 6-(4-((1H-indazol-5-yl)amino)pyrimidin-2-yl)-N-(1-hydroxypropan-2-yl)-1H-indole-2-carboxamide | OH in step 1 of Example 1 was replaced with (bromo-indole-carboxylic acid); and $NH_2$ in step 4 was replaced with $H_2N$-(1-hydroxypropan-2-yl) | $^1$H NMR (400 MHz, CD$_3$OD) δ 8.38 (s, 1H), 8.24-8.09 (m, 3H), 7.84 (d, J = 8.5 Hz, 2H), 7.67 (t, J = 11.5 Hz, 2H), 7.22 (s, 1H), 6.85 (d, J = 7.0 Hz, 1H), 4.22 (dd, J = 12.6, 6.1 Hz, 1H), 3.65-3.60 (m, 2H), 1.28 (d, J = 6.8 Hz, 4H). MS m/z (ESI): 428.2 [M + H]. |

TABLE 1-continued

| No. | Compound Structure | Compound Name | Starting material or regent different from that in Example 1 | Characterization Data |
|---|---|---|---|---|
| TDI01177 | 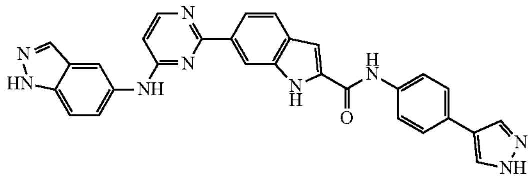 [SMILES: O=C(Nc1ccc(-c2cn[nH]c2)cc1)c1cc2ccc(-c3nccc(Nc4ccc5[nH]ncc5c4)n3)cc2[nH]1] | 6-(4-((1H-indazol-5-yl)amino)pyrimidin-2-yl)-N-(4-(1H-pyrazol-4-yl)phenyl)-1H-indole-2-carboxamide | 6-Br-benzothiophene-2-carboxylic acid in step 1 of Example 1 was replaced with 6-Br-indole-2-carboxylic acid; and 3-aminotetrahydrofuran in step 4 was replaced with 4-(1-Boc-pyrazol-4-yl)aniline (Reg-1-16-e) | $^1$H NMR (400 MHz, CD$_3$OD) δ 7.99 (s, 2H), 7.80 (t, J = 6.9 Hz, 3H), 7.67 (d, J = 8.1 Hz, 2H), 7.37-7.25 (m, 1H), 6.96 (s, 2H), 6.38 (d, J = 7.3 Hz, 1H), 5.01 (d, J = 16.9 Hz, 2H), 4.82 (s, 2H), 3.82 (s, 3H). MS m/z (ESI): 385.2 [M + H]. |
| TDI01178 | 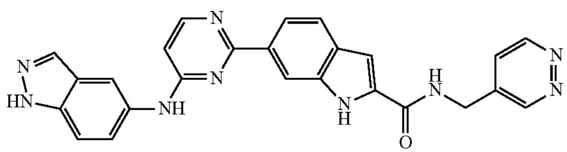 [SMILES: O=C(NCc1ccnnc1)c1cc2ccc(-c3nccc(Nc4ccc5[nH]ncc5c4)n3)cc2[nH]1] | 6-(4-((1H-indazol-5-yl)amino)pyrimidin-2-yl)-N-(pyridazin-4-ylmethyl)-1H-indole-2-carboxamide | 6-Br-benzothiophene-2-carboxylic acid in step 1 of Example 1 was replaced with 6-Br-indole-2-carboxylic acid; and 3-aminotetrahydrofuran in step 4 was replaced with 4-pyridylmethylamine·2HCl. | $^1$H NMR (400 MHz, DMSO-d$_6$) δ 12.38 (s, 1H), 11.11 (s, 1H), 9.41 (t, J = 5.9 Hz, 1H), 9.28-9.15 (m, 2H), 8.30 (m, J = 40.4, 33.4 Hz, 5H), 7.91 (s, 2H), 7.72-7.60 (m, 3H), 7.34 (s, 1H), 6.89 (s, 1H), 4.62 (d, J = 5.8 Hz, 2H). MS m/z (ESI): 462.1 [M + H]. |

TABLE 1-continued

| No. | Compound Structure | Compound Name | Starting material or regent different from that in Example 1 | Characterization Data |
|---|---|---|---|---|
| TDI01180 | 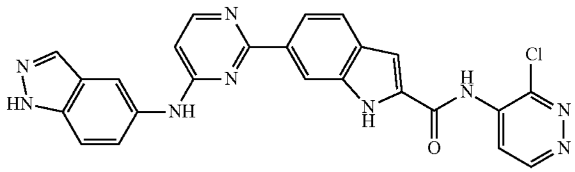 [SMILES: O=C(Nc1ccnnc1Cl)c1cc2ccc(-c3nccc(Nc4ccc5[nH]ncc5c4)n3)cc2[nH]1] | 6-(4-((1H-indazol-5-yl)amino)pyrimidin-2-yl)-N-(3-chloropyridazin-4-yl)-1H-indole-2-carboxamide | 6-bromobenzothiophene-2-carboxylic acid in step 1 of Example 1 was replaced with 6-bromoindole-2-carboxylic acid; and H$_2$N in step 4 was replaced with 3-amino-chloropyridazine | $^1$H NMR (400 MHz, CD$_3$OD) δ 9.07 (d, J = 5.4 Hz, 1H), 8.61 (d, J = 5.4 Hz, 1H), 8.41 (s, 1H), 8.35-8.04 (m, 3H), 7.96 (d, J = 8.3 Hz, 1H), 7.90 (s, 1H), 7.70 (d, J = 7.5 Hz, 2H), 7.51 (s, 1H), 6.91 (s, 1H). MS m/z (ESI): 482.1 [M + H]. |
| TDI01181 | 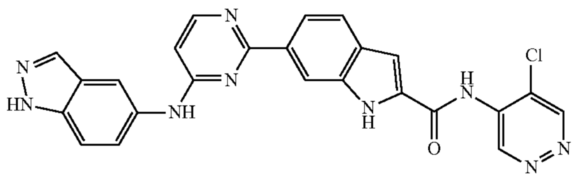 [SMILES: O=C(Nc1cnncc1Cl)c1cc2ccc(-c3nccc(Nc4ccc5[nH]ncc5c4)n3)cc2[nH]1] | 6-(4-((1H-indazol-5-yl)amino)pyrimidin-2-yl)-N-(5-chloropyridazin-4-yl)-1H-indole-2-carboxamide | 6-bromobenzothiophene-2-carboxylic acid in step 1 of Example 1 was replaced with 6-bromoindole-2-carboxylic acid; and H$_2$N in step 4 was replaced with tetrahydrofuran-3-amine | $^1$H NMR (400 MHz, DMSO-d$_6$) δ 13.2-13.10 (m, 1H), 12.49 (s, 1H), 10.66 (s, 1H), 9.64 (s, 1H), 9.44 (s, 1H), 8.49 (s, 1H), 8.35 (d, J = 6.4 Hz, 1H), 8.18 (s, 1H), 8.06 (d, J = 7.4 Hz, 1H), 7.91 (d, J = 8.0 Hz, 1H), 7.63 (s, 3H), 6.80 (s, 1H). MS m/z (ESI): 482.2 [M + H]. |
| TDI01182 | 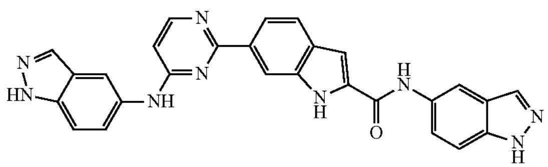 [SMILES: O=C(Nc1ccc2[nH]ncc2c1)c1cc2ccc(-c3nccc(Nc4ccc5[nH]ncc5c4)n3)cc2[nH]1] | 6-(4-((1H-indazol-5-yl)amino)pyrimidin-2-yl)-N-(1H-indazol-5-yl)-1H-indole-2-carboxamide | 6-bromobenzothiophene-2-carboxylic acid in step 1 of Example 1 was replaced with 6-bromoindole-2-carboxylic acid; and H$_2$N in step 4 was replaced with N-Boc protected aminoindazole | $^1$H NMR (400 MHz, DMSO-d$_6$) δ 13.18 (s, 2H), 12.41 (s, 1H), 10.94 (s, 1H), 10.44 (s, 1H), 8.45 (s, 1H), 8.35 (d, J = 6.8 Hz, 1H), 8.29 (s, 1H), 8.16 (d, J = 42.0 Hz, 3H), 7.95 (m, J = 17.1, 8.5 Hz, 2H), 7.74-7.61 (m, 3H), 7.58 (d, J = 12.7 Hz, 2H), 6.87 (d, J = 6.3 Hz, 1H). MS m/z (ESI): 486.1 [M + H]. |

TABLE 1-continued

| No. | Compound Structure | Compound Name | Starting material or regent different from that in Example 1 | Characterization Data |
|---|---|---|---|---|
| TDI01187 | 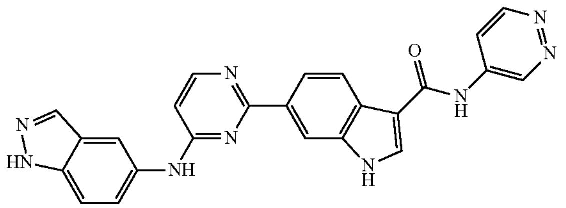 [SMILES: O=C(Nc1ccnnc1)c1c[nH]c2cc(-c3nccc(Nc4ccc5[nH]ncc5c4)n3)ccc12] | 6-(4-((1H-indazol-5-yl)amino)pyrimidin-2-yl)-N-(pyridazin-4-yl)-1H-indole-3-carboxide | Br-benzothiophene-2-COOH in step 1 of Example 1 was replaced with Br-indole-3-COOH; and H₂N-tetrahydrofuran-3-amine in step 4 was replaced with H₂N-pyridazin-4-amine | ¹H NMR (400 MHz, CD₃OD) δ 9.55 (s, 1H), 9.23 (d, J = 5.0 Hz, 1H), 8.78 (d, J = 4.7 Hz, 1H), 8.58 (s, 1H), 8.50 (d, J = 8.5 Hz, 1H), 8.41 (s, 1H), 8.22 (d, J = 7.2 Hz, 2H), 8.16 (s, 1H), 8.04 (dd, J = 3.5, 1.4 Hz, 1H), 7.86-7.57 (m, 2H), 6.92 (s, 1H). MS m/z (ESI): 448.2 [M + H]. |
| TDI01188 | 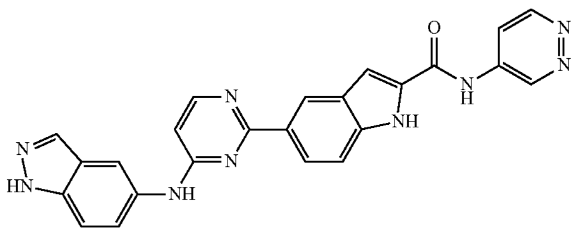 [SMILES: O=C(Nc1ccnnc1)c1cc2cc(-c3nccc(Nc4ccc5[nH]ncc5c4)n3)ccc2[nH]1] | 5-(4-((1H-indazol-5-yl)amino)pyrimidin-2-yl)-N-(pyridazin-4-yl)-1H-indole-2-carboxamide | Br-benzothiophene-2-COOH in step 1 of Example 1 was replaced with Br-indole-2-COOH; and H₂N-tetrahydrofuran-3-amine in step 4 was replaced with H₂N-pyridazin-4-amine | ¹H NMR (400 MHz, DMSO-d₆) δ 13.23 (s, 1H), 12.46 (s, 1H), 11.09 (s, 1H), 10.93 (s, 1H), 9.60 (d, J = 1.6 Hz, 1H), 9.17 (d, J = 6.0 Hz, 1H), 8.70 (s, 1H), 8.36 (d, J = 6.8 Hz, 1H), 8.21 (dt, J = 22.4, 7.2 Hz, 4H), 7.68 (dd, J = 28.8, 19.2 Hz, 4H), 6.86 (d, J = 6.4 Hz, 1H). MS m/z (ESI): 448.2 [M + H]. |
| TDI01189 | 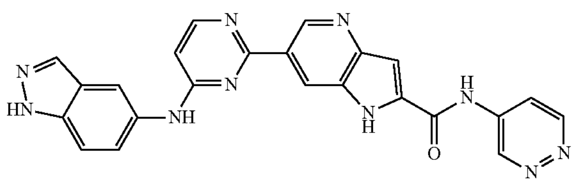 [SMILES: O=C(Nc1ccnnc1)c1cc2ncc(-c3nccc(Nc4ccc5[nH]ncc5c4)n3)cc2[nH]1] | 6-(4-((1H-indazol-5-yl)amino)pyrimidin-2-yl)-N-(pyridazin-4-yl)-1H-pyrrolo[3,2-b]pyridine-2-carboxamide | Br-benzothiophene-2-COOH in step 1 of Example 1 was replaced with Br-pyrrolo[3,2-b]pyridine-2-COOH; and H₂N-tetrahydrofuran-3-amine in step 4 was replaced with H₂N-pyridazin-4-amine | ¹H NMR (400 MHz, DMSO-d₆) δ 13.08 (s, 2H), 12.78 (s, 1H), 11.14 (s, 1H), 10.07 (s, 1H), 9.61 (s, 1H), 9.46 (s, 1H), 9.18 (d, J = 6.0 Hz, 1H), 8.83 (s, 1H), 8.40 (d, J = 6.1 Hz, 1H), 8.21 (d, J = 3.3 Hz, 1H), 8.15 (s, 1H), 7.76 (s, 1H), 7.61 (t, J = 8.4 Hz, 2H), 6.78 (d, J = 6.1 Hz, 1H). MS m/z (ESI): 449.1 [M + H]. |

TABLE 1-continued

| No. | Compound Structure | Compound Name | Starting material or regent different from that in Example 1 | Characterization Data |
|---|---|---|---|---|
| TDI01191 | 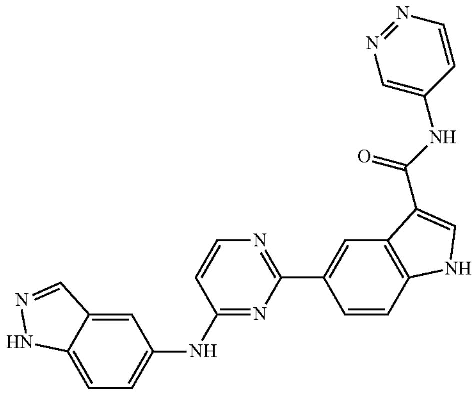 [SMILES: O=C(Nc1ccnnc1)c1c[nH]c2ccc(-c3nccc(Nc4ccc5[nH]ncc5c4)n3)cc12] | 5-(4-((1H-indazol-5-yl)amino)-pyrimidin-2-yl)-N-(pyridazin-4-yl)-1H-indole-3-carboxamide | OH in step 1 of Example 1 was replaced with Br-benzothiophene-COOH; indole-3-COOH replaced with Br-indole-3-COOH; and H₂N-pyridazine replacing amine in step 4 | $^{1}$H NMR (400 MHz, CD$_3$OD) δ 9.58 (s, 1H), 9.33 (s, 1H), 9.23 (d, J = 5.2 Hz, 1H), 8.59 (s, 1H), 8.54 (d, J = 4.8 Hz, 1H), 8.41 (s, 1H), 8.27-8.25 (m, 2H), 8.15 (d, J = 8.8 Hz, 1H), 7.78 (d, J = 8.8 Hz, 1H), 7.71 (d, J = 8.8 Hz, 1H), 7.63 (s, 1H), 6.93 (d, J = 6.0 Hz, 1H). MS m/z (ESI): 448.2 [M + H]. |
| TDI01193 | 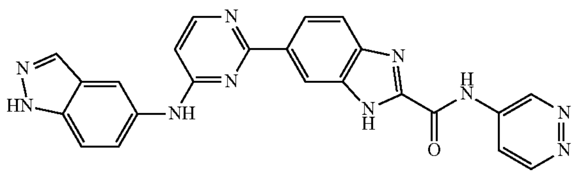 [SMILES: O=C(Nc1ccnnc1)c1nc2ccc(-c3nccc(Nc4ccc5[nH]ncc5c4)n3)cc2[nH]1] | 6-(4-((1H-indazol-5-yl)amino)-pyrimidin-2-yl)-N-(pyridazin-4-yl)-1H-benzo[d]-imidazole-2-carboxamide | OH in step 1 of Example 1 was replaced with Br-benzothiophene-COOH; benzimidazole-2-COOH; and H₂N-pyridazine in step 4 | $^{1}$H NMR (400 MHz, CD$_3$OD) δ 9.68 (d, J = 2.3 Hz, 1H), 9.21 (d, J = 6.2 Hz, 1H), 8.68 (s, 1H), 8.54 (dd, J = 6.1, 2.6 Hz, 1H), 8.24 (m, 4H), 7.95 (d, J = 8.5 Hz, 1H), 7.72 (d, J = 8.3 Hz, 1H), 7.65 (s, 1H), 6.94 (d, J = 6.2 Hz, 1H). MS m/z (ESI): 449.0 [M + H]. |
| TDI01199 | 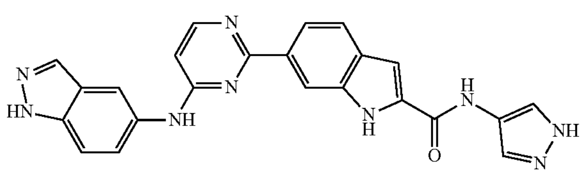 [SMILES: O=C(Nc1cn[nH]c1)c1cc2ccc(-c3nccc(Nc4ccc5[nH]ncc5c4)n3)cc2[nH]1] | 6-(4-((1H-indazol-5-yl)amino)-pyrimidin-2-yl)-N-(1H-pyrazol-4-yl)-1H-indole-2-carboxamide | OH in step 1 of Example 1 was replaced with Br-benzothiophene-COOH; indole-2-COOH; and aminopyrazole replacing NH₂ in step 4 | $^{1}$H NMR (400 MHz, DMSO-d$_6$) δ 13.23 (s, 1H), 12.40 (s, 1H), 11.02 (s, 1H), 10.66 (s, 1H), 8.42 (s, 1H), 8.33 (d, J = 6.8 Hz, 1H), 8.21 (s, 2H), 7.95-7.92 (m, 2H), 7.88 (s, 2H), 7.70-7.64 (m, 2H), 7.40 (s, 1H), 6.87 (d, J = 5.2 Hz, 1H). MS m/z (ESI): 436.1 [M + H]. |

TABLE 1-continued

| No. | Compound Structure | Compound Name | Starting material or reagent different from that in Example 1 | Characterization Data |
|---|---|---|---|---|
| TDI01200 | (structure shown) | tert-butyl 4-(6-(4-((1H-indazol-5-yl)amino)pyrimidin-2-yl)-1H-indole-2-carboxamido)-1H-pyrazole-1-carboxylate | (structures shown) OH in step 1 of Example 1 was replaced with Br-containing compound; and NH₂ in step 4 was replaced with Boc-pyrazolyl amine | ¹H NMR (400 MHz, CD₃OD) δ 8.58 (s, 1H), 8.54 (s, 1H), 8.30 (d, J = 6.0 Hz, 1H), 8.25 (s, 1H), 8.19-8.09 (m, 2H), 7.99 (s, 1H), 7.76 (d, J = 8.4 Hz, 1H), 7.66-7.60 (m, 2H), 7.29 (s, 1H), 6.66 (d, J = 6.0 Hz, 1H), 1.66 (s, 9H), MS m/z (ESI): 536.1 [M + H]. |
| TDI01201 | (structure shown) | 6-(4-((1H-indazol-5-yl)amino)pyrimidin-2-yl)-1-methyl-N-(pyridazin-4-yl)-1H-indole-2-carboxamide | The preparation started from step 3 of Example 1, (structures shown) — in step 3 was replaced with pinacol boronate ester of N-methylindole carboxylate; and NH₂ in step 4 was replaced with H₂N-pyridazine / tetrahydrofuranyl amine | ¹H NMR (400 MHz, DMSO-d₆) δ 11.24 (s, 1H), 10.97 (s, 1H), 9.57 (s, 1H), 9.19 (d, J = 5.6 Hz, 1H), 8.54 (s, 1H), 8.40 (d, J = 6.4 Hz, 1H), 8.24 (s, 2H), 8.17 (s, 1H), 8.04 (d, J = 8.4 Hz, 1H), 7.95 (d, J = 8.4 Hz, 1H), 7.67 (d, J = 8.4 Hz, 1H), 7.61-7.57 (m, 2H), 6.89 (d, J = 6.0 Hz, 1H), 4.11 (s, 3H), MS m/z (ESI): 462.2 [M + H]. |

TABLE 1-continued

| No. | Compound Structure | Compound Name | Starting material or regent different from that in Example 1 | Characterization Data |
|---|---|---|---|---|
| TDI01213 | 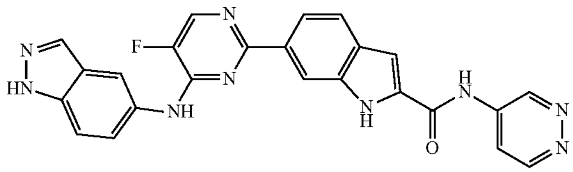 [SMILES: O=C(Nc1ccnnc1)c1cc2ccc(-c3ncc(F)c(Nc4ccc5[nH]ncc5c4)n3)cc2[nH]1] | 6-(4-((1H-indazol-5-yl)amino)-5-fluoropyrimidin-2-yl)-N-(pyridazin-4-yl)-1H-indole-2-carboxamide | (Reg-1-1) and (Reg-1-12); OH in step 1 of Example 1 was replaced with corresponding acids; in step 3 was replaced with corresponding amine; NH₂ in step 4 was replaced with H₂N-pyridazine | ¹H NMR (400 MHz, CD₃OD + DMSO-d₆) δ 9.64 (s, 1H), 9.19 (s, 1H), 8.53–8.47 (m, 2H), 8.41 (d, J = 3.6 Hz, 1H), 8.36 (s, 1H), 8.22 (s, 1H), 8.16 (d, J = 8.0 Hz, 1H), 7.85 (d, J = 8.8 Hz, 2H), 7.70 (d, J = 8.8 Hz, 1H), 7.57 (s, 1H). MS m/z (ESI): 466.1 [M + H]. |
| TDI01214 | 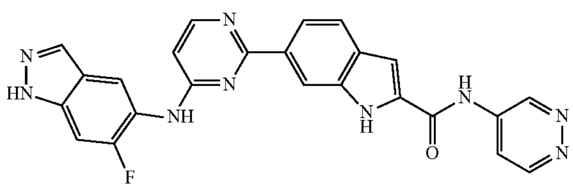 [SMILES: O=C(Nc1ccnnc1)c1cc2ccc(-c3nccc(Nc4cc5cn[nH]c5cc4F)n3)cc2[nH]1] | 6-(4-((6-fluoro-1H-indazol-5-yl)amino)pyrimidin-2-yl)-N-(pyridazin-4-yl)-1H-indole-2-carboxamide | (Reg-1-1) and (Reg-1-17); OH in step 1 of Example 1 was replaced with corresponding acids; in step 3 was replaced with corresponding amine; NH₂ in step 4 was replaced with H₂N-pyridazine | ¹H NMR (400 MHz, DMSO-d₆) δ 12.35 (s, 1H), 11.02 (s, 1H), 9.91 (s, 1H), 9.60 (s, 1H), 9.14 (d, J = 5.2 Hz, 1H), 8.43 (s, 1H), 8.39 (d, J = 6.0 Hz, 1H), 8.27–8.14 (m, 3H), 8.02 (d, J = 8.0 Hz, 1H), 7.83 (d, J = 8.4 Hz, 1H), 7.60 (s, 1H), 7.55 (d, J = 10.8 Hz, 1H), 6.78 (d, J = 3.6 Hz, 1H). MS m/z (ESI): 466.1 [M + H]. |

TABLE 1-continued

| No. | Compound Structure | Compound Name | Starting material or regent different from that in Example 1 | Characterization Data |
|---|---|---|---|---|
| TDI01215 | 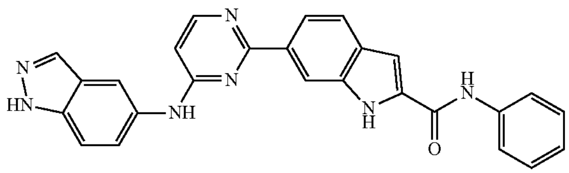 [SMILES: O=C(Nc1ccccc1)c1cc2ccc(-c3nccc(Nc4ccc5[nH]ncc5c4)n3)cc2[nH]1] | 6-(4-((1H-indazol-5-yl)amino)pyrimidin-2-yl)-N-phenyl-1H-indole-2-carboxamide | 6-bromobenzothiophene-2-carboxylic acid OH in step 1 of Example 1 was replaced with 6-bromo-1H-indole-2-carboxylic acid; and tetrahydrofuran-3-amine NH$_2$ in step 4 was replaced with aniline H$_2$N-phenyl | $^1$H NMR (400 MHz, DMSO-d$_6$) δ 13.22 (s, 1H), 12.40 (s, 1H), 10.85 (s, 1H), 10.39 (s, 1H), 8.45 (s, 1H), 8.34 (d, J = 6.8 Hz, 1H), 8.20 (s, 2H), 7.98 (d, J = 8.4 Hz, 1H), 7.91 (d, J = 8.4 Hz, 1H), 7.83 (d, J = 9.2 Hz, 2H), 7.56 (s, 1H), 7.40 (t, J = 7.6 Hz, 2H), 7.14 (t, J = 7.2 Hz, 1H), 6.86 (d, J = 5.6 Hz, 1H). MS m/z (ESI): 446.1 [M + H]. |
| TDI01221 | 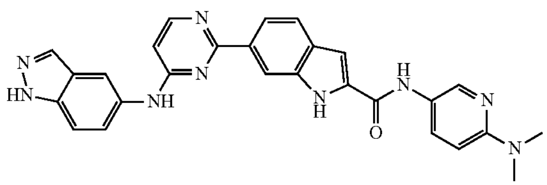 [SMILES: CN(C)c1ccc(NC(=O)c2cc3ccc(-c4nccc(Nc5ccc6[nH]ncc6c5)n4)cc3[nH]2)cn1] | 6-(4-((1H-indazol-5-yl)amino)pyrimidin-2-yl)-N-(6-(dimethylamino)pyridin-3-yl)-1H-indole-2-carboxamide | 6-bromobenzothiophene-2-carboxylic acid OH in step 1 of Example 1 was replaced with 6-bromo-1H-indole-2-carboxylic acid; and tetrahydrofuran-3-amine NH$_2$ in step 4 was replaced with N,N-dimethyl-5-aminopyridin-2-amine | $^1$H NMR (400 MHz, DMSO-d$_6$) δ 13.21 (s, 1H), 12.41 (s, 1H), 10.76 (s, 2H), 10.52 (s, 1H), 8.56 (s, 1H), 8.45 (s, 1H), 8.34 (d, J = 6.7 Hz, 1H), 8.20 (s, 2H), 8.11 (s, 1H), 8.00 (d, J = 8.3 Hz, 1H), 7.91 (d, J = 8.5 Hz, 1H), 7.66 (d, J = 8.8 Hz, 2H), 7.62 (s, 1H), 7.49 (s, 1H), 7.11 (s, 1H), 6.84 (s, 1H), 3.15 (s, 7H). MS m/z (ESI): 490.1 [M + H]. |

TABLE 1-continued

| No. | Compound Structure | Compound Name | Starting material or regent different from that in Example 1 | Characterization Data |
|---|---|---|---|---|
| TDI01231 | 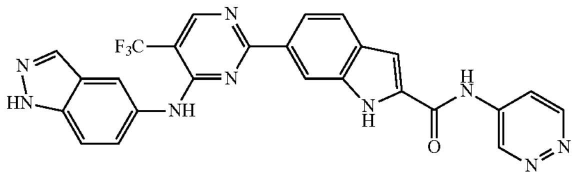 [SMILES: O=C(Nc1ccnnc1)c1cc2ccc(-c3ncc(C(F)(F)F)c(Nc4ccc5[nH]ncc5c4)n3)cc2[nH]1] | 6-(4-((1H-indazol-5-yl)amino)-5-(trifluoromethyl)-pyrimidin-2-yl)-N-(pyridazin-4-yl)-1H-indole-2-carboxamide | OH in step 1 of Example 1 was replaced with (Reg-1-1) and (Reg-1-23); in step 3 was replaced with NH₂ in step 4 was replaced with | ¹H NMR (400 MHz, DMSO-d₆) δ 13.16 (s, 1H), 12.31 (s, 1H), 11.06 (s, 1H), 9.58 (d, 1H), 9.17 (m, 2H), 8.75 (s, 1H), 8.45 (s, 1H), 8.26 (dd, 1H), 8.14 (s, 1H), 7.95 (dd, 1H), 7.88 (s, 1H), 7.76 (d, 1H), 7.60 (m, 3H). MS m/z (ESI): 516.2 [M + H]. |
| TDI01232 | 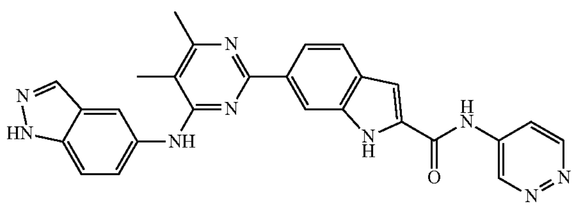 [SMILES: Cc1nc(-c2ccc3cc(C(=O)Nc4ccnnc4)[nH]c3c2)nc(Nc2ccc3[nH]ncc3c2)c1C] | 6-(4-((1H-indazol-5-yl)amino)-5,6-dimethyl-pyrimidin-2-yl)-N-(pyridazin-4-yl)-1H-indole-2-carboxamide | OH in step 1 of Example 1 was replaced with (Reg-1-1) and (Reg-1-13); in step 3 was replaced with NH₂ in step 4 was replaced with H₂N | ¹H NMR (400 MHz, DMSO-d₆) δ 13.16 (s, 1H), 12.45 (s, 1H), 10.98 (s, 1H), 9.58 (s, 2H), 9.14 (s, 1H), 8.29 (s, 1H), 8.17 (s, 2H), 8.00 (s, 1H), 7.89 (d, J = 8.4 Hz, 2H), 7.64 (s, 2H), 7.59 (s, 1H), 2.58 (s, 3H), 2.31 (s, 3H). MS m/z (ESI): 476.3 [M + H]. |

TABLE 1-continued

| No. | Compound Structure | Compound Name | Starting material or regent different from that in Example 1 | Characterization Data |
|---|---|---|---|---|
| TDI01248 | 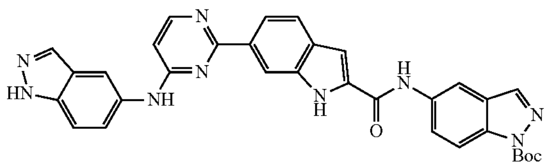 [SMILES: CC(C)(C)OC(=O)n1ncc2cc(NC(=O)c3cc4ccc(-c5nccc(Nc6ccc7[nH]ncc7c6)n5)cc4[nH]3)ccc21] | tert-butyl 5-(6-(4-((1H-indazol-5-yl)amino)pyrimidin-2-yl)-1H-indole-2-carboxamido)-1H-indazole-1-carboxylate | OH in step 1 of Example 1 was replaced with (Br-benzothiophene-COOH) and (Br-indole-6-COOH); NH$_2$ in step 4 was replaced with (Boc-aminobenzaldehyde-NH$_2$ tetrahydrofuran) | $^1$H NMR (400 MHz, CD$_3$OD + DMSO-d$_6$) 8.46 (s, 1H), 8.36 (s, 1H), 8.26–8.20 (t 2H), 8.13 (d, J = 9.5 Hz, 2H), 8.07 (d, J = 9.0 Hz, 2H), 7.82 (t, J = 8.9 Hz, 2H), 7.63 (d, J = 8.8 Hz, 1H), 7.58 (d, J = 8.9 Hz, 1H), 7.47 (s, 1H), 7.40 (s, 1H), 6.69 (d, J = 6.1 Hz, 1H), 1.76 (s, 9H). MS m/z (ESI): 586.2 [M + H]. |
| TDI01250 | 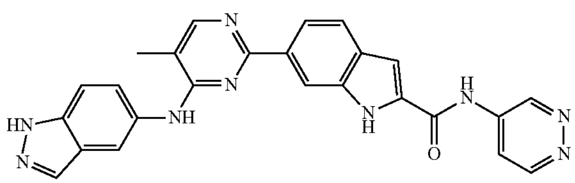 [SMILES: Cc1cnc(-c2ccc3cc(C(=O)Nc4ccnnc4)[nH]c3c2)nc1Nc1ccc2[nH]ncc2c1] | 6-(4-((1H-indazol-5-yl)amino)-5-methylpyrimidin-2-yl)-N-(pyridazin-4-yl)-1H-indole-2-carboxamide | OH in step 1 of Example 1 was replaced with (Br-benzothiophene-COOH) and (Br-indole-6-COOH); in step 3 was replaced with (Reg-1-1) and (Reg-1-14); NH$_2$ in step 4 was replaced with H$_2$N-pyridazine | $^1$H NMR (400 MHz, DMSO-d$_6$) δ 13.17 (br, 1H), 12.52 (s, 1H), 11.04 (s, 1H), 9.95 (br, 1H), 9.59 (d, J = 4.0 Hz, 1H), 9.16 (d, J = 8.0 Hz, 1H), 8.31 (d, J = 5.2 Hz, 2H), 8.22–8.18 (m, 2H), 8.05 (s, 1H), 7.91 (d, J = 8.6 Hz, 1H), 7.85 (d, J = 7.9 Hz, 1H), 7.68 (s, 2H), 7.61 (s, 1H), 2.36 (s, 3H). MS m/z (ESI): 462.3 [M + H]. |

TABLE 1-continued

| No. | Compound Structure | Compound Name | Starting material or regent different from that in Example 1 | Characterization Data |
|---|---|---|---|---|
| TDI01251 | 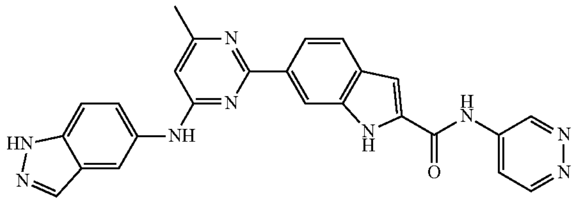 [SMILES: Cc1cc(Nc2ccc3[nH]ncc3c2)nc(-c2ccc3cc(C(=O)Nc4ccnnc4)[nH]c3c2)n1] | 6-(4-((1H-indazol-5-yl)amino)-6-methyl-pyrimidin-2-yl)-N-(pyridazin-4-yl)-1H-indole-2-carboxamide | OH in step 1 of Example 1 was replaced with (Reg-1-1); in step 3 was replaced with (Reg-1-15); and NH₂ in step 4 was replaced with | ¹H NMR (400 MHz, DMSO-d₆) δ 13.20 (s, 1H), 12.55 (s, 1H), 11.11 (s, 1H), 10.78 (s, 1H), 9.62 (d, J = 2.0 Hz, 1H), 9.18 (d, J = 6.0 Hz, 1H), 8.43 (d, J = 6.0 Hz, 1H), 8.20 (d, J = 40.4, 13.2 Hz, 3H), 7.97 (d, J = 8.8 Hz, 2H), 7.71-7.47 (m, 3H), 6.71 (s, 1H), 2.54 (s, 3H). MS m/z: (ESI): 462.1 [M + H]. |
| TDI01258 | 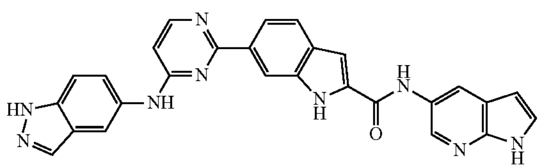 [SMILES: O=C(Nc1cnc2[nH]ccc2c1)c1cc2ccc(-c3nccc(Nc4ccc5[nH]ncc5c4)n3)cc2[nH]1] | 6-(4-((1H-indazol-5-yl)amino)-pyrimidin-2-yl)-N-(1H-pyrrolo[2,3-b]pyridin-5-yl)-1H-indole-2-carboxamide | OH in step 1 of Example 1 was replaced with ; and NH₂ in step 4 was replaced with | ¹H NMR (400 MHz, DMSO-d₆) δ 13.14 (s, 1H), 12.41 (s, 1H), 11.64 (s, 1H), 10.91 (s, 1H), 10.46 (s, 1H), 8.52 (d, J = 2.3 Hz, 1H), 8.44 (s, 1H), 8.35 (dd, J = 16.0, 4.5 Hz, 2H), 8.20 (s, 1H), 7.94 (dd, J = 8.8 Hz, 2H), 7.72-7.48 (m, 5H), 6.87 (s, 1H), 6.49 (dd, J = 3.3, 1.8 Hz, 1H). MS m/z (ESI): 486.2 [M + H]. |

TABLE 1-continued

| No. | Compound Structure | Compound Name | Starting material or regent different from that in Example 1 | Characterization Data |
|---|---|---|---|---|
| TDI01275 | 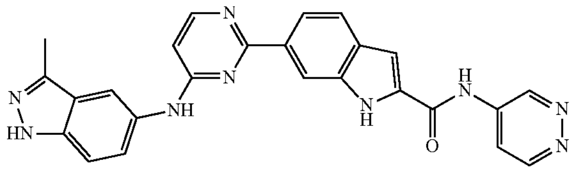 [SMILES: Cc1n[nH]c2ccc(Nc3ccnc(-c4ccc5cc(C(=O)Nc6ccnnc6)[nH]c5c4)n3)cc12] | 6-(4-((3-methyl-1H-indazol-5-yl)amino)pyrimidin-2-yl)-N-(pyridazin-4-yl)-1H-indole-2-carboxamide | OH in step 1 of Example 1 was replaced with (Reg-1-1) and (Reg-1-25); in step 3 was replaced with and NH₂ in step 4 was replaced with H₂N- | ¹H NMR (400 MHz, DMSO-d₆) δ 12.82-12.59 (m, 1H), 12.43 (s, 1H), 10.99 (s, 1H), 10.37 (s, 1H), 9.60 (s, 1H), 9.14 (d, J = 5.6 Hz, 1H), 8.50 (s, 1H), 8.35 (d, J = 6.4 Hz, 1H), 8.18 (d, J = 3.6 Hz, 2H), 8.09 (d, J = 8.4 Hz, 1H), 7.91 (d, J = 8.4 Hz, 1H), 7.62 (s, 1H), 7.55 (s, 1H), 6.78 (d, J = 5.6 Hz, 1H), 2.54 (s, 3H). MS m/z (ESI): 462.2 [M + H]. |
| TDI01276 | 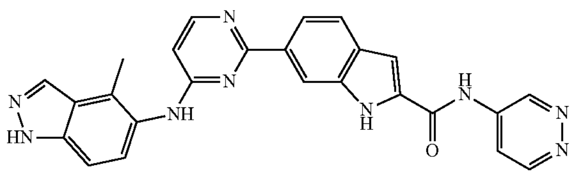 [SMILES: Cc1c(Nc2ccnc(-c3ccc4cc(C(=O)Nc5ccnnc5)[nH]c4c3)n2)ccc2[nH]ncc12] | 6-(4-((4-methyl-1H-indazol-5-yl)amino)pyrimidin-2-yl)-N-(pyridazin-4-yl)-1H-indole-2-carboxamide | OH in step 1 of Example 1 was replaced with (Reg-1-1) and (Reg-1-26); in step 3 was replaced with and NH₂ in step 4 was replaced with H₂N- | ¹H NMR (400 MHz, DMSO-d₆) δ 13.22 (s, 1H), 12.48 (s, 1H), 11.00 (s, 1H), 9.59 (d, J = 2.3 Hz, 1H), 9.15 (d, J = 6.0 Hz, 1H), 8.34 (s, 1H), 8.29 (d, J = 6.7 Hz, 1H), 8.24 (s, 1H), 8.20-8.16 (m, 1H), 7.90 (s, 2H), 7.61 (s, 1H), 7.50 (d, J = 8.7 Hz, 1H), 7.39 (s, d, J = 8.2 Hz, 1H), 2.50 (s, 3H). MS m/z (ESI): 462.2 [M + H]. |

TABLE 1-continued

| No. | Compound Structure | Compound Name | Starting material or regent different from that in Example 1 | Characterization Data |
|---|---|---|---|---|
| TDI01278 | (structure) | 6-(2-((1H-indazol-5-yl)amino)-5-(trifluoromethyl)-pyrimidin-4-yl)-N-(pyridazin-4-yl)-1H-indole-2-carboxamide | OH in step 1 of Example 1 was replaced with (Reg-1-1) and OH; in step 3 was replaced with (Reg-1-24) and NH₂ in step 4 was replaced with (tetrahydrofuran-3-amine). | ¹H NMR (400 MHz, DMSO-d₆) δ 12.98 (s, 1H), 12.26 (s, 1H), 11.04 (s, 1H), 10.34 (s, 1H), 9.59 (d, 1H), 9.17 (d, 1H), 8.86 (s, 1H), 8.24 (m, 2H), 8.03 (s, 1H), 7.88 (d, 1H), 7.76 (s, 1H), 7.63 (s, 2H), 7.50 (d, 1H), 7.34 (d, 1H). MS m/z (ESI): 516.2 [M + H]. |

TABLE 1-continued

| No. | Compound Name | Compound Structure | Starting material or regent different from that in Example 1 | Characterization Data |
|---|---|---|---|---|
| TDI01282 | 6-(2-((1H-indazol-5-yl)amino)-5,6-dimethyl-pyrimidin-4-yl)-N-(pyridazin-4-yl)-1H-indole-2-carboxamide | 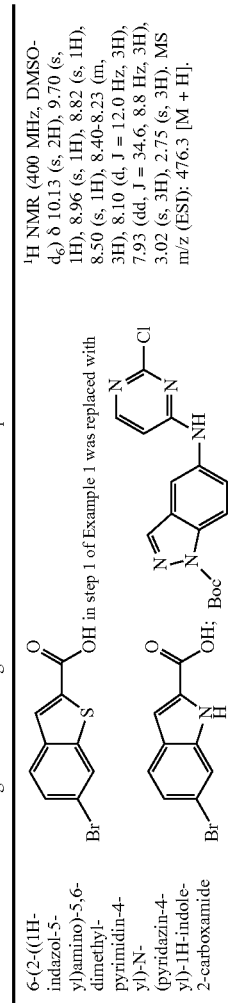 | 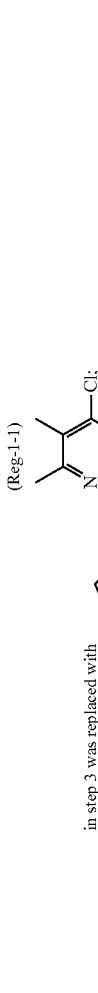 OH in step 1 of Example 1 was replaced with <br> (Reg-1-1) <br> ; <br> (Reg-1-22) <br> in step 3 was replaced with 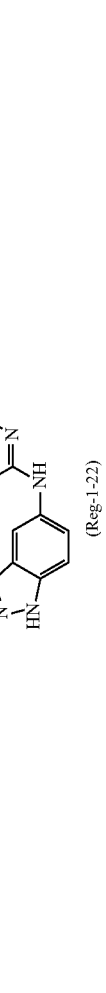 | ¹H NMR (400 MHz, DMSO-d₆) δ 10.13 (s, 2H), 9.70 (s, 1H), 8.96 (s, 1H), 8.82 (s, 1H), 8.50 (s, 1H), 8.40-8.23 (m, 3H), 8.10 (d, J = 12.0 Hz, 3H), 7.93 (dd, J = 34.6, 8.8 Hz, 3H), 3.02 (s, 3H), 2.75 (s, 3H). MS m/z (ESI): 476.3 [M + H]. |
| TDI01285 | 5-(4-((1H-indazol-5-yl)amino)-pyrimidin-2-yl)-N-isopropyl-1H-indole-3-carboxamide | 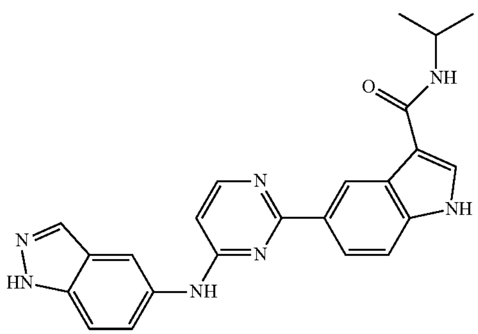 [SMILES: CC(C)NC(=O)c1c[nH]c2ccc(-c3nccc(Nc4ccc5[nH]ncc5c4)n3)cc12] | $\mathrm{H_2N}$—<img>—NH₂ in step 4 was replaced with H₂N—<img> in step 1 of Example 1 was replaced with <img> ; and 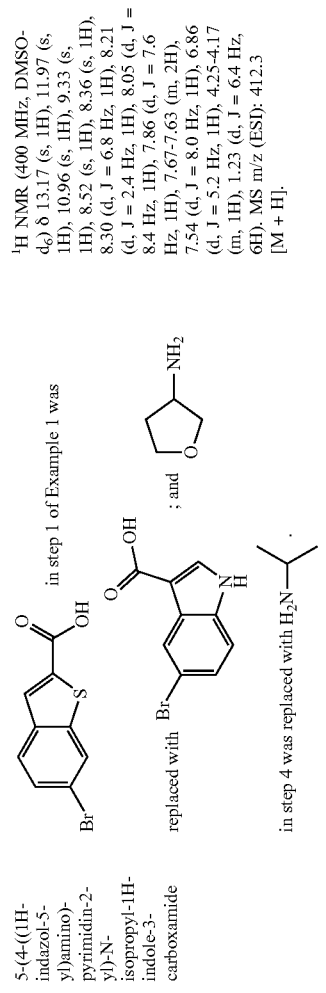 in step 4 was replaced with H₂N—<img>. | ¹H NMR (400 MHz, DMSO-d₆) δ 13.17 (s, 1H), 11.97 (s, 1H), 10.96 (s, 1H), 9.33 (s, 1H), 8.52 (s, 1H), 8.36 (s, 1H), 8.30 (d, J = 6.8 Hz, 1H), 8.21 (d, J = 2.4 Hz, 1H), 8.05 (d, J = 8.4 Hz, 1H), 7.86 (d, J = 7.6 Hz, 1H), 7.67-7.63 (m, 2H), 7.54 (d, J = 8.0 Hz, 1H), 6.86 (d, J = 5.2 Hz, 1H), 4.25-4.17 (m, 1H), 1.23 (d, J = 6.4 Hz, 6H). MS m/z (ESI): 412.3 [M + H]. |

TABLE 1-continued

| No. | Compound Structure | Compound Name | Starting material or regent different from that in Example 1 | Characterization Data |
|---|---|---|---|---|
| TDI01289 | 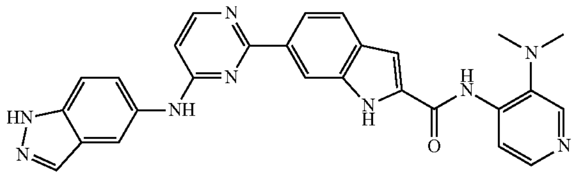 [SMILES: CN(C)c1cnccc1NC(=O)c1cc2ccc(-c3nccc(Nc4ccc5[nH]ncc5c4)n3)cc2[nH]1] | 6-(4-((1H-indazol-5-yl)amino)pyrimidin-2-yl)-N-(3-(dimethylamino)pyridin-4-yl)-1H-indole-2-carboxamide | OH in step 1 of Example 1 was replaced with 6-bromobenzothiophene-2-carboxylic acid and replaced with 6-bromo-1H-indole-2-carboxylic acid; NH2 in step 4 was replaced with 3-(dimethylamino)pyridin-4-amine | $^1$H NMR (400 MHz, DMSO-$d_6$) δ 13.17 (s, 1H), 12.57 (s, 1H), 10.49 (s, 1H), 10.08 (s, 1H), 8.63 (s, 1H), 8.57-8.52 (m, 2H), 8.50 (s, 1H), 8.36 (d, J = 6.4 Hz, 1H), 8.23 (s, 1H), 8.18 (s, 1H), 8.06 (d, J = 8.4 Hz, 1H), 7.92 (d, J = 8.8 Hz, 1H), 7.66-7.61 (m, 3H), 6.81 (d, J = 6.4 Hz, 1H), 2.86 (s, 6H). MS m/z (ESI): 490.2 [M + H]. |
| TDI01290 | 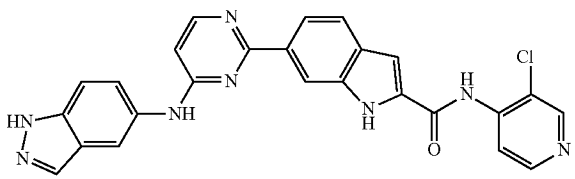 [SMILES: O=C(Nc1ccncc1Cl)c1cc2ccc(-c3nccc(Nc4ccc5[nH]ncc5c4)n3)cc2[nH]1] | 6-(4-((1H-indazol-5-yl)amino)pyrimidin-2-yl)-N-(3-chloropyridin-4-yl)-1H-indole-2-carboxamide | OH in step 1 of Example 1 was replaced with 6-bromobenzothiophene-2-carboxylic acid and replaced with 6-bromo-1H-indole-2-carboxylic acid; NH2 in step 4 was replaced with 3-chloropyridin-4-amine | $^1$H NMR (400 MHz, DMSO-$d_6$) δ 13.16 (s, 1H), 12.48 (s, 1H), 10.65 (s, 1H), 10.24 (s, 1H), 8.73 (s, 1H), 8.56 (d, J = 5.3 Hz, 1H), 8.46 (s, 1H), 8.34 (d, J = 6.6 Hz, 1H), 8.19 (s, 2H), 8.01 (d, J = 8.3 Hz, 1H), 7.92 (t, J = 6.0 Hz, 2H), 7.65 (t, J = 9.0 Hz, 2H), 7.59 (s, 1H), 6.83 (s, 1H). MS m/z (ESI): 481.1 [M + H]. |
| TDI01291 | 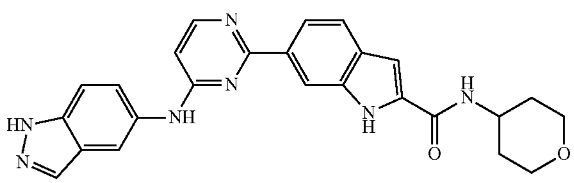 [SMILES: O=C(NC1CCOCC1)c1cc2ccc(-c3nccc(Nc4ccc5[nH]ncc5c4)n3)cc2[nH]1] | 6-(4-((1H-indazol-5-yl)amino)pyrimidin-2-yl)-N-(tetrahydro-2H-pyran-4-yl)-1H-indole-2-carboxamide | OH in step 1 of Example 1 was replaced with 6-bromobenzothiophene-2-carboxylic acid and replaced with 6-bromo-1H-indole-2-carboxylic acid; NH2 in step 4 was replaced with tetrahydro-2H-pyran-4-amine | $^1$H NMR (400 MHz, DMSO-$d_6$) δ 10.84 (br, 1H), 8.51 (d, J = 7.7 Hz, 1H), 8.41 (s, 1H), 8.33 (d, J = 6.8 Hz, 1H), 8.20 (s, 1H), 7.95 (d, J = 8.4 Hz, 1H), 7.85 (d, J = 8.5 Hz, 1H), 7.68-7.61 (m, 2H), 7.30 (s, 1H), 6.85 (d, J = 6.1 Hz, 1H), 3.92 (d, J = 8.0 Hz, 3H), 3.43 (t, J = 12.0 Hz, 2H), 1.81 (dt, J = 11.8, 7.8 Hz, 2H), 1.62 (d, J = 12.0 Hz, 2H). MS m/z (ESI): 454.3 [M + H]. |

TABLE 1-continued

| No. | Compound Structure | Compound Name | Starting material or regent different from that in Example 1 | Characterization Data |
|---|---|---|---|---|
| TDI01292 | 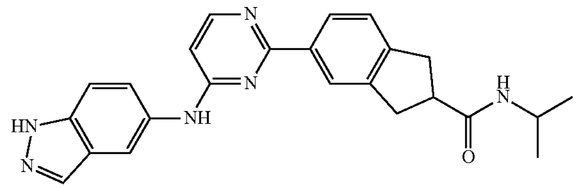 [SMILES: CC(C)NC(=O)C1Cc2ccc(-c3nccc(Nc4ccc5[nH]ncc5c4)n3)cc2C1] | 6-(4-((1H-indazol-5-yl)amino)-pyrimidin-2-yl)-N-isopropyl-indoline-2-carboxamide | (methyl 6-bromobenzothiophene-2-carboxylate) in step 2 of Example 1 was replaced with (methyl 6-bromoindoline-2-carboxylate); and (tetrahydrofuran-3-amine) NH₂ in step 4 was replaced with isopropylamine. | ¹H NMR (400 MHz, DMSO-d₆) δ 13.19 (s, 1H), 10.34 (s, 1H), 9.88 (s, 1H), 8.30 (d, J = 6.4 Hz, 1H), 8.17 (d, J = 25.2 Hz, 2H), 7.95 (s, 1H), 7.72 (d, J = 8.0 Hz, 1H), 7.56 (dd, J = 35.6, 28.5 Hz, 3H), 7.25-7.14 (m, 1H), 6.77 (s, 1H), 4.26 (d, J = 9.2 Hz, 1H), 3.89 (d, J = 12 Hz, 1H), 2.89 (s, 2H), 1.24 (s, 3H), 1.14-1.04 (m, 3H). MS m/z (ESI): 414.2 [M + H]. |
| TDI01294 | 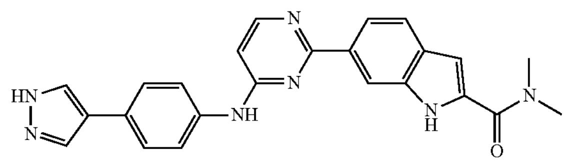 | 6-(4-(4-(1H-pyrazol-4-yl)phenyl)-pyrimidin-2-yl)-amino)-N,N-dimethyl-1H-indole-2-carboxamide | 6-bromobenzothiophene-2-carboxylic acid OH in step 1 of Example 1 was replaced with 6-bromoindole-2-carboxylic acid OH; (Reg-1-16) was used to replace (Reg-1-1) in step 3; and tetrahydrofuran-3-amine NH₂ in step 4 was replaced with dimethylamine —NH. | ¹H NMR (400 MHz, DMSO-d₆) δ 12.11 (s, 1H), 10.61 (s, 1H), 8.46 (s, 1H), 8.36 (d, J = 6.4 Hz, 1H), 8.08 (s, 2H), 7.99 (d, J = 8.8 Hz, 1H), 7.84-7.78 (m, 3H), 7.72 (d, J = 8.8 Hz, 2H), 7.00 (s, 1H), 6.85 (d, J = 6.4 Hz, 1H), 3.10 (s, 6H). MS m/z (ESI): 424.2 [M + H]. |

TABLE 1-continued

| No. | Compound Structure | Compound Name | Starting material or regent different from that in Example 1 | Characterization Data |
|---|---|---|---|---|
| TDI01296 | 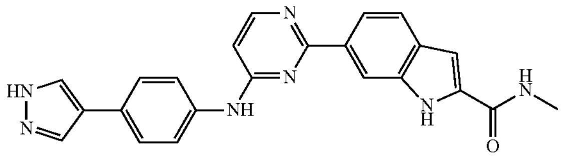 [SMILES: CNC(=O)c1cc2ccc(-c3nccc(Nc4ccc(-c5cn[nH]c5)cc4)n3)cc2[nH]1] | 6-(4-((4-(1H-pyrazol-4-yl)phenyl)-amino)-pyrimidin-2-yl)-N-methyl-1H-indole-2-carboxamide | 6-bromo-benzothiophene-2-carboxylic acid OH was used to replace OH in step 1 of Example 1 was replaced with 6-bromo-1H-indole-2-carboxylic acid (N-Boc pyrazole phenyl) (Reg-1-16); 2-chloro-4-((1H-indole)amino)pyrimidine Boc (Reg-1-1) was used to replace tetrahydrofuran-3-yl-NH₂ in step 3; and methylamine hydrochloride was used to replace in step 4. | ¹H NMR (400 MHz, DMSO-d₆) δ 12.15 (s, 1H), 10.57 (s, 1H), 8.62 (d, J = 4.6 Hz, 1H), 8.46 (s, 1H), 8.35 (d, J = 6.6 Hz, 1H), 8.08 (s, 2H), 7.98 (d, J = 8.4 Hz, 1H), 7.81 (d, J = 8.4 Hz, 3H), 7.71 (s, 1H), 6.83 (d, J = 6.5 Hz, 1H), 2.85 (d, J = 4.5 Hz, 3H). MS m/z (ESI): 410.2 [M + H]. |
| TDI01299 | 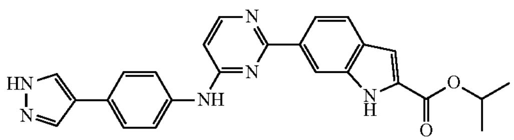 [SMILES: CC(C)OC(=O)c1cc2ccc(-c3nccc(Nc4ccc(-c5cn[nH]c5)cc4)n3)cc2[nH]1] | isopropyl 6-(4-((4-(1H-pyrazol-4-yl)phenyl)-amino)-pyrimidin-2-yl)-1H-indole-2-carboxylate | 6-bromo-benzothiophene-2-carboxylic acid OH was used to replace OH in step 1 of Example 1 was replaced with 6-bromo-1H-indole-2-carboxylic acid (N-Boc pyrazole phenyl) (Reg-1-16); 2-chloro-4-((1H-indole)amino)pyrimidine Boc (Reg-1-1) was used to replace tetrahydrofuran-3-yl-NH₂ in step 3; and isopropanol was used to replace in step 4. | ¹H NMR (400 MHz, CD₃OD) δ 8.46 (s, 1H), 8.24 (d, J = 7.3 Hz, 1H), 8.06 (s, 2H), 7.92 (s, 1H), 7.88 (d, J = 8.3 Hz, 1H), 7.78 (s, 4H), 7.28 (s, 1H), 6.94 (d, J = 7.2 Hz, 1H), 5.34–5.25 (m, 1H), 1.44 (d, J = 6.2 Hz, 6H). MS m/z (ESI): 439.2 [M + H]. |

TABLE 1-continued

| No. | Compound Structure | Compound Name | Starting material or regent different from that in Example 1 | Characterization Data |
|---|---|---|---|---|
| TDI01314 | 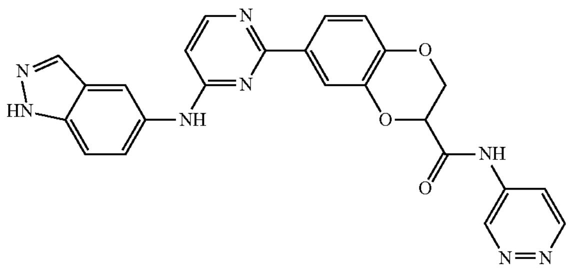 [SMILES: O=C(Nc1ccnnc1)C1COc2ccc(-c3nccc(Nc4ccc5[nH]ncc5c4)n3)cc2O1] | 7-(4-((1H-indazol-5-yl)amino)pyrimidin-2-yl)-N-(pyridazin-4-yl)-2,3-dihydrobenzo[b][1,4]dioxine-2-carboxamide | OH in step 1 of Example 1 was replaced with (TDI01314-1); and in step 4 was replaced with | $^1$H NMR (400 MHz, CD$_3$OD) δ 9.40 (s, 1H), 9.15 (d, J = 6.1 Hz, 1H), 8.57 (d, J = 7.1 Hz, 1H), 8.47 (d, J = 3.1 Hz, 1H), 8.35 (d, J = 3.7 Hz, 1H), 8.18 (d, J = 7.2 Hz, 1H), 8.13 (s, 1H), 7.92 (s, 1H), 7.74 (s, 1H), 7.68 (d, J = 8.2 Hz, 1H), 7.15 (d, J = 8.6 Hz, 1H), 6.87 (s, 1H), 5.16 (s, 1H), 4.60 (d, J = 3.8 Hz, 2H). MS m/z (ESI): 467.2 [M + H]. |
| TDI01315 | 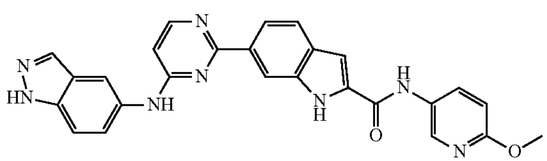 [SMILES: COc1ccc(NC(=O)c2cc3ccc(-c4nccc(Nc5ccc6[nH]ncc6c5)n4)cc3[nH]2)cn1] | 6-(4-((1H-indazol-5-yl)amino)pyrimidin-2-yl)-N-(6-methoxypyridin-3-yl)-1H-indole-2-carboxamide | OH in step 1 of Example 1 was replaced with ; and in step 4 was replaced with | $^1$H NMR (400 MHz, DMSO-d$_6$) δ 13.16 (s, 1H), 12.37 (s, 1H), 10.67 (s, 1H), 10.45 (s, 1H), 8.58 (d, J = 2.4 Hz, 1H), 8.45 (s, 1H), 8.34 (d, J = 6.4 Hz, 1H), 8.20 (d, J = 6.4 Hz, 2H), 8.08 (dd, J = 8.8, 2.4 Hz, 1H), 8.00 (d, J = 8.4 Hz, 1H), 7.90 (d, J = 8.4 Hz, 1H), 7.65 (t, J = 8.8 Hz, 2H), 7.50 (s, 1H), 6.89 (d, J = 8.8 Hz, 1H), 6.82 (d, J = 6.4 Hz, 1H), 3.86 (s, 3H). MS m/z (ESI): 477.2 [M + H]. |

TABLE 1-continued

| No. | Compound Name | Starting material or regent different from that in Example 1 | Characterization Data |
|---|---|---|---|
| TD101316 | 6-(4-((1H-indazol-5-yl)amino)pyrimidin-2-yl)-N-(1-methyl-piperidin-4-yl)-1H-pyrazol-4-yl)-1H-indole-2-carboxamide | (structures shown: 6-bromobenzothiophene-2-carboxylic acid OH in step 1 of Example 1 was replaced with 6-bromo-1H-indole-2-carboxylic acid OH; and in step 4 was replaced with 4-(1-methylpiperidin-4-yl)-1H-pyrazol-4-amine and 3-aminotetrahydrofuran) | $^1$H NMR (400 MHz, DMSO-$d_6$) δ 13.02 (s, 1H), 12.01 (s, 1H), 10.51 (s, 1H), 9.58 (s, 1H), 8.55 (s, 1H), 8.35 (d, 1H), 8.30 (s, 1H), 8.15 (t, 2H), 8.06 (s, 1H), 7.75 (d, 1H), 7.65 (s, 1H), 7.59 (s, 2H), 7.32 (s, 1H), 6.65 (d, 1H), 4.13 (m, 1H), 2.86 (d, 2H), 2.21 (s, 3H), 2.00 (m, 6H). MS m/z (ESI): 533.2 [M + H]. |
| TD101317 | 6-(4-((1H-indazol-5-yl)amino)pyrimidin-2-yl)-N-(1'-methyl-[1,4'-bipiperidin]-4-yl)-1H-indole-2-carboxamide | (structures shown: 6-bromobenzothiophene-2-carboxylic acid OH in step 1 of Example 1 was replaced with 6-bromo-1H-indole-2-carboxylic acid OH; and in step 4 was replaced with 1'-methyl-[1,4'-bipiperidin]-4-amine HCl) | $^1$H NMR (400 MHz, CD$_3$OD) δ 8.45 (s, 1H), 8.26 (d, J = 6.0 Hz, 1H), 8.22 (s, 1H), 8.12-8.06 (m, 2H), 7.69 (d, J = 8.5 Hz, 1H), 7.65-7.57 (m, 2H), 7.16 (s, 1H), 6.63 (d, J = 6.0 Hz, 1H), 3.95-3.90 (m, 1H), 3.11-3.01 (m, 4H), 2.45-2.40 (m, 2H), 2.39 (s, 3H), 2.30-2.19 (m, 2H), 2.04-1.94 (m, 4H), 1.72-1.64 (m, 5H). MS m/z (ESI): 550.3 [M + H]. |

TABLE 1-continued

| No. | Compound Name | Starting material or regent different from that in Example 1 | Characterization Data |
|---|---|---|---|
| TDI01318 | 6-(4-((1H-indazol-5-yl)amino)-pyrimidin-2-yl)-N-(1'-methyl-[1,4'-bipiperidin]-3-yl)-1H-indole-2-carboxamide | OH in step 1 of Example 1 was replaced with (6-bromobenzothiophene-2-carboxylic acid) and (6-bromo-1H-indole-2-carboxylic acid); in step 4 was replaced with 3-amino-tetrahydrofuran and 1'-methyl-[1,4'-bipiperidin]-3-amine HCl | ¹H NMR (400 MHz, DMSO-d₆) δ 12.23 (s, 1H), 9.90 (s, 2H), 8.78 (d, J = 6.6 Hz, 1H), 8.43 (s, 1H), 8.34 (d, J = 6.6 Hz, 1H), 8.24 (s, 1H), 8.18 (s, 1H), 7.99 (d, J = 8.7 Hz, 1H), 7.84 (d, J = 8.4 Hz, 1H), 7.64 (t, J = 10.5 Hz, 2H), 7.30 (s, 1H), 6.82 (d, J = 6.0 Hz, 1H), 4.30 (s, 1H), 2.99 (s, 6H), 2.79 (s, 3H), 2.33 (s, 2H), 1.95 (dd, J = 36.5, 12.4 Hz, 8H). MS m/z (ESI): 550.3 [M + H]. |
| TDI01319 | (6-(4-((1H-indazol-5-yl)amino)-pyrimidin-2-yl)-1H-indol-2-yl)(4-(4-methyl-piperazin-1-yl)piperidin-1-yl)methanone | OH in step 1 of Example 1 was replaced with (6-bromobenzothiophene-2-carboxylic acid) and (6-bromo-1H-indole-2-carboxylic acid); in step 4 was replaced with 3-amino-tetrahydrofuran and 1-methyl-4-(piperidin-4-yl)piperazine | ¹H NMR (400 MHz, CD₃OD) δ 8.45 (s, 1H), 8.26 (d, J = 6.0 Hz, 1H), 8.22 (s, 1H), 8.08 (dd, J = 5.8, 2.6 Hz, 2H), 7.72 (d, J = 8.5 Hz, 1H), 7.61 (q, J = 8.9 Hz, 2H), 6.89 (s, 1H), 6.66 (d, J = 6.1 Hz, 1H), 4.97 (s, 6H), 4.56 (s, 3H), 3.96 (s, 4H), 2.76 (s, 4H), 2.50 (s, 3H). MS m/z (ESI): 536.3 [M + H]. |

TABLE 1-continued

| No. | Compound Name | Compound Structure | Starting material or regent different from that in Example 1 | Characterization Data |
|---|---|---|---|---|
| TDI01320 | (6-(4-((1H-indazol-5-yl)amino)-pyrimidin-2-yl)-1H-indol-2-yl)(9-methyl-3,9-diazaspiro[5.5]undecan-3-yl)methanone | 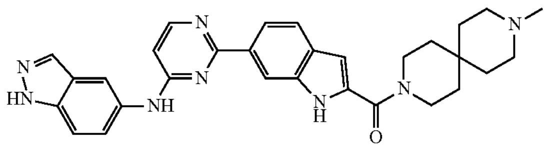 [SMILES: CN1CCC2(CC1)CCN(C(=O)c1cc3ccc(-c4nccc(Nc5ccc6[nH]ncc6c5)n4)cc3[nH]1)CC2] | Br-[benzothiophene]-C(O)OH in step 1 of Example 1 was replaced with Br-[indole-N-H]-C(O)OH; and [3-aminotetrahydrofuran] in step 4 was replaced with [9-methyl-3,9-diazaspiro[5.5]undecane] | $^{1}$H NMR (400 MHz, DMSO-$d_6$) δ 12.18 (s, 1H), 9.27 (s, 2H), 8.40 (s, 1H), 8.33 (d, J = 6.8 Hz, 1H), 8.19 (s, 2H), 7.95 (s, 2H), 7.81 (d, J = 8.6 Hz, 1H), 7.66 (d, J = 8.9 Hz, 1H), 7.62-7.56 (m, 1H), 6.86 (s, 2H), 3.29 (s, 2H), 3.09 (s, 2H), 2.79 (d, J = 4.5 Hz, 3H), 1.94 (d, J = 14.2 Hz, 2H), 1.71 (s, 2H), 1.49 (d, J = 26.0 Hz, 4H). MS m/z (ESI): 521.3 [M + H]. |
| TDI01324 | 6-(4-((4-(1H-pyrazol-4-yl)phenyl)-amino)-pyrimidin-2-yl)-N-cyclopropyl-1H-indole-2-carboxamide | 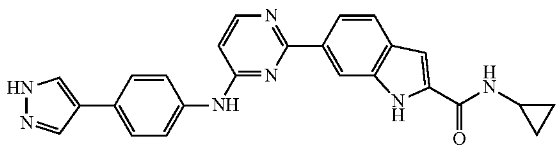 [SMILES: O=C(NC1CC1)c1cc2ccc(-c3nccc(Nc4ccc(-c5cn[nH]c5)cc4)n3)cc2[nH]1] | Br-[benzothiophene]-C(O)OH in step 1 of Example 1 was replaced with Br-[indole-N-H]-C(O)OH; BocN-[pyrazole]-[phenyl]-[pyrimidine-Cl]-NH (Reg-1-16) was used to replace BocN-[indazole]-NH-[pyrimidine-Cl] (Reg-1-1) in step 3; and [3-aminotetrahydrofuran]-NH$_2$ in step 4 was replaced with cyclopropylamine. | $^{1}$H NMR (400 MHz, DMSO-$d_6$) δ 12.09 (s, 1H), 10.55-10.29 (br, 1H), 8.61 (d, J = 4.0 Hz, 1H), 8.47 (s, 1H), 8.35 (d, J = 6.4 Hz, 1H), 8.07 (s, 2H), 7.98 (s, 1H), 7.79 (d, J = 8.0 Hz, 3H), 7.70 (d, J = 8.5 Hz, 2H), 7.19 (s, 1H), 6.81 (d, J = 6.8 Hz, 1H), 2.89 (d, J = 3.9 Hz, 1H), 0.75 (q, J = 7.0 Hz, 2H), 0.64-0.59 (m, 2H). MS m/z (ESI): 436.2 [M + H]. |

TABLE 1-continued

| No. | Compound Structure | Compound Name | Starting material or regent different from that in Example 1 | Characterization Data |
|---|---|---|---|---|
| TDI01329 | 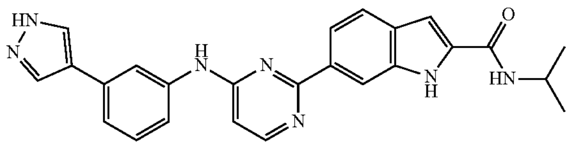 [SMILES: CC(C)NC(=O)c1cc2ccc(-c3nccc(Nc4cccc(-c5cn[nH]c5)c4)n3)cc2[nH]1] | 6-(4-((3-(1H-pyrazol-4-yl)phenyl)amino)pyrimidin-2-yl)-N-isopropyl-1H-indole-2-carboxamide | Br–[benzothiophene]–C(O)OH in step 1 of Example 1 was replaced with Br–[indole]–C(O)OH; (Reg-1-38) was used to replace [chloropyrimidine-indazole-Boc] (Reg-1-1) in step 3 was replaced with [Boc-pyrazole-phenyl-NH-pyrimidine-Cl]; and H$_2$N–[tetrahydrofuran] was replaced with H$_2$N-isobutyl in step 4. | $^1$H NMR (400 MHz, DMSO-d$_6$) δ 12.04 (s, 1H), 10.46 (s, 1H), 8.45 (s, 1H), 8.38 (dd, J = 7.2, 3.6 Hz, 2H), 8.12-8.00 (m, 3H), 7.97 (s, 1H), 7.77 (d, J = 8.4 Hz, 1H), 7.65 (s, 1H), 7.50-7.41 (m, 2H), 7.25 (s, 1H), 6.83 (d, J = 6.4 Hz, 1H), 4.18-4.13 (m, 1H), 1.21 (d, J = 6.4 Hz, 6H). MS m/z (ESI): 438.2 [M + H]. |
| TDI01330 | 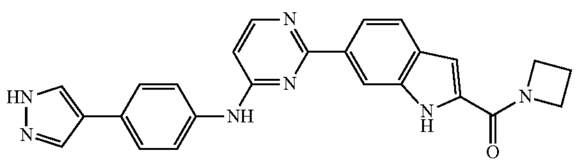 [SMILES: O=C(c1cc2ccc(-c3nccc(Nc4ccc(-c5cn[nH]c5)cc4)n3)cc2[nH]1)N1CCC1] | (6-(4-((4-(1H-pyrazol-4-yl)phenyl)amino)pyrimidin-2-yl)-1H-indol-2-yl)(azetidin-1-yl)methanone | Br–[benzothiophene]–C(O)OH in step 1 of Example 1 was replaced with Br–[indole]–C(O)OH; (Reg-1-6) [BocN-pyrazole-phenyl-NH-pyrimidine-Cl] was used to replace (Reg-1-1) [BocN-indazole-pyrimidine-Cl] in step 3; and H$_2$N–[tetrahydrofuran] in step 4 was replaced with HCl·HN–[azetidine]. | $^1$H NMR (400 MHz, DMSO-d$_6$) δ 12.19 (s, 1H), 10.77 (s, 1H), 8.48 (s, 1H), 8.35 (d, J = 6.7 Hz, 1H), 8.08 (s, 2H), 7.98 (d, J = 8.5 Hz, 1H), 7.88-7.76 (m, 3H), 7.72 (d, J = 8.5 Hz, 2H), 6.96-6.84 (m, 2H), 4.57 (s, 2H), 4.13 (s, 2H), 2.42-2.33 (m, 2H). MS m/z (ESI): 436.2 [M + H]. |

| No. | Compound Structure | Compound Name | Starting material or regent different from that in Example 1 | Characterization Data |
|---|---|---|---|---|
| TDI01331 | ![structure] | (6-(4-((4-(1H-pyrazol-4-yl)phenyl)amino)pyrimidin-2-yl)-1H-indol-2-yl)(morpholino)methanone | ![Br-benzothiophene-COOH] in step 1 of Example 1 was replaced with ![Br-indole-COOH]; in step 3 was replaced with (Reg-1-1) and (Reg-1-16); ![tetrahydrofuran-NH2] in step 4 was replaced with ![morpholine] | $^1$H NMR (400 MHz, CD$_3$OD) δ 8.41 (s, 1H), 8.20 (d, J = 7.2 Hz, 1H), 8.05 (s, 2H), 7.87 (s, 2H), 7.83 (d, J = 13.2 Hz, 2H), 7.75 (d, J = 8.4 Hz, 2H), 6.95 (s, 1H), 6.91 (d, J = 7.2 Hz, 1H), 3.86 (s, 4H), 3.76 (d, J = 4.4 Hz, 4H). MS m/z (ESI): 466.2 [M + H]. |

TABLE 1-continued

| No. | Compound Structure | Compound Name | Starting material or regent different from that in Example 1 | Characterization Data |
|---|---|---|---|---|
| TDI01332 | 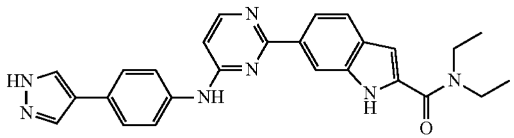 [SMILES: CCN(CC)C(=O)c1cc2ccc(-c3nccc(Nc4ccc(-c5cn[nH]c5)cc4)n3)cc2[nH]1] | 6-(4-(4-((1H-pyrazol-4-yl)phenyl)amino)pyrimidin-2-yl)-N,N-diethyl-1H-indole-2-carboxamide | OH in step 1 of Example 1 was replaced with Br-benzothiophene-COOH and Br-indole-COOH; in step 3 was replaced with (Reg-1-1) and (Reg-1-16); NH₂ in step 4 was replaced with HN(Et)₂ and 3-aminotetrahydrofuran | ¹H NMR (400 MHz, DMSO-d₆) δ 12.18 (s, 1H), 10.89-10.62 (br, 1H), 8.45 (s, 1H), 8.36 (s, 1H), 8.10 (d, J = 3.6 Hz, 2H), 7.96 (s, 1H), 7.91-7.75 (m, 3H), 7.73 (d, J = 7.9 Hz, 2H), 6.91 (s, 2H), 1.24 (s, 6H). MS m/z (ESI): 452.2 [M + H]. |
| TDI01333 | 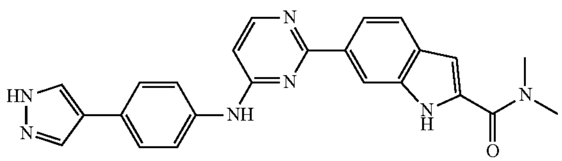 | 6-(4-(4-((1H-pyrazol-4-yl)phenyl)amino)pyrimidin-2-yl)-N,N-dimethylbenzo[b]thiophene-2-carboxamide | Cl in step 3 of Example 1 was replaced with (Reg-1-1) and (Reg-1-16); NH₂ in step 4 was replaced with HN(Me)₂ and 3-aminotetrahydrofuran | ¹H NMR (400 MHz, DMSO-d₆) δ 9.87 (s, 1H), 8.93 (s, 1H), 8.44-8.39 (m, 2H), 8.06 (t, J = 4.1 Hz, 2H), 7.89 (s, 1H), 7.79 (d, J = 8.4 Hz, 2H), 7.67 (d, J = 8.5 Hz, 2H), 6.78 (d, J = 6.0 Hz, 1H), 3.27 (s, 3H), 3.09 (s, 3H). MS m/z (ESI): 441.1 [M + H]. |

TABLE 1-continued

| No. | Compound Structure | Compound Name | Starting material or regent different from that in Example 1 | Characterization Data |
|---|---|---|---|---|
| TDI01334 | (structure) | 6-(4-((4-(1H-pyrazol-4-yl)phenyl)-aminothieno[3,2-d]pyrimidin-2-yl)-N,N-dimethyl-1H-indole-2-carboxamide | (Br-benzothiophene-COOH) in step 1 of Example 1 was replaced with (Br-indole-COOH); (Reg-1-1) in step 3 was replaced with (Reg-1-33); and NH$_2$ in step 4 was replaced with (dimethylaminotetrahydrofuran amine). | $^1$H NMR (400 MHz, DMSO-d$_6$) δ 11.92 (s, 1H), 10.09 (s, 1H), 8.56 (s, 1H), 8.29 (d, J = 5.2 Hz, 1H), 8.14 (d, J = 8.0 Hz, 1H), 8.09 (s, 2H), 7.92 (d, J = 8.0 Hz, 2H), 7.75-7.71 (m, 4H), 7.56 (d, J = 5.2 Hz, 1H), 6.95 (s, 1H), 2.54 (s, 6H). MS m/z (ESI): 480.2 [M + H]. |

TABLE 1-continued

| No. | Compound Structure | Compound Name | Starting material or regent different from that in Example 1 | Characterization Data |
|---|---|---|---|---|
| TDI01335 | (structure) | (6-(4-((4-(1H-pyrazol-4-yl)phenyl)amino)pyrimidin-2-yl)-1H-indol-2-yl)(3-methoxyazetidin-1-yl)methanone | Br—(benzothiophene)-C(=O)OH in step 1 of Example 1 was replaced with Br—(indole)-C(=O)OH; (Reg-1-1) in step 3 was replaced with (Reg-1-16) and (tetrahydrofuran-3-yl)-NH₂ in step 4 was replaced with 3-methoxyazetidine·HCl | ¹H NMR (400 MHz, DMSO-d₆) δ 12.16 (s, 1H), 10.46 (s, 1H), 8.49 (s, 1H), 8.36 (d, J = 6.5 Hz, 1H), 8.07 (s, 2H), 8.01 (d, J = 8.7 Hz, 1H), 7.81 (d, J = 8.5 Hz, 3H), 7.71 (d, J = 8.5 Hz, 2H), 6.96 (s, 1H), 6.82 (d, J = 6.4 Hz, 1H), 4.73 (s, 1H), 4.44-4.27 (m, 4H), 3.92 (d, J = 7.5 Hz, 1H), 3.28 (s, 3H). MS m/z (ESI): 466.2 [M + H]. |

TABLE 1-continued

| No. | Compound Structure | Compound Name | Starting material or regent different from that in Example 1 | Characterization Data |
|---|---|---|---|---|
| TDI01336 | (structure) | 6-(4-((4-(1H-pyrazol-4-yl)phenyl)-amino)-pyrimidin-2-yl)-N,N-bis(2-methoxyethyl)-1H-indole-2-carboxamide | OH in step 1 of Example 1 was replaced with (Reg-1-1) and (Reg-1-16) structures; in step 3 was replaced with; and NH₂ in step 4 was replaced with (tetrahydrofuran-3-amine) and bis(2-methoxyethyl)amine | ¹H NMR (400 MHz, DMSO-d₆) δ 12.00 (s, 1H), 10.27 (s, 1H), 8.49 (s, 1H), 8.36 (d, J = 6.3 Hz, 1H), 8.09-8.01 (m, 3H), 7.79 (dd, J = 17.6, 8.4 Hz, 3H), 7.69 (d, J = 8.5 Hz, 2H), 6.93 (s, 1H), 6.79 (d, J = 6.3 Hz, 1H), 3.61 (s, 8H), 3.29 (s, 6H). MS m/z (ESI): 512.2 [M + H]. |

TABLE 1-continued

| No. | Compound Structure | Compound Name | Starting material or regent different from that in Example 1 | Characterization Data |
|---|---|---|---|---|
| TDI01337 | (structure) | 6-(4-(4-(1H-pyrazol-4-yl)phenyl)amino)-pyrimidin-2-yl)-N-(tetrahydro-furan-3-yl)-1H-indole-2-carboxamide | (structure) OH in step 1 of Example 1 was replaced with (structure) OH; and (Reg-1-16) Cl was used to replace (Reg-1-1) Cl in step 3. | ¹H NMR (400 MHz, CD₃OD) δ 8.40 (s, 1H), 8.19 (d, J = 6.8 Hz, 1H), 8.03 (s, 2H), 7.89-7.82 (m, 3H), 7.79-7.68 (m, 3H), 7.25 (s, 1H), 6.90 (d, J = 6.8 Hz, 1H), 4.63-4.59 (m, 1H), 4.02-3.96 (m, 2H), 3.88-3.82 (m, 1H), 3.78-3.76 (m, 1H), 2.38-2.28 (m, 1H), 2.07-2.00 (m, 1H). MS m/z (ESI): 466.2 [M + H]. |

TABLE 1-continued

| No. | Compound Structure | Compound Name | Starting material or regent different from that in Example 1 | Characterization Data |
|---|---|---|---|---|
| TDI01338 | (structure shown) | 6-(4-((4-(1H-pyrazol-4-yl)phenyl)amino)-pyrimidin-2-yl)-N-(tetrahydro-2H-pyran-4-yl)-1H-indole-2-carboxamide | OH in step 1 of Example 1 was replaced with Br-benzothiophene-COOH and Br-indole-COOH (Reg-1-1); in step 3 was replaced with (Reg-1-16) 2-chloro-4-(4-(Boc-pyrazol-4-yl)phenylamino)pyrimidine; and NH$_2$ in step 4 was replaced with tetrahydrofuran-3-amine and 4-amino-tetrahydropyran·HCl. | $^1$H NMR (400 MHz, DMSO-d$_6$) δ 12.23 (s, 1H), 10.89 (s, 1H), 8.52 (d, J = 7.8 Hz, 1H), 8.44 (s, 1H), 8.34 (d, J = 6.8 Hz, 1H), 8.09 (s, 2H), 7.94 (d, J = 8.7 Hz, 1H), 7.86 (d, J = 8.5 Hz, 1H), 7.79 (d, J = 7.5 Hz, 2H), 7.74 (d, J = 8.5 Hz, 2H), 7.31 (s, 1H), 6.89 (d, J = 6.8 Hz, 1H), 3.92 (s, 1H), 3.89 (s, 1H), 3.45-3.39 (m, 3H), 1.81 (d, J = 12.6 Hz, 2H), 1.67-1.62 (m, 1H), 1.62-1.56 (m, 1H). MS m/z (ESI): 480.2 [M + H] |

TABLE 1-continued

| No. | Compound Structure | Compound Name | Starting material or regent different from that in Example 1 | Characterization Data |
|---|---|---|---|---|
| TDI01339 | (structure shown) | 6-(4-((4-(1H-pyrazol-4-yl)phenyl)-amino)-pyrimidin-2-yl)-N-(1-methyl-pyrrolidin-3-yl)-1H-indole-2-carboxamide | Br-benzothiophene-2-COOH in step 1 of Example 1 was replaced with Br-indole-2-COOH (Boc); (Reg-1-16) was used to replaced (Reg-1-1) in step 3; and 3-aminotetrahydrofuran-NH$_2$ in step 4 was replaced with 1-methylpyrrolidin-3-amine. | $^1$H NMR (400 MHz, DMSO-d$_6$) δ 12.07 (s, 1H), 10.31 (s, 1H), 10.15 (s, 1H), 8.90 (d, J = 52.4 Hz, 1H), 8.51 (s, 1H), 8.36 (d, J = 5.6 Hz, 1H), 8.06 (d, J = 12.0 Hz, 3H), 7.93-7.73 (m, 2H), 7.68 (d, J = 7.6 Hz, 1H), 7.27 (s, 1H), 6.78 (d, J = 5.6 Hz, 1H), 4.71 (s, 2H), 3.09-3.02 (m, 1H), 2.91 (d, J = 12.4 Hz, 3H), 2.77 (s, 1H), 2.33 (s, 3H), 2.11 (s, 2H). MS m/z (ESI): 479.2 [M + H]. |

TABLE 1-continued

| No. | Compound Structure | Compound Name | Starting material or regent different from that in Example 1 | Characterization Data |
|---|---|---|---|---|
| TD101340 | (structure) | 6-(4-((2-methoxy-4-(1H-pyrazol-4-yl)phenyl)amino)pyrimidin-2-yl)-N,N-dimethyl-1H-indole-2-carboxamide | OH in step 1 of Example 1 was replaced with (Br-benzothiophene-COOH) and (Br-indole-COOH); (Reg-1-1) in step 3 was replaced with (Reg-1-32) and NH₂ in step 4 was replaced with HN-(tetrahydrofuran). | ¹H NMR (400 MHz, CD₃OD) δ 8.37 (s, 1H), 8.17 (d, J = 7.3 Hz, 1H), 8.09 (s, 2H), 7.86-7.82 (m, 2H), 7.41-7.32 (m, 2H), 7.01 (s, 1H), 3.98 (s, 3H), 3.30 (s, 6H). MS m/z (ESI): 454.2 [M + H]. |
| TD101341 | (structure) | 6-(4-((2-fluoro-4-(1H-pyrazol-4-yl)phenyl)amino)pyrimidin-2-yl)-N,N-dimethyl-1H-indole-2-carboxamide | OH in step 1 of Example 1 was replaced with (Br-benzothiophene-COOH) and (Br-indole-COOH); (Reg-1-1) in step 3 was replaced with (Reg-1-29) and NH₂ in step 4 was replaced with HN-(tetrahydrofuran). | ¹H NMR (400 MHz, DMSO-d₆) δ 11.96 (s, 1H), 9.96 (s, 1H), 8.46-8.36 (m, 2H), 8.15 (s, 2H), 8.09-7.94 (m, 2H), 7.73 (d, J = 8.4 Hz, 1H), 7.66 (d, J = 12.5 Hz, 1H), 7.57 (d, J = 8.5 Hz, 1H), 6.94 (s, 1H), 6.86 (s, 1H), 3.08 (s, 6H). MS m/z (ESI): 442.2 [M + H]. |

TABLE 1-continued

| No. | Compound Structure | Compound Name | Starting material or regent different from that in Example 1 | Characterization Data |
|---|---|---|---|---|
| TDI01342 | (structure shown) | 6-(4-((4-(1H-pyrazol-4-yl)phenyl)amino)pyrimidin-2-yl)-N-(2-methoxyethyl)-N-methyl-1H-indole-2-carboxamide | (Br-benzothiophene-2-COOH) in step 1 of Example 1 was replaced with (Br-indole-2-COOH); (Reg-1-1) in step 3 was replaced with (Reg-1-16) and NH2 in step 4 was replaced with HN-CH2CH2-OMe (N-methyl) | $^1$H NMR (400 MHz, DMSO-d$_6$) δ 8.42 (s, 1H), 8.30 (d, J = 7.2 Hz, 1H), 8.10 (s, 2H), 7.90 (s, 2H), 7.77 (s, 4H), 7.61 (t, J = 10.0 Hz, 1H), 7.05 (s, 1H), 6.93 (d, J = 7.2 Hz, 1H), 3.60 (t, J = 5.6 Hz, 2H), 3.37 (s, 1H), 3.29 (s, 3H), 3.07 (s, 3H), 2.78 (s, 1H). MS m/z (ESI): 468.2 [M + H]. |

TABLE 1-continued

| No. | Compound Structure | Compound Name | Starting material or regent different from that in Example 1 | Characterization Data |
|---|---|---|---|---|
| TDI01343 | (structure) | (6-4-((4-(1H-pyrazol-4-yl)phenyl)amino)-pyrimidin-2-yl)-1H-indol-2-yl)(4-methyl-piperazin-1-yl)methanone | Br-[benzothiophene]-COOH in step 1 of Example 1 was replaced with Br-[indole]-COOH; (Reg-1-1) in step 3 was replaced with (Reg-1-16); and NH₂-tetrahydrofuran in step 4 was replaced with HN(4-methylpiperazine). | ¹H NMR (400 MHz, DMSO-d₆) δ 12.14 (s, 1H), 10.34 (s, 1H), 10.06 (s, 1H), 8.49 (s, 1H), 8.37 (d, J = 6.4 Hz, 1H), 8.06 (s, 2H), 8.04 (s, 1H), 7.80 (d, J = 8.0 Hz, 3H), 7.69 (d, J = 8.4 Hz, 2H), 7.02 (s, 1H), 6.81 (d, J = 6.0 Hz, 1H), 4.61 (s, 2H), 3.52 (s, 4H), 3.16 (s, 2H), 2.88 (s, 3H). MS m/z (ESI): 479.2 [M + H]. |

TABLE 1-continued

| No. | Compound Name | Compound Structure | Starting material or regent different from that in Example 1 | Characterization Data |
|---|---|---|---|---|
| TDI01344 | 6-(4-(4-(1H-pyrazol-4-yl)phenyl)-amino)-pyrimidin-2-yl)-N-methyl-N-(oxetan-3-1)-1H-indole-2-carboxamide | (structure shown) | OH in step 1 of Example 1 was replaced with Br-benzothiophene-COOH and Br-indole-COOH (Boc-protected); in step 3 was replaced with (Reg-1-1) and (Reg-1-16); and NH$_2$ in step 4 was replaced with HN-oxetan-3-yl and tetrahydrofuran-3-amine. | $^1$H NMR (400 MHz, CD$_3$OD + DMSO-d$_6$) δ 8.56 (s, 1H), 8.34 (d, J = 5.8 Hz, 1H), 8.17 (d, J = 8.5 Hz, 1H), 8.03 (s, 2H), 7.84 (d, J = 8.5 Hz, 2H), 7.75 (d, J = 8.4 Hz, 1H), 7.66 (d, J = 8.5 Hz, 1H), 6.92 (s, 1H), 6.68 (d, J = 5.9 Hz, 2H), 4.85 (dt, J = 17.3, 6.9 Hz, 4H), 4.12 (s, 1H), 3.40 (s, 3H). MS m/z (ESI): 466.2 [M + H]. |

TABLE 1-continued

| No. | Compound Structure | Compound Name | Starting material or regent different from that in Example 1 | Characterization Data |
|---|---|---|---|---|
| TDI01344-2A | (structure) | 6-(4-((4-(1H-pyrazol-4-yl)phenyl)amino)-pyrimidin-2-yl)-N-(1,3-dihydroxy-propan-2-yl)-N-methyl-1H-indole-2-carboxamide | (see below) | ¹H NMR (400 MHz, DMSO-d₆) δ 12.40 (s, 1H), 10.40 (s, 1H), 8.81 (s, 2H), 8.51 (s, 1H), 8.38 (d, J = 6.4 Hz, 1H), 8.07 (s, 2H), 7.87 (d, J = 8.5 Hz, 1H), 7.79 (d, J = 8.3 Hz, 2H), 7.70 (d, J = 8.5 Hz, 2H), 7.43 (s, 1H), 6.83 (d, J = 6.4 Hz, 1H), 5.70-5.40 (m, 2H), 4.56 (dd, J = 12.9, 5.0 Hz, 2H), 3.81 (dd, J = 13.0, 4.9 Hz, 2H), 3.59 (d, J = 4.9 Hz, 1H), 2.73 (s, 3H), MS m/z (ESI): 484.2 [M + H]. |

Starting material or regent: OH in step 1 of Example 1 was replaced with Br-benzothiophene-COOH and Br-indole-COOH; (Reg-1-1) and (Reg-1-16) in step 3 was replaced with (chloropyrimidinyl-aminophenyl-BocN-pyrazole structures); and NH₂ in step 4 was replaced with HN-(tetrahydrofuran-3-yl) and HN-(oxetan-3-yl)methyl.

TABLE 1-continued

| No. | Compound Structure | Compound Name | Starting material or regent different from that in Example 1 | Characterization Data |
|---|---|---|---|---|
| TDI01345 | (structure) | 6-(4-((4-(1H-pyrazol-4-yl)phenyl)amino)pyrimidin-2-yl)-N-methyl-N-(pyrrolidin-3-yl)-1H-indole-2-carboxamide | OH in step 1 of Example 1 was replaced with (Br-benzothiophene-COOH), (Br-indole-COOH) (Reg-1-1); in step 3 was replaced with (Reg-1-16); and NH$_2$ in step 4 was replaced with (tetrahydrofuran-3-amine) and (N-Boc-pyrrolidin-3-amine). | $^1$H NMR (400 MHz, DMSO-d$_6$) δ 12.02 (s, 1H), 8.89 (s, 1H), 8.79 (s, 1H), 8.51 (s, 1H), 8.37 (d, 1H), 8.06 (d, 3H), 7.79 (q, 3H), 7.68 (d, 2H), 7.00 (s, 1H), 6.77 (d, 1H), 5.17 (m, 1H), 3.47 (m, 1H), 3.23 (dd, 4H), 2.25 (m, 2H), 2.11 (m, 2H). MS m/z (ESI): 479.2 [M + H]. |

TABLE 1-continued

| No. | Compound Structure | Compound Name | Starting material or regent different from that in Example 1 | Characterization Data |
|---|---|---|---|---|
| TDI01346 | 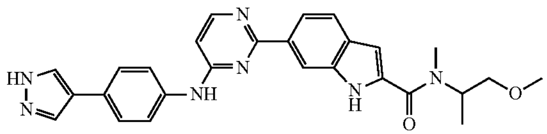 [SMILES: COCC(C)N(C)C(=O)c1cc2ccc(-c3nccc(Nc4ccc(-c5cn[nH]c5)cc4)n3)cc2[nH]1] | 6-(4-((4-(1H-pyrazol-4-yl)phenyl)amino)pyrimidin-2-yl)-N-(1-methoxypropan-2-yl)-N-methyl-1H-indole-2-carboxamide | Br—[benzothiophene]-C(O)OH in step 1 of Example 1 was replaced with Br—[indole]-C(O)OH; and (Reg-1-1) [4-(1H-pyrazol-4-yl, Boc)phenyl-NH-pyrimidine-2-Cl] | $^1$H NMR (400 MHz, CD$_3$OD) δ 8.40 (s, 1H), 8.20 (d, J = 7.2 Hz, 1H), 8.03 (s, 2H), 7.87-7.73 (m, 6H), 6.98 (d, J = 16.0 Hz, 1H), 6.90 (d, J = 7.2 Hz, 1H), 3.67-3.54 (m, 1H), 3.35 (s, 3H), 3.30 (s, 3H), 3.00 (s, 2H), 1.26 (d, J = 6.8 Hz, 3H). MS m/z (ESI): 482.2 [M + H]. |
| TDI01347 | 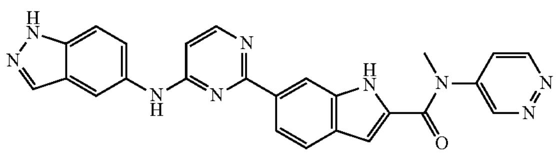 [SMILES: CN(C(=O)c1cc2ccc(-c3nccc(Nc4ccc5[nH]ncc5c4)n3)cc2[nH]1)c1ccnnc1] | 6-(4-((1H-indazol-5-yl)amino)pyrimidin-2-yl)-N-methyl-N-(pyridazin-4-yl)-1H-indole-2-carboxamide | Br—[benzothiophene]-C(O)OH in step 1 of Example 1 was replaced with Br—[indole]-C(O)OH; and (Reg-1-16) [indazole(Boc)-NH-pyrimidine-2-Cl]; NH$_2$ in step 4 was replaced with HN(Me)-[tetrahydrofuran-3-yl] with [pyridazin-4-yl-NH(Me)] in step 4 was replaced with | $^1$H NMR (400 MHz, DMSO-d$_6$) δ 12.33 (s, 1H), 10.61 (s, 1H), 9.28 (d, J = 2.1 Hz, 1H), 9.23 (d, J = 5.7 Hz, 1H), 8.43 (s, 1H), 8.34 (d, J = 6.5 Hz, 1H), 8.19 (d, J = 13.4 Hz, 2H), 7.95 (d, J = 8.6 Hz, 1H), 7.78 (dd, J = 5.7, 2.7 Hz, 1H), 7.70 (d, J = 8.5 Hz, 1H), 7.63 (q, J = 8.8 Hz, 2H), 6.82 (d, J = 6.5 Hz, 1H), 6.39 (s, 1H), 3.59 (s, 3H). MS m/z (ESI): 462.2 [M + H]. |

TABLE 1-continued

| No. | Compound Structure | Compound Name | Starting material or regent different from that in Example 1 | Characterization Data |
|---|---|---|---|---|
| TDI01348 | 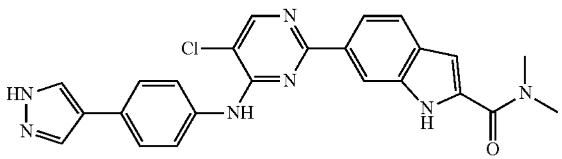 | 6-(4-((4-(1H-pyrazol-4-yl)phenyl)amino)-5-chloropyrimidin-2-yl)-N,N-dimethyl-1H-indole-2-carboxamide | OH in step 1 of Example 1 was replaced with (Reg-1-1) and (Reg-1-34); in step 3 was replaced with and NH₂ in step 4 was replaced with HN | ¹H NMR (400 MHz, DMSO-d₆) δ 11.85 (s, 1H), 9.45 (s, 1H), 9.09 (s, 1H), 8.53 (s, 1H), 8.46 (s, 1H), 8.08 (s, 2H), 8.02 (d, J = 8.8 Hz, 1H), 7.84 (d, J = 8.8 Hz, 2H), 7.68 (dd, J = 8.8, 4.0 Hz, 3H), 6.92 (s, 1H), 2.77 (d, J = 4.8 Hz, 6H). MS m/z (ESI): 458.1 [M + H]. |
| TDI01348 P-2 | 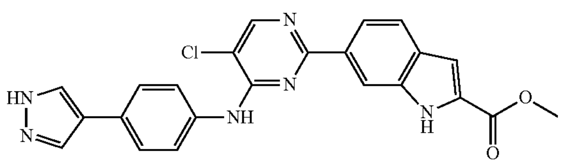 | methyl 6-(4-((4-(1H-pyrozol-4-yl)phenyl)amino)-5-chloropyrimidin-2-yl)-1H-indole-2-carboxylate | OH in step 1 of Example 1 was replaced with (Reg-1-1) and (Reg-1-34); in step 3 was replaced with and step 4 was performed according to the esterification reaction in step 1. | ¹H NMR (400 MHz, DMSO-d₆) δ 12.24 (s, 1H), 9.15 (s, 1H), 8.55 (s, 1H), 8.46 (s, 1H), 8.09 (s, 2H), 8.05 (d, J = 8.8 Hz, 1H), 7.83 (d, J = 8.8 Hz, 2H), 7.71 (dd, J = 16.8, 8.8 Hz, 3H), 7.20 (s, 1H), 3.90 (s, 3H). MS m/z (ESI): 445.1 [M + H]. |

TABLE 1-continued

| No. | Compound Structure | Compound Name | Starting material or regent different from that in Example 1 | Characterization Data |
|---|---|---|---|---|
| TDI01350 | 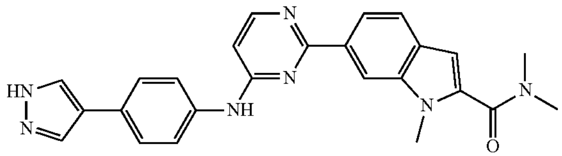 | 6-(4-((4-(1H-pyrazol-4-yl)phenyl)amino)pyrimidin-2-yl)-N,N,1-trimethyl-1H-indole-2-carboxamide | OH in step 1 of Example 1 was replaced with Br-[benzothiophene-COOH], Br-[1-methylindole-COOH]; (Reg-1-1) Boc-indazole-NH, (Reg-1-16) BocN-pyrazole-phenyl-NH; in step 3 was replaced with tetrahydrofuran-NH2 | ¹H NMR (400 MHz, CD₃OD) δ 8.40 (s, 1H), 8.23 (d, J = 7.2 Hz, 1H), 8.03 (s, 2H), 7.95 (d, J = 8.4 Hz, 1H), 7.85 (d, J = 8.4 Hz, 2H), 7.74 (d, J = 7.6 Hz, 3H), 6.91 (d, J = 7.2 Hz, 1H), 6.83 (s, 1H), 3.91 (s, 3H), 3.19 (s, 6H). MS m/z (ESI): 438.4 [M + H]. |
| TDI01353 | 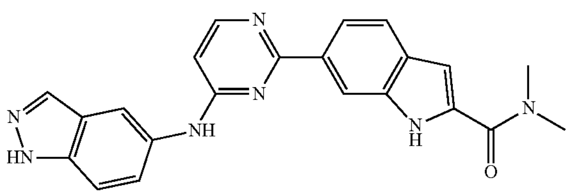 [SMILES: CN(C)C(=O)c1cc2ccc(-c3nccc(Nc4ccc5[nH]ncc5c4)n3)cc2[nH]1] | 6-(4-((1H-indazol-5-yl)amino)pyrimidin-2-yl)-N,N-dimethyl-1H-indole-2-carboxamide | OH in step 1 of Example 1 was replaced with Br-[benzothiophene-COOH], Br-[indole-COOH] and tetrahydrofuran-NH2; NH2 in step 4 was replaced with HN- | ¹H NMR (400 MHz, DMSO-d₆) δ 12.17 (s, 1H), 10.91 (s, 1H), 8.41 (s, 1H), 8.33 (d, J = 6.7 Hz, 1H), 8.20 (s, 2H), 7.94 (d, J = 8.4 Hz, 1H), 7.83 (d, J = 8.5 Hz, 1H), 7.66 (t, J = 10.1 Hz, 2H), 6.99 (s, 1H), 6.87 (d, J = 6.5 Hz, 1H), 3.32 (s, 3H), 3.10 (s, 3H). MS m/z (ESI): 398.1 [M + H]. |

TABLE 1-continued

| No. | Compound Structure | Compound Name | Starting material or regent different from that in Example 1 | Characterization Data |
|---|---|---|---|---|
| TDI01354 | 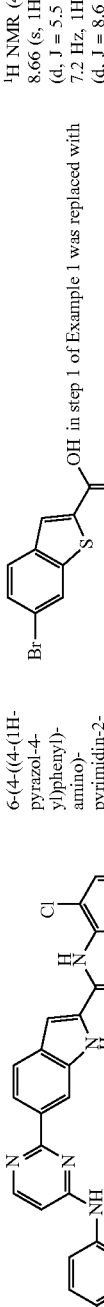 | 6-(4-((4-(1H-pyrazol-4-yl)phenyl)amino)-pyrimidin-2-yl)-N-(3-chloropyridin-4-yl)-1H-indole-2-carboxamide | 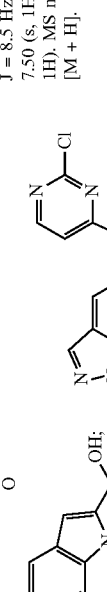 in step 3 was replaced with (Reg-1-16) and NH$_2$ in step 4 was replaced with 3-chloropyridin-4-amine | $^1$H NMR (400 MHz, CD$_3$OD) δ 8.66 (s, 1H), 8.47 (s, 2H), 8.40 (d, J = 5.5 Hz, 1H), 8.23 (d, J = 7.2 Hz, 1H), 8.03 (s, 2H), 7.98 (d, J = 8.6 Hz, 1H), 7.91 (d, J = 8.5 Hz, 1H), 7.76 (s, 4H), 7.50 (s, 1H), 6.93 (d, J = 7.2 Hz, 1H). MS m/z (ESI): 507.3 [M + H]. |

TABLE 1-continued

| No. | Compound Structure | Compound Name | Starting material or regent different from that in Example 1 | Characterization Data |
|---|---|---|---|---|
| TDI01355 | (structure shown) | 6-(4-((1H-pyrazol-4-yl)phenyl)-amino)-pyrimidin-2-yl)-N-methyl-N-(2,2,2-trifluoroethyl)-1H-indole-2-carboxamide | (reagents shown: Br-benzothiophene-COOH replacing starting OH in step 1; Boc-indazole-NH-pyrimidine-Cl (Reg-1-1) and Boc-pyrazole-phenyl-NH-pyrimidine-Cl (Reg-1-16) replacing in step 3; and tetrahydrofuran-CH$_2$-N(CF$_3$CH$_2$)H·HCl replacing NH$_2$ in step 4) | $^1$H NMR (400 MHz, DMSO-d$_6$) δ 12.10 (s, 1H), 10.07 (s, 1H), 8.52 (s, 1H), 8.37 (d, J = 6.4 Hz, 1H), 8.18-7.99 (m, 3H), 7.93-7.76 (m, 3H), 7.68 (d, J = 8.0 Hz, 2H), 7.11 (s, 1H), 6.76 (d, J = 5.6 Hz, 1H), 2.77 (d, J = 4.8 Hz, 2H), 2.55 (s, 3H), MS m/z (ESI): 492.1 [M + H]. |

TABLE 1-continued

| No. | Compound Structure | Compound Name | Starting material or regent different from that in Example 1 | Characterization Data |
|---|---|---|---|---|
| TDI01357 | 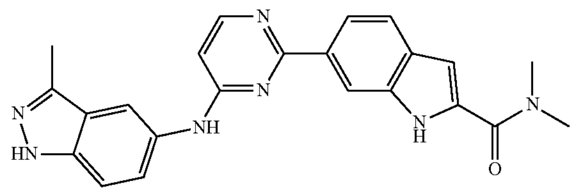 [SMILES: Cc1n[nH]c2ccc(Nc3ccnc(-c4ccc5cc(C(=O)N(C)C)[nH]c5c4)n3)cc12] | N,N-dimethyl-6-(4-((3-methyl-1H-indazol-5-yl)amino)pyrimidin-2-yl)-1H-indole-2-carboxamide | OH in step 1 of Example 1 was replaced with (structure of 6-bromobenzothiophene-2-carboxylic acid) and (structure of 6-bromoindole-2-carboxylic acid); in step 3 was replaced with (Reg-1-1, N-Boc indazolyl-NH-chloropyrimidine) and (Reg-1-20, 3-methyl-indazolyl-NH-chloropyrimidine); NH₂ in step 4 was replaced with dimethylamine hydrochloride. | ¹H NMR (400 MHz, DMSO-d₆) δ 12.71 (s, 1H), 12.08 (s, 1H), 10.67-10.44 (m, 1H), 8.43 (s, 1H), 8.32 (d, J = 6.4 Hz, 1H), 8.21 (s, 1H), 8.01 (d, J = 8.4 Hz, 1H), 7.79 (d, J = 8.4 Hz, 1H), 7.54 (s, 2H), 6.79 (s, 1H), 3.32 (s, 3H), 3.09 (s, 3H), 2.53 (s, 3H). MS m/z (ESI): 412.3 [M + H]. |
| TDI01360 | 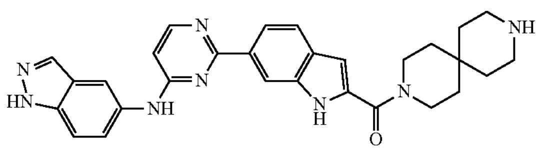 [SMILES: O=C(c1cc2ccc(-c3nccc(Nc4ccc5[nH]ncc5c4)n3)cc2[nH]1)N1CCC2(CCNCC2)CC1] | (6-(4-((1H-indazol-5-yl)amino)pyrimidin-2-yl)-1H-indol-2-yl)(3,9-diazaspiro[5.5]undecan-3-yl)methanone | OH in step 1 of Example 1 was replaced with (structure of 6-bromobenzothiophene-2-carboxylic acid) and (structure of 6-bromoindole-2-carboxylic acid); NH₂ in step 4 with (tetrahydrofuran-3-amine) was replaced with (NBoc-diazaspiro) ; and then the product was obtained by removal of Boc protection using TFA. | ¹H NMR (400 MHz, DMSO-d₆) δ 12.34 (s, 1H), 11.74 (s, 1H), 8.92 (s, 2H), 8.44 (s, 1H), 8.30 (d, J = 7.0 Hz, 2H), 8.22 (s, 1H), 8.02 (d, J = 8.5 Hz, 1H), 7.85 (d, J = 8.5 Hz, 1H), 7.75 (s, 1H), 7.69 (d, J = 8.6 Hz, 2H), 7.15 (s, 1H), 6.88 (s, 1H), 3.72 (s, 4H), 3.05 (s, 4H), 1.71 (s, 4H), 1.57 (s, 4H). MS m/z (ESI): 507.3 [M + H]. |

TABLE 1-continued

| No. | Compound Structure | Compound Name | Starting material or regent different from that in Example 1 | Characterization Data |
|---|---|---|---|---|
| TDI01360 P-1 | 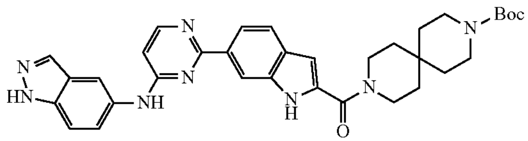 [SMILES: CC(C)(C)OC(=O)N1CCC2(CC1)CCN(C(=O)c1cc3ccc(-c4nccc(Nc5ccc6[nH]ncc6c5)n4)cc3[nH]1)CC2] | tert-butyl 9-(6-(4-((1H-indazol-5-yl)amino)-pyrimidin-2-yl)-1H-indole-2-carbonyl)-3,9-diazaspiro[5.5]undecan-3-carboxylate | OH in step 1 of Example 1 was replaced with [6-bromobenzothiophene-2-carboxylic acid] and [6-bromo-1H-indole-2-carboxylic acid]; and in step 4 was replaced with 3,9-diazaspiro[5.5]undecane (NBoc) | $^1$H NMR (400 MHz, CD$_3$OD) δ 8.44 (s, 1H), 8.26 (d, J = 6.0 Hz, 1H), 8.21 (s, 1H), 8.08 (s, 2H), 7.70 (d, J = 8.6 Hz, 1H), 7.59 (s, 2H), 6.83 (s, 1H), 6.63 (d, J = 6.0 Hz, 1H), 3.84 (s, 4H), 3.45 (s, 4H), 1.63 (s, 4H), 1.55 (s, 4H), 1.46 (s, 9H). MS m/z (ESI): 607.5 [M + H]. |
| TDI01363 | 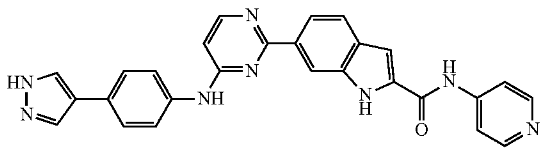 [SMILES: O=C(Nc1ccncc1)c1cc2ccc(-c3nccc(Nc4ccc(-c5cn[nH]c5)cc4)n3)cc2[nH]1] | 6-(4-(4-(1H-pyrazol-4-yl)phenyl)-amino)-pyrimidin-2-yl)-N-(pyridin-4-yl)-1H-indole-2-carboxamide | OH in step 1 of Example 1 was replaced with [6-bromobenzothiophene-2-carboxylic acid] and [6-bromo-1H-indole-2-carboxylic acid]; in step 3 was replaced with (Reg-1-1) and (Reg-1-16); and NH$_2$ in step 4 was replaced with [tetrahydrofuran-3-amine] and [4-aminopyridine]. | $^1$H NMR (400 MHz, DMSO-d$_6$) δ 12.38 (s, 1H), 11.40 (s, 1H), 9.96 (s, 1H), 8.75 (d, 2H), 8.58 (s, 1H), 8.39 (d, 1H), 8.28 (d, 2H), 8.15 (d, 1H), 8.05 (s, 2H), 7.89 (d, 1H), 7.83 (d, 2H), 7.68 (d, 3H), 6.76 (d, 1H). MS m/z (ESI): 473.2 [M + H]. |

TABLE 1-continued

| No. | Compound Structure | Compound Name | Starting material or regent different from that in Example 1 | Characterization Data |
|---|---|---|---|---|
| TDI01368 | 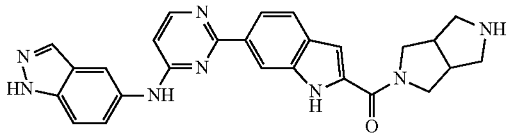 [SMILES: O=C(c1cc2ccc(-c3nccc(Nc4ccc5[nH]ncc5c4)n3)cc2[nH]1)N1CC2CNCC2C1] | (6-(4-((1H-indazol-5-yl)amino)-pyrimidin-2-yl)-1H-indol-2-yl)(hexahydro-pyrrolo[3,4-c]pyrrol-2(1H)-yl)methanone | OH in step 1 of Example 1 was replaced with [structure with Br, S, OH]; [structure with Br, indole, NH, OH]; and then the product was obtained by removal of Boc using TFA. | $^1$H NMR (400 MHz, CD$_3$OD + DMSO-d$_6$) δ 8.43 (s, 1H), 8.31 (d, J = 7.1 Hz, 2H), 8.21 (s, 1H), 7.91 (s, 2H), 7.70 (d, J = 7.5 Hz, 2H), 7.10 (s, 1H), 7.03 (s, 1H), 3.82 (d, J = 75.6 Hz, 4H), 3.46 (d, J = 12.0 Hz, 3H), 3.18 (d, J = 10.2 Hz, 3H). MS m/z (ESI): 480.3 [M + H]. |
| TDI01369 | 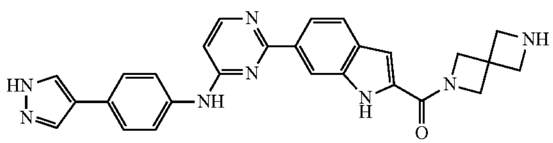 [SMILES: O=C(c1cc2ccc(-c3nccc(Nc4ccc(-c5cn[nH]c5)cc4)n3)cc2[nH]1)N1CC2(CNC2)C1] | (6-(4-(4-((1H-pyrazol-4-yl)phenyl)-amino)-pyrimidin-2-yl)-1H-indol-2-yl)(2,6-diazaspiro[3.3]heptan-2-yl)methanone | OH in step 1 of Example 1 was replaced with [structure with Br, S, OH]; [structure with Br, indole, NH, OH]; in step 3 was replaced with (Reg-1-1); (Reg-1-16); and NH$_2$ in step 4 was replaced with [Boc-spiro structure]; and then the product was obtained by removal of Boc using TFA. | $^1$H NMR (400 MHz, CD$_3$OD) δ 8.44 (s, 1H), 8.22 (d, J = 7.0 Hz, 1H), 8.02 (s, 2H), 7.90 (s, 2H), 7.75 (s, 4H), 6.99 (s, 1H), 6.91 (d, J = 7.2 Hz, 1H), 4.35 (s, 4H), 1.40-1.27 (m, 4H). MS m/z (ESI): 477.1 [M + H]. |

TABLE 1-continued

| No. | Compound Name | Compound Structure | Starting material or regent different from that in Example 1 | Characterization Data |
|---|---|---|---|---|
| TDI01370 | 6-(4-((1H-pyrazol-4-yl)phenyl)-amino)-thieno[3,2-d]pyrimidin-2-yl)-N-isopropyl-1H-indole-2-carboxamide | 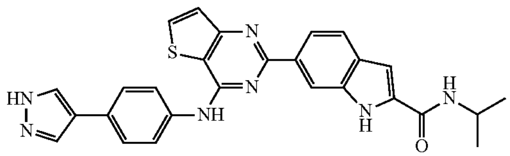 [SMILES: CC(C)NC(=O)c1cc2ccc(-c3nc(Nc4ccc(-c5cn[nH]c5)cc4)c4sccc4n3)cc2[nH]1] | OH in step 1 of Example 1 was replaced with (Reg-1-1); in step 3 was replaced with and | $^1$H NMR (400 MHz, CD$_3$OD) δ 8.45 (s, 1H), 8.35 (d, J = 5.6 Hz, 1H), 8.06 (s, 2H), 7.96 (d, J = 8.8 Hz, 1H), 7.83 (d, J = 8.4 Hz, 1H), 7.76 (d, J = 8.8 Hz, 4H), 7.57 (d, J = 5.6 Hz, 1H), 7.19 (s, 1H), 4.29-4.22 (m, 1H), 1.29 (d, J = 6.4 Hz, 6H). MS m/z (ESI): 494.2 [M + H]. |
| TDI01372 | 6-(4-((1H-indazol-5-yl)amino)-pyrimidin-2-yl)-N-(3-chloropyridin-4-yl)benzo[b]-thiophene-2-carboxamide | 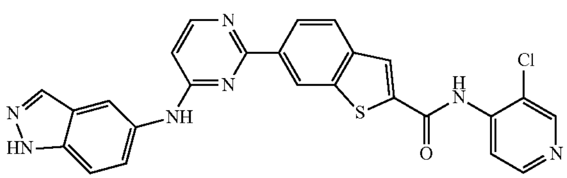 [SMILES: O=C(Nc1ccncc1Cl)c1cc2ccc(-c3nccc(Nc4ccc5[nH]ncc5c4)n3)cc2s1] | NH$_2$ in step 4 of Example 1 was replaced with (Reg-1-33) | $^1$H NMR (400 MHz, DMSO-d$_6$) δ 10.59 (s, 1H), 10.46 (s, 1H), 8.95 (s, 1H), 8.74 (s, 1H), 8.56 (d, J = 5.2 Hz, 1H), 8.52 (s, 1H), 8.41 (d, J = 6.4 Hz, 1H), 8.36 (d, J = 8.5 Hz, 1H), 8.23 (d, J = 8.5 Hz, 1H), 8.15 (s, 2H), 7.89 (d, J = 5.3 Hz, 1H), 7.63 (dd, J = 21.8, 8.8 Hz, 2H), 6.85 (d, J = 6.4 Hz, 1H). MS m/z (ESI): 498.1 [M + H]. |

TABLE 1-continued

| No. | Compound Name | Starting material or regent different from that in Example 1 | Characterization Data |
|---|---|---|---|
| TDI01379 | 6-(4-((4-(1H-pyrazol-4-yl)phenyl)-aminoythieno[3.2-d]pyrimidin-2-yl)-N-methyl-1H-indole-2-carboxamide | OH in step 1 of Example 1 was replaced with (Reg-1-1) and (Reg-1-33) in step 3 was replaced with | ¹H NMR (400 MHz, CD₃OD) δ 8.46 (s, 1H), 8.35 (d, J = 5.6 Hz, 1H), 8.06 (s, 2H), 7.98 (dd, J = 8.8, 1.2 Hz, 1H), 7.83 (d, J = 8.8 Hz, 1H), 7.82-7.75 (m, 4H), 7.57 (d, J = 5.6 Hz, 1H), 7.11 (s, 1H), 2.96 (s, 3H). MS m/z (ESI): 466.1 [M + H]. |
| TDI01380 | (6-(4-((1H-indazol-5-yl)amino)-pyrimidin-2-yl)-1H-indol-2-yl)(3-(4-methyl-piperazin-1-yl)piperidin-1-yl)methanone | OH in step 1 of Example 1 was replaced with, and NH₂ in step 4 was replaced with methylamine hydrochloride. in step 4 was replaced with | ¹H NMR (400 MHz, DMSO-d₆) δ 12.21 (s, 1H), 10.86 (s, 1H), 8.41 (s, 1H), 8.34 (d, J = 6.7 Hz, 1H), 8.20 (s, 2H), 7.96 (d, J = 8.3 Hz, 1H), 7.82 (d, J = 8.5 Hz, 1H), 7.65 (t, J = 12.0 Hz, 2H), 6.87 (d, J = 11.1 Hz, 2H), 4.39 (s, 2H), 4.22 (s, 2H), 3.15 (s, 7H), 2.78 (s, 3H), 2.66 (s, 2H), 1.97 (s, 1H), 1.82 (s, 1H), 1.65-1.46 (m, 2H). MS m/z (ESI): 536.3 [M + H]. |

TABLE 1-continued

| No. | Compound Structure | Compound Name | Starting material or regent different from that in Example 1 | Characterization Data |
|---|---|---|---|---|
| TDI01385 | 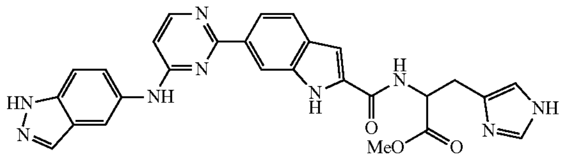 [SMILES: COC(=O)C(Cc1c[nH]cn1)NC(=O)c1cc2ccc(-c3nccc(Nc4ccc5[nH]ncc5c4)n3)cc2[nH]1] | methyl (6-(4-(((1H-indazol-5-yl)amino)-pyrimidin-2-yl)-1H-indole-2-carbonyl)-histidinate | ![structure]: Br-benzothiophene-2-COOH in step 1 of Example 1 was replaced with Br-indole-2-COOH; and tetrahydrofuran-3-amine (NH₂-THF-OH) in step 4 was replaced with methyl histidinate. | ¹H NMR (400 MHz, CD₃OD + DMSO-d₆) δ 8.89 (d, J = 5.2 Hz, 1H), 8.33 (s, 1H), 8.25-8.14 (m, 3H), 7.89-7.87 (m, 2H), 7.69 (d, J = 8.4 Hz, 1H), 7.62 (s, 1H), 7.40 (s, 1H), 7.27 (s, 1H), 6.89 (d, J = 4.4 Hz, 1H), 4.92-4.83 (m, 1H), 3.68 (s, 3H), 3.35-3.30 (m, 1H), 3.26-3.18 (m, 1H). MS m/z (ESI): 522.4 [M + H]. |
| TDI01388 | 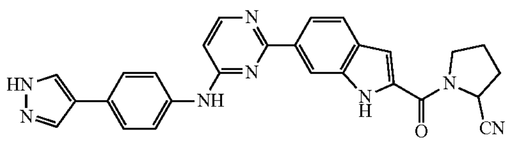 | 1-(6-(4-((1H-pyrazol-4-yl)phenyl)-amino)-pyrimidin-2-yl)-1H-indole-2-carbonyl)-pyrrolidine-2-carbonitrile | Br-benzothiophene-2-COOH in step 1 of Example 1 was replaced with Br-indole-2-COOH; (Reg-1-1) in step 3 was replaced with (Reg-1-16); and NH₂-THF in step 4 was replaced with HN-pyrrolidine-2-CN. | ¹H NMR (400 MHz, DMSO-d₆) δ 12.17 (s, 1H), 10.14 (s, 1H), 9.80 (s, 1H), 8.55 (s, 1H), 8.38 (d, J = 5.6 Hz, 1H), 8.06 (dd, J = 19.2, 11.2 Hz, 3H), 7.82 (t, J = 8.0 Hz, 3H), 7.69 (d, J = 8.0 Hz, 2H), 7.17 (s, 1H), 6.79 (d, J = 5.6 Hz, 1H), 5.03 (s, 1H), 4.71 (d, J = 7.2 Hz, 1H), 4.05 (s, 1H), 2.34 (s, 1H), 2.14 (s, 2H), 1.99 (s, 1H). MS m/z (ESI): 475.2 [M + H]. |

TABLE 1-continued

| No. | Compound Structure | Compound Name | Starting material or regent different from that in Example 1 | Characterization Data |
|---|---|---|---|---|
| TDI01390 | 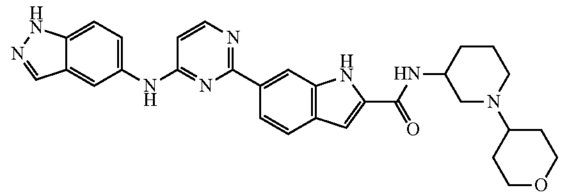 [SMILES: O=C(NC1CCCN(C2CCOCC2)C1)c1cc2ccc(-c3nccc(Nc4ccc5[nH]ncc5c4)n3)cc2[nH]1] | 6-(4-((1H-indazol-5-yl)amino)pyrimidin-2-yl)-N-(1-(tetrahydro-2H-pyran-4-yl)piperidin-3-yl)-1H-indole-2-carboxamide | OH in step 1 of Example 1 was replaced with Br-(benzothiophene-COOH) OH; and Br-(indole-COOH) OH; and H₂N-(tetrahydrofuran-3-amine) NH₂ in step 4 was replaced with H₂N-(piperidin-3-amine with tetrahydropyran) HCl | ¹H NMR (400 MHz, DMSO-d₆) δ 12.21 (s, 1H), 10.53 (s, 1H), 9.70 (s, 1H), 8.76 (d, J = 7.6 Hz, 1H), 8.44 (s, 1H), 8.34 (d, J = 6.5 Hz, 1H), 8.24 (s, 1H), 8.18 (s, 1H), 8.00 (d, J = 8.5 Hz, 1H), 7.83 (d, J = 8.5 Hz, 1H), 7.63 (q, J = 8.8 Hz, 2H), 7.29 (s, 1H), 6.81 (d, J = 6.5 Hz, 1H), 4.30 (s, 1H), 3.99 (d, J = 10.9 Hz, 2H), 3.38-3.28 (m, 4H), 2.92-2.77 (m, 2H), 2.00 (d, J = 8.4 Hz, 4H), 1.85-1.58 (m, 4H), 1.31-1.19 (m, 1H). MS m/z (ESI): 537.3 [M + H]. |
| TDI01393 | 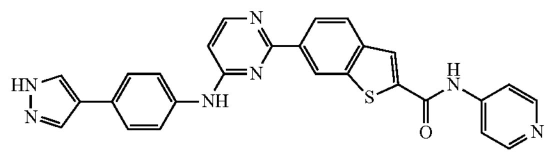 [SMILES: O=C(Nc1ccncc1)c1cc2ccc(-c3nccc(Nc4ccc(-c5cn[nH]c5)cc4)n3)cc2s1] | 6-(4-(4-(1H-pyrazol-4-yl)phenyl)-amino)pyrimidin-2-yl)-N-(pyridin-4-yl)benzo[b]-thiophene-2-carboxamide | Cl in step 3 of Example 1 was replaced with (Reg-1-1) and (Reg-1-16); NH₂ in step 4 was replaced with H₂N-pyridine | ¹H NMR (400 MHz, DMSO-d₆) δ 11.74 (s, 1H), 9.95 (s, 1H), 9.03 (s, 1H), 8.79 (d, J = 6.8 Hz, 2H), 8.61 (s, 1H), 8.46 (dd, J = 12.2, 7.6 Hz, 2H), 8.27 (dd, J = 17.7, 7.7 Hz, 3H), 8.06 (s, 2H), 7.79 (d, J = 8.3 Hz, 2H), 7.69 (s, 2H), 6.81 (d, J = 6.0 Hz, 1H). MS m/z (ESI): 490.2 [M + H]. |

TABLE 1-continued

| No. | Compound Structure | Compound Name | Starting material or reagent different from that in Example 1 | Characterization Data |
|---|---|---|---|---|
| TDI01397 | (structure shown) | 6-(4-((4-(1H-pyrazol-4-yl)phenyl)amino)pyrimidin-2-yl)-N-(pyridin-3-yl)-1H-indole-2-carboxamide | In step 1 of Example 1 was replaced with 6-bromobenzothiophene-2-carboxylic acid and 6-bromo-1H-indole-2-carboxylic acid; in step 3 was replaced with (Reg-1-1) and (Reg-1-16); and in step 4 was replaced with 3-aminopyridine (and tetrahydrofuran-3-amine). | $^1$H NMR (400 MHz, DMSO-d$_6$) δ 12.35 (s, 1H), 10.69 (s, 1H), 10.37 (s, 1H), 9.08 (s, 1H), 8.53 (s, 1H), 8.45-8.31 (m, 3H), 8.07 (s, 3H), 7.90 (d, J = 8.2 Hz, 1H), 7.82 (d, J = 1.5 Hz, 2H), 7.71 (d, J = 7.9 Hz, 2H), 7.57 (s, 2H), 6.82 (d, J = 6.1 Hz, 1H). MS m/z (ESI): 473.1 [M + H]. |

TABLE 1-continued

| No. | Compound Structure | Compound Name | Starting material or regent different from that in Example 1 | Characterization Data |
|---|---|---|---|---|
| TDI01398 | (structure) | 1-(6-(4-((1H-pyrazol-4-yl)phenyl)amino)pyrimidin-2-yl)-1H-indole-2-carbonyl)azetidine-3-carbonitrile | OH in step 1 of Example 1 was replaced with (Br-benzothiophene-2-carboxylic acid) and (Br-indole-2-carboxylic acid); in step 3 was replaced with (Reg-1-1) and (Reg-1-16); in step 4 was replaced with (3-aminotetrahydrofuran) and (3-cyanoazetidine) | $^1$H NMR (400 MHz, CD$_3$OD) δ 8.43 (s, 1H), 8.21 (d, J = 7.2 Hz, 1H), 8.03 (s, 2H), 7.92 (d, J = 8.4 Hz, 1H), 7.88-7.86 (m, 1H), 7.81-7.73 (m, 4H), 7.00 (s, 1H), 6.92 (d, J = 7.2 Hz, 1H), 4.55 (s, 2H), 4.39 (s, 2H), 3.91-3.85 (m, 1H). MS m/z (ESI): 461.2 [M + H]. |

TABLE 1-continued

| No. | Compound Structure | Compound Name | Starting material or regent different from that in Example 1 | Characterization Data |
|---|---|---|---|---|
| TDI01402 | (structure shown) | 6-(4-((4-(1H-pyrazol-4-yl)phenyl)amino)-pyrimidin-2-yl)-N-ethyl-N-methyl-1H-indole-2-carboxamide | OH in step 1 of Example 1 was replaced with (Br-benzothiophene-2-carboxylic acid) and (Br-indole-2-carboxylic acid); in step 3 was replaced with (Reg-1-1) and (Reg-1-16); NH₂ in step 4 was replaced with HN-(tetrahydrofuran-3-yl)ethyl. | ¹H NMR (400 MHz, DMSO-d₆) δ 12.16 (s, 1H), 10.79 (s, 1H), 8.44 (s, 1H), 8.35 (d, J = 6.7 Hz, 1H), 8.09 (s, 2H), 7.96 (d, J = 8.5 Hz, 1H), 7.81 (dd, J = 17.7, 7.6 Hz, 3H), 7.73 (d, J = 8.5 Hz, 2H), 6.98 (s, 1H), 6.87 (d, J = 6.6 Hz, 1H), 3.61 (s, 3H), 3.31 (s, 2H), 1.23 (s, 3H). MS m/z (ESI): 438.2 [M + H]. |

TABLE 1-continued

| No. | Compound Structure | Compound Name | Starting material or regent different from that in Example 1 | Characterization Data |
|---|---|---|---|---|
| TDI01404 | (structure) | (6-(4-((1H-indazol-5-yl)amino)-thieno[3,2-d]pyrimidin-2-yl)-1H-indol-2-yl)(3,9-diazaspiro[5.5]undecan-3-yl)methanone | (Reg-1-1) in step 1 of Example 1 was replaced with (structure); in step 3 was replaced with (Reg-1-4); and (structure) in step 4 was replaced with (structure); and then the product was obtained by deprotection with HCl. | $^1$H NMR (400 MHz, CD$_3$OD) δ 9.28 (s, 1H), 8.57 (s, 1H), 8.31 (d, J = 8.4 Hz, 1H), 8.14 (s, 1H), 8.01 (s, 1H), 7.72 (d, J = 8.4 Hz, 1H), 7.67 (d, J = 5.6 Hz, 1H), 7.61 (d, J = 8.8 Hz, 1H), 7.57 (d, J = 8.4 Hz, 1H), 7.49 (d, J = 5.6 Hz, 1H), 6.80 (s, 1H), 3.95-3.79 (m, 4H), 3.46-3.41 (m, 4H), 1.57-1.52 (m, 8H), 1.47 (s, 9H). MS m/z (ESI): 563.2 [M + H]. |

TABLE 1-continued

| No. | Compound Structure | Compound Name | Starting material or regent different from that in Example 1 | Characterization Data |
|---|---|---|---|---|
| TDI01405 | 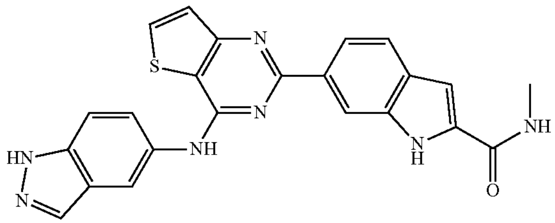 [SMILES: CNC(=O)c1cc2ccc(-c3nc(Nc4ccc5[nH]ncc5c4)c4sccc4n3)cc2[nH]1] | 6-(4-((1H-indazol-5-yl)amino)-thieno[3,2-d]pyrimidin-2-yl)-N-methyl-1H-indole-2-carboxamide |  in step 1 of Example 1 was replaced with ; in step 3 was replaced with (Reg-1-4); and —NH₂ in step 4 was replaced with methylamine hydrochloride. | ¹H NMR (400 MHz, DMSO-d₆) δ 13.16 (s, 1H), 11.95 (s, 1H), 10.07 (s, 1H), 8.60-8.49 (m, 2H), 8.28-8.08 (m, 4H), 7.73 (dd, J = 15.3, 8.8 Hz, 2H), 7.65 (d, J = 8.8 Hz, 1H), 7.52 (d, J = 5.4 Hz, 1H), 7.12 (s, 1H), 2.84 (d, J = 4.4 Hz, 3H). MS m/z (ESI): 440.3 [M + H]. |

TABLE 1-continued

| No. | Compound Structure | Compound Name | Starting material or regent different from that in Example 1 | Characterization Data |
|---|---|---|---|---|
| TDI01406 | (structure) | 6-(4-((1H-indazol-5-yl)amino)thieno[3,2-d]pyrimidin-2-yl)-N,N-dimethyl-1H-indole-2-carboxamide | (Br-benzothiophene-2-carboxylic acid) OH in step 1 of Example 1 was replaced with (Br-indole-2-carboxylic acid) OH; in step 3 was replaced with (Reg-1-1) and (Reg-1-4); -NH$_2$ in step 4 was replaced with dimethylamine hydrochloride. | $^1$H NMR (400 MHz, DMSO-d$_6$) δ 13.17 (s, 1H), 11.94 (s, 1H), 8.51 (s, 1H), 8.18 (m, 3H), 7.88-7.41 (m, 4H), 6.94 (s, 1H), 3.09 (s, 6H). MS m/z (ESI): 454.1 [M + H]. |

TABLE 1-continued

| No. | Compound Structure | Compound Name | Starting material or regent different from that in Example 1 | Characterization Data |
|---|---|---|---|---|
| TD101415 | | 6-(4-(4-(1H-pyrazol-4-yl)phenyl)-amino)-pyrimidin-2-yl)-N-ethyl-N-(2-hydroxyethyl)-1H-indole-2-carboxamide | OH in step 1 of Example 1 was replaced with (Reg-1-1) and (Reg-1-16); in step 3 was replaced with NH$_2$ in step 4 was replaced with | $^1$H NMR (400 MHz, CD$_3$OD) δ 8.40 (s, 1H), 8.20 (d, J = 7.2 Hz, 1H), 8.03 (s, 2H), 7.87 (s, 2H), 7.75 (s, 4H), 7.04 (s, 1H), 6.90 (d, J = 7.2 Hz, 1H), 3.84 (d, J = 5.0 Hz, 2H), 3.77 (s, 4H), 1.32 (s, 3H). MS m/z (ESI): 468.1 [M + H]. |
| TD101417 | | 6-(4-((1H-indazol-5-yl)amino)-pyrimidin-2-yl)-N,N-diethyl-benzo[b]thiophene-2-carboxamide | NH$_2$ in step 4 of Example 1 was replace with diethylamine. | $^1$H NMR (400 MHz, DMSO-d$_6$) δ 13.12 (s, 1H), 10.31 (s, 2H), 8.89 (s, 1H), 8.39 (d, J = 6.3 Hz, 1H), 8.33 (d, J = 8.4 Hz, 1H), 8.12 (dd, J = 14.6, 9.1 Hz, 3H), 7.80 (s, 1H), 7.61 (d, J = 13.3 Hz, 2H), 6.80 (d, J = 6.2 Hz, 1H), 3.54-3.52 (m, 4H), 1.22-1.20 (m, 6H). MS m/z (ESI): 443.2 [M + H]. |

TABLE 1-continued

| No. | Compound Structure | Compound Name | Starting material or regent different from that in Example 1 | Characterization Data |
|---|---|---|---|---|
| TDI01421 | (structure shown) | 6-(4-((4-(1H-pyrazol-4-yl)phenyl)-amino)-pyrimidin-2-yl)-N-methyl-N-(pyridin-4-yl)-1H-indole-2-carboxamide | Br—(benzothiophene-2-COOH) —OH in step 1 of Example 1 was replaced with Br—(indole-2-COOH) —OH; in step 3 was replaced with (Reg-1-1) and (Reg-1-16); —NH$_2$ in step 4 was replaced with (tetrahydrofuran-3-amine) and (N-methyl-pyridin-4-amine). | $^1$H NMR (400 MHz, DMSO-d$_6$) δ 12.35 (s, 1H), 10.42 (s, 1H), 8.68 (d, J = 6.6 Hz, 2H), 8.48 (s, 1H), 8.36 (d, J = 6.4 Hz, 1H), 8.07 (s, 2H), 7.98 (d, J = 8.4 Hz, 1H), 7.79 (d, J = 8.3 Hz, 2H), 7.71 (dd, J = 10.2, 5.5 Hz, 5H), 6.82 (d, J = 6.5 Hz, 1H), 6.58 (s, 1H), 3.62 (s, 3H). MS m/z (ESI): 487.2 [M + H]. |

TABLE 1-continued
| No. | Compound Structure | Compound Name | Starting material or regent different from that in Example 1 | Characterization Data |
|---|---|---|---|---|
| TD101422 | 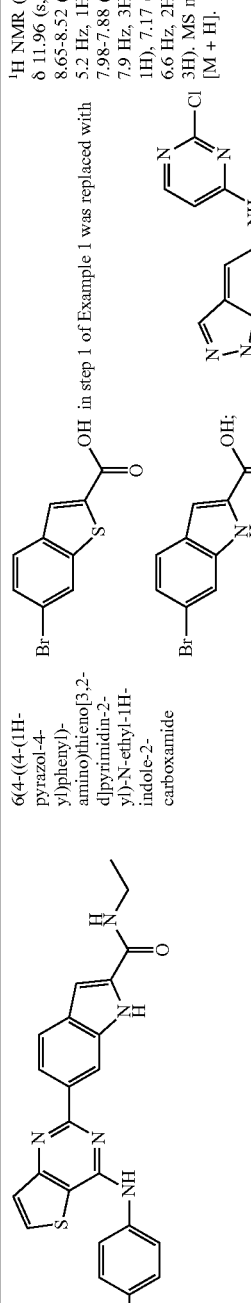 | 6-(4-((1H-pyrazol-4-yl)phenyl)-aminothieno[3,2-d]pyrimidin-2-yl)-N-ethyl-1H-indole-2-carboxamide | (see structures at right) | $^1$H NMR (400 MHz, DMSO-d$_6$) δ 11.96 (s, 1H), 10.12 (s, 1H), 8.65-8.52 (m, 2H), 8.30 (d, J = 5.2 Hz, 1H), 8.20-8.06 (m, 3H), 7.98-7.88 (m, 2H), 7.74 (t, J = 7.9 Hz, 3H), 7.57 (d, J = 5.3 Hz, 1H), 7.17 (s, 1H), 3.35 (d, J = 6.6 Hz, 2H), 1.17 (t, J = 7.1 Hz, 3H). MS m/z (ESI): 480.3 [M + H]. |

TABLE 1-continued

| No. | Compound Name | Starting material or regent different from that in Example 1 | Characterization Data |
|---|---|---|---|
| TDI01423 | 6-(4-((4-(1H-pyrazol-4-yl)phenyl)amino)thieno[3,2-d]pyrimidin-2-yl)-N-(tetrahydrofuran-3-yl)-1H-indole-2-carboxamide | (Reg-1-1) and (Reg-1-33) in step 3 was replaced with | $^1$H NMR (400 MHz, CD$_3$OD) δ 8.41 (s, 1H), 8.36 (d, J = 4.4 Hz, 1H), 8.05 (s, 2H), 7.92 (d, J = 8.0 Hz, 1H), 7.81 (d, J = 8.4 Hz, 1H), 7.80-7.72 (m, 4H), 7.56 (d, J = 4.8 Hz, 1H), 7.21 (s, 1H), 4.63-4.61 (m, 1H), 4.05-3.95 (m, 2H), 3.87-3.85 (m, 1H), 3.80-3.73 (m, 1H), 2.38-2.28 (m, 1H), 2.05-2.03 (m, 1H), MS m/z (ESI): 522.2 [M + H]. |

TABLE 1-continued

| No. | Compound Structure | Compound Name | Starting material or regent different from that in Example 1 | Characterization Data |
|---|---|---|---|---|
| TDI01424 | 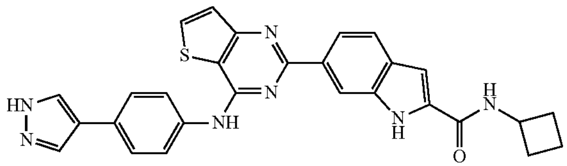 [SMILES: O=C(NC1CCC1)c1cc2ccc(-c3nc(Nc4ccc(-c5cn[nH]c5)cc4)c4sccc4n3)cc2[nH]1] | 6-(4-((4-(1H-pyrazol-4-yl)phenyl)-amino)-thieno[3,2-d]pyrimidin-2-yl)-N-cyclobutyl-1H-indole-2-carboxamide | OH in step 1 of Example 1 was replaced with structure (Reg-1-1); in step 3 was replaced with structure (Reg-1-33); and NH₂ in step 4 was replaced with cyclobutyl-NH₂. | ¹H NMR (400 MHz, CD₃OD) δ 8.46 (s, 1H), 8.40 (s, 1H), 8.08 (brs, 2H), 7.96 (d, J = 8.4 Hz, 1H), 7.86 (d, J = 8.4 Hz, 1H), 7.80-7.72 (m, 4H), 7.61 (d, J = 4.8 Hz, 1H), 7.22 (s, 1H), 4.58-4.51 (m, 1H), 2.39-2.37 (m, 2H), 2.21-2.12 (m, 2H), 1.85-1.76 (m, 2H), MS m/z (ESI): 506.3 |

TABLE 1-continued

| No. | Compound Name | Starting material or regent different from that in Example 1 | Characterization Data |
|---|---|---|---|
| TDI01425 | (6-(4-((4-(1H-pyrazol-4-yl)phenyl)amino)-pyrimidin-2-yl)-1H-indol-2-yl)(3,9-diazaspiro[5.5]undecan-3-yl)methanone | Br—[benzothiophene-2-COOH] in step 1 of Example 1 was replaced with Br—[indole-2-COOH]; (Reg-1-1) [2-chloropyrimidin-4-yl-NH-indazole-Boc]; in step 3 was replaced with (Reg-1-16) [2-chloropyrimidin-4-yl-NH-phenyl-pyrazole-BocN]; [tetrahydrofuran-3-yl-NH2] in step 4 was replaced with [Boc-diazaspiro-NH]; and then the product was obtained by removal of Boc using TFA. | $^1$H NMR (400 MHz, CD$_3$OD) δ 8.37 (s, 1H), 8.18 (d, J = 7.2 Hz, 1H), 8.03 (s, 2H), 7.84 (s, 2H), 7.71 (d, J = 7.9 Hz, 4H), 6.94-6.83 (m, 2H), 3.84 (s, 4H), 3.22 (s, 4H), 1.91-1.75 (m, 4H), 1.69 (s, 4H). MS m/z (ESI): 533.3 [M + H]. |

TABLE 1-continued

| No. | Compound Structure | Compound Name | Starting material or regent different from that in Example 1 | Characterization Data |
|---|---|---|---|---|
| TDI01428 | 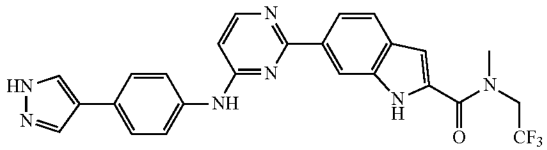 | 6-(4-((4-(1H-pyrazol-4-yl)phenyl)-amino)-pyrimidin-2-yl)-N-methyl-N-(2,2,2-trifluoroethyl)-benzo[b]-thiophene-2-carboxamide | Cl in step 3 of Example 1 (Reg-1-1) was replaced with (Reg-1-16); and NH$_2$ in step 4 was replaced with HN–CH$_2$CF$_3$ | $^1$H NMR (400 MHz, DMSO-d$_6$) δ 9.89 (s, 1H), 8.96 (s, 1H), 8.42 (d, J = 6.3 Hz, 2H), 8.08 (d, J = 16.4 Hz, 3H), 7.78 (d, J = 6.6 Hz, 2H), 7.68 (d, J = 7.6 Hz, 2H), 6.78 (d, J = 5.6 Hz, 1H), 4.47 (d, J = 9.1 Hz, 2H), 3.41 (s, 3H). MS m/z (ESI): 509.2 [M + H]. |
| TDI01439 | 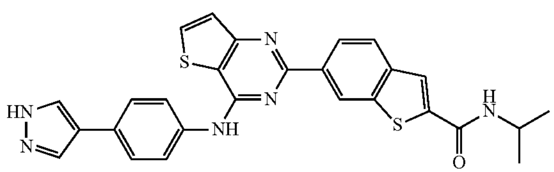 [SMILES: CC(C)NC(=O)c1cc2ccc(-c3nc(Nc4ccc(-c5cn[nH]c5)cc4)c4sccc4n3)cc2s1] | 6-(4-((4-(1H-pyrazol-4-yl)phenyl)-amino)thieno[3,2-d]pyrimidin-2-yl)-N-isopropyl-benzo[b]thiophene-2-carboxamide | Cl in step 3 of Example 1 (Reg-1-1) was replaced with (Reg-1-33); and NH$_2$ in step 4 was replaced with isopropylamine. | $^1$H NMR (400 MHz, DMSO-d$_6$) δ 9.99 (s, 1H), 8.97 (s, 1H), 8.59 (d, J = 7.2 Hz, 1H), 8.46 (d, J = 8.8 Hz, 1H), 8.30 (d, J = 5.6 Hz, 1H), 8.18 (s, 1H), 8.15-8.02 (m, 3H), 7.88 (d, J = 8.8 Hz, 2H), 7.72 (d, J = 8.8 Hz, 2H), 7.57 (d, J = 5.6 Hz, 1H), 4.13-4.08 (m, 1H), 1.21 (d, J = 6.4 Hz, 6H). MS m/z (ESI): 511.1 [M + H]. |

TABLE 1-continued

| No. | Compound Structure | Compound Name | Starting material or regent different from that in Example 1 | Characterization Data |
|---|---|---|---|---|
| TDI01456 | (structure) | 6-(4-((4-(1H-pyrazol-4-yl)phenyl)amino)pyrimidin-2-yl)-N-(2,2,2-trifluoroethyl)-benzo[b]thiophene-2-carboxamide | (Reg-1-1) and (Reg-1-16); NH₂ in step 4 was replaced with trifluoroethylamine. | ¹H NMR (400 MHz, DMSO-d₆) δ 9.93 (s, 1H), 9.49 (t, J = 6.3 Hz, 1H), 8.96 (s, 1H), 8.42 (dd, J = 6.6, 3.6 Hz, 2H), 8.29 (s, 1H), 8.13 (d, J = 8.5 Hz, 1H), 8.07 (s, 2H), 7.78 (d, J = 8.5 Hz, 2H), 7.68 (d, J = 8.6 Hz, 2H), 6.79 (d, J = 6.0 Hz, 1H), 4.17-4.11 (m, 2H). MS m/z (ESI): 495.1 [M + H]. |
| TDI01471 | (structure) | (6-(4-((4-(1H-pyrazol-4-yl)phenyl)amino)pyrimidin-2-yl)benzo[b]thiophen-2-yl)(3,3-difluoroazetidin-1-yl)methanone | (Reg-1-1) and (Reg-1-16); NH₂ in step 4 was replaced with 3,3-difluoroazetidine HCl. | ¹H NMR (400 MHz, CD₃OD) δ 8.91 (s, 1H), 8.41-8.34 (m, 2H), 8.20 (d, J = 8.4 Hz, 1H), 8.11 (s, 2H), 8.01 (s, 1H), 7.80-7.76 (m, 4H), 6.96 (d, J = 6.8 Hz, 2H), 5.07 (s, 4H). MS m/z (ESI): 489.1 [M + H]. |

TABLE 1-continued

| No. | Compound Structure | Compound Name | Starting material or regent different from that in Example 1 | Characterization Data |
|---|---|---|---|---|
| TDI01500 | (structure) | 1-(6-(4-((1H-pyrazol-4-yl)phenyl)-amino)-pyrimidin-2-yl)benzo[b]thiophene-2-carbonyl)azetidine-3-carbonitrile | Cl in step 3 of Example 1 (Reg-1-1) was replaced with (Reg-1-16) and NH₂ was replaced with (azetidine-CN) | ¹H NMR (400 MHz, DMSO-d₆) δ 9.86 (s, 1H), 8.95 (s, 1H), 8.44-8.40 (m, 2H), 8.11-8.03 (m, 3H), 7.96 (s, 1H), 7.78 (d, J = 8.2 Hz, 2H), 7.67 (d, J = 8.4 Hz, 2H), 6.78 (d, J = 5.9 Hz, 1H), 4.86 (s, 2H), 4.41 (s, 1H), 4.27 (s, 1H), 3.97 (d, J = 7.4 Hz, 1H). MS m/z (ESI): 478.1 [M + H]. |
| TDI01525 | (structure) | (6-(4-((1H-pyrazol-4-yl)phenyl)aminothieno[3,2-d]pyrimidin-2-yl)benzo[b]thiophen-2-yl)(3,3-difluoroazetidin-1-yl)methanone | Cl in step 3 of Example 1 (Reg-1-1) was replaced with (Reg-1-33) and NH₂ was replaced with (3,3-difluoroazetidine·HCl) | ¹H NMR (400 MHz, DMSO-d₆) δ 9.85 (s, 1H), 9.01 (s, 1H), 8.52 (dd, J = 8.5, 1.4 Hz, 1H), 8.44 (s, 2H), 8.27 (d, J = 5.4 Hz, 1H), 8.07 (d, J = 8.5 Hz, 1H), 8.00 (s, 1H), 7.89 (d, J = 8.6 Hz, 2H), 7.71 (d, J = 8.6 Hz, 1H), 7.56 (d, J = 5.4 Hz, 1H), 5.08 (s, 2H), 4.60 (s, 2H). MS m/z (ESI): 545.1 [M + H]. |

TABLE 1-continued

| No. | Compound Structure | Compound Name | Starting material or regent different from that in Example 1 | Characterization Data |
|---|---|---|---|---|
| TDI01801 | (structure) | 6-(4-((1H-indazol-5-yl)amino)-6-methoxypyrimidin-2-yl)-N-(pyridazin-4-yl)-1H-indole-2-carboxamide | OH in step 1 of Example 1 was replaced with (Reg-1-1); in step 3 was replaced with (Reg-1-82); NH₂ in step 4 was replaced with (structure) | $^1$H NMR (400 MHz, DMSO-d$_6$) δ 12.29 (s, 1H), 11.10 (s, 1H), 9.91 (s, 1H), 9.60 (s, 1H), 9.20 (d, J = 6.0 Hz, 1H), 8.30 (s, 1H), 8.22 (s, 1H), 8.18 (s, 1H), 8.07 (s, 1H), 7.89 (d, J = 8.4 Hz, 1H), 7.74 (d, 8.8 Hz, 1H), 7.61 (s, 1H), 7.55 (t, J = 8.7 Hz, 2H), 6.93 (s, 1H), 4.01 (s, 3H). MS m/z (ESI): 478.2 [M + H]. |

TABLE 1-continued

| No. | Compound Structure | Compound Name | Starting material or regent different from that in Example 1 | Characterization Data |
|---|---|---|---|---|
| TDI01803 | 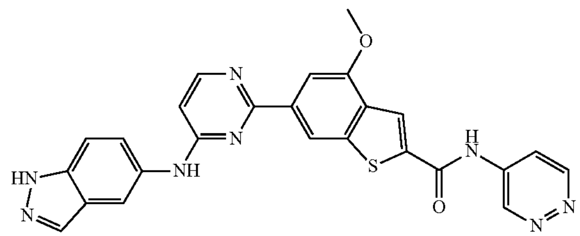 [SMILES: COc1cc(-c2nccc(Nc3ccc4[nH]ncc4c3)n2)cc2sc(C(=O)Nc3ccnnc3)cc12] | 6-(4-((1H-indazol-5-yl)amino)pyrimidin-2-yl)-4-methoxy-N-(pyridazin-4-yl)benzo[b]thiophene-2-carboxamide | The synthesis started from step 2 of Example 1. [methyl 6-bromo-4-methoxybenzo[b]thiophene-2-carboxylate] in step 2 of Example 1 was replaced with [structure], and H₂N-pyridazine in step 4 was replaced with 3-aminotetrahydrofuran. | ¹H NMR (400 MHz, DMSO-d₆) δ 13.04 (s, 1H), 11.06 (s, 1H), 9.72 (s, 1H), 9.55 (s, 1H), 9.11 (d, J = 5.8 Hz, 1H), 8.61 (d, J = 6.3 Hz, 2H), 8.57 (d, J = 3.9 Hz, 1H), 8.40 (d, J = 5.8 Hz, 1H), 8.31 (s, 1H), 8.10 (dd, J = 5.9, 2.6 Hz, 1H), 8.06 (s, 1H), 8.01 (s, 1H), 7.78 (t, J = 7.6 Hz, 1H), 7.58 (dd, J = 16.2, 8.8 Hz, 2H), 7.40-7.37 (m, 1H), 6.73 (d, J = 5.9 Hz, 1H), 4.12 (s, 3H). MS m/z (ESI): 494.9 [M + H]. |
| TDI01804 | 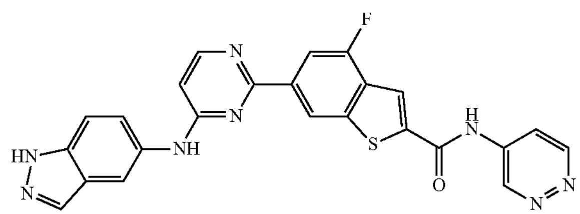 [SMILES: O=C(Nc1ccnnc1)c1cc2c(F)cc(-c3nccc(Nc4ccc5[nH]ncc5c4)n3)cc2s1] | 6-(4-((1H-indazol-5-yl)amino)pyrimidin-2-yl)-4-fluoro-N-(pyridazin-4-yl)benzo[b]thiophene-2-carboxamide | The synthesis started from step 2 of Example 1. [methyl 6-bromo-4-fluorobenzo[b]thiophene-2-carboxylate] in step 2 of Example 1 was replaced with [structure], and H₂N-pyridazine in step 4 was replaced with 3-aminotetrahydrofuran. | ¹H NMR (400 MHz, DMSO-d₆) δ 13.06 (s, 1H), 11.12 (s, 1H), 9.73 (s, 1H), 9.53 (s, 1H), 9.13 (d, J = 5.9 Hz, 1H), 8.86 (s, 1H), 8.58 (s, 1H), 8.39 (d, J = 5.8 Hz, 1H), 8.11 (dd, J = 14.1, 9.3 Hz, 4H), 7.59 (dd, J = 17.7, 8.8 Hz, 2H), 6.73 (d, J = 5.8 Hz, 1H). MS m/z (ESI): 482.8 [M + H]. |

TABLE 1-continued

| No. | Compound Structure | Compound Name | Starting material or regent different from that in Example 1 | Characterization Data |
|---|---|---|---|---|
| TDI01808 | 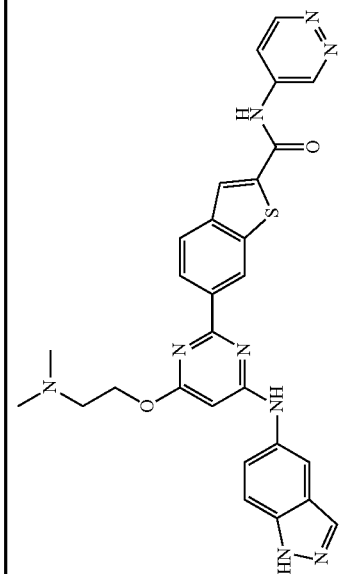 | 6-(4-((1H-indazol-5-yl)amino)-6-(2-(dimethylamino)ethoxy)-pyrimidin-2-yl)-N-(pyridazin-4-yl)benzo[b]-thiophene-2-carboxamide |  (Reg-1-1) in step 3 of Example 1 was replaced with  (Reg-1-31); and [tetrahydrofuran-3-yl]-NH$_2$ in step 4 was replaced with 4-aminopyridazine | $^1$H NMR (400 MHz, CD$_3$OD) δ 9.60 (s, 1H), 9.27 (d, J = 5.9 Hz, 1H), 8.68 (s, 2H), 8.43 (s, 1H), 8.18–8.04 (m, 4H), 7.58 (dd, J = 27.2, 8.7 Hz, 2H), 6.99 (s, 1H), 3.79–3.71 (m, 1H), 3.67 (s, 2H), 3.27–3.22 (m, 1H), 3.03 (s, 6H). MS m/z (ESI): 552.3 [M + H]. |

TABLE 1-continued

| No. | Compound Name | Compound Structure | Starting material or regent different from that in Example 1 | Characterization Data |
|---|---|---|---|---|
| TDI01811 | 6-(4-((1H-indazol-5-yl)amino)-6-(dimethyl-amino)-pyrimidin-2-yl)-N-(pyridazin-4-yl)-1H-indole-2-carboxamide | (structure shown) | OH in step 1 of Example 1 was replaced with (Reg-1-1); in step 3 was replaced with (Reg-1-83); and NH₂ in step 4 was replaced with (tetrahydrofuran-3-amine and 4-aminopyridazine) | ¹H NMR (400 MHz, DMSO-d₆) δ 13.08 (s, 1H), 12.50 (s, 1H), 11.04 (s, 1H), 9.62 (s, 1H), 9.14 (d, J = 6.0 Hz, 1H), 8.22-8.07 (m, 4H), 7.97 (d, J = 8.3 Hz, 1H), 7.74 (d, J = 8.2 Hz, 1H), 7.65 (s, 1H), 7.58 (s, 2H), 6.80 (s, 1H), 3.27 (s, 6H). MS m/z (ESI): 490.7 [M + H]. |

TABLE 1-continued

| No. | Compound Structure | Compound Name | Starting material or regent different from that in Example 1 | Characterization Data |
|---|---|---|---|---|
| TDI01813 | (structure) | 6-(4-((1H-indazol-5-yl)amino)-5-methoxy-pyrimidin-2-yl)-N-(pyridazin-4-yl)-1H-indole-2-carboxamide | (structures): Br-substituted benzothiophene-2-carboxylic acid OH in step 1 of Example 1 was replaced with Br-substituted 1H-indole-2-carboxylic acid OH; (Reg-1-1) in step 3 was replaced with (Reg-1-80); and H₂N-pyridazine NH₂ in step 4 was replaced with H₂N-tetrahydrofuran | ¹H NMR (400 MHz, DMSO-d₆) δ 13.22 (s, 1H), 12.50 (s, 1H), 11.18 (s, 1H), 10.27 (s, 1H), 9.59 (s, 1H), 9.23 (s, 1H), 8.31 (s, 2H), 8.19 (s, 2H), 8.09 (s, 1H), 7.91 (d, J = 11.8 Hz, 2H), 7.76 (d, J = 8.9 Hz, 1H), 7.64 (d, J = 8.7 Hz, 2H), 4.10 (s, 3H). MS m/z (ESI): 477.9 [M + H]. |

TABLE 1-continued

| No. | Compound Structure | Compound Name | Starting material or regent different from that in Example 1 | Characterization Data |
|---|---|---|---|---|
| TDI01814 | (structure shown) | 6-(4-((1H-indazol-5-yl)amino)pyrimidin-2-yl)-N-(1-(pyridin-4-yl)piperidin-4-yl)-1H-indole-2-carboxamide | 6-bromobenzo[b]thiophene-2-carboxylic acid in step 1 of Example 1 was replaced with 6-bromo-1H-indole-2-carboxylic acid; and 1-(pyridin-4-yl)piperidin-4-amine·2HCl in step 4 was replaced with 4-amino-1-(pyridin-4-yl)piperidine | $^1$H NMR (400 MHz, DMSO-$d_6$) δ 13.35 (s, 1H), 12.20 (s, 1H), 10.70 (s, 1H), 8.51 (d, J = 7.9 Hz, 1H), 8.42 (s, 1H), 8.33 (d, J = 6.5 Hz, 1H), 8.30-8.17 (m, 4H), 7.96 (d, J = 8.8 Hz, 1H), 7.82 (d, J = 8.5 Hz, 1H), 7.64-7.62 (m, 2H), 7.28-7.26 (m, 3H), 6.82 (d, J = 6.4 Hz, 1H), 4.29-4.26 (m, 3H), 3.42-3.36 (m, 2H), 2.05-2.02 (m, 2H), 1.63-1.60 (m, 2H). MS m/z (ESI): 529.9 [M + H]. |
| TDI01815 | (structure shown) | (6-(4-((1H-indazol-5-yl)amino)pyrimidin-2-yl)-1H-indol-2-yl)(4-(pyridin-4-yl)piperazin-1-yl)methanone | 6-bromobenzo[b]thiophene-2-carboxylic acid in step 1 of Example 1 was replaced with 6-bromo-1H-indole-2-carboxylic acid; and 1-(pyridin-4-yl)piperidin-4-amine·2HCl in step 4 was replaced with 1-(pyridin-4-yl)piperazine | $^1$H NMR (400 MHz, DMSO-$d_6$) δ 13.42 (s, 1H), 12.15 (s, 1H), 8.47 (s, 1H), 8.36-8.24 (m, 4H), 8.17 (s, 1H), 8.04 (d, J = 7.5 Hz, 1H), 7.80 (d, J = 8.6 Hz, 1H), 7.65-7.60 (m, 2H), 7.18 (d, J = 7.3 Hz, 2H), 7.00 (s, 1H), 6.76 (s, 1H), 4.02 (s, 2H), 3.88 (s, 2H). MS m/z (ESI): 515.9 [M + H]. |

TABLE 1-continued

| No. | Compound Name | Compound Structure | Starting material or regent different from that in Example 1 | Characterization Data |
|---|---|---|---|---|
| TDI01818 | 6-(4-((4-(1H-pyrazol-4-yl)phenyl)amino)pyrimidin-2-yl)-1H-indole-2-carboxamide | (structure shown) | Br-benzothiophene-2-carboxylic acid OH in step 1 of Example 1 was replaced with Br-indole-2-carboxylic acid OH; in step 3 was replaced with (Reg-1-1) 2-chloro-4-(1-Boc-indazol-5-ylamino)pyrimidine and (Reg-1-16) 2-chloro-4-(4-(1-Boc-pyrazol-4-yl)phenylamino)pyrimidine; and tetrahydrofuran-3-amine -NH$_2$ in step 4 was replaced with a solution of ammonia in methanol. | $^1$H NMR (400 MHz, CD$_3$OD) δ 8.45 (s, 1H), 8.24 (d, J = 6.8 Hz, 1H), 8.01 (s, 2H), 7.94 (d, J = 8.0 Hz, 1H), 7.83 (d, J = 8.0 Hz, 1H), 7.77 (s, 2H), 7.72 (d, J = 8.0 Hz, 2H), 7.20 (s, 1H), 6.83 (d, J = 6.8 Hz, 1H). MS m/z (ESI): 396.0 [M + H]. |

TABLE 1-continued

| No. | Compound Structure | Compound Name | Starting material or regent different from that in Example 1 | Characterization Data |
|---|---|---|---|---|
| TDI01819 | (structure shown) | 6-(4-((4-(1H-pyrazol-4-yl)phenyl)amino)-pyrimidin-2-yl)-3-chloro-N-methyl-1H-indole-2-carboxamide | OH (Br-benzothiophene-2-carboxylic acid) in step 1 of Example 1 was replaced with (3-chloro-6-bromo-1H-indole-2-carboxylic acid); (Reg-1-1) in step 3 was replaced with (Reg-1-16); and (tetrahydrofuran-3-yl)-NH₂ in step 4 was replaced with methylamine hydrochloride. | ¹H NMR (400 MHz, CD₃OD) δ 8.44 (s, 1H), 8.25 (d, J = 6.9 Hz, 1H), 8.02 (s, 2H), 8.00 (d, J = 8.0 Hz, 1H), 7.84 (d, J = 8.0 Hz, 1H), 7.78-7.71 (m, 4H), 6.89 (d, J = 6.9 Hz, 1H). MS m/z (ESI): 444.0 [M + H]. |

TABLE 1-continued

| No. | Compound Name | Compound Structure | Starting material or regent different from that in Example 1 | Characterization Data |
|---|---|---|---|---|
| TDI01820 | 6-(4-((1H-pyrazol-4-yl)phenyl)-amino)-pyrimidin-2-yl)-3-chloro-N,N-dimethyl-1H-indole-2-carboxamide | [structure] | [structure: Br-benzothiophene-COOH] in step 1 of Example 1 was replaced with [structure: Br-3-chloroindole-COOH]; in step 3 was replaced with (Reg-1-1) and (Reg-1-16); and NH₂ in step 4 was replaced with HN-tetrahydrofuran. | ¹H NMR (400 MHz, CD₃OD) δ 8.39 (s, 1H), 8.23 (d, J = 8.0 Hz, 1H), 8.03 (s, 1H), 7.98 (d, J = 8.0 Hz, 1H), 7.84 (d, J = 8.0 Hz, 1H), 7.80-7.70 (m, 4H), 6.93 (d, J = 8.0 Hz, 1H), 5.35 (s, 1H), 3.17 (s, 6H). MS m/z (ESI): 457.8 [M + H]. |

| No. | Compound Structure | Compound Name | Starting material or regent different from that in Example 1 | Characterization Data |
|---|---|---|---|---|
| TDI01821 | (structure shown) | 6-(4-((4-(1H-pyrazol-4-yl)phenyl)amino)-pyrimidin-2-yl)-5-chloro-N-methyl-1H-indole-2-carboxamide | The synthesis started from step 2 of Example 1. (methyl 6-bromobenzothiophene-2-carboxylate) in step 2 of Example 1 was replaced with (ethyl 6-bromo-5-chloro-1H-indole-2-carboxylate); (Reg-1-1) in step 3 was replaced with (Reg-1-16); and NH₂-tetrahydrofuran in step 4 was replaced with MeNH₂. | ¹H NMR (400 MHz, DMSO-d₆) δ 12.23 (s, 1H), 10.99 (s, 1H), 8.70 (s, 1H), 8.45 (d, J = 6.8 Hz, 1H), 8.05 (s, 2H), 7.99 (s, 1H), 7.84 (s, 1H), 7.67 (m, J = 14.1 Hz, 4H), 7.17 (s, 1H), 6.98 (s, 1H), 2.85 (d, J = 4.5 Hz, 3H). MS m/z (ESI): 443.8 [M + H]. |

TABLE 1-continued

| No. | Compound Structure | Compound Name | Starting material or regent different from from that in Example 1 | Characterization Data |
|---|---|---|---|---|
| TDI01822 | 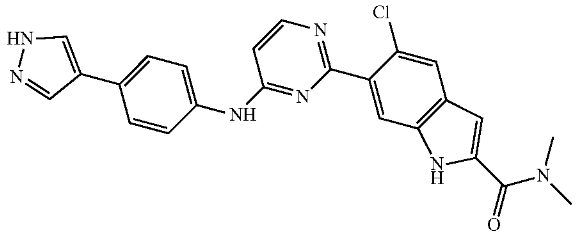 [SMILES: CN(C)C(=O)c1cc2cc(Cl)c(-c3nccc(Nc4ccc(-c5cn[nH]c5)cc4)n3)cc2[nH]1] | 6-(4-((4-(1H-pyrazol-4-yl)phenyl)-amino)-pyrimidin-2-yl)-5-chloro-N,N-dimethyl-1H-indole-2-carboxamide | The synthesis started from step 2 of Example 1. in step 2 of Example 1 was replaced with (Reg-1-1) and (Reg-1-16) in step 3 was replaced with and NH₂ in step 4 was replaced with | $^1$H NMR (400 MHz, DMSO-d$_6$) δ 12.20 (s, 1H), 11.10 (s, 1H), 8.46 (d, J = 6.9 Hz, 1H), 8.06 (s, 2H), 7.95 (s, 1H), 7.87 (s, 1H), 7.67 (m, J = 12.8 Hz, 4H), 7.03-6.97 (m, 2H), 3.31 (d, J = 14.5 Hz, 3H), 3.08 (s, 3H). MS m/z (ESI): 457.7 [M + H]. |

TABLE 1-continued

| No. | Compound Name | Compound Structure | Starting material or regent different from that in Example 1 | Characterization Data |
|---|---|---|---|---|
| TDI01823 | 6-(4-((4-(1H-pyrazol-4-yl)phenyl)amino)-5-methoxy-pyrimidin-2-yl)-N,N-diethyl-1H-indole-2-carboxamide | [structure] | 6-bromobenzo[b]thiophene-2-carboxylic acid in step 1 of Example 1 was replaced with 6-bromo-1H-indole-2-carboxylic acid; (Reg-1-1) was replaced with (Reg-1-36); in step 3 was replaced with HN(Et)₂ | ¹H NMR (400 MHz, DMSO-d₆) δ 11.97 (s, 1H), 8.37 (s, 1H), 8.12 (s, 1H), 8.07 (s, 1H), 7.94 (d, J = 8.0 Hz, 2H), 7.75 (d, J = 8.0 Hz, 1H), 7.68 (d, J = 8.0 Hz, 1H), 6.85 (s, 1H), 4.05 (s, 3H), 3.56 (s, 4H), 1.24 (s, 6H). MS m/z (ESI): 482.0 [M + H]. |
| TDI01824 | 6-(4-((1H-indazol-5-yl)amino)pyrimidin-2-yl)-3-chloro-N-(pyridazin-4-yl)-1H-indole-2-carboxamide | [structure] | 6-bromobenzo[b]thiophene-2-carboxylic acid in step 1 of Example 1 was replaced with 6-bromo-3-chloro-1H-indole-2-carboxylic acid; and 3-aminotetrahydrofuran in step 4 was replaced with 4-aminopyridazine | ¹H NMR (400 MHz, DMSO-d₆) δ 13.16 (d, J = 25.7 Hz, 1H), 12.69 (s, 1H), 10.92 (s, 1H), 10.38 (s, 1H), 9.51 (s, 1H), 9.18 (s, 1H), 8.49 (s, 1H), 8.37 (d, J = 6.4 Hz, 1H), 8.15 (d, J = 20.0 Hz, 4H), 7.85 (s, 1H), 7.62 (d, J = 8.6 Hz, 2H), 6.80 (s, 1H). MS m/z (ESI): 481.9 [M + H]. |

TABLE 1-continued

| No. | Compound Name | Starting material or regent different from that in Example 1 | Characterization Data |
|---|---|---|---|
| TDI01829C | 6-(4-(4-((1H-pyrazol-4-yl)phenyl)-amino)-pyrimidin-2-yl)-N-(3-iodopyridin-4-yl)-1H-indole-2-carboxamide | OH in step 1 of Example 1 was replaced with (Reg-1-1) and (Reg-1-16); in step 3 was replaced with NH₂ | ¹H NMR (400 MHz, DMSO-d₆) δ 12.42 (s, 1H), 11.71 (s, 1H), 10.04 (s, 1H), 8.99 (s, 1H), 8.58 (dd, J = 28.0, 22.8 Hz, 2H), 8.38 (d, J = 6.3 Hz, 1H), 8.07 (s, 2H), 7.90 (dd, J = 22.7, 14.4 Hz, 2H), 7.81 (d, J = 4.8 Hz, 2H), 7.67 (dd, J = 26.4, 7.9 Hz, 2H), 7.52 (s, 1H), 7.20 (m, 1H), 6.82 (s, 1H). MS m/z (ESI): 598.8 [M + H]. |
| TDI01836 | 4-(6-(4-((1H-indazol-5-yl)amino)-pyrimidin-2-yl)-1H-indole-2-carbonyl)-1,1-dimethylpiperazin-1-ium chloride | OH in step 1 of Example 1 was replaced with and with in step 4 was replaced with | ¹H NMR (400 MHz, DMSO-d₆) δ 13.18 (s, 1H), 12.20 (s, 1H), 10.02 (s, 1H), 8.46 (s, 1H), 8.34 (d, J = 6.3 Hz, 1H), 8.25 (s, 1H), 8.18 (s, 1H), 8.04 (s, 1H), 7.80 (d, J = 8.5 Hz, 1H), 7.62 (t, J = 9.7 Hz, 2H), 7.02 (s, 1H), 6.79 (s, 1H), 4.62 (s, 2H), 4.15 (s, 2H), 3.97 (s, 2H), 3.54 (s, 6H), 3.23 (s, 1H), 2.87 (s, 1H). MS m/z (ESI): 467.2 [M − Cl]. |

TABLE 1-continued

| No. | Compound Structure | Compound Name | Starting material or regent different from that in Example 1 | Characterization Data |
|---|---|---|---|---|
| TDI01840 | 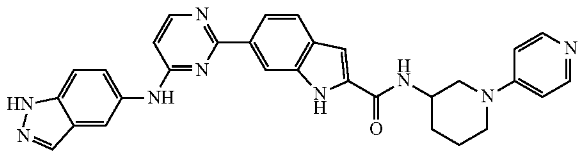 [SMILES: O=C(NC1CCCN(c2ccncc2)C1)c1cc2ccc(-c3nccc(Nc4ccc5[nH]ncc5c4)n3)cc2[nH]1] | 6-(4-((1H-indazol-5-yl)amino)-pyrimidin-2-yl)-N-(1-(pyridin-4-yl)piperidin-3-yl)-1H-indole-2-carboxamide | OH in step 1 of Example 1 was replaced with [6-bromo-benzothiophene-2-carboxylic acid] and [6-bromo-1H-indole-2-carboxylic acid]; in step 4 was replaced with [3-aminotetrahydrofuran] and [1-(pyridin-4-yl)piperidin-3-amine] | $^1$H NMR (400 MHz, DMSO-$d_6$) δ 13.30 (s, 1H), 12.11 (s, 1H), 10.40-10.24 (m, 1H), 8.64 (d, J = 7.0 Hz, 1H), 8.46 (s, 1H), 8.33 (d, J = 6.3 Hz, 1H), 8.21 (d, J = 29.1 Hz, 3H), 8.03 (d, J = 8.4 Hz, 1H), 7.79 (d, J = 8.3 Hz, 1H), 7.62 (t, J = 8.2 Hz, 2H), 7.27 (s, 3H), 6.76 (s, 1H), 4.24 (d, J = 11.7 Hz, 1H), 3.97 (s, 1H), 3.31-3.30 (m, 1H), 3.28 (s, 1H), 2.04 (s, 1H), 1.92 (s, 1H), 1.81 (d, J = 11.7 Hz, 1H), 1.63 (s, 1H). MS m/z (ESI): 530.0 [M + H]. |
| TDI01841 | 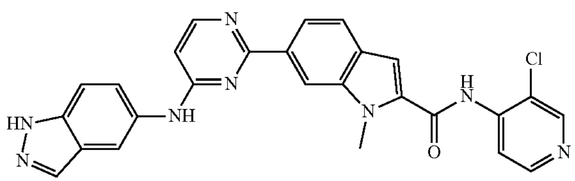 [SMILES: Cn1c(C(=O)Nc2ccncc2Cl)cc2ccc(-c3nccc(Nc4ccc5[nH]ncc5c4)n3)cc21] | 6-(4-((1H-indazol-5-yl)amino)-pyrimidin-2-yl)-N-(3-chloropyridin-4-yl)-1-methyl-1H-indole-2-carboxamide | The synthesis started from step 2 of Example 1. In step 2 of Example 1 was replaced with [methyl 6-bromo-benzothiophene-2-carboxylate] and [methyl 6-bromo-1-methyl-1H-indole-2-carboxylate]; NH$_2$ in step 4 was replaced with [3-aminotetrahydrofuran] and [3-chloropyridin-4-amine] | $^1$H NMR (400 MHz, DMSO-$d_6$) δ 10.80 (s, 1H), 10.30 (s, 1H), 8.74 (s, 1H), 8.57 (s, 2H), 8.40 (d, J = 6.2 Hz, 1H), 8.20 (d, J = 23.4 Hz, 2H), 8.07 (d, J = 8.5 Hz, 1H), 7.95 (t, J = 7.1 Hz, 2H), 7.68 (d, J = 8.8 Hz, 1H), 7.61 (s, 1H), 7.54 (s, 1H), 6.87 (d, J = 6.7 Hz, 1H), 5.33 (s, 1H), 4.14 (s, 3H). MS m/z (ESI): 494.8 [M + H]. |

| No. | Compound Structure | Compound Name | Starting material or regent different from that in Example 1 | Characterization Data |
|---|---|---|---|---|
| TDI01844 | 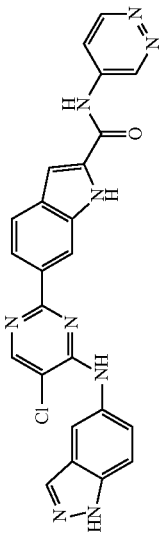 | 6-(4-((1H-indazol-5-yl)amino)-5-chloropyrimidin-2-yl)-N-(pyridazin-4-yl)-1H-indole-2-carboxamide | ![Br-benzothiophene-COOH] in step 1 of Example 1 was replaced with ![Br-indole-COOH]; ![Reg-1-1] in step 3 was replaced with ![Reg-1-81] and ![tetrahydrofuran-NH2] in step 4 was replaced with ![aminopyridazine]. | $^1$H NMR (400 MHz, DMSO-d$_6$) δ 13.12 (d, J = 8.0 Hz, 1H), 12.25 (s, 1H), 10.97 (s, 1H), 9.58 (s, 1H), 9.19 (d, J = 26.2 Hz, 2H), 8.53 (s, 1H), 8.43 (s, 1H), 8.22 (s, 1H), 8.15 (s, 1H), 8.09 (s, 1H), 8.01 (d, J = 8.6 Hz, 1H), 7.75 (dd, J = 19.5, 13.8 Hz, 2H), 7.58 (d, J = 17.9 Hz, 1H). MS m/z (ESI): 481.9 [M + H]. |

TABLE 1-continued

| No. | Compound Structure | Compound Name | Starting material or regent different from that in Example 1 | Characterization Data |
|---|---|---|---|---|
| TDI01845 | 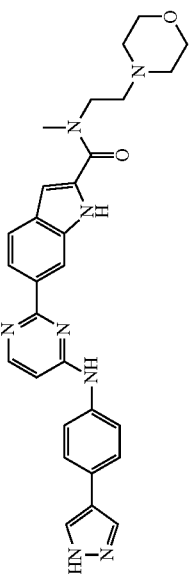 | 6-(4-((4-(1H-pyrazol-4-yl)phenyl)amino)-pyrimidin-2-yl)-N-methyl-N-(2-morpholino-ethyl)-1H-indole-2-carboxamide | 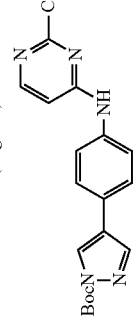 OH in step 1 of Example 1 was replaced with OH; (Reg-1-1) in step 3 was replaced with (Reg-1-16) and NH₂ in step 4 was replaced with | ¹H NMR (400 MHz, DMSO-d₆) δ 12.03 (s, 1H), 10.1 (s, 1H), 9.61 (s, 1H), 8.53 (s, 1H), 8.37 (d, J = 6.0 Hz, 1H), 8.05 (s, 2H), 7.81 (t, J = 8.0 Hz, 2H), 7.68 (d, J = 8.0 Hz, 2H), 7.10 (s, 1H), 6.78 (d, J = 6.0 Hz, 1H), 4.02-3.93 (m, 5H), 3.75-3.59 (m, 6H), 3.25-3.10 (m, 4H). MS m/z (ESI): 522.7 [M + H]. |

TABLE 1-continued

| No. | Compound Name | Compound Structure | Starting material or regent different from that in Example 1 | Characterization Data |
|---|---|---|---|---|
| TDI01847 | 6-(4-((1H-indazol-5-yl)amino)-pyrimidin-2-yl)-N-(1-(3-chloropyridin-4-yl)piperidin-4-yl)-1H-indole-2-carboxamide | (structure shown) | (bromobenzothiophene-2-carboxylic acid) OH in step 1 of Example 1 was replaced with (6-bromoindole-2-carboxylic acid) OH; and (4-amino-1-(3-chloropyridin-4-yl)piperidine) in step 4 was replaced with (3-aminotetrahydrofuran). | $^1$H NMR (400 MHz, DMSO-d$_6$) δ 13.02 (s, 1H), 11.92 (s, 1H), 9.59 (s, 1H), 8.52 (s, 1H), 8.46 (d, J = 8.0 Hz, 1H), 8.41 (s, 1H), 8.38-8.28 (m, 3H), 8.14 (d, J = 8.5 Hz, 2H), 7.71 (d, J = 8.3 Hz, 1H), 7.59 (s, 1H), 7.24 (s, 1H), 7.10 (d, J = 5.5 Hz, 1H), 6.65 (d, J = 5.9 Hz, 1H), 4.07 (s, 1H), 3.62 (d, J = 12.4 Hz, 2H), 2.94 (t, J = 11.7 Hz, 2H), 1.99 (d, J = 10.6 Hz, 2H), 1.85-1.73 (m, 2H). MS m/z (ESI): 563.6 [M + H]. |

TABLE 1-continued

| No. | Compound Structure | Compound Name | Starting material or regent different from that in Example 1 | Characterization Data |
|---|---|---|---|---|
| TDI01847B | 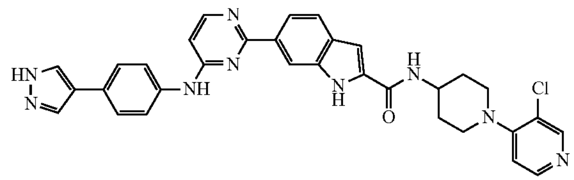 [SMILES: O=C(NC1CCN(c2ccncc2Cl)CC1)c1cc2ccc(-c3nccc(Nc4ccc(-c5cn[nH]c5)cc4)n3)cc2[nH]1] | 6-(4-((4-(1H-pyrazol-4-yl)phenyl)amino)-pyrimidin-2-yl)-N-(1-(3-chloropyridin-4-yl)piperidin-4-yl)-1H-indole-2-carboxamide | OH in step 1 of Example 1 was replaced with [structure with Br, S, OH] and [structure with Br, N-H, OH]; in step 3 was replaced with (Reg-1-1) and (Reg-1-16); and NH₂ in step 4 was replaced with [tetrahydrofuran-3-amine structure] | $^{1}$H NMR (400 MHz, DMSO-d$_6$) δ 12.05 (s, 1H), 10.11 (s, 1H), 8.52-8.48 (m, 3H), 8.36 (d, J = 6.0 Hz, 2H), 8.13 (s, 1H), 8.06-8.04 (m, 3H), 7.82 (d, J = 8.0 Hz, 2H), 7.77 (d, J = 8.0 Hz, 1H), 7.68 (d, J = 8.0 Hz, 2H), 7.27 (s, 1H), 7.20 (d, J = 8.0 Hz, 1H), 6.76 (d, J = 6.0 Hz, 1H), 4.13 (d, J = 8.0 Hz, 1H), 3.78 (d, J = 12.0 Hz, 2H), 3.07 (t, J = 12.0 Hz, 2H), 2.02-1.99 (m, 2H), 1.82-1.74 (m, 2H). MS m/z (ESI): 589.8 [M + H]. |

TABLE 1-continued

| No. | Compound Structure | Compound Name | Starting material or regent different from that in Example 1 | Characterization Data |
|---|---|---|---|---|
| TDI01848 | (structure) | (R)-6-(4-((1H-indazol-5-yl)amino)-pyrimidin-2-yl)-N-(1-(6-(trifluoromethyl)-pyridin-3-yl)ethyl)-1H-indole-2-carboxamide | (structures) ...OH in step 1 of Example 1 was replaced with (structure) ; and in step 4 was replaced with H$_2$N-(structure) | $^1$H NMR (400 MHz, DMSO-d$_6$), δ 13.17 (d, J = 14.0 Hz, 1H), 12.18 (s, 1H), 9.15 (s, 1H), 8.85 (s, 1H), 8.41 (s, 1H), 8.32 (d, J = 6.5 Hz, 1H), 8.18 (s, 2H), 8.11 (d, J = 8.0 Hz, 1H), 8.03-7.89 (m, 3H), 7.85 (s, 1H), 7.63 (s, 2H), 7.38 (s, 1H), 6.79 (s, 1H), 5.33 (d, J = 6.9 Hz, 1H), 1.59 (d, J = 6.9 Hz, 3H). MS m/z (ESI): 442.9 [M + H]. |
| TDI01849 | (structure) | (R)-6-(4-((1H-indazol-5-yl)amino)-pyrimpidin-2-yl)-N-(1-(pyridin-4-yl)ethyl)-1H-indole-2-carboxamide | (structures) ...OH in step 1 of Example 1 was replaced with (structure) ; and in step 4 was replaced with H$_2$N-(structure) | $^1$H NMR (400 MHz, DMSO-d$_6$), δ 13.14 (s, 1H), 12.17 (s, 1H), 9.17 (d, J = 6.5 Hz, 1H), 8.71 (s, 2H), 8.42 (s, 1H), 8.32 (d, J = 6.5 Hz, 1H), 8.19 (d, J = 13.8 Hz, 2H), 7.98 (s, 1H), 7.86 (d, J = 8.3 Hz, 1H), 7.74 (s, 2H), 7.63 (t, J = 9.2 Hz, 3H), 7.42 (s, 1H), 6.80 (s, 1H), 5.30 (m, 1H), 1.56 (d, J = 6.9 Hz, 3H). MS m/z (ESI): 475.0 [M + H]. |

TABLE 1-continued

| No. | Compound Structure | Compound Name | Starting material or regent different from that in Example 1 | Characterization Data |
|---|---|---|---|---|
| TDI01849 B | 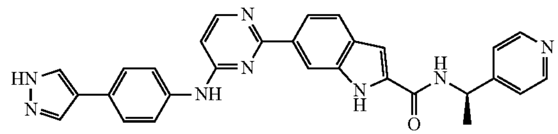 [SMILES: C[C@@H](NC(=O)c1cc2ccc(-c3nccc(Nc4ccc(-c5cn[nH]c5)cc4)n3)cc2[nH]1)c1ccncc1] | (R)-6-(4-((1H-pyrazol-4-yl)phenyl)amino)-pyrimidin-2-yl)-N-(1-(pyridin-4-yl)ethyl)-1H-indole-2-carboxamide | 6-Bromobenzothiophene-2-carboxylic acid in step 1 of Example 1 was replaced with 6-bromo-1H-indole-2-carboxylic acid; (Reg-1-1) in step 3 was replaced with (Reg-1-16) and NH₂ in step 4 was replaced with (R)-1-(pyridin-4-yl)ethan-1-amine. | ¹H NMR (400 MHz, DMSO-d₆) δ 12.28 (s, 1H), 10.97 (s, 1H), 9.29 (d, J = 8.0 Hz, 1H), 8.85 (d, J = 8.0 Hz, 2H), 8.41 (s, 1H), 8.34 (d, J = 6.0 Hz, 1H), 8.09 (s, 2H), 8.02 (d, J = 8.0 Hz, 2H), 7.93 (s, 2H), 7.76-7.72 (m, 3H), 7.47 (s, 1H), 6.90 (d, J = 8.0 Hz, 1H), 5.42-5.34 (m, 1H), 1.59 (d, J = 8.0 Hz, 3H). MS m/z (ESI): 500.9 [M + H]. |

TABLE 1-continued

| No. | Compound Structure | Compound Name | Starting material or regent different from that in Example 1 | Characterization Data |
|---|---|---|---|---|
| TDI01852 | 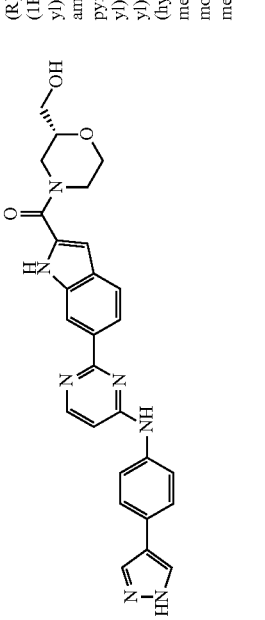 | (R)-(6-4-((1H-pyrazol-4-yl)phenyl)-amino)-pyrimidin-2-yl)-1H-indol-2-yl)(2-(hydroxy-methyl)-morpholino)-methanone | 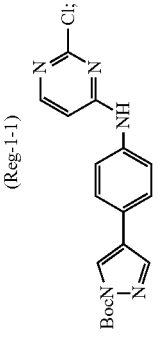 in step 1 of Example 1 was replaced with ; in step 3 was replaced with (Reg-1-1) (Reg-1-16) and NH$_2$ in step 4 was replaced with . | $^1$H NMR (400 MHz, DMSO-d$_6$) δ 12.27 (s, 1H), 8.42 (s, 1H), 8.34 (d, J = 8.0 Hz, 1H), 8.10 (s, 2H), 7.94 (d, J = 8.0 Hz, 1H), 7.85 (d, J = 8.0 Hz, 1H), 7.72 (m, 3H), 6.94 (s, 1H), 6.89 (d, J = 8.0 Hz, 1H), 4.41 (m, 1H), 4.28 (m, 2H), 3.91 (m, 2H), 3.56-3.46 (m, 4H). MS m/z (ESI): 496.0 [M + H]. |

TABLE 1-continued
| No. | Compound Structure | Compound Name | Starting material or regent different from that in Example 1 | Characterization Data |
|---|---|---|---|---|
| TDI01853 | 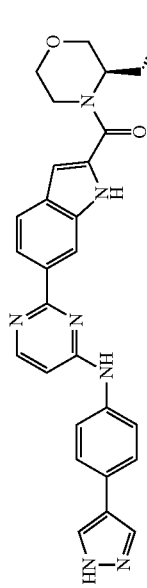 | (R)-(6-(4-((1H-pyrazol-4-yl)phenyl)-amino)-pyrimidin-2-yl)-1H-indol-2-yl)(3-(hydroxy-methyl)-mor-pholino)-methanone | 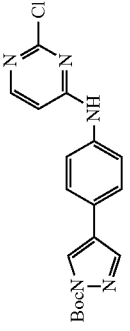 | $^{1}$H NMR (400 MHz, DMSO-d$_6$) δ 12.09 (s, 1H), 8.47 (s, 1H), 8.35 (d, J = 8.0 Hz, 1H), 8.07 (s, 1H), 8.01 (d, J = 8.0 Hz, 1H), 7.79 (s, 2H), 7.70 (d, J = 8.0 Hz, 1H), 6.97 (s, 1H), 6.81 (d, J = 8.0 Hz, 1H), 4.41 (s, 1H), 4.17 (d, J = 12.0 Hz, 1H), 3.93-3.88 (m, 2H), 3.76-3.72 (m, 2H), 3.67-3.64 (m, 4H). MS m/z (ESI): 495.7 [M + H]. |

TABLE 1-continued

| No. | Compound Structure | Compound Name | Starting material or regent different from that in Example 1 | Characterization Data |
|---|---|---|---|---|
| TDI01854 | (structure) | 6-(4-((4-(1H-pyrazol-4-yl)phenyl)-amino)-pyrimidin-2-yl)-N-(isoxazol-4-yl)-1H-indole-2-carboxmide | (see scheme: Br-benzothiophene-2-COOH replacing step 1; Br-indole-2-COOH; Reg-1-1 and Reg-1-16 replacing step 3; isoxazol-4-amine and 3-aminotetrahydrofuran replacing step 4) | $^1$H NMR (400 MHz, DMSO-d$_6$) δ 12.92 (s, 1H), 12.16 (s, 1H), 10.98 (s, 1H), 9.70 (s, 1H), 9.28 (s, 1H), 8.81 (s, 1H), 8.58 (s, 1H), 8.38 (d, J = 5.7 Hz, 1H), 8.16 (d, J = 8.3 Hz, 2H), 7.83 (m, 3H), 7.65 (d, J = 8.3 Hz, 2H), 7.40 (s, 1H), 6.71 (d, J = 5.7 Hz, 1H). MS m/z (ESI): 462.8 [M + H]. |

TABLE 1-continued

| No. | Compound Structure | Compound Name | Starting material or regent different from that in Example 1 | Characterization Data |
|---|---|---|---|---|
| TDI01855 | (structure shown) | (R)-6-(4-((1H-pyrazol-4-yl)phenyl)amino)pyrimidin-2-yl)-N-(1-aminopropan-2-yl)-1H-indole-2-carboxamide | (Reg-1-1) and (Reg-1-16) reagents shown; in step 1 of Example 1 was replaced with 6-bromobenzothiophene-2-carboxylic acid and 6-bromo-1H-indole-2-carboxylic acid; in step 3 was replaced with the chloropyrimidine-aniline-Boc-pyrazole intermediates; NH$_2$ in step 4 was replaced with the tetrahydrofuran-amine and (R)-N-Boc-1,2-diaminopropane | $^1$H NMR (400 MHz, DMSO-d$_6$) δ 11.99 (s, 1H), 9.64 (s, 1H), 8.56 (s, 2H), 8.37 (d, J = 8.0 Hz, 1H), 8.29 (s, 1H), 8.13 (d, J = 8.0 Hz, 1H), 8.03 (s, 2H), 7.84 (d, J = 8.0 Hz, 2H), 7.71 (d, J = 8.0 Hz, 1H), 7.65 (d, J = 8.0 Hz, 2H), 7.21 (s, 1H), 6.68 (d, J = 8.0 Hz, 1H), 4.27-4.20 (m, 1H), 2.91 (d, J = 8.0 Hz, 2H), 1.22 (d, J = 8.0 Hz, 3H). MS m/z (ESI): 453.0 [M + H]. |

TABLE 1-continued

| No. | Compound Structure | Compound Name | Starting material or regent different from that in Example 1 | Characterization Data |
|---|---|---|---|---|
| TDI01856 | (structure) | (S)-6-(4-((1H-pyrazol-4-yl)phenyl)-amino)-pyrimidin-2-yl)-N-(1-aminopropan-2-yl)-1H-indole-2-carboxamide | (Reg-1-1) in step 1 of Example 1 was replaced with (structures); in step 3 was replaced with (Reg-1-16); and (structure) in step 4 was replaced with (structure) | $^1$H NMR (400 MHz, DMSO-$d_6$) δ 12.00 (s, 1H), 9.64 (s, 1H), 8.58 (d, J = 8.0 Hz, 1H), 8.55 (s, 1H), 8.37 (d, J = 8.0 Hz, 1H), 8.32 (s, 1H), 8.12 (d, J = 8.0 Hz, 1H), 8.03 (s, 2H), 7.84 (d, J = 8.0 Hz, 2H), 7.71 (d, J = 8.0 Hz, 1H), 7.65 (d, J = 8.0 Hz, 2H), 7.21 (s, 1H), 6.68 (d, J = 8.0 Hz, 1H), 4.27-4.20 (m, 1H), 2.89 (d, J = 8.0 Hz, 2H), 1.23 (d, J = 8.0 Hz, 3H). MS m/z (ESI): 452.8 [M + H]. |

TABLE 1-continued
| No. | Compound Structure | Compound Name | Starting material or regent different from that in Example 1 | Characterization Data |
|---|---|---|---|---|
| TDI01862 | 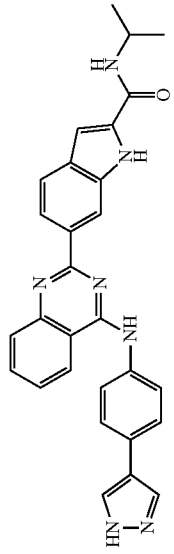 | 6-(4-((4-(1H-pyrazol-4-yl)phenyl)-amino)-quinazolin-2-yl)-N-isopropyl-1H-indole-2-carboxamide | (shown at right) | $^1$H NMR (400 MHz, DMSO-$d_6$) δ 12.13 (s, 1H), 8.68 (s, 1H), 8.56 (s, 1H), 8.38 (s, 1H), 8.14 (s, 3H), 8.00 (s, 3H), 7.79 (s, 3H), 7.26 (s, 1H), 4.14 (s, 1H), 1.28-1.18 (m, 6H). MS m/z (ESI): 488.0 [M + H]. |

TABLE 1-continued

| No. | Compound Structure | Compound Name | Starting material or reagent different from that in Example 1 | Characterization Data |
|---|---|---|---|---|
| TDI01867 | (structure) | 6-(4-((4-(1H-pyrazol-4-yl)phenyl)amino)-5-methoxy-pyrimidin-2-yl)-N-isopropyl-1H-indole-2-carboxamide | (Br-benzothiophene-2-COOH) OH in step 1 of Example 1 was replaced with (Br-indole-2-COOH) OH; (Reg-1-1 structure with 2-chloropyrimidine-NH-indazole-Boc) in step 3 was replaced with (Reg-1-36 structure: 2-chloro-5-methoxy-pyrimidine-NH-phenyl-pyrazole-Boc); (3-aminotetrahydrofuran) NH$_2$ in step 4 was replaced with H$_2$N-isopropyl | $^1$H NMR (400 MHz, DMSO-d$_6$) δ 11.86 (s, 1H), 9.18 (s, 1H), 8.41 (s, 1H), 8.32 (d, J = 7.7 Hz, 1H), 8.15 (s, 1H), 8.02 (dd, J = 16.7, 11.8 Hz, 5H), 7.67 (t, J = 8.8 Hz, 3H), 7.19 (s, 1H), 4.16-4.11 (m, 1H), 4.02 (s, 3H), 1.20 (d, J = 6.5 Hz, 6H). MS m/z (ESI): 468.0 [M + H]. |

TABLE 1-continued

| No. | Compound Structure | Compound Name | Starting material or regent different from that in Example 1 | Characterization Data |
|---|---|---|---|---|
| TD101868 | | 6-(4-((4-(1H-pyrazol-4-yl)phenyl)amino)-5-methoxy-pyrimidin-2-yl)-N-methyl-N-(2,2,2-trifluoroethyl)-1H-indole-2-carboxamide | Br-[benzothiophene-2-carboxylic acid]-OH in step 1 of Example 1 was replaced with Br-[indole-2-carboxylic acid]-OH; (Reg-1-1) in step 3 was replaced with (Reg-1-36); NH₂-[tetrahydrofuran-3-yl] in step 4 was replaced with F₃C-CH₂-NH·HCl. | ¹H NMR (400 MHz, DMSO-d₆) δ 12.84 (s, 1H), 11.92 (s, 1H), 8.92 (s, 1H), 8.46 (s, 1H), 8.18 (s, 1H), 8.04 (dd, J = 21.7, 8.6 Hz, 4H), 7.67 (dd, J = 21.6, 8.4 Hz, 3H), 7.07 (s, 1H), 4.49 (d, J = 8.2 Hz, 2H), 4.01 (s, 3H), 3.45 (s, 3H). MS m/z (ESI): 521.9 [M + H]. |

TABLE 1-continued

| No. | Compound Structure | Compound Name | Starting material or regent different from that in Example 1 | Characterization Data |
|---|---|---|---|---|
| TDI01872 | 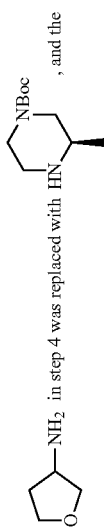 | (R)-(6-(4-((4-(1H-pyrazol-4-yl)phenyl)amino)-pyrimidin-2-yl)-1H-indol-2-yl)(2-methyl-piperazin-1-yl)methanone | Br-[benzothiophene]-C(O)OH in step 1 of Example 1 was replaced with Br-[indole]-C(O)OH; (Reg-1-1) [2-chloro-pyrimidine-NH-indazole-Boc] in step 3 was replaced with (Reg-1-16) [2-chloro-pyrimidine-NH-phenyl-pyrazole-BocN], and the HN-[tetrahydrofuran]-NH₂ in step 4 was replaced with HN-[piperidine]-NBoc, final product was obtained by removal of Boc using 4N hydrochoric acid/dioxane solution in the final step. | ¹H NMR (400 MHz, DMSO-d₆) δ 12.34 (s, 1H), 11.13 (s, 1H), 9.07 (s, 1H), 8.67 (s, 1H), 8.40 (s, 1H), 8.33 (s, 1H), 8.11 (s, 2H), 7.90 (s, 2H), 7.76 (s, 3H), 7.03 (s, 1H), 6.93 (s, 1H), 4.91 (s, 1H), 4.47 (d, J = 14.1 Hz, 2H), 3.27 (s, 2H), 3.10 (d, J = 10.9 Hz, 2H), 1.41 (d, J = 6.7 Hz, 3H), 1.25 (s, 1H). MS m/z (ESI): 478.9 [M + H]. |

TABLE 1-continued

| No. | Compound Structure | Compound Name | Starting material or regent different from that in Example 1 | Characterization Data |
|---|---|---|---|---|
| TDI01878 | 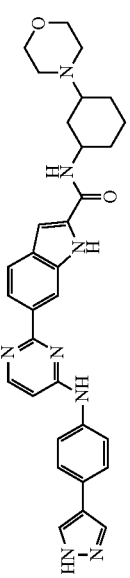 | 6-(4-((4-(1H-pyrazol-4-yl)phenyl)amino)-pyrimidin-2-yl)-N-(3-morpholino-cyclohexyl)-1H-indole-2-carboxamide | 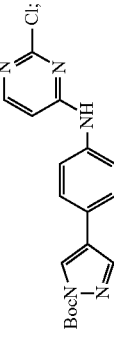 in step 1 of Example 1 was replaced with 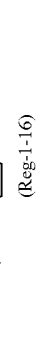 in step 3 was replaced with (Reg-1-16) and ... in step 4 was replaced with ... | $^1$H NMR (400 MHz, DMSO-$d_6$) δ 12.23 (s, 1H), 10.78 (s, 1H), 8.67 (s, 1H), 8.47 (s, 1H), 8.37 (d, J = 6.5 Hz, 1H), 8.09 (s, 2H), 7.98 (s, 1H), 7.87-7.79 (m, 2H), 7.73 (d, J = 7.8 Hz, 2H), 7.46-7.21 (m, 2H), 7.06 (d, J = 51.1 Hz, 1H), 6.87 (s, 1H), 4.41 (s, 1H), 4.01 (d, J = 12.4 Hz, 2H), 3.78-3.57 (m, 3H), 3.45 (d, J = 12.0 Hz, 2H), 3.12 (dd, J = 21.1, 11.5 Hz, 2H), 2.17 (dd, J = 66.0, 24.1 Hz, 2H), 1.96-1.73 (m, 3H), 1.61 (d, J = 7.8 Hz, 1H), 1.52-1.35 (m, 2H). MS m/z (ESI): 562.9 [M + H]. |

TABLE 1-continued

| No. | Compound Structure | Compound Name | Starting material or regent different from that in Example 1 | Characterization Data |
|---|---|---|---|---|
| TDI01880 | 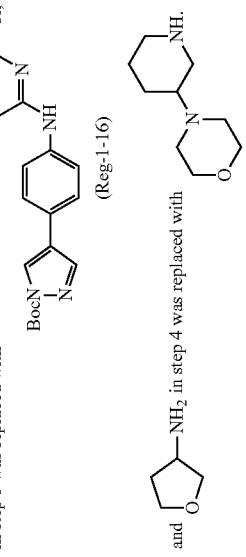 | (6-(4-((4-((1H-pyrazol-4-yl)phenyl)-amino)-pyrimidin-2-yl)-1H-indol-2-yl)(3-morpholino-piperidin-1-yl)methanone |  in step 1 of Example 1 was replaced with  (Reg-1-1); in step 3 was replaced with  (Reg-1-16); and  in step 4 was replaced with . | $^1$H NMR (400 MHz, DMSO-d$_6$) δ 12.16 (s, 1H), 9.89 (d, J = 7.3 Hz, 2H), 8.48 (s, 1H), 8.36 (d, J = 6.4 Hz, 1H), 8.11-7.97 (m, 3H), 7.81 (d, J = 8.0 Hz, 3H), 7.70 (d, J = 8.2 Hz, 3H), 6.98 (s, 1H), 6.82 (d, J = 4.5 Hz, 1H), 4.69 (s, 2H), 4.34 (d, J = 6.2 Hz, 3H), 4.04 (d, J = 11.7 Hz, 3H), 3.71 (s, 3H), 3.49-3.24 (m, 7H), 2.24 (s, 1H), 1.93 (d, J = 12.1 Hz, 1H), 1.79 (d, J = 10.0 Hz, 1H), 1.59 (s, 1H). MS m/z (ESI): 548.6 [M + H]. |

TABLE 1-continued

| No. | Compound Structure | Compound Name | Starting material or regent different from that in Example 1 | Characterization Data |
|---|---|---|---|---|
| TDI01882 | 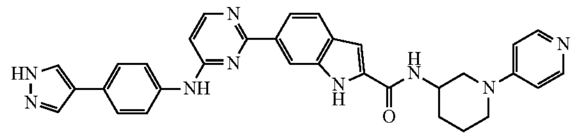 [SMILES: O=C(NC1CCCN(c2ccncc2)C1)c1cc2ccc(-c3nccc(Nc4ccc(-c5cn[nH]c5)cc4)n3)cc2[nH]1] | 6-(4-((4-(1H-pyrazol-4-yl)phenyl)-amino)-pyrimidin-2-yl)-N-(1-(pyridin-4-yl)piperidin-3-yl)-1H-indole-2-carboxamide | Br-[benzothiophene-2-COOH] in step 1 of Example 1 was replaced with Br-[indole-2-COOH]; (Reg-1-1) in step 3 was replaced with (Reg-1-16) and H$_2$N-[tetrahydrofuran-3-yl] in step 4 was replaced with H$_2$N-[1-(pyridin-4-yl)piperidin-3-yl]. | $^1$H NMR (400 MHz, DMSO-d$_6$) δ 13.28 (s, 1H), 12.18 (s, 1H), 8.68 (s, 1H), 8.48 (s, 1H), 8.36 (s, 1H), 8.24 (s, 2H), 8.04 (d, J = 28.6 Hz, 3H), 7.83 (s, 3H), 7.70 (d, J = 7.9 Hz, 2H), 7.26 (d, J = 23.9 Hz, 3H), 6.81 (s, 1H), 4.26 (s, 1H), 4.14 (d, J = 13.3 Hz, 4H), 1.93 (dd, J = 52.9, 42.3 Hz, 4H). MS m/z (ESI): 556.0 [M + H]. |

TABLE 1-continued

| No. | Compound Structure | Compound Name | Starting material or regent different from that in Example 1 | Characterization Data |
|---|---|---|---|---|
| TDI01884 | 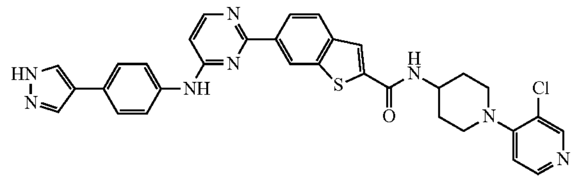 [SMILES: O=C(NC1CCN(c2ccncc2Cl)CC1)c1cc2ccc(-c3nccc(Nc4ccc(-c5cn[nH]c5)cc4)n3)cc2s1] | 6-(4-((4-(1H-pyrazol-4-yl)phenyl)amino)-pyrimidin-2-yl)-N-(1-(3-chloropyridin-4-yl)piperidin-4-yl)benzo[b]thiophene-2-carboxamide | Cl in step 3 of Example 1 (Reg-1-1) was replaced with (Reg-1-16) and NH₂ in step 4 was replaced with | ¹H NMR (400 MHz, DMSO-d₆) δ 10.19 (s, 2H), 8.93 (s, 1H), 8.81 (s, 1H), 8.67 (s, 1H), 8.40 (dd, J = 19.9, 7.4 Hz, 3H), 8.23 (s, 1H), 8.13 (d, J = 8.2 Hz, 1H), 8.08 (s, 1H), 7.78 (d, J = 8.1 Hz, 2H), 7.70 (d, J = 8.2 Hz, 2H), 7.36 (s, 1H), 6.83 (s, 1H), 4.16 (s, 1H), 4.01 (s, 2H), 3.28 (s, 2H), 2.05 (d, J = 11.6 Hz, 2H), 1.78 (dd, J = 21.7, 10.7 Hz, 2H). MS m/z (ESI): 606.9 [M + H]. |

TABLE 1-continued

| No. | Compound Structure | Compound Name | Starting material or regent different from that in Example 1 | Characterization Data |
|---|---|---|---|---|
| TDI01885 | 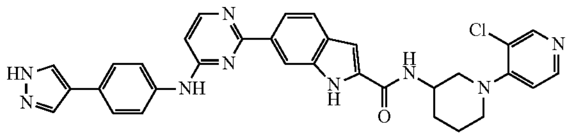 [SMILES: O=C(NC1CCCN(c2ccncc2Cl)C1)c1cc2ccc(-c3nccc(Nc4ccc(-c5cn[nH]c5)cc4)n3)cc2[nH]1] | (6-(4-((4-((1H-pyrazol-4-yl)phenyl)-amino)-pyrimidin-2-yl)-1H-indol-2-yl)(4-(3-chloropyridin-4-yl)piperazin-1-yl)methanone | OH in step 1 of Example 1 was replaced with (Reg-1-1) and (Reg-1-16); in step 3 was replaced with and NH₂ in step 4 was replaced with | ¹H NMR (400 MHz, DMSO-d₆) δ 12.20 (s, 1H), 10.56 (s, 1H), 8.59 (s, 1H), 8.48 (s, 1H), 8.41 (s, 1H), 8.36 (s, 1H), 8.10 (d, J = 22.4 Hz, 3H), 8.02 (s, 1H), 7.91-7.77 (m, 3H), 7.72 (s, 1H), 7.23 (s, 1H), 7.00 (s, 1H), 6.84 (s, 1H), 4.00 (s, 4H), 3.54 (s, 4H). MS m/z (ESI): 575.8 [M + H]. |
| TDI01675 | 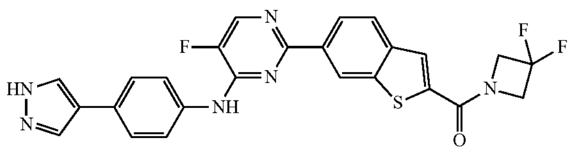 [SMILES: O=C(c1cc2ccc(-c3ncc(F)c(Nc4ccc(-c5cn[nH]c5)cc4)n3)cc2s1)N1CC(F)(F)C1] | (6-(4-((4-((1H-pyrazol-4-yl)phenyl)-amino)-5-fluoro-pyrimidin-2-yl)benzo[b]-thiophen-2-yl)(3,3-difluoroazetidin-1-yl)methanone | Cl in step 3 of Example 1 was replaced with (Reg-1-40) and NH₂ in step 4 was replaced with HCl | ¹H NMR (400 MHz, DMSO-d₆) δ 9.73 (s, 1H), 8.89 (s, 1H), 8.53 (d, J = 2.9 Hz, 1H), 8.37 (d, J = 8.4 Hz, 1H), 8.12-8.04 (m, 3H), 8.00 (s, 1H), 7.90 (d, J = 8.2 Hz, 2H), 7.70 (d, J = 8.2 Hz, 2H), 5.08 (s, 2H), 4.59 (s, 2H). MS m/z (ESI): 507.0 [M + H]. |

TABLE 1-continued

| No. | Compound Structure | Compound Name | Starting material or regent different from that in Example 1 | Characterization Data |
|---|---|---|---|---|
| TDI01691 | (structure shown) | (6-(4-((4-(1H-pyrazol-4-yl)phenyl)amino)-pyrimidin-2-yl)-1-methyl-N-(1,1,1-trifluoropropan-2-yl)-1H-indole-2-carboxamide | (reagents shown) in step 1 of Example 1 was replaced with (structure shown); in step 3 was replaced with (structures shown) (Reg-1-16) in step 4 was replaced with (structure shown). | ¹H NMR (400 MHz, DMSO-d₆) δ 9.05 (d, J = 8.8 Hz, 1H), 8.53 (s, 1H), 8.40 (d, J = 6.4 Hz, 1H), 8.08 (s, 3H), 7.94-7.67 (m, 5H), 7.33 (s, 1H), 6.83 (s, 1H), 4.90-4.84 (m, 1H), 4.09 (s, 3H), 1.39 (d, J = 7.0 Hz, 3H). MS m/z (ESI): 506.2 [M + H]. |

Example 2: preparation of 6-(4-((1H-indazol-5-yl)amino)pyrimidin-2-yl)-N-isopropylbenzofuran-2-carboxamide (TDI01102)

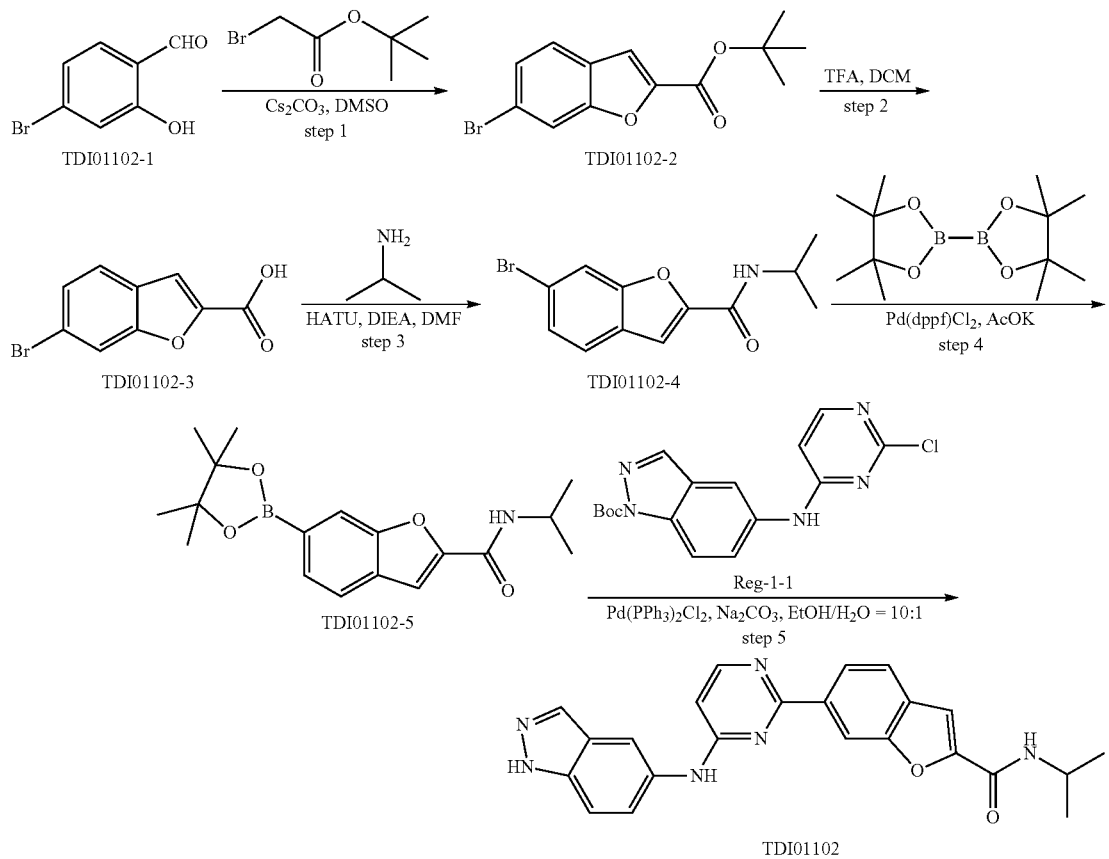

Step 1:
Compound TDI01102-1 (3.6 g, 17.9 mmol) and tert-butyl 2-bromoacetate (5.38 g, 27.6 mmol) were dissolved in dimethyl sulfoxide (100 mL), cesium carbonate (17.51 g, 53.7 mmol) was added, and the reaction was placed in an oil bath at 100° C., and allowed to proceed for 3 hours. Thin layer chromatography (petroleum ether) indicated the reaction was complete. The reaction solution was cooled to room temperature, extracted with ethyl acetate (100 mL×3) and water, respectively, washed with saturated brine (100 mL×3), dried over anhydrous sodium sulfate, and concentrated under reduced pressure to afford compound TDI01102-2 (4.0 g, brown solid, crude product).

$^1$H NMR (400 MHz, CDCl$_3$) δ 7.75 (s, 1H), 7.52 (d, J=8.4 Hz, 1H), 7.41 (m, H), 7.38 (s, 1H), 1.62 (s, 9H).

Step 2:
Compound TDI01102-2 (4.0 g, 13.47 mmol) was dissolved in anhydrous dichloromethane (40 mL), trifluoroacetic acid (10 mL) was added, and the reaction was performed at room temperature for 4 hours. Thin layer chromatography (petroleum ether) indicated the reaction was complete. The reaction solution was concentrated under reduced pressure, and the crude was dissolved in dichloromethane, and then concentrated to afford compound TDI01102-3 (3.0 g, yellow solid, crude product).

$^1$H NMR (400 MHz, DMSO-d$_6$) δ 13.63 (s, 1H), 8.06 (s, 1H), 7.76 (d, J=8.4 Hz, 1H), 7.69 (s, 1H), 7.53 (m, 1H). MS m/z (ESI): 239.0 [M−H].

Step 3:
Compound TDI01102-3 (400 mg, 1.66 mmol) and isopropylamine (119 mg, 2.0 mmol) were dissolved in N,N-dimethylformamide (10 mL), HATU (762 mg, 2.0 mmol) and diisopropylethylamine (1.07 g, 8.3 mmol) were added, and the reaction was performed at room temperature for 3 hours. Thin layer chromatography (petroleum ether:ethyl acetate=1:1) indicated the reaction was complete. Water (100 mL) was slowly added to the reaction solution, a large amount of solid precipitated, and was stirred for 30 minutes before filtered to afford compound TDI01102-4 (400 mg, yellow solid, crude product). MS m/z (ESI): 282.0/283.0 [M+H].

Step 4:
Compound TDI01102-4 (400 mg, 1.42 mmol) and bis(pinacolato)diboron (440 mg, 1.7 mmol) were dissolved in 1,4-dioxane (50 mL), potassium acetate (424 mg, 4.26 mmol) and Pd(dppf)Cl$_2$ (52 mg, 0.071 mmol) were added, purge with argon was performed for 3 times, and the reaction was placed in an oil bath at 90° C., and allowed to proceed for 4 hours. Thin layer chromatography (petroleum ether:ethyl acetate=4:1) indicated the reaction was complete. The reaction solution was cooled to room temperature, concentrated under reduced pressure, and the residue was separated and purified by column chromatography (petroleum ether:ethyl acetate=5:1 to 2:1), to afford compound TDI01102-5 (360 mg, yellow solid, crude product).

$^1$H NMR (400 MHz, CDCl$_3$) δ 7.94 (s, 1H), 7.72 (d, J=7.6 Hz, 1H), 7.66 (d, J=7.6 Hz, 1H), 7.45 (s, 1H), 6.46 (d, J=7.6 Hz, 1H), 4.31 (m, 1H), 1.37 (s, 12H), 1.31 (d, J=6.6 Hz, 6H). MS m/z (ESI): 330.2 [M+H].

Step 5:

Compound Reg-1-1 (300 mg, 0.87 mmol) and TDI01102-5 (360 mg, 1.10 mmol) were dissolved in a mixture of ethanol/water (10:1) (30 mL), sodium carbonate (184 mg, 1.74 mmol) and Pd(PPh$_3$)$_2$Cl$_2$ (63.0 mg, 0.09 mmol) were added, purge with argon was performed for 3 times, and the reaction was placed in an oil bath at 110° C. overnight. LC-MS indicated the reaction was complete. The reaction solution was cooled to room temperature, filtered, and concentrated under reduced pressure. The residue was purified by preparative liquid chromatography to afford compound TDI01102 (100 mg, yellow solid, yield: 27.9%).

$^1$H NMR (400 MHz, DMSO-d$_6$) δ 13.11 (s, 1H), 10.66 (s, 1H), 8.63 (d, J=8.0 Hz, 1H), 8.44 (s, 1H), 8.40 (d, J=8.0 Hz, 1H), 8.24 (d, J=8.0 Hz, 1H), 8.16 (s, 1H), 8.11 (s, 1H), 7.97 (d, J=8.0 Hz, 1H), 7.67-7.60 (m, 3H), 6.86 (d, J=8.0 Hz, 1H), 4.14 (m, 1H), 1.21 (d, J=8.0 Hz, 6H). MS m/z (ESI): 413.2 [M+H].

The compounds in Table 2 were prepared according to methods similar to that described in Example 2.

TABLE 2

| No. | Compound Structure | Compound Name | Starting material or regent different from that in Example 2 | Characterization Data |
|---|---|---|---|---|
| TDI01104 | (structure) | 6-(4-((1H-indazol-5-yl)amino)pyrimidin-2-yl)-N-isopropylbenzo[b]thiophene-2-carboxamide | The preparation started from step 3 of Example 2, and (6-bromobenzofuran-2-carboxylic acid) in step 3 was replaced with (6-bromobenzo[b]thiophene-2-carboxylic acid). | $^1$H NMR (400 MHz, CD$_3$OD) δ 8.76 (s, 1H), 8.24 (d, J = 7.2 Hz, 1H), 8.19-8.11 (m, 4H), 8.07 (s, 1H), 7.69 (s, 1H), 7.61 (s, 1H), 6.92 (d, J = 8.0 Hz, 1H), 4.25-4.19 (m, 1H), 1.29 (d, J = 6.4 Hz, 6H). MS m/z (ESI): 429.3 [M + H]. |
| TDI01108 | (structure) | 6-(4-((1H-indazol-5-yl)amino)pyrimidin-2-yl)-N-isopropyl-1H-indole-2-carboxamide | The preparation started from step 3 of Example 2, and (6-bromobenzofuran-2-carboxylic acid) in step 3 was replaced with (6-bromo-1H-indole-2-carboxylic acid). | $^1$H NMR (400 MHz, CD$_3$OD) δ 8.44 (s, 1H), 8.25 (d, J = 4.0 Hz, 1H), 8.20 (s, 1H), 8.09-8.06 (m, 2H), 7.69 (d, J = 8.0 Hz, 1H), 7.61 (m, 2H), 7.13 (s, 1H), 6.62 (d, J = 4.0 Hz, 1H), 4.28-4.21 (m, 1H), 1.30 (s, 3H), 1.28 (s, 3H). MS m/z (ESI): 412.2 [M + H]. |
| TDI01109 | (structure) | 6-(4-((1H-indazol-5-yl)amino)pyrimidin-2-yl)-N-methylbenzo[b]thiophene-2-carboxamide | The preparation started from step 3 of Example 2, and (6-bromobenzofuran-2-carboxylic acid) in step 3 was replaced with (6-bromobenzo[b]thiophene-2-carboxylic acid); isopropylamine in step 3 was replaced with methylamine. | $^1$H NMR (400 MHz, DMSO-d$_6$) δ 13.08 (s, 1H), 10.28 (s, 1H), 8.88 (d, J = 19.2 Hz, 2H), 8.39-8.34 (m, 2H), 8.17-8.11 (m, 3H), 7.61 (d, J = 10.0 Hz, 2H), 7.31-7.06 (m, 1H), 6.81 (s, 1H), 2.83 (s, 3H). MS m/z (ESI): 401.1 [M + H]. |

TABLE 2-continued

| No. | Compound Structure | Compound Name | Starting material or regent different from that in Example 2 | Characterization Data |
|---|---|---|---|---|
| TDI01110 | 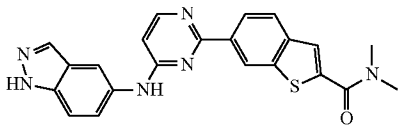 [SMILES: CN(C)C(=O)c1cc2ccc(-c3nccc(Nc4ccc5[nH]ncc5c4)n3)cc2s1] | 6-(4-((1H-indazol-5-yl)amino)pyrimidin-2-yl)-N,N-dimethylbenzo[b]thiophene-2-carboxamide | The preparation started from step 3 of Example 2, and Br—[benzofuran-2-carboxylic acid] was replaced with Br—[benzothiophene-2-carboxylic acid] ; isopropylamine was replaced with dimethylamine in step 3. | $^1$H NMR (400 MHz, CD$_3$OD) δ 8.78 (s, 1H), 8.24 (m, 3H), 8.13 (d, J = 4.0 Hz, 2H), 7.82 (s, 1H), 7.69 (d, J = 12 Hz, 1H), 7.62 (s, 1H), 6.88 (d, J = 8.0 Hz, 1H), 3.17 (s, 6H). MS m/z (ESI): 415.1 [M + H]. |
| TDI01111 | 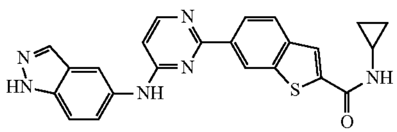 [SMILES: O=C(NC1CC1)c1cc2ccc(-c3nccc(Nc4ccc5[nH]ncc5c4)n3)cc2s1] | 6-(4-((1H-indazol-5-yl)amino)pyrimidin-2-yl)-N-cyclopropylbenzo[b]thiophene-2-carboxamide | The preparation started from step 3 of Example 2, and Br—[benzofuran-2-carboxylic acid] was replaced with Br—[benzothiophene-2-carboxylic acid] ; isopropylamine was replaced with cyclopropylamine in step 3. | $^1$H NMR (400 MHz, DMSO-d$_6$) δ 13.12 (s, 1H), 10.25 (s, 1H), 8.87 (m, 1H), 8.39 (d, J = 4.0 Hz, 1H), 8.32 (d, J = 8.0 Hz, 1H), 8.13-8.08 (m, 4H), 7.61 (m, 2H), 6.79 (d, J = 4.0 Hz, 1H), 2.87 (s, 1H), 0.75 (d, J = 4.0 Hz, 2H), 0.62 (s, 2H). MS m/z (ESI): 427.2 [M + H]. |
| TDI01112 | 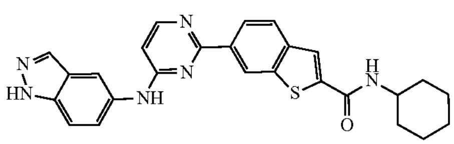 [SMILES: O=C(NC1CCCCC1)c1cc2ccc(-c3nccc(Nc4ccc5[nH]ncc5c4)n3)cc2s1] | 6-(4-((1H-indazol-5-yl)amino)pyrimidin-2-yl)-N-cyclohexylbenzo[b]thiophene-2-carboxamide | The preparation started from step 3 of Example 2, and Br—[benzofuran-2-carboxylic acid] was replaced with Br—[benzothiophene-2-carboxylic acid] ; isopropylamine was replaced with cyclohexylamine. | $^1$H NMR (400 MHz, DMSO-d$_6$) δ 13.15 (s, 1H), 10.27 (s, 1H), 8.88 (s, 1H), 8.60 (d, J = 8.0 Hz, 1H), 8.39 (d, J = 4.0 Hz, 1H), 8.31 (s, 1H), 8.21 (s, 1H), 8.13 (s, 2H), 8.10 (d, J = 8.0 Hz, 1H), 7.63 (d, J = 8.0 Hz, 1H), 7.59 (s, 1H), 6.80 (d, J = 4.0 Hz, 1H), 3.77 (s, 1H), 1.87 (s, 2H), 1.76 (s, 2H), 1.65-1.59 (m, 1H), 1.34 (s, 4H), 1.17 (s, 1H). MS m/z (ESI): 469.1 [M + H]. |

TABLE 2-continued

| No. | Compound Structure | Compound Name | Starting material or regent different from that in Example 2 | Characterization Data |
|---|---|---|---|---|
| TD101114 | (structure) | 6-(4-((1H-indazol-5-yl)amino)pyrimidin-2-yl)-N-(1-methylpiperidin-4-yl)benzo[b]thiophene-2-carboxamide | The preparation started from step 3 of Example 2, and (6-bromobenzofuran-2-carboxylic acid) in step 3 was replaced with (6-bromobenzo[b]thiophene-2-carboxylic acid); and (isopropylamine) was replaced with (4-amino-1-methylpiperidine). | $^1$H NMR (400 MHz, CD$_3$OD) δ 8.86 (s, 1H), 8.42-8.35 (m, 1H), 8.29 (d, J = 6.0 Hz, 1H), 8.13 (s, 1H), 8.04 (d, J = 17.2 Hz, 1H), 7.97 (d, J = 8.4 Hz, 1H), 7.59 (s, 2H), 6.66 (d, J = 6.0 Hz, 1H), 3.92-3.87 (m, 1H), 2.97-2.95 (m, 2H), 2.33 (s, 3H), 2.22-2.19 (m, 2H), 2.01-1.98 (m, 2H), 1.78-1.68 (m, 2H). MS m/z (ESI): 484.3 [M + H]. |
| TD101115 | (structure) | 6-(4-((1H-indazol-5-yl)amino)pyrimidin-2-yl)-N-(pyridin-3-yl)benzo[b]thiophene-2-carboxamide | The preparation started from step 3 of Example 2, and (6-bromobenzofuran-2-carboxylic acid) in step 3 was replaced with (6-bromobenzo[b]thiophene-2-carboxylic acid); and (isopropylamine) was replaced with (3-aminopyridine). | $^1$H NMR (400 MHz, DMSO-d$_6$) δ 11.07 (s, 1H), 10.41 (s, 1H), 9.12 (s, 1H), 8.96 (s, 1H), 8.50 (s, 2H), 8.42-8.36 (m, 3H), 8.23 (d, J = 8.4 Hz, 1H), 8.17-8.15 (m, 2H), 7.68-7.59 (m, 3H), 6.84 (d, J = 6.4 Hz, 1H). MS m/z (ESI): 464.2 [M + H]. |

TABLE 2-continued

| No. | Compound Structure | Compound Name | Starting material or regent different from that in Example 2 | Characterization Data |
|---|---|---|---|---|
| TDI01122 | 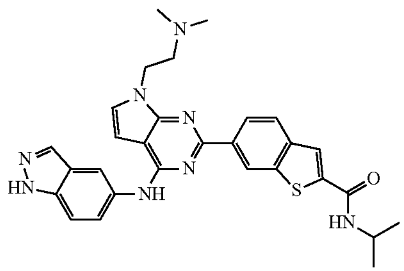 [SMILES: CC(C)NC(=O)c1cc2ccc(-c3nc(Nc4ccc5[nH]ncc5c4)c4ccn(CCN(C)C)c4n3)cc2s1] | 6-(4-((1H-indazol-5-yl)amino)-7-(2-(dimethylamino)ethyl)-7H-pyrrolo[2,3-d]pyrimidin-2-yl)-N-isopropylbenzo[b]thiophene-2-carboxamide | The preparation started from step 3 of Example 2, and step 3 was replaced with [structure: 6-bromobenzofuran-2-carboxylic acid]; [structure: Boc-protected 6-bromobenzo[b]thiophene-2-carboxylic acid] in step 5 was replaced with [structure: 2-chloro-4-((indazol-5-yl)amino)pyrimidine, BocN]; replaced with [structure: chloropyrrolopyrimidine with dimethylaminoethyl and indazolylamino, Reg-1-9]. | $^1$H NMR (400 MHz, DMSO-$d_6$) δ 9.62 (s, 1H), 9.57 (s, 1H), 9.00 (s, 1H), 8.58 (d, J = 7.8 Hz, 1H), 8.50 (d, J = 8.5 Hz, 1H), 8.32 (s, 1H), 8.17 (s, 1H), 8.12 (s, 1H), 8.03 (d, J = 8.5 Hz, 1H), 7.77 (d, J = 9.1 Hz, 1H), 7.62 (d, J = 8.9 Hz, 1H), 7.40 (d, J = 3.5 Hz, 1H), 6.81 (s, 1H), 4.69 (s, 2H), 4.13-4.07 (m, 1H), 3.67 (d, J = 5.6 Hz, 2H), 2.91 (d, J = 4.2 Hz, 6H), 1.21 (d, J = 6.6 Hz, 6H). MS m/z (ESI): 539.1 [M + H]. |

TABLE 2-continued

| No. | Compound Structure | Compound Name | Starting material or regent different from that in Example 2 | Characterization Data |
|---|---|---|---|---|
| TDI01128 | 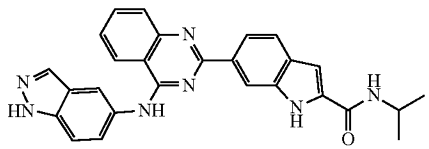 [SMILES: CC(C)NC(=O)c1cc2ccc(-c3nc(Nc4ccc5[nH]ncc5c4)c4ccccc4n3)cc2[nH]1] | 6-(4-((1H-indazol-5-yl)amino)quinazolin-2-yl)-N-isopropyl-1H-indole-2-carboxamide | The preparation started from step 3 of Example 2, and Br—[benzofuran-2-carboxylic acid with Br] in step 3 was replaced with [6-bromo-1H-indole-2-carboxylic acid]; [2-chloro-N-(1-Boc-indazol-5-yl)pyrimidin-4-amine] replaced with [2-chloro-4-((1-Boc-indazol-5-yl)amino)quinazoline] (Reg-1-2) in step 5 was. | ¹H NMR (400 MHz, DMSO-d₆) δ 13.09 (s, 1H), 11.82 (s, 1H), 9.87 (s, 1H), 8.58 (d, J = 7.6 Hz, 2H), 8.36 (s, 1H), 8.26 (d, J = 7.6 Hz, 1H), 8.21 (d, J = 8.8 Hz, 2H), 7.96-7.90 (m, 1H), 7.85 (d, J = 3.2 Hz, 2H), 7.67 (dd, J = 8.4, 2.8 Hz, 2H), 7.61-7.54 (m, 1H), 7.18 (s, 1H), 4.17-4.12 (m, 1H), 1.21 (d, J = 6.4 Hz, 6H). MS m/z (ESI): 462.2 [M + H]. |

TABLE 2-continued

| No. | Compound Structure | Compound Name | Starting material or regent different from that in Example 2 | Characterization Data |
|---|---|---|---|---|
| TDI01135 | 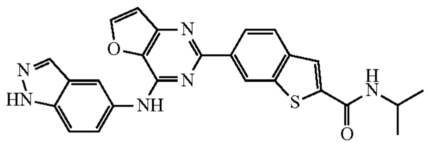 [SMILES: CC(C)NC(=O)c1cc2ccc(-c3nc(Nc4ccc5[nH]ncc5c4)c4occc4n3)cc2s1] | 6-(4-((1H-indazol-5-yl)amino)furo[3,2-d]pyrimidin-2-yl)-N-isopropylbenzo[b]thiophene-2-carboxamide | The preparation started from step 3 of Example 2, and Br-[benzofuran-2-carboxylic acid-OH] in step 3 was replaced with Br-[benzothiophene-2-carboxylic acid-OH]; [2-chloropyrimidine-NH-indazole-Boc] (Reg-1-1) in step 5 was replaced with [2-chlorofuropyrimidine-NH-indazole-Boc] (Reg-1-3). | $^1$H NMR (400 MHz, CD$_3$OD) δ 8.74 (s, 1H), 8.27-8.19 (m, 3H), 8.11 (s, 1H), 8.01 (d, J = 7.6 Hz, 2H), 7.76 (dd, J = 8.8, 1.6 Hz, 1H), 7.65 (d, J = 8.8 Hz, 1H), 7.09 (d, J = 2.0 Hz, 1H), 4.25-4.19 (m, 1H), 1.29 (d, J = 6.4 Hz, 6H). MS m/z (ESI): 469.1 [M + H]. |

TABLE 2-continued

| No. | Compound Structure | Compound Name | Starting material or regent different from that in Example 2 | Characterization Data |
|---|---|---|---|---|
| TDI01136 | (structure) | 6-(4-((1H-indazol-5-yl)amino)thieno[3,2-d]pyrimidin-2-yl)-N-isopropylbenzo[b]thiophene-2-carboxamide | The preparation started from step 3 of Example 2, and (structure with Br, OH, O on benzofuran-2-carboxylic acid) in step 3 was replaced with (structure with Br, OH, O on benzothiophene-2-carboxylic acid); (2-chloropyrimidin-4-yl amino indazole with BocN) (Reg-1-1) in step 5 was replaced with (2-chlorothieno[3,2-d]pyrimidin-4-yl amino indazole with BocN) (Reg-1-4). | $^1$H NMR (400 MHz, DMSO-$d_6$) δ 13.25 (s, 1H), 10.25 (s, 1H), 8.94 (s, 1H), 8.61 (d, J = 8.0 Hz, 1H), 8.41 (d, J = 8.0 Hz, 1H), 8.26 (d, J = 4.0 Hz, 1H), 8.18-8.14 (m, 3H), 8.06 (d, J = 8.0 Hz, 1H), 7.71-7.65 (m, 2H), 7.54 (d, J = 4.0 Hz, 1H), 4.15-4.06 (m, 1H), 1.21 (d, J = 8.0 Hz, 6H). MS m/z (ESI): 485.1 [M + H]. |

TABLE 2-continued

| No. | Compound Structure | Compound Name | Starting material or regent different from that in Example 2 | Characterization Data |
|---|---|---|---|---|
| TDI01141 | (structure shown) | 6-(4-((1H-indazol-5-yl)amino)thieno[3,2-d]pyrimidin-2-yl)-N-isopropyl-1H-indole-2-carboxamide | The preparation started from step 3 of Example 2, and Br—[benzofuran-2-carboxylic acid with OH] in step 3 was replaced with Br—[indole-2-carboxylic acid with BocN] (Reg-1-4); and [2-chloropyrimidine-NH-indazole-BocN] (Reg-1-1) in step 5 was replaced with [2-chlorothienopyrimidine-NH-indazole-BocN]. | $^1$H NMR (400 MHz, DMSO-$d_6$) δ 13.26 (s, 1H), 12.11 (s, 1H), 10.80 (s, 1H), 8.46 (s, 1H), 8.40 (d, J = 7.2 Hz, 1H), 8.33 (d, J = 4.0 Hz, 1H), 8.21 (s, 1H), 8.15 (s, 1H), 8.04 (d, J = 8.0 Hz, 1H), 7.80 (d, J = 8.0 Hz, 1H), 7.70 (s, 2H), 7.56 (d, J = 4.0 Hz, 1H), 7.26 (s, 1H), 4.20-4.12 (m, 1H), 1.22 (d, J = 6.4 Hz, 6H). MS m/z (ESI): 468.2 [M + H]. |

TABLE 2-continued

| No. | Compound Name | Compound Structure | Starting material or regent different from that in Example 2 | Characterization Data |
|---|---|---|---|---|
| TDI01142 | 6-(4-((1H-indazol-5-yl)amino)thieno[2,3-d]pyrimidin-2-yl)-N-isopropyl-1H-indole-2-carboxamide | (structure) | The preparation started from step 3 of Example 2, and Br-[benzofuran-2-carboxylic acid] was replaced with Br-[indole-2-carboxylic acid]; (Reg-1-1) in step 5 was replaced with (Reg-1-5). | ¹H NMR (400 MHz, DMSO-d₆) δ 11.18 (s, 1H), 9.79 (s, 1H), 8.37 (m, 3H), 8.15 (m, 1H), 8.00-7.86 (m, 2H), 7.67 (s, 2H), 7.20 (s, 1H), 1.22 (s, 6H). MS m/z (ESI): 468.1 [M + H]. |

TABLE 2-continued

| No. | Compound Structure | Compound Name | Starting material or regent different from that in Example 2 | Characterization Data |
|---|---|---|---|---|
| TDI01143 | (structure) | 6-(4-((1H-indazol-5-yl)amino)-7H-pyrrolo[2,3-d]pyrimidin-2-yl)-N-isopropyl-1H-indole-2-carboxamide | The preparation started from step 3 of Example 2, and Br—(6-bromo-benzofuran-2-carboxylic acid) in step 3 was replaced with (6-bromo-1H-indole-2-carboxylic acid OH); (Reg-1-1) in step 5 was replaced with (Reg-1-6). | $^1$H NMR (400 MHz, CD$_3$OD) δ 8.47 (s, 1H), 8.32 (s, 1H), 8.13 (d, J = 9.5 Hz, 2H), 7.84 (d, J = 7.8 Hz, 1H), 7.70-7.59 (m, 2H), 7.13 (d, 2H), 6.54 (s, 1H), 4.25 (m, J = 12.6, 6.3 Hz, 1H), 1.30 (s, 3H), 1.28 (s, 3H); MS m/z (ESI): 451.1 [M + H]. |

TABLE 2-continued

| No. | Compound Structure | Compound Name | Starting material or regent different from that in Example 2 | Characterization Data |
|---|---|---|---|---|
| TDI01149 | (structure) | 6-(7-((1H-indazol-5-yl)amino)thiazolo[4,5-d]pyrimidin-5-yl)-N-isopropyl-1H-indole-2-carboxamide | The preparation started from step 3 of Example 2, and (structure with Br, OH, C=O, O) in step 3 was replaced with (structure with Br, OH, C=O, N-H) (Reg-1-1) in step 5 was replaced with (structure with Cl, N, NH, BocN) (Reg-1-7). | $^1$H NMR (400 MHz, DMSO-d$_6$) δ 13.08 (s, 1H), 11.90 (s, 1H), 10.22 (s, 1H), 9.34 (s, 1H), 8.53 (s, 1H), 8.44 (s, 1H), 8.32 (d, J = 7.6 Hz, 1H), 8.19 (s, 1H), 8.15 (d, J = 8.4 Hz, 1H), 7.97 (d, J = 8.4 Hz, 1H), 7.70 (d, J = 8.4 Hz, 1H), 7.63 (d, J = 8.8 Hz, 1H), 7.21 (s, 1H), 4.16-4.13 (m, 1H), 1.21 (d, J = 6.4 Hz, 6H). MS m/z (ESI): 469.1 [M + H]. |

TABLE 2-continued

| No. | Compound Name | Starting material or regent different from that in Example 2 | Characterization Data |
|---|---|---|---|
| TDI01218 | 6-(4-((1H-indazol-5-yl)amino)-7H-phenyl-7H-pyrrolo[2,3-d]pyrimidin-2-yl)-N-isopropylbenzo[b]thiophene-2-carboxamide | The preparation started from step 3 of Example 2, and [structures shown] in step 3 was replaced with (Reg-1-1) in [structure shown] step 5 was replaced with [structure shown] (Reg-1-10). | $^1$H NMR (400 MHz, CD$_3$OD) δ 8.94 (s, 1H), 8.85 (d, J = 8.7 Hz, 1H), 8.53 (d, J = 8.4 Hz, 1H), 8.22 (s, 1H), 7.98 (s, 2H), 7.96-7.85 (m, 2H), 7.70 (s, 1H), 7.62 (t, J = 7.5 Hz, 2H), 7.47 (s, 2H), 7.16 (d, J = 8.7 Hz, 1H), 7.10 (s, 1H), 4.23 (s, 1H), 1.30 (d, J = 6.5 Hz, 6H). MS m/z (ESI): 544.2 [M + H]. |
| TDI01262 | 6-(4-((1H-indazol-5-yl)amino)pyrimidin-2-yl)-N-(2-(dimethylamino)pyridin-4-yl)benzo[b]thiophene-2-carboxamide | The preparation started from step 3 of Example 2, and [structure shown] Br in step 3 was replaced with [structures shown] ; was replaced with [structure shown]. | $^1$H NMR (400 MHz, DMSO-d$_6$) δ 13.07 (s, 1H), 10.78 (s, 1H), 9.72 (s, 1H), 8.99 (s, 1H), 8.48 (dd, J = 12.2, 5.8 Hz, 2H), 8.40 (d, J = 5.8 Hz, 1H), 8.15 (dd, J = 18.3, 9.8 Hz, 3H), 8.03 (d, J = 5.8 Hz, 1H), 7.60 (s, 2H), 7.13 (s, 2H), 6.73 (d, J = 5.8 Hz, 1H), 3.08 (s, 5H). MS m/z (ESI): 507.3 [M + H]. |

TABLE 2-continued

| No. | Compound Name | Compound Structure | Starting material or regent different from that in Example 2 | Characterization Data |
|---|---|---|---|---|
| TDI01280 | 6-(4-((4-(1H-pyrazol-4-yl)phenyl)amino)pyrimidin-2-yl)-N-isopropyl-1H-indole-2-carboxamide | 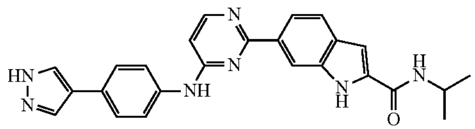 [SMILES: CC(C)NC(=O)c1cc2ccc(-c3nccc(Nc4ccc(-c5cn[nH]c5)cc4)n3)cc2[nH]1] | The preparation started from step 3 of Example 2, and Br-benzofuran-COOH in step 3 was replaced with Br-indole-COOH; and 2-chloro-pyrimidine-NH-phenyl-indazole-Boc (Reg-1-1) in step 5 was replaced with 2-chloro-pyrimidine-NH-phenyl-pyrazole-Boc (Reg-1-16). | $^1$H NMR (400 MHz, CD$_3$OD) δ 8.42 (s, 1H), 8.20 (d, J = 7.2 Hz, 1H), 8.04 (s, 2H), 7.86 (s, 4H), 7.76 (s, 2H), 7.22 (s, 1H), 6.91 (d, J = 7.2 Hz, 1H), 4.25 (dt, J = 13.2, 6.5 Hz, 1H), 1.29 (d, J = 6.6 Hz, 7H). MS m/z (ESI): 438.3 [M + H]. |
| TDI01327 | 7-(4-((1H-indazol-5-yl)amino)pyrimidin-2-yl)-N-isopropylquinoline-2-carboxamide | 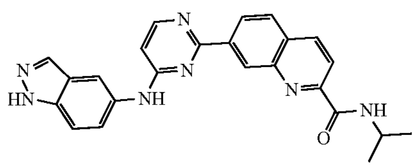 [SMILES: CC(C)NC(=O)c1ccc2ccc(-c3nccc(Nc4ccc5[nH]ncc5c4)n3)cc2n1] | The preparation started from step 3 of Example 2, and Br-benzofuran-COOH in step 3 was replaced with Br-quinoline-COOH. | $^1$H NMR (400 MHz, DMSO-d$_6$) δ 13.12 (s, 1H), 10.03 (s, 1H), 9.16 (s, 1H), 8.68-8.58 (m, 3H), 8.45 (d, J = 6.1 Hz, 1H), 8.29-8.15 (m, 4H), 7.63 (d, J = 8.8 Hz, 1H), 7.57 (d, J = 9.5 Hz, 1H), 6.81 (d, J = 6.1 Hz, 1H), 4.20 (d, J = 7.9 Hz, 1H), 1.29 (d, J = 6.6 Hz, 6H). MS m/z (ESI): 424.2 [M + H]. |

| No. | Compound Structure | Compound Name | Starting material or regent different from that in Example 2 | Characterization Data |
|---|---|---|---|---|
| TDI01392 | 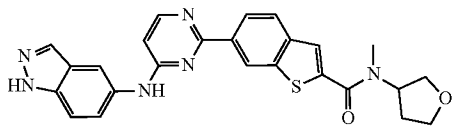 [SMILES: CN(C(=O)c1cc2ccc(-c3nccc(Nc4ccc5[nH]ncc5c4)n3)cc2s1)C1CCOC1] | 6-(4-((1H-indazol-5-yl)amino)pyrimidin-2-yl)-N-methyl-N-(tetrahydrofuran-3-yl)benzo[b]thiophene-2-carboxamide | The preparation started from step 3 of Example 2, and 5-bromobenzofuran-2-carboxylic acid was replaced with 6-bromobenzo[b]thiophene-2-carboxylic acid, H₂N-isobutyl was replaced with N-methyl-tetrahydrofuran-3-amine in step 3 | $^1$H NMR (400 MHz, DMSO-d$_6$) δ 9.69 (s, 1H), 8.94 (s, 1H), 8.43 (d, J = 8.4 Hz, 1H), 8.39 (d, J = 5.6 Hz, 1H), 8.18 (s, 1H), 8.10 (s, 1H), 8.06 (d, J = 8.4 Hz, 1H), 7.83 (s, 1H), 7.62-7.57 (m, 2H), 6.71 (d, J = 5.6 Hz, 1H), 5.08-5.02 (m, 1H), 4.03-3.97 (m, 1H), 3.87-3.83 (m, 1H), 3.77-3.71 (m, 1H), 3.63-3.57 (m, 1H), 3.08 (s, 3H), 2.32-2.24 (m, 1H), 2.04-1.97 (m, 1H). MS m/z (ESI): 471.1 [M + H]. |
| TDI01394 | 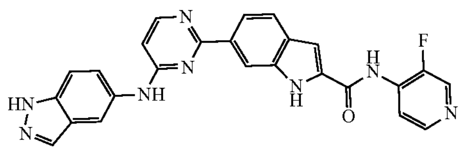 [SMILES: O=C(Nc1ccncc1F)c1cc2ccc(-c3nccc(Nc4ccc5[nH]ncc5c4)n3)cc2[nH]1] | 6-(4-((1H-indazol-5-yl)amino)pyrimidin-2-yl)-N-(3-fluoropyridin-4-yl)-1H-indole-2-carboxamide | The preparation started from step 3 of Example 2, and 5-bromobenzofuran-2-carboxylic acid was replaced with 6-bromo-1H-indole-2-carboxylic acid, H₂N-isobutyl was replaced with 3-fluoropyridin-4-amine in step 3 | $^1$H NMR (400 MHz, DMSO-d$_6$) δ 13.04 (s, 1H), 12.20 (s, 1H), 10.48 (s, 1H), 9.63 (s, 1H), 8.63 (s, 1H), 8.56 (s, 1H), 8.43 (d, J = 5.2 Hz, 1H), 8.36 (d, J = 5.8 Hz, 1H), 8.29 (s, 1H), 8.23-8.12 (m, 1H), 8.02-7.96 (m, 1H), 7.80 (d, J = 8.5 Hz, 1H), 7.59 (d, J = 10.5 Hz, 1H), 6.68 (d, J = 5.9 Hz, 1H). MS m/z (ESI): 465.2 [M + H]. |

TABLE 2-continued

| No. | Compound Structure | Compound Name | Starting material or regent different from that in Example 2 | Characterization Data |
|---|---|---|---|---|
| TDI01410 | 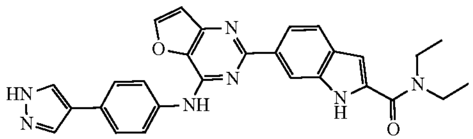 [SMILES: CCN(CC)C(=O)c1cc2ccc(-c3nc(Nc4ccc(-c5cn[nH]c5)cc4)c4occc4n3)cc2[nH]1] | 6-(4-((4-(1H-pyrazol-4-yl)phenyl)amino)furo[3,2-d]pyrimidin-2-yl)-N,N-diethyl-1H-indole-2-carboxamide | The preparation started from step 3 of Example 2, and 6-Br-benzofuran-2-carboxylic acid was replaced with 6-Br-indole-2-carboxylic acid; 2-chloro-N-(1-Boc-indazol-5-yl)pyrimidin-4-amine (Reg-1-1) in step 5 was replaced with 2-chloro-N-(4-(1-Boc-pyrazol-4-yl)phenyl)furo[3,2-d]pyrimidin-4-amine (Reg-1-44). isopropylamine in step 3 was replaced with N-ethylethanamine. | $^1$H NMR (400 MHz, DMSO-d$_6$) δ 12.90 (s, 1H), 11.84 (s, 1H), 9.97 (s, 1H), 8.55 (s, 1H), 8.37 (s, 1H), 8.16 (d, J = 8.5 Hz, 2H), 8.02 (d, J = 8.6 Hz, 3H), 7.69 (t, J = 7.6 Hz, 3H), 7.15 (s, 1H), 6.83 (s, 1H), 3.60 (s, 2H), 3.31 (s, 2H), 1.23 (s, 6H). MS m/z (ESI): 492.0 [M + H]. |

TABLE 2-continued

| No. | Compound Structure | Compound Name | Starting material or regent different from that in Example 2 | Characterization Data |
|---|---|---|---|---|
| TDI01434 | (structure) | (6-(4-((1H-pyrazol-4-yl)phenyl)amino)pyrimidin-2-yl)-1H-indol-2-yl)(3,3-difluoroazetidin-1-yl)methanone | The preparation started from step 3 of Example 2, and Br—[benzofuran-2-carboxylic acid with OH] in step 3 was replaced with Br—[indole-2-carboxylic acid with OH]; (Reg-1-1) in step 5 was replaced with [2-chloro-N-(1-Boc-indazol-5-yl)pyrimidin-4-amine] (Reg-1-1) in step 5 was replaced with [2-chloro-4-((4-(1-Boc-pyrazol-4-yl)phenyl)amino)pyrimidine]; NH₂-iPr in step 3 was replaced with 3,3-difluoroazetidine·HCl 16; | ¹H NMR (400 MHz, DMSO-d₆) δ 12.89 (s, 1H), 12.07 (s, 1H), 9.65 (s, 1H), 8.58 (s, 1H), 8.38 (d, J = 5.8 Hz, 1H), 8.15 (d, J = 8.4 Hz, 1H), 7.92 (s, 1H), 7.83 (d, J = 8.2 Hz, 2H), 7.72 (d, J = 8.5 Hz, 1H), 7.65 (d, J = 8.4 Hz, 2H), 6.97 (s, 1H), 6.69 (d, J = 5.8 Hz, 1H), 5.02 (s, 2H), 4.59 (s, 2H). MS m/z (ESI): 472.0 [M + H]. |
| TDI01434B | (structure) | (6-(4-((1H-indazol-5-yl)amino)pyrimidin-2-yl)-1H-indol-2-yl)(3,3-difluoroazetidin-1-yl)methanone | The preparation started from step 3 of Example 2, and Br—[benzofuran-2-carboxylic acid with OH] in step 3 was replaced with Br—[indole-2-carboxylic acid with OH]; NH₂-iPr in step 3 was replaced with 3,3-difluoroazetidine·HCl. | ¹H NMR (400 MHz, DMSO-d₆) δ 13.04 (s, 1H), 12.09 (s, 1H), 9.69 (s, 1H), 8.53 (s, 1H), 8.35 (d, J = 5.7 Hz, 1H), 8.27 (s, 1H), 8.14 (d, J = 7.2 Hz, 2H), 7.73 (d, J = 8.4 Hz, 1H), 7.60 (s, 1H), 6.98 (s, 2H), 6.68 (d, J = 5.7 Hz, 1H), 5.02 (s, 2H), 4.60 (s, 2H). MS m/z (ESI): 445.9 [M + H]. |

TABLE 2-continued

| No. | Compound Structure | Compound Name | Starting material or regent different from that in Example 2 | Characterization Data |
|---|---|---|---|---|
| TDI01526 | 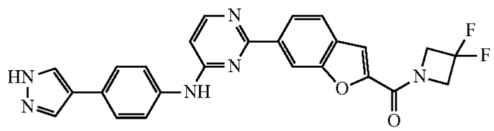 [SMILES: O=C(c1cc2ccc(-c3nccc(Nc4ccc(-c5cn[nH]c5)cc4)n3)cc2o1)N1CC(F)(F)C1] | (6-(4-(4-(1H-pyrazol-4-yl)phenyl)amino)pyrimidin-2-yl)benzofuran-2-yl)(3,3-difluoroazetidin-1-yl)methanone | The preparation started from step 3 of Example 2, and H₂N-iPr in step 3 was replaced with 3,3-difluoroazetidine·HCl (Reg-1-16); (Reg-1-1) in step 5 was replaced with BocN-pyrazole-C₆H₄-NH-pyrimidine-Cl. | ¹H NMR (400 MHz, DMSO-d6) δ 10.13 (s, 1H), 8.54 (s, 1H), 8.42 (d, J = 6.4 Hz, 1H), 8.34 (dd, J = 8.4, 1.2 Hz, 1H), 8.08 (s, 2H), 7.94 (d, J = 8.4 Hz, 1H), 7.77 (d, J = 8.4 Hz, 2H), 7.73-7.63 (m, 3H), 6.82 (d, J = 6.4 Hz, 1H), 5.11 (s, 2H), 4.56 (s, 2H). MS m/z (ESI): 473.2 [M + H]. |

TABLE 2-continued

| No. | Compound Structure | Compound Name | Starting material or regent different from that in Example 2 | Characterization Data |
|---|---|---|---|---|
| TDI01581 | (structure shown) | (6-(4-((4-(1H-pyrazol-4-yl)phenyl)amino)-1,3,5-triazin-2-yl)-1H-indol-2-yl)(3,3-difluoroazetidin-1-yl)methanone | The preparation started from step 3 of Example 2, and 6-bromobenzofuran-2-carboxylic acid was replaced with 6-bromo-1H-indole-2-carboxylic acid in step 3; 2-chloro-N-(1-Boc-indazol-5-yl)pyrimidin-4-amine (Reg-1-1) in step 5 was replaced with 4-chloro-N-(4-(1-Boc-1H-pyrazol-4-yl)phenyl)-1,3,5-triazin-2-amine (Reg-1-41); isopropylamine in step 3 was replaced with 3,3-difluoroazetidine hydrochloride. | $^1$H NMR (400 MHz, DMSO-$d_6$) δ 12.21 (s, 1H), 10.28 (s, 1H), 8.82 (s, 1H), 8.64 (s, 1H), 8.17 (d, J = 8.9 Hz, 1H), 8.05 (s, 2H), 7.80 (t, J = 12.1 Hz, 3H), 7.65 (s, 2H), 7.02 (s, 1H), 5.06 (s, 2H), 4.60 (s, 2H). MS m/z (ESI): 472.7 [M + H]. |

TABLE 2-continued

| No. | Compound Structure | Compound Name | Starting material or regent different from that in Example 2 | Characterization Data |
|---|---|---|---|---|
| TDI01582 | 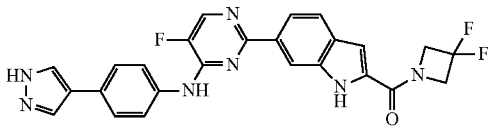 [SMILES: O=C(c1cc2ccc(-c3ncc(F)c(Nc4ccc(-c5cn[nH]c5)cc4)n3)cc2[nH]1)N1CC(F)(F)C1] | (6-(4-((4-(1H-pyrazol-4-yl)phenyl)amino)-5-fluoropyrimidin-2-yl)-1H-indol-2-yl)(3,3-difluoroazetidin-1-yl)methanone | The preparation started from step 3 of Example 2, and 6-bromo-1H-indole-2-carboxylic acid in step 3 was replaced with the corresponding indole; 2-chloro-N-(1H-indazol-5-yl)pyrimidin-4-amine (Reg-1-1) in step 5 was replaced with 2-chloro-5-fluoro-N-(4-(1-Boc-1H-pyrazol-4-yl)phenyl)pyrimidin-4-amine (Reg-1-40); 3,3-difluoroazetidine hydrochloride in step 3 was used. | ¹H NMR (400 MHz, DMSO-d₆) δ 12.05 (s, 1H), 9.66 (s, 1H), 8.48 (s, 2H), 8.06 (d, J = 6.0 Hz, 3H), 7.94 (d, J = 8.4 Hz, 2H), 7.70 (dd, J = 13.3, 8.6 Hz, 3H), 6.96 (s, 1H), 4.96 (d, J = 16.2 Hz, 2H), 4.57 (s, 2H). MS m/z (ESI): 489.6 [M + H]. |
| TDI01825B | 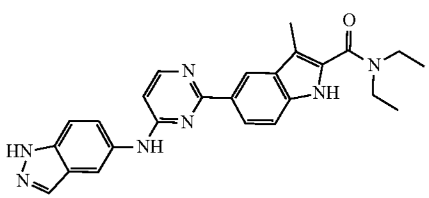 [SMILES: CCN(CC)C(=O)c1[nH]c2ccc(-c3nccc(Nc4ccc5[nH]ncc5c4)n3)cc2c1C] | 5-(4-((1H-indazol-5-yl)aminopyrimidin-2-yl)-N,N-diethyl-3-methyl-1H-indole-2-carboxamide | The preparation started from step 3 of Example 2, and 6-bromo-3-methyl-1H-indole-2-carboxylic acid in step 3 was used; diethylamine in step 3 was replaced with isopropylamine. | ¹H NMR (400 MHz, DMSO-d₆) δ 13.03 (s, 1H), 11.41 (s, 1H), 9.59 (s, 1H), 8.65 (s, 1H), 8.33 (d, J = 4 Hz, 1H), 8.24 (d, J = 12 Hz, 1H), 8.08 (s, 1H), 7.56 (m, 1H), 7.42 (d, J = 8.4Hz, 2H) 6.63 (d, J = 6 Hz, 1H), 3.44 (s, 4H), 2.31 (s, 3H), 1.13 (s, 6H). MS m/z (ESI): 440.0 [M + H]. |

TABLE 2-continued

| No. | Compound Structure | Compound Name | Starting material or regent different from that in Example 2 | Characterization Data |
|---|---|---|---|---|
| TDI01825C | 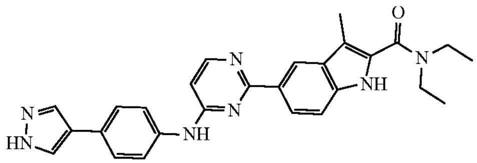 [SMILES: CCN(CC)C(=O)c1[nH]c2ccc(-c3nccc(Nc4ccc(-c5cn[nH]c5)cc4)n3)cc2c1C] | 5-(4-((4-(1H-pyrazol-4-yl)phenyl)amino)pyrimidin-2-yl)-N, N-diethyl-3-methyl-1H-indole-2-carboxamide | The preparation started from step 3 of Example 2, and [6-bromobenzofuran-2-carboxylic acid] in step 3 was replaced with [5-bromo-3-methyl-1H-indole-2-carboxylic acid]; (Reg-1-1) in step 5 was replaced with [Boc-pyrazole-phenyl-chloropyrimidine] (Reg-1-16); [isopropylamine] in step 3 was replaced with [diethylamine]. | $^1$H NMR (400 MHz, DMSO-d$_6$) δ11.42 (s, 1H), 9.62 (s, 1H), 8.64 (s, 1H), 8.37 (s, 1H), 8.25 (s, 1H), 8.16 (s, 1H), 8.06 (s, 1H), 7.82 (s, 2H), 7.67 (s, 2H), 7.43 (s, 1H), 6.66 (s, 1H), 3.45 (s, 4H), 2.30 (s, 3H), 1.13 (s, 6H). MS m/z (ESI): 466.0 [M + H]. |

TABLE 2-continued

| No. | Compound Structure | Compound Name | Starting material or regent different from that in Example 2 | Characterization Data |
|---|---|---|---|---|
| TDI01832 | 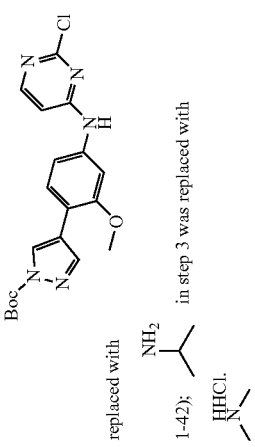 | 6-(4-((3-methoxy-4-(1H-pyrazol-4-yl)phenyl)amino)pyrimidin-2-yl)-N,N-dimethyl-1H-indole-2-carboxamide | The preparation started from step 3 of Example 2, and Br—[6-bromobenzofuran-2-carboxylic acid] in step 3 was replaced with Br—[6-bromo-1H-indole-2-carboxylic acid]; (Reg-1-1) in step 5 was replaced with [2-chloro-N-(1-Boc-1H-indazol-5-yl)pyrimidin-4-amine] (Reg-1-42); [Boc-pyrazole-methoxyphenyl-2-chloropyrimidin-4-amine] in step 3 was replaced with isopropylamine·HCl. | $^1$H NMR (400 MHz, DMSO-d$_6$) δ 11.85 (s, 1H), 9.68 (s, 1H), 8.54 (s, 1H), 8.4 (d, J = 5.6 Hz), 8.17 (m, 2H) 8.02 (m, 7.79 (s, 1H), 7.70 (d, J = 8.4Hz, 1H), 7.63 (d, J = 8.4 Hz, 1H), 7.32 (d, J = 9.6 Hz, 1H), 6.93 (s, 1H), 6.71 (d, J = 6 Hz, 1H), 3.96 (s, 3H), 2.55 (s, 6H). MS m/z (ESI): 454.0 [M + H]. |

TABLE 2-continued

| No. | Compound Structure | Compound Name | Starting material or regent different from that in Example 2 | Characterization Data |
|---|---|---|---|---|
| TDI01833 | 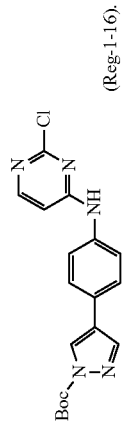 | N-(4-(1H-pyrazol-4-yl)phenyl)-2-(2-(methylsulfonyl)-1H-indol-6-yl)pyrimidin-4-amine | The preparation started from step 4 of Example 2, and Br-[6-bromo-N-isopropylbenzofuran-2-carboxamide] in step 3 was replaced with Br-[6-bromo-2-(methylsulfonyl)-1H-indole]; [2-chloro-N-(1-Boc-indazol-5-yl)pyrimidin-4-amine] in step 5 was replaced with [2-chloro-N-(4-(1-Boc-1H-pyrazol-4-yl)phenyl)pyrimidin-4-amine] (Reg-1-16). | $^1$H NMR (400 MHz, DMSO-$d_6$) δ 12.73 (s, 1H), 10.29 (s, 1H), 8.52 (s, 1H), 8.39 (d, J = 6.3 Hz, 1H), 8.13 (d, J = 8.0 Hz, 1H), 8.07 (s, 1H), 7.88 (d, J = 8.0 Hz, 1H), 7.79 (d, J = 8.0 Hz, 2H), 7.69 (d, J = 8.0 Hz, 2H), 7.24 (s, 1H), 6.81 (d, J = 6.3 Hz, 1H), 3.39 (s, 3H). MS m/z (ESI): 430.9 [M + H]. |

TABLE 2-continued

| No. | Compound Structure | Compound Name | Starting material or regent different from that in Example 2 | Characterization Data |
|---|---|---|---|---|
| TDI01837 | 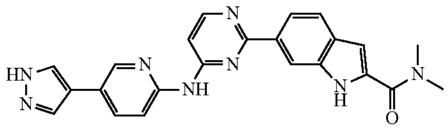 [SMILES: CN(C)C(=O)c1cc2ccc(-c3nccc(Nc4ccc(-c5cn[nH]c5)cn4)n3)cc2[nH]1] | 6-(4-((5-((1H-pyrazol-4-yl)pyridin-2-yl)amino)pyrimidin-2-yl)-N, N-dimethyl-1H-indole-2-carboxamide | The preparation started from step 3 of Example 2, and Br—[benzofuran-2-carboxylic acid with OH] in step 3 was replaced with Br—[indole-2-carboxylic acid with OH]; [2-chloro-pyrimidin-4-yl)amino indazole with BocN] was replaced with (Reg-1-1) in step 5 was replaced with [Boc-pyrazole-pyridine-NH-pyrimidine-Cl] (Reg-1-52). [isopropylamine NH₂ HCl] in step 3 was replaced with [dimethylamine HCl] | ¹H NMR (400 MHz, DMSO-d₆) δ 12.08 (s, 1H), 11.03 (s, 1H), 8.72 (s, 1H), 8.58-8.45 (m, 2H), 8.30-7.96 (m, 5H), 7.82 (d, J = 8.0 Hz, 1H), 7.62 (s, 1H), 6.99 (s, 1H), 3.34 (s, 3H), 3.09 (s, 3H). MS m/z (ESI): 424.7 [M + H]. |

TABLE 2-continued

| No. | Compound Structure | Compound Name | Starting material or regent different from that in Example 2 | Characterization Data |
|---|---|---|---|---|
| TDI01842 | 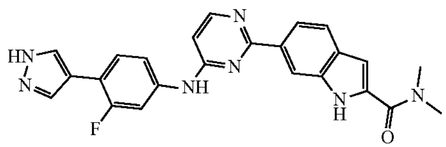 [SMILES: CN(C)C(=O)c1cc2ccc(-c3nccc(Nc4ccc(-c5cn[nH]c5)c(F)c4)n3)cc2[nH]1] | 6-(4-((3-fluoro-4-(1H-pyrazol-4-yl)phenyl)amino)pyrimidin-2-yl)-N,N-dimethyl-1H-indole-2-carboxamide | The preparation started from step 3 of Example 2, and Br-[benzofuran-2-carboxylic acid with OH] in step 3 was replaced with Br-[indole-2-carboxylic acid with OH]; (Reg-1-1) in step 5 was replaced with [Boc-pyrazole-phenyl-F with 2-chloropyrimidin-4-amine] (Reg-1-39). [isopropylamine HHCl] in step 3 was replaced with dimethylamine. | $^1$H NMR (400 MHz, DMSO-$d_6$) δ 13.03 (s, 1H), 11.88 (s, 1H), 9.86 (s, 1H), 8.53 (s, 1H), 8.43 (d, J = 5.7 Hz, 1H), 8.11 (d, J = 8.3 Hz, 1H), 8.03 (s, 2H), 7.91 (d, J = 13.7 Hz, 1H), 7.74 (dd, J = 16.5, 8.3 Hz, 2H), 7.60 (d, J = 8.5 Hz, 1H), 6.94 (s, 1H), 6.72 (d, J = 5.7 Hz, 1H), 3.40 (s, 3H) 3.08 (s, 3H) MS m/z (ESI): 441.8 [M + H]. |

TABLE 2-continued

| No. | Compound Structure | Compound Name | Starting material or regent different from that in Example 2 | Characterization Data |
|---|---|---|---|---|
| TDI01842B | (structure) | (3,3-difluoroazetidin-1-yl)(6-(4-((3-fluoro-4-(1H-pyrazol-4-yl)phenyl)amino)pyrimidin-2-yl)-1H-indol-2-yl)methanone | The preparation started from step 3 of Example 2, and Br-(benzofuran-COOH) was replaced with Br-(indole-COOH); (Reg-1-1) in step 5 was replaced with (Boc-pyrazole-phenyl-F-pyrimidine-Cl-NH) (Reg-1-39). in step 3 was replaced with (3-fluoroazetidine-NH₂·HCl). | ¹H NMR (400 MHz, DMSO-d₆) δ 13.04 (s, 1H), 12.10 (s, 1H), 9.92 (s, 1H), 8.55 (s, 1H), 8.43 (d, J = 5.6 Hz, 1H), 8.26-7.86 (m, 4H), 7.75 (t, J = 8.3 Hz, 2H), 7.61 (d, J = 8.3 Hz, 1H), 6.98 (s, 1H), 6.74 (d, J = 5.6 Hz, 1H), 5.04 (s, 2H), 4.59 (s, 2H). MS m/z (ESI): 489.9 [M + H]. |

TABLE 2-continued

| No. | Compound Structure | Compound Name | Starting material or regent different from that in Example 2 | Characterization Data |
|---|---|---|---|---|
| TDI01864 | 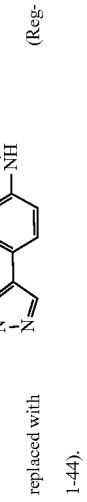 | 6-(4-((4-(1H-pyrazol-4-yl)phenyl)amino)furo[3,2-d]pyrimidin-2-yl)-N-isopropyl-1H-indole-2-carboxamide | The preparation started from step 3 of Example 2, and Br—[benzofuran-2-carboxylic acid, OH] in step 3 was replaced with Br—[indole-2-carboxylic acid, OH]; (Reg-1-1) in step 5 was replaced with [furo[3,2-d]pyrimidine intermediate with Boc-pyrazole] (Reg-1-44). | $^1$H NMR (400 MHz, DMSO-d$_6$) δ 12.88 (s, 1H), 11.83 (s, 1H), 9.96 (s, 1H), 8.54 (s, 1H), 8.37 (s, 1H), 8.30 (d, J = 7.8 Hz, 1H), 8.16 (d, J = 8.5 Hz, 1H), 8.02 (d, J = 8.4 Hz, 4H), 7.68 (d, J = 8.4 Hz, 3H), 7.20 (s, 1H), 7.15 (s, 1H), 4.15 (dd, J = 13.5, 6.7 Hz, 1H), 1.21 (d, J = 6.6 Hz, 6H). MS m/z (ESI): 478.0 [M + H]. |

TABLE 2-continued

| No. | Compound Structure | Compound Name | Starting material or regent different from that in Example 2 | Characterization Data |
|---|---|---|---|---|
| TDI01865 | 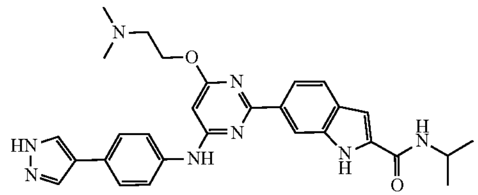 [SMILES: CC(C)NC(=O)c1cc2ccc(-c3nc(Nc4ccc(-c5cn[nH]c5)cc4)cc(OCCN(C)C)n3)cc2[nH]1] | 6-(4-((4-(1H-pyrazol-4-yl)phenyl)amino)-6-(2-(dimethylamino)ethoxy)pyrimidin-2-yl)-N-isopropyl-1H-indole-2-carboxamide | The preparation started from step 3 of Example 2, and Br-[benzofuran-2-carboxylic acid with OH/C=O] in step 3 was replaced with Br-[indole-2-carboxylic acid with OH/C=O, NH]; (Reg-1-1) in step 5 was replaced with [2-chloro-pyrimidine-indazole BocN structure] (Reg-1-51). | $^1$H NMR (400 MHz, DMSO-d$_6$) δ 11.88 (s, 1H), 9.81 (s, 1H), 9.65 (s, 1H), 8.35 (d, J = 7.8 Hz, 1H), 8.14 (s, 1H), 8.02 (s, 1H), 7.76-7.68 (m, 3H), 7.59 (d, J = 8.3 Hz, 2H), 7.22 (s, 1H), 7.00 (s, 1H), 6.67 (s, 1H), 5.34 (d, J = 4.6 Hz, 1H), 4.72 (s, 2H), 4.15 (d, J = 6.9 Hz, 1H), 3.61 (s, 3H), 2.91 (d, J = 3.7 Hz, 3H), 2.02-1.97 (m, 2H), 1.21 (d, J = 6.6 Hz, 6H). MS m/z (ESI): 524.8 [M + H]. |

TABLE 2-continued

| No. | Compound Structure | Compound Name | Starting material or regent different from that in Example 2 | Characterization Data |
|---|---|---|---|---|
| TDI01879 | (structure shown) | 6-(4-((4-(1H-pyrazol-4-yl)phenyl)amino)pyrimidin-2-yl)-N,N-diethyl-3-methyl-1H-indole-2-carboxamide | The preparation started from step 3 of Example 2, and Br—(benzofuran-2-carboxylic acid OH) in step 3 was replaced with Br—(3-methyl-1H-indole-2-carboxylic acid OH); BocN—(2-chloropyrimidin-4-yl)indazol-5-amine (Reg-1-1) in step 5 was replaced with Boc-pyrazole-phenyl-NH-(2-chloropyrimidin-4-yl) (Reg-1-16); NH$_2$-isopropylamine in step 3 was replaced with HN(Et)$_2$ diethylamine. | $^1$H NMR (400 MHz, DMSO-d$_6$) δ 11.49 (s, 1H), 9.63 (s, 1H), 8.46-8.35 (m, 4H), 8.11 (s, 1H), 7.82 (d, J = 8 Hz 2H), 6.67 (d, J = 5.6 Hz 2H), 3.5 (m, 4H), 2.25 (s, 3H), 1.10 (m, 6H). MS m/z (ESI): 466.0 [M + H]. |

TABLE 2-continued

| No. | Compound Structure | Compound Name | Starting material or regent different from that in Example 2 | Characterization Data |
|---|---|---|---|---|
| TDI01898 | (structure) | 6-(4-((1H-indazol-5-yl)amino)-6-benzylpyrimidin-2-yl)-N-isopropyl-1H-indole-2-carboxamide | The preparation started from step 3 of Example 2, and 6-bromobenzofuran-2-carboxylic acid in step 3 was replaced with 6-bromo-1H-indole-2-carboxylic acid; 2-chloro-N-(1-Boc-1H-indazol-5-yl)pyrimidin-4-amine (Reg-1-1) in step 5 was replaced with 6-benzyl-2-chloro-N-(1-Boc-1H-indazol-5-yl)pyrimidin-4-amine (Reg-1-53). | $^1$H NMR (400 MHz, DMSO-d$_6$) δ 13.09 (s, 1H), 12.02 (s, 1H), 8.42 (d, J = 29.2 Hz, 2H), 8.25 (s, 1H), 8.16 (s, 1H), 8.04 (s, 1H), 7.78 (s, 1H), 7.59 (s, 2H), 7.41 (s, 3H), 7.28 (d, J = 25.8 Hz, 2H), 6.43 (s, 1H), 4.16 (dd, J = 13.7, 6.8 Hz, 2H), 3.12-3.07 (m, 1H), 1.20 (dd, J = 17.9, 6.9 Hz, 6H). MS m/z (ESI): 501.6 [M + H]. |

TABLE 2-continued

| No. | Compound Structure | Compound Name | Starting material or regent different from that in Example 2 | Characterization Data |
|---|---|---|---|---|
| TDI01899 | 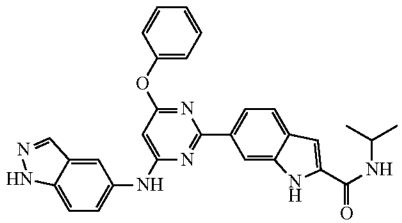 [SMILES: CC(C)NC(=O)c1cc2ccc(-c3nc(Nc4ccc5[nH]ncc5c4)cc(Oc4ccccc4)n3)cc2[nH]1] | 6-(4-((1H-indazol-5-yl)amino)-6-phenoxypyrimidin-2-yl)-N-isopropyl-1H-indole-2-carboxamide | The preparation started from step 3 of Example 2, and Br—[benzofuran-2-carboxylic acid with OH] in step 3 was replaced with Br—[indole-2-carboxylic acid with OH]; [2-chloropyrimidin-4-amine with BocN-indazole] (Reg-1-1) in step 5 was replaced with [2-chloro-6-phenoxy-N-(1-Boc-indazol-5-yl)pyrimidin-4-amine] (Reg-1-54). | $^1$H NMR (400 MHz, DMSO-d$_6$) δ 11.91 (s, 1H), 9.85 (s, 1H), 8.35 (d, J = 7.8 Hz, 1H), 8.14 (s, 1H), 7.90 (s, 1H), 7.79 (s, 1H), 7.73 (d, J = 8.4 Hz, 1H), 7.66 (d, J = 8.5 Hz, 1H), 7.56 (t, J = 7.8 Hz, 2H), 7.41 (t, J = 8.0 Hz, 2H), 7.30 (dd, J = 17.6, 8.4 Hz, 3H), 7.22 (s, 1H), 7.00 (s, 1H), 5.34 (d, J = 4.2 Hz, 1H), 4.18-4.13 (m, 1H), 1.23 (d, J = 7.2 Hz, 6H). MS m/z (ESI): 504.0 [M + H]. |

TABLE 2-continued

| No. | Compound Name | Starting material or regent different from that in Example 2 | Characterization Data |
|---|---|---|---|
| TDI01900 | 6-(4-((1H-indazol-5-yl)amino)-6-(phenylamino)pyrimidin-2-yl)-N-isopropyl-1H-indole-2-carboxamide | The preparation started from step 3 of Example 2, and Br—[benzofuran-2-carboxylic acid with OH] in step 3 was replaced with Br—[indole-2-carboxylic acid with OH]; (Reg-1-1) in step 5 was replaced with [2-chloro-4-(1H-indazol-5-ylamino)pyrimidine with BocN indazole] and [6-chloro-N-phenyl-pyrimidin-4-amine with Boc-indazole] (Reg-1-55). | $^1$H NMR (400 MHz, DMSO-d$_6$) δ 13.04 (s, 1H), 12.05 (s, 1H), 8.40 (s, 1H), 8.21 (d, J = 9.9 Hz, 2H), 8.04 (s, 2H), 7.83 (s, 1H), 7.62 (d, J = 57.7 Hz, 6H), 7.34-7.24 (m, 3H), 7.09 (s, 1H), 6.72 (s, 1H), 4.15 (s, 1H), 1.21 (d, J = 6.5 Hz, 6H). MS m/z (ESI): 503.0 [M + H]. |
| TDI01901 | N-(2-(2-methyl-1H-indol-6-yl)pyrimidin-4-yl)-1H-indazol-5-amine | The preparation started from step 4 of Example 2, and Br—[benzofuran-2-carboxamide with isopropyl] in step 3 was replaced with Br—[2-methyl-indole]. | $^1$H NMR (400 MHz, DMSO-d$_6$) δ 13.02 (s, 1H), 11.17 (s, 1H), 9.52 (s, 1H), 8.34 (s, 2H), 8.31 (d, J = 5.8 Hz, 1H), 8.19 (s, 1H), 8.14 (s, 1H), 8.03 (d, J = 8.5 Hz, 1H), 7.56 (s, 2H), 7.46 (d, J = 8.2 Hz, 1H), 6.60 (d, J = 5.8 Hz, 1H), 6.18 (s, 1H), 2.43 (s, 3H). MS m/z (ESI): 341.1 [M + H]. |

TABLE 2-continued

| No. | Compound Structure | Compound Name | Starting material or regent different from that in Example 2 | Characterization Data |
|---|---|---|---|---|
| TDI01914 | (structure) | (6-(4-((1H-pyrazol-4-yl)phenyl)amino)-5-methoxypyrimidin-2-yl)-1H-indol-2-yl)(3,3-difluoroazetidin-1-yl)methanone | The preparation started from step 3 of Example 2, and Br—(benzofuran-2-carboxylic acid OH) in step 3 was replaced with Br—(indole-2-carboxylic acid OH, NH); (Reg-1-1) in step 5 was replaced with (Reg-1-36); NH$_2$–isopropyl in step 3 was replaced with F–(azetidine)–NHHCl; and the final product was obtained by removal of Boc using 4N hydrochloric acid/dioxane solution in final step. | $^1$H NMR (400 MHz, DMSO-d$_6$) δ 12.91 (s, 1H), 11.99 (s, 1H), 9.31 (s, 1H), 8.93 (s, 1H), 8.47 (s, 1H), 8.18 (s, 1H), 8.07 (d, J = 8.5 Hz, 1H), 8.02 (d, J = 8.4 Hz, 2H), 7.93 (s, 1H), 7.67 (dd, J = 16.0, 8.4 Hz, 3H), 6.95 (s, 1H), 5.01 (s, 2H), 4.57 (s, 2H), 4.01 (s, 3H). MS m/z (ESI): 501.6 [M + H]. |

Example 3: preparation of 6-(4-((1H-indazol-5-yl)oxy)pyrimidin-2-yl)-N-(pyridazin-4-yl)-1H-indole-2-carboxamide (TDI01212)

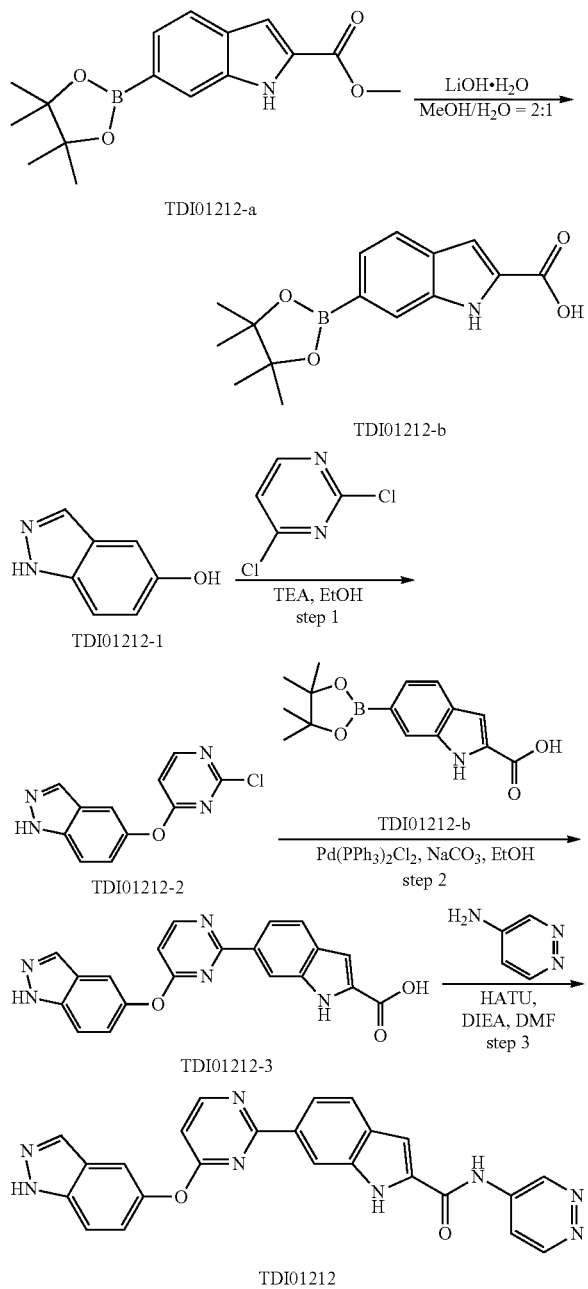

Preparation of Intermediate TDI01212-b

Intermediate TDI01212-a was prepared according to steps 1 and 2 of Example 1, wherein

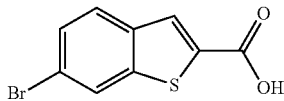

in step 1 was replaced with

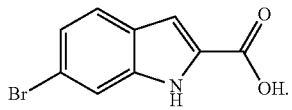 [SMILES: O=C(O)c1cc2ccc(Br)cc2[nH]1]

Intermediate TDI01212-a (3.00 g, 9.97 mmol) was dissolved in a mixture of methanol and water (2:1) (60 mL), lithium hydroxide monohydrate (4.19 g, 99.7 mmol) was added, and the reaction was performed at room temperature overnight. LC-MS indicated the reaction was complete. The reaction solution was concentrated under reduced pressure to remove methanol, the pH of the aqueous phase was adjusted to 3 with 6N HCl, a large amount of solid precipitated, and was stirred for 30 minutes before filtered to obtain intermediate TDI01212-b (2.1 g, yellow solid, yield: 73.2%).

$^1$H NMR (400 MHz, DMSO-$d_6$) δ 11.89 (s, 1H), 7.82 (s, 1H), 7.64 (d, J=8.0 Hz, 1H), 7.34 (d, J=8.0 Hz, 1H), 7.09 (s, 1H), 1.30 (s, 12H).

Step 1:

Compound TDI01212-1 (600 mg, 3.36 mmol), 2,4-dichloropyrimidine (736 mg, 3.70 mmol), TEA (1.36 g, 10 mmol) and anhydrous ethanol (20 mL) were added to a 50 mL flask, and the reaction was warmed to 80° C., and allowed to proceed overnight. Thin layer chromatography (methanol/dichloromethane =1:10) indicated the reaction was complete. The reaction solution was concentrated to give a crude product, and the crude product was added to 20 mL MTBE and 7.5 mL anhydrous ethanol. The mixture was warmed to 50° C., and triturated to afford TDI01212-2 (1.2 g, yellow solid, yield: 87%).

$^1$H NMR (400 MHz, DMSO-$d_6$) δ 13.33 (s, 1H), 8.61 (d, J=5.7 Hz, 1H), 8.11 (s, 1H), 7.67-7.63 (m, 2H), 7.25 (dd, J=9.0, 2.0 Hz, 1H), 7.14 (d, J=5.7 Hz, 1H). MS m/z (ESI): 247 [M+H].

Step 2:

Compound TDI01212-2 (1 g, 4 mmol), TDI01212-b (1.44 g, 4.8 mmol), Pd(PPh$_3$)Cl$_2$ (0.28 g, 0.4 mmol), Na$_2$CO$_3$ (0.85 g, 8 mmol), 40 mL ethanol and 5 mL water were added to a 100 mL flask, purge with argon was performed for 3 times, and the reaction was warmed to 105° C. and allowed to proceed for 4 h. The reaction was cooled to 50° C., 0.32 g sodium hydroxide was added, and the reaction was continued for 1 h. LC-MS indicated the reaction was complete. The reaction solution was concentrated under reduced pressure, the pH was adjusted to 3-4, and the solution was filtered to give a solid (1.5 g). 20 mL MTBE was added to obtain slurry, and the slurry was dried to afford compound TDI01212-3 (0.4 g, yellow solid, yield: 27%).

$^1$H NMR (400 MHz, DMSO-$d_6$) δ 13.26 (s, 1H), 12.05 (s, 1H), 8.74 (d, J=5.7 Hz, 1H), 8.38 (s, 1H), 8.13 (s, 1H), 7.92 (d, J=8.6 Hz, 1H), 7.66 (d, J=8.6 Hz, 3H), 7.51 (d, J=6.9 Hz, 2H), 7.34 (d, J=9.2 Hz, 2H), 7.09 (s, 1H), 6.91 (d, J=5.7 Hz, 1H). MS m/z (ESI): 372 [M+H].

Step 3:

Compound TDI01212-3 (200 mg, 0.54 mmol), pyridazin-4-amine (61.6 mg, 0.64 mmol), HATU (244 mg, 0.64 mmol), DIEA (280 mg, 2.16 mmol) and 12 mL DMF were added to a 25 mL flask, and the reaction was performed at room temperature for 3 h. LC-MS indicated the reaction was complete. The reaction solution was cooled to room temperature, and added to 100 mL water. The precipitated solid was filtered and dried before purified by preparative liquid chromatography to afford TDI01212 (50 mg, yellow solid, yield: 13.8%).

¹H NMR (400 MHz, DMSO-d₆) δ 13.28 (s, 1H), 12.27 (s, 1H), 11.08 (s, 1H), 9.58 (d, J=2.0 Hz, 1H), 9.19 (d, J=6.2 Hz, 1H), 8.76 (d, J=5.7 Hz, 1H), 8.41 (s, 1H), 8.28 (dd, J=6.0, 2.5 Hz, 1H), 8.13 (s, 1H), 7.96 (d, J=8.5 Hz, 1H), 7.77 (d, J=8.5 Hz, 1H), 7.72-7.66 (m, 2H), 7.57 (s, 1H), 7.34 (dd, J=8.9, 2.1 Hz, 1H), 6.93 (d, J=5.7 Hz, 1H). MS m/z (ESI): 449.1 [M+H].

Example 4: preparation of 7-(4-((1H-indazol-5-yl)amino) pyrimidin-2-yl)-N-isopropyl-2,3-dihydrobenzo[b][1,4]dioxine-2-carboxamide (TDI01103)

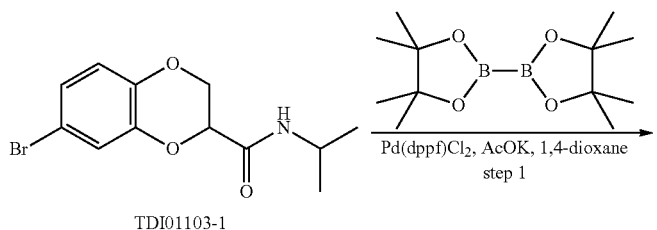

TDI01103-1

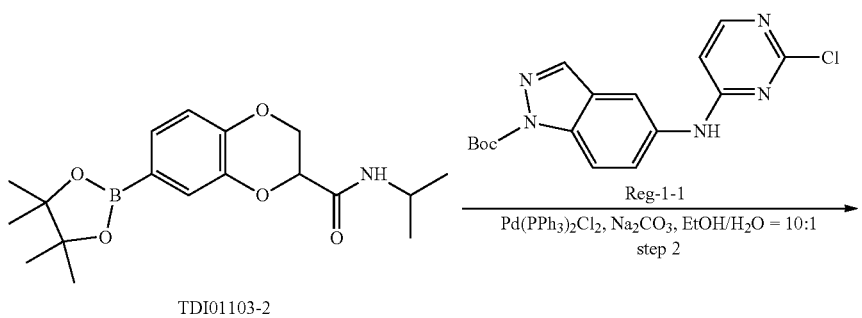

TDI01103-2

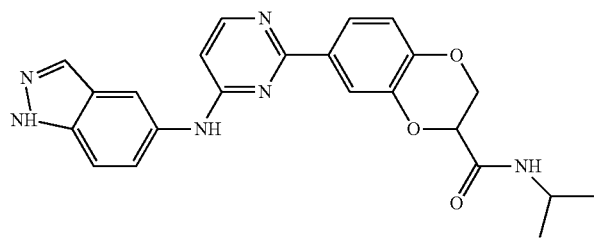

TDI01103

Step 1:

Compound TDI01103-1 (250 mg, 0.84 mmol) and bis(pinacolato)diboron (254 mg, 1.00 mmol) were dissolved in 1,4-dioxane (15 mL), potassium acetate (247 mg, 2.52 mmol) and Pd(dppf)Cl₂ (61.5 mg, 0.08 mmol) were added, purge with argon was performed for 3 times, and the reaction was allowed to proceed overnight in an oil bath at 80° C. Thin layer chromatography (petroleum ether:ethyl acetate=1:1) indicated the reaction was complete. The reaction solution was cooled to room temperature, concentrated under reduced pressure, and the residue was purified by preparative chromatography (petroleum ether:ethyl acetate=1:1) to afford compound TDI01103-2 (240 mg, yellow solid, yield: 82.8%).

¹H NMR (400 MHz, CDCl₃) δ 7.43 (d, J=1.2 Hz, 1H), 7.35 (dd, J=8.0, 1.2 Hz, 1H), 6.91 (d, J=8.0 Hz, 1H), 6.40 (s, 1H), 4.63-4.55 (m, 2H), 4.15-4.08 (m, 2H), 1.33 (s, 12H), 1.21 (d, J=6.4 Hz, 3H), 1.14 (d, J=6.4 Hz, 3H). MS m/z (ESI): 348.2 [M+H].

Step 2:

Compound TDI01103-2 (240 mg, 0.68 mmol) and Reg-1-1 (200 mg, 0.57 mmol) were dissolved in a mixture of ethanol/water (10:1) (22 mL), sodium carbonate (120 mg, 1.14 mmol) and Pd(PPh₃)₂Cl₂ (42.1 mg, 0.06 mmol) were added, purge with argon was performed for 3 times, and the reaction was allowed to proceed overnight in an oil bath at 110° C. LC-MS indicated the reaction was complete. The reaction solution was cooled to room temperature, filtered, concentrated under reduced pressure, and the residue was purified by preparative liquid chromatography to afford compound TDI01103 (18.5 mg, yellow solid, yield: 9.4%).

¹H NMR (400 MHz, CD₃OD) δ 8.16 (d, J=7.2 Hz, 1H), 8.13 (s, 1H), 7.95 (d, J=7.6 Hz, 1H), 7.86 (s, 1H), 7.73 (d, J=8.4 Hz, 1H), 7.67 (d, J=8.8 Hz, 1H), 7.59 (s, 1H), 7.11 (d, J=8.8 Hz, 1H), 6.84 (d, J=6.4 Hz, 1H), 4.80-4.77 (m, 1H), 4.53-4.50 (m, 1H), 4.36-4.31 (m, 1H), 4.07-4.01 (m, 1H), 1.19 (d, J=6.4 Hz, 3H), 1.13 (d, J=6.4 Hz, 3H). MS m/z (ESI): 431.2 [M+H].

Example 5: preparation of 2-(4-((1H-indazol-5-yl)amino) pyrimidin-2-yl)-N-isopropylbenzo[b]thiophene-6-carboxamide (TDI01106)

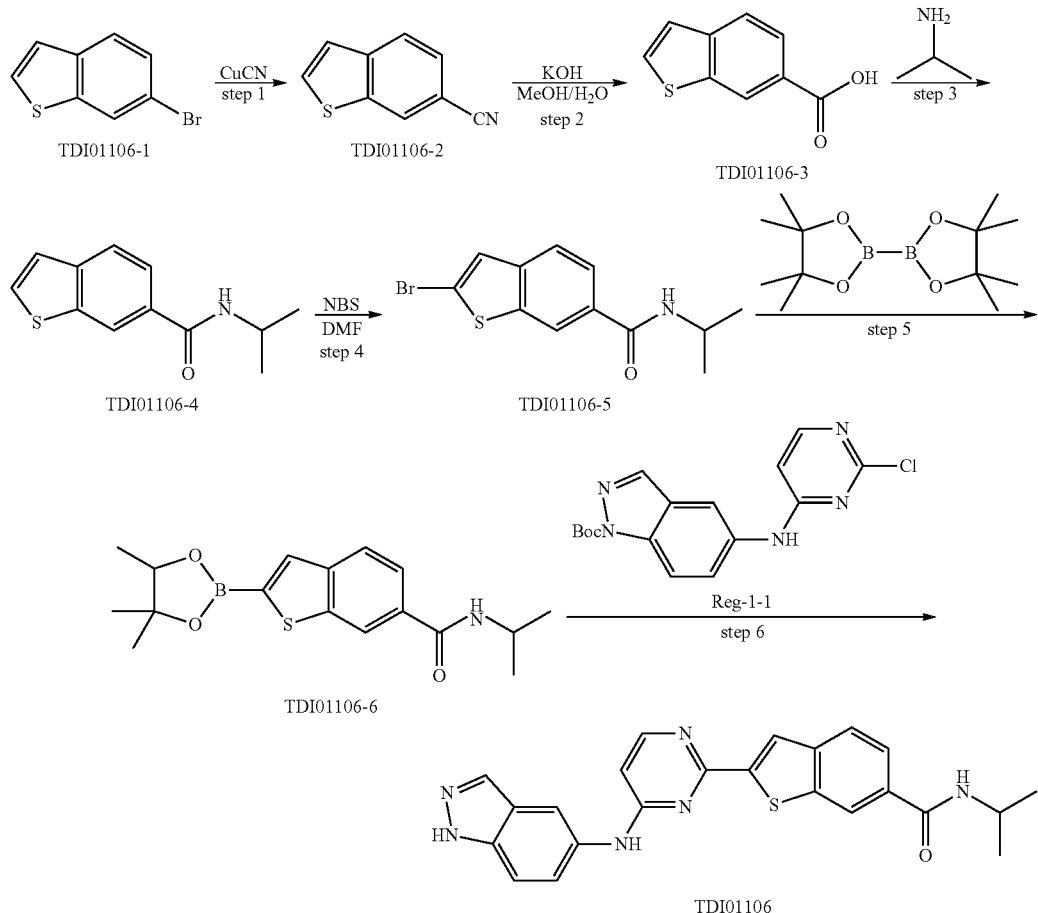

Step 1:

Compound TDI01106-1 (2.50 g, 7.04 mmol) and CuCN (1.58 g, 17.6 mmol) were dissolved in N-methylpyrrolidone (25 mL), the reaction was performed under microwave at 200° C. for 1 hour. Thin layer chromatography (petroleum ether:ethyl acetate=5:1) indicated the reaction was complete. The reaction solution was cooled to room temperature, followed by addition of water (100 mL), and was extracted with ethyl acetate (50 mL×3). The combined organic phase was washed with saturated brine (80 mL×3), dried over anhydrous sodium sulfate, filtered, concentrated under reduced pressure, and the residue was purified by column chromatography (petroleum ether:ethyl acetate=20:1), to afford compound TDI01106-2 (1.00 g, yellow solid, yield: 54.1%).

$^1$H NMR (400 MHz, CDCl$_3$) δ 8.22 (s, 1H), 7.90 (d, J=8.4 Hz, 1H), 7.72 (d, J=5.6 Hz, 1H), 7.60 (dd, J=8.4, 1.2 Hz, 1H), 7.42 (d, J=5.6 Hz, 1H).

Step 2:

Compound TDI01106-2 (800 mg, 5.09 mmol) and potassium hydroxide (2.85 g, 50.9 mmol) were dissolved in a mixture of methanol/water (2:1) (30 mL), and the reaction was performed in an oil bath at 120° C. overnight. Thin layer chromatography (petroleum ether:ethyl acetate=1:1) indicated the reaction was complete. The reaction solution was cooled to room temperature, and concentrated under reduced pressure to remove methanol before water (50 mL) was added. The pH was adjusted to 2 with 4N HCl, a large amount of solid precipitated, and was filtered after stir at room temperature for 30 minutes. The solid was dissolved in methanol, and the solution was concentrated under reduced pressure to afford compound TDI01106-3 (900 mg, yellow solid, yield: 99.2%).

$^1$H NMR (400 MHz, CDCl$_3$) δ 8.70 (s, 1H), 8.10 (dd, J=8.4, 1.2 Hz, 1H), 7.90 (d, J=8.4 Hz, 1H), 7.70 (d, J=5.4 Hz, 1H), 7.42 (d, J=5.4 Hz, 1H). MS m/z (ESI): 179.1 [M+H].

Step 3:

Compound TDI01106-3 (900 mg, 5.06 mmol) and isopropylamine (358 mg, 6.07 mmol) were dissolved in N,N-dimethylformamide (40 mL), HATU (2.31 g, 6.07 mmol) and diisopropylethylamine (2.61 g, 20.2 mmol) were added, and the reaction was performed at room temperature overnight. Thin layer chromatography (petroleum ether:ethyl acetate=1:1) indicated the reaction was complete. The reaction solution was added with water (50 mL), and extracted with ethyl acetate (80 mL×2). The organic phase was combined, successively washed with a saturated aqueous solution of ammonium chloride (100 mL×2) and saturated brine (80 mL×3), dried over anhydrous sodium sulfate, filtered, and concentrated under reduced pressure to afford compound TDI01106-4 (1.06 g, yellow solid, yield: 95.5%).

$^1$H NMR (400 MHz, CDCl$_3$) δ 8.33 (s, 1H), 7.84 (d, J=8.4 Hz, 1H), 7.71 (dd, J=8.4, 1.2 Hz, 1H), 7.58 (d, J=5.4 Hz,

1H), 7.37 (d, J=5.4 Hz, 1H), 6.03 (s, 1H), 4.37-4.29 (m, 1H), 1.29 (d, J=6.4 Hz, 6H). MS m/z (ESI): 220.1 [M+H].

Step 4:

Compound TDI01106-4 (1.06 g, 4.84 mmol) was dissolved in N,N-dimethylformamide (40 mL), N-bromosuccinimide (1.89 g, 10.7 mmol) was added, and the reaction solution was slowly warmed to 80° C., and was allowed to proceed at this temperature for 1 hour. Thin layer chromatography (petroleum ether:ethyl acetate=1:1) indicated the reaction was complete. The reaction solution was cooled to room temperature, and slowly added to water (100 mL), and a large amount of solid precipitated. The solid was filtered after stir at room temperature for 30 minutes, and purified by column chromatography (petroleum ether:ethyl acetate=1:1) to afford compound TDI01106-5 (1.10 g, yellow solid, yield: 75.8%).

$^1$H NMR (400 MHz, CDCl$_3$) δ 8.32 (s, 1H), 7.86 (d, J=8.4 Hz, 1H), 7.81-7.76 (m, 1H), 7.58 (s, 1H), 5.99 (s, 1H), 4.38-4.29 (m, 1H), 1.30 (d, J=6.4 Hz, 6H). MS m/z (ESI): 298.0/300.0 [M+H].

Step 5:

Compound TDI01106-5 (1.00 g, 3.34 mmol) and bis(pinacolato)diboron (1.02 g, 4.01 mmol) were dissolved in 1,4-dioxane (40 mL), potassium acetate (980 mg, 10.0 mmol) and Pd(dppf)Cl$_2$ (242 mg, 0.33 mmol) were added, purge with argon was performed for 3 times, and the reaction was performed in an oil bath at 80° C. overnight. Thin layer chromatography (petroleum ether:ethyl acetate=1:1) indicated the reaction was complete. The reaction solution was cooled to room temperature, concentrated under reduced pressure, and the residue was separated and purified by column chromatography (petroleum ether:ethyl acetate=10:1 to 2:1) to afford compound TDI01106-6 (450 mg, yellow solid, yield: 39.1%). MS m/z (ESI): 346.1 [M+H].

Step 6:

Compound Reg-1-1 (200 mg, 0.58 mmol) and TDI01106-6 (240 mg, 0.69 mmol) were dissolved in a mixture of ethanol/water (10:1) (22 mL), sodium carbonate (123 mg, 1.16 mmol) and Pd(PPh$_3$)$_2$Cl$_2$ (42.0 mg, 0.06 mmol) were added, purge with argon was performed for 3 times, and the reaction was performed in an oil bath at 110° C. overnight. LC-MS indicated the reaction was complete. The reaction solution was cooled to room temperature, filtered, concentrated under reduced pressure, and the residue was purified by preparative liquid chromatography to afford compound TDI01106 (87.1 mg, yellow solid, yield: 35.1%).

$^1$H NMR (400 MHz, CD$_3$OD) δ 8.81 (s, 1H), 8.70-8.65 (m, 1H), 8.46 (s, 1H), 8.27 (d, J=7.2 Hz, 1H), 8.11 (s, 1H), 8.06 (s, 1H), 7.69 (d, J=8.8 Hz, 2H), 7.58 (d, J=8.4 Hz, 1H), 6.89 (d, J=7.2 Hz, 1H), 4.27-4.20 (m, 1H), 1.27 (d, J=6.4 Hz, 6H). MS m/z (ESI): 429.2 [M+H].

Example 6: preparation of 6-(4-((1H-indazol-5-yl)amino)pyridin-2-yl)-N-isopropylbenzo[b]thiophene-2-carboxamide (TDI01117)

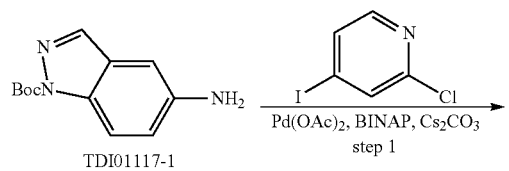

TDI01117-1

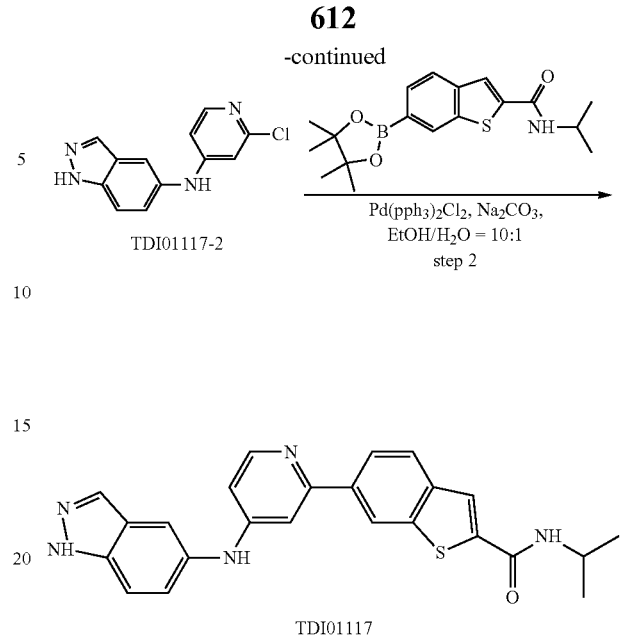

Step 1:

Compound TDI01117-1 (500 mg, 2.15 mmol) and 2-chloro-4-iodopyridine (615 mg, 2.58 mmol) were dissolved in toluene (20 mL), palladium acetate (24.1 mg, 0.11 mmol), BINAP (137 mg, 0.22 mmol) and cesium carbonate (1.40 g, 4.30 mmol) were added, purge with argon was performed for 3 times, and the reaction was performed in an oil bath at 90° C. overnight. Thin layer chromatography (petroleum ether:ethyl acetate=1:1) indicated the reaction was complete. The reaction solution was cooled to room temperature, and filtered. The filtrate was concentrated under reduced pressure, and the crude product was purified by column chromatography (petroleum ether:ethyl acetate=10:1 to 1:1) to afford compound TDI01117-2 (350 mg, yellow solid, yield: 47.3%).

$^1$H NMR (400 MHz, DMSO-d$_6$) δ 13.09 (s, 1H), 9.00 (s, 1H), 8.05 (s, 1H), 7.93 (d, J=6.0 Hz, 1H), 7.59-7.58 (m, 2H), 7.23-7.18 (m, 1H), 6.75 (dd, J=6.0, 2.0 Hz, 1H), 6.70 (d, J=1.6 Hz, 1H).

Step 2:

Compound TDI01117-2 (200 mg, 0.82 mmol) and N-isopropyl-6-(4,4,5,5-tetramethyl-1,3,2-dioxaborolan-2-yl)benzo[b]thiophene-2-carboxamide (339 mg, 0.98 mmol, for preparation thereof, please refer to the synthesis of the corresponding intermediate in the preparation of TDI01104 in Table 2) were dissolved in a mixture of ethanol/water (10:1) (33 mL), sodium carbonate (174 mg, 1.64 mmol) and Pd(PPh$_3$)$_2$Cl$_2$ (56.2 mg, 0.08 mmol) were added, purge with argon was performed for 3 times, and the reaction was performed in an oil bath at 110° C. overnight. LC-MS indicated the reaction was complete. The reaction solution was cooled to room temperature, filtered, and concentrated under reduced pressure. The residue was purified by preparative liquid chromatography to afford compound TDI01117 (85.0 mg, yellow solid, yield: 24.3%).

$^1$H NMR (400 MHz, CD$_3$OD) δ 8.38 (s, 1H), 8.17 (d, J=7.2 Hz, 1H), 8.14-8.07 (m, 2H), 8.05 (s, 1H), 7.84 (s, 1H), 7.76-7.71 (m, 2H), 7.40 (d, J=8.8 Hz, 1H), 7.29 (s, 1H), 7.06 (s, 1H), 4.25-4.18 (m, 1H), 1.29 (d, J=6.4 Hz, 6H). MS m/z (ESI): 428.2 [M+H].

Example 7: preparation of 6-(5-((1H-indazol-5-yl)amino)-1,3,4-thiadiazol-2-yl)-N-isopropylbenzo[b]thiophene-2-carboxamide (TDI01139)

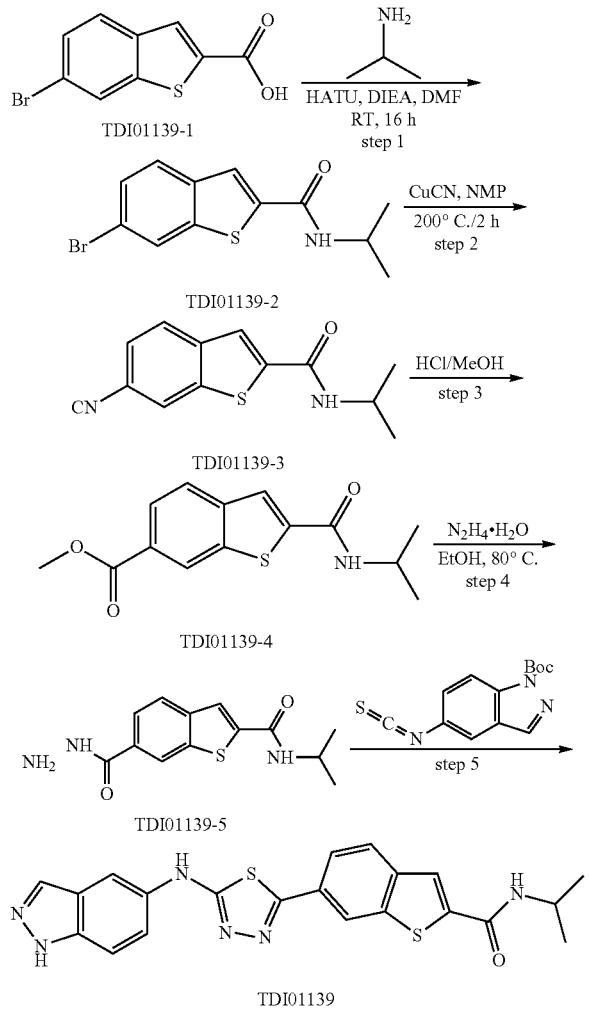

Step 1:

Compound TDI01139-1 (600 mg, 2.34 mmol) and isopropylamine (166 mg, 2.81 mmol) were dissolved in N,N-dimethylformamide (20 mL), HATU (1.07 g, 2.81 mmol) and diisopropylethylamine (1.21 g, 9.36 mmol) were added, and the reaction was performed at room temperature overnight. Thin layer chromatography (petroleum ether:ethyl acetate=2:1) indicated the reaction was complete. The reaction solution was diluted with ethyl acetate (80 mL), and successively washed with water (50 mL×2), a saturated aqueous solution of ammonium chloride (80 mL×2) and saturated brine (80 mL×3). The organic phase was dried over anhydrous sodium sulfate, filtered, and concentrated under reduced pressure to afford compound TDI01139-2 (700 mg, yellow solid, yield: 99.5%).

$^1$H NMR (400 MHz, CDCl$_3$) δ 8.00 (s, 1H), 7.68-7.66 (m, 2H), 7.49 (dd, J=8.8, 1.6 Hz, 1H), 5.89 (s, 1H), 4.33-4.25 (m, 1H), 1.29 (d, J=6.4 Hz, 6H).

Step 2:

Compound TDI01139-2 (600 mg, 2.01 mmol) and CuCN (271 mg, 3.01 mmol) were dissolved in N-methylpyrrolidone (15 mL), and the reaction was performed under microwave at 200° C. for 2 hours. Thin layer chromatography (petroleum ether:ethyl acetate=2:1) indicated the reaction was complete. The reaction solution was diluted with ethyl acetate (80 mL), and successively washed with water (80 mL×2) and saturated brine (100 mL×2). The organic phase was dried over anhydrous sodium sulfate, filtered and concentrated. The residue was purified by column chromatography (petroleum ether:ethyl acetate=10:1 to 2:1) to afford compound TDI01139-3 (350 mg, yellow solid, yield: 71.4%).

$^1$H NMR (400 MHz, DMSO-d$_6$) δ 8.70 (d, J=7.2 Hz, 1H), 8.66 (s, 1H), 8.21 (s, 1H), 8.12 (d, J=8.4 Hz, 1H), 7.80 (d, J=8.4 Hz, 1H), 4.11-4.06 (m, 1H), 1.20 (d, J=6.4 Hz, 6H).

Step 3:

Compound TDI01139-3 (350 mg, 1.43 mmol) was dissolved in hydrochloric acid-methanol solution (20 mL), and the reaction was performed at 100° C. overnight. Thin layer chromatography (petroleum ether:ethyl acetate=2:1) showed that some starting materials remained. The reaction solution was directly concentrated under reduced pressure, and the crude product was purified by column chromatography (petroleum ether:ethyl acetate=10:1 to 6:1) to afford compound TDI01139-4 (100 mg, white solid, yield: 25.2%).

$^1$H NMR (400 MHz, CDCl$_3$) δ 8.58 (s, 1H), 8.04 (dd, J=8.4, 1.2 Hz, 1H), 7.86 (d, J=8.4 Hz, 1H), 7.76 (s, 1H), 5.92 (d, J=6.0 Hz, 1H), 4.33-4.28 (m, 1H), 3.97 (s, 3H), 1.30 (d, J=6.4 Hz, 6H). MS m/z (ESI): 278.1 [M+H].

Step 4:

Compound TDI01139-4 (100 mg, 0.36 mmol) was dissolved in ethanol (5 mL), hydrazine hydrate (181 mg, 3.60 mmol) was added, and the reaction solution was slowly warmed to 80° C., and allowed to proceed at this temperature overnight. Thin layer chromatography (petroleum ether:ethyl acetate=2:1) indicated the reaction was complete. The reaction solution was cooled to room temperature, and concentrated under reduced pressure to afford compound TDI01139-5 (70 mg, yellow solid, yield: 70.0%).

$^1$H NMR (400 MHz, DMSO-d$_6$) δ 9.88 (s, 1H), 8.60 (d, J=7.6 Hz, 1H), 8.44 (s, 1H), 8.15 (s, 1H), 7.98 (d, J=8.4 Hz, 1H), 7.86 (d, J=8.4 Hz, 1H), 4.54 (s, 2H), 4.11-4.04 (m, 1H), 1.19 (d, J=6.4 Hz, 6H).

Step 5:

Compound TDI01139-5 (70.0 mg, 0.25 mmol) and tert-butyl 5-isothiocyanato-1H-indazole-1-carboxylate (69.5 mg, 0.25 mmol) were dissolved in dichloromethane (5 mL), and the reaction solution was stirred at room temperature. Concentrated sulfuric acid (0.5 mL) was then slowly added to the reaction solution, and the reaction was performed at room temperature for 5 hours. LC-MS indicated the reaction was complete. The reaction solution was concentrated under reduced pressure, and the pH was adjusted to 9 with saturated aqueous sodium carbonate. The precipitated solid was filtered, and purified by high-performance liquid chromatography to afford compound TDI01139 (4.2 mg, yellow solid, yield: 3.7%).

$^1$H NMR (400 MHz, DMSO-d$_6$) δ 13.03 (s, 1H), 10.56 (s, 1H), 8.60 (d, J=7.6 Hz, 1H), 8.50 (s, 1H), 8.27 (s, 1H), 8.16 (s, 1H), 8.08-8.01 (m, 2H), 7.98 (d, J=8.4 Hz, 1H), 7.56 (d, J=8.8 Hz, 1H), 7.43 (d, J=8.8 Hz, 1H), 4.12-4.07 (m, 1H), 1.20 (d, J=6.4 Hz, 6H). MS m/z (ESI): 435.1 [M+H].

Example 8: preparation of N-(2-(2-((isopropylamino) methyl)-1H-indol-6-yl)pyrimidin-4-yl)-1H-indazol-5-amine (TDI01155)

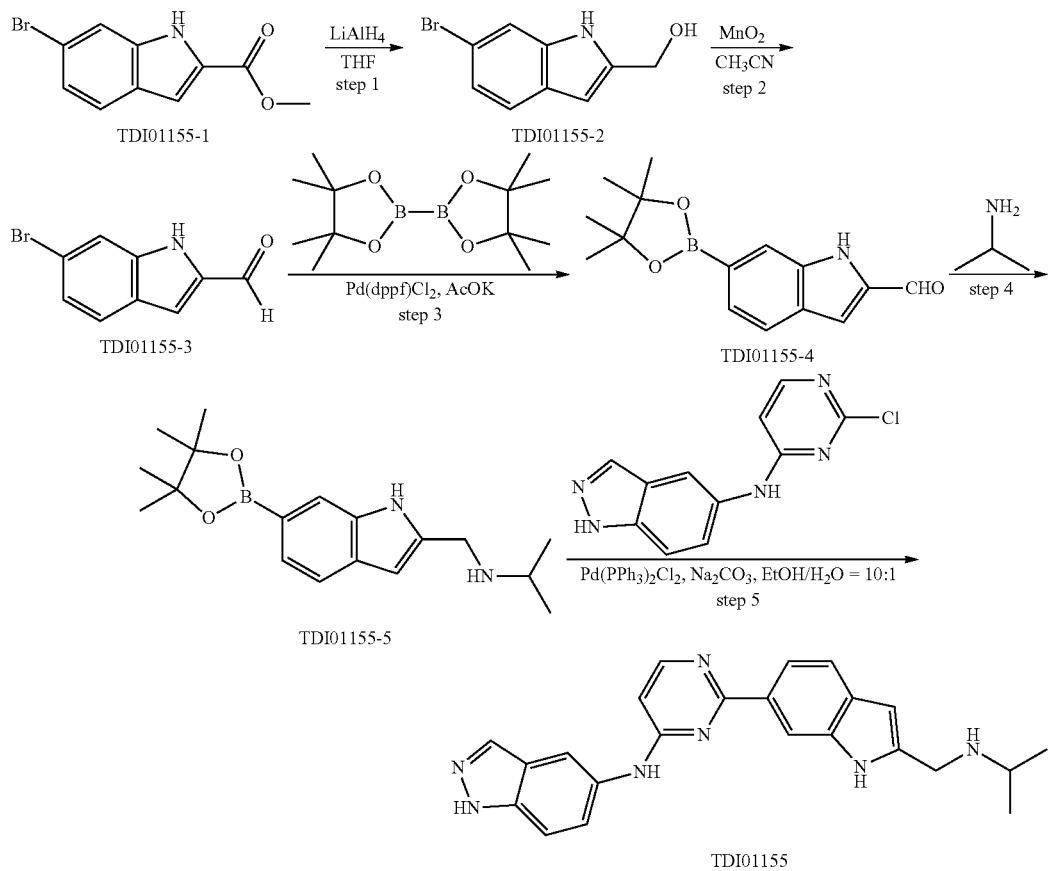

Step 1:

Compound TDI01155-1 (600 mg, 2.36 mmol) was dissolved in tetrahydrofuran (20 mL), LiAlH$_4$ (269.3 mg, 7.09 mmol) was slowly added at 0° C., the reaction was slowly warmed to room temperature after being stirred for 30 minutes, and was further stirred at room temperature for 5 h. LC-MS assay indicated the reaction was complete. Water (0.27 mL), NaOH (15% aq., 0.27 mL) and water (0.81 mL) were successively added to the above reaction mixture, which was stirred at room temperature for 30 min, then dried over anhydrous Mg$_2$SO$_4$, and filtered. The filter cake was washed, and the filtrate was collected and concentrated under reduced pressure to afford compound TDI01155-2 (600 mg, crude product).

$^1$H NMR (400 MHz, CDCl$_3$) δ 8.43 (s, 1H), 7.49 (s, 1H), 7.42 (d, J=8.4 Hz, 1H), 7.20 (m, 1H), 6.36 (s, 1H), 4.93-4.74 (m, 2H), 3.86-3.68 (m, 1H). MS m/z (ESI): 228.0 [M+H].

Step 2:

Compound TDI01155-2 (600 mg, 2.65 mmol) was dissolved in acetonitrile (20 mL), MnO$_2$ (692 mg, 7.96 mmol) was added, and the reaction was stirred at room temperature overnight. Thin layer chromatography (petroleum ether: ethyl acetate=5:1) and LC-MS assay indicated the reaction was complete. The reaction solution was concentrated under reduced pressure, and the residue was purified by column chromatography (petroleum ether:ethyl acetate=10:1 to 1:1) to afford compound TDI01155-3 (520 mg, yellow solid, yield: 87.6%).

$^1$H NMR (400 MHz, CDCl$_3$) δ 9.86 (s, 1H), 9.22 (s, 1H), 7.65 (s, 1H), 7.61 (d, J=8.4 Hz, 1H), 7.30-7.28 (m, 1H), 7.25 (br, 1H). MS m/z (ESI): 224.0/226.0 [M+H].

Step 3:

Compound TDI01155-3 (200 mg, 0.89 mmol) and bis (pinacolato)diboron (272 mg, 1.07 mmol) were dissolved in 1,4-dioxane (20 mL), potassium acetate (262.5 mg, 2.68 mmol) and Pd(dppf)Cl$_2$ (33 mg, 0.045 mmol) were added, purge with argon was performed for 3 times, and the reaction was performed in an oil bath at 90° C. overnight. Thin layer chromatography (petroleum ether:ethyl acetate=5:1) indicated the reaction was complete. The reaction solution was cooled to room temperature, concentrated under reduced pressure, and the residue was purified by column chromatography (petroleum ether:ethyl acetate=10:1 to 1:1) to afford compound TDI01155-4 (200 mg, yellow solid, yield: 82.6%).

$^1$H NMR (400 MHz, CDCl$_3$) δ 9.87 (s, 1H), 9.04 (s, 1H), 7.94 (s, 1H), 7.75 (d, J=8.0 Hz, 1H), 7.59 (d, J=8.0 Hz, 1H), 7.27 (br, 1H), 1.38 (s, 12H). MS m/z (ESI): 272.1 [M+H].

Step 4:

Compound TDI01155-4 (200 mg, 0.74 mmol) and isopropylamine (53 mg, 0.89 mmol) were dissolved in 1,2-dichloroethane (10 mL), and glacial acetic acid (10 drops) was added. After the reaction was stirred at room temperature for 1 h, sodium triacetoxyborohydride (471 mg, 2.22 mmol) was added. The reaction was stirred at room temperature overnight. Thin layer chromatography (dichloromethane/methanol=10:1) indicated the reaction was complete. The solvent was removed by concentration under reduced pressure, and the residue was purified by column chromatography (dichloromethane:methanol=10:1 to 1:1) to afford compound TDI01155-5 (185 mg, yellow solid, yield: 58.9%).

¹H NMR (400 MHz, CDCl₃) δ 10.53 (s, 1H), 8.00 (s, 1H), 7.55-7.50 (m, 2H), 6.54 (s, 1H), 4.29 (s, 2H), 3.11-3.05 (m, 1H), 1.38 (d, J=6.4 Hz, 6H), 1.35 (s, 12H). MS m/z (ESI): 315.2 [M+H].

Step 5:

Compound Reg-1-21 (170 mg, 0.49 mmol) and compound TDI01155-5 (185 mg, 0.59 mmol) were dissolved in a mixture of ethanol/water (10:1) (20 mL), sodium carbonate (104 mg, 0.98 mmol) and Pd(PPh₃)₂Cl₂ (35 mg, 0.049 mmol) were added, purge with argon was performed for 3 times, and the reaction was performed in an oil bath at 110° C. overnight. LC-MS indicated the reaction was complete. The reaction solution was cooled to room temperature, filtered, and concentrated under reduced pressure. The residue was purified by liquid chromatography to afford compound TDI01155 (85 mg, yellow solid, yield: 21.4%).

¹H NMR (400 MHz, DMSO-d₆) δ 12.05 (s, 1H), 11.03 (s, 1H), 9.15 (s, 2H), 8.38-8.34 (m, 2H), 8.19 (s, 2H), 7.94 (d, J=8.4 Hz, 1H), 7.80 (d, J=8.4 Hz, 1H), 7.68 (d, J=8.8 Hz, 1H), 7.62 (br, 1H), 6.88 (d, J=5.6 Hz, 1H), 6.76 (s, 1H), 4.42-4.41 (m, 2H), 3.41-3.33 (m, 1H), 1.32 (s, 3H), 1.30 (s, 3H). MS m/z (ESI): 398.1 [M+H].

Example 9: preparation of 6-(4-((1H-indazol-5-yl)amino)pyrimidin-2-yl)-N-(pyrazin-2-yl)-1H-indole-2-carboxamide (TDI01160)

Step 1:

Compound TDI01160-1 (1000 mg, 4.17 mmol) and pyrazin-2-amine (476 mg, 5.01 mmol) were dissolved in tetrahydrofuran (20 mL), pyridine (501 mg, 6.255 mmol) and phosphorus oxychloride (770 mg, 5.01 mmol) were added, and the reaction was performed at room temperature overnight. LC-MS indicated the reaction was complete. The reaction solution was slowly added to water (15 mL) under stirring, filtered, and the residue was rinsed with warmed methanol (50 mL) to afford crude product TDI01160-2 (260 mg, yellow solid, yield: 19.67%).

¹H NMR (400 MHz, DMSO-d₆) δ 12.02 (s, 1H), 11.24 (s, 1H), 9.47 (s, 1H), 8.52-8.40 (m, 2H), 7.67 (dd, J=8.7, 4.1 Hz, 3H), 7.22 (dd, J=8.6, 1.2 Hz, 1H). MS m/z (ESI): 317.0 [M+H].

Step 2:

Compound TDI01160-2 (260 mg, 0.82 mmol) and bis(pinacolato)diboron (417 mg, 1.64 mmol) were dissolved in 1,4-dioxane (8 mL), potassium acetate (242 mg, 2.49 mmol) and palladium acetate (10 mg, 0.04 mmol) were added, purge with argon was performed for 3 times, and the reaction was performed under microwave radiation at 110° C. for 1 h. LC-MS indicated the reaction was complete. The reaction solution was cooled to room temperature, filtered followed by addition of water (5 mL), successively washed with dichloromethane (10 mL×3) and saturated brine (5 mL×2), dried over anhydrous sodium sulfate, concentrated before

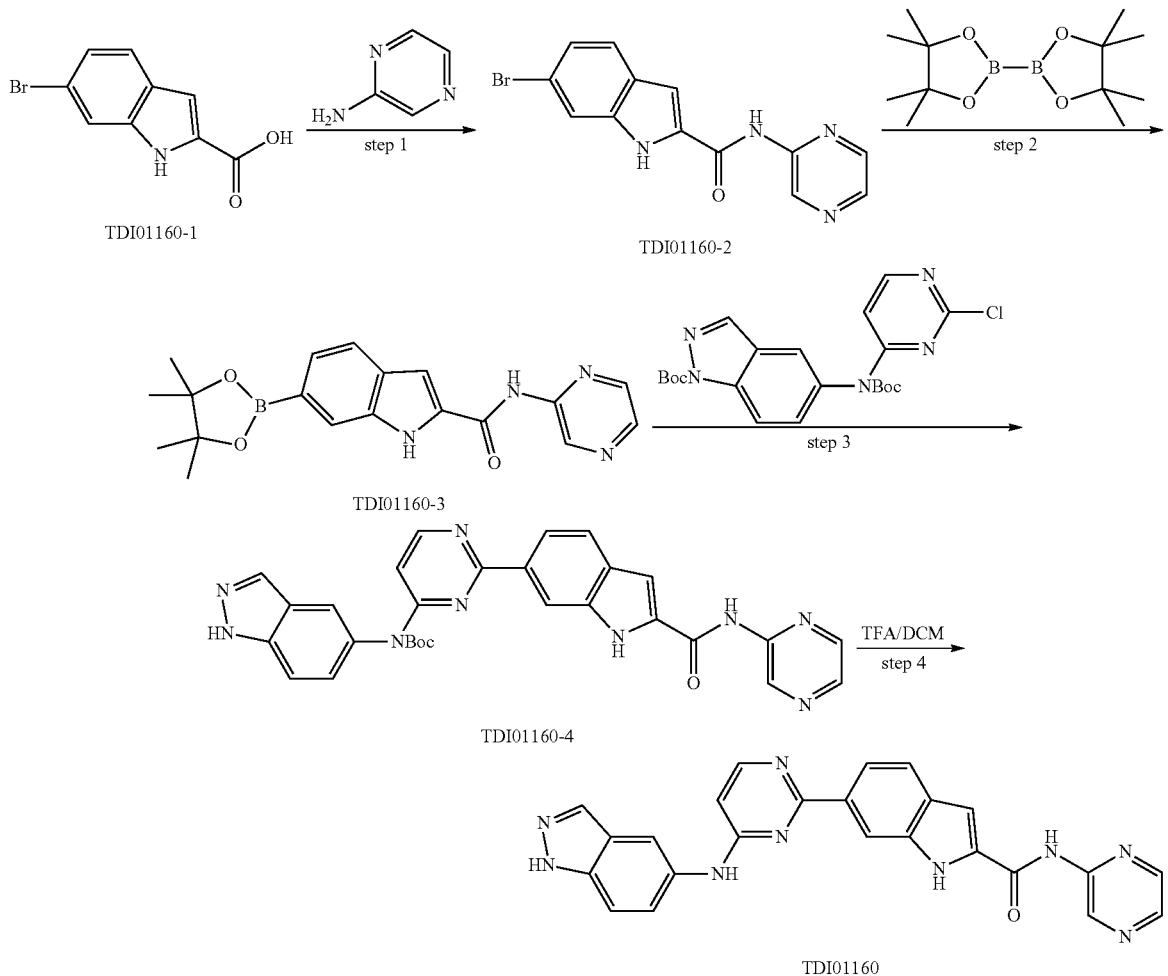

separated and purified by column chromatography (dichloromethane:methanol=100:0 to 20:1), to afford compound TDI01160-3 (80 mg, yellow solid, yield: 26.8%). MS m/z (ESI): 365.2 [M+H].

Step 3:

Compound TDI01160-3 (66 mg, 0.147 mmol) and Reg-1-27 (80 mg, 0.22 mmol) were dissolved in 1,4-dioxane:water=5:1 (2.4 mL in total), sodium carbonate (32 mg, 0.249 mmol) and Pd(PPh$_3$)$_2$Cl$_2$ (11 mg, 0.015 mmol) were added, purge with argon was performed for 3 times, and the reaction was performed under microwave radiation at 110° C. for 1 h. LC-MS indicated the reaction was complete. The reaction solution was cooled to room temperature, filtered followed by addition of water (5 mL), washed with dichloromethane (10 mL×3) and saturated brine (5 mL×2), dried over anhydrous sodium sulfate, and concentrated before purified by thin layer chromatography (dichloromethane:methanol=10:1), to afford compound TDI01160-4 (30 mg, yellow solid, yield: 37.3%). MS m/z (ESI): 548.3 [M+H].

Step 4:

Trifluoroacetic acid (1 mL) was added to a solution of TDI01160-4 (30 mg, 0.055 mmol) in dichloromethane (3 mL), and the reaction was performed at room temperature for 2 hours. LC-MS indicated the reaction was complete. The reaction solution was cooled to room temperature, concentrated under reduced pressure, and the residue was purified by preparative liquid chromatography to afford compound TDI01160 (5.4 mg, yellow solid, yield: 22.0%).

$^1$H NMR (400 MHz, DMSO-do) δ 13.14 (s, 1H), 12.37 (s, 1H), 11.31 (s, 1H), 10.36 (s, 1H), 9.51 (s, 1H), 8.48 (dd, J=21, 9, 6.7 Hz, 3H), 8.35 (d, J=6.4 Hz, 1H), 8.20 (d, J=18.1 Hz, 2H), 8.05 (d, J=8.4 Hz, 1H), 7.86 (d, J=8.6 Hz, 1H), 7.77 (s, 1H), 7.64 (d, J=8.4 Hz, 2H), 6.78 (d, J=6.4 Hz, 1H). MS m/z (ESI): 448.2 [M+H].

The compound in following table 3 was prepared according to a method similar to that described in Example 9.

Example 10: preparation of 6-(3-((1H-indazol-5-yl)amino)pyrrolidin-1-yl)-N-(pyridazin-4-yl)-1H-indole-2-carboxamide (TDI01209)

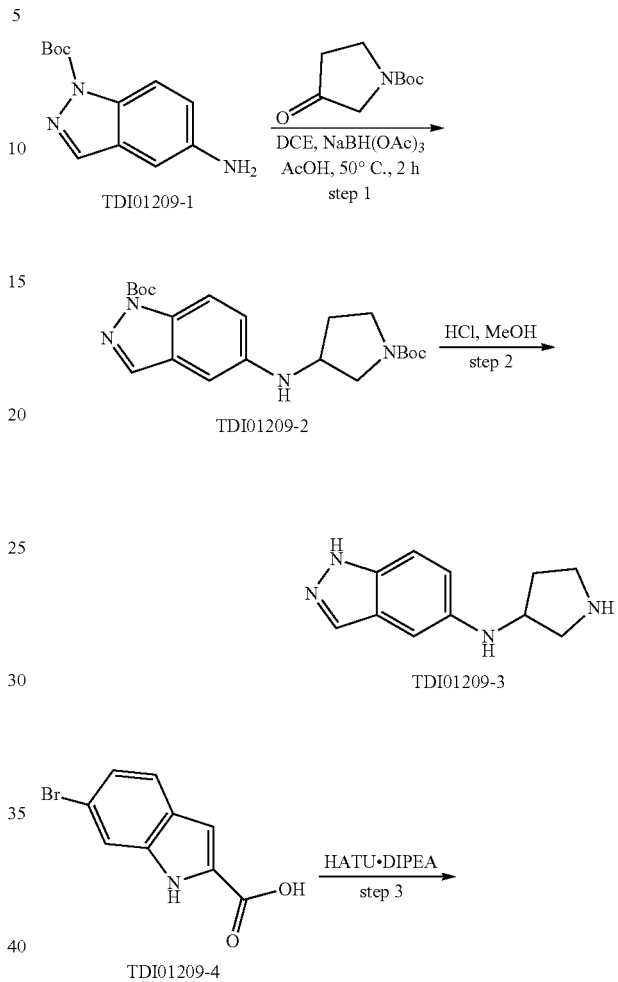

TABLE 3

| No. | Compound Structure | Compound Name | Starting material or regent different from that in Example 9 | Characterization Data |
|---|---|---|---|---|
| TDI01236 | (structure shown) | 7-(4-((1H-indazol-5-yl)amino)pyrimidin-2-yl)-N-(pyridazin-4-yl)quinoline-2-carboxamide | (structure) in step 1 of Example 9 was replaced with (structure); and (structure) in step 4 was replaced with (structure) | $^1$H NMR (400 MHz, DMSO-d$_6$) δ 11.53 (s, 1H), 9.84 (d, J = 18.4 Hz, 2H), 9.32 (s, 1H), 9.21 (s, 1H), 8.72 (t, J = 10 Hz, 2H), 8.47 (d, J = 5.9 Hz, 1H), 8.39 (s, 1H), 8.33-8.22 (m, 3H), 8.19 (s, 1H), 7.64 (s, 1H), 6.80 (d, J = 5.8 Hz, 1H). MS m/z (ESI): 460.3 [M + H]. |

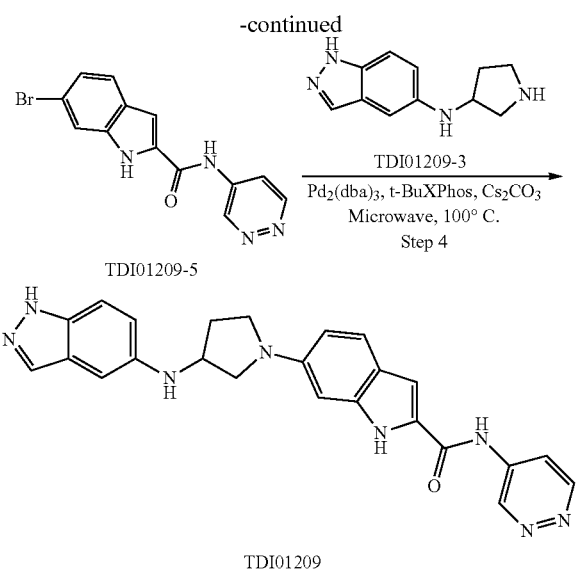

Step 1:

Compound TDI01209-1 (1.0 g, 4.3 mmol), tert-butyl 3-oxopyrrolidine-1-carboxylate (800 mg, 4.3 mmol), 1,2-dichloroethane (30 mL) and glacial acetic acid (8 drops) were added to a 50 mL single neck flask, and the reaction was performed at room temperature (15-25° C.) for 1.5 h. Sodium triacetoxyborohyride (2.73 g, 12.9 mmol) was then added, and the reaction was performed at 50° C. for 2 h. The reaction solution was added with 40 mL water, and extracted with dichloromethane (15 mL×2). The organic phase was combined, washed with saturated brine, dried over anhydrous sodium sulfate, and purified by column chromatography (petroleum ether:ethyl acetate=10:1-7:1) to afford TDI01209-2 (1.44 g, light yellow solid, yield: 83.7%).

$^1$H NMR (400 MHz, CDCl$_3$) δ 8.04-7.94 (m, 2H), 6.88 (dd, J=8.9, 2.1 Hz, 1H), 6.78 (d, J=1.9 Hz, 1H), 3.47 (s, 4H), 2.22 (s, 1H), 1.95 (d, J=9.0 Hz, 1H), 1.71 (s, 9H), 1.46 (s, 10H), 1.26 (t, J=7.1 Hz, 1H). MS m/z (ESI): 403.2 [M+H].

Step 2:

Compound TDI01209-2 (1.44 g, 3.58 mmol) and 30 mL hydrochloride methanol solution (3 mol/L) were added to a 50 mL single neck flask, and the reaction was warmed to 50° C., and allowed to proceed for 1 h. The reaction solution was concentrated under reduced pressure to remove methanol, followed by addition of methanol (20 mL), and sodium methoxide solid was added until the pH is basic. The reaction solution was filtered to collect filtrate, which was then evaporated to dryness to afford compound TDI01209-3 (1.14 g, grey solid, crude product).

$^1$H NMR (400 MHz, DMSO-d$_6$) δ 9.70 (s, 1H), 9.48 (s, 1H), 8.15 (s, 1H), 7.76 (s, 1H), 7.65 (d, J=8.9 Hz, 1H), 7.43 (d, J=8.5 Hz, 1H), 3.48 (ddd, J=19.5, 11.2, 5.2 Hz, 3H), 3.24 (dd, J=12.1, 6.2 Hz, 1H), 3.08-3.02 (m, 1H), 2.25-2.14 (m, 2H), 1.20 (t, J=7.3 Hz, 2H). MS m/z (ESI): 203.2 [M+H].

Step 3:

Compound TDI01209-4 (1 g, 4.167 mmol) and 4-aminopyridazine (475 mg, 4.999 mmol) were dissolved in N,N-dimethylformamide (40 mL), HATU (1.586 g, 4.167 mmol) and diisopropylethylamine (1.612 g, 12.501 mmol) were added, and the reaction was performed at room temperature for 16 h. After completion of the reaction, water (50 mL) was added, and a large amount of solid precipitated, and was filtered after being stirred for 30 min to afford compound TDI01209-5 (1.17 g, yellow solid, yield: 88.9%). MS m/z (ESI): 316.9 [M+H].

Step 4:

Compound TDI01209-5 (250 mg, 0.788 mmol), TDI01209-3 (175 mg, 0.867 mmol), Pd$_2$(dba)$_3$ (75 mg, 0.0788 mmol), t-BuXPhos (67 mg, 0.1576 mmol), cesium carbonate (770 mg, 2.364 mmol) and tert-butanol (10 mL) were added to a microwave tube, and the reaction was performed under microwave radiation at 110° C. for 2.5 h. The reaction solution was dissolved in methanol (20 mL), and concentrated to dryness after insoluble materials were filtered off. The residue was purified by high-performance liquid chromatography to afford TDI01209 (12.66 mg, yellow solid, yield: 3.7%).

$^1$H NMR (400 MHz, DMSO-d$_6$) δ 12.07 (s, 1H), 11.00 (s, 1H), 9.60 (d, J=2.1 Hz, 1H), 9.15 (d, J=6.0 Hz, 1H), 8.93 (s, 2H), 8.22 (dd, J=6.0, 2.7 Hz, 1H), 8.13 (s, 1H), 7.92 (d, J=8.6 Hz, 1H), 7.77 (s, 1H), 7.70 (d, J=9.0 Hz, 1H), 7.64 (d, J=1.3 Hz, 1H), 7.53 (dd, J=8.6, 1.8 Hz, 1H), 6.98 (dd, J=9.0, 2.0 Hz, 1H), 6.86 (d, J=1.8 Hz, 1H), 4.15 (m, 1H), 3.48 (m, 1H), 3.33 (m, 2H), 3.12 (m, 1H), 2.26 (dd, J=14.0, 7.7 Hz, 1H), 1.95 (m, 1H). MS m/z (ESI): 439.1 [M+H].

Compound TDI01219 (6-(3-((1H-indazol-5-yl)amino)pyrrolidin-1-yl)-N-isopropyl-1H-indole-2-carboxamide) was prepared according to a method similar to that described in Example 10:

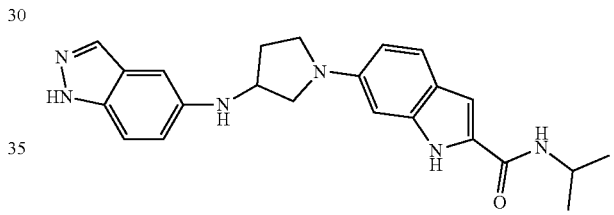

$^1$H NMR (400 MHz, DMSO-d$_6$) δ 11.66 (s, 1H), 8.86 (s, 2H), 8.30 (d, J=7.92 Hz, 1H), 8.10 (s, 1H), 7.77 (d, J=8.6 Hz, 1H), 7.70 (s, 1H), 7.65 (d, J=9.0 Hz, 1H), 7.42 (dd, J=8.6, 1.9 Hz, 1H), 7.23 (d, J=1.4 Hz, 1H), 6.95 (dd, J=9.0, 2.0 Hz, 1H), 6.83 (d, J=1.8 Hz, 1H), 5.87 (s, 1H), 4.14 (d, J=6.6 Hz, 2H), 3.35 (s, 2H), 3.12 (d, J=4.52 Hz, 1H), 2.36-2.21 (m, 2H), 1.95 (d, J=4.8 Hz, 1H), 1.21 (d, J=6.6 Hz, 6H). MS m/z (ESI): 403.2 [M+H].

Example 11: preparation of 1-(6-(4-((1H-indazol-5-yl)amino)pyrimidin-2-yl)-1H-indol-1-yl)ethan-1-one (TDI01229)

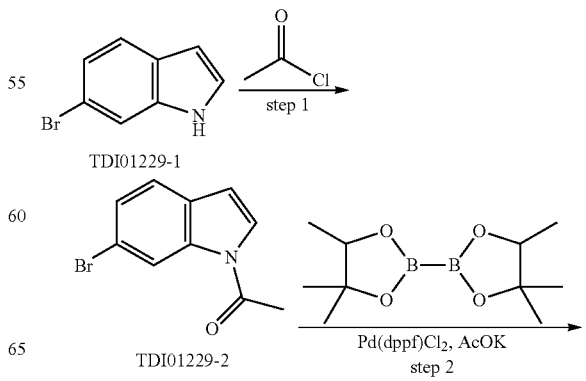

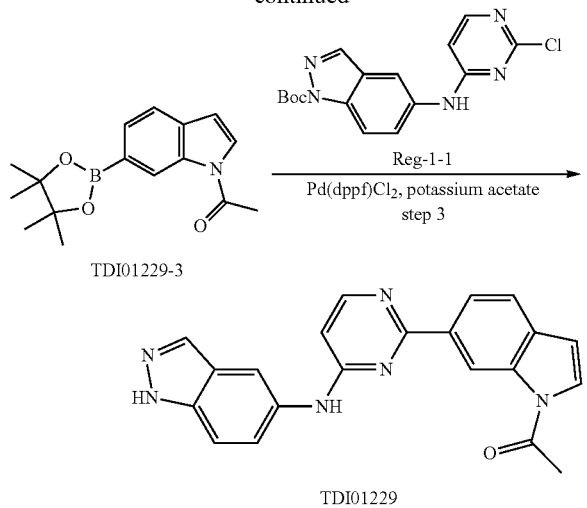

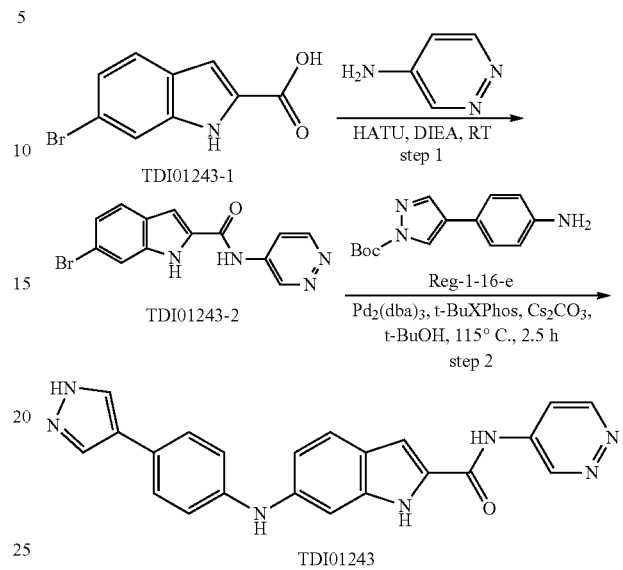

Example 12: preparation of 6-(04-(1H-pyrazol-4-yl)phenyl)amino)-N-(pyridazin-4-yl)-1H-indole-2-carboxamide (TDI01243)

Step 1:

Compound TDI01229-1 (3 g, 15.3 mmol) was dissolved in anhydrous acetonitrile (100 mL), acetyl chloride (9.69 g, 61.2 mmol) and cesium carbonate (19.95 g, 61.2 mmol) were added, and the reaction was performed at 50° C. for 5 hours. LC-MS assay indicated the reaction was complete. The reaction solution was cooled to room temperature, filtered, concentrated under reduced pressure, and the residue was purified by column chromatography (petroleum ether:ethyl acetate=20:1) to afford compound TDI01229-2 (1 g, brow solid, crude product).

$^1$H NMR (400 MHz, CDCl$_3$) δ 8.66 (s, 1H), 7.40 (d, J=3.0 Hz, 1H), 7.39-7.37 (m, 1H), 6.60 (d, J=3.7 Hz, 1H), 2.62 (s, 3H). MS m/z (ESI): 240.0 [M+H].

Step 2:

Compound TDI01229-2 (1 g, 4.2 mmol) and bis(pinacolato)diboron (1.60 g, 6.3 mmol) were dissolved in 1,4-dioxane (40 mL), potassium acetate (1.23 g, 12.6 mmol) and Pd(dppf)Cl$_2$ (462 mg, 0.63 mmol) were added, purge with argon was performed for 3 times, and the reaction was performed in an oil bath at 90° C. overnight. Thin layer chromatography (petroleum ether:ethyl acetate=4:1) indicated the reaction was complete. The reaction solution was cooled to room temperature, concentrated under reduced pressure, and the residue was purified by column chromatography (petroleum ether:ethyl acetate=10:1) to afford compound TDI01229-3 (372 mg, white solid, yield: 20.8%). MS m/z (ESI): 286.1 [M+H].

Step 3:

To a mixed solution of compound TDI01229-3 (300 mg, 0.87 mmol) and Reg-1-1 (372 mg, 1.3 mmol) in ethanol/water (10:1) (11 mL), potassium acetate (170 mg, 1.738 mmol) and Pd(dppf)Cl$_2$ (63.0 mg, 0.087 mmol) were added, purge with argon was performed, and the reaction was performed under microwave radiation at 110° C. for 1 h. LC-MS indicated the reaction was complete. The reaction solution was cooled to room temperature, filtered, concentrated under reduced pressure, and the residue was purified by liquid chromatography to afford compound TDI01229 (3.99 mg, yellow solid, yield: 1.2%).

$^1$H NMR (400 MHz, CD$_3$OD) δ 8.42 (dd, J=30.4, 13.8 Hz, 4H), 8.27-8.14 (m, 3H), 7.99 (s, 1H), 7.69 (s, 2H), 6.90 (s, 1H), 2.57 (s, 3H). MS m/z (ESI): 369.3 [M+H].

Step 1:

TDI01243-1 (1.0 g, 4.17 mmol) and N,N-dimethylformamide (10 mL) were successively added to a 50 mL single neck flask, HATU (2.38 g, 5.0 mmol) and DIEA (1.72 mL, 10.43 mmol) were cautiously added under stirring, and the reaction was performed in an oil bath at 50° C. for 1 h. After the reaction was complete, the reaction solution was slowly poured into water (20 mL) under stirring. A large amount of solid precipitated, and was filtered after being stirred for 30 min. The solid was washed with water as well as a mixed solvent of petroleum ether and ethyl acetate (v/v=20/1) for several times, to afford TDI01243-2 (1.26 g, grey-yellow solid, yield: 95.5%).

$^1$H NMR (400 MHz, DMSO-d$_6$) δ 12.08 (s, 1H), 10.83 (s, 1H), 9.56 (s, 1H), 9.10 (d, J=5.9 Hz, 1H), 8.12 (dd, J=5.5, 2.2 Hz, 1H), 7.73 (d, J=8.5 Hz, 1H), 7.66 (s, 1H), 7.54 (s, 1H), 7.25 (d, J=8.5 Hz, 1H). MS m/z (ESI): 317.0 [M+H].

Step 2:

Compound TDI01243-2 (190.3 mg, 0.6 mmol), Reg-1-16-e (130 mg, 0.5 mmol), Pd$_2$(dba)$_3$ (50 mg, 0.05 mmol), t-BuXPhos (106 mg, 0.25 mmol), cesium carbonate (325.8 mg, 1 mmol) and 10 mL tert-butanol were added to a 25 mL microwave tube, purge with argon was performed for 4 times, and the reaction was performed under microwave radiation at 115° C. for 2.5 h. LC-MS assay indicated the reaction was complete. The reaction solution was filtered, and concentrated under reduced pressure. The obtained solid was rinsed with 30 mL water and 30 mL dichloromethane to give 0.3 g solid, which was purified by preparative chromatography to afford TDI01243 (6.90 mg, dark brown solid, yield: 1.7%).

$^1$H NMR (400 MHz, DMSO-d$_6$) δ 11.51 (s, 1H), 10.64 (s, 1H), 9.56 (s, 1H), 9.06 (d, J=5.9 Hz, 1H), 8.28 (s, 1H), 8.12 (d, J=3.3 Hz, 1H), 7.96 (s, 2H), 7.57 (d, J=8.5 Hz, 1H), 7.50 (d, J=8.3 Hz, 2H), 7.45 (s, 1H), 7.17 (s, 1H), 7.13 (d, J=8.4 Hz, 2H), 6.89 (d, J=8.9 Hz, 1H), 6.57 (s, 1H). MS m/z (ESI): 396.1 [M+H].

Example 13: preparation of 6-(2-((1H-indazol-6-yl)amino)pyrimidin-4-yl)-N-(pyridazin-4-yl)-1H-indole-2-carboxamide (TDI01249)

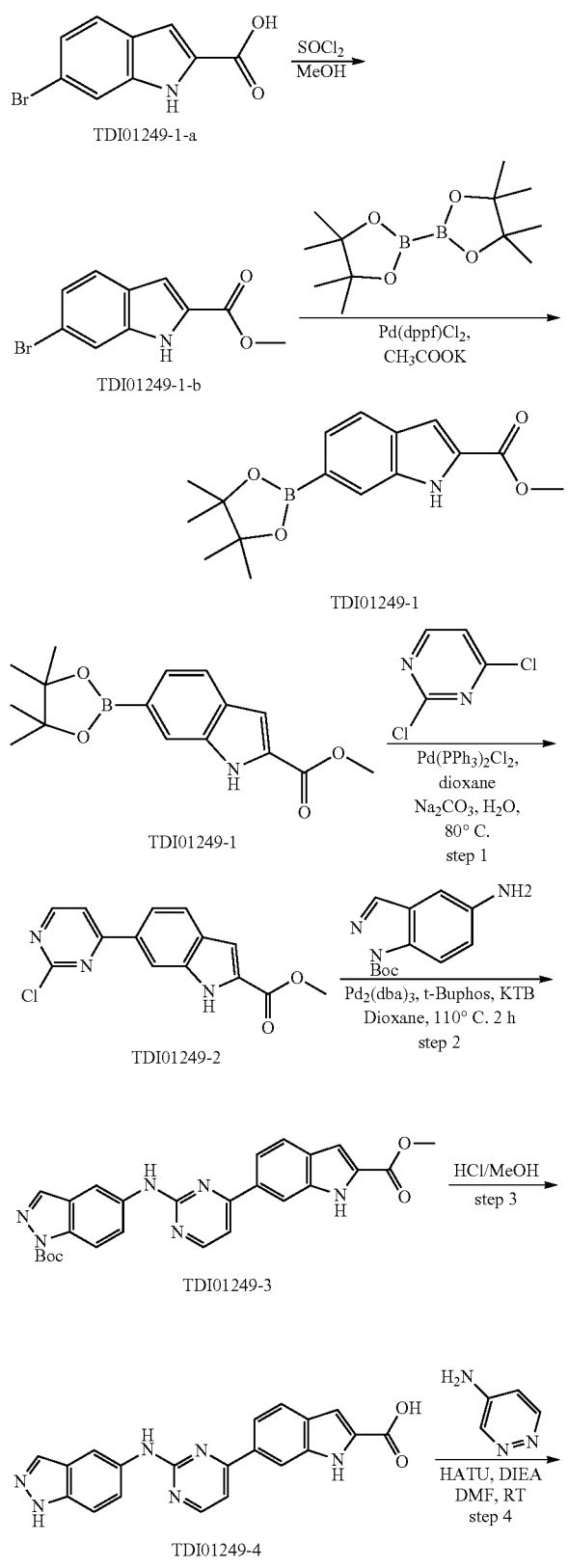

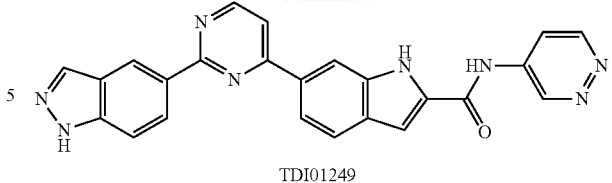

Preparation of TDI01249-1:

TDI01249-1-a (2 g, 8.33 mmol) and methanol (20 mL) were added to a 100 mL flask, thionyl chloride (1.98 g, 16.66 mmol) was added, and then the reaction was performed at 60° C. for 3 hours. Thin layer chromatography (petroleum ether:ethyl acetate=10:1) indicated the reaction was complete. The reaction solution was concentrated to give a crude product, and the crude product was dissolved in dichloromethane (100 mL). The dichloromethane phase was washed with a saturated aqueous solution of sodium hydrogen carbonate twice (50 mL for each time). The dichloromethane phase was then washed with saturated brine, dried over anhydrous sodium sulfate, filtered, and concentrated to obtain TDI01249-1-b (2.149 g, brown solid, yield: 100%).

$^1$H NMR (400 MHz, CDCl$_3$) δ 7.59 (s, 1H), 7.54 (d, J=8.5 Hz, 1H), 7.25 (d, J=8.6 Hz, 1H), 7.18 (s, 1H), 3.96 (s, 3H).

TDI01249-1-b (2 g, 7.87 mmol) and bis(pinacolato)diboron (3.0 g, 11.81 mmol) were dissolved in 1,4-dioxane (20 mL), potassium acetate (2.32 g, 23.61 mmol) and Pd(dppf)Cl$_2$ (130 mg, 0.157 mmol) were added, purge with argon was performed for 3 times, and the reaction was placed in an oil bath at 80° C. overnight. Thin layer chromatography (petroleum ether:ethyl acetate=20:1) indicated the reaction was complete. The reaction solution was cooled to room temperature, concentrated under reduced pressure, and the residue was separated and purified by column chromatography (petroleum ether:ethyl acetate=100:1 to 5:1) to afford TDI01249-1 (2.0 g, white solid, yield: 84.37%).

$^1$H NMR (400 MHz, CDCl$_3$) δ 9.08-8.93 (m, 1H), 7.97-7.86 (m, 1H), 7.69 (d, J=8.1 Hz, 1H), 7.61-7.52 (m, 1H), 7.21 (dd, J=2.1, 1.0 Hz, 1H), 3.95 (s, 3H), 1.37 (s, 12H). MS m/z (ESI): 302.2 [M+H].

Step 1:

Compound TDI01249-1 (2 g, 6.64 mmol), 2,4-dichloropyrimidine (1.08 g, 7.30 mmol), Pd(PPh$_3$)$_2$Cl$_2$ (47 mg, 0.07 mmol), sodium carbonate (1.40 g, 13.28 mmol), 60 mL dioxane and 15 mL water were added to a 250 mL single neck flask, purge with argon was performed for 4 times, and the reaction was warmed to 105° C., and allowed to proceed for 3 h. LC-MS indicated the reaction was complete. The reaction solution was cooled followed by concentration under reduced pressure to remove dioxane, 100 mL water was added, and the solution was stirred at room temperature for 1 h. The reaction mixture was filtered to give a yellow solid (2.3 g), which was rinsed with dichloromethane (80 mL×4) to afford TDI01249-2 (0.62 g, yellow solid, yield: 32.6%).

$^1$H NMR (400 MHz, DMSO-d$_6$) δ 12.33 (s, 1H), 8.78 (d, J=5.2 Hz, 1H), 8.34 (s, 1H), 8.13 (d, J=5.3 Hz, 1H), 7.89 (d, J=8.4 Hz, 1H), 7.83 (d, J=8.5 Hz, 1H), 7.24 (s, 1H), 3.91 (s, 3H). MS m/z (ESI): 288.0 [M+H].

Step 2:

Compound TDI01249-2 (400 mg, 1.39 mmol), tert-butyl 5-amino-1H-indazole-1-carboxylate (200 mg, 0.86 mmol), Pd$_2$(dba)$_3$ (85.6 mg, 0.09 mmol), 2-di-tert-butylphosphino-2',4',6'-triisopropyl-biphenyl (182.4 mg, 0.43 mmol), potassium tert-butoxide (193 mg, 1.72 mmol) and 80 mL dioxane were added to a 250 mL single neck flask, purge with argon was performed for 4 times, and the reaction was warmed to 110° C., and allowed to proceed for 3 h. 20 mg Pd$_2$(dba)$_3$, 40 mg 2-di-tert-butylphosphino-2',4',6'-triisopropyl-biphenyl and 50 mg potassium tert-butoxide were supplemented, and the reaction was continued for 1 h. LC-MS indicated the reaction was complete. The reaction solution was concentrated under reduced pressure to remove dioxane, 80 mL ethyl acetate was added, and filtered to obtain the filtrate, which was purified to afford TDI01249-3 (100 mg, yellow solid, yield: 24%).

$^1$H NMR (400 MHz, DMSO-d$_6$) δ 12.31 (s, 1H), 9.92 (s, 1H), 8.58 (d, J=5.2 Hz, 1H), 8.55 (d, J=1.5 Hz, 1H), 8.46 (s, 1H), 8.35 (s, 1H), 8.03 (s, 1H), 7.94 (dd, J=9.2, 1.8 Hz, 1H), 7.91-7.88 (m, 1H), 7.84 (s, 1H), 7.45 (d, J=5.3 Hz, 1H), 7.25 (d, J=1.2 Hz, 1H), 3.92 (s, 3H), 1.67 (s, 9H). MS m/z (ESI): 485.1 [M+H].

Step 3:

Compound TDI01249-3 (100 mg, 0.135 mmol) and 2 mol/L hydrochloric acid/methanol (5 mL) were added to a 100 mL single neck flask. The reaction was warmed to 60° C., and allowed to proceed for 1.5 h. LC-MS indicated the reaction was complete. The reaction solution was cooled to room temperature, 10 mL 2 mol/L aqueous solution of sodium hydroxide was added, and the reaction was warmed to 60° C., and allowed to proceed for 0.5 h. LC-MS indicated the reaction was complete. The reaction solution was cooled to room temperature, and the pH was adjusted to above 12 with concentrated hydrochloric acid. Methanol was removed through concentration under reduced pressure, 20 mL water was then added, and the reaction was filtered after stirring, the solid obtained after filtration was dried to afford compound TDI01249-4 (50 mg, yellow solid, yield: 23.8%).

$^1$H NMR (400 MHz, DMSO-d$_6$) δ 12.22 (s, 1H), 9.82 (s, 1H), 8.57 (d, J=5.4 Hz, 1H), 8.39 (s, 2H), 8.15 (s, 1H), 7.92 (d, J=1.1 Hz, 1H), 7.87 (s, 1H), 7.72 (dd, J=10.6, 9.0 Hz, 1H), 7.60 (s, 1H), 7.46 (d, J=5.4 Hz, 1H), 7.22 (s, 1H). MS m/z (ESI): 371.0 [M+H].

Step 4:

Compound TDI01249-4 (50 mg, 0.135 mmol), pyridazin-4-amine (15.4 mg, 0.162 mmol), HATU (61.7 mg, 0.162 mmol), DIEA (70 mg, 0.54 mmol) and 4 mL N,N-dimethylformamide were added to a 25 mL single neck flask, and the reaction was performed at room temperature for 0.5 h. LC-MS indicated the reaction was complete. The reaction solution was cooled to room temperature, and added to 20 mL water to give a solid, which was dried and purified by preparative chromatography to afford TDI01249 (14.38 mg, yellow solid, yield: 23.8%).

$^1$H NMR (400 MHz, DMSO-d$_6$) δ 12.89 (s, 1H), 12.33 (s, 1H), 10.94 (s, 1H), 9.62 (d, J=17.6 Hz, 2H), 9.14 (d, J=5.8 Hz, 1H), 8.54 (d, J=5.2 Hz, 1H), 8.36 (d, J=5.8 Hz, 2H), 8.18 (d, J=3.2 Hz, 1H), 8.08 (s, 1H), 7.90 (s, 2H), 7.69 (s, 1H), 7.61 (s, 1H), 7.51 (d, J=8.8 Hz, 1H), 7.38 (d, J=5.2 Hz, 1H). MS m/z (ESI): 448.0 [M+H].

Example 14: preparation of 6-(2-((1H-indazol-5-yl)amino)-6-methylpyrimidin-4-yl)-N-(pyridazin-4-yl)-1H-indole-2-carboxamide (TDI01261)

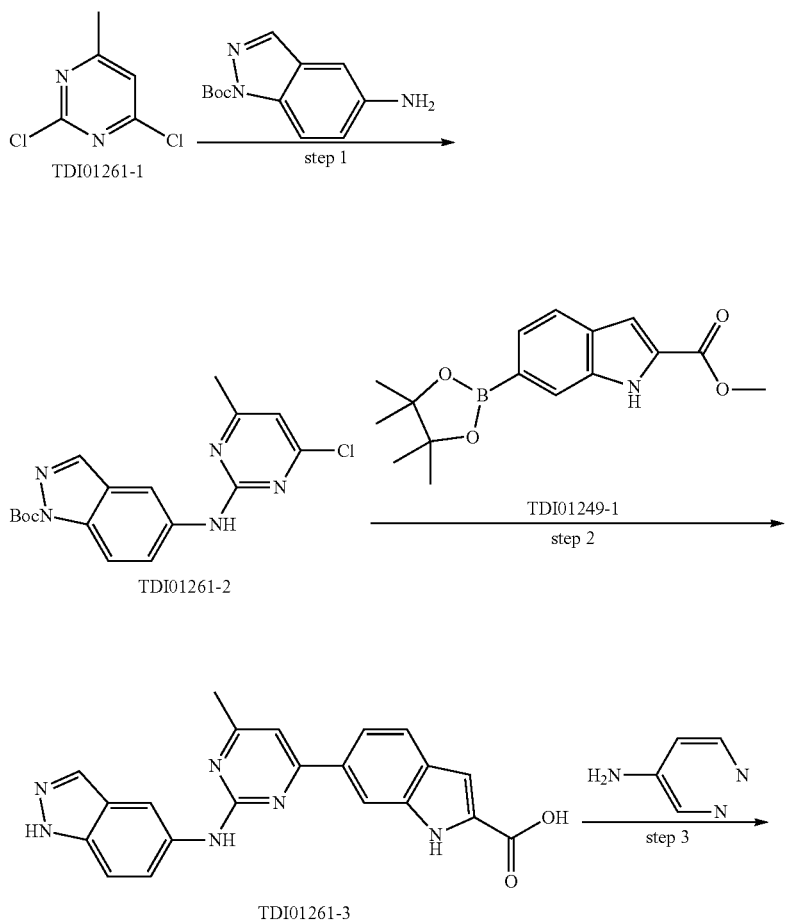

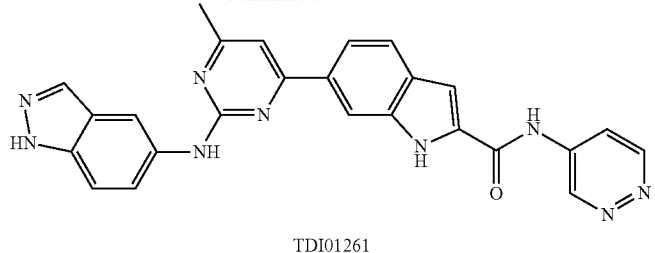

TDI01261

Step 1:

Compound TDI01261-1 (2.0 g, 8.58 mmol) and tert-butyl 5-amino-1H-indazole-1-carboxylate (1.68 g, 10.296 mmol) were dissolved in N,N-dimethylformamide (150 mL), diisopropylethylamine (4.427 g, 34.32 mmol) was added, and the reaction was slowly warmed to 100° C., and allowed to proceed at this temperature for 16 hours. Thin layer chromatography (petroleum ether:ethyl acetate=2:1) indicated the reaction was complete. The reaction solution was slowly poured into water (900 mL), stirred for 30 minutes followed by filtration. The residue was separated and purified by column chromatography (petroleum ether:ethyl acetate=1:0 to 1:1), to afford compound TDI01261-2 (300 mg, light yellow solid).

$^1$H NMR (400 MHz, DMSO-$d_6$) δ 10.18 (s, 1H), 8.40 (s, 1H), 8.37 (s, 1H), 7.98 (d, J=9.2 Hz, 1H), 7.77 (dd, J=9.2, 1.6 Hz, 1H), 6.92 (s, 1H), 2.40 (s, 3H), 1.65 (s, 8H). MS m/z (ESI): 360.0 [M+H].

Step 2:

Compound TDI01261-2 (300 mg, 0.836 mmol) and TDI01249-1 (299 mg, 1.672 mmol) were dissolved in a mixed solution of ethanol:water (10:1) (30 mL), sodium carbonate (177 mg, 1.672 mmol) and Pd(PPh$_3$)$_2$Cl$_2$ (59 mg, 0.0836 mmol) were added, purge with argon was performed for 3 times, and the reaction was perform in an oil bath at 110° C. overnight. LC-MS indicated the reaction was complete. The reaction solution was cooled to room temperature, filtered, and concentrated under reduced pressure. The residue was dissolved in dichloromethane (500 mL), washed with water (500 mL×3), the pH of the aqueous phase was adjusted to 2 with concentrated hydrochloric acid (3 mL), and compound TDI01261-3 (110 mg, yellow solid, yield: 32.7%) was obtained by filtration.

$^1$H NMR (400 MHz, DMSO-$d_6$) δ 12.20 (s, 1H), 9.90 (s, 1H), 8.33 (d, J=5.6 Hz, 2H), 8.12 (s, 1H), 7.87 (d, J=8.4 Hz, 1H), 7.81 (d, J=8.4 Hz, 1H), 7.71-7.66 (m, 1H), 7.56 (d, J=8.8 Hz, 1H), 7.42 (s, 1H), 7.17 (s, 1H), 2.09 (s, 3H). MS m/z (ESI): 385.1 [M+H].

Step 3:

Compound TDI01261-3 (100 mg, 0.26 mmol) and pyridazin-4-amine (30 mg, 0.313 mmol) were dissolved in N,N-dimethylformamide (10 mL), HATU (120 mg, 0.313 mmol) and diisopropylethylamine (130 mg, 1.04 mmol) were added, and the reaction was performed at room temperature overnight. LC-MS indicated the reaction was complete. The reaction solution was cooled to room temperature, filtered, concentrated under reduced pressure, and the residue was purified by liquid chromatography to afford compound TDI01261 (11.02 mg, yellow solid, yield: 10.2%).

$^1$H NMR (400 MHz, DMSO-$d_6$) δ 13.07-12.76 (m, 1H), 12.35 (s, 1H), 11.07 (s, 1H), 9.61 (s, 2H), 9.18 (d, J=5.6 Hz, 1H), 8.39 (d, J=20.0 Hz, 2H), 8.26 (d, J=3.6 Hz, 1H), 8.09 (s, 1H), 7.90 (s, 2H), 7.72 (d, J=8.8 Hz, 1H), 7.63 (s, 1H), 7.51 (d, J=8.8 Hz, 1H), 7.32 (s, 1H), 2.46 (s, 3H). MS m/z (ESI): 462.1 [M+H].

Example 15: preparation of 6-(5-((1H-indazol-5-yl)amino)-1,3,4-thiadiazol-2-yl)-N-isopropyl-1H-indole-2-carboxamide (TDI01147)

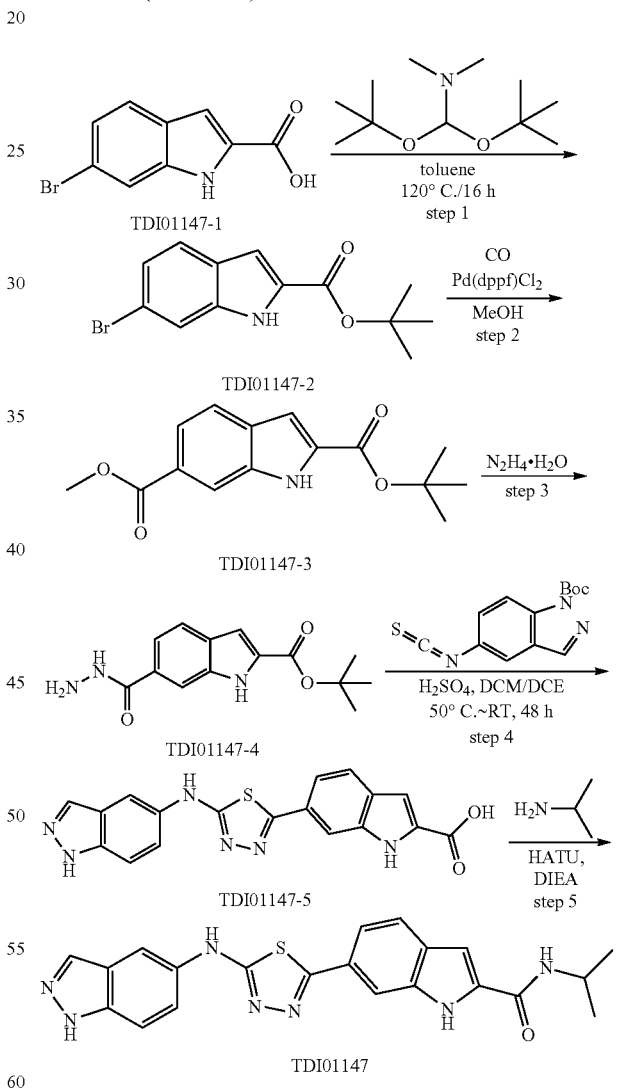

Step 1:

Compound TDI01147-1 (2.00 g, 8.33 mmol) was dissolved in anhydrous toluene (30 mL), 1,1-di-tert-butoxy-N,N-dimethylmethanamine (4.56 g, 22.5 mmol) was slowly added under reflux, and the reaction was performed in an oil bath at 120° C. overnight. Thin layer chromatography (petroleum ether:ethyl acetate=4:1) indicated the reaction was complete. The reaction solution was cooled to room temperature, concentrated under reduced pressure, and the crude product was separated and purified by column chromatography (petroleum ether:ethyl acetate=15:1) to afford compound TDI01147-2 (1.85 g, white solid, yield: 75.2%).

$^1$H NMR (400 MHz, CDCl$_3$) δ 8.95 (s, 1H), 7.59 (s, 1H), 7.53 (d, J=8.4 Hz, 1H), 7.24 (dd, J=8.4, 1.6 Hz, 1H), 7.10 (d, J=1.2 Hz, 1H), 1.62 (s, 9H).

Step 2:
Compound TDI01147-2 (1.85 g, 6.27 mmol) was dissolved in methanol (150 mL), triethylamine (1.90 g, 18.8 mmol) and Pd(dppf)Cl$_2$ (461 mg, 0.63 mmol) were added, purge with CO were performed for 3 times, and the reaction was placed in an oil bath at 80° C. overnight. Thin layer chromatography (petroleum ether:ethyl acetate=4:1) indicated the reaction was complete. The reaction solution was cooled to room temperature, and concentrated under reduced pressure. The residue was diluted with dichloromethane (150 mL), successively washed with water (150 mL) and saturated brine (150 mL×2), dried over anhydrous sodium sulfate, filtered, and concentrated under reduced pressure. The crude product was separated and purified by column chromatography (ethyl acetate/petroleum ether=6.2%-8.5%) to afford compound TDI01147-3 (620 mg, yellow solid, yield: 36.0%).

$^1$H NMR (400 MHz, CDCl$_3$) δ 9.10 (s, 1H), 8.18 (s, 1H), 7.82 (dd, J=8.4, 1.2 Hz, 1H), 7.70 (d, J=8.4 Hz, 1H), 7.16 (d, J=1.2 Hz, 1H), 3.95 (s, 3H), 1.63 (s, 9H).

Step 3:
Compound TDI01147-3 (570 mg, 2.07 mmol) was dissolved in ethanol (12 mL), hydrazine hydrate (3 mL) was added, and the reaction was performed under microwave radiation at 90° C. for 1 hour. LC-MS indicated half of the starting material was converted as the product. The reaction solution was diluted with ethyl acetate (80 mL), successively washed with water (100 mL) and saturated brine (100 mL×2), dried over anhydrous sodium sulfate, filtered, and concentrated under reduced pressure. The crude product was rinsed with ethyl acetate to afford compound TDI01147-4 (300 mg, yellow solid, yield: 52.6%).

$^1$H NMR (400 MHz, DMSO-d$_6$) δ11.98 (s, 1H), 9.76 (s, 1H), 7.95 (s, 1H), 7.67 (d, J=8.4 Hz, 1H), 7.52 (dd, J=8.4, 1.2 Hz, 1H), 7.08 (s, 1H), 4.49 (s, 2H), 1.58 (s, 9H).

Step 4:
Compound TDI01147-4 (250 mg, 0.91 mmol) was dissolved in a mixed solution of anhydrous dichloromethane/1,2-dichloroethane (2:1) (15 mL), compound tert-butyl 5-isothiocyanato-1H-indazole-1-carboxylate (250 mg, 0.91 mmol) was added, and the reaction solution was slowly warmed to 50° C., and allowed to proceed at this temperature for 16 hours. The reaction solution was cooled to room temperature, concentrated sulfuric acid was slowly added thereto under stirring, and the reaction was performed at room temperature for 6 hours. LC-MS indicated the reaction was complete. The reaction solution was concentrated under reduced pressure, the crude product was diluted with water (30 mL), and the pH was adjusted to 9 with saturated aqueous sodium carbonate. A large amount of solid precipitated, and was filtered after being stirred at room temperature for 1 hour. The solid was dissolved in toluene and then concentrated to afford compound TDI01147-5 (250 mg, yellow solid, yield: 73.3%).

$^1$H NMR (400 MHz, DMSO-d$_6$) δ 13.02 (s, 2H), 12.00 (s, 1H), 10.46 (s, 1H), 8.27 (s, 1H), 8.07 (s, 1H), 7.91 (s, 1H), 7.77 (d, J=8.4 Hz, 1H), 7.60-7.54 (m, 2H), 7.43 (d, J=8.6 Hz, 1H), 7.15 (s, 1H). MS m/z (ESI): 377.1 [M+H].

Step 5:
Compound TDI01147-5 (100 mg, 0.27 mmol) was dissolved in N,N-dimethylformamide (6 mL), and HATU (122 mg, 0.32 mmol) and diisopropylethylamine (139 mg, 1.08 mmol) were added. After reaction at room temperature for 30 minutes, isopropylamine (18.8 mg, 0.32 mmol) was added, and the reaction was continued at room temperature overnight. LC-MS indicated the reaction was complete. The reaction solution was slowly added to water (20 mL), a large amount of solid precipitated, and was filtered after being stirred for 30 min. The solid was purified by high-performance liquid chromatography to afford compound TDI01147 (6.03 mg, yellow solid, yield: 5.4%).

$^1$H NMR (400 MHz, DMSO-d$_6$) δ 13.01 (s, 1H), 11.79 (s, 1H), 10.44 (s, 1H), 8.34 (d, J=7.6 Hz, 1H), 8.27 (s, 1H), 8.07 (s, 1H), 7.90 (s, 1H), 7.73 (d, J=8.4 Hz, 1H), 7.56 (d, J=8.4 Hz, 2H), 7.43 (d, J=8.8 Hz, 1H), 7.22 (s, 1H), 4.17-4.12 (m, 1H), 1.21 (d, J=6.4 Hz, 6H). MS m/z (ESI): 418.1 [M+H].

Example 16: preparation of 6-(3-((1H-indazol-5-yl)amino)piperidin-1-yl)-N-(pyridazin-4-yl)-1H-indole-2-carboxamide (TDI01234)

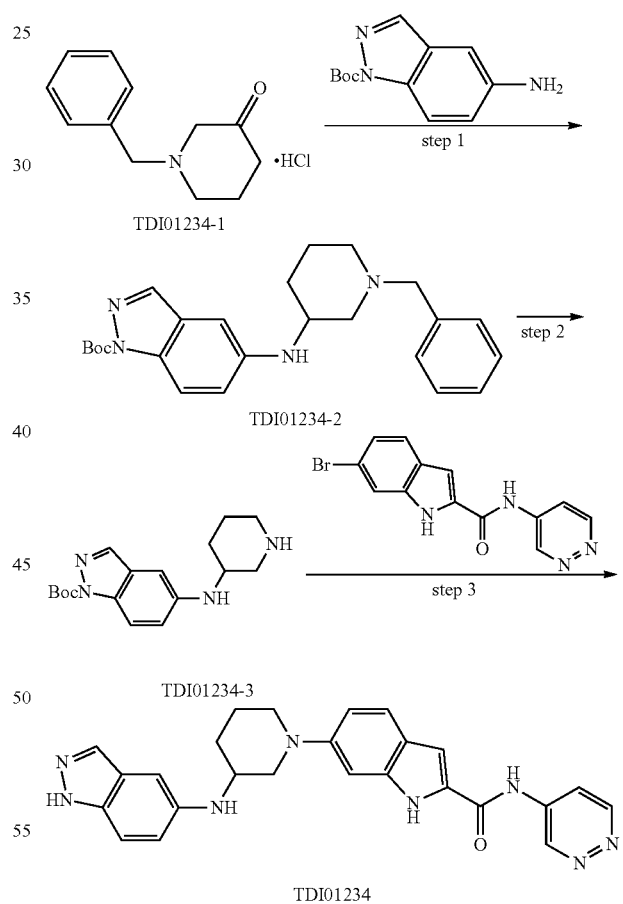

Step 1:
Compound TDI01234-1 (2.0 g, 8.86 mmol) was dissolved in 1,2-dichloroethane (150 mL), triethylamine (746 mg, 7.38 mmol) was added, and the reaction solution was warmed to 30° C. and stirred for 1.5 hours. Tert-butyl 5-amino-1H-indazole-1-carboxylate (1.72 g, 7.38 mmol) and acetic acid (443 mg, 7.38 mmol) were then added, after stir of 0.5 hour, sodium triacetoxyborohydride (4.69 g, 22.14 mmol) was added, and the reaction was maintained at 30° C. overnight. Thin layer chromatography (dichloromethane:methanol=60:1) assay indicated the reaction was complete. The reaction solution was dissolved in dichloromethane (1500 mL), successively washed with water (150 mL×2) and saturated brine (150 mL), and the organic phase was dried over anhydrous sodium sulfate, concentrated, and purified by column chromatography (dichloromethane:methanol=1:0 to 60:1), to afford compound TDI01234-2 (1.0 g, brown yellow solid).

¹H NMR (400 MHz, CDCl₃) δ 7.96 (s, 1H), 7.93 (d, J=8.8 Hz, 1H), 7.30 (dd, J=13.6, 5.2 Hz, 4H), 7.24 (dd, J=5.2, 3.2 Hz, 1H), 6.88 (dd, J=8.8, 2.1 Hz, 1H), 6.75 (d, J=1.6 Hz, 1H), 4.16 (s, 1H), 3.66-3.44 (m, 3H), 2.57 (d, J=120.0 Hz, 4H), 1.70 (s, 11H), 1.59 (s, 2H). MS m/z (ESI): 407.3 [M+H].

Step 2:

Compound TDI01234-2 (0.6 g, 1.478 mmol) was dissolved in methanol (50 mL), palladium/carbon (100 mg) was added, purge with hydrogen was performed for 3 times, and the reaction was placed in an oil bath at 35° C. overnight. LC-MS indicated the reaction was complete. The reaction solution was cooled to room temperature, filtered, concentrated under reduced pressure, and purified by column chromatography (dichloromethane:methanol=1:0 to 10:1), to afford compound TDI01234-3 (200 mg, off-white solid).

¹H NMR (400 MHz, CDCl₃) δ 7.98 (s, 1H), 7.93 (d, J=8.8 Hz, 1H), 6.94-6.88 (m, 1H), 6.83-6.78 (m, 1H), 4.09 (s, 1H), 3.56 (s, 1H), 3.33-3.19 (m, 1H), 2.99-2.90 (m, 1H), 2.81 (d, J=8.0 Hz, 1H), 2.68 (dd, J=11.2, 7.1 Hz, 1H), 1.84 (dd, J=13.6, 6.7 Hz, 2H), 1.71 (s, 9H), 1.59 (dd, J=19.2, 13.9 Hz, 3H). MS m/z (ESI): 317.3 [M+H].

Step 3:

6-bromo-N-(pyridazin-4-yl)-1H-indole-2-carboxamide was prepared according to step 3 of Example 2, with

being replaced with

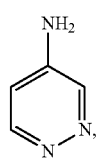

and

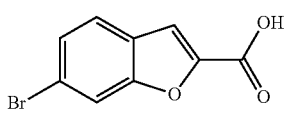

being replaced with

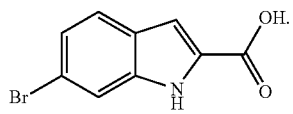 [SMILES: O=C(O)c1cc2ccc(Br)cc2[nH]1]

Compound TDI01234-3 (400 mg, 1.27 mmol) and 6-bromo-N-(pyridazin-4-yl)-1H-indole-2-carboxamide (400 mg, 1.27 mmol) were dissolved in dimethyl sulfoxide (10 mL). Pd₂(dba)₃ (120 mg, 0.127 mmol), t-BuXPhos (823 mg, 2.53 mmol) and cesium carbonate (268.4 mg, 0.63 mmol) were then added, and the reaction was performed under microwave radiation and the protection of argon for 2 hours. LC-MS indicated the reaction was complete. The reaction solution was cooled to room temperature, slowly added to water (80 mL), and filtered. The filter cake was rinsed with dichloromethane:ethyl acetate=1:1 (20 mL×2), and the residue was purified by liquid chromatography to afford compound TDI01234 (2.58 mg, yellow solid).

¹H NMR (400 MHz, DMSO-d₆) δ 12.06 (s, 1H), 11.05 (s, 1H), 10.20 (s, 1H), 9.61 (s, 1H), 9.10 (s, 2H), 8.95 (s, 1H), 8.18 (s, 1H), 8.07 (s, 1H), 7.87 (d, J=8.4 Hz, 1H), 7.76 (s, 1H), 7.66 (d, J=9.6 Hz, 1H), 7.51 (d, J=8.8 Hz, 1H), 6.98 (d, J=8.4 Hz, 1H), 6.89 (s, 1H), 3.24 (s, 1H), 2.87 (s, 1H), 1.95 (d, J=46.4 Hz, 3H), 1.74 (s, 2H), 1.52 (s, 2H). MS m/z (ESI): 451.3 [M−H].

Example 17: preparation of 6-((3-(1H-pyrazol-4-yl)phenyl)amino)-N-(pyridazin-4-yl)-1H-indole-2-carboxamide (TDI01245)

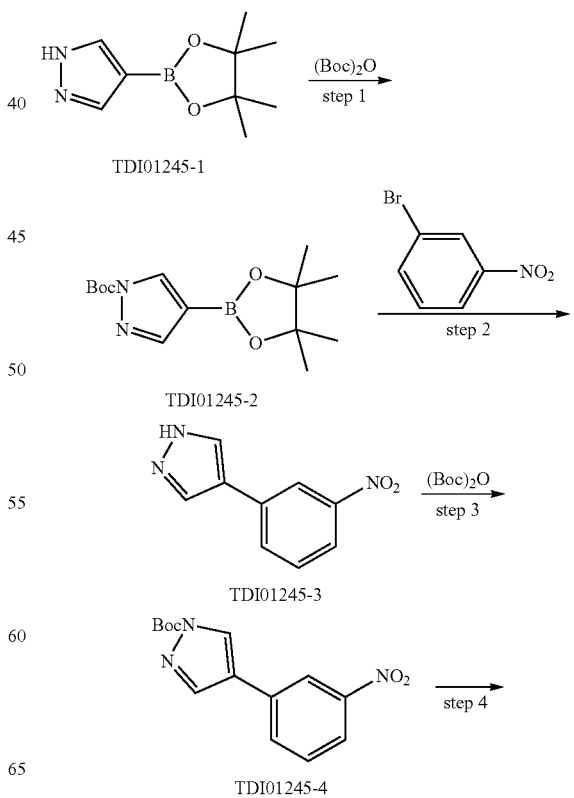

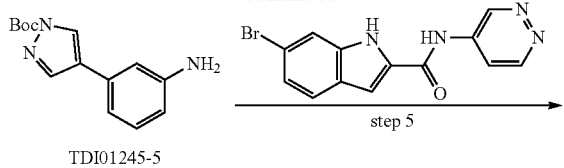

Step 1:

Compound TDI01245-1 (5.0 g, 25.77 mmol) was dissolved in dichloromethane (100 mL), diisopropylethylamine (13.30 g, 100.08 mmol) and 4-dimethylaminopyridine (1.57 g, 12.88 mmol) were added, and di-red-butyl dicarbonate (11.24 g, 51.55 mmol) was added after the reaction was stirred at room temperature for 10 minutes. Thin layer chromatography (petroleum ether:ethyl acetate=3:1) indicated the reaction was complete. The reaction solution was dissolved in dichloromethane (400 mL), and successively washed with water (500 mL×2) and saturated brine (500 mL). The organic phase was dried over anhydrous sodium sulfate, concentrated, and purified by column chromatography (petroleum ether:ethyl acetate=1:0 to 10:1), to afford compound TDI01245-2 (4.58 g, white solid).

$^1$H NMR (400 MHz, CDCl$_3$) δ 8.42-8.34 (m, 1H), 7.93 (s, 1H), 1.65 (s, 9H), 1.34 (s, 12H). Step 2:

Compound TDI01245-2 (5.0 g, 17.01 mmol) and 1-bromo-3-nitrobenzene (2.863 g, 14.17 mmol) were dissolved in a mixed solution of 1,4-dioxane/water (8:1) (500 mL), potassium carbonate (3.91 g, 28.34 mmol) and Pd(dppf)Cl$_2$ (497 mg, 0.708 mmol) were added, purge with argon was performed for 3 times, and the reaction was placed in an oil bath at 110° C. overnight. LC-MS indicated the reaction was complete. The reaction solution was cooled to room temperature, filtered, and concentrated under reduced pressure. The residue was dissolved in dichloromethane (500 mL), and successively washed with water (500 mL×2) and saturated brine (500 mL). The organic phase was dried over anhydrous sodium sulfate, concentrated, and purified by column chromatography (dichloromethane:methanol=1:0 to 50:1) to afford compound TDI01245-3 (850 mg, yellow solid).

$^1$H NMR (400 MHz, DMSO-d$_6$) δ 13.14 (s, 1H), 8.44 (d, J=11.2 Hz, 2H), 8.20-8.06 (m, 2H), 8.03 (dd, J=8.0, 1.6 Hz, 1H), 7.65 (t, J=8.0 Hz, 1H). MS m/z (ESI): 190.3 [M+H].

Step 3:

Compound TDI01245-3 (850 mg, 4.497 mmol) was dissolved in dichloromethane (100 mL), diisopropylethylamine (2.32 g, 17.989 mmol) and 4-dimethylaminopyridine (274 mg, 2.249 mmol) were added, and di-tert-butyl dicarbonate (1.96 g, 8.995 mmol) was added after the reaction was stirred at room temperature for 10 minutes. Thin layer chromatography (dichloromethane) indicated the reaction was complete. The reaction solution was dissolved in dichloromethane (400 mL), and successively washed with water (250 mL×2) and saturated brine (250 mL). The organic phase was dried over anhydrous sodium sulfate, concentrated, and purified by column chromatography (petroleum ether:dichloromethane =10:1 to 1:1), to afford compound TDI01245-4 (820 mg, white solid).

$^1$H NMR (400 MHz, CDCl$_3$) δ 8.43 (s, 1H), 8.38 (t, J=1.6 Hz, 1H), 8.16 (dd, J=8.0, 1.2 Hz, 1H), 7.85 (d, J=7.6 Hz, 1H), 7.59 (t, J=8.0 Hz, 1H), 7.26 (s, 1H), 1.70 (s, 9H).

Step 4:

Compound TDI01245-4 (820 mg, 2.837 mmol) was dissolved in methanol (100 mL), palladium/carbon (100 mg) was added, purge with hydrogen was performed for 3 times, and the reaction was placed in an oil bath at 35° C. overnight. LC-MS indicated the reaction was complete. The reaction solution was cooled to room temperature, filtered, concentrated under reduced pressure, and purified by column chromatography (dichloromethane:methanol=1:0 to 100:1) to afford compound TDI01245-5 (650 mg, off-white solid).

$^1$H NMR (400 MHz, CDCl$_3$) δ 8.25 (s, 1H), 7.95 (s, 1H), 7.18 (t, J=7.6 Hz, 1H), 6.92 (d, J=7.6 Hz, 1H), 6.84 (s, 1H), 6.63 (d, J=8.0 Hz, 1H), 3.71 (s, 2H), 1.67 (s, 9H). MS m/z (ESI): 249.0 [M−H].

Step 5:

Compound TDI01245-5 (300 mg, 1.158 mmol) and 6-bromo-N-(pyridazin-4-yl)-1H-indole-2-carboxamide (the preparation method thereof is as described in Example 12) (366 mg, 1.158 mmol) were dissolved in tert-butanol (8 mL). Pd$_2$(dba)$_3$ (110 mg, 0.116 mmol), t-BuXPhos (753 mg, 2.316 mmol) and cesium carbonate (245.5 mg, 0.579 mmol) were added, and the reaction was performed under microwave radiation at 115° C. and the protection of argon for 2 hours. LC-MS indicated the reaction was complete. The reaction solution was rotary evaporated to dryness, slurried in dichloromethane (20 mL), and filtered. The residue was purified by liquid chromatography to afford compound TDI01245 (53.25 mg, brownish red solid).

$^1$H NMR (400 MHz, DMSO-d$_6$) δ 11.55 (s, 1H), 10.81 (s, 1H), 9.56 (s, 1H), 9.13 (s, 1H), 8.23 (s, 2H), 7.98 (s, 2H), 7.58 (d, J=8.8 Hz, 1H), 7.47 (s, 1H), 7.37 (s, 1H), 7.25 (s, 2H), 7.09 (d, J=7.6 Hz, 1H), 6.93 (dd, J=21.2, 7.9 Hz, 2H). MS m/z (ESI): 396.2 [M−H].

Example 18: preparation of 6-(4-((1H-indazol-5-yl)amino)pyrimidin-2-yl)-N-(1,3,4-thiadiazol-2-yl)-1H-indole-2-carboxamide (TDI01247)

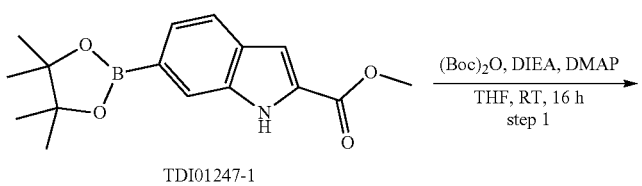

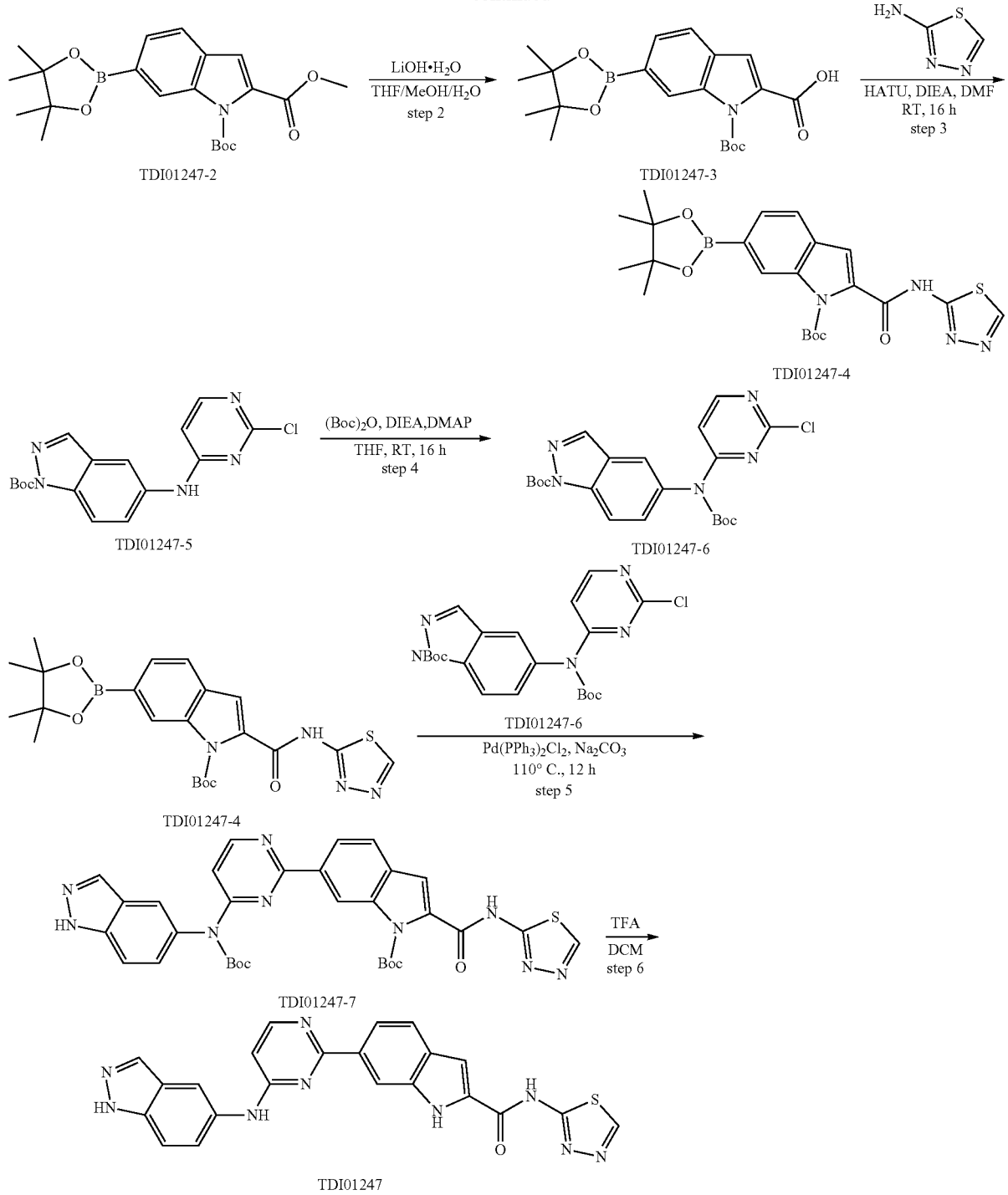

Step 1:

Compound TDI01247-1 (the preparation thereof is as described in Example 13) (3.00 g, 9.97 mmol) was dissolved in tetrahydrofuran (50 mL), diisopropylethylamine (5.15 g, 39.9 mmol) and dimethylaminopyridine (182 mg, 1.50 mmol) were added, di-tert-butyl dicarbonate (3.25 g, 14.9 mmol) was added with stirring at room temperature, and the reaction was performed at room temperature overnight. Thin layer chromatography (petroleum ether:ethyl acetate=5:1) indicated the reaction was complete. The reaction solution was diluted with water (80 mL), and extracted with ethyl acetate (100 mL×2). The organic phase was combined, successively washed with 0.5M HCl (80 mL×2) and saturated brine (100 mL×2), dried over anhydrous sodium sulfate, filtered, and concentrated to afford compound TDI01247-2 (2.8 g, yellow solid, yield: 70%).

$^1$H NMR (400 MHz, CDCl$_3$) δ 8.58 (s, 1H), 7.69 (d, J=8.0 Hz, 1H), 7.59 (d, J=8.0 Hz, 1H), 7.07 (s, 1H), 3.93 (s, 3H), 1.63 (s, 9H), 1.36 (s, 12H).

Step 2:

Compound TDI01247-2 (2.8 g, 6.98 mmol) was dissolved in a mixed solution of tetrahydrofuran/methanol/water (2:2:1) (25 mL), lithium hydroxide (2.93 g, 69.8 mmol) was added, and the reaction was performed at room temperature overnight. LC-MS indicated the reaction was complete. The reaction solution was concentrated under reduced pressure, and the crude product was purified by column chromatography (dichloromethane/methanol=12:1) to afford compound TDI01247-3 (1.3 g, yellow solid, yield: 48.3%).

$^1$H NMR (400 MHz, DMSO-$d_6$) δ 11.89 (s, 1H), 8.37 (s, 1H), 7.70 (d, J=8.0 Hz, 1H), 7.58 (d, J=8.0 Hz, 1H), 7.20 (s, 1H), 1.57 (s, 9H), 1.32 (s, 12H). MS m/z (ESI): 388.2 [M+H].

Step 3:

Compound TDI01247-3 (800 mg, 2.07 mmol) was dissolved in N,N-dimethylformamide (10 mL), and HATU (945 mg, 2.48 mmol) and diisopropylethylamine (1.07 g, 8.28 mmol) were added. After stirring at room temperature for 30 min, 1,3,4-thiadiazol-2-amine (250 mg, 2.48 mmol) was added, and the reaction was continued at room temperature overnight. LC-MS and thin layer chromatography (petroleum ether:ethyl acetate=1:1) indicated the reaction was complete. The reaction solution was washed with ethyl acetate (80 mL), and successively washed with water (60 mL×2) and saturated brine (80 mL×2). The organic phase was dried over anhydrous sodium sulfate, filtered, and concentrated under reduced pressure. The crude product was separated and purified by column chromatography (ethyl acetate/petroleum ether=10%-50%) to afford compound TDI01247-4 (100 mg, yellow solid, yield: 10.3%).

$^1$H NMR (400 MHz, CDCl$_3$) δ 11.45 (s, 1H), 8.86 (s, 1H), 8.65 (s, 1H), 7.74 (d, J=8.0 Hz, 1H), 7.66 (d, J=8.0 Hz, 1H), 7.39 (s, 1H), 1.60 (s, 9H), 1.37 (s, 12H). MS m/z (ESI): 471.2 [M+H].

Step 4:

Compound TDI01247-5 (6.00 g, 17.4 mmol) was dissolved in tetrahydrofuran (150 mL), diisopropylethylamine (8.98 g, 69.6 mmol) and dimethylaminopyridine (212 mg, 1.74 mmol) were added. Di-tert-butyl dicarbonate (4.55 g, 20.9 mmol) was slowly added under stirring at room temperature, and the reaction was performed at room temperature overnight. Thin layer chromatography (petroleum ether: ethyl acetate=1:1) indicated the reaction was complete. The reaction solution was diluted with water (80 mL), and extracted with ethyl acetate(100 mL×2) The organic phase was combined, successively washed with 0.5M HCl (150 mL×2) and saturated brine (200 mL×2), dried over anhydrous sodium sulfate, filtered, and concentrated to afford compound TDI01247-6 (Reg-1-27, 7.0 g, yellow solid, yield: 90.9%).

$^1$H NMR (400 MHz, DMSO-$d_6$) δ 8.63 (d, J=6.0 Hz, 1H), 8.45 (s, 1H), 8.13 (d, J=8.8 Hz, 1H), 8.02 (d, J=6.0 Hz, 1H), 7.82 (d, J=2.0 Hz, 1H), 7.50 (dd, J=8.8, 2.0 Hz, 1H), 1.67 (s, 9H), 1.36 (s, 9H).

Step 5:

Compound TDI01247-4 (100 mg, 0.21 mmol) and TDI01247-6 (78.9 mg, 0.18 mmol) were dissolved in a mixed solution of ethanol/water (8:1) (9 mL), sodium carbonate (38.2 mg, 0.36 mmol) and Pd(PPh$_3$)$_2$Cl$_2$ (14.0 mg, 0.02 mmol) were added, purge with argon was performed for 3 times, and the reaction was placed in an oil bath at 110° C., and allowed to proceed overnight. LC-MS indicated the reaction was complete. The reaction solution was cooled to room temperature, filtered, concentrated under reduced pressure, and the residue was purified by preparative thin layer chromatography (ethyl acetate) to afford compound TDI01247-7 (50 mg, yellow oil, yield: 51.0%). MS m/z (ESI): 554.2 [M+H].

Step 6:

Compound TDI01247-7 (50 mg, 0.09 mmol) was dissolved in dichloromethane (2 mL), trifluoroacetic acid (1 mL) was added at room temperature, and the reaction was performed in an oil bath at 40° C. for 2 hours. LC-MS indicated the reaction was complete. The reaction solution was concentrated under reduced pressure, and the crude product was separated and purified by high-performance liquid chromatography (trifluoroacetic acid) to afford compound TDI01247 (8.23 mg, yellow solid, yield: 20.1%).

$^1$H NMR (400 MHz, CD$_3$OD, DMSO-$d_6$) δ 9.12 (s, 1H), 8.42 (s, 1H), 8.23 (d, J=7.2 Hz, 1H), 8.18 (s, 2H), 7.95 (d, J=8.4 Hz, 2H), 7.90 (d, J=8.8 Hz, 1H), 7.71 (d, J=8.8 Hz, 2H), 7.63 (s, 2H), 6.90 (d, J=6.8 Hz, 1H). MS m/z (ESI): 454.1 [M+H].

Example 19: preparation of 1-(6-(4-((1H-indazol-5-yl)amino)pyrimidin-2-yl)-1H-indol-1-yl)-2-(4-methylpiperazin-1-yl)ethan-1-one (TDI01230)

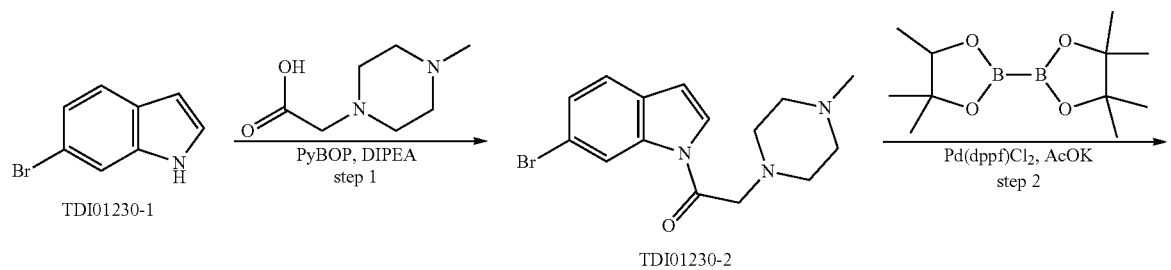

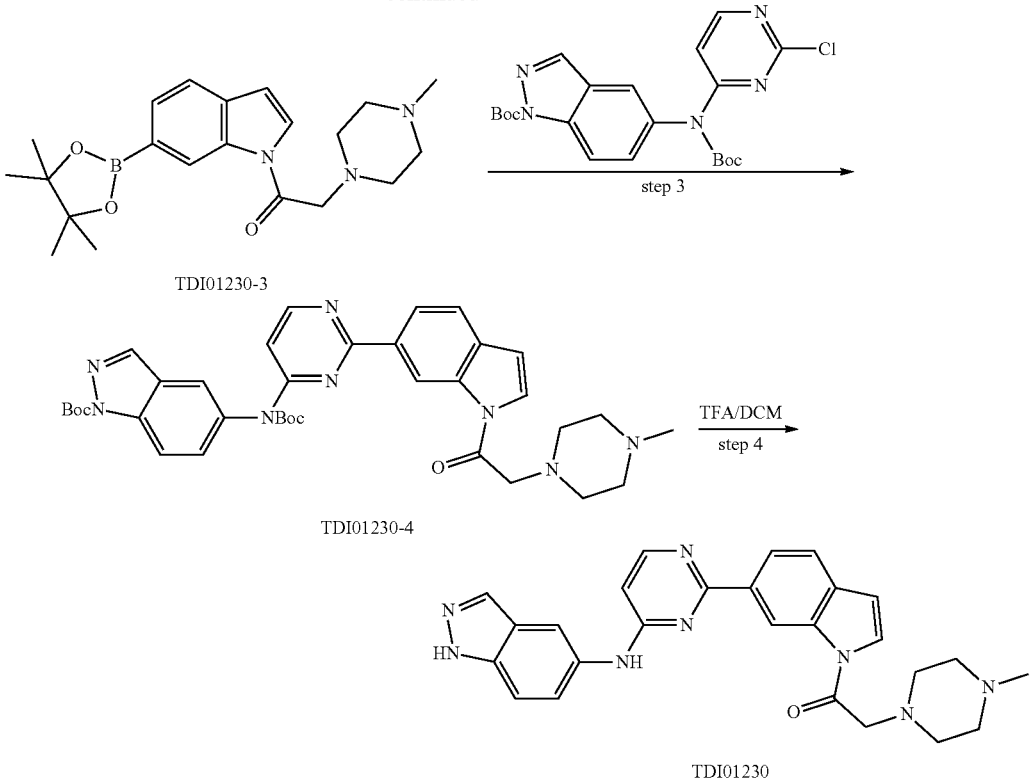

Step 1:

Compound 2-(4-methylpiperazin-1-yl)acetic acid (2.4 g, 15.3 mmol) was dissolved in N,N-dimethylformamide (10 mL), PyBOP (7.9 g, 15.3 mmol) was added, and the reaction solution was stirred at ambient temperature for 1 hour. TDI01230-1 (2 g, 10.2 mmol) and DIPEA (3.9 g, 30.6 mmol) were then added, and the reaction was continued at ambient temperature for 2 h. LC-MS indicated the reaction was complete. The reaction solution was added with water (25 mL), and extracted with dichloromethane (50 mL×3). The organic phase was washed with saturated brine (10 mL×2), dried over anhydrous sodium sulfate, and concentrated, followed by purification by column chromatography (dichloromethane:methanol=100:0 to 20:1), to afford compound TDI01230-2 (600 g, yellow solid, crude product, yield: 11.6%).

$^1$H NMR (400 MHz, DMSO-$d_6$) δ 8.51 (s, 1H), 7.95 (d, J=3.8 Hz, 1H), 7.60 (d, J=8.3 Hz, 1H), 7.46 (d, J=1.7 Hz, 1H), 6.76 (d, J=3.7 Hz, 1H), 3.89 (s, 2H), 2.70 (d, J=5.7 Hz, 8H), 2.38 (s, 3H). MS m/z (ESI): 336.1 [M+H].

Step 2:

Compound TDI01230-2 (600 mg, 1.79 mmol) and bis(pinacolato)diboron (908 mg, 6.3 mmol) were dissolved in 1,4-dioxane (10 mL), potassium acetate (527 mg, 5.37 mmol) and Pd(dppf)Cl$_2$ (132 mg, 0.18 mmol) were added, purge with argon was performed for 3 times, the reaction was placed in an oil bath at 110° C., and allowed to proceed overnight. Thin layer chromatography (petroleum ether:ethyl acetate=20:1) indicated the reaction was complete. The reaction solution was cooled to room temperature, concentrated under reduced pressure, and the residue was purified by column chromatography (dichloromethane/methanol=100:0 to 20:1), to afford compound TDI01230-3 (300 mg, brown solid, yield: 43.8%). MS m/z (ESI): 384.3 [M+H].

Step 3:

Compound TDI01230-3 (100 mg, 0.225 mmol) and tert-butyl 5-((tert-butoxycarbonyl)(2-chloropyrimidin-4-yl)amino)-1H-indazole-1-carboxylate (for preparation process thereof, please refer to Example 18) (129 mg, 0.337 mmol) were dissolved in a mixed solution of tetrahydrofuran/water (1:2) (3 mL), potassium phosphate (96 mg, 0.45 mmol) and chloro(2-dicyclohexylphosphino-2',4',6'-triisopropyl-1,1'-biphenyl)[2-(2'-amino-1,1'-biphenyl)]palladium (II) (4 mg, 0.005 mmol) were added, purge with argon was performed, and the reaction was placed in an oil bath at 60° C., and allowed to proceed for 2 h. LC-MS indicated the reaction was complete. The reaction solution was cooled to room temperature followed by addition of water (5 mL), and then extracted with dichloromethane (5 mL×3). The organic phase was extracted with saturated brine (5 mL×2), dried over anhydrous sodium sulfate, and concentrated followed by purification by thin layer chromatography (dichloromethane:methanol=15:1) to afford compound TDI01230-4 (30 mg, yellow solid, yield: 20.0%). MS m/z (ESI): 369.3 [M+H].

Step 4:

Trifluoroacetic acid (1.5 mL) was added to a solution of TDI01230-4 (30 mg, 0.045 mmol) in dichloromethane (3 mL), and the reaction was performed at room temperature for 2 hours. LC-MS indicated the reaction was complete. The reaction solution was cooled to room temperature, concentrated under reduced pressure, and the residue was purified by liquid chromatography to afford compound TDI01230 (7.13 mg, yellow solid, yield: 34.0%).

$^1$H NMR (400 MHz, DMSO-d$_6$) δ 10.47 (s, 1H), 9.77 (s, 1H), 9.55 (s, 1H), 8.64 (s, 1H), 8.44-8.31 (m, 2H), 8.26 (d, J=7.8 Hz, 1H), 8.09 (s, 1H), 7.81 (d, J=7.9 Hz, 1H), 7.63 (d, J=8.5 Hz, 1H), 7.52 (d, J=8.0 Hz, 1H), 6.95-6.78 (m, 2H), 4.14 (s, 2H), 3.47 (s, 2H), 3.20 (s, 4H), 2.85 (s, 3H), 2.73 (s, 2H). MS m/z (ESI): 467.3 [M+H].

Example 20: preparation of 2-(5-(4-((1H-indazol-5-yl)amino)pyrimidin-2-yl)isoindolin-2-yl)-N-(pyridazin-4-yl)acetamide (TDI01238)

hours. LC-MS indicated the reaction was complete. Water (25 mL) and dichloromethane (30 mL) were added to the reaction solution, and precipitation occurred. The filter cake was obtained after filtration, washed with water and n-hexane, and dried to afford compound TDI01238-2 (950 mg, brown solid, yield: 52.78%).

$^1$H NMR (400 MHz, DMSO-d$_6$) δ 10.97 (s, 1H), 9.30 (dd, 1H), 9.07 (dd, 1H), 7.92 (dd, 1H), 4.37 (s, 2H). MS m/z (ESI): 172.1 [M+H].

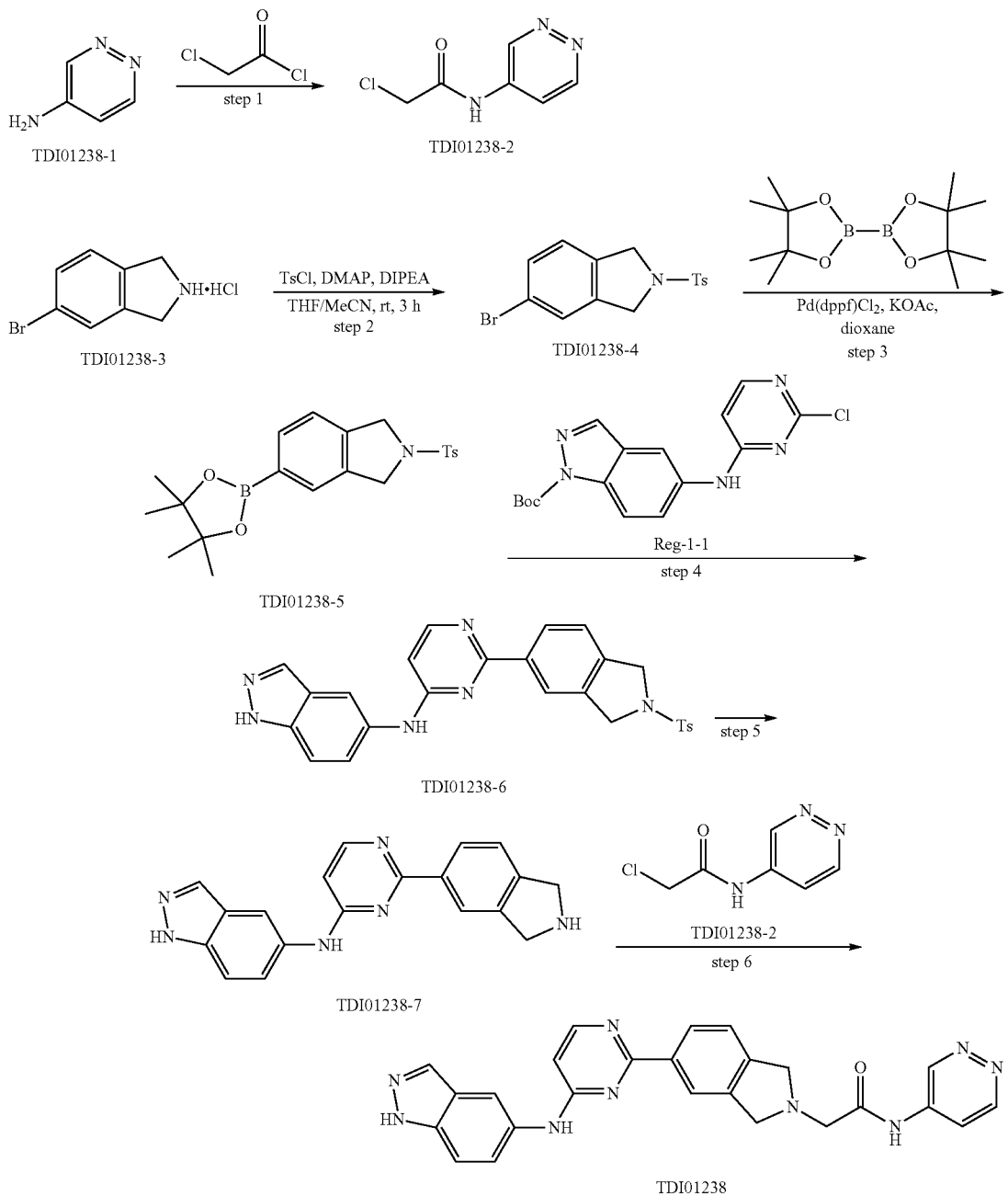

Step 1:

Compound TDI01238-1 (1 g, 10.526 mmol), chloroacetyl chloride (1.3 g, 11.504 mmol) and triethylamine (1.17 g, 11.584 mmol) were dissolved in dichloromethane (10 mL), and the reaction was performed at room temperature for 3

Step 2:

Compound TDI01238-3 (500 mg, 2.132 mmol), 4-tosyl chloride (447 mg, 2.345 mmol), 4-dimethylaminopyridine (78 mg, 0.6396 mmol), diisopropylethylamine (825 mg, 6.396 mmol) and tetrahydrofuran/acetonitrile (20/8 mL)

were mixed, and reacted at room temperature for 16 h. After the reaction was complete, the reaction solution was concentrated to dryness, and the residue was added with water, followed by extraction with ethyl acetate (20 mL×2). The organic phase was combined, washed with saturated brine, dried over anhydrous sodium sulfate, and then concentrated to dryness. The residue was rinsed with petroleum ether to afford compound TDI01238-4 (700 mg, white solid, yield: 93.58%).

$^1$H NMR (400 MHz, CDCl$_3$) δ 7.76 (d, 2H), 7.33 (dd, 4H), 7.03 (d, 1H), 4.57 (d, 4H), 2.41 (s, 3H). MS m/z (ESI): 352.1 [M+H].

Step 3:

Compound TDI01238-4 (700 mg, 1.988 mmol) and bis(pinacolato)diboron (757 mg, 2.983 mmol) were dissolved in 1,4-dioxane (20 mL), potassium acetate (584 mg, 5.964 mmol) and Pd(dppf)Cl$_2$ (146 mg, 0.199 mmol) were added, purge with argon was performed for 3 times, and the reaction was placed in an oil bath at 105° C., and allowed to proceed for 4 h. After the reaction was complete, the reaction solution was filtered, and the filtrate was concentrated under reduced pressure to dryness. The residue was added with water, and extracted with dichloromethane (20 mL×2). The organic phase was combined, washed with saturated brine, dried over anhydrous sodium sulfate, and then concentrated to dryness. The residue was purified by column chromatography (petroleum ether:ethyl acetate=10:1) to afford compound TDI01238-5 (740 mg, white solid, yield: 93.3%).

$^1$H NMR (400 MHz, CDCl$_3$) δ 7.76 (d, 2H), 7.67 (d, 1H), 7.61 (s, 1H), 7.30 (d, 2H), 7.17 (d, 1H), 4.62 (d, 4H), 2.39 (s, 3H), 1.32 (s, 12H). MS m/z (ESI): 400.2 [M+H].

Step 4:

Compound TDI01238-5 (0.5 g, 1.253 mmol) and Reg-1-1 (288 mg, 0.835 mmol) were dissolved in a mixed solution of ethanol/water (8/1 mL), sodium carbonate (266 mg, 2.505 mmol) and Pd(PPh$_3$)$_2$Cl$_2$ (59 mg, 0.0835 mmol) were added, purge with argon was performed for 3 times, the reaction was placed in an oil bath at 100° C., and allowed to proceed for 2 h. After the reaction was complete, the reaction solution was filtered, and the filtrate was concentrated under reduced pressure to dryness. The residue was added with water, and extracted with ethyl acetate (20 mL×3). The organic phase was combined, washed with saturated brine, dried over anhydrous sodium sulfate, and then concentrated to dryness. The residue was purified by column chromatography (dichloromethane:methanol=30:1-20:1) to afford compound TDI01238-6 (260 mg, yellow oil, yield: 64.68%).

$^1$H NMR (400 MHz, CDCl$_3$) δ 8.30 (dd, 1H), 8.20 (s, 0.5H), 8.09 (d, 1H), 7.77 (dd, 2.5H), 7.68 (m, 1H), 7.55 (dd, 1H), 7.47 (d, 0.5H), 7.32 (m, 5H), 7.17 (d, 0.3H), 7.02 (s, 0.4H), 6.49 (dd, 0.7H), 4.65 (dd, 4H), 2.40 (d, 3H). MS m/z (ESI): 483.3 [M+H].

Step 5:

Compound TDI01238-6 (245 mg, 0.508 mmol) and hydrobromic acid (5 mL) were placed in an oil bath at 95° C., and reacted for 6 h. After the reaction was complete, the reaction solution was concentrated under reduced pressure to dryness, toluene (10 mL) was added to dissolve the residue, and the resulted solution was then concentrated under reduced pressure to dryness, to afford compound TDI01238-7 (150 mg, yellow solid, yield: 90.36%).

$^1$H NMR (400 MHz, DMSO-d$_6$) δ 11.47 (s, 1H), 9.69 (s, 2H), 9.48 (s, 1H), 8.40 (d, 1H), 8.19 (s, 2H), 7.70 (m, 2H), 7.49 (d, 1H), 7.13 (d, 1H), 4.67 (s, 3H), 4.53 (t, 2H). MS m/z (ESI): 329.2 [M+H].

Step 6:

Compound TDI01238-7 (100 mg, 0.244 mmol), TDI01238-2 (37 mg, 0.219 mmol) and N,N-diisopropylethylamine (94 mg, 0.732 mmol) were dissolved in acetonitrile (4 mL), and the reaction was performed in an oil bath at 70° C. for 3 h. After the reaction was complete, insoluble was removed by filtration, the filtrate was evaporated to dryness, and the residue was purified by preparative thin layer chromatography (dichloromethane:methanol=10:1), to give a crude product (50 mg), which was further purified by high-performance liquid chromatography to afford compound TDI01238 (13.17 mg, yellow solid, yield: 11.65%).

$^1$H NMR (400 MHz, DMSO-d$_6$) δ 13.07 (s, 1H), 11.30 (s, 1H), 9.92 (s, 1H), 9.36 (s, 1H), 9.14 (d, 1H), 8.36 (m, 2H), 8.19 (s, 1H), 8.11 (s, 1H), 7.97 (m, 1H), 7.57 (dd, 2H), 6.75 (d, 1H), 4.84 (s, 3H), 4.60 (s, 1H). MS m/z (ESI): 464.3 [M+H].

Example 21: preparation of 5-(4-((1H-indazol-5-yl)amino)pyrimidin-2-yl)-N-(pyridazin-4-yl)isoindoline-2-carboxamide (TDI01237)

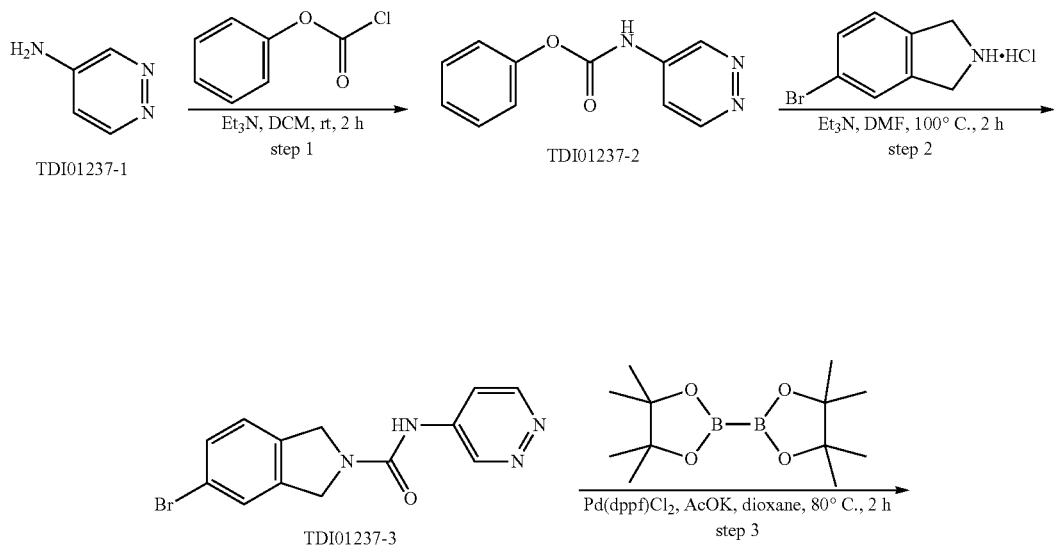

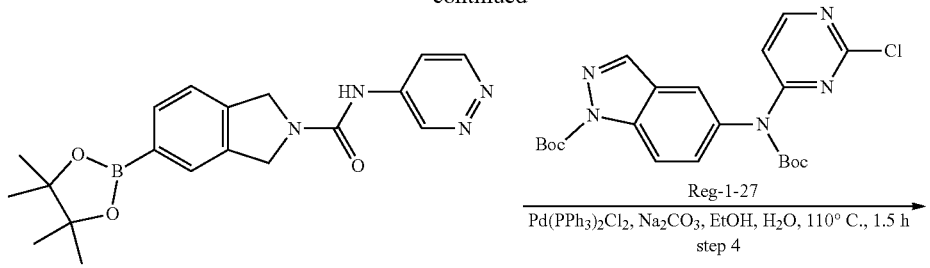

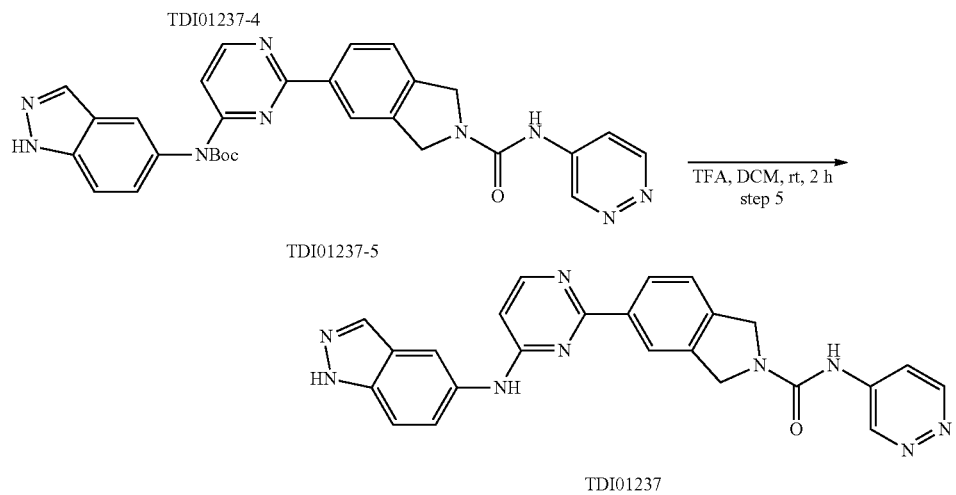

Step 1:

Under ice bath cooling, phenyl chloroformate (1.24 g, 7.89 mmol) was added to a solution of TDI01237-1 (500 mg, 5.27 mmol) and triethylamine (1.06 g, 10.54 mmol) in dichloromethane (10 mL), and the reaction was performed at room temperature for 2 h. LC-MS indicated the reaction was complete. The reaction was quenched by adding water (15 mL), extracted with dichloromethane (30 mL), washed with saturated brine (15 mL), dried, and concentrated to afford TDI01237-2 (600 mg, crude product). MS m/z (ESI): 216.1 [M+H].

Step 2:

Compound TDI01237-2 (410 mg, 1.91 mmol) and 5-bromoisoindoline hydrochloride (895 mg, 3.82 mmol) were dissolved in N,N-dimethylformamide (5 mL), triethylamine (2 mL) was added, and the reaction was performed in an oil bath at 100° C. for 1 h. LC-MS indicated the reaction was complete. Water (15 mL) was slowly added to the reaction solution, and a large amount of solid precipitated. The mixture was stirred for 30 min, filtered, and the solid thus obtained was TDI01237-3 (380 mg, wine red solid, yield: 62.56%). MS m/z (ESI): 319.2 [M+H].

Step 3:

Compound TDI01237-3 (350 mg, 1.09 mmol) and bis(pinacolato)diboron (558 mg, 2.19 mmol) were dissolved in dioxane (12 mL), potassium acetate (323 mg, 3.29 mmol) and Pd(dppf)Cl$_2$ (81 mg, 0.11 mmol) were added, purge with argon was performed for 3 times, the reaction was placed in an oil bath, and allowed to proceed overnight. Thin layer chromatography (dichloromethane/methanol=10:1) indicated the reaction was complete. The reaction solution was cooled to room temperature, concentrated under reduced pressure, and the residue was separated by column chromatography (dichloromethane/methanol=20:1), to afford compound TDI01237-4 (120 mg, yellow solid, yield: 30.08%). MS m/z (ESI): 367.2 [M+H].

Step 4:

Compound TDI01237-4 (100 mg, 0.273 mmol) and intermediate Reg-1-27 (80 mg, 0.182 mmol) were dissolved in ethanol/water=5/2 (7 mL), sodium carbonate (58 mg, 0.546 mmol) and Pd(PPh$_3$)$_2$ (13 mg, 0.018 mmol) were added, purge with argon was performed for 3 times, and the reaction was performed under microwave radiation at 110° C. for 1.5 h. LC-MS indicated the reaction was complete. The reaction solution was cooled to room temperature, filtered, and concentrated followed by addition of water (5 mL). The solution was extracted with dichloromethane (15 mL), washed with saturated brine (5 mL), dried over anhydrous sodium sulfate, and concentrated followed by purification by thin layer chromatography (dichloromethane:methanol=10:1) to afford compound TDI01237-5 (30 mg, yellow solid, yield: 30.03%). MS m/z (ESI): 550.3 [M+H].

Step 5:

Trifluoroacetic acid (1 mL) was added to a solution of TDI01237-5 (30 mg, 0.055 mmol) in dichloromethane (3 mL), and the reaction was performed at room temperature for 2 hours. LC-MS indicated the reaction was complete. The reaction solution was cooled to room temperature, concentrated under reduced pressure, and the residue was purified by liquid chromatography to afford compound TDI01237 (2.13 mg, yellow solid, yield: 8.53%).

$^1$H NMR (400 MHz, DMSO-d$_6$) δ 10.09 (s, 1H), 9.79 (s, 1H), 9.46 (d, J=2.3 Hz, 1H), 9.11 (d, J=6.4 Hz, 1H), 8.36 (d, J=6.2 Hz, 1H), 8.29 (d, J=8.1 Hz, 2H), 8.19 (dd, J=7.4, 4.8 Hz, 2H), 8.12 (s, 1H), 7.62-7.53 (m, 3H), 6.76 (d, J=6.2 Hz, 1H), 4.95 (s, 4H). MS m/z (ESI): 450.2 [M+H].

The compounds in following table 4 were prepared according to methods similar to that described in Example 21.

TABLE 4

| No. | Compound Structure | Compound Name | Starting material or regent different from that in Example 21 | Characterization Data |
|---|---|---|---|---|
| TDI01374 | 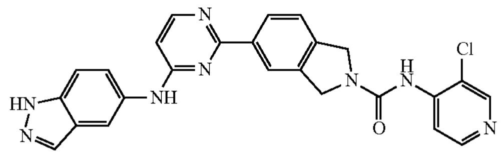 [SMILES: O=C(Nc1ccncc1Cl)N1Cc2ccc(-c3nccc(Nc4ccc5[nH]ncc5c4)n3)cc2C1] | 5-(4-((1H-indazol-5-yl)amino)pyrimidin-2-yl)-N-(3-chloropyridin-4-yl)isoindoline-2-carboxamide | 4-aminopyridine replaced with 4-amino-3-chloropyridine in synthesis step 1 of Example 21 | ¹H NMR (400 MHz, DMSO-d₆) δ 13.11 (s, 1H), 10.10 (s, 1H), 8.62 (s, 1H), 8.42 (d, J = 5.3 Hz, 1H), 8.36 (d, J = 6.2 Hz, 1H), 8.27 (d, J = 7.9 Hz, 2H), 8.12 (dd, J = 21.4, 17.9 Hz, 4H), 7.59 (dd, J = 17.4, 8.2 Hz, 3H), 6.76 (d, J = 6.2 Hz, 1H), 4.98 (s, 4H). MS m/z (ESI): 483.1 [M+H]. |
| TDI01376 | 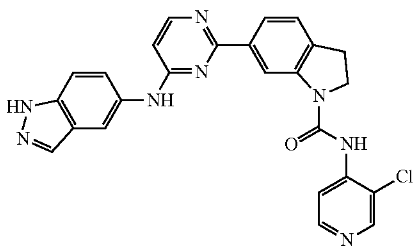 [SMILES: O=C(Nc1ccncc1Cl)N1CCc2ccc(-c3nccc(Nc4ccc5[nH]ncc5c4)n3)cc21] | 6-(4-((1H-indazol-5-yl)amino)pyrimidin-2-yl)-N-(3-chloropyridin-4-yl)indoline-1-carboxamide | 4-aminopyridine replaced with 3-amino-2-chloropyridine; isoindoline·HCl replaced with 5-bromoisoindoline·HCl in step 4 | ¹H NMR (400 MHz, DMSO-d₆) δ 11.06 (s, 1H), 8.89 (s, 1H), 8.74 (s, 1H), 8.55 (d, J = 5.2 Hz, 1H), 8.42 (s, 1H), 8.31 (d, J = 6.8 Hz, 1H), 8.18 - 8.12 (m, 2H), 7.87 (d, J = 7.7 Hz, 1H), 7.62 (d, J = 8.7 Hz, 1H), 7.55 (d, J = 8.5 Hz, 1H), 7.45 (d, J = 7.8 Hz, 1H), 6.91 (d, J = 6.4 Hz, 1H), 4.31 (t, J = 8.3 Hz, 2H), 3.30 (d, J = 8.2 Hz, 2H). MS m/z (ESI): 483.1 [M+H]. |
| TDI01403 | 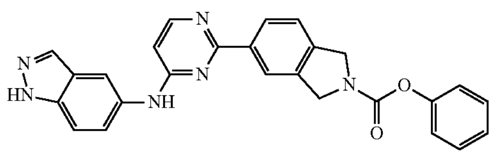 [SMILES: O=C(Oc1ccccc1)N1Cc2ccc(-c3nccc(Nc4ccc5[nH]ncc5c4)n3)cc2C1] | phenyl 5-(4-((1H-indazol-5-yl)amino)pyrimidin-2-yl)isoindoline-2-carboxylate | phenyl chloroformate was directly reacted with 5-bromoisoindoline·HCl in synthesis step 1 of Example 21. | ¹H NMR (400 MHz, CD₃OD) δ 8.23 (d, J = 7.2 Hz, 1H), 8.14 (d, J = 7.2 Hz, 3H), 8.08 (s, 1H), 7.68 (d, J = 6.0 Hz, 1H), 7.64 (t, J = 6.0 Hz, 2H), 7.41 (t, J = 8.0 Hz, 2H), 7.26 (t, J = 7.2 Hz, 1H), 7.20 (d, J = 8.0 Hz, 2H), 6.91 (d, J = 7.02 Hz, 1H), 5.08 (s, 2H), 4.90 (s, 2H). MS m/z (ESI): 449.1 [M+H]. |

TABLE 4-continued

| No. | Compound Name | Compound Structure | Starting material or regent different from that in Example 21 | Characterization Data |
|---|---|---|---|---|
| TDI01534 | phenyl 5-(4-((4-(1H-pyrazol-4-yl)phenyl)amino)pyrimidin-2-yl)isoindoline-2-carboxylate | [structure] | [phenyl chloroformate] was directly reacted with [5-bromoisoindoline·HCl]; in synthesis step 1 of Example 21; [2-chloro-N-Boc-indazol-5-amine with Boc] in step 4 was replaced with [2-chloro-4-((4-(1-Boc-pyrazol-4-yl)phenyl)amino)pyrimidine] | $^{1}$H NMR (400 MHz, DMSO-$d_6$) δ 10.23 (s, 1H), 8.40 (d, J = 6.4 Hz, 1H), 8.29 (d, J = 8.0 Hz, 2H), 8.08 (s, 2H), 7.77 (d, J = 8.0 Hz, 2H), 7.69 (d, J = 8.0 Hz, 2H), 7.59 (d, J = 8.0 Hz, 1H), 7.44 (t, J = 7.6 Hz, 2H), 7.29 - 7.22 (m, 3H), 6.83 (d, J = 6.0 Hz, 1H), 5.03 (d, J = 10.4 Hz, 2H), 4.84 (d, J = 12.0 Hz, 2H). MS m/z (ESI): 475.2 [M+H]. |

Example 22: preparation of 2-(6-(4-((1H-indazol-5-yl)amino)pyrimidin-2-yl)-1-oxoisoindolin-2-yl)-N-(pyridazin-4-yl)acetamide (TDI01239)

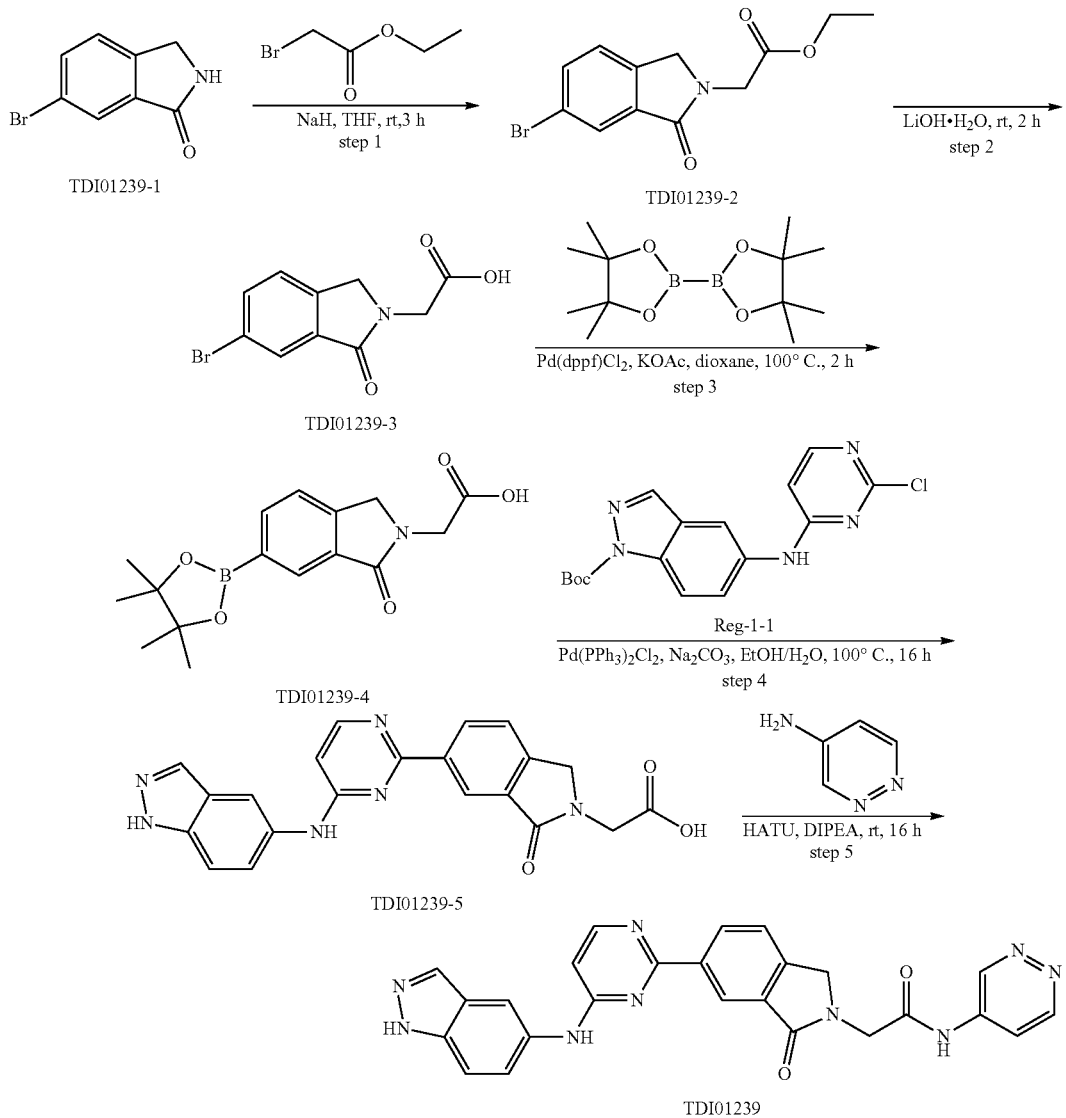

Step 1:
TDI01239-1 (500 mg, 2.358 mmol) was dissolved in tetrahydrofuran (24 mL), and cooled to 0° C. Under the protection of nitrogen, 60% NaH (236 mg, 5.895 mmol) was added to the above reaction solution, and the reaction was performed at room temperature for 1 h after the addition. Bromoethyl acetate was then added at 0° C., and the reaction was continued at room temperature for 2 h. LC-MS indicated the reaction was complete. After completion of the reaction, ice water and 1N HCl solution was added to quench the reaction, and the aqueous phase was extracted with ethyl acetate (15 mL). The combined organic phase was washed with saturated brine, dried over anhydrous sodium sulfate and concentrated to dryness to afford TDI01239-2 (700 mg, yellow solid, yield: 99.57%). MS m/z (ESI): 298.1 [M+H].

Step 2:
TDI01239-2 (700 mg, 2.357 mmol), lithium hydroxide monohydrate (297 mg, 7.071 mmol) were added to a mixed solution of tetrahydrofuran (10 mL) and water (10 mL), and the reaction was stirred at room temperature for 2 h. LC-MS indicated the reaction was complete. After pH was adjusted to 3 with dilute hydrochloric acid, the solution was extracted with ethyl acetate (2 mL). The organic phase was combined, washed with saturated brine, dried over anhydrous sodium sulfate, and concentrated to afford TDI01239-3 (600 mg, yellow solid, yield: 94.64%). MS m/z (ESI): 270.1 [M+H].

Step 3:
TDI01239-3 (0.3 g, 1.115 mmol) and bis(pinacolato)diboron (425 mg, 1.673 mmol) were dissolved in 1,4-dioxane (10 mL), potassium acetate (328 mg, 3.345 mmol) and Pd(dppf)Cl$_2$ (82 mg, 0.1115 mmol) were added, purge with argon was performed for 3 times, and the reaction was placed in an oil bath at 100° C., and allowed to proceed for 3 h. LC-MS indicated the reaction was complete. After the reaction was complete, the solution was filtered, and the filtrate was concentrated to afford TDI01239-4 (350 mg, black oil, crude product).

$^1$H NMR (400 MHz, DMSO-d$_6$) δ 7.96 (s, 1H), 7.90 (d, 1H), 7.64 (d, 1H), 4.55 (s, 2H), 4.27 (s, 2H), 1.32 (s, 12H). MS m/z (ESI): 318.2 [M+H].

Step 4:

TDI01239-4 (350 mg, 1.104 mmol) and Reg-1-1 (254 mg, 0.736 mmol) were dissolved in a mixed solution of ethanol (10 mL) and water (1.25 mL), sodium carbonate (234 mg, 2.208 mmol) and Pd(PPh$_3$)$_2$Cl$_2$ (52 mg, 0.0736 mmol) were added, purge with argon was performed for 3 times, and the reaction was placed in an oil bath at 100° C., and allowed to proceed for 16 h. LC-MS indicated the reaction was complete. The reaction solution was filtered, the filtrate was evaporated to dryness, and the residue was purified by column chromatography (dichloromethane:methanol=20:1-1:1) to afford TDI01239-5 (130 mg, light yellow solid, yield: 29.48%).

$^1$H NMR (400 MHz, CDCl$_3$) δ 9.88 (s, 1H), 8.63 (s, 1H), 8.55 (d, 1H), 8.36 (d, J=5.9 Hz, 1H), 8.20 (s, 1H), 8.04 (s, 1H), 7.69 (d, 1H), 7.57 (s, 2H), 6.75 (d, 1H), 4.62 (s, 2H), 3.87 (s, 2H). MS m/z (ESI): 401.2 [M+H].

Step 5:

TDI01239-5 (70 mg, 0.175 mmol) and 4-aminopyridazine (20 mg, 0.21 mmol) were dissolved in N,N-dimethylformamide (2 mL), HATU (66 mg, 0.175 mmol) and diisopropylethylamine (68 mg, 0.525 mmol) were added, and the reaction was performed at room temperature for 16 h. LC-MS indicated the reaction was complete. The solvent was evaporated to dryness, and the residue was purified by preparative chromatograph (dichloromethane:methanol:aqueous ammonia=8:1:10 drops) to give a crude product, which was purified by high-performance liquid chromatography to afford compound TDI01239 (5.29 mg, yellow solid, yield: 6.37%).

$^1$H NMR (400 MHz, DMSO-d$_6$) δ 11.10 (s, 1H), 10.32 (s, 1H), 9.33 (d, 1H), 9.11 (d, 1H), 8.65 (s, 1H), 8.55 (dd, 1H), 8.39 (d, 1H), 8.15 (s, 1H), 8.10 (s, 1H), 8.00 (dd, 1H), 7.84 (d, 1H), 7.62 (d, 1H), 7.55 (d, 1H), 6.81 (d, 1H), 4.70 (s, 2H), 4.56 (s, 2H). MS m/z (ESI): 478.2 [M+H].

The compound in following table 5 was prepared according to a method similar to that described in Example 22.

Example 23: preparation of N-(1H-indazol-5-yl)-2-(1-(1-methylpyrrolidin-3-yl)-1H-indol-6-yl)quinazolin-4-amine (TDI01272)

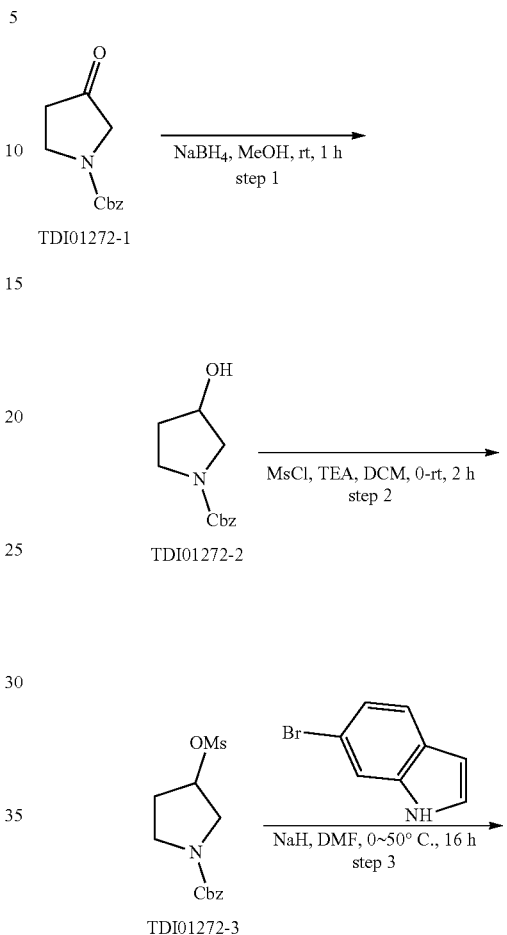

TABLE 5

| No. | Compound Structure | Compound Name | Starting material or regent different from that in Example 22 | Characterization Data |
|---|---|---|---|---|
| TDI01446 | | 2-(5-(4-((1H-indazol-5-yl)amino)pyrimidin-2-yl)-1-oxoisoindolin-2-yl)-N-isopropylacetamide | NH$_2$-pyridazine; in synthesis step 5 of Example 22 was replaced with isopropylamine. | $^1$H NMR (400 MHz, DMSO-d$_6$) δ 13.09 (s, 1H), 10.02 (s, 1H), 8.51 (s, 1H), 8.45 (d, J = 8.0 Hz, 1H), 8.39 (d, J = 6.0 Hz, 1H), 8.19 (s, 1H), 8.13 (s, 1H), 8.02 (d, J = 7.2 Hz, 1H), 7.85 (d, J = 8.0 Hz, 1H), 7.62-7.55 (m, 2H), 6.78 (d, J = 6.0 Hz, 1H), 4.63 (s, 2H), 4.16 (s, 2H), 3.90 - 3.85 (m, 1H), 1.08 (d, J = 6.4 Hz, 6H). MS m/z (ESI): 442.1 [M+H]. |

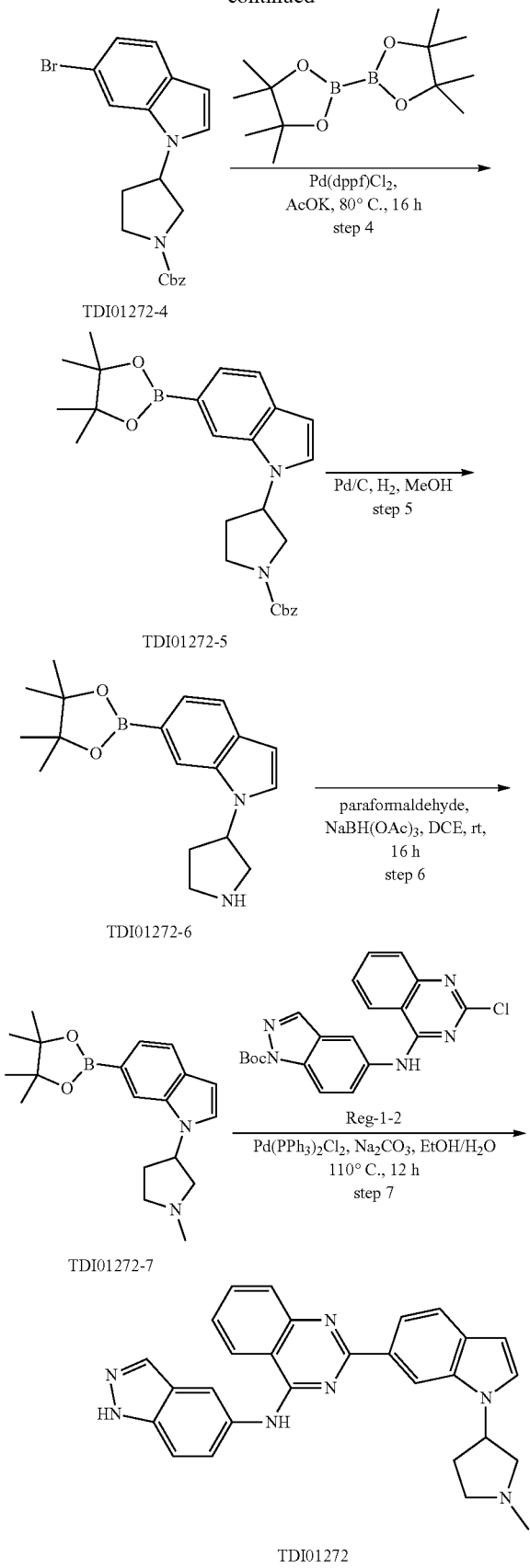

Step 1:
TDI01272-1 (10.0 g, 45.7 mmol) was dissolved in anhydrous methanol (100 mL), sodium borohydride (3.38 g, 91.4 mmol) was added in portions under cooling of an ice bath, and the reaction was performed at room temperature for 2 h. Thin layer chromatography (ethyl acetate) indicated the reaction was complete. The reaction solution was quenched by water (80 mL), and extracted with dichloromethane (300 mL). The combined organic phase was washed with saturated brine (300 mL), dried over anhydrous sodium sulfate, filtered, concentrated under reduced pressure, and the crude product was separated and purified by column chromatography (petroleum ether:ethyl acetate=1:1 to 0:1) to afford TDI01272-2 (5.20 g, yellow oil, yield: 51.9%).

$^1$H NMR (400 MHz, CDCl$_3$) δ 7.34-7.21 (m, 5H), 4.32-4.28 (m, 1H), 3.60 (s, 2H), 2.86-2.79 (m, 1H), 2.66-2.63 (m, 1H), 2.54-2.51 (m, 1H), 2.31-2.26 (m, 1H), 2.22-2.12 (m, 1H), 1.75-1.65 (m, 1H).

Step 2:
TDI01272-2 (5.20 g, 23.6 mmol) was dissolved in dichloromethane (150 mL), triethylamine (7.15 g, 70.8 mmol) was added, and methylsulfonyl chloride (4.04 g, 35.5 mmol) was added under ice bath cooling. The reaction was performed at room temperature for 3 h. Thin layer chromatography indicated the reaction was complete. The reaction solution was quenched by water (100 mL), and extracted with dichloromethane (300 mL). The combined organic phase was washed with saturated brine (400 mL), dried over anhydrous sodium sulfate, filtered, and concentrated under reduced pressure to afford TDI01272-3 (7.50 g, yellow oil, crude product).

$^1$H NMR (400 MHz, CDCl$_3$) δ 7.33-7.29 (m, 4H), 7.28-7.24 (m, 1H), 5.21-5.15 (m, 1H), 3.68 (d, J=12.8 Hz, 1H), 3.62 (d, J=12.8 Hz, 1H), 2.98 (s, 3H), 2.86-2.78 (m, 3H), 2.53-2.47 (m, 1H), 2.35-2.28 (m, 1H), 2.11-2.04 (m, 1H).

Step 3:
6-bromo-1H-indole (2.50 g, 12.8 mmol) was dissolved in N,N-dimethylformamide (40 mL), sodium hydride (1.03 g, 25.6 mmol) was added under ice bath cooling, and the reaction was performed at 0° C. for 30 minutes. TDI01272-3 (7.20 g, 24.1 mmol) was slowly added to the reaction solution, and the reaction was performed at 50° C. overnight. Thin layer chromatography (petroleum ether:ethyl acetate=5:1) indicated the reaction was complete. The reaction solution was quenched by water (100 mL), and extracted with ethyl acetate (200 mL). The combined organic phase was sequentially washed with a saturated aqueous solution of ammonium chloride (300 mL) and saturated brine (300 mL), dried over anhydrous sodium sulfate, filtered, and concentrated. The crude product was separated and purified by column chromatography (petroleum ether:ethyl acetate=20:1 to 8:1) to afford TDI01272-4 (4.10 g, yellow oil, yield: 80.4%).

$^1$H NMR (400 MHz, CDCl$_3$) δ 7.76 (s, 1H), 7.45 (d, J=8.4 Hz, 1H), 7.39 (d, J=7.2 Hz, 2H), 7.34 (dd, J=9.2, 6.0 Hz, 3H), 7.27 (s, 1H), 7.17 (dd, J=8.4, 1.6 Hz, 1H), 6.45 (d, J=3.2 Hz, 1H), 4.94-4.88 (m, 1H), 3.74 (d, J=12.8 Hz, 1H), 3.65 (d, J=12.8 Hz, 1H), 3.10-3.07 (m, 1H), 3.00-2.96 (m, 1H), 2.80-2.76 (m, 1H), 2.50-2.43 (m, 2H), 2.12-2.05 (m, 1H).

Step 4:
TDI01272-4 (2.00 g, 5.01 mmol) and bis(pinacolato)diboron (2.54 g, 10.0 mmol) were dissolved in 1,4-dioxane (40 mL), potassium acetate (4.90 g, 20.0 mmol) and Pd(dppf)Cl$_2$ (366 mg, 0.50 mmol) were added, purge with argon was performed for 3 times, and the reaction was performed in an oil bath (90° C.) overnight. Thin layer chromatography (petroleum ether:ethyl acetate=5:1) indicated the reaction was complete. The reaction solution was cooled to room temperature, concentrated under reduced pressure, and the residue was separated and purified by column chromatography (petroleum ether:ethyl acetate=20:1 to 8:1) to afford TDI01272-5 (2.10 g, yellow oil, yield: 93.9%).

$^1$H NMR (400 MHz, CDCl$_3$) δ 7.92 (s, 1H), 7.60 (d, J=8.0 Hz, 1H), 7.54-7.50 (m, 2H), 7.38 (d, J=7.2 Hz, 2H), 7.32 (t, J=7.2 Hz, 2H), 7.26-7.24 (m, 1H), 6.51 (d, J=3.2 Hz, 1H), 5.17-5.10 (m, 1H), 3.71 (d, J=12.8 Hz, 1H), 3.66 (d, J=12.8 Hz, 1H), 3.06-3.02 (m, 1H), 2.95-2.92 (m, 1H), 2.83-2.79 (m, 1H), 2.54-2.45 (m, 2H), 2.08-2.02 (m, 1H), 1.37 (s, 12H).

Step 5:

TDI01272-5 (2.10 g, 4.71 mmol) was dissolved in methanol (50 mL), Pd/C (210 mg) was added, and the reaction solution was purged with argon (3 times) and then hydrogen (3 times). The reaction was performed under an atmosphere of hydrogen at room temperature for 6 hours. Thin layer chromatography (petroleum ether:ethyl acetate=5:1) and LC-MS indicated the reaction was complete. The reaction solution was filtered, the filtrate was concentrated under reduced pressure, and the crude product was separated and purified by column chromatography (dichloromethane/methanol=20:1 to 10:1) to afford TDI01272-6 (550 mg, yellow oil, yield: 37.6%).

$^1$H NMR (400 MHz, CDCl$_3$) δ 7.91 (s, 1H), 7.63 (d, J=8.0 Hz, 1H), 7.56 (d, J=8.0 Hz, 1H), 7.30 (d, J=3.2 Hz, 1H), 6.53 (d, J=3.2 Hz, 1H), 5.14-5.08 (m, 1H), 3.41-3.36 (m, 1H), 3.31-3.25 (m, 1H), 3.17-3.10 (m, 2H), 2.43-2.34 (m, 1H), 2.16-2.09 (m, 1H), 1.38 (s, 12H). MS m/z (ESI): 313.3 [M+H].

Step 6:

TDI01272-6 (300 mg, 0.96 mmol) and paraformaldehyde (144 mg, 4.81 mmol) were dissolved in 1,2-dichloroethane (10 mL), acetic acid (5 drops) was added, and the reaction was stirred at room temperature for 1 hour followed by addition of NaBH(OAc)$_3$ (611 mg, 2.88 mmol). The reaction was performed at room temperature overnight. Thin layer chromatography (dichloromethane/methanol=10:1) and LC-MS indicated the reaction was complete. The reaction solution was quenched by water (40 mL), and extracted with dichloromethane (100 mL). The combined organic phase was sequentially washed with saturated aqueous sodium carbonate (100 mL) and saturated brine (160 mL), dried over anhydrous sodium sulfate, filtered, and concentrated. The crude product was separated and purified by preparative thin layer chromatography (dichloromethane/methanol=10:1) to afford TDI01272-7 (100 mg, yellow oil, yield: 31.9%).

$^1$H NMR (400 MHz, CDCl$_3$) δ 7.87 (s, 1H), 7.62 (d, J=8.0 Hz, 1H), 7.54 (d, J=8.0 Hz, 1H), 7.50 (d, I=3.2 Hz, 1H), 6.54 (d, J=3.2 Hz, 1H), 5.25-5.20 (m, 1H), 3.12-3.06 (m, 1H), 2.99-2.98 (m, 2H), 2.66-2.61 (m, 1H), 2.58-2.54 (m, 1H), 2.50 (s, 3H), 2.19-2.14 (m, 1H), 1.37 (s, 12H). MS m/z (ESI): 327.3 [M+H].

Step 7:

TDI01272-7 (98.8 mg, 0.303 mmol) and Reg-1-2 (100 mg, 0.253 mmol) were dissolved in a mixed solution of ethanol:water (8:1) (9 mL), sodium carbonate (53.6 mg, 0.506 mmol) and Pd(PPh$_3$)C$_{12}$ (17.6 mg, 0.025 mmol) were added, purge with argon was performed for 3 times, and the reaction was performed under microwave radiation (110° C.) for 1 hour. LC-MS indicated the reaction was complete. The reaction solution was cooled to room temperature, concentrated under reduced pressure, and the crude product was added with methanol and filtered. The resulted solid was purified by high-performance liquid chromatography to afford compound TDI01272 (86.9 mg, yellow solid, yield: 74.9%).

$^1$H NMR (400 MHz, CD$_3$OD) δ 8.60 (d, J=8.4 Hz, 1H), 8.44 (s, 1H), 8.23 (d, J=3.2 Hz, 2H), 8.13-8.06 (m, 2H), 7.99 (dd, J=8.4, 1.6 Hz, 1H), 7.84 (t, J=6.8 Hz, 1H), 7.79-7.74 (m, 4H), 6.73 (d, J=3.2 Hz, 1H), 5.50-5.43 (m, 1H), 3.99-3.58 (m, 4H), 3.03 (s, 3H), 2.73-2.68 (m, 1H), 2.52-2.47 (m, 1H). MS m/z (ESI): 460.2 [M+H].

Example 24: preparation of N-(2-(1-(2-(dimethylamino)ethyl)-1H-indol-6-yl)pyrimidin-4-yl)-1H-indazol-5-amine (TDI01287)

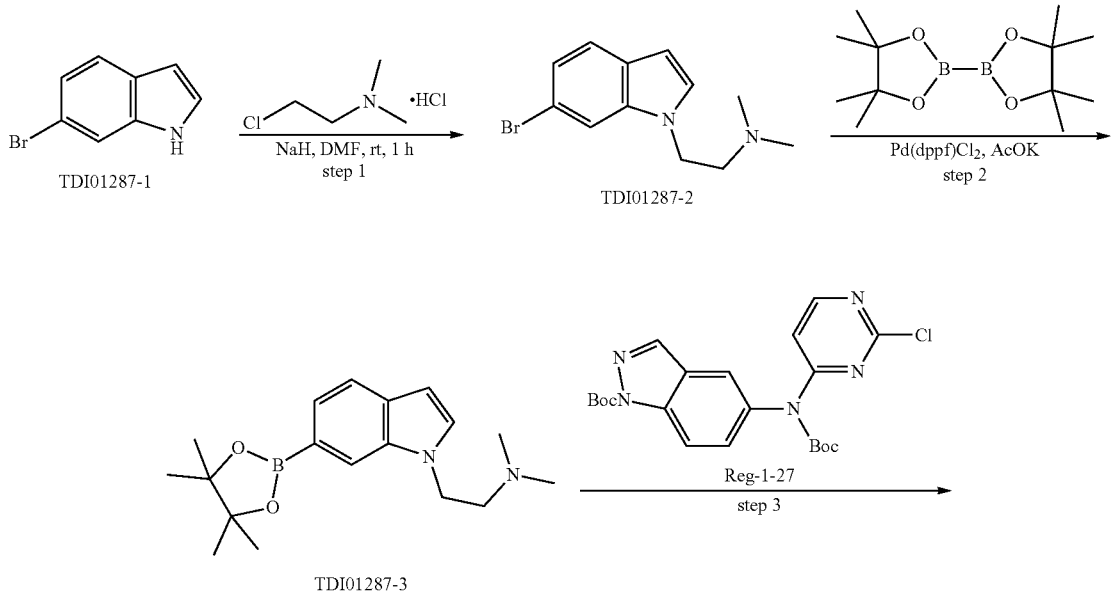

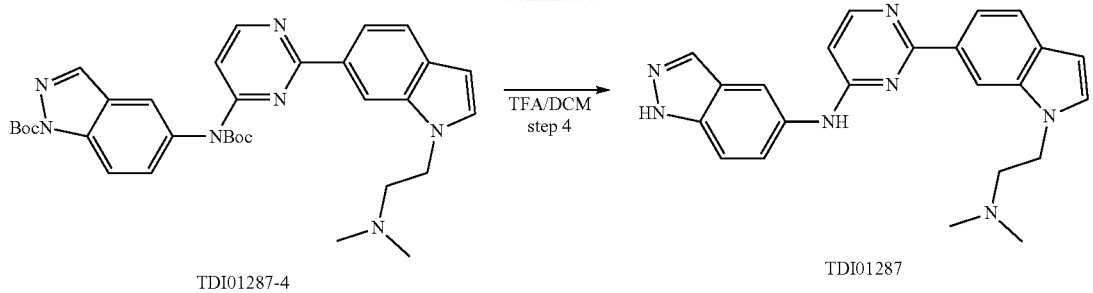

TDI01287-4 → TDI01287 (TFA/DCM, step 4)

Step 1:

Under ice bath cooling, NaH (612 mg, 15.3 mmol) was added to a solution of TDI01287-1 (1.0 g, 7.6 mmol) in N,N-dimethylformamide (10 mL). The reaction was warmed to room temperature and stirred for 1 h, and then dimethylaminoethyl chloride hydrochloride (1.1 g, 7.6 mmol) was added. The reaction was performed for 2 h. LC-MS indicated the reaction was complete. The reaction solution was added with water (25 mL), extracted with dichloromethane (150 mL), washed with saturated brine (30 mL), dried over anhydrous sodium sulfate, concentrated, and purified by column chromatography (dichloromethane:methanol=100:0 to 15:1) to afford TDI01287-2 (500 mg, yellow solid, yield: 12.23%). MS m/z (ESI): 267.1 [M+H].

Step 2:

TDI01287-2 (500 mg, 1.873 mmol) and bis(pinacolato)diboron (952 mg, 3.75 mmol) were dissolved in dioxane (8 mL), potassium acetate (368 mg, 3.75 mmol) and Pd(dppf)Cl$_2$ (138 mg, 0.187 mmol) were added, purge with argon was performed for 3 times, the reaction was placed in an oil bath at 90° C., and allowed to proceed overnight. Thin layer chromatography (dichloromethane:methanol=15:1) indicated the reaction was complete. The reaction solution was cooled to room temperature, concentrated under reduced pressure, and the residue was separated and purified by column chromatography (petroleum ether:ethyl acetate=4:1) to afford TDI01287-3 (360 mg, yellow solid, yield: 61.21%). MS m/z (ESI): 315.3 [M+H].

Step 3:

Compound Reg-1-27 (200 mg, 0.637 mmol) and TDI01287-3 (189 mg, 0.425 mmol) were dissolved in 1,4-dioxane/water=4/1 (5 mL), sodium carbonate (91 mg, 0.85 mmol) and 2-dicyclohexylphosphino-2',4',6'-triisopropylbiphenyl (40 mg, 0.085 mmol) and tris(dibenzylideneacetone)dipalladium (39 mg, 0.043 mmol) were added, purge with argon was performed for 3 times, and the reaction was performed under microwave radiation at 110° C. for 1 h. LC-MS indicated the reaction was complete. The reaction solution was cooled to room temperature, filtered, added with water (5 mL), extracted with dichloromethane (30 mL), washed with saturated brine (10 mL), dried over anhydrous sodium sulfate, and concentrated. The residue was purified by thin layer chromatography (dichloromethane:methanol=10:1) to afford TDI01287-4 (50 mg, yellow solid, yield: 15.79%). MS m/z (ESI): 498.4 [M+H].

Step 4:

Trifluoroacetic acid (1 mL) was added to a solution of TDI01287-4 (50 mg, 0.1 mmol) in dichloromethane (3 mL), and the reaction was performed at room temperature for 2 hours. LC-MS indicated the reaction was complete. The reaction solution was cooled to room temperature, concentrated under reduced pressure, and the residue was purified by liquid chromatography to afford compound TDI01287 (2.41 mg, yellow solid, yield: 6.07%).

$^1$H NMR (400 MHz, DMSO-d$_6$) δ 10.77 (s, 1H), 9.86 (s, 1H), 8.48 (s, 1H), 8.38 (d, J=6.6 Hz, 1H), 8.21 (s, 1H), 8.16 (s, 1H), 7.99 (d, J=8.2 Hz, 1H), 7.79 (d, J=8.4 Hz, 1H), 7.71 (s, 1H), 7.66 (d, J=8.8 Hz, 1H), 7.60 (d, J=8.8 Hz, 1H), 6.84 (d, J=3.8 Hz, 1H), 6.66 (d, J=3.0 Hz, 1H), 4.67 (t, J=6.7 Hz, 2H), 3.60 (t, J=6.3 Hz, 2H), 2.81 (s, 6H). MS m/z (ESI): 398.2 [M+H].

Example 25: preparation of N-(2-(2-methylisoindolin-5-yl)pyrimidin-4-yl)-1H-indazol-5-amine (TDI01288)

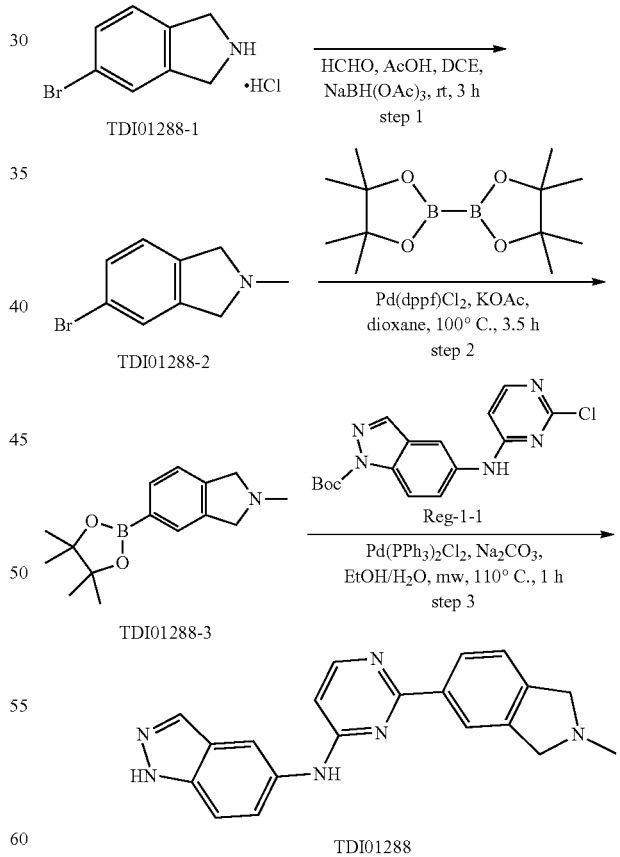

Step 1:

TDI01288-1 (450 mg, 1.919 mmol), 40% formaldehyde solution (576 mg, 7.676 mmol), DCE (20 mL) and glacial acetic acid (5 drops) were added to a 50 mL single neck flask, and the reaction was performed at room temperature for 1 h. Sodium triacetoxyborohyride (1.6 g, 7.676 mmol) was then added, and the reaction was continued at room temperature for 2 h. The reaction solution was filtered, and the filtrate was evaporated to dryness to afford TDI01288-2 (405 mg, black oil). MS m/z (ESI): 212.1 [M+H].

Step 2:

TDI01288-2 (400 mg, 1.896 mmol) and bis(pinacolato) diboron (963 mg, 3.791 mmol) were dissolved in dioxane (18 mL), potassium acetate (557 mg, 5.688 mmol) and Pd(dppf)Cl$_2$ (138 mg, 0.189 mmol) were added, purge with argon was performed for 3 times, and the reaction was placed in an oil bath at 100° C., and allowed to proceed for 3.5 h. After the reaction was complete, the mixture was filtered, and the filtrate was concentrated under reduced pressure. The residue was purified by column chromatography (dichloromethane:methanol=50:1-20:1) to afford TDI01288-3 (520 mg, black oil). MS m/z (ESI): 260.2 [M+H].

Step 3:

TDI01288-3 (300 mg, 1.159 mmol) and Reg-1-1 (200 mg, 0.579 mmol) were dissolved in a mixed solution of ethanol (8 mL) and water (1 mL), sodium carbonate (184 mg, 1.737 mmol) and Pd(PPh$_3$)$_2$Cl$_2$ (41 mg, 0.0579 mmol) were added, purge with argon was performed for 3 times, and the reaction was performed under microwave radiation (115° C.) for 3 h. The reaction solution was filtered, the filtrate was concentrated, and then purified by preparative thin layer chromatography (dichloromethane:methanol=5:1) to give a crude product (60 mg), which was then purified by high-performance liquid chromatography to afford compound TDI01288 (8.09 mg, yellow solid, yield: 4.04%).

$^1$H NMR (400 MHz, DMSO-d$_6$) δ 10.87 (s, 1H), 9.95 (s, 1H), 8.35 (m, 3H), 8.20 (s, 1H), 8.11 (s, 1H), 7.57 (m, 3H), 6.75 (d, 1H), 4.91 (m, 2H), 4.57 (s, 2H), 3.07 (s, 3H). MS m/z (ESI): 343.2 [M+H].

Example 26: preparation of methyl 2-(8-(4-((1H-indazol-5-yl)amino)pyrimidin-2-yl)-4-oxo-2,3,4,5-tetrahydro-1H-benzo[b][1,4]diazepin-1-yl)acetate (TDI01298)

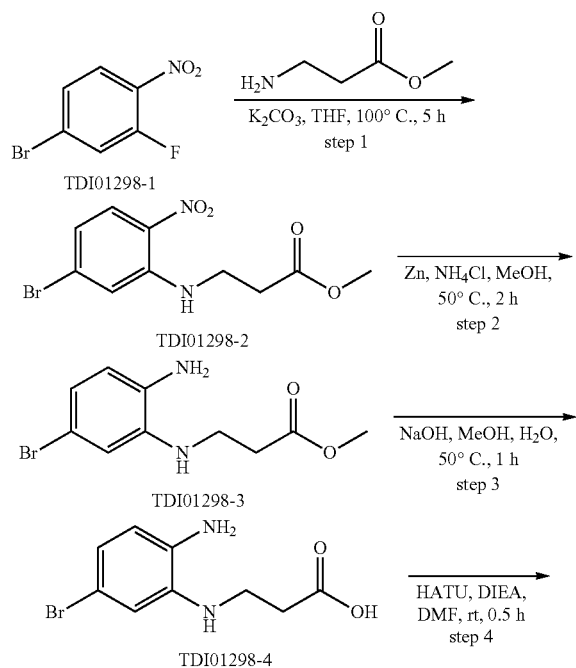

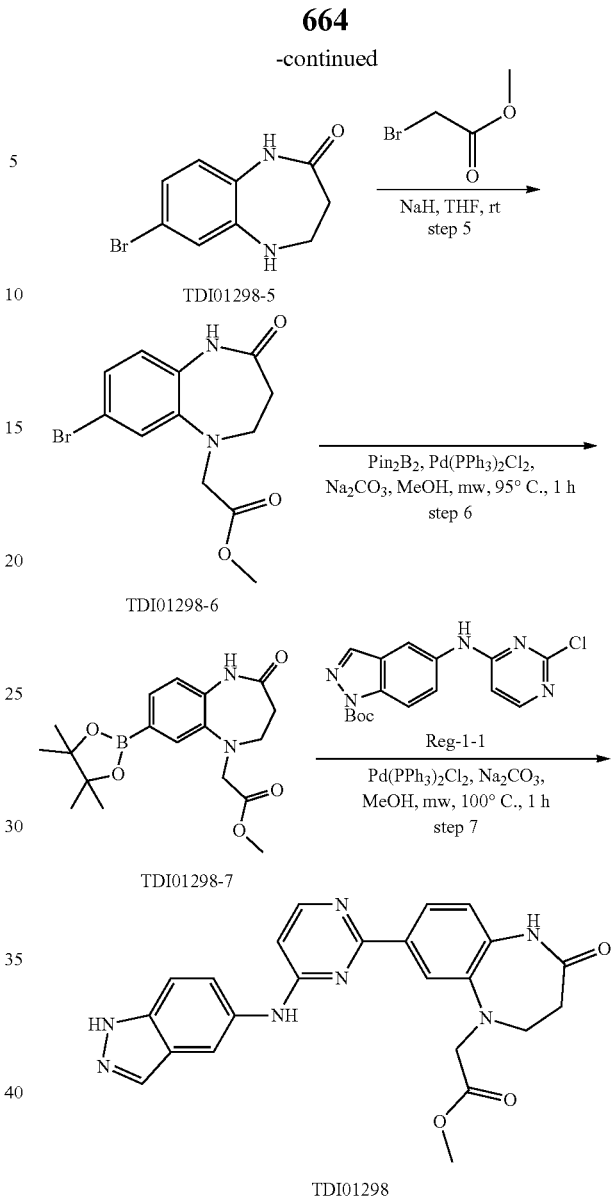

Step 1:

TDI01298-1 (6 g, 27.27 mmol), methyl 3-aminopropanoate (3.8 g, 27.27 mmol), potassium carbonate (11.29 g, 81.81 mmol) and tetrahydrofuran 60 mL were added to a 100 mL sealed tube. The reaction was warmed to 100° C., and allowed to proceed for 5 h. LC-MS indicated the reaction was complete. The reaction solution was filtered, and the filtrate was collected, and concentrated under reduced pressure to afford TDI01298-2 (8.5 g, yellow solid, yield: 100%). MS m/z (ESI): 305.1 [M+H].

Step 2:

TDI01298-2 (8.5 g, 28 mmol), zinc powder (18.2 g, 280 mmol), ammonium chloride (15 g, 280 mmol) and 260 mL methanol were added to a 500 mL flask. The reaction was warmed to 50° C., and allowed to proceed for 2 h. LC-MS indicated the reaction was complete. The reaction solution was filtered, and the filtrate was collected, and concentrated to dryness to give an oil, which was purified by column chromatography (petroleum ether:ethyl acetate=10:1-3:1), to afford TDI01298-3 (5.4 g, brown solid, yield: 70.7%).

¹H NMR (400 MHz, CDCl₃) δ 6.80-6.72 (m, 2H), 6.56 (d, J=8.1 Hz, 1H), 3.71 (s, 3H), 3.39 (t, J=6.3 Hz, 4H), 2.66 (t, J=6.3 Hz, 2H). MS m/z (ESI): 275.1 [M+H].

Step 3:

TDI01298-3 (5.0 g, 18.3 mmol), sodium hydroxide (2.2 g, 54.9 mmol), 100 mL methanol and 10 mL water were added to a 250 mL flask. The reaction was warmed to 50° C., and allowed to proceed for 1 h. LC-MS indicated the reaction was complete. The reaction solution was adjusted to pH 4-5 with concentrated hydrochloric acid, concentrated under reduced pressure to remove most of methanol, and filtered to collect the solid, so as to afford TDI01298-4 (4.4 g, brown solid, yield: 92.8%).

¹H NMR (400 MHz, DMSO-d₆) δ 6.55 (dd, J=8.1, 2.1 Hz, 1H), 6.47 (t, J=5.7 Hz, 2H), 3.23 (t, J=6.7 Hz, 2H), 2.53-2.49 (m, 2H). MS m/z (ESI): 259.1 [M+H].

Step 4:

TDI01298-4 (4 g, 15.44 mmol), HATU (7.06 g, 18.53 mmol), diisopropylethylamine (8.0 g, 61.8 mmol) and 150 mL N,N-dimethylformamide were added to a 250 mL flask, and the reaction was performed at room temperature for 0.5 h. LC-MS indicated the reaction was complete. The reaction solution was combined, added to 600 mL water, and extracted with ethyl acetate (600 mL). The organic phase was dried, concentrated under reduced pressure to give a brown red solid, which was rinsed with 10 mL ethyl acetate and 60 mL petroleum ether, to afford TDI01298-5 (3.8 g, brown solid, yield: 100%).

¹H NMR (400 MHz, DMSO-d₆) δ 9.49 (s, 1H), 6.91 (s, 1H), 6.80 (d, J=8.4 Hz, 1H), 6.73 (s, 1H), 6.01 (s, 1H), 2.71 (d, J=17.3 Hz, 1H), 2.52 (d, J=5.2 Hz, 3H). MS m/z (ESI): 241.1 [M+H].

Step 5:

Compound TDI01298-5 (800 mg, 3.32 mmol) and 40 mL tetrahydrofuran was added to a 100 mL flask. The reaction was cooled to 0=10° C., sodium hydride (146 mg, 3.65 mmol) was added, and the reaction was performed for 20 minutes. methyl 2-bromoacetate (813 mg, 5.31 mmol) was added, and the reaction was warmed to room temperature, and allowed to proceed for 0.5 h. TLC indicated the reaction was complete. The reaction solution was filtered, and the filtrate was collected, concentrated under reduced pressure to give a brown red oil, which was purified by column chromatography (petroleum ether:ethyl acetate=8:1~1:1) to afford TDI01298-6 (900 mg, brown red oil, yield: 86.5%).

¹H NMR (400 MHz, DMSO-d₆) δ 7.11 (d, J=2.1 Hz, 1H), 6.99 (dt, J=8.6, 5.3 Hz, 2H), 5.66 (s, 1H), 4.37 (s, 2H), 3.67 (s, 3H), 3.60-3.54 (m, 2H), 2.48-2.43 (m, 2H). MS m/z (ESI): 315.21 [M+H].

Step 6:

Compound TDI01298-6 (850 mg, 2.71 mmol), bis(pinacolato)diboron (826 mg, 3.25 mmol), Pd(PPh₃)₂Cl₂ (95 mg, 0.14 mmol), sodium carbonate (575 mg, 5.42 mmol) and 15 mL methanol were added to a 30 mL microwave tube. Purge with argon was performed for 4 times, the reaction was warmed to 95° C., and allowed to proceed for 1.5 h. LC-MS indicated the reaction was complete. The reaction solution was filtered, and the filtrate was concentrated under reduced pressure to give a dark brown oil, which was purified by column chromatography (petroleum ether:ethyl acetate=4:11:1) to obtain TDI01298-7 (650 mg, yellow solid, yield: 66.6%).

¹H NMR (400 MHz, DMSO-d₆) δ 7.34 (s, 1H), 7.18 (d, J=7.8 Hz, 1H), 7.07 (d, J=7.9 Hz, 1H), 5.34 (s, 1H), 4.38 (s, 2H), 3.68 (s, 3H), 3.57 (t, J=6.1 Hz, 2H), 2.41 (t, J=6.2 Hz, 2H), 1.28 (s, 12H). MS m/z (ESI): 361.3 [M+H].

Step 7:

Compound TDI01298-7 (240 mg, 0.67 mmol), Reg-1-1 (150 mg, 0.43 mmol), Pd(PPh₃)₂Cl₂ (28 mg, 0.04 mmol), sodium carbonate (92 mg, 0.86 mmol) and 12 mL methanol were added to a 30 mL microwave tube. The reaction solution was purged with argon for 1 minute, warmed to 100° C., and allowed to react under microwave radiation for 3 h. LC-MS indicated the reaction was complete. The reaction solution was filtered, and the filtrate was concentrated under reduced pressure to dryness to give a solid, which was washed with 5 mL ethyl acetate and 20 mL petroleum ether, to obtain 0.48 g solid. The solid was further purified by high-performance liquid chromatography to afford TDI01298 (62.97 mg, yellow solid, yield: 33%).

¹H NMR (400 MHz, DMSO-d₆) δ 10.48 (s, 1H), 8.32 (d, J=6.5 Hz, 1H), 8.15 (d, J=4.1 Hz, 2H), 7.85 (s, 1H), 7.76-7.72 (m, 1H), 7.61 (q, J=8.9 Hz, 2H), 7.28 (d, J=8.5 Hz, 1H), 6.80 (d, J=6.5 Hz, 1H), 4.46 (s, 2H), 3.70 (s, 3H), 3.68-3.62 (m, 4H). MS m/z (ESI): 444.3 [M+H].

Example 27: preparation of 6-(4-((1H-indazol-5-yl)amino)pyrimidin-2-yl)-N-(pyridin-2-yl)-1H-indole-2-carboxamide (TDI01311)

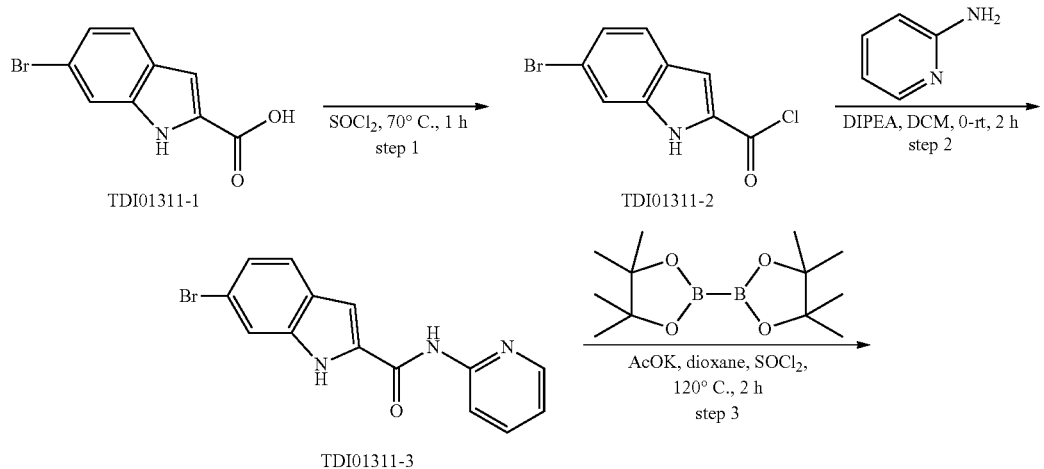

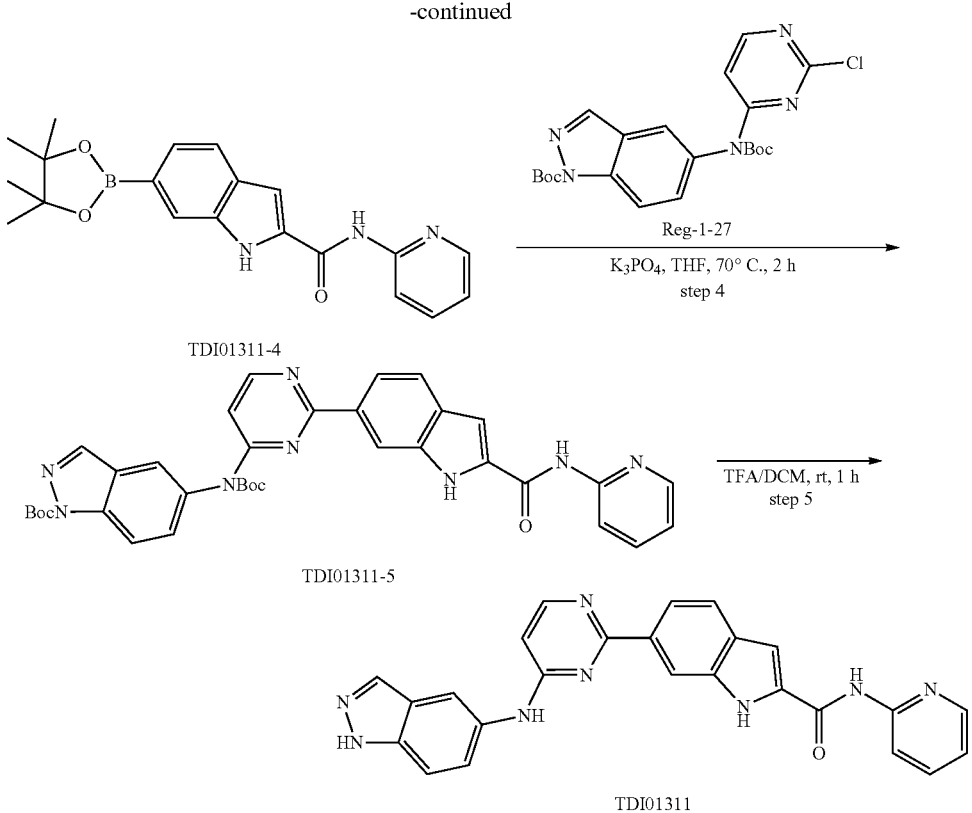

Step 1:

TDI01311-1 (2.4 g, 10 mmol) and thionyl chloride (10 mL) were sequentially added to a 25 mL flask, N,N-dimethylformamide (1 drop) was cautiously added under stirring, the reaction was warmed to 70° C. in an oil bath, and allowed to proceed for 1 h. After the reaction solution became clear, thionyl chloride was removed under reduced pressure. The residue was dissolved in dichloromethane (10 mL), and directly used in the next reaction.

Step 2:

2-aminopyridine (1.13 g, 12 mmol), diisopropylethylamine (3.88 g, 30 mmol) and dichloromethane (10 mL) were sequentially added to a 50 mL tree-neck flask, and purge with nitrogen was performed for 3 times. In an ice bath and under the protection of nitrogen, a solution of the product prepared in the last step in dichloromethane (10 mL) was cautiously added dropwise. After the dropwise addition, the reaction was stirred at 0° C. for 15 minutes, and then performed at room temperature for 2 hours after the ice bath was removed. LC-MS indicated the reaction was complete. At this point, a large amount of yellow solid precipitated, which was filtered, washed with a mixed solvent of water (20 mL) and petroleum ether:ethyl acetate (20 mL), and then washed with acetonitrile (20 mL), to afford the first batch of the product (yellow solid, 2.1 g). The filtrate was extracted with dichloromethane (60 mL), and the organic phase was successively washed with water (30 mL) and saturated brine (30 mL), dried over anhydrous sodium sulfate for half an hour, filtered, and concentrated to dryness to afford the second batch of the product (yellow product, 0.9 g). The two batches were both TDI01311-3 (3.0 g, yield: 94.9%, yellow solid). MS m/z (ESI): 316.1 [M+H].

Step 3:

TDI01311-3 (800 mg, 2.53 mmol), bis(pinacolato)diboron (964 mg, 3.80 mmol), potassium acetate (496 mg, 5.06 mmol), and dioxane (20 mL) were sequentially added to a 100 mL flask, and purge with nitrogen was performed for 3 times. Under the protection of nitrogen, Pd(dppf)Cl$_2$ (185 mg, 0.253 mmol) was cautiously added. After the addition was complete, the reaction was performed in an oil bath at 120° C. for 2 hours. After the reaction was complete, the reaction solution was cooled to room temperature, filtered to remove insoluble, and washed with ethyl acetate (10 mL×2). The filtrate was evaporated under reduced pressure to remove the solvent, and purified to afford TDI01311-4 (458 mg, yield: 50.0%).

$^1$H NMR (400 MHz, DMSO-d$_6$) δ 11.94 (s, 1H), 10.88 (s, 1H), 8.42 (d, J=3.6 Hz, 1H), 8.24 (d, J=8.4 Hz, 1H), 7.89-7.85 (m, 2H), 7.68-7.63 (m, 2H), 7.36 (d, J=8.1 Hz, 1H), 7.21-7.15 (m, 1H), 1.16 (s, 12H). MS m/z (ESI): 364.3 [M+H].

Step 4:

TDI01311-4 (200 mg, 0.449 mmol), Reg-1-27 (196 mg, 0.539 mmol), potassium phosphate (190 mg, 0.898 mmol), tetrahydrofuran (3 mL) and water (0.5 mL) were sequentially added to a 10 mL flask, purge with nitrogen was performed for 3 minutes, chloro(2-dicyclohexylphosphino-2′,4′,6′-triisopropyl-1,1′-biphenyl)[2-(2′-amino-1,1′-biphenyl)]palladium (II) (7 mg, 0.009 mmol) was cautiously added, and the reaction was performed in an oil bath at 70° C. for 2 hours. LC-MS indicated about 18% of the target product was formed. The reaction solution was cooled to room temperature, and then poured into 10 mL water. The solution was extracted with ethyl acetate (60 mL), and the organic phase was combined, washed with water (20 mL) and saturated brine (20 mL), dried over anhydrous sodium sulfate, filtered, and concentrated to give a crude product (85 mg), which was then separated by preparative thin layer chromatography to afford TDI01311-5 (25 mg, yellow solid, yield: 8.6%). MS m/z (ESI): 647.5 [M+H].

Step 5:

TDI01311-5 (20 mg, 0.03 mmol) and dichloromethane (1 mL) were sequentially added to a 10 mL flask, and trifluoroacetic acid (1 mL) was cautiously added dropwise under stirring. After the dropwise addition, the reaction was stirred at room temperature for 1 hour. LC-MS indicated the reaction was complete. The solvent was removed by evaporation under reduced pressure to afford compound TDI01311 (7.24 mg, yellow solid, yield: 41.9%).

$^1$H NMR (400 MHz, DMSO-$d_6$) δ 12.37 (s, 1H), 11.00 (s, 1H), 8.45 (s, 1H), 8.43 (d, J=3.8 Hz, 1H), 8.34 (d, J=6.7 Hz, 1H), 8.25 (d, J=8.3 Hz, 1H), 8.19 (s, 1H), 7.99 (d, J=8.7 Hz, 1H), 7.92-7.85 (m, 2H), 7.75 (d, J=1.2 Hz, 1H), 7.65 (t, J=9.5 Hz, 2H), 7.24 (s, 1H), 7.21 (dd, J=7.3, 5.5 Hz, 1H), 7.11 (s, 1H), 6.98 (s, 1H), 6.83 (d, J=6.4 Hz, 1H). MS m/z (ESI): 447.2 [M+H].

Example 28: preparation of 5-(4-((1H-indazol-5-yl)amino)pyrimidin-2-yl)-N-isopropylisoindoline-2-carboxamide (TDI01312)

saturated brine, dried over anhydrous sodium sulfate, and concentrated to afford TDI01312-2 (575 mg, brown solid, crude product).

$^1$H NMR (400 MHz, CDCl$_3$) δ 7.41 (m, 2H), 7.13 (m, 1H), 4.65 (d, 4H), 4.04 (m, 1H), 1.22 (t, 6H). MS m/z (ESI): 283.1 [M+H].

Step 2:

TDI01312-2 (300 mg, 1.064 mmol) and bis(pinacolato)diboron (405 mg, 1.596 mmol) were dissolved in dioxane (10 mL), potassium acetate (312 mg, 3.192 mmol) and Pd(dppf)Cl$_2$ (79 mg, 0.1064 mmol) were added, purge with argon was performed for 3 times, the reaction was placed in an oil bath at 100° C., and allowed to proceed for 2 h. After the reaction was complete, the reaction solution was filtered, and the filtrate was concentrated under reduced pressure to afford TDI01312-3 (400 mg, black solid, crude product). MS m/z (ESI): 331.3 [M+H].

Step 3:

Compound TDI01312-3 (400 mg, 1.212 mmol) and Reg-1-1 (279 mg, 0.808 mmol) were dissolved in a mixed solution of ethanol (8 mL) and water (1 mL), sodium carbonate (257 mg, 2.424 mmol) and Pd(PPh$_3$)$_2$Cl$_2$ (57 mg, 0.08 mmol) were added, purge with argon was performed for

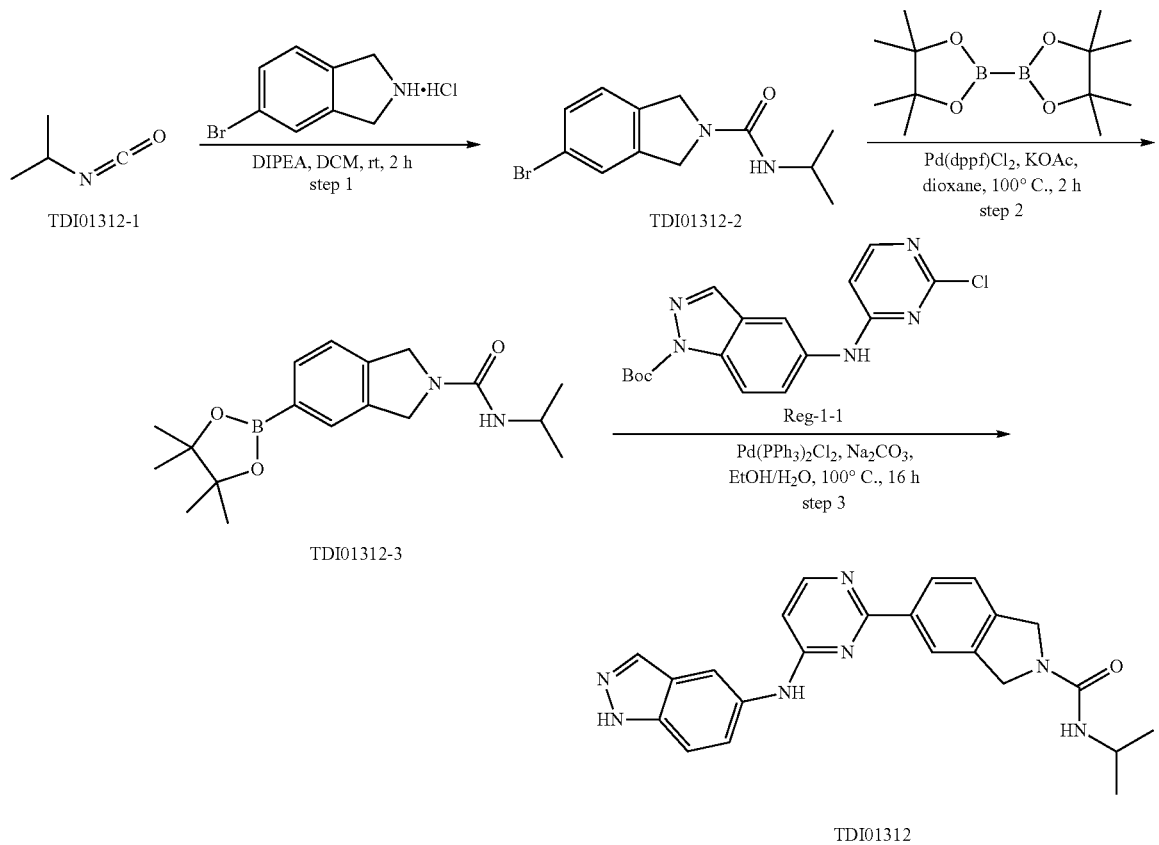

Step 1:

TDI01312-1 (150 mg, 1.765 mmol), 5-bromoisoindoline (620 mg, 2.647 mmol), diisopropylethylamine (341 mg, 2.647 mmol) and dichloromethane (9 mL) were added to a 50 mL single neck flask, and the reaction was performed at room temperature for 2 h. The reaction solution was added with 10 mL water, and extracted with dichloromethane (10 mL×2). The organic phase was combined, washed with 3 times, and the reaction was performed at 100° C. for 16 h. The reaction solution was filtered, and the filtrate was concentrated. Then the residue was purified by thin layer chromatography (dichloromethane:methanol=8:1, containing 1% aqueous ammonia), to afford a crude product (100 mg), which was then purified by high-performance liquid chromatography to afford compound TDI01312 (34.73 mg, yellow solid, yield: 10.43%).

¹H NMR (400 MHz, DMSO-d₆) δ 13.15 (s, 1H), 10.47 (s, 1H), 8.35 (d, 1H), 8.17 (dd, 4H), 7.62 (d, 1H), 7.54 (t, 2H), 6.81 (d, 1H), 6.05 (d, 1H), 4.67 (s, 4H), 3.83 (d, 1H), 1.12 (d, 6H). MS m/z (ESI): 414.2 [M+H].

The compounds in following table 6 were prepared according to methods similar to that described in Example 28.

TABLE 6

| No. | Compound Structure | Compound Name | Starting material or regent different from that in Example 28 | Characterization Data |
|---|---|---|---|---|
| TD101366 | (structure shown) | 5-(4-(4-((1H-pyrazol-4-yl)phenyl)amino)pyrimidin-2-yl)-N,N-dimethylisoindoline-2-carboxamide | in step 1 of Example 28 was replaced with (isopropyl isocyanate and dimethylcarbamoyl chloride); and in step 3 was replaced with (Boc-indazole chloropyrimidine and Boc-pyrazole-phenyl chloropyrimidine structures) | $^1$H NMR (400 MHz, CD$_3$OD) δ 8.24 (d, J = 7.2 Hz, 1H), 8.12 - 8.10 (m, 2H), 8.02 (s, 2H), 7.74 - 7.71 (m, 4H), 7.57 (d, J = 8.0 Hz, 1H), 6.94 (d, J = 7.2 Hz, 1H), 4.90 (s, 4H), 2.97 (s, 6H). MS m/z (ESI): 426.1 [M+H]. |

TABLE 6-continued

| No. | Compound Structure | Compound Name | Starting material or regent different from that in Example 28 | Characterization Data |
|---|---|---|---|---|
| TDI01375 | 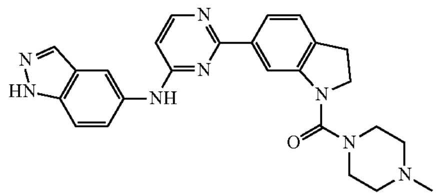 [SMILES: CN1CCN(C(=O)N2CCc3ccc(-c4nccc(Nc5ccc6[nH]ncc6c5)n4)cc32)CC1] | (6-(4-((1H-indazol-5-yl)amino)pyrimidin-2-yl)indolin-1-yl)(4-methylpiperazin-1-yl)methanone | in step 1 of Example 28 was replaced with | 1H NMR (400 MHz, DMSO-d6) δ 10.53 (s, 1H), 10.07 (s, 1H), 8.34 (d, J = 6.4 Hz, 2H), 8.20 (d, J = 9.6 Hz, 2H), 7.88 (d, J = 7.2 Hz, 1H), 7.61 (d, J = 8.8 Hz, 1H), 7.50 (d, J = 8.8 Hz, 1H), 7.43 (d, J = 7.2 Hz, 1H), 6.82 (d, J = 6.4 Hz, 1H), 4.04 (t, J = 8.8 Hz, 2H), 3.93 (d, J = 12.0 Hz, 2H), 3.46 (s, 2H), 3.18 (dd, J = 18.2, 9.6 Hz, 4H), 3.07 (s, 2H), 2.84 (s, 3H). MS m/z (ESI): 455.2 [M+H]. |
| TDI01383 | 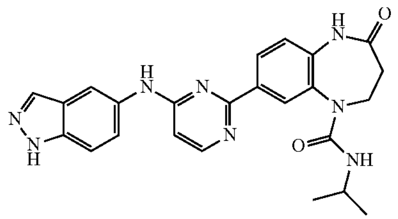 [SMILES: CC(C)NC(=O)N1CCC(=O)Nc2ccc(-c3nccc(Nc4ccc5[nH]ncc5c4)n3)cc21] | 8-(4-((1H-indazol-5-yl)amino)pyrimidin-2-yl)-N-isopropyl-4-oxo-2,3,4,5-tetrahydro-1H-benzo[b][1,4]diazepine-1-carboxamide | and in step 1 of Example 28 was replaced with in step 1 of Example 28 was replaced with | 1H NMR (400 MHz, DMSO-d6) δ 10.39 (s, 1H), 10.04 (s, 1H), 8.33 (d, J = 6.4 Hz, 1H), 8.28 - 8.19 (m, 2H), 8.15 (d, J = 8.4 Hz, 1H), 8.08 (s, 1H), 7.59 (d, J = 8.8 Hz, 1H), 7.52 (d, J = 9.3 Hz, 1H), 7.25 (d, J = 8.5 Hz, 1H), 6.78 (d, J = 6.4 Hz, 1H), 5.98 (d, J = 7.9 Hz, 1H), 3.94 (t, J = 6.5 Hz, 2H), 3.80 (s, 1H), 2.47 (d, J = 6.7 Hz, 2H), 0.97 (d, J = 6.6 Hz, 6H). MS m/z (ESI): 457.2 [M+H]. |

TABLE 6-continued

| No. | Compound Structure | Compound Name | Starting material or regent different from that in Example 28 | Characterization Data |
|---|---|---|---|---|
| TDI01411 | (structure) | 5-(4-((4-(1H-pyrazol-4-yl)phenyl)amino)pyrimidin-2-yl)-N-ethylisoindoline-2-carboxamide | (isopropyl isocyanate) in step 1 of Example 28 was replaced with (ethyl isocyanate) and (Reg-1-1); in step 3 was replaced with (Reg-1-16) | $^1$H NMR (400 MHz, DMSO-$d_6$) δ 9.99 (s, 1H), 9.59 (s, 1H), 8.37 (d, J = 6.4 Hz, 1H), 8.33 - 8.22 (m, 2H), 8.04 (s, 2H), 7.75 (d, J = 8.8 Hz, 2H), 7.65 (d, J = 8.8 Hz, 2H), 7.49 (d, J = 7.2 Hz, 1H), 6.77 (d, J = 6.4 Hz, 1H), 6.39 (s, 1H), 4.67 (d, J = 8.8 Hz, 4H), 2.77 (d, J = 4.8 Hz, 2H), 1.07 (t, J = 7.2 Hz, 3H). MS m/z (ESI): 426.5 [M+H]. |

Example 29: preparation of 2-(5-(4-((1H-indazol-5-yl)amino)thieno[3,2-d]pyrimidin-2-yl)isoindolin-2-yl)-N-isopropylacetamide (TDI01271)

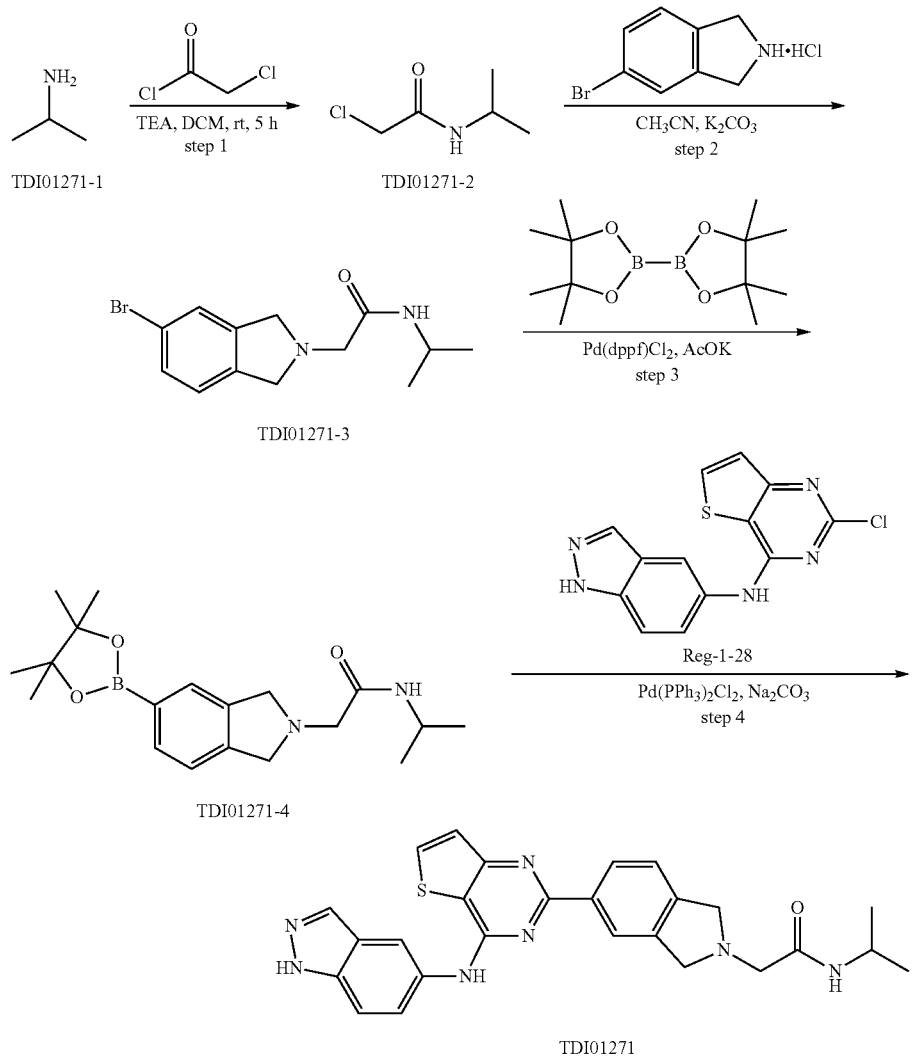

Step 1:

TDI01271-1 (1.0 g, 16.95 mmol) was dissolved in anhydrous dichloromethane (20 mL), and triethylamine (1.88 g, 18.64 mmol) and chloroacetyl chloride (2.1 g, 18.64 mmol) were slowly added dropwise. The reaction was performed at room temperature for 5 hours. LC-MS indicated the reaction was complete. The reaction solution was concentrated under reduced pressure, and the crude product was extracted with saturated dichloromethane (150 mL), and washed with saturated brine (100 mL). The organic phase was dried over anhydrous sodium sulfate, filtered, and concentrated to afford TDI01271-2 (440 mg, crude product).

$^1$H NMR (400 MHz, DMSO-$d_6$) δ 8.13 (s, 1H), 3.99 (s, 2H), 3.87-3.79 (m, 1H), 1.07 (d, J=6.4 Hz, 6H). MS m/z (ESI): 136.2 [M+H].

Step 2:

TDI01271-2 (400 mg, 2.96 mmol) and 5-bromoisoindoline hydrochloride (696.3 mg, 2.96 mmol) were dissolved in anhydrous acetonitrile (20 mL), potassium carbonate (1.7 g, 11.85 mmol) was added, and the reaction was performed at 90° C. overnight. LC-MS indicated the reaction was complete. The reaction solution was concentrated under reduced pressure, and the crude product was extracted with saturated dichloromethane (150 mL), and washed with saturated brine (150 mL). The organic phase was dried over anhydrous sodium sulfate, filtered, and concentrated to afford TDI01271-3 (400 mg, crude product).

$^1$H NMR (400 MHz, CDCl$_3$) δ 7.36 (d, J=4.0 Hz, 2H), 7.13-7.05 (m, 1H), 6.90 (s, 1H), 4.19-4.12 (m, 1H), 4.01 (s, 2H), 3.97 (s, 2H), 3.38 (s, 2H), 1.17 (d, J=6.8 Hz, 6H). MS m/z (ESI): 297.1 [M+H].

Step 3:

TDI01271-3 (400 mg, 1.347 mmol) and bis(pinacolato)diboron (648 mg, 2.694 mmol) were dissolved in 1,4-dioxane (20 mL), potassium acetate (528 mg, 5.388 mmol) and Pd(dppf)Cl$_2$ (98 mg, 0.1347 mmol) were added, purge with argon was performed for 3 times, and the reaction was placed in an oil bath at 80° C., and allowed to proceed overnight. LC-MS indicated the reaction was complete. The reaction solution was cooled to room temperature, concentrated under reduced pressure, and the residue was separated and purified by column chromatography to afford TDI01271-4 (300 mg, white solid, yield: 64.7%). MS m/z (ESI): 345.3 [M+H].

Step 4:

TDI01271-4 (274.3 mg, 0.797 mmol) and Reg-1-28 (200 mg, 0.665 mmol) were dissolved in a mixed solvent of ethanol/water (10:1) (22 mL), sodium carbonate (141 mg, 1.329 mmol) and Pd(PPh$_3$)$_2$Cl$_2$ (47 mg, 0.0665 mmol) were added, purge with argon was performed for 3 times, and the reaction was placed in an oil bath at 110° C., and allowed to proceed overnight. LC-MS indicated the reaction was complete. The reaction solution was concentrated under reduced pressure, and the crude product was purified by high-performance liquid chromatography to afford compound TDI01271 (40.0 mg, yellow solid, yield: 10.4%).

$^1$H NMR (400 MHz, DMSO-d$_6$) δ 13.13 (s, 1H), 11.03 (s, 1H), 9.92 (s, 1H), 8.45 (d, J=7.2 Hz, 1H), 8.39 (d, J=5.6 Hz, 2H), 8.22 (d, J=5.6 Hz, 1H), 8.14 (d, J=9.2 Hz, 2H), 7.69 (d, J=8.8 Hz, 1H), 7.62 (d, J=8.8 Hz, 1H), 7.53 (d, J=8.4 Hz, 1H), 7.50 (d, J=5.6 Hz, 1H), 4.92 (s, 2H), 4.63 (s, 2H), 4.23 (s, 2H), 3.99-3.90 (m, 1H), 1.13 (d, J=6.8 Hz, 6H). MS m/z (ESI): 484.2 [M+H].

Example 30: preparation of 2-(6-(4-((1H-indazol-5-yl)amino)pyrimidin-2-yl)-1H-indol-1-yl)-N-isopropylacetamide (TDI01286)

Step 1:

TDI01286-1 (1.0 g, 16.95 mmol) was dissolved in anhydrous dichloromethane (20 mL), and triethylamine (1.88 g, 18.64 mmol) and chloroacetyl chloride (2.1 g, 18.64 mmol) were slowly added dropwise. The reaction was performed at room temperature for 5 hours. LC-MS indicated the reaction was complete. The reaction solution was concentrated under reduced pressure, and the crude product was extracted with saturated dichloromethane (150 mL), and washed with saturated brine (100 mL) successively. The organic phase was dried over anhydrous sodium sulfate, filtered, and concentrated to afford TDI01286-2 (800 mg, crude product). MS m/z (ESI): 136.2 [M+H].

Step 2:

5-bromo-1H-indole (700 mg, 3.57 mmol) was dissolved in anhydrous DMF (10 mL), NaH (60%, 429 mg, 10.71 mmol) was added at 0° C., the reaction solution was slowly warmed to room temperature, and allowed to proceed overnight. Then TDI01286-2 (579 mg, 4.29 mmol) was added at room temperature, and the reaction was further stirred for 3 hours at room temperature. LC-MS indicated the reaction was complete. The reaction solution was slowly added to 100 mL water, and stirred at room temperature for 30 min. A large amount of solid precipitated, and was filtered by

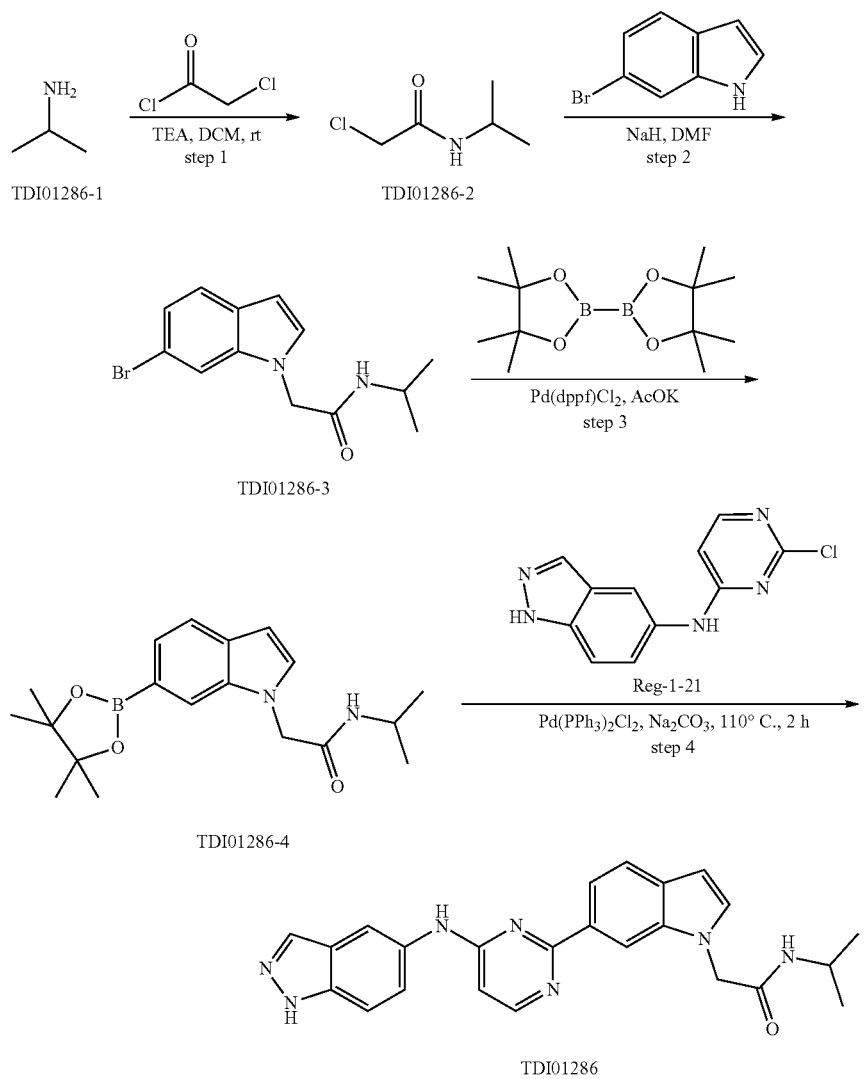

suction. The filter cake was washed, collected and dried to afford TDI01286-3 (800 mg, crude product).

$^1$H NMR (400 MHz, DMSO-d$_6$) δ 8.17 (d, J=7.2 Hz, 1H), 7.61 (s, 1H), 7.50 (d, J=8.4 Hz, 1H), 7.33 (d, J=3.2 Hz, 1H), 7.15 (d, J=8.4 Hz, 1H), 6.46 (d, J=2.8 Hz, 1H), 4.77 (s, 2H), 3.88-3.80 (m, 1H), 1.09 (d, J=6.4 Hz, 6H). MS m/z (ESI): 297.2 [M+H].

Step 3:

TDI01286-3 (500 mg, 1.695 mmol) and bis(pinacolato)diboron (861 mg, 3.390 mmol) were dissolved in dioxane (20 mL), potassium acetate (664.4 mg, 6.780 mmol) and Pd(dppf)Cl$_2$ (124 mg, 0.1695 mmol) were added, purge with argon was performed for 3 times, the reaction was placed in an oil bath at 80° C., and allowed to proceed overnight. Thin layer chromatography indicated the reaction was complete. The reaction solution was cooled to room temperature, concentrated under reduced pressure, and the residue was separated and purified by column chromatography to afford TDI01286-4 (400 mg, yellow solid, yield: 69%). MS m/z (ESI): 343.3 [M+H].

Step 4:

Reg-1-21 (300 mg, 0.87 mmol) and TDI01286-4 (357 mg, 1.04 mmol) were dissolved in a mixture of ethanol/water (10:1)(15 mL), sodium carbonate (184 mg, 1.74 mmol) and Pd(PPh$_3$)$_2$Cl$_2$ (61.0 mg, 0.087 mmol) were added, purge with argon was performed for 3 times, and the reaction was performed under microwave radiation at 110° C. for 2 hours. LC-MS indicated the reaction was complete. The reaction solution was cooled to room temperature, filtered, concentrated under reduced pressure, and the residue was purified by liquid chromatography to afford compound TDI01286 (30 mg, yellow solid, yield: 8.1%).

$^1$H NMR (400 MHz, CD$_3$OD) δ 8.46 (s, 1H), 8.30 (d, J=6.0 Hz, 2H), 8.16 (d, J=8.4 Hz, 1H), 8.10 (s, 1H), 7.67-7.58 (m, 3H), 7.39 (d, J=3.2 Hz, 1H), 6.63 (d, J=6.0 Hz, 1H), 6.54 (d, J=3.2 Hz, 1H), 4.89 (s, 2H), 3.97-3.90 (m, 1H), 1.10 (d, J=6.4 Hz, 6H). MS m/z (ESI): 426.4 [M+H].

The compound in following table 7 was prepared according to a method similar to that described in Example 30.

TABLE 7

| No. | Compound Structure | Compound Name | Starting material or regent different from that in Example 30 | Characterization Data |
|---|---|---|---|---|
| TDI01358 | | 2-(8-(4-((1H-indazol-5-yl)amino)pyrimidin-2-yl)-4-oxo-2,3,4,5-tetrahydro-1H-benzo[b][1,4]diazepin-1-yl)-N-isopropylacetamide | 6-bromo-1H-indole in synthesis step 2 of Example 30 was replaced with | $^1$H NMR (400 MHz. DMSO-d$_6$) δ 10.65 (s. 1H). 8.34 (d. .7=6.6 Hz. 1H). 8.15 (d. .7 =8.0 Hz, 2H). 7.91 (dd. J = 10.8. 4.7 Hz. 2H), 7.83 (dd. J = 8.4. 1.8 Hz. 1H). 7.62 (dd. J = 19.5, 8.9 Hz. 2H). 7.44 (d.J=8.4 Hz. 1H). 6.84 (d. .7=6.6 Hz. 1H). 4.28 (s. 2H). 3.82 (d. .7 = 7.0 Hz. 1H). 3.66 (t. J = 6.4 Hz. 2H). 2.47 (d. .7= 6.5 Hz, 2H). 1.03 (d. 7=6.6 Hz, 6H). MS m/z (ESI): 471.3 [M+H], |

Example 31: preparation of 1-(6-(4-((1H-indazol-5-yl)amino)pyrimidin-2-yl)indolin-1-yl)-2-(4-methylpiperazin-1-yl)ethanone (TDI01326)

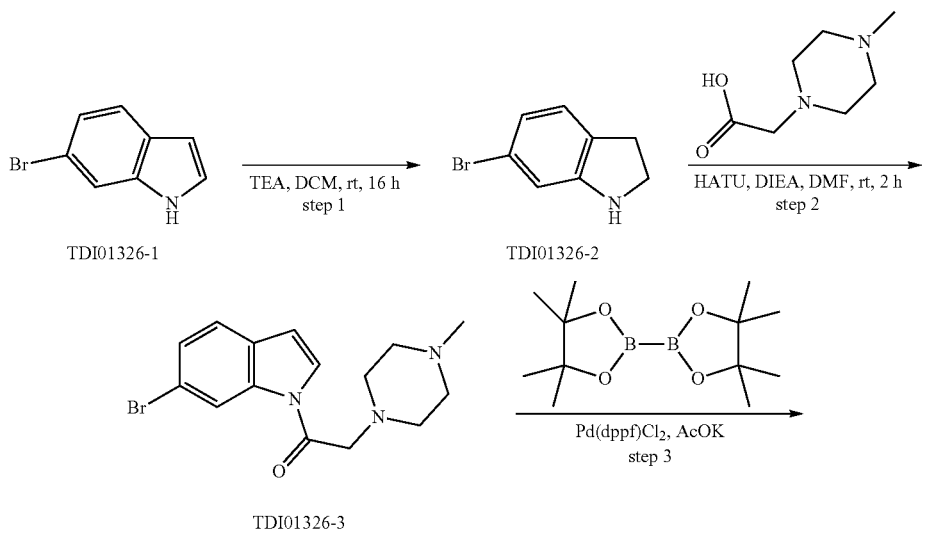

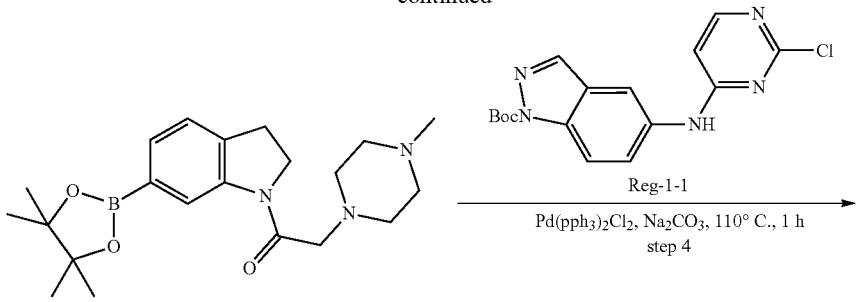

Step 1:

TDI01326-1 (5.0 g, 25.64 mmol) was dissolved in dichloromethane (400 mL), trifluoroacetic acid (27.5 mL) was added, and then triethylsilane (10.5 mL, 64.1 mmol) was added. The reaction was performed at room temperature for 16 hours. Thin layer chromatography indicated the reaction was complete. The reaction system was slowly added with aqueous ammonia to adjust the pH to about 9, followed by supplementary addition of dichloromethane (200 mL), and was successively washed with water (750 mL) and saturated brine (250 mL). The organic phase was dried over anhydrous sodium sulfate, concentrated under reduced pressure, and the residue was separated and purified by column chromatography to afford TDI01326-2 (3.6 g, light yellow oil).

$^1$H NMR (400 MHz, CDCl$_3$) δ 6.93 (d, J=7.6 Hz, 1H), 6.78 (dd, J=7.6, 1.6 Hz, 1H), 6.73 (d, J=1.6 Hz, 1H), 3.56 (t, J=8.4 Hz, 2H), 2.96 (t, J=8.4 Hz, 2H). MS m/z (ESI): 200.1 [M+H].

Step 2:

TDI01326-2 (2.6 g, 13.2 mmol) was dissolved in N,N-dimethylformamide (100 mL), HATU (5.03 g, 13.2 mmol) and diisopropylethylamine (5.68 g, 44 mmol) were added. After stir of 30 minutes, 2-(4-methylpiperazin-1-yl)acetic acid (1.74 g, 11 mmol) was added, and the reaction was performed at room temperature for 2 hours. LC-MS indicated the reaction was complete. The reaction solution was dissolved in ethyl acetate (500 mL), and successively washed with water (500 mL) and saturated brine (250 mL). The organic phase was dried over anhydrous sodium sulfate, and concentrated under reduced pressure to afford TDI01326-3 (3.1 g, light yellow oil).

$^1$H NMR (400 MHz, DMSO-d$_6$) δ 7.96 (s, 2H), 7.20-7.17 (m, 1H), 2.90 (s, 6H), 2.74 (s, 6H), 2.69 (s, 5H). MS m/z (ESI): 338.3 [M+H].

Step 3:

TDI01326-3 (3.0 g, 8.90 mmol) and bis(pinacolato)diboron (3.4 g, 13.35 mmol) were dissolved in dioxane (100 mL), potassium acetate (2.62 g, 26.7 mmol) and Pd(dppf)Cl$_2$ (312 mg, 0.45 mmol) were added, purge with argon was performed for 3 times, the reaction was placed in an oil bath at 80° C., and allowed to proceed overnight. Thin layer chromatography indicated the reaction was complete. The reaction solution was cooled to room temperature, concentrated under reduced pressure, and the residue was purified by column chromatography to afford TDI01326-4 (2.0 g, brown yellow oil).

$^1$H NMR (400 MHz, CDCl$_3$) δ 8.61 (s, 1H), 7.49 (d, J=7.2 Hz, 1H), 7.20 (d, J=7.2 Hz, 1H), 4.08 (t, 1=8.0 Hz, 2H), 3.31 (s, 2H), 3.19 (t, 1=8.0 Hz, 2H), 2.81 (br.s, 5H), 2.47 (br.s, 3H), 2.03 (s, 3H), 1.32 (s, 12H).

Step 4:

TDI01326-4 (134 mg, 0.35 mmol) and Reg-1-1 (100 mg, 0.29 mmol) were dissolved in a mixed solution of ethanol/water (8:1) (2.7 mL), sodium carbonate (61.5 mg, 0.58 mmol) and Pd(PPh$_3$)$_2$Cl$_2$ (21.1 mg, 0.03 mmol) were added, purge with argon was performed for 3 times, and the reaction was performed under microwave radiation at 110° C. for 1 hour. LC-MS indicated the reaction was complete. The reaction solution was cooled to room temperature, concentrated under reduced pressure, and the residue was purified by high-performance liquid chromatography to afford compound TDI01326 (5.18 mg, yellow solid, yield: 3.8%).

$^1$H NMR (400 MHz, DMSO-d$_6$) δ 9.21 (s, 1H), 8.76 (s, 1H), 8.45 (s, 1H), 8.20 (d, J=7.2 Hz, 1H), 7.85 (d, J=7.6 Hz, 1H), 7.66 (d, 1=8.8 Hz, 1H), 7.51 (d, J=8.0 Hz, 2H), 6.94 (s, 1H), 4.24 (t, J=8.4 Hz, 2H), 3.67 (s, 2H), 3.50-3.48 (m, 4H), 3.37 (t, J=8.4 Hz, 2H), 3.16-3.02 (m, 4H), 2.96 (s, 3H). MS m/z (ESI): 469.3 [M+H].

Example 32: preparation of N-(2-(2,3,4,5-tetrahydrobenzo[b][1,4]oxazepin-7-yl)pyrimidin-4-yl)-1H-indazol-5-amine (TDI01264)

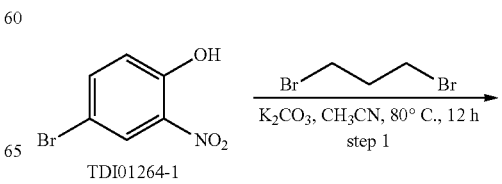

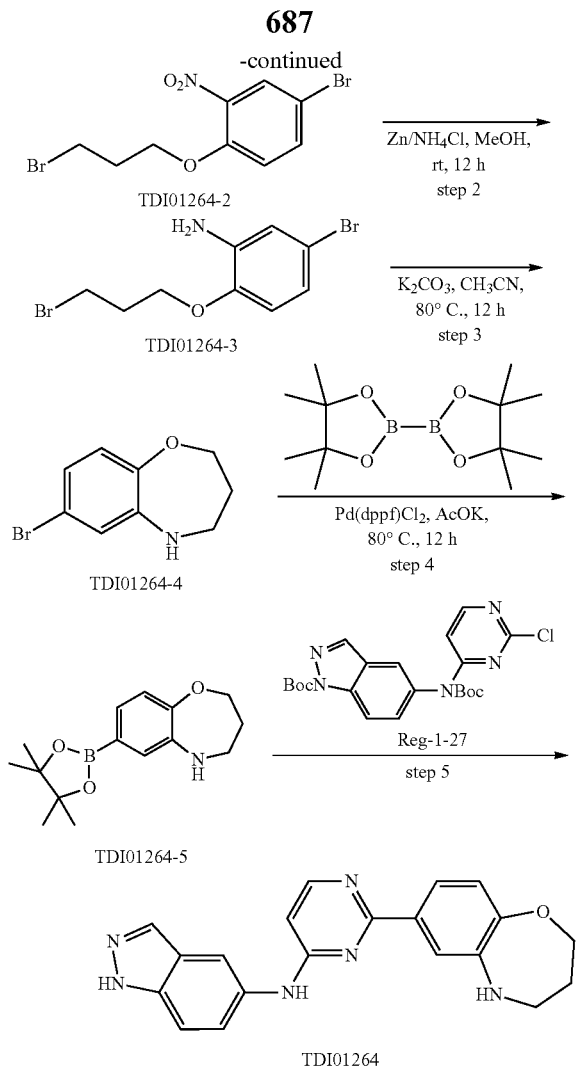

Step 1:
TDI01264-1 (3.0 g, 1.38 mmol) and 1,3-dibromopropane (8.35 g, 4.14 mmol) were dissolved in acetonitrile (100 mL), potassium carbonate (6.09 g, 4.14 mmol) was added, the reaction was placed in an oil bath at 80° C., and allowed to proceed for 12 h. LC-MS indicated the reaction was complete. The reaction solution was cooled to room temperature, filtered, concentrated under reduced pressure, and the residue was separated and purified by column chromatography to afford TDI01264-2 (3.2 g, brick red oil, 68.6%).

$^1$H NMR (400 MHz, CDCl$_3$) δ 7.98 (t, J=6.1 Hz, 1H), 7.64 (dd, J=8.9, 2.5 Hz, 1H), 7.01 (d, J=8.9 Hz, 1H), 4.25 (t, J=5.7 Hz, 2H), 3.65 (t, J=6.2 Hz, 2H), 2.48-2.27 (m, 2H).

Step 2:
TDI01264-2 (2.9 g, 8.56 mmol) was dissolved in methanol (100 mL), ammonium chloride (9.15 g, 171.10 mmol) was added, and then zinc powder (5.59 g, 85.6 mmol) was added in portions. The reaction was performed at ambient temperature for 12 h. LC-MS indicated the reaction was complete. The reaction solution was filtered, and concentrated under reduced pressure to give a crude product, which was separated by medium pressure preparative column chromatography to afford TDI01264-3 (0.9 g, brown solid, yield: 34.05%).

$^1$H NMR (400 MHz, CD$_3$OD) δ 7.54 (dd, J=8.9, 2.4 Hz, 1H), 7.50-7.46 (m, 1H), 7.04 (dt, J=11.0, 5.5 Hz, 1H), 4.10 (s, 2H), 3.46 (dd, J=13.7, 6.6 Hz, 2H), 2.23-2.12 (m, 2H). MS m/z (ESI): 307.9; 309.9 [M+H].

Step 3:
TDI01264-3 (0.7 g, 2.27 mmol) was dissolved in acetonitrile (100 mL), potassium carbonate (0.626 g, 4.53 mmol) was added, the reaction was placed in an oil bath at 80° C., and allowed to proceed for 12 h. LC-MS indicated the reaction was complete. The reaction solution was cooled to room temperature, filtered, concentrated under reduced pressure, and the residue was purified by column chromatography to afford TDI01264-4 (0.3 g, brown solid, yield: 58.06%).

$^1$H NMR (400 MHz, CD$_3$OD) δ 7.10 (d, J=2.3 Hz, 1H), 6.96 (dd, J=8.5, 2.4 Hz, 1H), 6.85 (d, 1=8.5 Hz, 1H), 4.07-4.00 (m, 2H), 3.25-3.16 (m, 2H), 2.05-1.99 (m, 2H). MS m/z (ESI): 228.0 [M+H].

Step 4:
TDI01264-4 (0.27 g, 1.18 mmol) and bis(pinacolato)diboron (0.599 g, 2.36 mmol) were dissolved in dioxane (30 mL), potassium acetate (0.347 g, 3.54 mmol) and Pd(dppf)Cl$_2$ (48 mg, 0.059 mmol) were added, purge with argon was performed for 3 times, the reaction was placed in an oil bath at 80° C., and allowed to proceed for 12 h. LC-MS indicated the reaction was complete. The reaction solution was cooled to room temperature, concentrated under reduced pressure, and the residue was separated and purified by column chromatography to afford TDI01264-5 (0.2 g, brown solid, yield: 61.40%). MS m/z (ESI): 276.2 [M+H].

Step 5:
TDI01264-5 (160 mg, 0.581 mmol) and Reg-1-27 (0.20 g, 0.465 mmol) were dissolved in a mixed solution of ethanol/water (10:1) (11 mL), sodium carbonate (0.18 g, 11.74 mmol) and Pd(PPh$_3$)$_2$Cl$_2$ (20.39 mg, 0.029 mmol) were added, purge with argon was performed for 3 times, the reaction was performed under microwave radiation at 110° C. for 2 h. LC-MS indicated the reaction was complete. The reaction solution was cooled to room temperature, filtered, concentrated under reduced pressure, and the crude product was separated by preparative liquid chromatography to afford TDI01264 (13.69 mg; yellow solid, yield: 6.57%).

$^1$H NMR (400 MHz, CD$_3$OD) δ 8.14 (d, J=6.7 Hz, 2H), 7.68 (d, J=8.3 Hz, 2H), 7.59 (s, 1H), 7.50 (d, J=8.2 Hz, 1H), 7.06 (d, J=8.4 Hz, 1H), 6.84 (s, 1H), 4.28-4.12 (m, 2H), 3.28 (s, 2H), 2.09-1.96 (m, 2H). MS m/z (ESI): 359.2 [M+H].

Example 33: preparation of 7-(4-((1H-indazol-5-yl)amino)pyrimidin-2-yl)-1,3,4,5-tetrahydro-2H-benzo[b][1,4]diazepin-2-one (TDI01265)

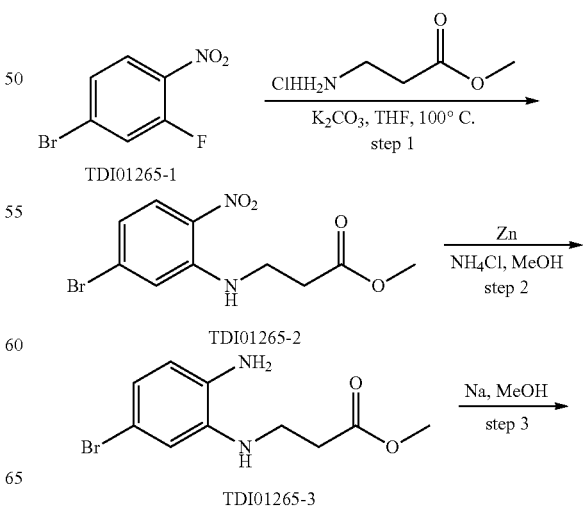

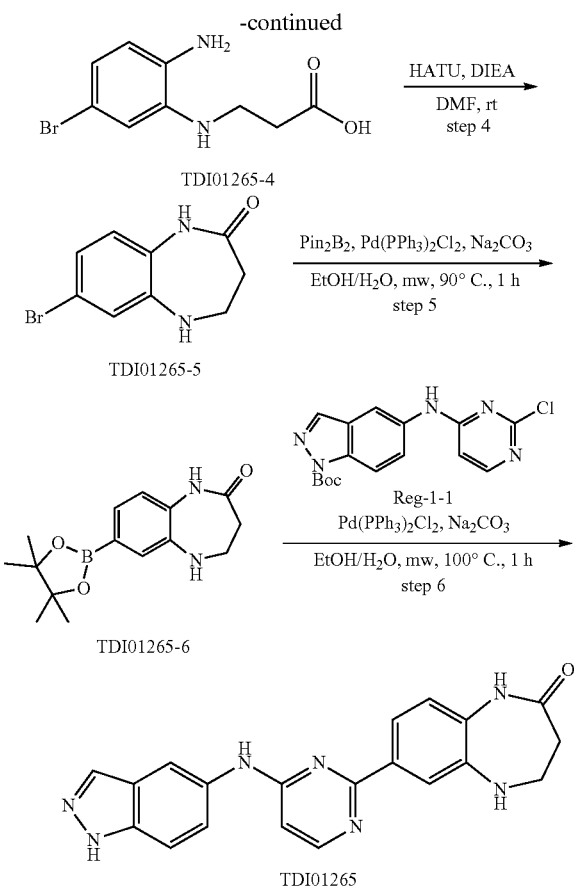

Step 1:

Compound TDI01265-1 (2 g, 9.1 mmol), methyl 3-aminopropanoate hydrochloride (1.27 g, 9.1 mmol), potassium carbonate (3.8 g, 27.3 mmol) and tetrahydrofuran (30 mL) were added to a 50 mL sealed tube. The reaction was warmed to 100° C. for 4.5 h. LC-MS indicated the reaction was complete. The reaction solution was filtered, and the filtrate was collected, and concentrated under reduced pressure to give a solid, which was purified by column chromatography (petroleum ether:ethyl acetate=20:1-8:1) to afford TDI01265-2 (1.8 g, yellow solid, yield: 65.2%).

$^1$H NMR (400 MHz, CDCl$_3$) δ 8.21 (s, 1H), 8.04 (d, J=9.1 Hz, 1H), 7.04 (d, J=1.8 Hz, 1H), 6.79 (dd, J=9.1, 1.9 Hz, 1H), 3.75 (s, 3H), 3.62 (dd, J=12.4, 6.5 Hz, 2H), 2.73 (t, J=6.6 Hz, 2H). MS m/z (ESI): 305.1 [M+H].

Step 2:

Compound TDI01265-2 (1.3 g, 4.29 mmol), zinc powder (2.79 g, 42.9 mmol), ammonium chloride (2.30 g, 42.9 mmol) and 50 mL methanol were added to a 100 mL flask, and the reaction was warmed to 50° C., and allowed to proceed for 2 h. LC-MS indicated the reaction was complete. The reaction solution was filtered, and the filtrate was collected, concentrated to dryness to give an oil, which was purified by column chromatography (petroleum ether:ethyl acetate=10:1-4:1) to afford TDI01265-3 (1 g, brown red oil, yield: 85.5%).

$^1$H NMR (400 MHz, CDCl$_3$) δ 6.80-6.71 (m, 2H), 6.55 (d, J=8.1 Hz, 1H), 3.71 (s, 3H), 3.39 (t, J=6.3 Hz, 2H), 2.65 (t, J=6.3 Hz, 2H). MS m/z (ESI): 275.1 [M+H].

Step 3:

15 mL methanol was added to a 100 mL flask, and cooled to 0° C. Sodium metal (0.25 g, 10.99 mmol) was added in portions, and the solid completely dissolve. TDI01265-3 (1.0 g, 3.66 mmol) and 15 mL methanol were added to another 100 mL flask, cooled to 0° C., and the freshly prepared solution of sodium methoxide was added dropwise. After the addition, the reaction was performed at room temperature overnight, and then warmed to 60° C., and allowed to proceed for 2 h. LC-MS indicated the reaction was complete. The reaction solution was cooled to 0-10° C., the pH was adjusted to 6 with a hydrochloride methanol solution. The reaction solution was concentrated under reduced pressure followed by addition of 20 mL anhydrous ethanol, and the solution was filtered to collect the filtrate, which was concentrated under reduced pressure to afford TDI01265-4 (0.98 g, brown red solid, yield: 100%). MS m/z (ESI): 259.0[M+H].

Step 4:

Compound TDI01265-4 (500 mg, 1.92 mmol), HATU (880 mg, 2.30 mmol), diisopropylethylamine (990 mg, 7.68 mmol) and 100 mL N,N-dimethylformamide were added to a 250 mL flask, and the reaction was performed at room temperature for 10 minutes. LC-MS indicated the reaction was complete. The reaction solution was added to 500 mL water, extracted with ethyl acetate (200 mL×2), and the organic phase was dried, and concentrated under reduced pressure to give a brown yellow oil, which was purified by column chromatography (petroleum ether:ethyl acetate=5:1-1:2) to afford TDI01265-5 (250 mg, brown red solid, yield: 53.9%).

$^1$H NMR (400 MHz, CDCl$_3$) δ 8.09 (s, 1H), 6.88 (d, J=6.9 Hz, 2H), 6.74 (d, J=8.3 Hz, 1H), 3.91 (s, 1H), 3.65 (d, J=1.5 Hz, 2H), 2.76-2.69 (m, 2H). MS m/z (ESI): 241.1 [M+H].

Step 5:

Compound TDI01265-5 (150 mg, 0.62 mmol), bis(pinacolato)diboron (190 mg, 0.75 mmol), Pd(PPh$_3$)$_2$Cl$_2$ (42 mg, 0.06 mmol), Na$_2$CO$_3$ (131 mg, 1.24 mmol), 10 mL ethanol and 2 mL water were added to a 25 mL flask, purge with argon was performed for 4 times, and the reaction was warmed to 100° C., and allowed to proceed for 2 h. LC-MS indicated the reaction was complete. The reaction solution was filtered, and the filtrate was concentrated under reduced pressure to give a solid, which was purified by column chromatography (petroleum ether:ethyl acetate=10:1-1:2) to afford TDI01265-6 (100 mg, off-white solid, yield: 56%).

$^1$H NMR (400 MHz, DMSO-d$_6$) δ 9.54 (s, 1H), 7.16 (s, 1H), 6.93 (d, J=7.9 Hz, 1H), 6.87 (d, J=7.8 Hz, 1H), 5.71 (s, 1H), 3.40 (d, J=5.7 Hz, 2H), 2.49-2.47 (m, 2H), 1.26 (s, 12H). MS m/z (ESI): 289.2 [M+H].

Step 6:

Compound TDI01265-6 (70 mg, 0.24 mmol), Reg-1-1 (70 mg, 0.20 mmol), Pd(PPh$_3$)$_2$Cl$_2$ (14 mg, 0.02 mmol), sodium carbonate (42 mg, 0.40 mmol), 15 mL ethanol and 2 mL water were added to a 30 mL microwave tube, the system was purged with argon for 1 minute, the reaction was warmed to 95° C., and performed under microwave radiation for 1 h, LC-MS indicated the reaction was complete. The reaction solution was filtered, and the filtrate was concentrated under reduced pressure to give a solid, which was purified by high-performance liquid chromatography to afford TDI01265 (8.95 mg, yellow solid, yield: 12%).

$^1$H NMR (400 MHz, DMSO-d$_6$) δ 12.99 (s, 1H), 9.57 (d, J=37.4 Hz, 2H), 8.28 (d, J=5.3 Hz, 1H), 8.13 (d, J=31.2 Hz, 2H), 7.82 (s, 1H), 7.64-7.54 (m, 3H), 6.99 (d, J=8.0 Hz, 1H), 6.62 (d, J=5.7 Hz, 1H), 5.94 (s, 1H), 3.47 (s, 2H), 2.57 (s, 2H). MS m/z (ESI): 372.3 [M+H].

Example 34: preparation of (6-(4-((4-(1H-pyrazol-4-yl)phenyl)amino)pyrimidin-2-yl)-1-methyl-1H-indol-2-yl)(3,3-difluoroazetidin-1-yl)methanone (TDI01470)

sulfate, filtered, and concentrated to afford compound TDI01470-2 (21 g, brown solid, yield: 94.01%). MS m/z (ESI): 266.1; 268.1 [M−H].

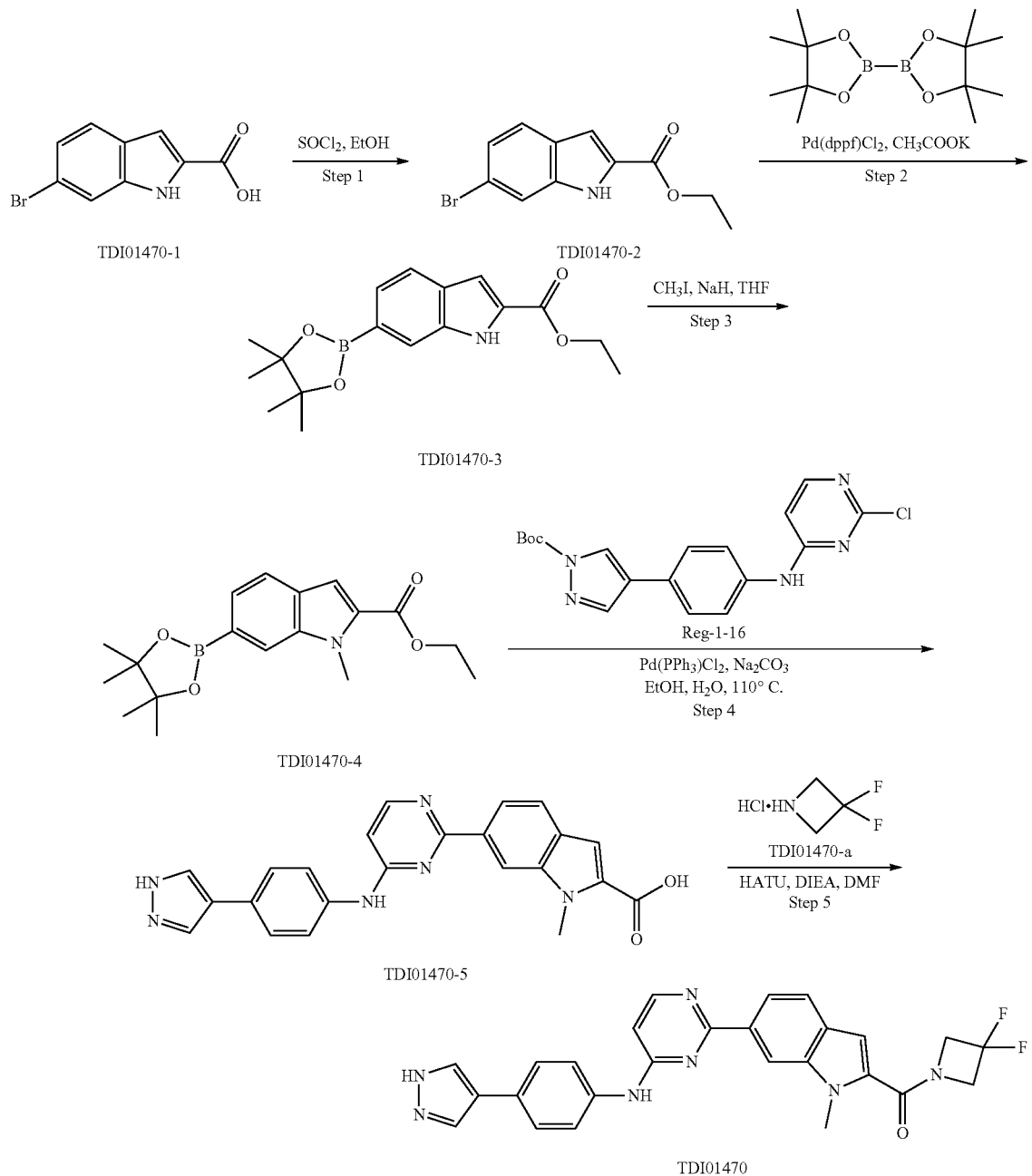

Step 1:

Compound TDI01470-1 (20 g, 83.31 mmol) and ethanol (200 mL) were added to a 500 mL flask, thionyl chloride (19.82 g, 166.63 mmol) was added, and then the reaction was performed at 60° C. for 3 hours. Thin layer chromatography (petroleum ether/ethyl acetate=10:1) assay indicated the reaction was complete. The reaction solution was concentrated to afford a crude product, which was dissolved in dichloromethane (500 mL), and the resulting solution was washed twice with a saturated aqueous solution of sodium bicarbonate (150 mL each). The organic phase was washed with saturated brine, then dried over anhydrous sodium Step 2:

Compound TDI01470-2 (21 g, 78.33 mmol) and bis(pinacolato)diboron (26.85 g, 105.74 mmol) were dissolved in 1,4-dioxane (200 mL), potassium acetate (23.06 g, 234.98 mmol) and Pd(dppf)Cl₂ (3.24 g, 3.91 mmol) were added, purge with argon was performed for 3 times, and the reaction was placed in an oil bath at 80° C. overnight. LC-MS indicated the reaction was complete. The reaction solution was cooled to room temperature, concentrated under reduced pressure, and the residue was purified by column chromatography (petroleum ether/ethyl acetate=100:1 to 5:1) to afford compound TDI01470-3 (17.5 g, white solid, yield: 70.89%).

$^1$H NMR (400 MHz, CDCl$_3$) δ 8.92 (s, 1H), 7.92 (s, 1H), 7.69 (d, J=8.1 Hz, 1H), 7.57 (d, J=8.1 Hz, 1H), 7.22-7.18 (m, 1H), 4.42 (q, J=7.1 Hz, 2H), 1.42 (t, J=7.1 Hz, 3H), 1.37 (s, 12H). MS m/z (ESI): 316.2 [M+H].

Step 3:

Compound TDI01470-3 (10.0 g, 31.8 mmol) was dissolved in tetrahydrofuran (250 mL), sodium hydride (1.91 g, 47.8 mmol) was added under ice bath cooling, and then the reaction was performed for 30 minutes. Iodomethane (13.5 g, 95.4 mmol) was slowly added to the reaction solution, and the reaction was performed at room temperature overnight. Thin layer chromatography (petroleum ether/ethyl acetate=5:1) indicated the reaction was complete. The reaction solution was quenched with water (100 mL), and extracted with ethyl acetate (150 mL×2). The combined organic phases were washed sequentially with a saturated aqueous solution of ammonium chloride (200 mL×2) and saturated brine (300 mL×2), dried over anhydrous sodium sulfate, filtered, and concentrated. The crude product was separated and purified by column chromatography (petroleum ether/ethyl acetate=15:1) to afford compound TDI01470-4 (6.5 g, yellow solid, yield: 62.5%).

$^1$H NMR (400 MHz, CDCl$_3$) δ 7.91 (s, 1H), 7.68-7.65 (m, 1H), 7.57 (d, J=8.0 Hz, 1H), 7.27 (s, 1H), 4.12 (s, 3H), 3.91 (s, 3H), 1.38 (s, 12H).

Step 4:

Compound Reg-1-16 (1.00 g, 2.70 mmol) and TDI01470-4 (1.33 g, 4.04 mmol) were dissolved in a mixed solution of ethanol/water (8:1) (120 mL), sodium carbonate (572 mg, 5.40 mmol) and Pd(PPh$_3$)Cl$_2$ (189 mg, 0.27 mmol) were added, purge with argon was performed for 3 times, and the reaction was placed in an oil bath at 110° C. overnight. LC-MS indicated the reaction was complete. The reaction solution was cooled to room temperature, and concentrated under reduced pressure. The residue was diluted with water (30 mL), and the pH was adjusted to 1 with 6N HCl. A large amount of solid precipitated, and was filtered. The solide was wahsed with methanol to afford compound TDI01470-5 (900 mg, yellow solid, crude product).

$^1$H NMR (400 MHz, DMSO-d$_6$) δ 11.54 (s, 1H), 8.77 (s, 1H), 8.38 (d, J=7.2 Hz, 1H), 8.14 (s, 2H), 8.03 (d, J=8.8 Hz, 1H), 7.92 (d, J=8.4 Hz, 1H), 7.80-7.69 (m, 4H), 7.33 (s, 1H), 7.07 (d, J=8.0 Hz, 1H), 4.16 (s, 3H).

Step 5:

Compound TDI01470-5 (300 mg, 0.73 mmol) was dissolved in N,N-dimethylformamide (6 mL), HATU (335 mg, 0.88 mmol) and DIEA (377 mg, 2.92 mmol) were added, and the reaction was performed at room temperature for 30 min. Then, compound TDI01470-a (114 mg, 0.88 mmol) was added, and the reaction was continued at room temperature for 2 hours. LC-MS indicated the reaction was complete. The reaction solution was concentrated under reduced pressure, and the crude product was purified by high performance liquid chromatography to afford compound TDI01470 (185 mg, yellow solid, yield: 52.1%).

$^1$H NMR (400 MHz, DMSO-d$_6$) δ 10.63 (s, 1H), 8.52 (s, 1H), 8.41 (d, J=6.4 Hz, 1H), 8.09 (s, 2H), 8.06 (dd, J=8.4, 1.2 Hz, 1H), 7.83 (d, J=8.4 Hz, 1H), 7.77 (d, J=8.0 Hz, 2H), 7.72 (d, J=8.4 Hz, 2H), 7.13 (s, 1H), 6.86 (d, J=6.4 Hz, 1H), 4.91 (s, 2H), 4.57 (s, 2H), 4.05 (s, 3H). MS m/z (ESI): 486.2 [M+H].

The compounds in following table 8 were prepared according to methods similar to that described in the synthetic route of TDI01470 in Example 34.

TABLE 8

| No. | Compound Structure | Compound Name | Starting material or regent different from that in the synthetic route of TDI01470 in Example 34 | Characterization Data |
|---|---|---|---|---|
| TDI01457 | 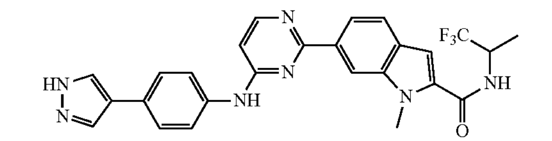 [SMILES: CC(NC(=O)c1cc2ccc(-c3nccc(Nc4ccc(-c5cn[nH]c5)cc4)n3)cc2n1C)C(F)(F)F] | 6-(4-(4-(1H-pyrazol-4-yl)phenyl)amino)pyrimidin-2-yl)-1-methyl-N-(1,1,1-trifluoropropan-2-yl)-1H-indole-2-carboxamide | | $^1$H NMR (400 MHz, DMSO-d$_6$) δ 10.44 (s, 1H), 9.07 (d, J = 8.8 Hz, 1H), 8.54 (s, 1H), 8.41 (d, J = 6.2 Hz, 1H), 8.10 (d, J = 7.4 Hz, 3H), 7.96 - 7.64 (m, 5H), 7.33 (s, 1H), 6.84 (d, J = 6.1 Hz, 1H), 4.90-4.85 (m, 1H), 4.09 (s, 3H), 1.40 (d, J = 6.5 Hz, 3H), MS m/z (ESI): 506.2 [M+H]. |
| TDI01504 | 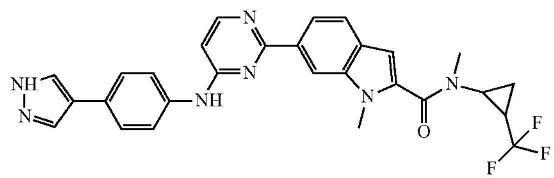 [SMILES: CN(C(=O)c1cc2ccc(-c3nccc(Nc4ccc(-c5cn[nH]c5)cc4)n3)cc2n1C)C1CC1C(F)(F)F] | 6-(4-(4-(1H-pyrazol-4-yl)phenyl)amino)pyrimidin-2-yl)-N,1-dimethyl-N-(2-(trifluoromethyl)cyclopropyl)-1H-indole-2-carboxamide | HCl in step 5 of the synthetic route of TDI01470 in Example 34 was replaced with | $^1$H NMR (400 MHz, CD$_3$OD) δ 8.42 (s, 1H), 8.24 (d, J = 7.2 Hz, 1H), 8.02 (t, J = 5.2 Hz, 2H), 7.98 (dd, J = 8.4, 1.2 Hz, 1H), 7.85 (d, J = 8.4 Hz, 1H), 7.77 - 7.71 (m, 4H), 6.95 (s, 1H), 6.89 (d, J = 8.5 Hz, 2H), 3.93 (s, 3H), 3.18 (s, 3H), 2.17 - 2.11 (m, 2H), 1.24 - 1.19 (m, 2H), MS m/z (ESI): 532.3 [M+H]. |
| TDI01505 | 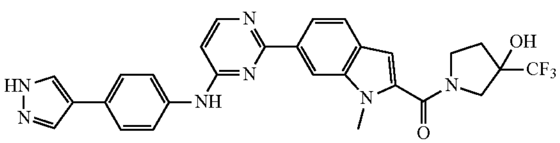 [SMILES: Cn1c(C(=O)N2CCC(O)(C(F)(F)F)C2)cc2ccc(-c3nccc(Nc4ccc(-c5cn[nH]c5)cc4)n3)cc21] | (6-(4-((4-(1H-pyrazol-4-yl)phenyl)amino)pyrimidin-2-yl)-1-methyl-1H-indol-2-yl)(3-hydroxy-3-(trifluoromethyl)pyrrolidin-1-yl)methanone | HCl in step 5 of the synthetic | $^1$H NMR (400 MHz, DMSO-d$_6$) δ 10.73 (s, 1H), 8.50 (s, 1H), 8.40 (d, J = 6.7 Hz, 1H), 8.10 (s, 2H), 8.04 (d, J = 8.3 Hz, 1H), 7.84 (d, J = 8.5 Hz, 1H), 7.77 (s, 2H), 7.73 (d, J = 8.5 Hz, 2H), 7.04 (d, J = 5.3 Hz, 1H), 6.87 (d, J = 6.6 Hz, 1H), 3.95 (s, 3H), 3.81-3.71 (m, 4H), 2.25-2.23 (m, 1H), 2.10-2.08 (m, 1H), MS m/z (ESI): 548.2 [M+H]. |
| TDI01506 | 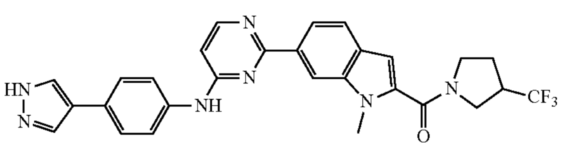 [SMILES: Cn1c(C(=O)N2CCC(C(F)(F)F)C2)cc2ccc(-c3nccc(Nc4ccc(-c5cn[nH]c5)cc4)n3)cc21] | (6-(4-((4-(1H-pyrazol-4-yl)phenyl)amino)pyrimidin-2-yl)-1-methyl-1H-indol-2-yl)(3-(trifluoromethyl)pyrrolidin-1-yl)methanone | route of TDI01470 in Example 34 was replaced with | $^1$H NMR (400 MHz, DMSO-d$_6$) δ 10.72 (s, 1H), 8.50 (s, 1H), 8.41 (d, J = 6.5 Hz, 1H), 8.10 (s, 2H), 8.04 (d, J = 8.6 Hz, 1H), 7.87 - 7.71 (m, 6H), 7.01 (d, J = 17.7 Hz, 1H), 6.88 (d, J = 6.4 Hz, 1H), 3.93 (s, 3H), 3.41-3.37 (m, 3H), 2.51-2.33 (m, 2H), 2.24-2.09 (m, 2H), MS m/z(ESI): 532.2 [M+H]. |

TABLE 8-continued

| No. | Compound Structure | Compound Name | Starting material or regent different from that in the synthetic route of TDI01470 in Example 34 | Characterization Data |
|---|---|---|---|---|
| TDI01507 | 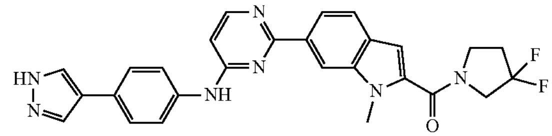 [SMILES: Cn1c(C(=O)N2CCC(F)(F)C2)cc2ccc(-c3nccc(Nc4ccc(-c5cn[nH]c5)cc4)n3)cc21] | (6-(4-((4-(1H-pyrazol-4-yl)phenyl)amino)pyrimidin-2-yl)-1-methyl-1H-indol-2-yl)(3,3-difluoropyrrolidin-1-yl)methanone | in step 5 of the synthetic route of TDI01470 in Example 34 was replaced with | ¹H NMR (400 MHz, CD₃OD) δ 8.42 (s, 1H), 8.24 (d, J = 7.2 Hz, 1H), 8.03 (s, 2H), 7.96 (d, J = 8.5 Hz, 1H), 7.89 (d, J = 8.5 Hz, 1H), 7.75 (d, J = 7.0 Hz, 4H), 7.03 (s, 1H), 6.92 (d, J = 7.2 Hz, 1H), 4.10 (d, J = 33.4 Hz, 2H), 4.00 (s, 5H), 2.52 (s, 2H), MS m/z (ESI): 500.3 |
| TDI01508 | 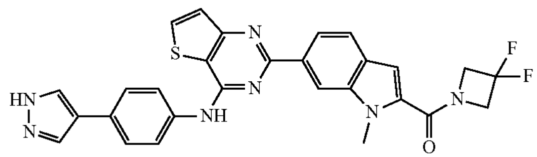 | (6-(4-((4-(1H-pyrazol-4-yl)phenyl)amino)thieno[3,2-d]pyrimidin-2-yl)-1-methyl-1H-indol-2-yl)(3,3-difluoroazetidin-1-yl)methanone | Reg-1-16 in step 4 of the synthetic route of TDI01470 in Example 34 was replaced with (Reg-1-33) | 1H NMR (400 MHz, DMSO-d₆) δ 10.71 (s, 1H), 8.56 (s, 1H), 8.40 (d, J = 5.3 Hz, 1H), 8.13 (d, J = 9.2 Hz, 3H), 7.92 - 7.70 (m, 6H), 7.60 (d, J = 5.4 Hz, 1H), 7.12 (s, 1H), 4.90 (s, 2H), 4.62 - 4.53 (m, 2H), 4.06 (s, 3H), MS m/z (ESI): 542.2 [M+H]. |
| TDI01512 | 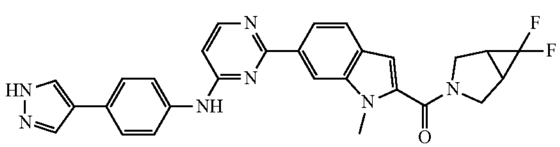 | (6-(4-((4-(1H-pyrazol-4-yl)phenyl)amino)pyrimidin-2-yl)-1-methyl-1H-indol-2-yl)(6,6-difluoro-3-azabicyclo[3.1.0]hexan-3-yl)methanone | in step 5 of the synthetic route of TDI01470 in Example 34 was replaced with | ¹H NMR (400 MHz, CD₃OD) δ 8.47 (s, 1H), 8.29 (d, J = 6.0 Hz, 1H), 8.15 (dd, J = 8.4, 1.2 Hz, 1H), 7.96 (s, 2H), 7.77 (d, J = 8.4 Hz, 2H), 7.71 (d, J = 8.4 Hz, 1H), 7.62 (d, J = 8.8 Hz, 2H), 6.84 (s, 1H), 6.66 (d, J = 6.0 Hz, 1H), 4.34 - 4.31 (m, 1H), 4.10-4.02 (m, 2H), 3.90 (s, 3H), 3.86 - 3.80 (m, 1H), 2.54 - 2.46 (m, 2H), MS m/z (ESI): 512.2 [M+H]. |

TABLE 8-continued

| No. | Compound Structure | Compound Name | Starting material or regent different from that in the synthetic route of TDI01470 in Example 34 | Characterization Data |
|---|---|---|---|---|
| TDI01513 | 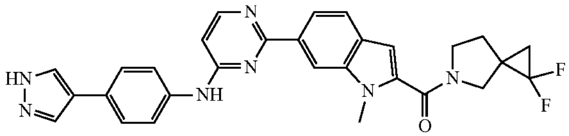 [SMILES: Cn1c(C(=O)N2CCC3(C2)CC3(F)F)cc2ccc(-c3nccc(Nc4ccc(-c5cn[nH]c5)cc4)n3)cc21] | (6-(4-{4-(1H-pyrazol-4-yl)phenyl)amino)pyrimidin-2-yl)-1-methyl-1H-indol-2-yl)(1,1-difluoro-5-azaspiro[2.4]heptan-5-yl)methanone | in step 5 of the synthetic route of TDI01470 in Example 34 was replaced with [structure] HCl | $^1$H NMR (400 MHz, CD$_3$OD) δ 8.41 (s, 1H), 8.24 (d, J = 7.2 Hz, 1H), 8.06 (s, 2H), 7.96 (d, J = 7.6 Hz, 1H), 7.87 (d, J = 8.4 Hz, 1H), 7.82 - 7.73 (m, 4H), 7.00 (d, J = 10.8 Hz, 1H), 6.92 (d, J = 7.2 Hz, 1H), 3.99 (s, 3H), 3.88 - 3.84 (m, 2H), 2.32 - 2.07 (m, 3H), 1.62 - 1.50 (m, 3H), MS m/z (ESI): 526.2 [M+H]. |
| TDI01514 | 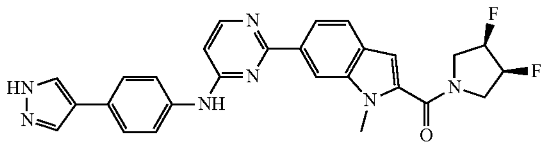 [SMILES: Cn1c(C(=O)N2C[C@@H](F)[C@@H](F)C2)cc2ccc(-c3nccc(Nc4ccc(-c5cn[nH]c5)cc4)n3)cc21] | (6-(4-((4-(1H-pyrazol-4-yl)phenyl)amino)pyrimidin-2-yl)-1-methyl-1H-indol-2-yl)((3S,4R)-3,4-difluoropyrrolidin-1-yl)methanone | in step 5 of the synthetic route of TDI01470 in Example 34 was replaced with [structure] HCl | $^1$H NMR (400 MHz, DMSO-d$_6$) δ 10.76 (s, 1H), 8.52 (s, 1H), 8.41 (d, J = 6.6 Hz, 1H), 8.12 - 8.03 (m, 3H), 7.86 - 7.71 (m, 5H), 7.08 (s, 1H), 6.89 (d, J = 6.7 Hz, 1H), 5.60 - 5.20 (m, 2H), 4.15 (m, 2H), 3.95 (s, 3H), 3.74 (d, J = 4.4 Hz, 2H), MS m/z (ESI): 500.2 [M+H]. |
| TDI01515 | 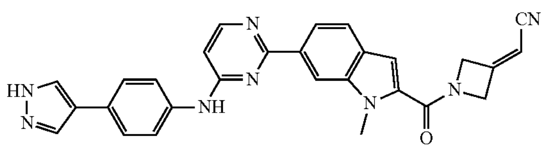 [SMILES: Cn1c(C(=O)N2CC(=CC#N)C2)cc2ccc(-c3nccc(Nc4ccc(-c5cn[nH]c5)cc4)n3)cc21] | 2-(1-(6-(4-((4-(1H-pyrazol-4-yl)phenyl)amino)pyrimidin-2-yl)-1-methyl-1H-indole-2-carbonyl)azetidin-3-ylidene)acetonitrile | in step 5 of the synthetic route of TDI01470 in Example 34 was replaced with [structure] HCl | $^1$H NMR (400 MHz, DMSO-d$_6$) δ 10.42 (s, 1H), 8.52 (s, 1H), 8.41 (d, J = 6.4 Hz, 1H), 8.08 (s, 3H), 7.83 - 7.76 (m, 3H), 7.70 (d, J = 8.4 Hz, 2H), 7.12 (s, 1H), 6.83 (d, J = 6.4 Hz, 1H), 5.96 (s, 1H), 5.26 (d, J = 43.3 Hz, 2H), 4.88 (d, J = 26.0 Hz, 2H), 4.05 (s, 3H), MS m/z (ESI): 487.2 [M+H]. |
| TDI01516 | 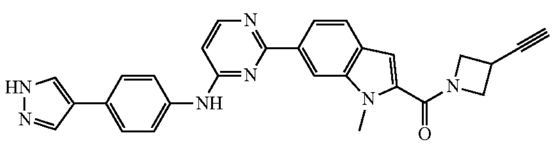 | (6-(4-((4-(1H-pyrazol-4-yl)phenyl)amino)pyrimidin-2-yl)-1-methyl-1H-indol-2-yl)(3-ethynylazetidin-1-yl)methanone | in step 5 of the synthetic route of TDI01470 in Example 34 was replaced with [structure] HCl | $^1$H NMR (400 MHz, DMSO-d$_6$) δ 8.51 (s, 2H), 8.40 (d, J = 6.4 Hz, 1H), 8.10 - 8.08 (m, 3H), 7.80 - 7.77 (m, 3H), 7.69 (d, J = 8.4 Hz, 2H), 7.01 (s, 1H), 6.80 (d, J = 6.4 Hz, 2H), 4.71 - 4.62 (m, 2H), 4.42 - 4.38 (m, 2H), 4.04 (s, 3H), 3.62 - 3.56 (m, 2H), MS m/z (ESI): 471.4 [M+H]. |

TABLE 8-continued

| No. | Compound Structure | Compound Name | Starting material or regent different from that in the synthetic route of TDI01470 | Characterization Data |
|---|---|---|---|---|
| TDI01517 | 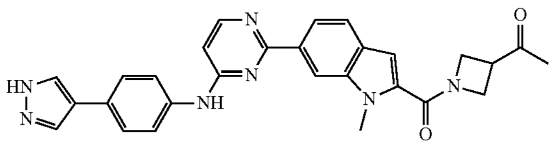 [SMILES: CC(=O)C1CN(C(=O)c2cc3ccc(-c4nccc(Nc5ccc(-c6cn[nH]c6)cc5)n4)cc3n2C)C1] | 1-(1-(6-(4-((1H-pyrazol-4-yl)phenyl)aminopyrimidin-2-yl)-1-methyl-1H-indole-2-carbonyl)azetidin-3-yl)ethan-1-one | in step 5 of the synthetic route of TDI01470 in Example 34 was replaced with [azetidine ketone HCl] | ¹H NMR (400 MHz, DMSO-d₆) δ 12.91 (s, 1H), 9.67 (s, 1H), 8.54 (s, 1H), 8.40 (d, J = 5.8 Hz, 1H), 8.18 (d, J = 8.3 Hz, 2H), 7.93 (s, 1H), 7.81 (d, J = 8.3 Hz, 2H), 7.74 (d, J = 8.4 Hz, 1H), 7.66 (d, J = 8.5 Hz, 2H), 6.97 (s, 1H), 6.71 (d, J = 5.8 Hz, 1H), 4.58 (s, 1H), 4.50 (s, 1H), 4.23 - 4.13 (m, 2H), 4.03 (s, 3H), 3.71 (d, J = 8.9 Hz, 1H), 2.19 (s, 3H). MS m/z (ESI): 492.3 [M+H]. |
| TDI01518 | 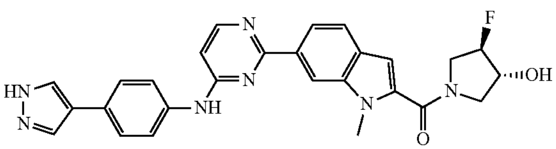 [SMILES: Cn1c(C(=O)N2C[C@@H](O)[C@H](F)C2)cc2ccc(-c3nccc(Nc4ccc(-c5cn[nH]c5)cc4)n3)cc21] | (6-(4-((1H-pyrazol-4-yl)phenyl)aminopyrimidin-2-yl)-1-methyl-1H-indol-2-yl)((3R,4R)-3-fluoro-4-hydroxypyrrolidin-1-yl)methanone | in step 5 of the synthetic route of TDI01470 in Example 34 was replaced with [3-fluoro-4-hydroxypyrrolidine HCl] | ¹H NMR (400 MHz, DMSO-d₆, D₂O) δ 8.46 (s, 1H), 8.37 (dd, J = 7.2, 1.6 Hz, 1H), 8.12 (s, 2H), 7.98 (d, J = 8.4 Hz, 1H), 7.90 (d, J = 8.4 Hz, 1H), 7.84 - 7.72 (m, 4H), 7.08 (d, J = 2.0 Hz, 1H), 6.94 (d, J = 7.2 Hz, 1H), 5.16 - 5.19 (m, 1H), 5.03 - 4.96 (m, 1H), 4.37 - 4.28 (m, 1H), 4.14 - 4.01 (m, 1H), 3.95 (s, 3H), 3.91 - 3.83 (m, 1H), 3.77 - 3.74 (m, 1H). MS m/z (ESI): 498.2 [M+H]. |
| TDI01519 | 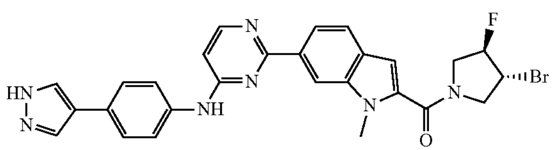 [SMILES: Cn1c(C(=O)N2C[C@@H](F)[C@H](Br)C2)cc2ccc(-c3nccc(Nc4ccc(-c5cn[nH]c5)cc4)n3)cc21] | (6-(4-((1H-pyrazol-4-yl)phenyl)aminopyrimidin-2-yl)-1-methyl-1H-indol-2-yl)(3-bromo-4-fluoropyrrolidin-1-yl)methanone | in step 5 of the synthetic route of TDI01470 in Example 34 was replaced with [3-bromo-4-fluoropyrrolidine HCl] | ¹H NMR (400 MHz, DMSO-d₆) δ 7.60 (s, 1H), 7.43 (d, J = 7.2 Hz, 1H), 7.23 (s, 2H), 7.15 (d, J = 8.4 Hz, 1H), 7.07 (d, J = 8.4 Hz, 1H), 6.98 - 6.92 (m, 4H), 6.25 - 6.18 (m, 1H), 6.11 (d, J = 7.2 Hz, 1H), 4.70 - 4.50 (m, 1H), 3.93 - 3.82 (m, 1H), 3.67 - 3.60 (m, 1H), 3.54 - 3.46 (m, 1H), 3.34 - 3.23 (m, 1H), 3.18 (s, 3H), 3.12 - 3.01 (m, 1H). MS m/z (ESI): 560.2 [M+H]. |
| TDI01520 | 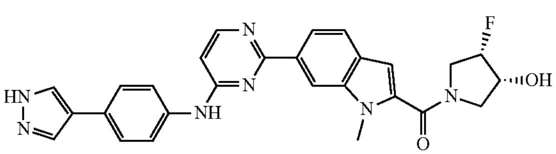 [SMILES: Cn1c(C(=O)N2C[C@@H](O)[C@@H](F)C2)cc2ccc(-c3nccc(Nc4ccc(-c5cn[nH]c5)cc4)n3)cc21] | (6-(4-((1H-pyrazol-4-yl)phenyl)aminopyrimidin-2-yl)-1-methyl-1H-indol-2-yl)((3S,4R)-3-fluoro-4-hydroxypyrrolidin-1-yl)methanone | in step 5 of the synthetic route of TDI01470 in Example 34 was replaced with [(3S,4R)-3-fluoro-4-hydroxypyrrolidine HCl] | ¹H NMR (400 MHz, DMSO-d₆) δ 7.59 (s, 1H), 7.42 (d, J = 7.2 Hz, 1H), 7.23 (s, 2H), 7.14 (d, J = 7.6 Hz, 1H), 7.10 - 7.00 (m, 2H), 6.99 - 6.92 (m, 3H), 6.17 (d, J = 10.0 Hz, 1H), 6.10 (d, J = 6.8 Hz, 1H), 4.42 - 4.17 (m, 2H), 3.70 - 3.53 (m, 1H), 3.27 - 3.19 (m, 1H), 3.16 (s, 3H), 3.07 (s, 1H), 2.88 - 2.72 (m, 1H). MS m/z (ESI): 498.2 [M+H]. |

TABLE 8-continued

| No. | Compound Structure | Compound Name | Starting material or regent different from that in the synthetic route of TDI01470 in Example 34 | Characterization Data |
|---|---|---|---|---|
| TDI01523 | 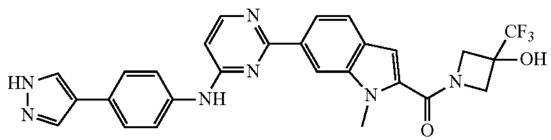 [SMILES: Cn1c(C(=O)N2CC(O)(C(F)(F)F)C2)cc2ccc(-c3nccc(Nc4ccc(-c5cn[nH]c5)cc4)n3)cc21] | (6-(4-((1H-pyrazol-4-yl)phenyl)amino)pyrimidin-2-yl)(3-hydroxy-3-(trifluoromethyl)azetidin-1-yl)methanone | in step 5 of the synthetic route of TDI01470 in Example 34 was replaced with (structure: 3-hydroxy-3-(trifluoromethyl)azetidine HCl) | $^1$H NMR (400 MHz, DMSO-d$_6$) δ 10.56 (s, 1H), 8.52 (s, 1H), 8.41 (d, J = 6.4 Hz, 1H), 8.12 - 8.04 (m, 3H), 7.83 (d, J = 8.4 Hz, 1H), 7.78 (d, J = 8.0 Hz, 2H), 7.71 (d, J = 8.4 Hz, 2H), 7.12 (s, 1H), 6.86 (d, J = 6.4 Hz, 1H), 4.76 - 4.70 (m, 1H), 4.46 - 4.44 (m, 1H), 4.35 - 4.33 (m, 1H), 4.14 - 4.10 (m, 1H), 4.05 (s, 3H). MS m/z (ESI): 534.3 [M+H]. |
| TDI01524 | 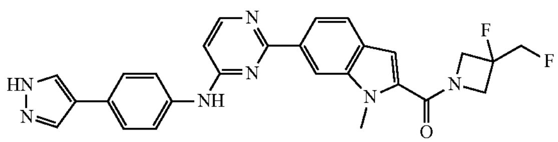 | (6-(4-((1H-pyrazol-4-yl)phenyl)amino)pyrimidin-2-yl)(3-fluoro-3-(fluoromethyl)azetidin-1-yl)methanone | in step 5 of the synthetic route of TDI01470 in Example 34 was replaced with (structure: 3-fluoro-3-(fluoromethyl)azetidine HCl) | $^1$H NMR (400 MHz, CD$_3$OD) δ 8.45 (s, 1H), 8.26 (d, J = 6.5 Hz, 1H), 8.06 (d, J = 8.6 Hz, 1H), 7.98 (s, 2H), 7.74 (s, 3H), 7.66 (d, J = 8.5 Hz, 2H), 7.00 (s, 1H), 6.77 (d, J = 6.5 Hz, 1H), 4.72 (d, J = 21.5 Hz, 2H), 4.64 (s, 2H), 4.44 - 4.25 (m, 2H), 4.07 (s, 3H). MS m/z (ESI): 500.3 [M+H]. |
| TDI01531 | 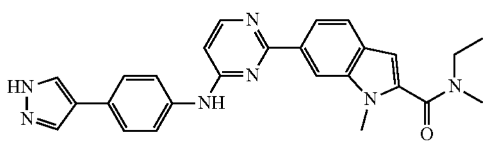 [SMILES: CCN(C)C(=O)c1cc2ccc(-c3nccc(Nc4ccc(-c5cn[nH]c5)cc4)n3)cc2n1C] | 6-(4-((1H-pyrazol-4-yl)phenyl)amino)pyrimidin-2-yl)-N-ethyl-N,1-dimethyl-1H-indole-2-carboxamide | in step 5 of the synthetic route of TDI01470 in Example 34 was replaced with ethylmethylamine. | $^1$H NMR (400 MHz, CD$_3$OD) δ 8.40 (s, 1H), 8.23 (d, J = 7.2 Hz, 1H), 8.04 (s, 2H), 7.96 (d, J = 8.5 Hz, 1H), 7.86 (d, J = 8.5 Hz, 3H), 7.76 (s, 2H), 6.91 (d, J = 7.2 Hz, 1H), 6.81 (d, J = 6.9 Hz, 1H), 3.90 (d, J = 3.4 Hz, 3H), 3.60 (dd, J = 50.8, 6.8 Hz, 2H), 3.16 (s, 3H), 1.33 - 1.20 (m, 3H). MS m/z (ESI): 452.3 [M+H]. |

TABLE 8-continued

| No. | Compound Structure | Compound Name | Starting material or regent different from that in the synthetic route of TDI01470 in Example 34 | Characterization Data |
|---|---|---|---|---|
| TDI01532 | 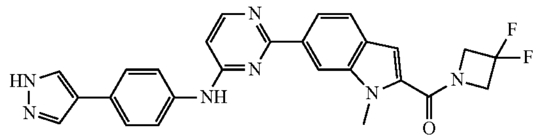 [SMILES: Cn1c(C(=O)N2CC(F)(F)C2)cc2ccc(-c3nccc(Nc4ccc(-c5cn[nH]c5)cc4)n3)cc21] | (6-(4-((1H-pyrazol-4-yl)phenyl)amino)-1,3,5-triazin-2-yl)-1-methyl-1H-indol-2-yl)(3,3-difluoroazetidin-1-yl)methanone | Reg-1-16 in step 4 of the synthetic route of TDI01470 in Example 34 was replaced with (Reg-1-41) | MS m/z (ESI): 487.2 [M+H]. |
| TDI01533 | 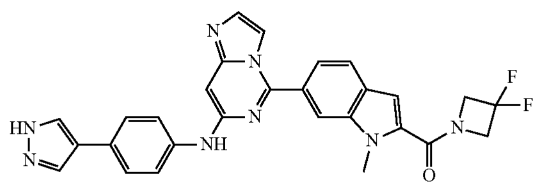 [SMILES: Cn1c(C(=O)N2CC(F)(F)C2)cc2ccc(-c3nc(Nc4ccc(-c5cn[nH]c5)cc4)cc4nccn34)cc21] | (6-(7-((4-(1H-pyrazol-4-yl)phenyl)amino)imidazo[1,2-c]pyrimidin-5-yl)-1-methyl-1H-indol-2-yl)(3,3-difluoroazetidin-1-yl)methanone | Reg-1-16 in Step 4 of the synthetic route of TDI01470 in Example 34 was replaced with (Reg-1-70) | $^1$H NMR (400 MHz, DMSO-d$_6$) 9.43 (s, 1H), 9.00 (s, 1H), 8.59 (s, 2H), 8.42 (s, 1H), 8.41 (d, J = 8.0 Hz, 1H), 7.94 (s, 1H), 7.78 - 7.82 (m, 3H), 7.09 (s, 1H), 7.01 (d, J = 8.0 Hz, 2H), 4.30 - 4.57 (m, 4H), 4.13 (s, 3H). MS m/z (ESI): 525.3 [M+H]. |

TABLE 8-continued

| No. | Compound Structure | Compound Name | Starting material or regent different from that in the synthetic route of TDI01470 in Example 34 | Characterization Data |
|---|---|---|---|---|
| TDI01538 | (structure) | (6-(4-((1H-pyrazol-4-yl)phenyl)amino)pyrimidin-2-yl)-1-methyl-1H-indol-2-yl)(3-(trifluoromethyl)azetidin-1-yl)methanone | in step 5 of the synthetic route of TDI01470 in Example 34 was replaced with (structure) HN-CF3 · HCl | $^1$H NMR (400 MHz, CD$_3$OD) δ 8.43 (s, 1H), 8.25 (d, J = 7.2 Hz, 1H), 8.04 (s, 2H), 7.97 (dd, J = 8.4, 1.2 Hz, 1H), 7.91 (d, J = 8.4 Hz, 1H), 7.87 - 7.71 (m, 4H), 7.06 (s, 1H), 6.94 (d, J = 7.2 Hz, 1H), 4.76 - 4.68 (m, 1H), 4.58 - 4.51 (m, 1H), 4.48 - 4.41 (m, 1H), 4.28 - 4.21 (m, 1H), 4.10 (s, 3H), 3.66 - 3.58 (m, 1H). MS m/z (ESI): 518.3 [M+H]. |

Compound TDI01434 was prepared according to a method similar to that described in Example 34, with step 3 omitted
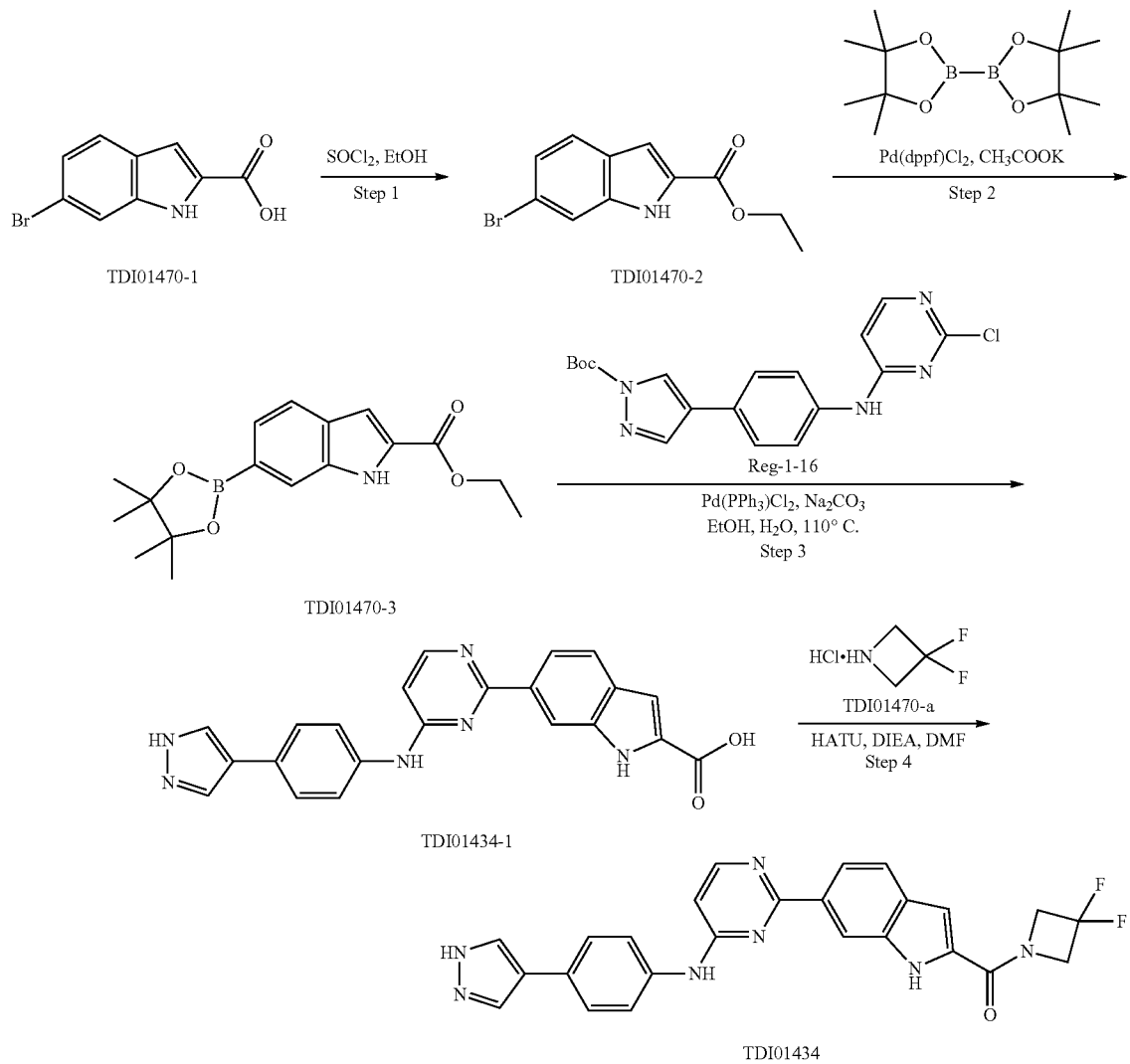
$^1$H NMR (400 MHz, DMSO-d$_6$) δ 12.28 (s, 1H), 10.61 (s, 1H), 8.48 (s, 1H), 8.35 (d, J=6.4 Hz, 1H), 8.07 (s, 2H), 8.00 (d, J=8.4 Hz, 1H), 7.83 (d, J=8.4 Hz, 1H), 7.79 (d, J=7.6 Hz, 2H), 7.71 (d, J=8.4 Hz, 2H), 7.03 (s, 1H), 6.85 (d, J=6.4 Hz, 1H), 5.03 (s, 2H), 4.58 (s, 2H). MS m/z (ESI): 472.1 [M+H].
The compounds in following table 9 were prepared according to methods similar to that described in the synthetic route of TDI01434 in Example 34.

TABLE 9

| No. | Compound Name | Compound Structure | Starting material or regent different from that in the synthetic route of TDI01434 in Example 34 | Characterization Data |
|---|---|---|---|---|
| TDI01381 | 6-(4-((1H-pyrazol-4-yl)phenyl)amino)pyrimidin-2-yl)-N-methyl-N-(tetrahydro-2H-pyran-4-yl)-1H-indole-2-carboxamide | 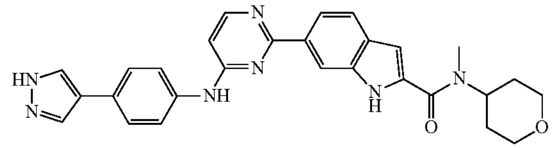 [SMILES: CN(C(=O)c1cc2ccc(-c3nccc(Nc4ccc(-c5cn[nH]c5)cc4)n3)cc2[nH]1)C1CCOCC1] | in step 4 of the synthetic route of TDI01434 in Example 34 was replaced with 4-(methylamino)tetrahydropyran | $^1$H NMR (400 MHz, CD3OD) δ 8.42 (s, 1H), 8.20 (d, J = 7.2 Hz, 1H), 8.03 (s, 2H), 7.88 (s, 3H), 7.74 (d, J = 7.7 Hz, 3H), 6.98 (s, 1H), 6.91 (d, J = 7.2 Hz, 1H), 4.05 (d, J = 8.3 Hz, 2H), 3.51 (s, 3H), 3.20 (s, 3H), 2.01 (s, 2H), 1.74 (d, J = 11.7 Hz, 2H). MS m/z (ESI): 494.3 [M + H]. |
| TDI01408 | 5-(4-((4-((1H-pyrazol-4-yl)phenyl)amino)pyrimidin-2-yl)-N,N-diethyl-1H-indole-2-carboxamide | 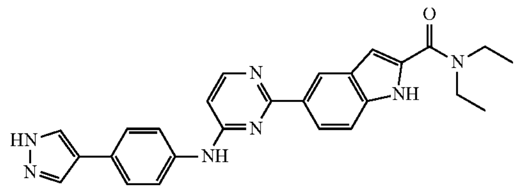 [SMILES: CCN(CC)C(=O)c1cc2cc(-c3nccc(Nc4ccc(-c5cn[nH]c5)cc4)n3)ccc2[nH]1] | 5-bromo-1H-indole-2-carboxylic acid in step 1 of the synthetic route of TDI01434 in Example 34 was replaced with 6-bromo-1H-indole-2-carboxylic acid; in step 4 was replaced with diethylamine. | $^1$H NMR (400 MHz, DMSO-d$_6$) δ 11.93 (s, 1H), 10.39 (s, 1H), 8.66 (s, 1H), 8.35 (d, J = 6.3 Hz, 1H), 8.17 (d, J = 8.7 Hz, 1H), 8.07 (s, 2H), 7.79 (d, J = 7.7 Hz, 2H), 7.71 (d, J = 8.4 Hz, 2H), 7.58 (d, J = 8.7 Hz, 1H), 6.99 (s, 1H), 6.80 (d, J = 6.1 Hz, 1H), 3.62-3.60 (m, 4H), 1.20-1.28 (m, 6H). MS m/z (ESI): 452.3 [M + H]. |
| TDI01418 | 6-(4-((4-((1H-pyrazol-4-yl)phenyl)amino)pyrimidin-2-yl)-N-(3-hydroxycyclobutyl)-N-methyl-1H-indole-2-carboxamide | 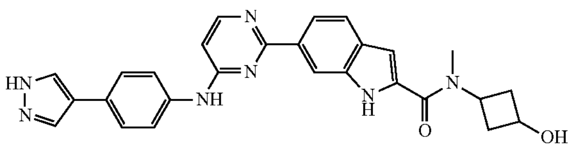 [SMILES: CN(C(=O)c1cc2ccc(-c3nccc(Nc4ccc(-c5cn[nH]c5)cc4)n3)cc2[nH]1)C1CC(O)C1] | in step 4 of the synthetic route of TDI01434 in Example 34 was replaced with 3-(methylamino)cyclobutanol | $^1$H NMR (400 MHz, DMSO-d$_6$) δ 12.19 (s, 1H), 10.89 (s, 1H), 8.42 (s, 1H), 8.35 (d, J = 6.5 Hz, 1H), 8.09 (s, 2H), 7.93 (s, 1H), 7.86 (s, 1H), 7.76 (d, J = 11.7 Hz, 4H), 6.89 (d, J = 6.3 Hz, 2H), 4.43 (d, J = 8.3 Hz, 1H), 3.85 (s, 1H), 3.15 (s, 3H), 2.13 (s, 3H). MS m/z (ESI): 480.3 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01419 | 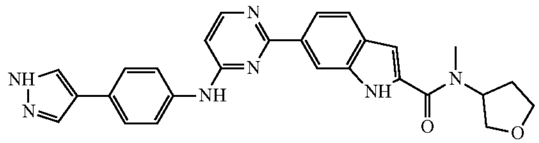 [SMILES: CN(C(=O)c1cc2ccc(-c3nccc(Nc4ccc(-c5cn[nH]c5)cc4)n3)cc2[nH]1)C1CCOC1] | 6-(4-((4-(1H-pyrazol-4-yl)phenyl)amino)pyrimidin-2-yl)-N-methyl-N-(tetrahydrofuran-3-yl)-1H-indole-2-carboxamide | in step 4 of the synthetic route of TDI01434 in Example 34 was replaced with | $^1$H NMR (400 MHz, CD$_3$OD) δ 8.60 (s, 1H), 8.38 (d, J = 2.8 Hz, 1H), 8.21 (d, J = 8.8 Hz, 1H), 8.07 (s, 2H), 7.90 (d, J = 8.4 Hz, 2H), 7.79 (d, J = 8.4 Hz, 1H), 7.72 (d, J = 8.4 Hz, 2H), 6.98 (s, 1H), 6.73 (d, J = 6.0 Hz, 1H), 5.35 (d, J = 8.8 Hz, 1H), 4.33 (s, 3H), 4.16-4.12 (m, 1H), 4.00-3.96 (m, 1H), 3.90-3.86 (m, 1H), 3.77-3.71 (m, 1H), 2.45-2.40 (m, 1H), 2.15-2.10 (m, 1H). MS m/z (ESI): 480.3 [M + H]. |
| TDI01420 | 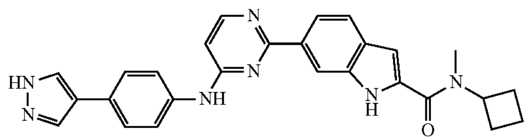 [SMILES: CN(C(=O)c1cc2ccc(-c3nccc(Nc4ccc(-c5cn[nH]c5)cc4)n3)cc2[nH]1)C1CCC1] | 6-(4-((4-(1H-pyrazol-4-yl)phenyl)amino)pyrimidin-2-yl)-N-cyclobutyl-N-methyl-1H-indole-2-carboxamide | in step 4 of the synthetic route of TDI01434 in Example 34 was replaced with | $^1$H NMR (400 MHz, DMSO-d$_6$) δ 12.12 (s, 1H), 10.64 (s, 1H), 8.41 (d, J = 34.4 Hz, 2H), 8.09 (s, 2H), 7.98 (s, 1H), 7.88-7.67 (m, 4H), 6.89 (d, J = 25.6 Hz, 2H), 4.93 (s, 1H), 3.15 (s, 3H), 2.33 (s, 2H), 2.16 (s, 2H), 1.68 (s, 2H). MS m/z (ESI): 464.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01426 | 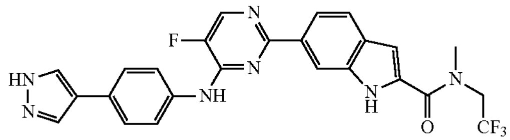 | 6-(4-((1H-pyrazol-4-yl)phenyl)amino)-5-fluoropyrimidin-2-yl)-N-methyl-N-(2,2,2-trifluoroethyl)-1H-indole-2-carboxamide | Reg-1-16 in step 3 of the synthetic route of TDI01434 in Example 34 was replaced with (Reg-1-40) | $^1$H NMR (400 MHz, DMSO-d$_6$) δ 11.99 (s, 1H), 9.65 (s, 1H), 8.48 (s, 2H), 8.06 (d, J = 4.9 Hz, 3H), 7.94 (d, J = 8.6 Hz, 2H), 7.70 (dd, J = 18.3, 8.6 Hz, 3H), 7.08 (s, 1H), 4.50 (s, 2H), 3.46 (s, 3H). MS m/z (ESI): 510.2 [M + H]. |
| TDI01429 | 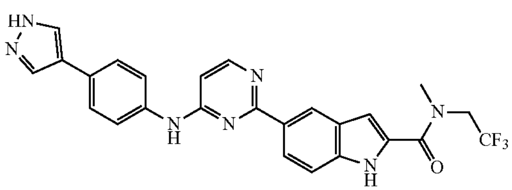 [SMILES: CN(CC(F)(F)F)C(=O)c1cc2cc(-c3nccc(Nc4ccc(-c5cn[nH]c5)cc4)n3)ccc2[nH]1] | 5-(4-((1H-pyrazol-4-yl)phenyl)amino)pyrimidin-2-yl)-N-methyl-N-(2,2,2-trifluoroethyl)-1H-indole-2-carboxamide | OH in step 1 of the synthetic route of TDI01434 in Example 34 was replaced with ; in step 4 was replaced with | $^1$H NMR (400 MHz, DMSO-d$_6$) δ 7.92 (s, 1H), 7.53 (s, 1H), 7.47-7.29 (m, 3H), 7.04-6.97 (m, 5H), 6.54 (s, 1H), 6.25-6.16 (m, 1H), 3.73 (s, 2H), 2.79 (s, 3H). MS m/z (ESI): 492.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01430 | 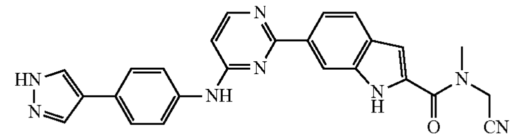 [SMILES: CN(CC#N)C(=O)c1cc2ccc(-c3nccc(Nc4ccc(-c5cn[nH]c5)cc4)n3)cc2[nH]1] | 6-(4-((1H-pyrazol-4-yl)phenyl)amino)pyrimidin-2-yl)-N-(cyanomethyl)-N-methyl-1H-indole-2-carboxamide | in step 4 of the synthetic route of TDI01434 in Example 34 was replaced with HCl·HN—CH₂CN. | ¹H NMR (400 MHz, DMSO-d₆) δ 12.25 (s, 1H), 10.50 (s, 1H), 8.49 (s, 1H), 8.37 (d, J = 6.4 Hz, 1H), 8.08 (s, 2H), 8.03 (d, J = 8.3 Hz, 1H), 7.82 (dd, J = 15.7, 8.1 Hz, 3H), 7.71 (d, J = 8.2 Hz, 2H), 7.13 (s, 1H), 6.84 (d, J = 6.3 Hz, 1H), 4.69 (s, 2H), 3.40 (s, 3H). MS m/z (ESI): 449.2 [M + H]. |
| TDI01431 | 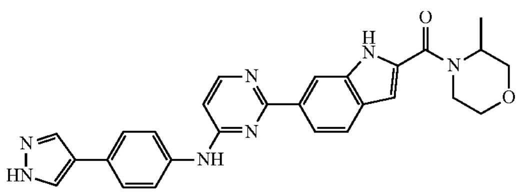 [SMILES: CC1COCCN1C(=O)c1cc2ccc(-c3nccc(Nc4ccc(-c5cn[nH]c5)cc4)n3)cc2[nH]1] | (6-(4-((1H-pyrazol-4-yl)phenyl)amino)pyrimidin-2-yl)-1H-indol-2-yl)(3-methylmorpholino)methanone | in step 4 of the synthetic route of TDI01434 in Example 34 was replaced with 3-methylmorpholine. | ¹H NMR (400 MHz, CD₃OD) δ 8.41 (s, 1H), 8.21 (d, J = 7.2 Hz, 1H), 8.03 (s, 2H), 7.88 (s, 2H), 7.75 (d, J = 7.4 Hz, 3H), 6.96-6.87 (m, 2H), 4.61 (s, 1H), 4.21 (d, J = 9.1 Hz, 1H), 3.95 (d, J = 7.2 Hz, 1H), 3.71 (dd, J = 14.6, 11.8 Hz, 2H), 3.56 (d, J = 6.8 Hz, 2H), 1.46 (d, J = 6.9 Hz, 3H). MS m/z (ESI): 480.3 [M + H]. |
| TDI01433 | 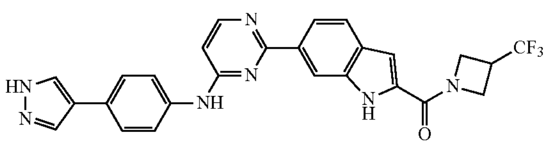 [SMILES: O=C(c1cc2ccc(-c3nccc(Nc4ccc(-c5cn[nH]c5)cc4)n3)cc2[nH]1)N1CC(C(F)(F)F)C1] | (6-(4-((1H-pyrazol-4-yl)phenyl)amino)pyrimidin-2-yl)-1H-indol-2-yl)(3-(trifluoromethyl)azetidin-1-yl)methanone | in step 4 of the synthetic route of TDI01434 in Example 34 was replaced with F₃C-azetidine·NHHCl. | ¹H NMR (400 MHz, DMSO-d₆) δ 12.16 (s, 1H), 10.26 (s, 1H), 8.51 (s, 1H), 8.36 (d, J = 6.3 Hz, 1H), 8.05 (d, J = 9.5 Hz, 3H), 7.80 (t, J = 8.6 Hz, 3H), 7.69 (d, J = 8.3 Hz, 2H), 7.03 (s, 1H), 6.79 (d, J = 5.9 Hz, 1H), 4.81 (s, 1H), 4.62 (s, 1H), 4.38 (s, 1H), 4.10 (s, 1H), 3.79 (dd, J = 3.5, 1.3 Hz, 1H). MS m/z (ESI): 504.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01435 | (structure) | (6-(4-((1H-pyrazol-4-yl)phenyl)amino)pyrimidin-2-yl)-1H-indol-2-yl)(3-(difluoromethyl)azetidin-1-yl)methanone | in step 4 of the synthetic route of TDI01434 in Example 34 was replaced with (3,3-difluoroazetidine HCl) with (3-(CHF$_2$)azetidine) | $^1$H NMR (400 MHz, CD$_3$OD) δ 8.42 (s, 1H), 8.20 (d, J = 1.1 Hz, 1H), 8.03 (s, 2H), 7.88 (dd, J = 18.4, 8.5 Hz, 2H), 7.74 (s, 3H), 6.99 (s, 1H), 6.90 (d, J = 7.1 Hz, 1H), 6.21 (dd, J = 57.6, 54.6 Hz, 1H), 4.73 (s, 1H), 4.60 (s, 1H), 4.22 (dd, J = 74.1, 31.0 Hz, 4H). MS m/z (ESI): 486.2 [M + H]. |
| TDI01436 | (structure) | (6-(4-((1H-pyrazol-4-yl)phenyl)amino)pyrimidin-2-yl)-1H-indol-2-yl)(3-(trifluoromethoxy)azetidin-1-yl)methanone | in step 4 of the synthetic route of TDI01434 in Example 34 was replaced with (3,3-difluoroazetidine HCl) with (3-(OCF$_3$)azetidine) | $^1$H NMR (400 MHz, DMSO-d$_6$) δ 8.53 (s, 1H), 8.37 (d, J = 6.1 Hz, 1H), 8.08 (d, J = 9.0 Hz, 3H), 7.82 (d, J = 8.0 Hz, 2H), 7.77 (d, J = 8.4 Hz, 1H), 7.70 (s, 2H), 6.97 (s, 1H), 6.75 (d, J = 5.8 Hz, 1H), 5.35 (s, 1H), 4.95 (s, 1H), 4.72 (s, 1H), 4.56 (s, 1H), 4.20 (s, 1H). MS m/z (ESI): 520.2 [M + H]. |
| TDI01437 | (structure) | (6-(4-((1H-pyrazol-4-yl)phenyl)amino)pyrimidin-2-yl)-1H-indol-2-yl)(3-hydroxyazetidin-1-yl)methanone | replaced with (3-hydroxyazetidine HCl) | $^1$H NMR (400 MHz, CD$_3$OD) δ 8.43 (s, 1H), 8.21 (d, J = 7.2 Hz, 1H), 8.03 (s, 2H), 7.92-7.84 (m, 2H), 7.75 (s, 4H), 6.99 (s, 1H), 6.91 (d, J = 7.2 Hz, 1H), 4.72-4.71 (m, 1H), 4.67 (s, 1H), 4.46 (s, 1H), 4.39 (s, 1H), 4.02 (s, 1H). MS m/z (ESI): 452.2 [M + H]. |
| TDI01438 | (structure) | (S)-(6-(4-((1H-pyrazol-4-yl)phenyl)amino)pyrimidin-2-yl)-1H-indol-2-yl)(3-hydroxypyrrolidin-1-yl)methanone | in step 4 of the synthetic route of TDI01434 in Example 34 was replaced with (S)-3-hydroxypyrrolidine | $^1$H NMR (400 MHz, CD$_3$OD) δ 8.42 (s, 1H), 8.20 (d, J = 7.2 Hz, 1H), 8.06 (s, 2H), 7.74 (m, 6H), 7.12 (d, J = 24.7 Hz, 1H), 6.90 (d, J = 7.2 Hz, 1H), 4.54 (d, J = 24.2 Hz, 1H), 4.14-3.67 (m, 4H), 2.22-1.97 (m, 2H). MS m/z (ESI): 466.1 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01441 | (structure) | (6-(4-((1H-pyrazol-4-yl)phenyl)aminopyrimidin-2-yl)-1H-indol-2-yl)(3-fluoro-3-methylazetidin-1-yl)methanone | (reagent structure) in step 4 of the synthetic route of TDI01434 in Example 34 was replaced with (reagent structure) | ¹H NMR (400 MHz, CD₃OD) δ 8.43 (s, 1H), 8.21 (d, J = 7.2 Hz, 1H), 8.03 (s, 2H), 7.90 (t, J = 8.1 Hz, 2H), 7.75 (s, 4H), 7.00 (s, 1H), 6.91 (d, J = 7.2 Hz, 1H), 4.65 (s, 2H), 4.29 (s, 2H), 1.70 (d, J = 21.6 Hz, 3H). MS m/z (ESI): 468.2 [M + H]. |
| TDI01442 | (structure) | 6-(4-((4-(1H-pyrazol-4-yl)phenyl)aminopyrimidin-2-yl)-N-(2-cyanoethyl)-N-methyl-1H-indole-2-carboxamide | (reagent structure) in step 4 of the synthetic route of TDI01434 in Example 34 was replaced with (reagent structure) | ¹H NMR (400 MHz, DMSO-d₆) δ 12.16 (s, 1H), 10.57 (s, 1H), 8.49 (s, 1H), 8.37 (d, J = 6.5 Hz, 1H), 8.08 (s, 2H), 8.01 (d, J = 8.4 Hz, 1H), 7.82 (d, J = 8.6 Hz, 3H), 7.71 (d, J = 8.5 Hz, 2H), 7.05 (s, 1H), 6.85 (d, J = 6.5 Hz, 1H), 3.39 (s, 4H), 2.93 (s, 3H). MS m/z (ESI): 463.3 [M + H]. |
| TDI01444 | (structure) | (6-(4-((1H-pyrazol-4-yl)phenyl)aminopyrimidin-2-yl)-1H-indol-2-yl)(3-(trifluoromethyl)pyrrolidin-1-yl)methanone | (reagent structure) in step 4 of the synthetic route of TDI01434 in Example 34 was replaced with (reagent structure) | ¹H NMR (400 MHz, CD₃OD) δ 8.44 (s, 1H), 8.21 (d, J = 7.2 Hz, 1H), 8.03 (s, 2H), 7.96-7.82 (m, 3H), 7.75 (d, J = 8.0 Hz, 3H), 7.15 (s, 1H), 6.92 (d, J = 7.2 Hz, 1H), 4.26 (d, J = 28.2 Hz, 2H), 3.99-3.83 (m, 2H), 2.35 (d, J = 41.6 Hz, 2H). MS m/z (ESI): 518.3 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01445 | (structure) | 1-(6-(4-((4-(1H-pyrazol-4-yl)phenyl)amino)pyrimidin-2-yl)-1H-indole-2-carbonyl)piperidine-4-carbonitrile | (3-fluoroazetidine HCl) in step 4 of the synthetic route of TDI01434 in Example 34 was replaced with (4-cyanopiperidine) | $^{1}$H NMR (400 MHz, CD$_3$OD) δ 8.38 (s, 1H), 8.19 (d, J = 7.1 Hz, 1H), 8.03 (s, 2H), 7.77 (dd, J = 42.4, 15.3 Hz, 6H), 6.99-6.84 (m, 2H), 4.10 (d, J = 12.3 Hz, 2H), 3.68 (s, 2H), 3.14 (s, 1H), 2.05 (s, 2H), 1.96-1.80 (m, 2H). MS m/z (ESI): 489.2 [M + H]. |
| TDI01447 | (structure) | (6-(4-((4-(1H-pyrazol-4-yl)phenyl)amino)pyrimidin-2-yl)-1H-indol-2-yl)(3-(4-methylpiperazin-1-yl)piperidin-1-yl)methanone | (3-fluoroazetidine HCl) in step 4 of the synthetic route of TDI01434 in Example 34 was replaced with (1-methyl-4-(piperidin-3-yl)piperazine) | $^{1}$H NMR (400 MHz, DMSO-d$_6$) δ 12.12 (s, 1H), 10.51 (s, 1H), 8.47 (s, 1H), 8.37 (d, J = 6.4 Hz, 1H), 8.07 (s, 2H), 8.02 (d, J = 8.5 Hz, 1H), 7.80 (d, J = 4.3 Hz, 3H), 7.71 (d, J = 8.3 Hz, 2H), 6.92-6.77 (m, 2H), 4.39 (s, 2H), 4.25 (d, J = 10.7 Hz, 2H), 3.02 (d, J = 80.3 Hz, 7H), 2.77 (s, 3H), 2.63 (s, 2H), 1.96 (s, 1H), 1.82 (s, 1H), 1.64-1.46 (m, 2H). MS m/z (ESI): 562.4 [M + H]. |
| TDI01448 | (structure) | 1-(6-(4-((4-(1H-pyrazol-4-yl)phenyl)amino)pyrimidin-2-yl)-1H-indole-2-carbonyl)pyrrolidine-3-carbonitrile | (3-fluoroazetidine HCl) in step 4 of the synthetic route of TDI01434 in Example 34 was replaced with (3-cyanopyrrolidine) | $^{1}$H NMR (400 MHz, CD$_3$OD) δ 8.44 (s, 1H), 8.21 (d, J = 7.1 Hz, 1H), 8.02 (s, 2H), 7.91 (s, 2H), 7.75 (s, 4H), 7.15 (d, J = 9.2 Hz, 1H), 6.90 (d, J = 7.2 Hz, 1H), 4.22-3.85 (m, 4H), 3.48 (d, J = 3.4 Hz, 1H), 2.41 (t, J = 26.9 Hz, 2H), MS m/z (ESI): 475.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01450 | 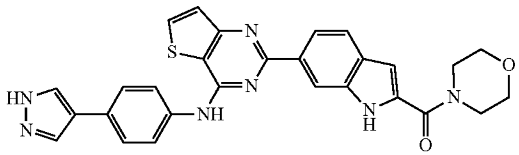 [SMILES: O=C(c1cc2ccc(-c3nc(Nc4ccc(-c5cn[nH]c5)cc4)c4sccc4n3)cc2[nH]1)N1CCOCC1] | (6-(4-((4-(1H-pyrazol-4-yl)phenyl)amino)thieno[3,2-d]pyrimidin-2-yl)-1H-indol-2-yl)(morpholino)methanone | (Reg-1-16) in step 3 of the synthetic route of TDI01434 in Example 34 was replaced with (Reg-1-33); in step 4 was replaced with morpholine. | $^1$H NMR (400 MHz, CD$_3$OD) δ 11.93 (s, 1H), 9.94 (s, 1H), 8.57 (s, 1H), 8.26 (d, J = 8.0 Hz, 1H), 8.15 (d, J = 8.0 Hz, 1H), 8.09 (s, 2H), 7.92 (d, J = 8.0 Hz, 2H), 7.71 (d, J = 8.0 Hz, 3H), 7.56 (s, 1H), 6.88 (s, 1H), 3.79-3.68 (m, 8H). MS m/z (ESI): 522.2 [M + H]. |
| TDI01451 | 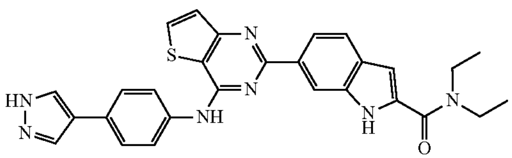 [SMILES: CCN(CC)C(=O)c1cc2ccc(-c3nc(Nc4ccc(-c5cn[nH]c5)cc4)c4sccc4n3)cc2[nH]1] | 6-(4-((4-(1H-pyrazol-4-yl)phenyl)amino)thieno[3,2-d]pyrimidin-2-yl)-N,N-diethyl-1H-indole-2-carboxamide | (Reg-1-16) in step 3 of the synthetic route of TDI01434 in Example 34 was replaced with (Reg-1-33); in step 4 was replaced with diethylamine hydrochloride. | $^1$H NMR (400 MHz, DMSO-d$_6$) δ 10.13 (s, 2H), 9.70 (s, 1H), 8.96 (s, 1H), 8.82 (s, 1H), 8.50 (s, 1H). 8.40-8.23 (m, 3H), 8.10 (d, J = 12.0 Hz, 3H), 7.93 (dd, J = 34.6, 8.8 Hz, 3H), 3.02 (s, 3H), 2.75 (s, 3H). MS m/z (ESI): 508.3 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01455 | 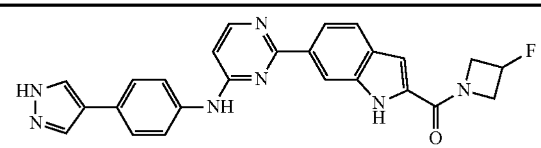 | (6-(4-((1H-pyrazol-4-yl)phenyl)amino)pyrimidin-2-yl)-1H-indol-2-yl)(3-fluoroazetidin-1-yl)methanone | in step 4 of the synthetic route of TDI01434 in Example 34 was replaced with ![structure] | $^1$H NMR (400 MHz, DMSO-$d_6$) δ 12.21 (s, 1H), 10.53 (s, 1H), 8.49 (s, 1H), 8.37 (d, J = 6.4 Hz, 1H), 8.08 (s, 2H), 8.01 (d, J = 8.8 Hz, 1H), 7.81 (dd, J = 8.8, 4.0 Hz, 3H), 7.71 (d, J = 8.8 Hz, 2H), 6.97 (s, 1H), 6.84 (d, J = 6.4 Hz, 1H), 5.54 (d, J = 57.6 Hz, 1H), 4.86 (s, 1H), 4.65 (s, 1H), 4.48 (s, 1H), 4.12 (s, 1H). MS m/z (ESI): 454.2 [M + H]. |
| TDI01458 | 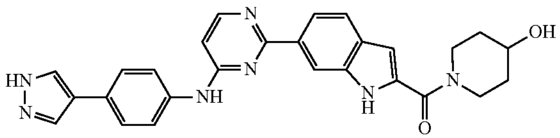 [SMILES: O=C(c1cc2ccc(-c3nccc(Nc4ccc(-c5cn[nH]c5)cc4)n3)cc2[nH]1)N1CCC(O)CC1] | (6-(4-((1H-pyrazol-4-yl)phenyl)amino)pyrimidin-2-yl)-1H-indol-2-yl)(4-hydroxypiperidin-1-yl)methanone | in step 4 of the synthetic route of TDI01434 in Example 34 was replaced with 4-hydroxypiperidine. | $^1$H NMR (400 MHz, DMSO-$d_6$) δ 12.04 (s, 1H), 10.32 (s, 1H), 8.47 (s, 1H), 8.36 (d, J = 6.3 Hz, 1H), 8.09-8.01 (m, 3H), 7.81-7.76 (m, 3H), 7.70 (d, J = 8.5 Hz, 2H), 6.85 (s, 1H), 6.80 (d, J = 6.2 Hz, 1H), 4.11-4.08 (m, 4H), 3.81-3.79 (m, 1H), 1.87-1.80 (m, 2H), 1.47-1.40 (m, 2H). MS m/z (ESI): 480.2 [M + H]. |
| TDI01461 | 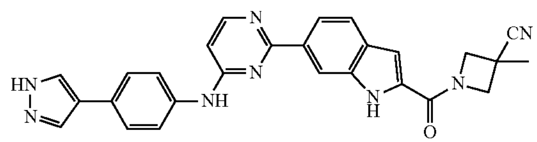 [SMILES: CC1(C#N)CN(C(=O)c2cc3ccc(-c4nccc(Nc5ccc(-c6cn[nH]c6)cc5)n4)cc3[nH]2)C1] | 1-(6-(4-((4-((1H-pyrazol-4-yl)phenyl)amino)pyrimidin-2-yl)-1H-indole-2-carbonyl)-3-methylazetidine-3-carbonitrile | in step 4 of the synthetic route of TDI01434 in Example 34 was replaced with ![structure] | $^1$H NMR (400 MHz, CD$_3$OD) δ 8.43 (s, 1H), 8.21 (d, J = 7.2 Hz, 1H), 8.03 (s, 2H), 7.89 (dd, J = 16.6, 8.6 Hz, 2H), 7.75 (s, 4H), 6.99 (s, 1H), 6.91 (d, J = 7.2 Hz, 1H), 4.77 (s, 1H), 4.55 (s, 2H), 4.18 (s, 1H), 1.76 (s, 3H). MS m/z (ESI): 475.3 [M + H]. |
| TDI01462 | 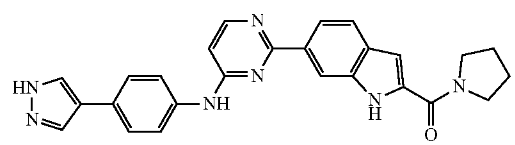 [SMILES: O=C(c1cc2ccc(-c3nccc(Nc4ccc(-c5cn[nH]c5)cc4)n3)cc2[nH]1)N1CCCC1] | (6-(4-((1H-pyrazol-4-yl)phenyl)amino)pyrimidin-2-yl)-1H-indol-2-yl)(pyrrolidin-1-yl)methanone | in step 4 of the synthetic route of TDI01434 in Example 34 was replaced with pyrrolidine. | $^1$H NMR (400 MHz, DMSO-$d_6$) δ 12.14 (s, 1H), 10.66 (s, 1H), 8.48 (s, 1H), 8.35 (d, J = 6.6 Hz, 1H), 8.08 (s, 2H), 7.98 (d, J = 8.5 Hz, 1H), 7.83 (d, J = 8.7 Hz, 3H), 7.72 (d, J = 8.4 Hz, 2H), 7.09 (s, 1H), 6.85 (d, J = 5.9 Hz, 1H), 3.86 (t, J = 6.5 Hz, 2H), 3.59 (s, 2H), 1.99 (d, J = 6.6 Hz, 2H), 1.93-1.86 (m, 2H). MS m/z (ESI): 466.3 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01463 | 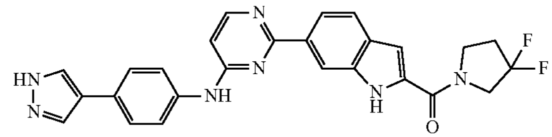 [SMILES: O=C(c1cc2ccc(-c3nccc(Nc4ccc(-c5cn[nH]c5)cc4)n3)cc2[nH]1)N1CCC(F)(F)C1] | (6-(4-((4-((1H-pyrazol-4-yl)phenyl)amino)pyrimidin-2-yl)-1H-indol-2-yl)(3,3-difluoropyrrolidin-1-yl)methanone | in step 4 of the synthetic route of TDI01434 in Example 34 was replaced with (3,3-difluoropyrrolidine·HCl). | $^1$H NMR (400 MHz, CD$_3$OD) δ 8.41 (s, 1H), 8.20 (d, J = 6.2 Hz, 1H), 8.03 (s, 2H), 7.97-7.56 (m, 6H), 7.13 (s, 1H), 6.90 (d, J = 6.4 Hz, 1H), 4.22-4.20 (m, 2H), 3.98-3.96 (m, 2H), 2.57-2.55 (m, 2H). MS m/z (ESI): 486.1 [M + H]. |
| TDI01464 | 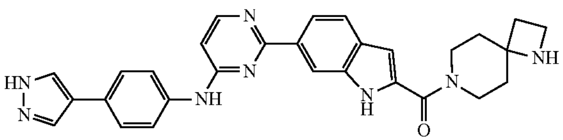 [SMILES: O=C(c1cc2ccc(-c3nccc(Nc4ccc(-c5cn[nH]c5)cc4)n3)cc2[nH]1)N1CCC2(CCN2)CC1] | (6-(4-((4-((1H-pyrazol-4-yl)phenyl)amino)pyrimidin-2-yl)-1H-indol-2-yl)(1,7-diazaspiro[3.5]nonan-7-yl)methanone | in step 4 of the synthetic route of TDI01434 in Example 34 was replaced with (Boc-protected diazaspiro compound); and then the product was obtained by removal of Boc using TFA. | $^1$H NMR (400 MHz, DMSO-d$_6$) δ 8.42 (s, 1H), 8.22 (d, J = 6.0 Hz, 1H), 8.06 (s, 2H), 7.89 (s, 2H), 7.80-7.75 (m, 4H), 6.97 (s, 1H), 6.92 (d, J = 5.6 Hz, 1H), 4.14-4.00 (m, 4H), 3.79-3.64 (m, 4H), 2.57-2.53 (m, 2H), 2.23-2.16 (m, 4H). MS m/z (ESI): 505.3 [M + H]. |
| TDI01465 | 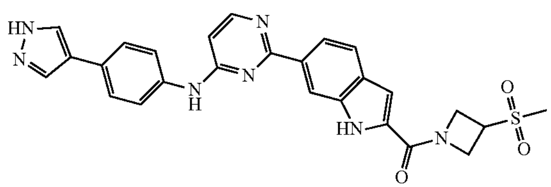 [SMILES: CS(=O)(=O)C1CN(C(=O)c2cc3ccc(-c4nccc(Nc5ccc(-c6cn[nH]c6)cc5)n4)cc3[nH]2)C1] | (6-(4-((4-((1H-pyrazol-4-yl)phenyl)amino)pyrimidin-2-yl)-1H-indol-2-yl)(3-(methylsulfonyl)azetidin-1-yl)methanone | in step 4 of the synthetic route of TDI01434 in Example 34 was replaced with (3-(methylsulfonyl)azetidine·HCl). | $^1$H NMR (400 MHz, CD$_3$OD) δ 8.41 (s, 1H), 8.20 (d, J = 7.2 Hz, 1H), 8.03 (s, 2H), 7.74 (s, 6H), 7.02 (s, 1H), 6.90 (d, J = 7.2 Hz, 1H), 4.45 (dd, J = 15.5, 11.5 Hz, 4H), 3.06 (s, 3H). MS m/z (ESI): 514.3 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01468 | | O7-(6-(4-((4-(1H-pyrazol-4-yl)phenyl)amino)pyrimidin-2-yl)-1H-indole-2-carbonyl)-1,7-diazaspiro[3.5]nonan-2-one | in step 4 of the synthetic route of TDI01434 in Example 34 was replaced with | ¹H NMR (400 MHz, CD₃OD) δ 8.41 (s, 1H), 8.21 (d, J = 7.2 Hz, 1H), 8.03 (s, 2H), 7.93-7.82 (m, 3H), 7.79-7.74 (m, 3H), 6.95 (s, 1H), 6.91 (d, J = 7.2 Hz, 1H), 4.00-3.93 (m, 2H), 3.85-3.76 (m, 2H), 2.81 (s, 2H), 1.99-1.87 (m, 4H). MS m/z (ESI): 519.3 [M + H]. |
| TDI01472 | 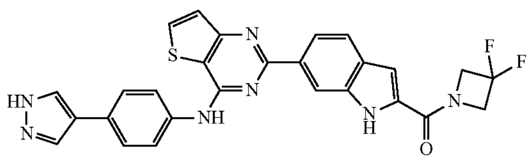 [SMILES: O=C(c1cc2ccc(-c3nc(Nc4ccc(-c5cn[nH]c5)cc4)c4sccc4n3)cc2[nH]1)N1CC(F)(F)C1] | (6-(4-((4-(1H-pyrazol-4-yl)phenyl)aminothieno[3,2-d]pyrimidin-2-yl)-1H-indol-2-yl)(3,3-difluoroazetidin-1-yl)methanone | (Reg-1-16) in step 3 of the synthetic route of TDI01434 in Example 34 was replaced with (Reg-1-33) | ¹H NMR (400 MHz, DMSO-d₆) δ 12.19 (s, 1H), 10.33 (s, 1H), 8.56 (s, 1H), 8.34 (d, J = 5.6 Hz, 1H), 8.19-8.08 (m, 3H), 7.90 (d, J = 8.8 Hz, 2H), 7.77 (dd, J = 21.2, 8.4 Hz, 3H), 7.58 (d, J = 5.6 Hz, 1H), 7.01 (s, 1H), 5.03 (s, 2H), 4.61 (s, 2H). MS m/z (ESI): 528.1 [M + H]. |
| TDI01473 | 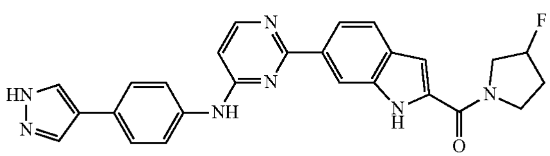 [SMILES: O=C(c1cc2ccc(-c3nccc(Nc4ccc(-c5cn[nH]c5)cc4)n3)cc2[nH]1)N1CCC(F)C1] | (6-(4-((4-(1H-pyrazol-4-yl)phenyl)amino)pyrimidin-2-yl)-1H-indol-2-yl)(3-fluoropyrrolidin-1-yl)methanone | in step 4 of the synthetic route of TDI01434 in Example 34 was replaced with | ¹H NMR (400 MHz, DMSO-d₆) δ 12.22 (s, 1H), 10.75 (s, 1H), 8.47 (s, 1H), 8.35 (d, J = 6.6 Hz, 1H), 8.09 (s, 2H), 7.97 (d, J = 8.4 Hz, 1H), 7.92-7.67 (m, 4H), 7.14 (d, J = 22.2 Hz, 1H), 6.87 (d, J = 6.6 Hz, 1H), 4.19-4.07 (m, 2H), 3.97-3.83 (m, 3H), 3.66 (s, 1H), 2.27 (d, J = 48.5 Hz, 2H). MS m/z (ESI): 468.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01477 | 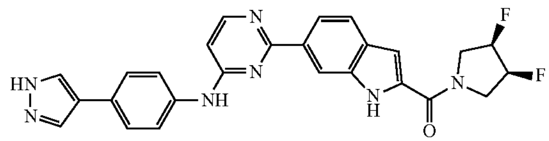 | (6-(4-((4-((1H-pyrazol-4-yl)phenyl)amino)pyrimidin-2-yl)-1H-indol-2-yl)((3S,4R)-3,4-difluoropyrrolidin-1-yl)methanone | in step 4 of the synthetic route of TDI01434 in Example 34 was replaced with | ¹H NMR (400 MHz, CD₃OD) δ 8.44 (s, 1H), 8.22 (d, J = 7.2 Hz, 1H), 8.03 (s, 2H), 7.94 (d, J = 8.5 Hz, 1H), 7.87 (d, J = 8.5 Hz, 1H), 7.76 (s, 4H), 7.17 (s, 1H), 6.92 (d, J = 7.2 Hz, 1H), 5.42 (m, 1H), 5.25 (m, 1H), 4.38 (m, 2H), 4.09 (m, 2H). MS m/z (ESI): 486.3 [M + H]. |
| TDI01478 | 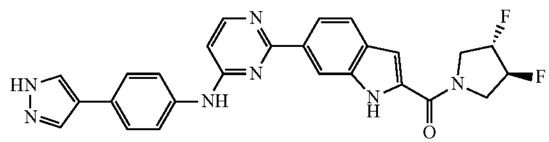 [SMILES: O=C(c1cc2ccc(-c3nccc(Nc4ccc(-c5cn[nH]c5)cc4)n3)cc2[nH]1)N1C[C@H](F)[C@@H](F)C1] | (6-(4-((4-((1H-pyrazol-4-yl)phenyl)amino)pyrimidin-2-yl)-1H-indol-2-yl)((3S,4S)-3,4-difluoropyrrolidin-1-yl)methanone | in step 4 of the synthetic route of TDI01434 in Example 34 was replaced with | ¹H NMR (400 MHz, CD₃OD) δ 8.52 (s, 1H), 8.29 (d, J = 6.0 Hz, 1H), 8.12 (dd, J = 8.5, 1.4 Hz, 1H), 7.96 (s, 2H), 7.79 (dd, J = 15.2, 8.5 Hz, 3H), 7.64 (d, J = 8.7 Hz, 2H), 7.12 (s, 1H), 6.67 (d, J = 6.0 Hz, 1H), 5.36 (s, 2H), 4.28 (s, 2H), 4.05 (d, J = 18.3 Hz, 2H). MS m/z (ESI): 486.2 [M + H]. |
| TDI01485 | 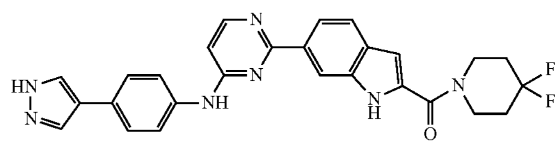 [SMILES: O=C(c1cc2ccc(-c3nccc(Nc4ccc(-c5cn[nH]c5)cc4)n3)cc2[nH]1)N1CCC(F)(F)CC1] | (6-(4-((4-((1H-pyrazol-4-yl)phenyl)amino)pyrimidin-2-yl)-1H-indol-2-yl)(4,4-difluoropiperidin-1-yl)methanone | in step 4 of the synthetic route of TDI01434 in Example 34 was replaced with | ¹H NMR (400 MHz, DMSO-d₆) δ 12.05 (s, 1H), 10.15 (s, 1H), 8.51 (s, 1H), 8.37 (d, J = 6.1 Hz, 1H), 8.10-8.04 (m, 3H), 7.82 (d, J = 8.4 Hz, 2H), 7.75 (d, J = 8.5 Hz, 1H), 7.68 (d, J = 8.5 Hz, 2H), 6.94 (s, 1H), 6.78 (d, J = 6.1 Hz, 1H), 3.87 (br. s, 4H), 2.12 (br. s, 4H). MS m/z (ESI): 500.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01486 | 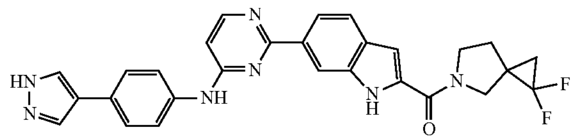 [SMILES: O=C(c1cc2ccc(-c3nccc(Nc4ccc(-c5cn[nH]c5)cc4)n3)cc2[nH]1)N1CCC2(C1)CC2(F)F] | (6-(4-((4-((1H-pyrazol-4-yl)phenyl)amino)pyrimidin-2-yl)-1H-indol-2-yl)(1,1-difluoro-5-azaspiro[2.4]heptan-5-yl)methanone | ![structure] in step 4 of the synthetic route of TDI01434 in Example 34 was replaced with ![structure]. | ¹H NMR (400 MHz, CD₃OD) δ 8.36 (s, 1H), 8.17 (d, J = 6.8 Hz, 1H), 8.02 (s, 2H), 7.93-7.58 (m, 6H), 7.06 (d, J = 14.4 Hz, 1H), 6.86 (d, J = 6.9 Hz, 1H), 4.18-3.69 (m, 4H), 2.21 (t, J = 32.1 Hz, 2H), 1.57 (s, 2H). MS m/z (ESI): 512.2 [M + H]. |
| TDI01487 | 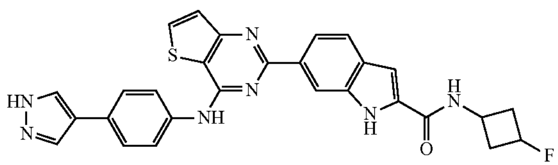 [SMILES: O=C(NC1CC(F)C1)c1cc2ccc(-c3nc(Nc4ccc(-c5cn[nH]c5)cc4)c4sccc4n3)cc2[nH]1] | 6-(4-((4-(1H-pyrazol-4-yl)phenyl)amino)thieno[3,2-d]pyrimidin-2-yl)-N-(3-fluorocyclobutyl)-1H-indole-2-carboxamide | (Reg-1-16) ![structure] and (Reg-1-33) ![structure] in step 3 [1H], of the synthetic route of TDI01434 in Example 34 was replaced with ![structure]; and in step 4 was replaced with ![structure]. | ¹H NMR (400 MHz, DMSO-d₆) δ 11.95 (s, 1H), 9.99 (s, 1H), 8.81 (s, 1H), 8.57 (s, 1H), 8.28 (s, 1H), 8.16 (s, 1H), 8.09 (s, 2H), 7.94 (d, J = 6.4 Hz, 2H), 7.76-7.71 (m, 3H), 7.56 (s, 1H), 7.24 (s, 1H), 5.39-5.25 (m, 1H), 4.97-4.84 (m, 1H), 4.69-4.57 (m, 1H), 4.09-4.03 (m, 1H), 2.83-2.73 (m, 2H). MS m/z (ESI): 524.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01489 | 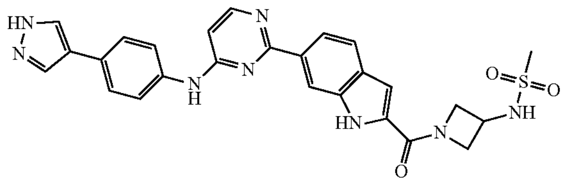 [SMILES: CS(=O)(=O)NC1CN(C(=O)c2cc3ccc(-c4nccc(Nc5ccc(-c6cn[nH]c6)cc5)n4)cc3[nH]2)C1] | N-(1-(6-(4-((1H-pyrazol-4-yl)phenyl)amino)pyrimidin-2-yl)-1H-indole-2-carbonyl)azetidin-3-yl)methanesulfonamide | in step 4 of the synthetic route of TDI01434 in Example 34 was replaced with | $^1$H NMR (400 MHz, CD$_3$OD) δ 8.43 (s, 1H), 8.22 (d, J = 6.9 Hz, 1H), 8.02 (s, 2H), 7.88 (q, J = 8.6 Hz, 2H), 7.73 (t, J = 8.2 Hz, 4H), 6.96 (s, 1H), 6.87 (d, J = 6.9 Hz, 1H), 4.52 (d, J = 31.4 Hz, 4H), 4.12 (s, 1H), 3.00 (s, 3H). MS m/z (ESI): 529.3 [M + H]. |
| TDI01490 | 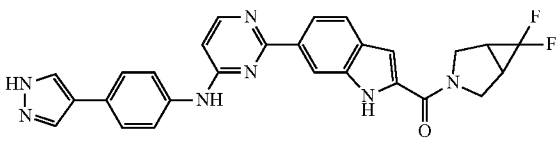 [SMILES: O=C(c1cc2ccc(-c3nccc(Nc4ccc(-c5cn[nH]c5)cc4)n3)cc2[nH]1)N1CC2C(C1)C2(F)F] | (6-(4-((1H-pyrazol-4-yl)phenyl)amino)pyrimidin-2-yl)-1H-indol-2-yl)(6,6-difluoro-3-azabicyclo[3.1.0]hexan-3-yl)methanone | in step 4 of the synthetic route of TDI01434 in Example 34 was replaced with | $^1$H NMR (400 MHz, DMSO-d$_6$) δ 12.08 (s, 1H), 10.30 (s, 1H), 8.50 (s, 1H), 8.35 (s, 1H), 8.06-8.03 (m, 3H), 7.81-7.80 (m, 3H), 7.70 (d, J = 8.0 Hz, 2H), 7.10 (s, 1H), 6.80 (d, J = 5.6 Hz, 1H), 4.25-4.20 (m, 2H), 4.156-4.13 (m, 1H), 3.90-3.86 (m, 1H), 2.79-2.74 (m 1H), 2.69-2.65 (m, 1H). MS m/z (ESI): 498.2 [M + H]. |
| TDI01495 | 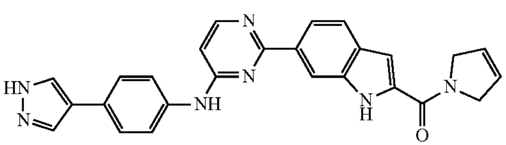 [SMILES: O=C(c1cc2ccc(-c3nccc(Nc4ccc(-c5cn[nH]c5)cc4)n3)cc2[nH]1)N1CC=CC1] | (6-(4-((1H-pyrazol-4-yl)phenyl)amino)pyrimidin-2-yl)-1H-indol-2-yl)(2,5-dihydro-1H-pyrrol-1-yl)methanone | in step 4 of the synthetic route of TDI01434 in Example 34 was replaced with | $^1$H NMR (400 MHz, DMSO-d$_6$) δ 11.93 (s, 1H), 9.67 (s, 1H), 8.59 (s, 1H), 8.38 (d, J = 5.8 Hz, 2H), 8.15 (d, J = 8.5 Hz, 1H), 8.04 (s, 1H), 7.85 (d, J = 8.3 Hz, 2H), 7.74 (d, J = 8.5 Hz, 1H), 7.66 (d, J = 8.5 Hz, 2H), 7.10 (s, 1H), 6.69 (d, J = 5.8 Hz, 1H), 6.03 (s, 2H), 4.70 (br. s, 2H), 4.40 (br, 2H). MS m/z (ESI): 448.2 [M + H]. |

TABLE 9-continued

| No. | Compound Structure | Compound Name | Starting material or regent different from that in the synthetic route of TDI01434 in Example 34 | Characterization Data |
|---|---|---|---|---|
| TDI01497 | 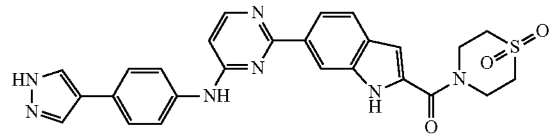 | (6-(4-((1H-pyrazol-4-yl)phenyl)amino)pyrimidin-2-yl)-1H-indol-2-yl)(1,1-dioxidothiomorpholino)methanone | in step 4 of the synthetic route of TDI01434 in Example 34 was replaced with | $^1$H NMR (400 MHz, DMSO-$d_6$) δ 12.13 (s, 1H), 10.41 (s, 1H), 8.48 (s, 1H), 8.36 (d, J = 6.4 Hz, 1H), 8.10-8.01 (m, 3H), 7.80 (d, J = 8.5 Hz, 3H), 7.70 (d, J = 8.6 Hz, 2H), 6.99 (d, J = 1.6 Hz, 1H), 6.81 (d, J = 6.4 Hz, 1H), 4.16 (br. s, 4H), 3.35 (br, 4H). MS m/z (ESI): 514.2 [M + H]. |
| TDI01498 | 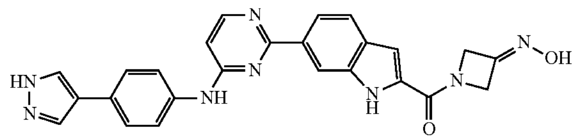 [SMILES: O=C(c1cc2ccc(-c3nccc(Nc4ccc(-c5cn[nH]c5)cc4)n3)cc2[nH]1)N1CC(=NO)C1] | (6-(4-((1H-pyrazol-4-yl)phenyl)amino)pyrimidin-2-yl)(3-(hydroxyimino)azetidin-1-yl)methanone | in step 4 of the synthetic route of TDI01434 in Example 34 was replaced with | $^1$H NMR (400 MHz, DMSO-$d_6$) δ 8.44 (s, 1H), 8.20 (d, J = 8.0 Hz, 1H), 8.04 (s, 2H), 7.90-7.86 (m, 3H), 7.74-7.72 (m, 3H), 7.03 (d, J = 12.0 Hz, 1H), 6.92 (d, J = 8.0 Hz, 1H), 5.83-5.81 (m, 4H). MS m/z (ESI): 465.2 [M + H]. |

Example 35: preparation of 1-(5-(4-((1H-indazol-5-yl)amino)pyrimidin-2-yl)isoindolin-2-yl)-2-(dimethylamino)ethan-1-one (TDI01364)

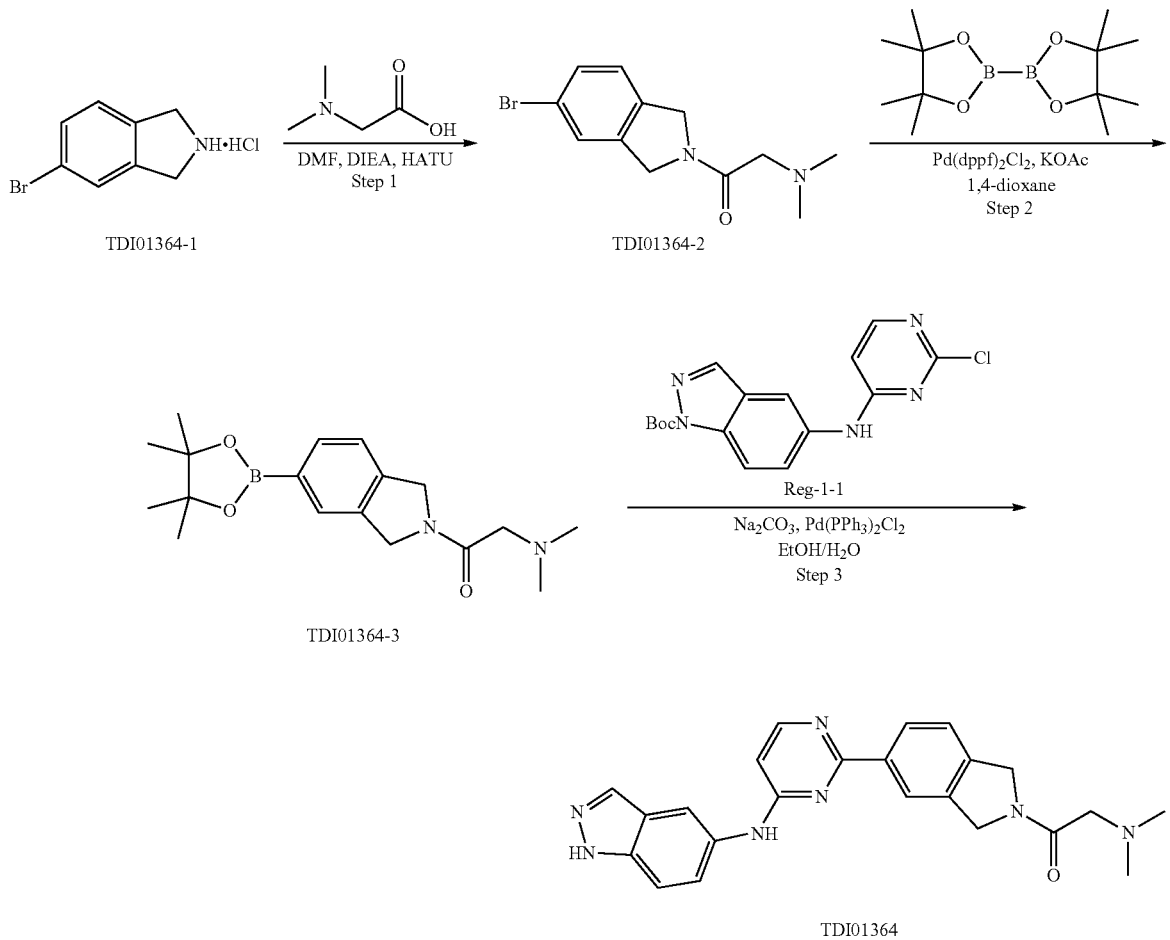

Step 1:

Compound TDI01364-1 (1.36 g, 5.82 mmol) and N,N-dimethylaminoacetic acid (500 mg, 4.85 mmol) were dissolved in N,N-dimethylformamide (50 mL), HATU (2.22 g, 5.82 mmol) and diisopropylethylamine (2.5 g, 19.4 mmol) were added, and the reaction was performed at room temperature overnight. LC-MS indicated the reaction was complete. The reaction solution was dissolved in ethyl acetate (250 mL), washed sequentially with water (250 mL×3) and saturated brine (250 mL×2), and the organic phase was dried over anhydrous sodium sulfate, and concentrated to afford compound TDI01364-2 (1.05 g, light yellow oil).

$^1$H NMR (400 MHz, DMSO-$d_6$) δ 7.59 (d, J=6.4 Hz, 1H), 7.48 (d, J=8.0 Hz, 1H), 7.34-7.30 (m, 1H), 4.87 (d, J=16.0 Hz, 2H), 4.62 (d, J=16.8 Hz, 2H), 3.15 (s, 2H), 2.25 (s, 6H). MS m/z (ESI): 283.1 [M+H].

Step 2:

Compound TDI01364-2 (1.0 g, 3.55 mmol) and bis(pinacolato)diboron (1.8 g, 7.09 mmol) were dissolved in 1,4-dioxane (100 mL), potassium acetate (1.04 g, 10.64 mmol) and Pd(dppf)Cl$_2$ (125 mg, 0.18 mmol) were added, purge with argon was performed for 3 times, and the reaction was placed in an oil bath at 80° C. overnight. LC-MS indicated the reaction was complete. The reaction solution was cooled to room temperature, concentrated under reduced pressure, and the residue was purified by column chromatography (dichloromethane:methanol=1:0 to 10:1), to afford compound TDI01364-3 (400 mg, light yellow oil).

$^1$H NMR (400 MHz, CDCl$_3$) δ 7.72 (d, J=14.4 Hz, 2H), 7.30 (d, J=7.2 Hz, 1H), 4.89 (d, J=18.4 Hz, 2H), 4.82 (d, J=4.8 Hz, 2H), 3.25 (s, 2H), 2.42 (s, 6H), 1.35 (s, 12H). MS m/z (ESI): 331.4 [M+H].

Step 3:

Compound TDI01364-3 (115 mg, 0.35 mmol) and Intermediate Reg-1-1 (100 mg, 0.29 mmol) were dissolved in a mixed solution of ethanol/water (10:1) (5 mL), sodium carbonate (62 mg, 0.58 mmol) and Pd(PPh$_3$)$_2$Cl$_2$ (21 mg, 0.03 mmol) were added, purge with argon was performed for 3 times, and the reaction was performed under microwave at 110° C. for 2 hours. LC-MS indicated the reaction was complete. The reaction solution was cooled to room temperature, and concentrated under reduced pressure. The residue was dissolved in dimethyl sulfoxide (5 mL), filtered, and the filtrate was purified by liquid chromatography, to afford compound TDI01364 (21.4 mg, white solid).

$^1$H NMR (400 MHz, DMSO-$d_6$) δ 13.02 (s, 1H), 9.62 (s, 1H), 8.36-8.30 (m, 2H), 8.28 (d, J=5.6 Hz, 1H), 8.18 (s, 1H), 8.09 (s, 1H), 7.57 (t, J=7.2 Hz, 2H), 7.48 (t, J=8.8 Hz, 1H), 6.68 (d, J=5.6 Hz, 1H), 4.97 (s, 2H), 4.73 (d, J=14.4 Hz, 2H), 3.18 (d, J=7.2 Hz, 2H), 2.27 (d, J=5.6 Hz, 6H). MS m/z (ESI): 414.2 [M+H].

Example 36: preparation of 5-(4-((1H-indazol-5-yl)amino)pyridin-2-yl)-N-(pyridazin-4-yl)-1H-indole-2-carboxamide (TDI01384)

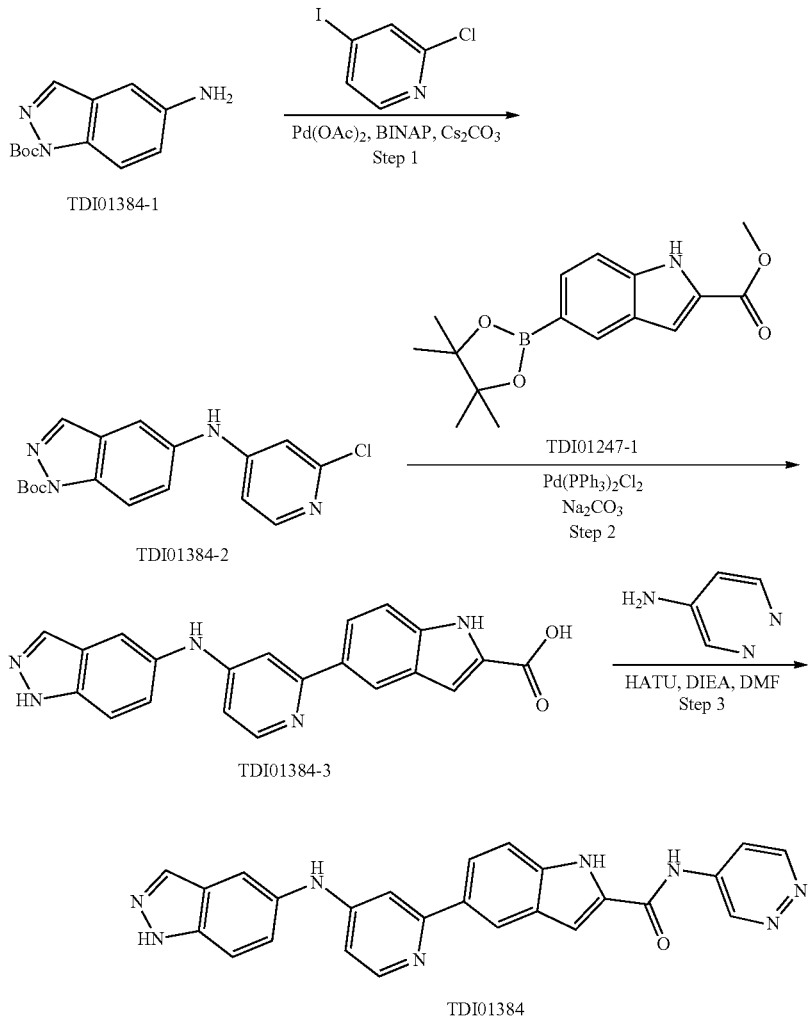

Step 1:
Compound TDI01384-1 (500 mg, 2.14 mmol), 2-chloro-4-iodopyridine (332 mg, 1.62 mmol), cesium carbonate (2.09 g, 6.42 mmol) and BINAP (68.49 mg, 0.11 mmol) were dissolved in toluene (20 mL), palladium acetate (24.70 mg, 0.11 mmol) was then added, and the reaction was placed in an oil bath at 100° C. for 4 hours. LC-MS indicated the reaction was complete. The reaction solution was cooled to room temperature, filtered, and separated by column chromatography (dichloromethane:methanol=100:1~10:1) to afford compound TDI01384-2 (170 mg, 23.0%, yellow solid). MS m/z (ESI): 345.1 [M+H].

Step 2:
Compound TDI01384-2 (170 mg, 0.493 mmol) and Intermediate TDI01247-1 (178.17 mg, 0.591 mmol) in Example 18 were dissolved in a mixed solution of ethanol/water (8:1) (45 mL), sodium carbonate (156.77 mg, 1.48 mmol) and Pd(PPh$_3$)$_2$Cl$_2$ (17.30 mg, 0.0247 mmol) were added, purge with argon was performed for 3 times, and the reaction was placed in an oil bath at 110° C. overnight. LC-MS indicated the reaction was complete. The reaction solution was cooled to room temperature, concentrated under reduced pressure, the residue was diluted with water (40 mL), and the pH was adjusted with 6N HCl to 1. A large amount of solid precipitated, which was filtered, and slurried with methanol to afford compound TDI01384-3 (100 mg, yellow solid, yield 43.20%). MS m/z (ESI): 370.1 [M+H].

Step 3:
Compound TDI01384-3 (90.0 mg, 0.243 mmol) was dissolved in N,N-dimethylformamide (5 mL), HATU (110 mg, 0.29 mmol) and diisopropylethylamine (94.22 mg, 0.73 mmol) were added, and the reaction was performed at room temperature for 30 min. Compound 4-aminopyridazine (27.81 mg, 0.29 mmol) was then added, and the reaction was continued at room temperature overnight. MS indicated the reaction was complete. The reaction solution was concentrated, and the solide was purified by high performance liquid chromatography (trifluoroacetic acid) to afford compound TDI01384 (13.32 mg, yellow solid, yield 12.24%).

$^1$H NMR (400 MHz, CD$_3$OD) δ 9.59 (s, 1H), 9.18 (d, J=6.5 Hz, 1H), 8.55 (s, 1H), 8.13 (s, 2H), 7.96-7.91 (m, 1H), 7.84 (s, 1H), 7.72 (d, J=8.6 Hz, 1H), 7.58 (s, 1H), 7.47 (d, J=7.4 Hz, 2H), 7.41 (d, J=7.4 Hz, 1H), 7.35 (d, J=8.2 Hz, 1H), 7.08-7.01 (m, 1H). MS m/z (ESI): 447.1 [M+H].

Example 37: preparation of 9-(6-(4-(OH-indazol-5-yl)amino)pyrimidin-2-yl)-1H-indole-2-carbonyl)-3,9-diaz-aspiro[5.5]undecane-3-carboximidamide (TDI01400)

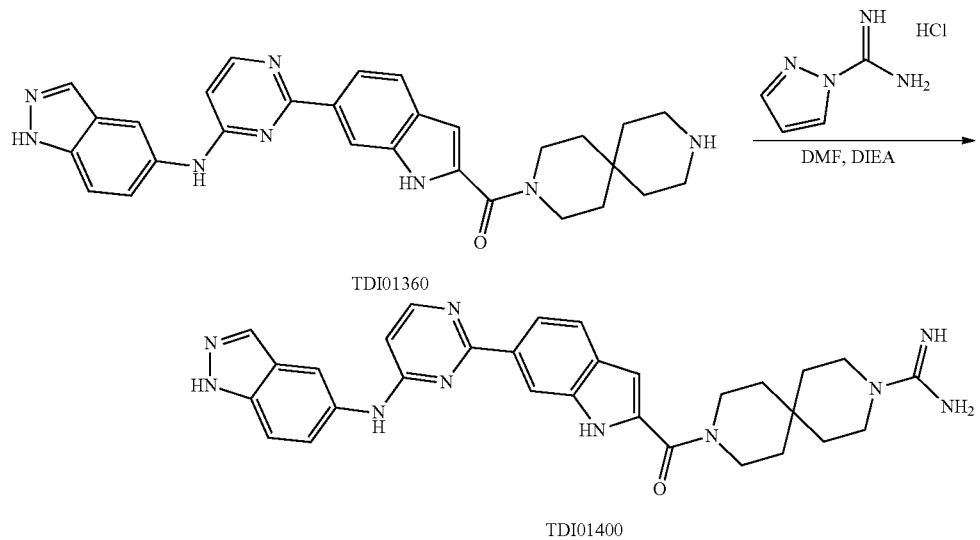

Compound TDI01360 (30.00 mg, 0.059 mmol) in Table 1 of Example 1, compound 1H-pyrazolecarboximidamide (10.42 mg, 0.071 mmol) and diisopropylethylamine (23 mg, 0.178 mmol) were dissolved in N,N-dimethylformamide (1 mL), and the reaction was stirred at ambient temperature overnight. The reaction solution was concentrated under reduced pressure, separated by preparative liquid chromatography, and lyophilized to afford target compound (8.04 mg, yield 24.25%).

$^1$H NMR (400 MHz, CD$_3$OD) δ 8.36 (s, 1H), 8.19 (d, J=7.2 Hz, 1H), 8.16 (s, 1H), 7.98 (s, 1H), 7.86 (s, 2H), 7.69 (s, 2H), 6.92 (s, 2H), 3.86 (s, 4H), 3.59-3.40 (m, 4H), 1.70 (s, 6H), 1.37 (s, 2H). MS m/z (ESI): 529.3 [M+H].

Example 38: preparation of (3,3-difluoroazetidin-1-yl)(1-methyl-6-(4-(04-(1-methyl-1H-pyrazol-4-yl)phenyl)amino)pyrimidin-2-yl)-1H-indol-2-yl)methanone (TDI01698)

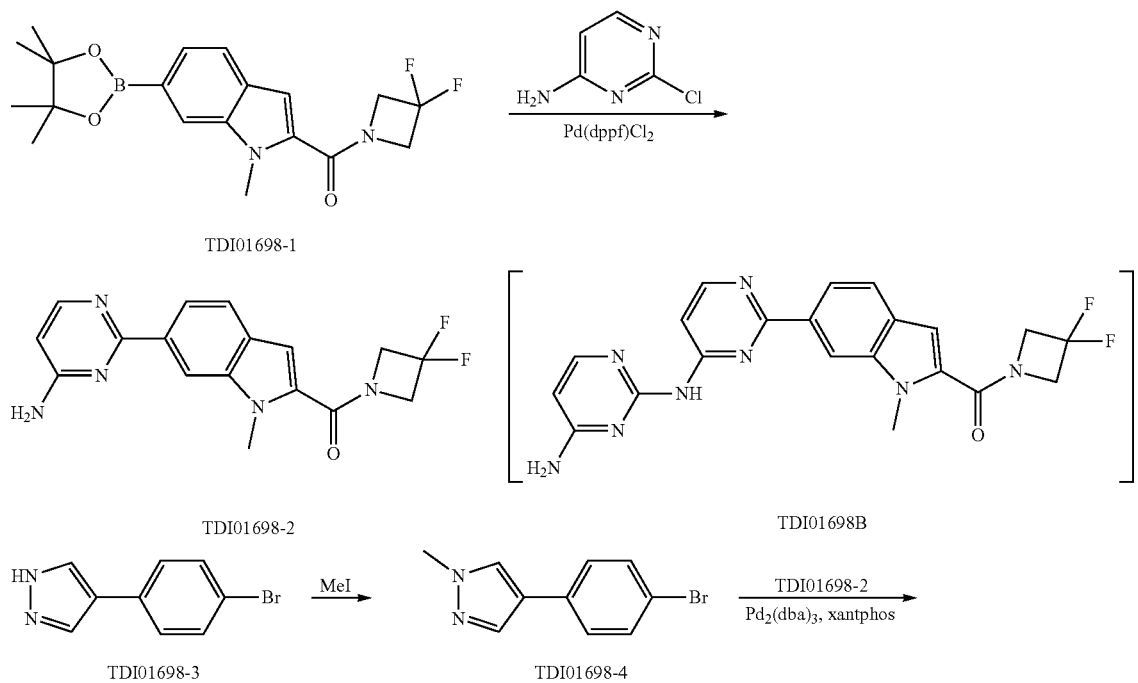

-continued

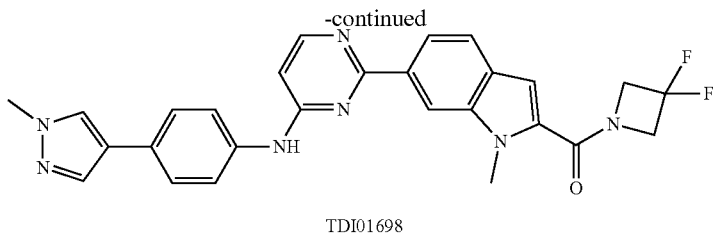

TDI01698

Compound TDI01698-1 was synthesized according to step 1 to step 3 of Example 46.

Step 1:

Compound TDI01698-1 (5 g, 13.3 mmol), 2-chloro-4-aminopyrimidine (1.7 g, 13 mmol) and potassium carbonate (5.38 g, 39 mmol) were mixed in a mixed solvent of 1,4-dioxane (100 mL) and water (10 mL), Pd(dppf)Cl$_2$ (952 mg, 1.3 mmol) was added, the flask was purged with N$_2$ 3 times, and the reaction solution was heated to reflux and reacted overnight. LC-MS indicated the product was a mixture of target product TDI01698-2 and byproduct TDI01699B. The reaction solution was cooled to room temperature, and filtered to remove salt impurities. The filtrate was concentrated under reduced pressure, and the crude product was separated by preparative flash chromatography (methanol/dichloromethane =0~4%), to afford compound TDI01698-2 (0.36 g, light brown solid, gross yield: 8%) and TDI01699B (0.1 g, light yellow solid, gross yield: 1.8%).

TDI01698-2: $^1$H NMR (400 MHz, DMSO-d$_6$) δ 8.45 (s, 1H), 8.19 (d, J=5.7 Hz, 1H), 8.14 (d, J=8.4 Hz, 1H), 7.66 (d, J=8.5 Hz, 1H), 7.04 (s, 1H), 6.90 (s, 2H), 6.36 (d, J=5.8 Hz, 1H), 4.84 (s, 2H), 4.58 (s, 2H), 4.00 (s, 3H).

Step 2:

Compound TDI01698-3 (223 mg, 1 mmol) was dissolved in DMF (3 mL), and cooled to 0° C. in an ice-water bath under protection of N$_2$. NaH (60%, 60 mg, 1.5 mmol) was added, and the reaction was stirred for 0.5 hour before addition of iodomethane (213 mg, 1.5 mmol). The reaction was stirred at room temperature overnight. LC-MS indicated the reaction was complete. Water (20 mL) was added, the mixture was stirred for 10 minutes, and filtered. The filter cake was washed with water (10 mL), dried under reduced pressure to afford compound TDI01698-4 (0.2 g, brown solid, yield: 84%).

$^1$H NMR (400 MHz, DMSO-d$_6$) δ 8.17 (s, 1H), 7.88 (s, 1H), 7.52 (s, 4H), 3.85 (s, 3H).

Step 3:

Compound TDI01698-2 (70 mg, 0.2 mmol), compound TDI01698-4 (48 mg, 0.2 mmol) and cesium carbonate (196 mg, 0.6 mmol) were mixed in 1,4-dioxane (3 mL), Pd$_2$(dba)$_3$ (37 mg, 0.04 mmol) and Xantphos (69 mg, 0.12 mmol) were added, the flask was purged with N$_2$ 3 times, and the reaction solution was heated to reflux and reacted overnight. LC-MS indicated the reaction was complete. The reaction solution was cooled to room temperature, and filtered to remove salt impurities. The filtrate was concentrated under reduced pressure, and the crude product was separated by preparative HPLC (acetonitrile/water (0.5% TFA)=20-60%, 30 minutes), to afford compound TDI01698 (10 mg, yellow solid, yield: 8%).

$^1$H NMR (400 MHz, DMSO-d$_6$) δ 10.59 (s, 1H), 8.52 (s, 1H), 8.40 (d, J=8.4 Hz, 1H), 8.14 (s, 1H), 8.06 (d, J=8.4 Hz, 1H), 7.88 (s, 1H), 7.82 (d, J=8.3 Hz, 1H), 7.77 (d, J=7.4 Hz, 2H), 7.66 (d, J=8.3 Hz, 2H), 7.12 (s, 1H), 6.85 (d, J=6.7 Hz, 1H), 4.89 (s, 2H), 4.57 (s, 2H), 4.05 (s, 3H), 3.88 (s, 3H). MS m/z (ESI): 500.1 [M+H].

Example 39: preparation of 1-(6-(4-((4-(1H-pyrazol-4-yl)phenyl)amino)pyrimidin-2-yl)-1H-indole-2-carbonyl)azetidine-3-carboxylic acid (TDI01466)

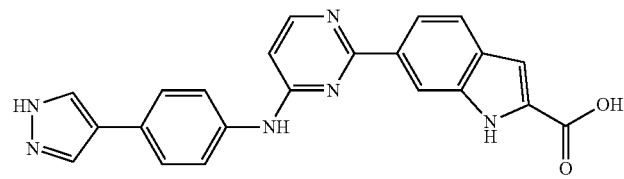

TDI01434-1

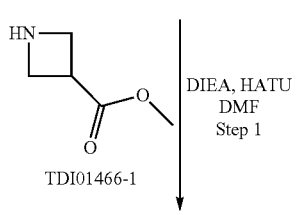

TDI01466-1

DIEA, HATU
DMF
Step 1

-continued

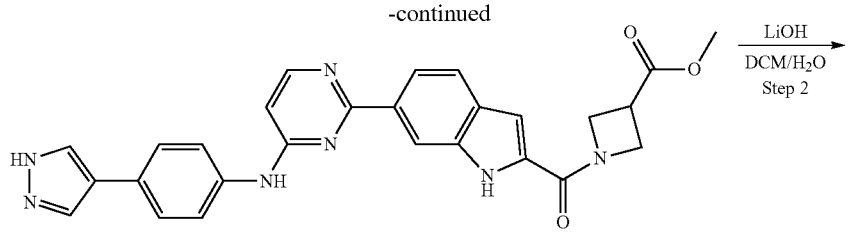

TDI01466-2

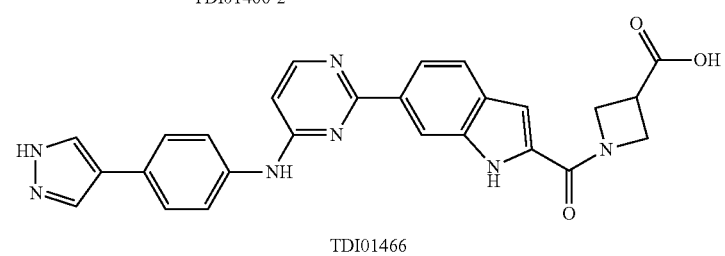

TDI01466

Step 1:
Compound TDI01466-2 was obtained by reacting Intermediate TDI01434-1, as a starting material, with Intermediate TDI01466-1, according to the synthetic method in step 5 of the synthetic process of TDI01434.

$^1$H NMR (400 MHz, DMSO-d$_6$) δ 12.10 (s, 1H), 8.54 (s, 1H), 8.36 (d, J=6.2 Hz, 1H), 8.14-8.02 (m, 3H), 7.92-7.64 (m, 5H), 6.91 (d, J=37.8 Hz, 2H), 4.74 (d, J=8.5 Hz, 1H), 4.61 (s, 1H), 4.31 (t, J=9.3 Hz, 1H), 4.15 (s, 1H), 3.61-3.59 (m, 1H), 3.38 (s, 3H). MS m/z (ESI): 494.2 [M+H].

Step 2:
Compound TDI01466-2 (50 mg, 0.1 mmol) was dissolved in (dichloromethane (10 mL)/water (5 mL)), LiOH (42 mg, 1.0 mmol) was then added, and the reaction was performed at 50° C. for 1 hour. LC-MS indicated the reaction was complete. The solvent was rotary evaporated to dryness, and 5 mL water was added. The mixture was filtered, and purified by preparative chromatography to afford compound TDI01466 (15 mg, yellow solid, 30.0%).

$^1$H NMR (400 MHz, DMSO-d$_6$) δ 12.26 (s, 1H), 10.75 (s, 1H), 8.46 (s, 1H), 8.35 (s, 1H), 8.09 (s, 2H), 7.97 (d, J=7.5 Hz, 1H), 7.83-7.74 (m, 5H), 6.99 (s, 1H), 6.87 (s, 1H), 4.75 (s, 1H), 4.62 (s, 1H), 4.31 (s, 1H), 4.16 (s, 1H), 3.60-3.59 (m, 1H). MS m/z (ESI): 480.2 [M+H].

Example 40: preparation of (5-(4-(04-(1H-pyrazol-4-yl)phenyl)amino)pyrimidin-2-yl)isoindolin-2-yl)(3,3-difluoroazetidin-1-yl)methanone (TDI01467)

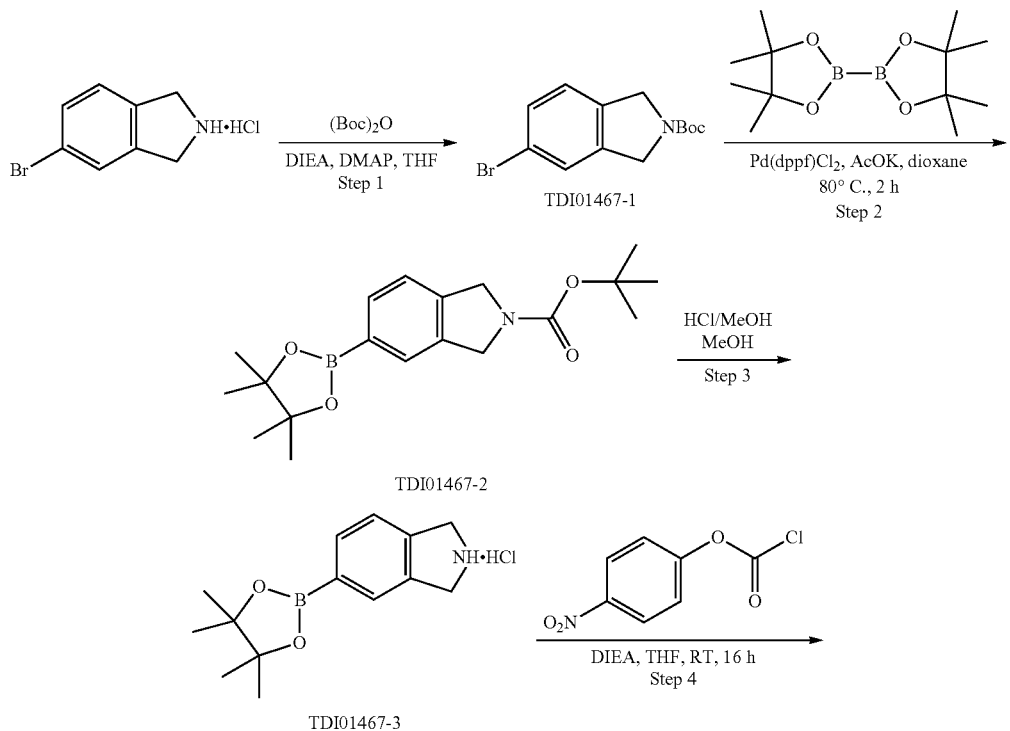

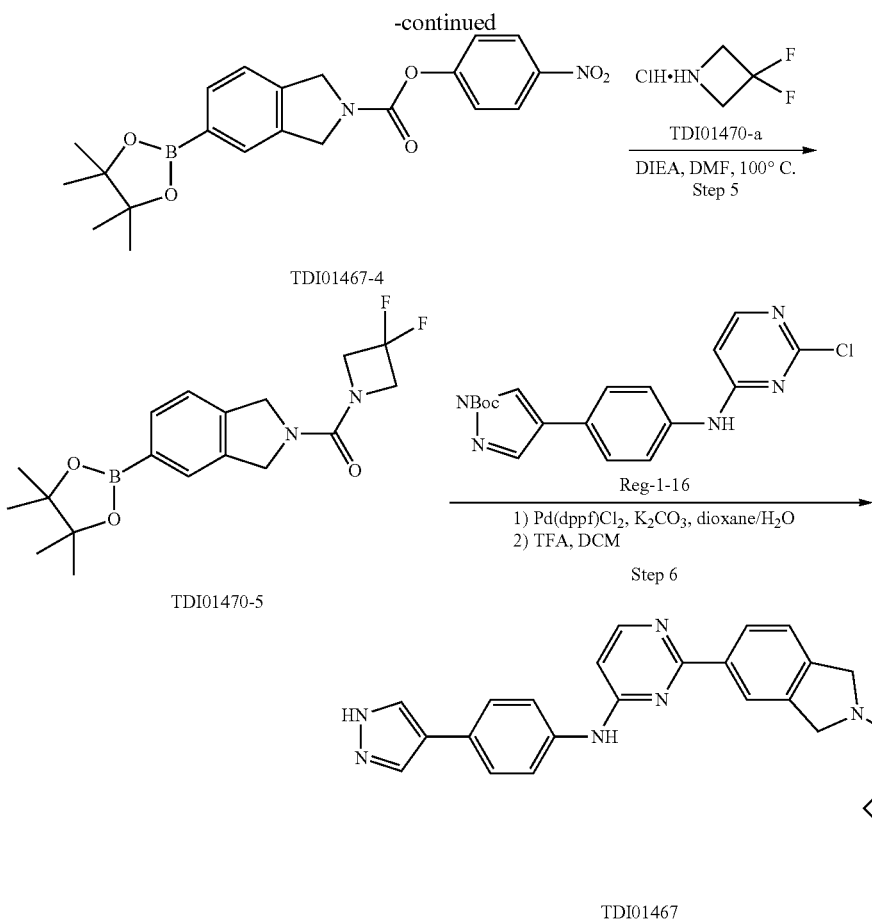

Step 1:

Compound 5-bromoisoindoline hydrochloride (5.0 g, 21.3 mmol) was dissolved in tetrahydrofuran (100 mL), di-tert-butyl dicarbonate (9.3 g, 42.6 mmol), diisopropylethylamine (11.0 g, 85.2 mmol) and 4-dimethylaminopyridine (123 mg, 1.06 mmol) were added, and the reaction was performed at room temperature overnight. Thin layer chromatography (petroleum ether/ethyl acetate=5:1) indicated the reaction was complete. The reaction solution was diluted with ethyl acetate (100 mL), and washed sequentially with saturated ammonium chloride (150 mL×2) and saturated sodium chloride (200 mL×2). The organic phase was dried over anhydrous sodium sulfate, filtered, and concentrated. The residue was purified by column chromatography (petroleum ether/ethyl acetate=10:1) to afford compound TDI01467-1 (2.7 g, white solid, yield 42.9%).

$^1$H NMR (400 MHz, CDCl$_3$) δ 7.42-7.36 (m, 2H), 7.15-7.08 (m, 1H), 4.63 (t, J=15.2 Hz, 4H), 1.51 (s, 9H).

Step 2:

Compound TDI01467-1 (2.70 g, 9.06 mmol) and bis(pinacolato)diboron (3.45 g, 13.6 mmol) were dissolved in 1,4-dioxane (100 mL), potassium acetate (2.67 g, 27.2 mmol) and Pd(dppf)Cl$_2$ (666 mg, 0.91 mmol) were added, purge with argon was performed for 3 times, and the reaction was placed in an oil bath at 100° C. overnight. Thin layer chromatography (petroleum ether/ethyl acetate=5:1) indicated the reaction was complete. The reaction solution was cooled to room temperature, and concentrated under reduced pressure. The residue was purified by column chromatography (petroleum ether/ethyl acetate=10:1) to afford compound TDI01467-2 ((3.0 g, white solid, yield 96.1%)

$^1$H NMR (400 MHz, CDCl$_3$) δ 7.72 (s, 1H), 7.71-7.65 (m, 1H), 7.29-7.23 (m, 1H), 4.70-4.62 (m, 4H), 1.52 (s, 9H), 1.35 (s, 12H).

Step 3:

Compound TDI01467-2 (1.00 g, 2.89 mmol) was dissolved in methanol(10 mL), a 3M hydrochloric acid methanol solution (10 mL) was added, and the reaction solution was stirred at room temperature overnight. Thin layer chromatography (petroleum ether/ethyl acetate=5:1) indicated the reaction was complete. The reaction solution was concentrated under reduced pressure to afford compound TDI01467-3 (800 mg, yellow solid, crude product).

$^1$H NMR (400 MHz, DMSO-d$_6$) δ9.95 (s, 1H), 7.71 (s, 1H), 7.65 (d, J=7.6 Hz, 1H), 7.42 (d, J=7.6 Hz, 1H), 4.54-4.47 (m, 4H), 1.17 (s, 12H).

Step 4:

Compound TDI01467-3 (800 mg, 2.84 mmol) was dissolved in tetrahydrofuran (20 mL), diisopropylethylamine (1.47 g, 11.4 mmol) was added, 4-nitrophenyl carbonochloridate (570 mg, 2.84 mmol) was added under ice bath cooling, and the reaction was continued at room temperature overnight. LC-MS indicated the reaction was complete. The reaction solution was diluted with ethyl acetate (50 mL), and successively washed with water (40 mL×2), saturated ammonium chloride (50 mL×2) and saturated sodium chloride (80 mL×2). The organic phase was dried over anhydrous sodium sulfate, filtered, and concentrated. The crude product was separated by column chromatography (petroleum ether/ethyl acetate=10:1) to afford compound TDI01467-4 (670 mg, yellow solid, yield 57.6%)

$^1$H NMR (400 MHz, CDCl$_3$) δ 8.32-8.25 (m, 2H), 8.19-8.14 (m, 1H), 7.42-7.37 (m, 2H), 7.36-7.29 (m, 1H), 6.91-6.86 (m, 1H), 4.95 (d, J=15.2 Hz, 2H), 4.85 (d, J=8.0 Hz, 2H), 1.37 (s, 12H). MS m/z (ESI): 411.2 [M+H].

Step 5:

Compound TDI01467-4 (400 mg, 0.98 mmol) and Intermediate TDI01470-a (151 mg, 1.17 mmol) were dissolved in N,N-dimethylformamide (10 mL), diisopropylethylamine (506 mg, 3.92 mmol) was added, and the reaction was performed in an oil bath at 100° C. for 24 hours. LC-MS indicated the reaction was complete. The reaction solution was diluted with ethyl acetate (40 mL), and successively washed with water (50 mL×2), saturated ammonium chloride (80 mL×2) and saturated sodium chloride (100 mL×2). The organic phase was dried over anhydrous sodium sulfate, filtered, and concentrated. The crude product was separated by column chromatography (petroleum ether/ethyl acetate=3:1) to afford compound TDI01467-5 (140 mg, yellow solid, yield 39.4%).

$^1$H NMR (400 MHz, CDCl$_3$) δ 7.74 (d, J=7.6 Hz, 1H), 7.71 (s, 1H), 7.28 (s, 1H), 4.74 (s, 2H), 4.72 (s, 2H), 4.39 (t, J=12.4 Hz, 4H), 1.35 (s, 12H). MS m/z (ESI): 365.1 [M+H].

Step 6:

Intermediate compound Reg-1-16 (90 mg, 0.174 mmol) and TDI01467-5 (95 mg, 0.262 mmol) were dissolved in a mixed solution of dioxane/water (10:1) (8.8 mL), potassium carbonate (48 mg, 0.348 mmol) and Pd(dppf)Cl$_2$ (12.7 mg, 0.017 mmol) were added, purge with argon was performed for 3 times, and the reaction was placed in an oil bath at 100° C. overnight. LC-MS indicated the starting material reacted completely. The reaction solution was concentrated under reduced pressure, the crude product was dissolved in dichloromethane (6 mL), trifluoroacetic acid (2 mL) was added, and the reaction was performed at room temperature for 2 hours. LC-MS indicated the reaction was complete. The reaction solution was concentrated under reduced pressure, and the crude product was purified by high performance liquid chromatography to afford compound TDI01467 (11.71 mg, yellow solid, yield 20.9%).

$^1$H NMR (400 MHz, DMSO-d$_6$) δ 10.25 (s, 1H), 8.38 (d, J=6.0 Hz, 1H), 8.24 (d, J=7.2 Hz, 2H), 8.06 (d, J=6.0 Hz, 2H), 7.75 (d, J=6.4 Hz, 2H), 7.68 (d, J=7.2 Hz, 2H), 7.53 (d, J=7.6 Hz, 1H), 6.82 (d, J=6.4 Hz, 1H), 4.77 (d, J=6.4 Hz, 4H), 4.49-4.41 (m, 4H). MS m/z (ESI): 474.3 [M+H].

Example 41: preparation of (5-(4-((1H-indazol-5-yl)amino)pyrimidin-2-yl)isoindolin-2-yl)(pyridin-4-yl)methanone (TDI01544)

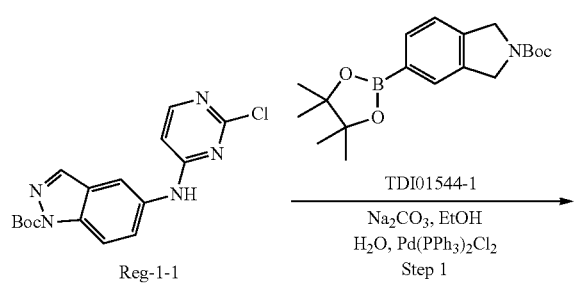

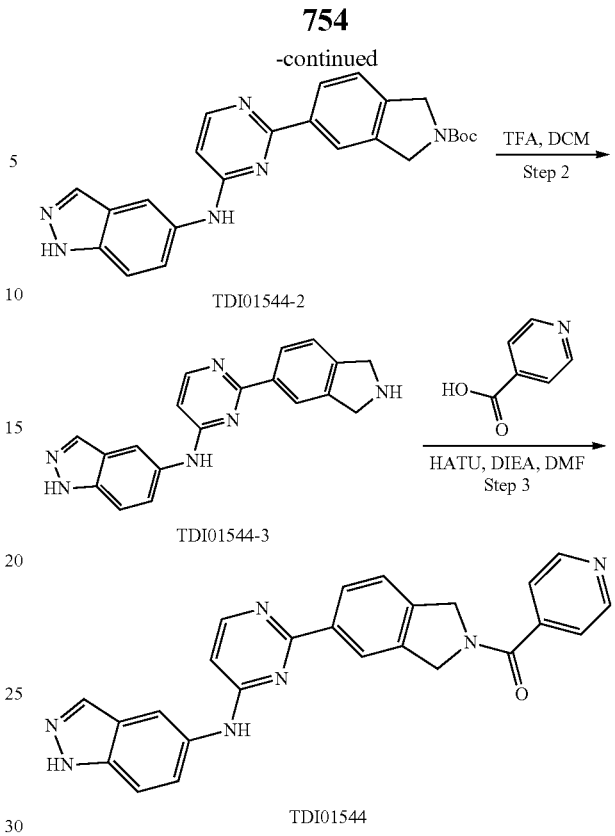

Step 1:

Intermediate compound Reg-1-1 (500 mg, 1.45 mmol) and TDI01544-1 (599 mg, 1.74 mmol) were dissolved in ethanol (30 mL) and water (3 mL), sodium carbonate (459.77 mg, 4.34 mmol) and Pd(PPh$_3$)$_2$Cl$_2$ (50.75 mg, 0.072 mmol) were added, and the reaction was refluxed at 110° C. under protection of nitrogen. LC-MS indicated the reaction was complete. The reaction solution was cooled to room temperature, and filtered through Celite. The filtrate was concentrated, and separated by column chromatography (dichloromethane:methanol=100:1-10:1) to afford compound TDI01544-2 (600 mg, yield 78.50%).

$^1$H NMR (400 MHz, CDCl$_3$) δ 8.35 (d, J=5.9 Hz, 1H), 8.33-8.19 (m, 2H), 8.08 (s, 1H), 7.76 (d, J=4.6 Hz, 1H), 7.48 (t, J=14.6 Hz, 2H), 7.39-7.32 (m, 1H), 7.28 (d, J=5.7 Hz, 1H), 4.70 (dd, J=18.6, 8.9 Hz, 4H), 1.54 (s, 9H). MS m/z ESI: 429.3 [M+H].

Step 2:

Compound TDI01544-2 (0.6 g, 1.41 mmol) was dissolved in dichloromethane (20 mL), trifluoroacetic acid (2 mL) was then added, and the reaction was stirred at 30° C. for 3 hours. LC-MS indicated the reaction was complete. The reaction solution was rotary evaporated to dryness to afford TDI01544-3 (0.35 g, brown oil, yield 76.12%).

$^1$H NMR (400 MHz, DMSO-d$_6$) δ8.38 (d, J=6.7 Hz, 1H), 8.22 (d, J=11.8 Hz, 2H), 8.18-8.09 (m, 2H), 7.65 (d, J=9.6 Hz, 2H), 7.56 (d, J=9.0 Hz, 1H), 6.89 (d, J=6.7 Hz, 1H), 4.72-4.57 (m, 4H). MS m/z ESI: 329.1 [M+H].

Step 3:

Compound TDI01544-3 (50 mg, 0.152 mmol) and 4-pyridinecarboxy acid (22.41 mg, 0.182 mmol) were dissolved in N,N-dimethylformamide (5 mL), HATU (69.16 mg, 0.182 mmol) and diisopropylethylamine (58.94 mg, 0.456 mmol) were added, and the reaction was performed at room temperature for 1 hour. LC-MS indicated the reaction was complete. The solvent was evaporated off under reduced pressure, and the crude product was separated by high performance liquid chromatography to afford compound TDI01544 (4.04 mg, yellow solid, yield 6.12%).

$^1$H NMR (400 MHz, DMSO-d$_6$) δ 10.38 (s, 1H), 8.87 (s, 1H), 8.73 (s, 1H), 8.34 (dd, J=17.0, 10.2 Hz, 2H), 8.25-8.17 (m, 1H), 8.17-8.06 (m, 3H), 7.57 (ddd, J=42.5, 24.1, 8.5 Hz, 4H), 6.79 (t, J=6.6 Hz, 1H), 4.99 (d, J=9.7 Hz, 2H), 4.93 (d, J=11.8 Hz, 2H). MS m/z ESI: 434.2 [M+H].

The compound in following table 10 was prepared according to a method similar to that described in Example 41.

TABLE 10

| No. | Compound Structure | Compound Name | Starting material or regent different from that in Example 41 | Characterization Data |
|---|---|---|---|---|
| TDI01545 | 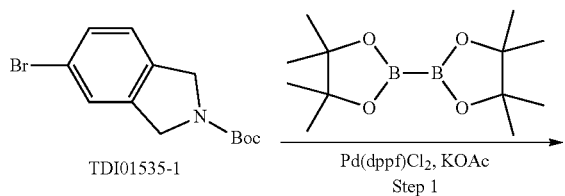 | (5-(4-((1H-indazol-5-yl)amino)pyrimidin-2-yl)isoindolin-2-yl)(pyridin-3-yl)methanone | in step 3 of Example 41 was replaced with | $^1$H NMR (400 MHz, DMSO-d$_6$) δ 10.19 (d, J = 16.3 Hz, 1H), 8.79 (s, 3H), 8.35 (dd, J = 12.8, 5.5 Hz, 2H), 8.25 (dd, J = 12.0, 8.2 Hz, 1H), 8.16-8.09 (m, 2H), 7.83 (d, J = 5.3 Hz, 1H), 7.69-7.57 (m, 4H), 6.78 (t, J = 6.8 Hz, 1H), 4.97 (d, J = 10.8 Hz, 2H), 4.86 (d, J = 12.1 Hz, 2H). MS m/z (ESI): 434.2 [M + H]. |

Example 42: preparation of pyridin-4-yl 5-(4-((4-(1H-pyrazol-4-yl)phenyl)amino)pyrimidin-2-yl)isoindoline-2-carboxylate (TDI01535)

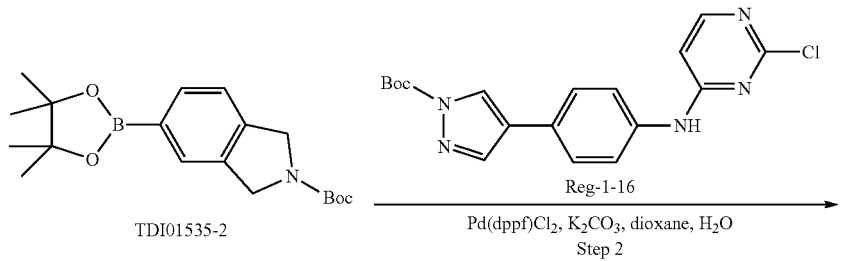

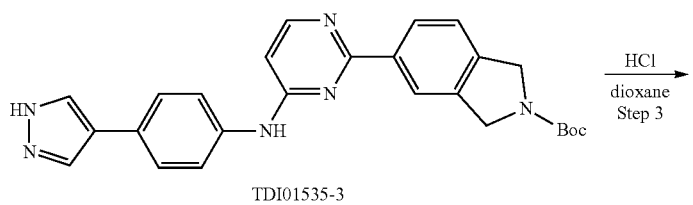

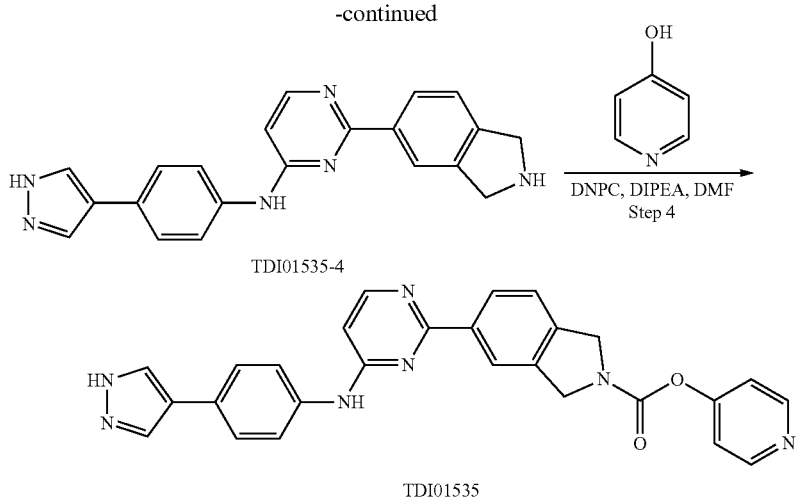

Step 1:

Compound TDI01535-1 (46 g, 0.15 mol) and bis(pinacolato)diboron (46 g, 0.18 mol) were dissolved in N,N-dimethylformamide (800 mL), potassium acetate (46 g, 0.47 mol) and Pd(dppf)Cl$_2$ (10 g, 14 mmol) were added, the flask was purged with nitrogen three times, and the reaction solution was stirred at 110° C. for 16 hours. LC-MS indicated the reaction was complete. The reaction solution was cooled to room temperature, and the reaction solvent was removed through rotary evaporation under vacuum. The residue was purified by column chromatography (petroleum ether:ethyl acetate=20:1 to 5:1) to afford compound TDI01535-2 (37 g, white solid, yield 73%).

$^1$H NMR (400 MHz, CDCl$_3$) δ 7.67-7.72 (m, 2H), 7.22-7.29 (m, 1H), 4.62-4.69 (m, 4H), 1.52 (s, 9H), 1.35 (s, 12H), MS m/z (ESI): 367.9 [M+Na].

Step 2:

Compound TDI01535-2 (5.17 g, 13.9 mmol) and compound Reg-1-16 (4.8 g, 13.9 mmol) were dissolved in a mixed solution of dioxane (100 mL) and water (10 mL), potassium carbonate (5.76 g, 41.7 mmol) was added, and the flask was purged with nitrogen three times. Pd(dppf)Cl$_2$ (3.05 g, 4.17 mmol) was added, the flask was purged with nitrogen three times again, and the reaction solution was stirred at 110° C. for 16 h. LC-MS indicated the reaction was complete. The reaction solution was cooled to room temperature, and the reaction solvent was removed through rotary evaporation under vacuum. The residue was purified by column chromatography (petroleum ether:ethyl acetate=4:1 to pure ethyl acetate) to afford compound TDI01535-3 (2.5 g, off-white solid).

$^1$H NMR (400 MHz, DMSO-d$_6$) δ 9.87 (s, 1H), 8.38 (d, J=6.0 Hz, 1H), 8.29-8.24 (m, 2H), 8.05 (s, 2H), 7.76 (d, J=8.4 Hz, 2H), 7.66 (d, J=8.5 Hz, 2H), 7.49 (d, J=4.5 Hz, 1H), 6.76 (d, J=6.0 Hz, 1H), 4.68 (t, J=9.9 Hz, 4H), 1.48 (s, 9H). MS m/z (ESI): 455.0 [M+H].

Step 3:

Compound TDI01535-3 (2.5 g, 5.5 mmol) was dissolved in dichloromethane (20 mL), a hydrochloric acid/dioxane solution (8 mL) was dropwise added, and a large amount of solid precipitated. The reaction was continually stirred at room temperature for 16 h. LC-MS indicated the reaction was complete. The reaction solvent was removed through rotary evaporation under vacuum to afford TDI01535-4 (2.2 g, yellow solid, crude product).

$^1$H NMR (400 MHz, DMSO-d$_6$) δ 10.01 (s, 1H), 9.58 (s, 2H), 8.39 (d, J=6.0 Hz, 1H), 8.34 (d, J=8.2 Hz, 2H), 8.04 (s, 2H), 7.76 (d, J=8.4 Hz, 2H), 7.66 (d, J=8.6 Hz, 2H), 7.59 (d, J=7.9 Hz, 1H), 6.80 (d, J=6.0 Hz, 1H), 4.61 (dd, J=10.7, 5.2 Hz, 4H). MS m/z (ESI): 354.7 [M+H].

Step 4:

Compound 4-hydroxypyridine (25 mg, 0.26 mmol) and DNPC (79 mg, 0.26 mmol) were dissolved in N,N-dimethylformamide (4 mL), diisopropylethylamine (134 mg, 1.04 mmol) was added, and the reaction was stirred at room temperature for 1 h. TDI01535-4 (92 mg, 0.26 mmol) was added, and the reaction was stirred at room temperature for 16 h. LC-MS indicated the reaction was complete, the reaction solvent was removed through rotary evaporation under vacuum, and the residue was purified by preparative liquid chromatography to afford compound TDI01535 (18.8 mg, yield 15.2%)

$^1$H NMR (300 MHz, DMSO-d$_6$) δ 10.45 (s, 1H), 8.35 (d, J=6.4 Hz, 1H), 8.19 (dd, J=23.5, 7.2 Hz, 4H), 8.04 (s, 2H), 7.69 (dd, J=20.8, 8.4 Hz, 4H), 7.56 (d, J=7.3 Hz, 1H), 6.85 (s, 1H), 6.42-6.33 (m, 2H), 4.99 (d, J=7.3 Hz, 4H). MS m/z (ESI): 475.6 [M+H].

The compounds in following table 11 were prepared according to methods similar to that described in Example 42.

TABLE 11

| No. | Compound Structure | Compound Name | Starting material or regent different from that in Example 42 | Characterization Data |
|---|---|---|---|---|
| TDI01543 | 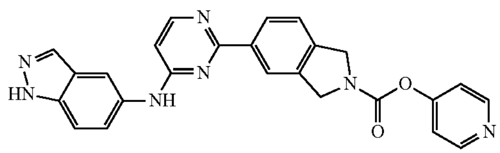 [SMILES: O=C(Oc1ccncc1)N1Cc2ccc(-c3nccc(Nc4ccc5[nH]ncc5c4)n3)cc2C1] | pyridin-4-yl 5-(4-((1H-indazol-5-yl)amino)pyrimidin-2-yl)isoindoline-2-carboxylate | in step 2 of Example 42 was replaced with (Reg-1-16) and (Reg-1-1). | $^1$H NMR (300 MHz, DMSO-d$_6$) δ 13.04 (s, 1H), 10.16 (s, 1H), 8.34-8.18 (m, 3H), 8.15-7.99 (m, 4H), 7.57 (t, J = 7.5 Hz, 3H), 6.73 (d, J = 6.0 Hz, 1H), 6.23 (d, J = 7.3 Hz, 2H), 4.97 (d, J = 7.0 Hz, 4H). MS m/z (ESI): 449.6 [M + H]. |
| TDI01551 | 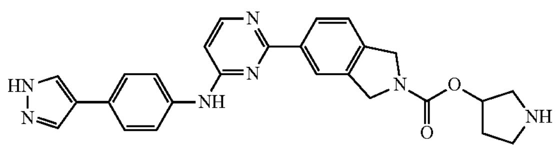 [SMILES: O=C(OC1CCNC1)N1Cc2ccc(-c3nccc(Nc4ccc(-c5cn[nH]c5)cc4)n3)cc2C1] | pyrrolidin-3-yl 5-(4-((4-(1H-pyrazol-4-yl)phenyl)amino)pyrimidin-2-yl)isoindoline-2-carboxylate | in step 4 of Example 42 was replaced with HO— and the final product was obtained by removal of Boc using a 4N hydrochloric acid/dioxane solution in the final step. | $^1$H NMR (300 MHz, DMSO-d$_6$) δ 11.88 (s, 1H), 8.96 (s, 3H), 8.41-8.15 (m, 6H), 7.78 (d, J = 15.8 Hz, 4H), 7.62 (t, J = 9.2 Hz, 1H), 7.20 (s, 1H), 6.98 (d, J = 6.7 Hz, 1H), 4.80 (d, J = 23.1 Hz, 4H), 3.72-3.51 (m, 2H), 3.44-3.28 (m, 1H), 3.18 (s, 2H), 2.95 (d, J = 31.8 Hz, 4H), 2.05 (dd, J = 21.5, 12.2 Hz, 4H), 1.75 (d, J = 48.5 Hz, 4H). MS m/z (ESI): 467.8 [M + H]. |

TABLE 11-continued

| No. | Compound Structure | Compound Name | Starting material or regent different from that in Example 42 | Characterization Data |
|---|---|---|---|---|
| TDI01552 | 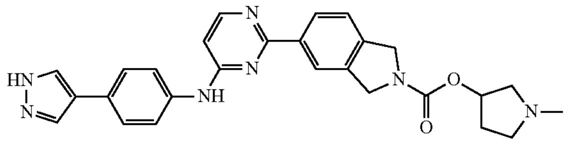 [SMILES: CN1CCC(OC(=O)N2Cc3ccc(-c4nccc(Nc5ccc(-c6cn[nH]c6)cc5)n4)cc3C2)C1] | 1-methylpyrrolidin-3-yl 5-(4-((4-(1H-pyrazol-4-yl)phenyl)amino)pyrimidin-2-yl)isoindoline-2-carboxylate | in step 4 of Example 42 was replaced with HO-(4-hydroxypyridine) and HO-(1-methylpyrrolidin-3-ol) | ¹H NMR (400 MHz, DMSO-d₆) δ 10.07 (s, 1H), 9.95 (s, 1H), 8.38 (d, J = 6.0 Hz, 1H), 8.31 (s, 1H), 8.04 (s, 2H), 7.75 (d, J = 6.1 Hz, 2H), 7.68-7.63 (m, 2H), 7.54-7.49 (m, 1H), 6.77 (d, J = 6.0 Hz, 1H), 5.31 (s, 1H), 4.83-4.72 (m, 4H), 3.75 (d, J = 7.5 Hz, 3H), 3.35-3.26 (m, 2H), 2.95 (d, J = 4.2 Hz, 2H), 2.88 (d, J = 4.1 Hz, 2H). MS m/z (ESI): 482.0 [M + H]. |
| TDI01555 | 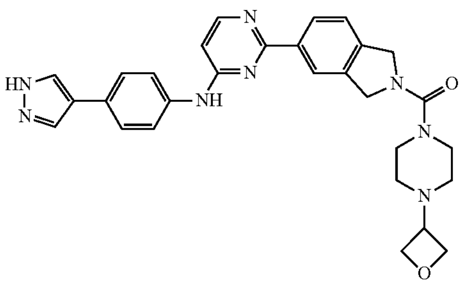 [SMILES: O=C(N1CCN(C2COC2)CC1)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(4-(oxetan-3-yl)piperazin-1-yl)methanone | in step 4 of Example 42 was replaced with 4-hydroxypyridine and 1-(oxetan-3-yl)piperazine | ¹H NMR (400 MHz, DMSO-d₆) δ 12.82 (s, 1H), 9.68 (s, 1H), 8.38 (d, J = 5.9 Hz, 1H), 8.29 (d, J = 7.7 Hz, 2H), 8.04 (s, 1H), 7.77 (d, J = 8.3 Hz, 2H), 7.64 (d, J = 8.4 Hz, 2H), 7.45 (d, J = 8.3 Hz, 1H), 6.72 (d, J = 5.9 Hz, 1H), 4.80 (d, J = 10.0 Hz, 4H), 4.53 (d, J = 34.5 Hz, 4H), 3.47 (s, 1H), 3.33 (s, 4H), 2.33 (s, 4H). MS m/z (ESI): 522.8 [M + H]. |
| TDI01557 | 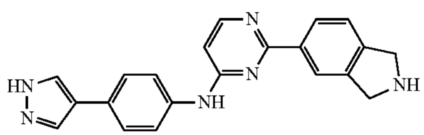 [SMILES: c1cc(Nc2ccc(-c3cn[nH]c3)cc2)nc(-c2ccc3c(c2)CNC3)n1] | N-(4-(1H-pyrazol-4-yl)phenyl)-2-(isoindolin-5-yl)pyrimidin-4-amine | Intermediate TDI01535-4 | ¹H NMR (400 MHz, DMSO-d₆) δ 10.01 (s, 1H), 9.58 (s, 2H), 8.39 (d, J = 6.0 Hz, 1H), 8.34 (d, J = 8.2 Hz, 2H), 8.04 (s, 2H), 7.76 (d, J = 8.4 Hz, 2H), 7.66 (d, J = 8.6 Hz, 2H), 7.59 (d, J = 7.9 Hz, 1H), 6.80 (d, J = 6.0 Hz, 1H), 4.61 (dd, J = 10.7, 5.2 Hz, 4H). MS m/z (ESI): 354.7 [M + H]. |
| TDI01557B | 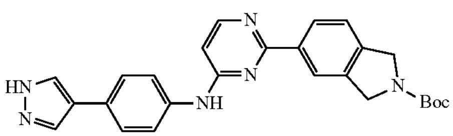 [SMILES: CC(C)(C)OC(=O)N1Cc2ccc(-c3nccc(Nc4ccc(-c5cn[nH]c5)cc4)n3)cc2C1] | tert-butyl 5-(4-((4-(1H-pyrazol-4-yl)phenyl)amino)pyrimidin-2-yl)isoindoline-2-carboxylate | Intermediate TDI01535-3 | ¹H NMR (400 MHz, DMSO-d₆) δ 9.87 (s, 1H), 8.38 (d, J = 6.0 Hz, 1H), 8.29-8.24 (m, 2H), 8.05 (s, 2H), 7.76 (d, J = 8.4 Hz, 2H), 7.66 (d, J = 8.5 Hz, 2H), 7.49 (d, J = 4.5 Hz, 1H), 6.76 (d, J = 6.0 Hz, 1H), 4.68 (t, J = 9.9 Hz, 4H), 1.48 (s, 9H). MS m/z (ESI): 455.0 [M + H]. |

TABLE 11-continued

| No. | Compound Structure | Compound Name | Starting material or regent different from that in Example 42 | Characterization Data |
|---|---|---|---|---|
| TDI01571B | 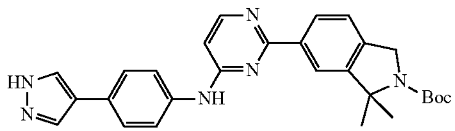 | tert-butyl 6-(4-((4-(1H-pyrazol-4-yl)phenyl)amino)pyrimidin-2-yl)-1,1-dimethylisoindoline-2-carboxylate | The compound was synthesized according to step 1 to step 2 of Example 42, and [structure with Boc-isoindoline-Br] in step 1 of Example 42 was replaced with [Br-isoindoline-Boc structure] | $^1$H NMR (400 MHz, DMSO-d$_6$) δ 8.39 (d, J = 6.2 Hz, 1H), 8.18 (s, 3H), 8.06 (s, 2H), 7.74 (s, 2H), 7.67 (s, 2H), 7.50 (s, 1H), 6.80 (s, 1H), 4.67 (d, J = 8.5 Hz, 2H), 1.67 (d, J = 5.9 Hz, 6H), 1.49 (d, J = 12.9 Hz, 9H). MS m/z (ESI): 482.8 [M + H]. |
| TDI01562 | 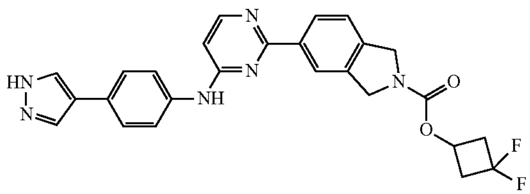 [SMILES: O=C(OC1CC(F)(F)C1)N1Cc2ccc(-c3nccc(Nc4ccc(-c5cn[nH]c5)cc4)n3)cc2C1] | 3,3-difluorocyclobutyl 5-(4-((4-(1H-pyrazol-4-yl)phenyl)amino)pyrimidin-2-yl)isoindoline-2-carboxylate | [4-hydroxypyridine structure] in step 4 of Example 42 was replaced with HO-[3,3-difluorocyclobutyl] | $^1$H NMR (400 MHz, DMSO-d$_6$) δ 9.73 (s, 1H), 8.37 (d, J = 5.7 Hz, 1H), 8.33-8.27 (m, 2H), 8.03 (s, 2H), 7.76 (d, J = 8.2 Hz, 2H), 7.64 (d, J = 8.3 Hz, 2H), 7.60-7.36 (m, 2H), 6.73 (d, J = 5.8 Hz, 1H), 4.75 (dd, J = 23.4, 12.7 Hz, 4H), 3.12-3.05 (m, 2H), 2.76 (td, J = 13.6, 6.6 Hz, 2H). MS m/z (ESI): 489.0 [M + H]. |

TABLE 11-continued

| No. | Compound Structure | Compound Name | Starting material or regent different from that in Example 42 | Characterization Data |
|---|---|---|---|---|
| TDI01580 | 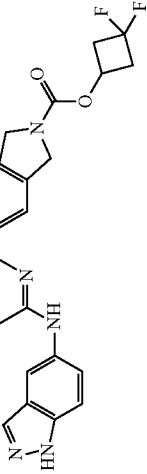 | 3,3-difluorocyclobutyl 5-(4-((1H-indazol-5-yl)amino)pyrimidin-2-yl)isoindoline-2-carboxylate | 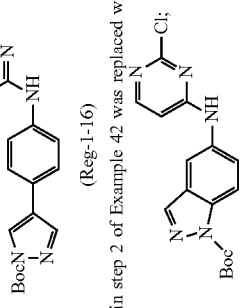 (Reg-1-16) in step 2 of Example 42 was replaced with [structure] (Reg-1-1); [structure] in step 4 was replaced with HO-[cyclobutyl-F,F]. | $^1$H NMR (400 MHz, DMSO-d$_6$) δ 13.15 (s, 1H), 10.43 (s, 1H), 8.34 (d, J = 6.3 Hz, 1H), 8.21 (d, J = 10.8 Hz, 2H), 8.13 (s, 2H), 7.62 (d, J = 8.7 Hz, 1H), 7.56 (d, J = 4.1 Hz, 2H), 6.80 (d, J = 6.1 Hz, 1H), 4.92 (s, 1H), 4.76 (dd, J = 22.3, 7.3 Hz, 4H), 3.12-3.05 (m, 2H), 2.79-2.71 (m, 2H). MS m/z (ESI): 462.6 [M + H]. |

TABLE 11-continued

| No. | Compound Structure | Compound Name | Starting material or regent different from that in Example 42 | Characterization Data |
|---|---|---|---|---|
| TDI01609 | (structure shown) | 3,3-difluorocyclobutyl 5-((4-(1H-pyrazol-4-yl)phenyl)amino)-5-fluoropyrimidin-2-yl)isoindoline-2-carboxylate | (Reg-1-16) in step 2 of Example 42 was replaced with (Reg-1-40); in step 4 was replaced with 3,3-difluorocyclobutanol | $^1$H NMR (400 MHz, DMSO-$d_6$) δ 9.68 (s, 1H), 8.47 (s, 1H), 8.22 (d, J = 8.9 Hz, 2H), 8.07 (s, 2H), 7.88 (d, J = 7.8 Hz, 2H), 7.63 (dd, J = 26.8, 8.6 Hz, 2H), 7.47 (d, J = 7.7 Hz, 1H), 4.92 (s, 1H), 4.73 (dd, J = 23.6, 12.3 Hz, 4H), 3.09 (d, J = 6.9 Hz, 2H), 2.81-2.69 (m, 2H). MS m/z (ESI): 506.5 [M + H]. |

| No. | Compound Structure | Compound Name | Starting material or regent different from that in Example 42 | Characterization Data |
|---|---|---|---|---|
| TDI01613 | (structure) | 3,3-difluorocyclobutyl 5-(4-((1H-indazol-5-yl)amino)-5-fluoropyrimidin-2-yl)isoindoline-2-carboxylate | (Reg-1-16) in step 2 of Example 42 was replaced with (Reg-1-12); in step 4 was replaced with 3,3-difluorocyclobutanol | $^1$H NMR (400 MHz, DMSO-$d_6$) δ 13.04 (s, 1H), 9.72 (s, 1H), 8.44 (s, 1H), 8.19 (t, J = 8.9 Hz, 3H), 8.12 (s, 1H), 7.73 (d, J = 7.7 Hz, 1H), 7.59 (d, J = 8.8 Hz, 1H), 7.43 (d, J = 5.9 Hz, 1H), 4.91 (s, 1H), 4.71 (dd, J = 22.7, 9.6 Hz, 4H), 3.07 (d, J = 5.1 Hz, 2H), 2.75 (dd, J = 13.2, 6.9 Hz, 2H). MS m/z (ESI): 480.7 [M + H]. |
| TDI01620 | (structure) | (1s,4s)-quinuclidin-3-yl 6-(4-((4-(1H-pyrazol-4-yl)phenyl)amino)pyrimidin-2-yl)-3,4-dihydroisoquinoline-2(1H)-carboxylate | in step 1 of Example 42 was replaced with N-Boc tetrahydroisoquinoline bromide; in step 4 was replaced with quinuclidinol | $^1$H NMR (400 MHz, DMSO-$d_6$) δ 10.34 (s, 1H), 9.68 (s, 1H), 8.37 (d, J = 6.3 Hz, 1H), 8.11 (d, J = 7.7 Hz, 3H), 8.06 (s, 2H), 7.74 (d, J = 8.3 Hz, 2H), 7.67 (d, J = 8.4 Hz, 2H), 7.42 (s, 1H), 6.82 (d, J = 6.2 Hz, 1H), 4.94 (s, 1H), 4.77-4.62 (m, 2H), 3.78-3.59 (m, 4H), 3.35-3.23 (m, 3H), 3.19 (s, 2H), 2.95 (s, 2H), 2.29 (s, 1H), 2.07 (s, 1H), 1.96-1.72 (m, 3H). MS m/z (ESI): 521.8 [M + H]. |

TABLE 11-continued

| No. | Compound Structure | Compound Name | Starting material or regent different from that in Example 42 | Characterization Data |
|---|---|---|---|---|
| TDI01621 | 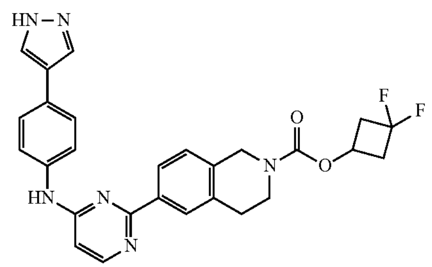 [SMILES: O=C(OC1CC(F)(F)C1)N1CCc2cc(-c3nccc(Nc4ccc(-c5cn[nH]c5)cc4)n3)ccc2C1] | 3,3-difluorocyclobutyl 6-(4-((4-(1H-pyrazol-4-yl)phenyl)amino)pyrimidin-2-yl)-3,4-dihydroisoquinoline-2(1H)-carboxylate | in step 1 of Example 42 was replaced with ; in step 4 was replaced with | $^1$H NMR (400 MHz, DMSO-d$_6$) δ 10.55 (s, 1H), 8.37 (d, J = 6.5 Hz, 1H), 8.08 (s, 4H), 7.70 (t, J = 7.7 Hz, 4H), 7.43 (d, J = 7.5 Hz, 1H), 6.85 (d, J = 6.6 Hz, 1H), 4.87 (s, 1H), 4.67 (d, J = 24.4 Hz, 2H), 3.68 (s, 2H), 3.04 (dt, J = 14.7, 7.5 Hz, 2H), 2.94 (s, 2H), 2.73 (dt, J = 19.4, 12.3 Hz, 2H). MS m/z (ESI): 503.1 [M + H]. |
| TDI01634 | 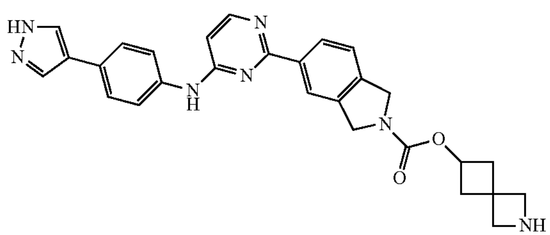 [SMILES: O=C(OC1CC2(CNC2)C1)N1Cc2ccc(-c3nccc(Nc4ccc(-c5cn[nH]c5)cc4)n3)cc2C1] | 2-azaspiro[3.3]heptan-6-yl 5-(4-((4-(1H-pyrazol-4-yl)phenyl)amino)pyrimidin-2-yl)isoindoline-2-carboxylate | in step 4 of Example 42 was replaced with ; and the final product was obtained by removal of Boc using a 4N hydrochloric acid/dioxane solution in the final step. | $^1$H NMR (400 MHz, DMSO-d$_6$) δ 9.91 (s, 1H), 8.57 (s, 2H), 8.38 (d, J = 5.7 Hz, 1H), 8.32-8.25 (m, 2H), 8.05 (s, 2H), 7.76 (d, J = 7.8 Hz, 2H), 7.66 (d, J = 8.0 Hz, 2H), 7.50 (s, 1H), 6.77 (s, 1H), 4.88-4.84 (m, 1H), 4.72 (t, J = 12.9 Hz, 4H), 4.00 (d, J = 19.8 Hz, 4H), 2.68 (s, 2H), 2.33 (s, 2H). MS m/z (ESI): 493.9 [M + H] |

| No. | Compound Structure | Compound Name | Starting material or regent different from that in Example 42 | Characterization Data |
|---|---|---|---|---|
| TDI01656 | 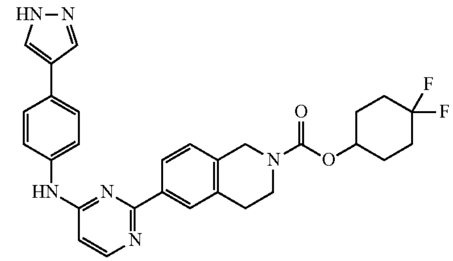 [SMILES: O=C(OC1CCC(F)(F)CC1)N1CCc2cc(-c3nccc(Nc4ccc(-c5cn[nH]c5)cc4)n3)ccc2C1] | 4,4-difluorocyclohexyl 6-(4-(4-(1H-pyrazol-4-yl)phenyl)amino)pyrimidin-2-yl)-3,4-dihydroisoquinoline-2(1H)-carboxylate | in step 4 of Example 42 was replaced with | 1H NMR (400 MHz, DMSO-$d_6$) δ 10.62 (s, 1H), 8.37 (d, J = 6.5 Hz, 1H), 8.08 (s, 4H), 7.70 (t, J = 6.7 Hz, 4H), 7.45 (d, J = 8.4 Hz, 1H), 6.86 (d, J = 6.6 Hz, 1H), 4.84 (s, 1H), 4.66 (s, 2H), 3.68 (s, 2H), 2.94 (s, 2H), 2.10-1.91 (m, 4H), 1.91-1.70 (m, 4H). MS m/z (ESI): 531.1 [M + H]. |
| TDI01667 | 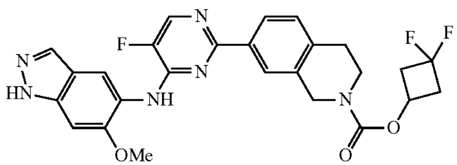 [SMILES: COc1cc2[nH]ncc2cc1Nc1nc(-c2ccc3c(c2)CN(C(=O)OC2CC(F)(F)C2)CC3)ncc1F] | 3,3-difluorocyclobutyl 7-(5-fluoro-4-((6-methoxy-1-indazol-5-yl)amino)pyrimidin-2-yl)-3,4-dihydroisoquinoline-2(1H)-carboxylate | in step 1 of Example 42 was replaced with; in step 2 was replaced with (Reg-1-88); in step 4 was replaced with | 1H NMR (400 MHz, DMSO-$d_6$) δ 12.95 (s, 1H), 8.82 (s, 1H), 8.40 (d, J = 3.4 Hz, 1H), 8.16 (d, J = 9.3 Hz, 1H), 8.01 (s, 1H), 7.95 (s, 1H), 7.91 (d, J = 8.0 Hz, 1H), 7.23 (d, J = 7.9 Hz, 1H), 7.10 (s, 1H), 4.84 (d, J = 5.1 Hz, 1H), 4.58 (d, J = 34.7 Hz, 2H), 3.87 (s, 3H), 3.60 (s, 2H), 3.11-2.95 (m, 2H), 2.82 (s, 2H), 2.73 (d, J = 11.8 Hz, 2H). MS m/z (ESI): 524.7 [M + H]. |

TABLE 11-continued

| No. | Compound Structure | Compound Name | Starting material or regent different from that in Example 42 | Characterization Data |
|---|---|---|---|---|
| TDI01672 | 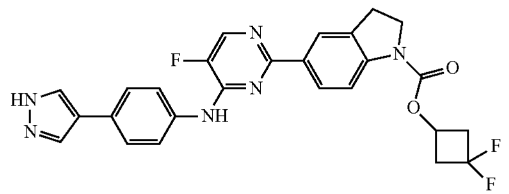 [SMILES: O=C(OC1CC(F)(F)C1)N1CCc2cc(-c3ncc(F)c(Nc4ccc(-c5cn[nH]c5)cc4)n3)ccc21] | 3,3-difluorocyclobutyl 5-(4-((4-(1H-pyrazol-4-yl)phenyl)amino)-5-fluoropyrimidin-2-yl)indoline-1-carboxylate | in step 1 of Example 42 was replaced with (structures shown); in step 2 was replaced with (Reg-1-16) and (Reg-1-40); in step 4 was replaced with (structure) | $^1$H NMR (400 MHz, DMSO-d$_6$) δ 9.56 (s, 1H), 8.85 (s, 1H), 8.41 (s, 1H), 8.36 (d, J = 3.5 Hz, 1H), 8.01-7.89 (m, 4H), 7.81 (d, J = 8.4 Hz, 2H), 6.52 (d, J = 8.2 Hz, 1H), 6.01 (s, 1H), 5.25-5.19 (m, 1H), 3.51 (t, J = 8.3 Hz, 2H), 3.23-3.18 (m, 2H), 3.07-2.96 (m, 4H). MS m/z (ESI): 506.5 [M + H]. |
| TDI01951 | 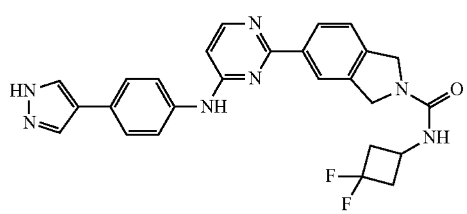 [SMILES: O=C(NC1CC(F)(F)C1)N1Cc2ccc(-c3nccc(Nc4ccc(-c5cn[nH]c5)cc4)n3)cc2C1] | 5-(4-((4-(1H-pyrazol-4-yl)phenyl)amino)pyrimidin-2-yl)-N-(3,3-difluorocyclobutyl)isoindoline-2-carboxamide | in step 4 of Example 42 was replaced with (structure) NH$_2$·HCl. | $^1$H NMR (400 MHz, DMSO-d$_6$) δ 10.46 (s, 1H), 8.39 (d, J = 6.4 Hz, 1H), 8.25-8.17 (m, 2H), 8.08 (s, 2H), 7.72 (dd, J = 21.9, 8.6 Hz, 4H), 7.56 (d, J = 8.0 Hz, 1H), 6.84 (t, J = 6.2 Hz, 2H), 4.71 (d, J = 4.7 Hz, 4H), 4.12-4.03 (m, 1H), 2.87 (ddd, J = 14.2, 9.8, 3.7 Hz, 2H), 2.70 (dt, J = 19.0, 6.6 Hz, 2H). MS m/z (ESI): 487.8 [M + H]. |

TABLE 11-continued

| No. | Compound Structure | Compound Name | Starting material or regent different from that in Example 42 | Characterization Data |
|---|---|---|---|---|
| TDI01957 | 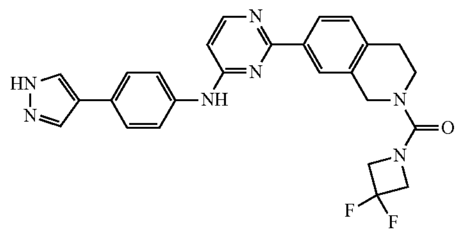 [SMILES: O=C(N1CCc2ccc(-c3nccc(Nc4ccc(-c5cn[nH]c5)cc4)n3)cc2C1)N1CC(F)(F)C1] | (7-(4-((4-(1H-pyrazol-4-yl)phenyl)amino)pyrimidin-2-yl)-3,4-dihydroisoquinolin-2(1H)-yl)(3,3-difluoroazetidin-1-yl)methanone | [structures: 5-bromoisoindoline-2-Boc and 7-bromo-tetrahydroisoquinoline-2-Boc] in step 1 of Example 42 was replaced with; [structures: 4-hydroxypyridine and 3,3-difluoroazetidine·HCl] in step 4 was replaced with NHHCl. | $^1$H NMR (400 MHz, DMSO-d$_6$) δ 10.54 (s, 0H), 8.37 (d, J = 8.0 Hz, 1H), 8.08-8.05 (m, 4H), 7.74-7.67 (m, 4H), 7.41 (d, J = 8.0 Hz, 1H), 6.85 (d, J = 8.0 Hz, 1H), 4.57 (s, 2H), 4.41 (t, J = 13.0 Hz, 4H), 3.55 (t, J = 6.0 Hz, 2H), 2.91 (t, J = 6.0 Hz, 2H). MS m/z (ESI): 487.6 [M + H]. |
| TDI01959 | 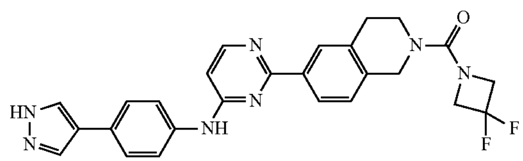 | (6-(4-((4-(1H-pyrazol-4-yl)phenyl)amino)pyrimidin-2-yl)-3,4-dihydroisoquinolin-2(1H)-yl)(3,3-difluoroazetidin-1-yl)methanone | [structures: 5-bromoisoindoline-2-Boc and 6-bromo-tetrahydroisoquinoline-2-Boc] in step 1 of Example 42 was replaced with; [structures: 4-hydroxypyridine and 3,3-difluoroazetidine·HCl] in step 4 was replaced with NHHCl. | $^1$H NMR (300 MHz, DMSO-d$_6$) δ 12.89 (s, 1H), 9.68 (s, 1H), 8.34 (d, J = 5.8 Hz, 1H), 8.14 (d, J = 5.1 Hz, 2H), 8.01 (s, 2H), 7.75 (d, J = 8.2 Hz, 2H), 7.62 (d, J = 8.2 Hz, 2H), 7.32 (d, J = 8.4 Hz, 1H), 6.70 (d, J = 5.9 Hz, 1H), 4.53 (s, 2H), 4.40 (t, J = 12.9 Hz, 4H), 3.55 (s, 2H), 2.92 (s, 2H). MS m/z (ESI): 488.1 [M + H]. |

TABLE 11-continued

| No. | Compound Structure | Compound Name | Starting material or regent different from that in Example 42 | Characterization Data |
|---|---|---|---|---|
| TDI01974 | 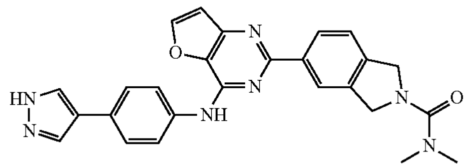 [SMILES: CN(C)C(=O)N1Cc2ccc(-c3nc(Nc4ccc(-c5cn[nH]c5)cc4)c4occc4n3)cc2C1] | 5-(4-(4-(1H-pyrazol-4-yl)phenyl)amino)furo[3,2-d]pyrimidin-2-yl)-N,N-dimethylisoindoline-2-carboxamide | (Reg-1-16)<br><br>in step 2 of Example 42 was replaced with<br><br>(OH-pyridine)<br><br>in step 4 was replaced with<br><br>HHCl (dimethylamine). | 1H NMR (400 MHz, DMSO-d6) δ 10.01 (s, 1H), 8.39 (d, 2.2 Hz, 1H), 8.31 (d, J = 5.7 Hz, 2H), 8.06 (s, 2H), 7.95 (d, J = 8.6 Hz, 2H), 7.67 (d, J = 8.6 Hz, 2H), 7.43 (d, J = 8.4 Hz, 1H), 7.13 (d, J = 2.2 Hz, 1H), 4.78 (d, J = 13.9 Hz, 4H), 2.87 (s, 6H). MS m/z (ESI): 466.0 [M + H]. |
| TDI01861 | 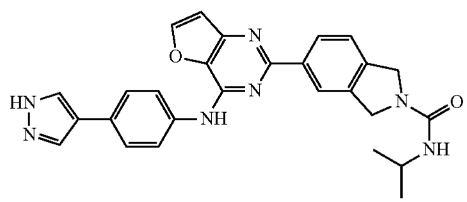 [SMILES: CC(C)NC(=O)N1Cc2ccc(-c3nc(Nc4ccc(-c5cn[nH]c5)cc4)c4occc4n3)cc2C1] | 5-(4-(4-(1H-pyrazol-4-yl)phenyl)amino)furo[3,2-d]pyrimidin-2-yl)-N-isopropylisoindoline-2-carboxamide | (Reg-1-16)<br><br>in step 2 of Example 42 was replaced with<br><br>(OH-pyridine)<br><br>(Reg-1-44);<br><br>in step 4 was replaced with NH2HCl. | 1H NMR (400 MHz, DMSO-d6) δ 10.09 (s, 1H), 8.41 (s, 1H), 8.33-8.27 (m, 2H), 8.07 (s, 2H), 7.93 (d, J = 8.2 Hz, 2H), 7.66 (d, J = 8.2 Hz, 2H), 7.45 (d, J = 7.9 Hz, 1H), 7.15 (s, 1H), 6.04 (d, J = 6.7 Hz, 2H), 4.66 (d, J = 11.8 Hz, 4H), 3.83 (s, 1H), 1.12 (d, J = 6.5 Hz, 6H). MS m/z (ESI): 479.9 [M + H]. |

Example 43: preparation of N-(4-(1H-pyrazol-4-yl)phenyl)-2-(2-(ethylsulfonyl)isoindolin-5-yl)pyrimidin-4-amine (TDI01558)

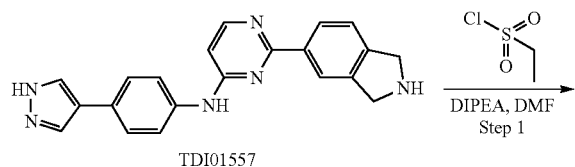

Step 1:

Compound TDI01557 (80 mg, 0.224 mmol) was dissolved in N,N-dimethylformamide (5 mL), diisopropylethylamine (144 mg, 1.12 mmol) and ethanesulfonyl chloride (28 mg, 0.224 mmol) were added, and the reaction was stirred at room temperature for 16 h. LC-MS indicated the reaction was complete. The reaction solvent was removed through rotary evaporation under vacuum, and the residue was purified by preparative liquid chromatography to afford compound TDI01558 (65 mg, yield 65%).

$^1$H NMR (400 MHz, DMSO-$d_6$) δ 10.28 (s, 1H), 8.38 (d, J=6.3 Hz, 1H), 8.25 (d, J=9.6 Hz, 2H), 8.06 (s, 2H), 7.71 (dd, J=28.0, 8.4 Hz, 4H), 7.54 (d, J=7.9 Hz, 1H), 6.83 (d, J=5.4 Hz, 1H), 4.78 (d, J=10.1 Hz, 4H), 3.23 (q, J=7.4 Hz, 2H), 1.25 (t, J=7.4 Hz, 3H). MS m/z (ESI): 447.1 [M+H].

The compound in following table 12 was prepared according to a method similar to that described in Example 43.

TABLE 12

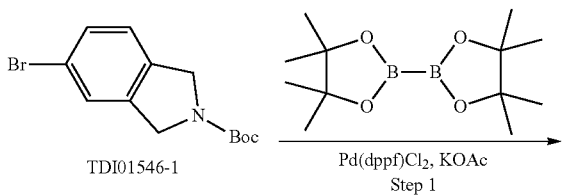

| TDI01559 | structure | benzyl 5-(4-((4-(1H-pyrazol-4-yl)phenyl)amino)pyrimidin-2-yl)isoindolin-2-carboxylate |
|---|---|---|
| TDI01559 | in step 1 of Example 43 was replaced with | $^1$H NMR (400 MHz, DMSO-$d_6$) δ 10.30 (s, 2H), 8.38 (d, J = 6.3 Hz, 1H), 8.24 (d, J = 9.2 Hz, 2H), 8.06 (s, 2H), 7.72 (dd, J = 27.9, 7.6 Hz, 4H), 7.55 (t, J = 9.1 Hz, 1H), 7.39 (ddd, J = 23.8, 13.8, 7.0 Hz, 5H), 6.83 (d, J = 6.0 Hz, 1H), 5.18 (s, 2H), 4.80 (dd, J = 21.6, 10.7 Hz, 4H). MS m/z(ESI): 489.0 [M + H]. |

Example 44: preparation of (5-(4-((4-(1H-pyrazol-4-yl)phenyl)amino)pyrimidin-2-yl)isoindolin-2-yl)(7-azaspiro[3.5]nonan-2-yl)methanone (TDI01546)

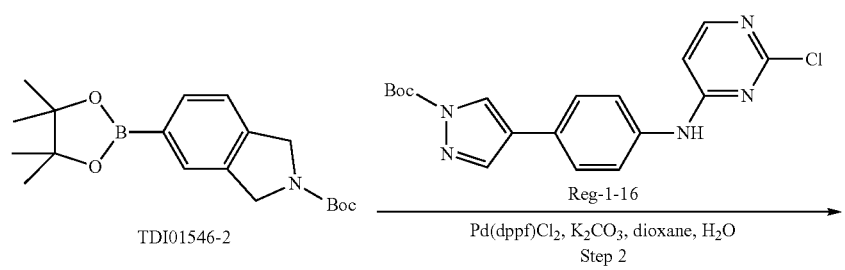

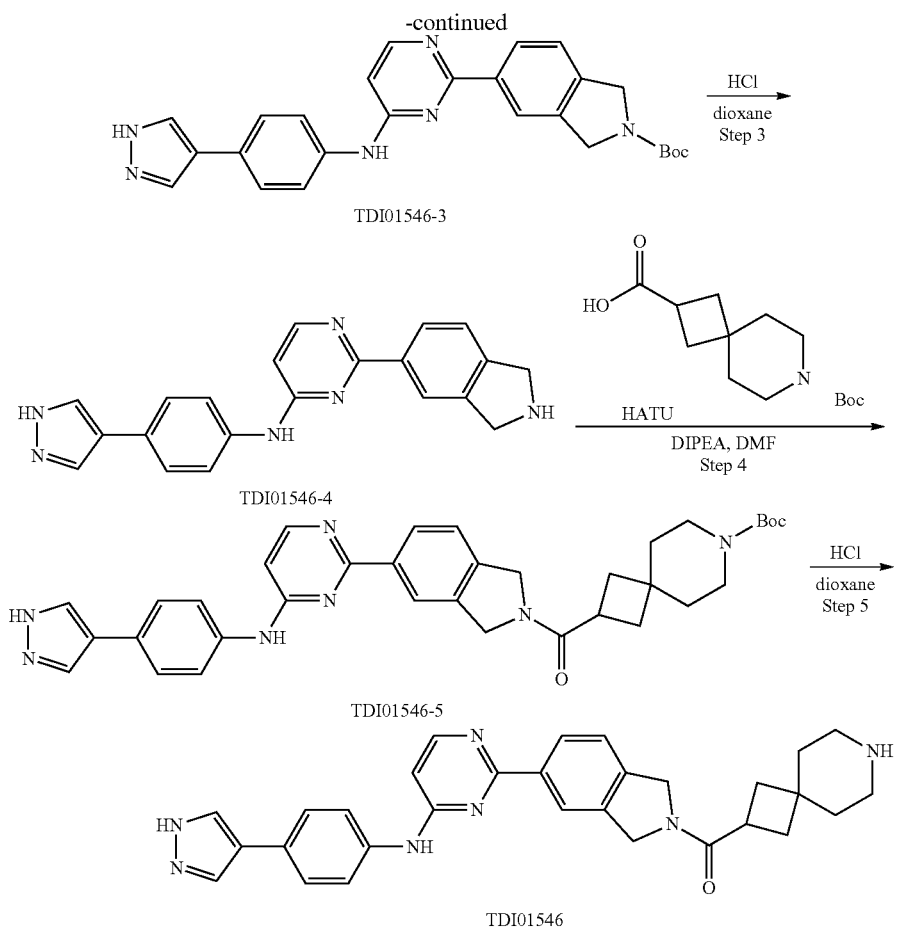

The synthesis of Step 1 to Step 3 of Example 44 was performed according to Step 1 to Step 2 of Example 42.

Step 4:

Compound TDI01546-4 (30 mg, 0.085 mmol) and HATU (39 mg, 0.102 mmol) were dissolved in N,N-dimethylformamide (3 mL), 7-(tert-butoxycarbonyl)-7-azaspiro[3,5]nonane-2-carboxylic acid (23 mg, 0.085 mmol) and diisopropylethylamine (32 mg, 0.255 mmol) were added, and the reaction was stirred at room temperature for 2 h. The reaction solution was diluted with water (10 mL), extracted with dichloromethane (20 mL×3), dried over anhydrous sodium sulfate, filtered, and concentrated under reduced pressure. The residue was purified by flash column chromatography (dichloromethane:methanol=20:1) to afford compound TDI01546-5 (43 mg, yellow oil, crude product).

MS m/z (ESI): 605.8 [M+H]

Step 5:

Compound TDI01546-5 (43 mg, 0.071 mmol) was dissolved in dichloromethane (5 mL), a hydrochloric acid/dioxane solution (3 mL) was added, and the reaction was performed at room temperature for 16 h. The reaction solution was concentrated under reduced pressure, and the residue was purified by preparative liquid chromatography to afford compound TDI01546 (17 mg, yellow solid, yield 48%).

$^1$H NMR (301 MHz, DMSO-d$_6$) δ 10.22 (s, 1H), 8.38 (d, J=5.6 Hz, 2H), 8.30-8.16 (m, 2H), 8.06 (s, 2H), 7.71 (dd, J=24.1, 7.0 Hz, 4H), 7.59-7.46 (m, 1H), 6.81 (d, J=5.9 Hz, 1H), 4.82 (s, 2H), 4.73 (d, J=8.6 Hz, 2H), 3.45-3.27 (m, 1H), 2.99 (d, J=28.4 Hz, 4H), 2.21-1.95 (m, 4H), 1.80 (s, 2H), 1.65 (s, 2H). MS m/z (ESI): 505.8 [M+H].

The compounds in following table 13 were prepared according to methods similar to that described in Example 44.

TABLE 13

| No. | Compound Structure | Compound Name | Starting material or regent different from that in Example 44 | Characterization Data |
|---|---|---|---|---|
| TDI01553 | 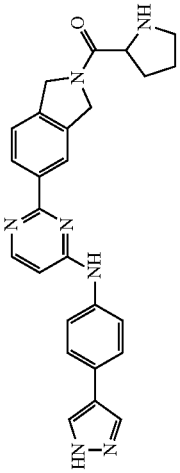 | 5-(4-((4-(1H-pyrazol-4-yl)phenyl)amino)pyrimidin-2-yl)-2-prolylisoindoline | 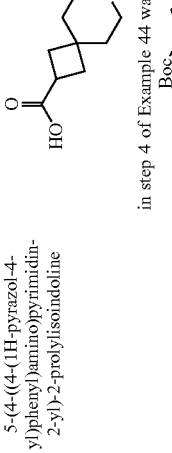 in step 4 of Example 44 was replaced with Boc-N-[prolyl]-COOH | ¹H NMR (400 MHz, DMSO-d₆) δ 10.07 (s, 1H), 9.41 (s, 1H), 8.67 (s, 1H), 8.52-8.22 (m, 3H), 8.05 (s, 2H), 7.86-7.52 (m, 4H), 6.80 (d, J = 6.1 Hz, 1H), 5.11-4.76 (m, 4H), 4.56 (s, 1H), 3.28 (dd, J = 31.9, 5.1 Hz, 2H), 2.54 (s, 2H), 1.97 (s, 2H). MS m/z (ESI): 451.7 [M + H]. |
| TDI01554 | 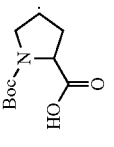 | 1-(5-(4-((4-(1H-pyrazol-4-yl)phenyl)amino)pyrimidin-2-yl)isoindolin-2-yl)-2,6-diaminohexan-1-one | 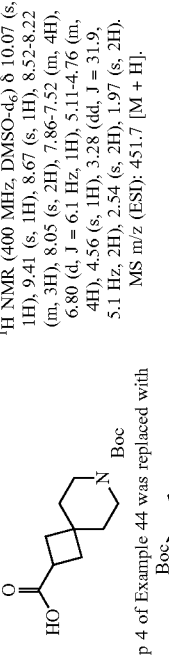 in step 4 of Example 44 was replaced with Boc-NH-CH(COOH)-(CH₂)₄-NHBoc | ¹HNMR (400 MHz, DMSO-d₆) δ 9.72 (s, 1H), 8.39-8.31 (m, 5H), 8.28 (s, 2H), 8.04 (s, 1H), 7.77 (d, J = 7.1 Hz, 2H), 7.65 (d, J = 8.5 Hz, 2H), 7.58-7.47 (m, 1H), 6.74 (d, J = 5.9 Hz, 1H), 5.11 (s, 1H), 4.94 (s, 1H), 4.82-4.71 (m, 3H), 3.64 (s, 1H), 3.51 (s, 7H), 2.78 (s, 2H), 1.56 (t, J = 37.2 Hz, 8H). MS m/z (ESI): 482.8 [M + H]. |
| TDI01560 | 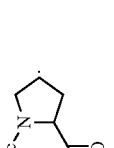 | (5-(4-((4-(1H-pyrazol-4-yl)phenyl)amino)pyrimidin-2-yl)isoindolin-2-yl)(tetrahydro-2H-pyran-4-yl)methanone | 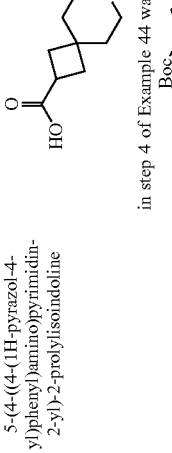 in step 4 of Example 44 was replaced with tetrahydropyran-4-carboxylic acid; and Step 5 was omitted. | ¹H NMR (301 MHz, DMSO-d₆) δ 10.50 (s, 1H), 8.38 (d, J = 4.8 Hz, 1H), 8.29-8.15 (m, 2H), 8.08 (s, 2H), 7.84-7.64 (m, 4H), 7.56 (t, J = 6.7 Hz, 1H), 6.85 (d, J = 6.3 Hz, 1H), 5.04 (s, 2H), 4.74 (d, J = 7.7 Hz, 2H), 3.90 (d, J = 10.7 Hz, 2H), 3.41 (s, 2H), 2.83 (d, J = 4.7 Hz, 1H), 1.66 (s, 4H). MS m/z (ESI): 466.8 [M + H]. |

TABLE 13-continued

| No. | Compound Structure | Compound Name | Starting material or regent different from that in Example 44 | Characterization Data |
|---|---|---|---|---|
| TDI01561 | 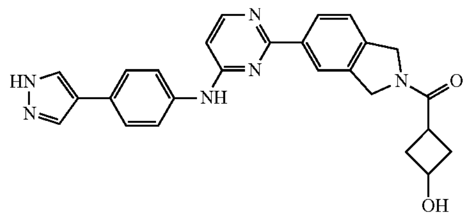 [SMILES: O=C(C1CC(O)C1)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(3-hydroxycyclobutyl)methanone | in step 4 of Example 44 was replaced with HO-C(=O)-cyclobutyl-OH; and Step 5 was omitted. | $^1$HNMR (400 MHz, DMSO-d$_6$) δ 8.38 (d, J = 6.2 Hz, 1H), 8.27 (s, 3H), 8.07 (s, 1H), 7.75 (s, 2H), 7.68 (s, 2H), 7.53 (s, 2H), 6.80 (s, 2H), 4.87 (d, J = 8.2 Hz, 2H), 4.73 (d, J = 12.8 Hz, 2H), 4.02 (s, 2H), 2.79 (s, 1H), 2.45 (d, J = 6.6 Hz, 1H), 2.02 (dd, J = 19.8, 9.6 Hz, 4H). MS m/z (ESI): 452.8 [M + H]. |
| TDI01563 | 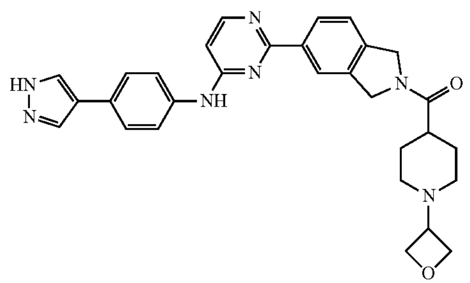 [SMILES: O=C(C1CCN(C2COC2)CC1)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(1-(oxetan-3-yl)piperidin-4-yl)methanone | in step 4 of Example 44 was replaced with HO-C(=O)-piperidine-N-Boc; and Step 5 was omitted. | $^1$H NMR (400 MHz, DMSO-d$_6$) δ 10.31 (s, 1H), 10.03 (s, 1H), 8.39 (dd, 6.1, 1.7 Hz, 1H), 8.34-8.24 (m, 2H), 8.05 (d, J = 3.5 Hz, 2H), 7.76 (d, J = 5.7 Hz, 2H), 7.71-7.62 (m, 2H), 7.57-7.50 (m, 1H), 6.79 (d, J = 5.3 Hz, 1H), 5.05 (d, J = 4.7 Hz, 2H), 4.83-4.68 (m, 6H), 4.40 (s, 1H), 3.48 (d, J = 11.3 Hz, 2H), 2.90 (s, 3H), 2.06 (d, J = 14.0 Hz, 2H), 1.89 (dd, J = 25.6, 12.8 Hz, 2H). MS m/z (ESI): 521.8 [M + H]. |
| TDI01570 | 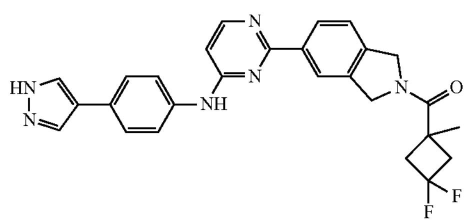 [SMILES: CC1(C(=O)N2Cc3ccc(-c4nccc(Nc5ccc(-c6cn[nH]c6)cc5)n4)cc3C2)CC(F)(F)C1] | (5-(4-((4-(1H-pyrazol-4-yl)phenyl)amino)pyrimidin-2-yl)isoindolin-2-yl)(3,3-difluoro-1-methylcyclobutyl)methanone | in step 4 of Example 44 was replaced with HO-C(=O)-C(CH$_3$)-cyclobutyl-F,F; and Step 5 was omitted. | $^1$H NMR (400 MHz, DMSO-d$_6$) δ 10.20 (s, 1H), 8.38 (d, J = 6.1 Hz, 1H), 8.25 (dd, J = 14.0, 5.5 Hz, 2H), 8.06 (s, 2H), 7.81-7.63 (m, 4H), 7.54 (dd, J = 20.3, 7.9 Hz, 1H), 6.81 (d, J = 5.7 Hz, 1H), 4.91-4.77 (m, 4H), 3.16 (d, J = 16.0 Hz, 2H), 2.56 (s, 2H), 1.49 (s, 3H). MS m/z (ESI): 486.6 [M + H]. |

TABLE 13-continued

| No. | Compound Structure | Compound Name | Starting material or regent different from that in Example 44 | Characterization Data |
|---|---|---|---|---|
| TD101575 | 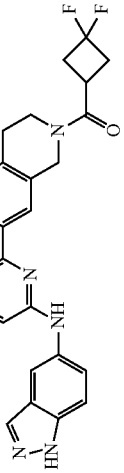 | (7-(4-((1H-indazol-5-yl)amino)pyrimidin-2-yl)-3,4-dihydroisoquinolin-2(1H)-yl)(3,3-difluorocyclobutyl)methanone | 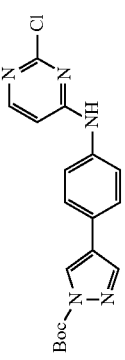 in step 1 of Example 44 was replaced with the Br-isoquinoline Boc; (Reg-1-16) in step 2 was replaced with the Cl-pyrimidine indazole Boc (Reg-1-1); the spiro Boc HO-carboxylic acid in step 4 was replaced with the difluorocyclobutyl F,F HO-carboxylic acid; and Step 5 was omitted. | $^1$H NMR (400 MHz, DMSO-$d_6$) δ 10.85 (s, 1H), 8.34 (d, J = 8.0 Hz, 1H), 8.19-8.02 (m, 4H), 7.66-7.63 (m, 1H), 7.55 (d, J = 8.0 Hz, 1H), 7.42 (t, J = 8.0 Hz, 1H), 6.85 (t, J = 8.0 Hz, 1H), 4.73 (d, J = 8.0 Hz, 2H), 3.77-3.66 (m, 2H), 3.46-3.35 (m, 1H), 3.00-2.69 (m, 6H). MS m/z (ESI): 460.7 [M + H]. |

TABLE 13-continued

| No. | Compound Structure | Compound Name | Starting material or regent different from that in Example 44 | Characterization Data |
|---|---|---|---|---|
| TDI01588 | 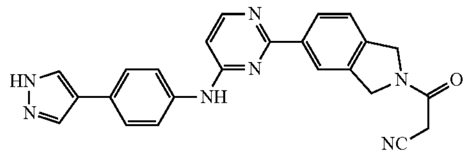 [SMILES: N#CCC(=O)N1Cc2ccc(-c3nccc(Nc4ccc(-c5cn[nH]c5)cc4)n3)cc2C1] | 3-(5-(4-((4-(1H-pyrazol-4-yl)phenyl)amino)pyrimidin-2-yl)isoindolin-2-yl)-3-oxopropanenitrile | in step 4 of Example 44 was replaced with HO—C(=O)—CH₂—CN; and Step 5 was omitted. | $^1$H NMR (400 MHz, DMSO-$d_6$) δ 10.03 (s, 1H), 8.38 (d, J = 6.0 Hz, 1H), 8.31-8.23 (m, 2H), 8.05 (s, 2H), 7.74 (s, 2H), 7.67 (d, J = 5.0 Hz, 2H), 7.57-7.52 (m, 1H), 6.78 (d, J = 5.8 Hz, 1H), 4.90 (d, J = 1.1 Hz, 2H), 4.77 (d, J = 14.1 Hz, 2H), 4.11 (s, 2H). MS m/z (ESI): 422.1 [M + H]. |
| TDI01594 | 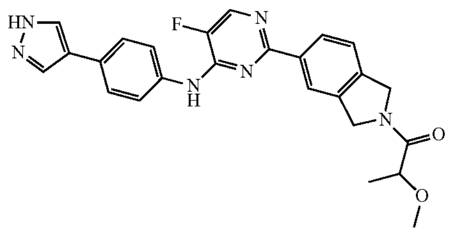 [SMILES: COC(C)C(=O)N1Cc2ccc(-c3ncc(F)c(Nc4ccc(-c5cn[nH]c5)cc4)n3)cc2C1] | 1-(5-(4-((4-(1H-pyrazol-4-yl)phenyl)amino)-5-fluoropyrimidin-2-yl)isoindolin-2-yl)-2-methoxypropan-1-one | (Reg-1-16) in step 2 of Example 44 was replaced with (Reg-1-40); in step 4 was replaced with and Step 5 was omitted. | $^1$H NMR (400 MHz, DMSO-$d_6$) δ 9.69 (s, 1H), 8.48 (s, 1H), 8.27-8.21 (m, 2H), 8.07 (s, 2H), 7.92-7.85 (m, 2H), 7.67 (d, J = 5.9 Hz, 2H), 7.48 (t, J = 8.2 Hz, 1H), 5.03 (d, J = 10.7 Hz, 1H), 4.93 (d, J = 8.7 Hz, 1H), 4.79-4.72 (m, 2H), 4.21-4.17 (m, 1H), 3.25 (s, 3H), 1.28 (d, J = 6.4 Hz, 3H). MS m/z (ESI): 458.7 [M + H]. |

TABLE 13-continued

| No. | Compound Structure | Compound Name | Starting material or regent different from that in Example 44 | Characterization Data |
|---|---|---|---|---|
| TD101594B | 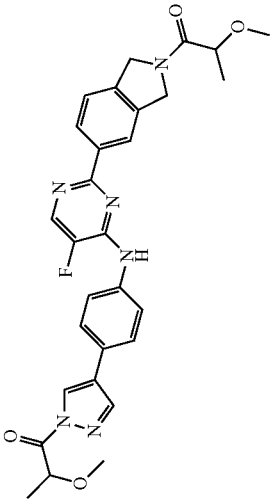 | 1-(4-(4-((5-fluoro-2-(2-(2-methoxypropanoyl)isoindolin-5-yl)pyrimidin-4-yl)amino)phenyl)-1H-pyrazol-1-yl)-2-methoxypropan-1-one | (Reg-1-16) in step 2 of Example 44 was replaced with (Reg-1-40) and in step 4 of Example 44 was replaced with and Step 5 was omitted. | ¹H NMR (400 MHz, DMSO-d₆) δ 9.74 (d, J = 41.4 Hz, 1H), 8.91-8.50 (m, 1H), 8.27-8.20 (m, 2H), 8.07 (s, 1H), 7.99-7.94 (m, 1H), 7.87 (d, J = 6.7 Hz, 2H), 7.67 (d, J = 6.0 Hz, 1H), 7.48 (t, J = 8.4 Hz, 1H), 5.07 (d, J = 16.9 Hz, 1H), 4.93 (d, J = 9.7 Hz, 1H), 4.81-4.72 (m, 2H), 4.22-4.17 (m, 2H), 3.29 (d, J = 31.0 Hz, 6H), 1.48-1.22 (m, 6H). MS m/z (ESI): 544.5 [M + H]. |
| TD101597B | 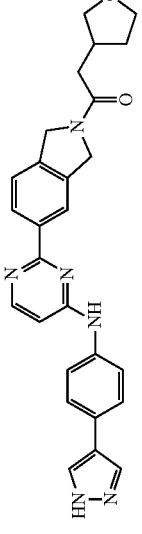 | 1-(5-(4-((4-(1H-pyrazol-4-yl)phenyl)amino)pyrimidin-2-yl)isoindolin-2-yl)-2-(tetrahydrofuran-3-yl)ethan-1-one | in step 4 of Example 44 was replaced with and Step 5 was omitted. | 1H NMR (400 MHz, DMSO-d₆) δ 8.38 (d, J = 6.4 Hz, 1H), 8.28-8.23 (m, 2H), 8.06 (s, 2H), 7.75 (d, J = 8.4 Hz, 2H), 7.67 (d, J = 6.4 Hz, 2H), 7.54 (t, J = 8.4 Hz, 1H), 6.80 (d, J = 6.2 Hz, 2H), 4.93 (d, J = 6.7 Hz, 2H), 4.74 (d, J = 12.7 Hz, 3H), 3.88 (t, J = 6.7 Hz, 2H), 3.75 (dd, J = 13.5, 8.3 Hz, 2H), 3.65 (dd, J = 15.2, 7.5 Hz, 2H), 3.31 (d, J = 7.3 Hz, 1H), 2.08 (s, 1H), 1.56 (s, 1H). MS m/z (ESI): 466.8 [M + H]. |

TABLE 13-continued

| No. | Compound Structure | Compound Name | Starting material or regent different from that in Example 44 | Characterization Data |
|---|---|---|---|---|
| TD101618A | 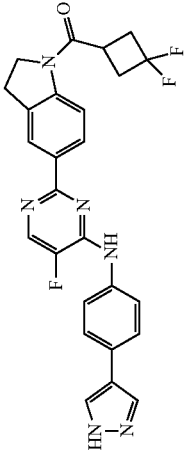 | (5-(4-((1H-pyrazol-4-yl)phenyl)amino)-5-fluoropyrimidin-2-yl)indolin-1-yl)(3,3-difluorocyclobutyl)methanone | 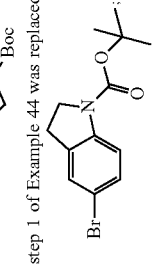 in step 1 of Example 44 was replaced with (Reg-1-16) in step 2 was replaced with (Reg-1-40) in step 4 was replaced with and Step 5 was omitted. | ¹H NMR (400 MHz, DMSO-d₆) δ 9.68 (s, 1H), 8.44 (d, J = 3.6 Hz, 1H), 8.21-8.10 (m, 3H), 8.07 (s, 2H), 7.87 (d, J = 8.4 Hz, 2H), 7.66 (d, J = 8.4 Hz, 2H), 4.12 (t, J = 8.0 Hz, 2H), 3.38-3.32 (m, 1H), 3.23 (t, J = 8.5 Hz, 2H), 2.92-2.84 (m, 4H). MS m/z (ESI): 491.1 [M + H]. |

TABLE 13-continued

| No. | Compound Structure | Compound Name | Starting material or regent different from that in Example 44 | Characterization Data |
|---|---|---|---|---|
| TDI01628 | 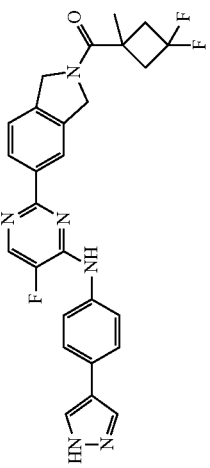 | (5-(4-((4-(1H-pyrazol-4-yl)phenyl)amino)-5-fluoropyrimidin-2-yl)isoindolin-2-yl)(3,3-difluoro-1-methylcyclobutyl)methanone | 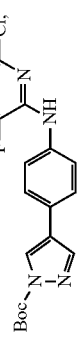<br>(Reg-1-16)<br>in step 2 of Example 44 was replaced with<br>(Reg-1-40)<br>in step 4 was replaced with<br>and Step 5 was omitted. | $^1$H NMR (400 MHz, DMSO-d$_6$) δ 9.68 (s, 1H), 8.48 (s, 1H), 8.28-8.19 (m, 2H), 8.07 (s, 2H), 7.93-7.83 (m, 2H), 7.73-7.63 (m, 2H), 7.46 (dd, J = 20.5, 7.8 Hz, 1H), 4.81 (dd, J = 31.0, 11.6 Hz, 4H), 3.20-3.09 (m, 2H), 2.54 (s, 2H), 1.49 (s, 3H). MS m/z (ESI): 505.0 [M + H]. |

TABLE 13-continued

| No. | Compound Name / Structure | Starting material or regent different from that in Example 44 | Characterization Data |
|---|---|---|---|
| TDI01655 | (7-(4-((4-(1H-pyrazol-4-yl)phenyl)amino)-5-fluoropyrimidin-2-yl)-3,4-dihydroisoquinolin-2(1H)-yl)(3,3-difluoro-1-methylcyclobutyl)methanone | in step 1 of Example 44 was replaced with Boc-protected bromo-indane and Boc-protected bromo-tetrahydroisoquinoline; (Reg-1-16) in step 2 was replaced with (Reg-1-40); in step 4 was replaced with Boc-spiro piperidine carboxylic acid and 3,3-difluoro-1-methylcyclobutane carboxylic acid, and Step 5 was omitted. | $^1$H NMR (400 MHz, DMSO-d$_6$) δ 9.67 (s, 1H), 8.96 (s, 1H), 8.46 (s, 1H), 8.12 (d, J = 45.0 Hz, 4H), 7.88 (d, J = 8.0 Hz, 2H), 7.65 (d, J = 7.6 Hz, 2H), 7.31 (d, J = 7.8 Hz, 1H), 4.71 (s, 1H), 4.57 (s, 1H), 3.72 (s, 1H), 3.57 (s, 1H), 3.12-3.06 (m, 2H), 2.89 (d, J = 24.0 Hz, 2H), 2.65 (d, J = 15.8 Hz, 2H), 1.43 (d, J = 28.2 Hz, 3H). MS m/z (ESI): 518.6 [M + H]. |

TABLE 13-continued

| No. | Compound Structure | Compound Name | Starting material or regent different from that in Example 44 | Characterization Data |
|---|---|---|---|---|
| TDI01657 | (structure) | (6-(4-((4-(1H-pyrazol-4-yl)phenyl)amino)-5-fluoropyrimidin-2-yl)-3,4-dihydroisoquinolin-2(1H)-yl)(4,4-difluorocyclohexyl)methanone | (structure: Br-indoline-N-Boc) in step 1 of Example 44 was replaced with (structure: Br-tetrahydroisoquinoline-N-Boc); (structure: 2-chloropyrimidine with NH-phenyl-pyrazole-N-Boc) (Reg-1-16) in step 2 was replaced with (structure: spiro compound with N-Boc and carboxylic acid) in step 4 was replaced with (structure: 4,4-difluorocyclohexane carboxylic acid); and Step 5 was omitted. | 1H NMR (400 MHz, DMSO-d$_6$) δ 9.68 (s, 1H), 8.46 (d, J = 3.3 Hz, 1H), 8.09 (d, J = 8.0 Hz, 2H), 8.06 (s, 1H), 7.87 (d, J = 8.5 Hz, 2H), 7.84-7.78 (m, 1H), 7.65 (d, J = 8.1 Hz, 1H), 7.58-7.49 (m, 1H), 7.32 (d, J = 8.2 Hz, 1H), 4.67 (s, 2H), 3.80-3.72 (m, 2H), 2.97-2.93 (m, 2H), 2.04-1.86 (m, 5H), 1.81-1.71 (m, 2H), 1.67-1.56 (m, 2H). MS m/z (ESI): 533.1 [M + H]. |

TABLE 13-continued

| No. | Compound Structure | Compound Name | Starting material or regent different from that in Example 44 | Characterization Data |
|---|---|---|---|---|
| TDI01658 | (structure) | (7-(4-((1H-pyrazol-4-yl)phenyl)amino)-5-fluoropyrimidin-2-yl)-3,4-dihydroisoquinolin-2(1H)-yl)(4,4-difluorocyclohexyl)methanone | (structures shown) in step 1 of Example 44 was replaced with (structure); (Reg-1-16) in step 2 was replaced with (structure) (Reg-1-40) in step 4 was replaced with (structure); and Step 5 was omitted. | $^1$H NMR (400 MHz, DMSO-$d_6$) δ 9.66 (s, 1H), 8.96 (s, 1H), 8.46 (s, 1H), 8.09 (t, J = 22.0 Hz, 4H), 7.88 (d, J = 6.7 Hz, 2H), 7.65 (d, J = 8.1 Hz, 2H), 7.31 (d, J = 6.2 Hz, 1H), 4.85 (s, 1H), 4.70 (s, 1H), 3.80 (s, 1H), 3.71 (s, 1H), 3.10 (d, J = 6.1 Hz, 2H), 2.83 (s, 1H), 2.10-1.86 (m, 4H), 1.77 (s, 2H), 1.62 (d, J = 12.6 Hz, 2H). MS m/z (ESI): 532.6 [M + H]. |

TABLE 13-continued

| No. | Compound Structure | Compound Name | Starting material or regent different from that in Example 44 | Characterization Data |
|---|---|---|---|---|
| TDI01665 | (structure) | (8-(4-((4-(1H-pyrazol-4-yl)phenyl)amino)-5-fluoropyrimidin-2-yl)-2,3-dihydrobenzo[f][1,4]oxazepin-4(5H)-yl)(3,3-difluorocyclobutyl)methanone | (structures shown) in step 1 of Example 44 was replaced with (structure); in step 2 was replaced with (structure) (Reg-1-40); in step 4 was replaced with (structure); and Step 5 was omitted. | ¹H NMR (400 MHz, DMSO-d₆) δ 9.72 (s, 1H), 8.48 (s, 1H), 8.09 (s, 2H), 7.94-7.89 (m, 1H), 7.85 (d, J = 8.5 Hz, 2H), 7.79 (s, 1H), 7.66 (d, J = 8.3 Hz, 2H), 7.48 (dd, J = 72.6, 7.7 Hz, 1H), 4.67 (d, J = 12.0 Hz, 2H), 4.18 (s, 2H), 3.90 (s, 2H), 3.28 (dd, J = 19.2, 7.3 Hz, 1H), 2.76 (dd, J = 27.6, 14.9 Hz, 4H). MS m/z (ESI): 520.6 [M + H]. |

| No. | Compound Structure | Compound Name | Starting material or regent different from that in Example 44 | Characterization Data |
|---|---|---|---|---|
| TDI01674 | 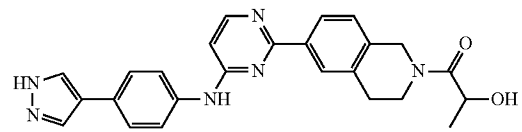 [SMILES: CC(O)C(=O)N1CCc2cc(-c3nccc(Nc4ccc(-c5cn[nH]c5)cc4)n3)ccc2C1] | 1-(6-(4-((4-(1H-pyrazol-4-yl)phenyl)amino)pyrimidin-2-yl)-3,4-dihydroisoquinolin-2(1H)-yl)-2-hydroxypropan-1-one | Br–[indoline]–N–Boc in step 1 of Example 44 was replaced with Br–[tetrahydroisoquinoline]–N–Boc; and HO–[spiro]–C(O)OH was replaced with HO–CH(CH₃)–C(O)OH in step 4 was replaced with and Step 5 was omitted. | ¹H NMR (400 MHz, DMSO-d₆) δ 10.65 (s, 1H), 8.37 (d, J = 6.6 Hz, 1H), 8.14-8.02 (s, 1H), 7.77-7.65 (m, 4H), 7.50-7.39 (m, 1H), 6.87 (d, J = 6.5 Hz, 1H), 4.95-4.74 (m, 2H), 4.73 (d, J = 9.6 Hz, 1H), 4.58-4.50 (m, 2H), 3.89-3.76 (m, 2H), 3.04-2.85 (m, 2H), 1.28-1.16 (m, 3H). MS m/z (ESI): 440.8 [M + H]. |
| TDI01676 | 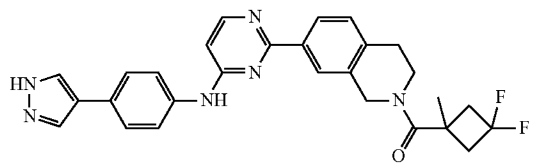 [SMILES: CC1(C(=O)N2CCc3ccc(-c4nccc(Nc5ccc(-c6cn[nH]c6)cc5)n4)cc3C2)CC(F)(F)C1] | (7-(4-((4-(1H-pyrazol-4-yl)phenyl)amino)pyrimidin-2-yl)-3,4-dihydroisoquinolin-2(1H)-yl)(3,3-difluoro-1-methylcyclobutyl)methanone | Br–[indoline]–N–Boc in step 1 of Example 44 was replaced with Br–[tetrahydroisoquinoline]–N–Boc; and HO–[spiro]–C(O)OH was replaced with difluoromethylcyclobutyl acid in step 4 was replaced with and Step 5 was omitted. | ¹H NMR (400 MHz, DMSO-d₆) δ 10.79-10.08 (s, 1H), 8.38 (d, J = 6.4 Hz, 1H), 8.08 (s, 4H), 7.77-7.66 (m, 4H), 7.40 (s, 1H), 6.83 (s, 1H), 4.75 (s, 1H), 4.60 (s, 1H), 3.75 (s, 1H), 3.60 (s, 1H), 3.09-2.92 (m, 4H), 2.68 (s, 2H), 1.45 (d, J = 26.7 Hz, 3H). MS m/z (ESI): 500.8 [M + H]. |

TABLE 13-continued

| No. | Compound Structure | Compound Name | Starting material or regent different from that in Example 44 | Characterization Data |
|---|---|---|---|---|
| TDI01965 | 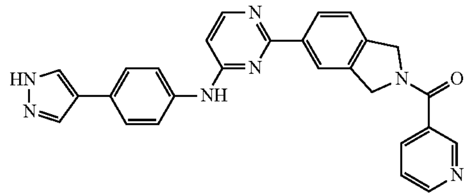 [SMILES: O=C(c1cccnc1)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(pyridin-3-yl)methanone | ![structure] in step 4 of Example 44 was replaced with ![structure] and Step 5 was omitted. | ¹H NMR (400 MHz, DMSO-d₆) δ 12.88 (s, 1H), 9.84 (d, J = 8.9 Hz, 1H), 8.86 (s, 1H), 8.74-8.69 (m, 1H), 8.41-8.28 (m, 3H), 8.12-7.98 (m, 3H), 7.79 (t, J = 8.9 Hz, 2H), 7.64 (dd, J = 12.9, 8.6 Hz, 2H), 7.57-7.41 (m, 2H), 6.77 (t, J = 6.2 Hz, 1H), 4.95 (dd J = 23.6, 15.8 Hz, 4H). MS m/z (ESI): 459.6 [M + H]. |
| TDI01966 | 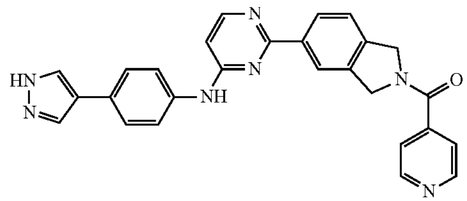 [SMILES: O=C(c1ccncc1)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(pyridin-4-yl)methanone | ![structure] in step 4 of Example 44 was replaced with ![structure] and Step 5 was omitted. | ¹H NMR (400 MHz, DMSO-d₆) δ 13.13 (s, 1H), 9.76 (d, J = 10.1 Hz, 1H), 8.79-8.73 (m, 3H), 8.41-8.28 (m, 3H), 8.03 (d, J = 9.0 Hz, 2H), 7.83-7.75 (m, 4H), 7.63 (dd, J = 7.1, 2.8 Hz, 4H), 6.77-6.73 (m, 1H), 4.97 (d, J = 14.0 Hz, 2H), 4.85 (d, J = 17.9 Hz, 2H). MS m/z (ESI): 459.6 [M + H]. |

TABLE 13-continued

| No. | Compound Structure | Compound Name | Starting material or regent different from that in Example 44 | Characterization Data |
|---|---|---|---|---|
| TDI01967 | 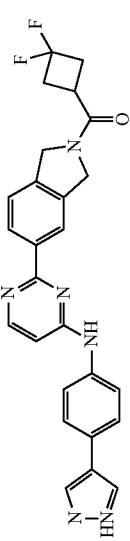 | (5-(4-((1H-indazol-5-yl)amino)pyrimidin-2-yl)isoindolin-2-yl)(3,3-difluorocyclobutyl) methanone | (Reg-1-16) in step 2 of Example 44 was replaced with (Reg-1-1) and in step 4 was replaced with and Step 5 was omitted. | $^1$H NMR (400 MHz, DMSO-$d_6$) δ 13.19 (s, 1H), 10.60 (s, 1H), 8.35 (d, J = 6.1 Hz, 1H), 8.23-8.11 (m, 4H), 7.60 (dd, J = 32.2, 8.4 Hz, 3H), 6.82 (d, J = 5.0 Hz, 1H), 4.92 (s, 2H), 4.77 (d, J = 9.8 Hz, 2H), 3.32-3.27 (m, 1H), 2.86 (dd, J = 16.4, 8.4 Hz, 4H). MS m/z (ESI): 447.0 [M + H]. |
| TDI01968A | 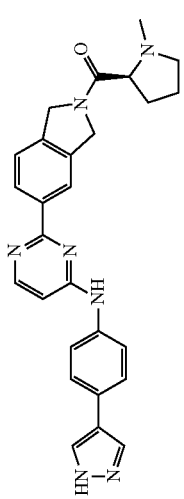 | 5-(4-((4-(1H-pyrazol-4-yl)phenyl)amino)pyrimidin-2-yl)-2-(methyl-L-prolyl)isoindoline | in step 4 of Example 44 was replaced with and Step 5 was omitted. | $^1$H NMR (400 MHz, DMSO-$d_6$) δ 10.06 (s, 1H), 9.71 (s, 1H), 8.41-8.37 (m, 1H), 8.33 (d, J = 4.4 Hz, 1H), 8.05 (d, J = 3.3 Hz, 2H), 7.75 (d, J = 4.2 Hz, 2H), 7.69-7.63 (m, 2H), 7.57 (t, J = 8.5 Hz, 1H), 6.79 (d, J = 6.1 Hz, 1H), 5.07 (d, J = 14.2 Hz, 2H), 4.91 (dd, J = 14.7, 7.6 Hz, 2H), 3.64 (s, 1H), 2.85 (d, J = 4.4 Hz, 3H), 2.67 (s, 2H), 2.07 (dd, J = 62.3, 20.0 Hz, 4H). MS m/z (ESI): 466.1 [M + H]. |

TABLE 13-continued

| No. | Compound Structure | Compound Name | Starting material or regent different from that in Example 44 | Characterization Data |
|---|---|---|---|---|
| TDI01968B | 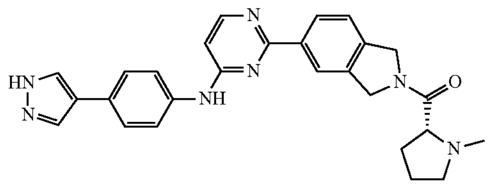 [SMILES: CN1CCC[C@@H]1C(=O)N1Cc2ccc(-c3nccc(Nc4ccc(-c5cn[nH]c5)cc4)n3)cc2C1] | 5-(4-((4-(1H-pyrazol-4-yl)phenyl)amino)pyrimidin-2-yl)-2-(methyl-D-prolyl)isoindoline | [spiro piperidine-Boc carboxylic acid structure]; in step 4 of Example 44 was replaced with [N-methyl-D-proline structure] and Step 5 was omitted. | $^1$H NMR (400 MHz, DMSO-$d_6$) δ 10.22 (s, 1H), 9.72 (s, 1H), 8.41-8.38 (m, 1H), 8.30 (dd, J = 16.6, 8.3 Hz, 2H), 8.06 (d, J = 3.2 Hz, 2H), 7.75 (s, 2H), 7.70-7.65 (m, 2H), 7.59 (t, J = 8.6 Hz, 1H), 6.83 (d, J = 6.2 Hz, 1H), 5.05 (t, J = 23.5 Hz, 2H), 4.91 (dd, J = 14.7, 6.7 Hz, 2H), 3.21-3.14 (m, 1H), 2.86 (d, J = 2.6 Hz, 3H), 2.68 (s, 2H), 2.23-1.84 (m, 4H). MS m/z (ESI): 465.7 [M + H]. |
| TDI01969 | 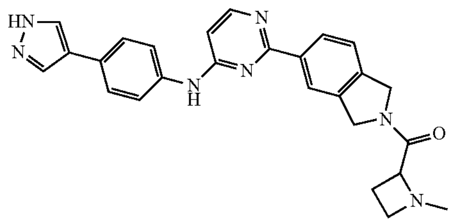 [SMILES: CN1CCC1C(=O)N1Cc2ccc(-c3nccc(Nc4ccc(-c5cn[nH]c5)cc4)n3)cc2C1] | (5-(4-((4-(1H-pyrazol-4-yl)phenyl)amino)pyrimidin-2-yl)isoindolin-2-yl)(1-methylazetidin-2-yl)methanone | [spiro piperidine-Boc carboxylic acid structure]; in step 4 of Example 44 was replaced with [1-methylazetidine-2-carboxylic acid] and Step 5 was omitted. | $^1$H NMR (400 MHz, DMSO-$d_6$) δ 9.97 (d, J = 32.8 Hz, 3H), 8.40-8.28 (m, 4H), 8.04 (d, J = 2.8 Hz, 2H), 7.77-7.73 (m, 2H), 7.67-7.63 (m, 2H), 7.55 (d, J = 7.6 Hz, 1H), 6.77 (d, J = 5.9 Hz, 1H), 5.36 (d, J = 7.5 Hz, 1H), 4.91-4.81 (m, 4H), 4.01 (d, J = 5.8 Hz, 2H), 2.85 (d, J = 3.7 Hz, 5H). MS m/z (ESI): 452.0 [M + H]. |
| TDI01973 | 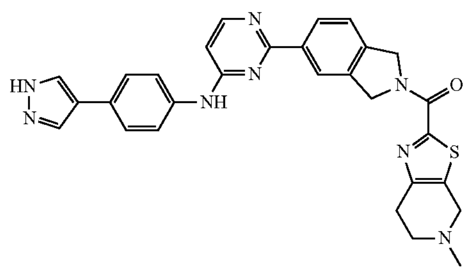 [SMILES: CN1CCc2nc(C(=O)N3Cc4ccc(-c5nccc(Nc6ccc(-c7cn[nH]c7)cc6)n5)cc4C3)sc2C1] | (5-(4-((4-(1H-pyrazol-4-yl)phenyl)amino)pyrimidin-2-yl)isoindolin-2-yl)(5-methyl-4,5,6,7-tetrahydrothiazolo[5,4-c]pyridin-2-yl)methanone | [spiro piperidine-Boc carboxylic acid structure]; in step 4 of Example 44 was replaced with [5-methyl-tetrahydrothiazolopyridine-2-carboxylic acid] and Step 5 was omitted. | $^1$H NMR (400 MHz, DMSO-$d_6$) δ 10.35 (s, 1H), 10.00 (s, 1H), 8.37 (dd, J = 20.8, 14.4 Hz, 3H), 8.06 (s, 2H), 7.77 (d, J = 5.6 Hz, 2H), 7.64 (dd, J = 25.3, 7.4 Hz, 3H), 6.80 (d, J = 5.4 Hz, 1H), 5.46 (d, J = 6.9 Hz, 2H), 5.03 (d, J = 12.6 Hz, 2H), 4.81 (s, 1H), 4.53 (s, 1H), 3.81 (s, 1H), 3.57 (s, 1H), 3.25 (s, 2H), 3.01 (s, 3H). MS m/z (ESI): 535.1 [M + H]. |

TABLE 13-continued

| No. | Compound Structure | Compound Name | Starting material or regent different from that in Example 44 | Characterization Data |
|---|---|---|---|---|
| TDI01976 | 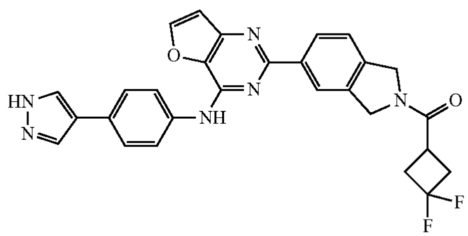 [SMILES: O=C(C1CC(F)(F)C1)N1Cc2ccc(-c3nc(Nc4ccc(-c5cn[nH]c5)cc4)c4occc4n3)cc2C1] | (5-(4-(4-((1H-pyrazol-4-yl)phenyl)amino)furo[3,2-d]pyrimidin-2-yl)isoindolin-2-yl)(3,3-difluorocyclobutyl)methanone | (Reg-1-16) in step 2 of Example 44 was replaced with (Reg-1-44); in Step 4 was replaced with and Step 5 was omitted. | $^1$H NMR (400 MHz, DMSO-d$_6$) δ 10.30 (s, 1H), 8.45 (s, 1H), 8.30 (dd, J = 15.2, 6.9 Hz, 2H), 8.09 (d, J = 2.3 Hz, 2H), 7.92 (dd, J = 8.2, 3.0 Hz, 2H), 7.68 (dd, J = 8.4, 3.1 Hz, 2H), 7.53-7.47 (m, 1H), 7.16 (s, 1H), 4.90 (d, J = 11.0 Hz, 2H), 4.76 (d, J = 17.2 Hz, 2H), 3.32-3.27 (m, 1H), 2.90-2.83 (m, 4H). MS m/z (ESI): 512.6 [M + H]. |

TABLE 13-continued

| No. | Compound Structure | Compound Name | Starting material or regent different from that in Example 44 | Characterization Data |
|---|---|---|---|---|
| TDI01978 | 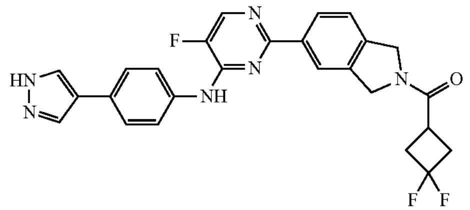 [SMILES: O=C(C1CC(F)(F)C1)N1Cc2ccc(-c3ncc(F)c(Nc4ccc(-c5cn[nH]c5)cc4)n3)cc2C1] | (5-(4-((1H-pyrazol-4-yl)phenyl)amino)-5-fluoropyrimidin-2-yl)isoindolin-2-yl)(3,3-difluorocyclobutyl)methanone | (Reg-1-16) in step 2 of Example 44 was replaced with (Reg-1-40); and in Step 4 was replaced with the 3,3-difluorocyclobutyl carboxylic acid; and Step 5 was omitted. | 1H NMR (400 MHz, DMSO-d$_6$) δ 9.68 (s, 1H), 8.47 (d, J = 2.6 Hz, 1H), 8.23 (dd, J = 16.6, 8.4 Hz, 2H), 8.07 (s, 2H), 7.94-7.81 (m, 2H), 7.66 (dd, J = 8.4, 3.8 Hz, 2H), 7.47 (dd, J = 15.2, 8.0 Hz, 1H), 4.89 (d, J = 9.6 Hz, 2H), 4.74 (d, J = 15.1 Hz, 2H), 3.31-3.26 (m, 1H), 2.86 (dd, J = 16.4, 8.4 Hz, 4H). MS m/z (ESI): 490.9 [M + H]. |
| TDI01989 | 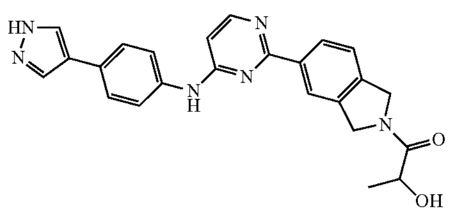 [SMILES: CC(O)C(=O)N1Cc2ccc(-c3nccc(Nc4ccc(-c5cn[nH]c5)cc4)n3)cc2C1] | 1-(5-(4-((4-((1H-pyrazol-4-yl)phenyl)amino)pyrimidin-2-yl)isoindolin-2-yl)-2-hydroxypropan-1-one | in step 4 of Example 44 was replaced with 2-hydroxypropanoic acid; and Step 5 was omitted. | 1H NMR (400 MHz, DMSO-d$_6$) δ 10.07 (s, 1H), 8.39 (d, J = 6.0 Hz, 1H), 8.28 (dd, J = 13.6, 5.1 Hz, 2H), 8.06 (s, 2H), 7.79-7.65 (m, 3H), 7.58-7.50 (m, 1H), 6.79 (d, J = 5.6 Hz, 1H), 5.10 (dd, J = 15.4, 6.0 Hz, 1H), 4.98 (dd, J = 14.9, 6.7 Hz, 1H), 4.82-4.71 (m, 2H), 4.45-4.40 (m, 1H), 3.15 (dd, J = 7.3, 4.2 Hz, 1H), 1.30-1.26 (m, 3H). MS m/z (ESI): 426.9 [M + H]. |

Example 45: preparation of (5-(4-(44-(1H-pyrazol-4-yl)phenyl)amino)pyrimidin-2-yl)isoindolin-2-yl)(3,3-difluorocyclobutyl)methanone (TDI01944)

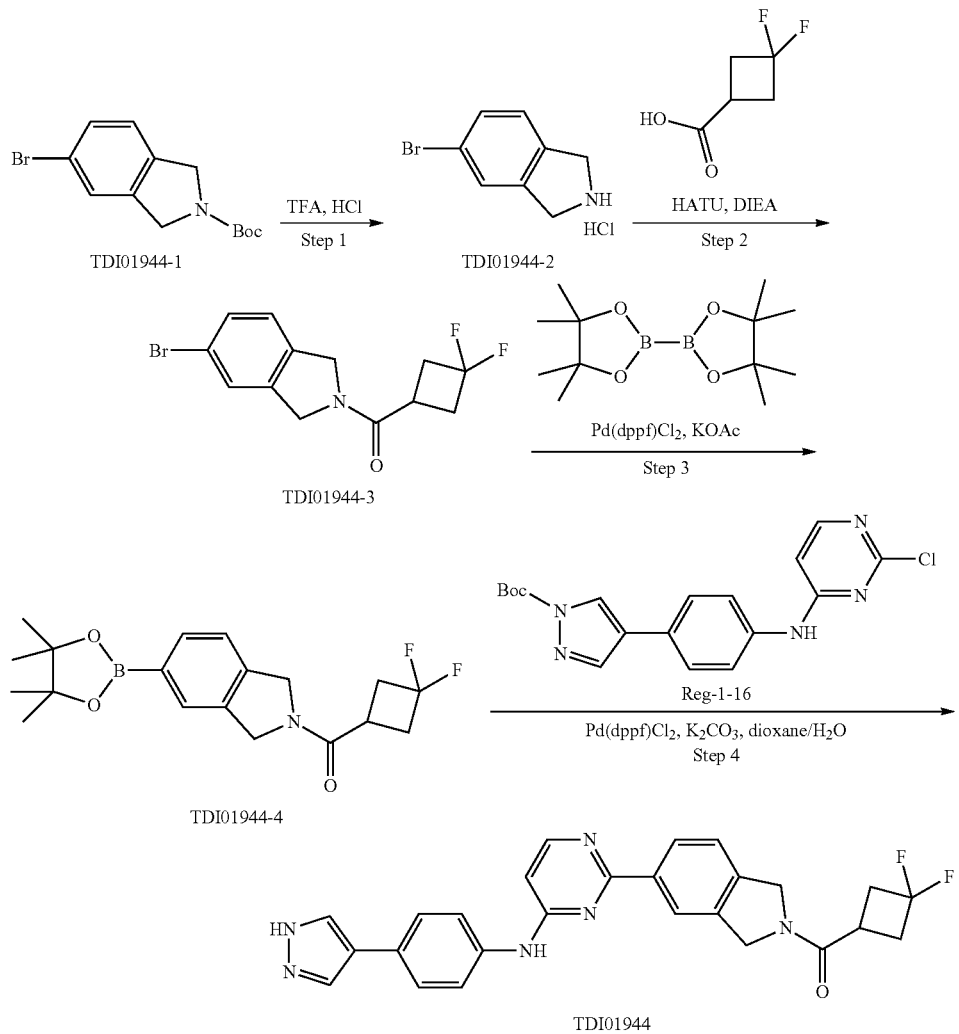

Step 1:

Compound TDI01944-1 (20 g, 67 mmol) was dissolved in dichloromethane (20 mL), trifluoroacetic acid (50 mL) was added, and the reaction solution was stirred at room temperature for 16 hours. The reaction solvent and trifluoroacetic acid were removed through rotary evaporation under vacuum, and the residue was added with 20 mL water and 40 mL concentrated hydrochloric acid. A solid precipitated, and was filtered and dried to afford compound TDI01944-2 (15.3 g, grey solid).

$^1$H NMR (400 MHz, CDCl$_3$) δ 7.39 (s, 1H), 7.34 (d, J=8.2 Hz, 1H), 7.12 (d, J=8.0 Hz, 1H), 4.22 (d, J=14.1 Hz, 4H). MS m/z (ESI): 197.9, 199.8 [M-Cl]$^+$.

Step 2:

Compound 3,3-difluorocyclobutanecarboxylic acid (3.1 g, 23 mmol) was dissolved in N,N-dimethylformamide (100 mL), HATU (9.5 g, 25 mmol), diisopropylethylamine (8.7 g, 67 mmol) and TDI01944-2 (4.5 g, 19 mmol) were successively added, and the reaction was continually stirred at room temperature for 16 hours. The reaction solvent was removed through rotary evaporation under vacuum, the residue was dissolved in 20 mL dichloromethane, washed with water (20 mL×3), and then the organic phase was concentrated until a solid precipitated. After the solid precipitated completely, it was filtered and dried to afford TDI01944-3 (4.2 g, grey solid, crude product, 70% yield).

MS m/z (ESI): 315.7, 317.8 [M+H].

Step 3:

Compound TDI01944-3 (4.1 g, 13 mmol) and bis(pinacolato)diboron (4.1 g, 16 mmol) were dissolved in N,N-dimethylformamide (100 mL), potassium acetate (4.1 g, 16 mmol) and Pd(dppf)Cl$_2$ (0.95 g, 1.3 mmol) were added, the flask was purged with nitrogen three times, and the reaction solution was stirred at 110° C. for 16 hours. LC-MS indicated the reaction was complete. The reaction solution was cooled to room temperature, and the reaction solvent was removed through rotary evaporation under vacuum. The residue was purified by column chromatography (petroleum ether:ethyl acetate=5:1), to afford compound TDI01944-4 (3.8 g, white solid, 81% yield).

$^1$H NMR (400 MHz, CDCl$_3$) δ 7.73-7.79 (m, 2H), 728-7.35 (m, 1H), 4.78-4.85 (m, 4H), 3.09-3.17 (m, 1H), 2.94-3.05 (m, 2H), 2.80-2.85 (m, 2H), 1.38 (s, 12H). MS m/z (ESI): 363.9 [M+H].

Step 4:

Compound TDI01944-4 (3.72 g, 10.0 mmol) and compound Reg-1-16 (3.63 g, 10.0 mmol) were dissolved in a mixed solution of dioxane (80 mL) and water (8 mL), potassium carbonate (4.15 g, 30.0 mmol) was added, and the flask was purged with nitrogen three times. Pd(dppf)Cl$_2$ (1.46 g, 2.0 mmol) was added, the flask was purged with nitrogen three times again, and the reaction solution was stirred at 110° C. for 16 h. LC-MS indicated the reaction was complete. The reaction solution was cooled to room temperature, and the reaction solvent was removed through rotary evaporation under vacuum. The residue was purified by column chromatography (petroleum ether:ethyl acetate=4:1 to pure ethyl acetate) to afford compound TDI01944 (1.35 g, off-white solid, 28.7% yield).

$^1$H NMR (400 MHz, DMSO-d$_6$) δ 12.90 (s, 1H), 9.68 (s, 1H), 8.38 (dd, J=5.8, 1.2 Hz, 1H), 8.36-8.28 (m, 2H), 8.16 (s, 1H), 7.92 (s, 1H), 7.77 (d, J=6.7 Hz, 2H), 7.64 (dd, J=8.6, 3.5 Hz, 2H), 7.49 (dd, J=15.4, 8.0 Hz, 1H), 6.73 (d, J=5.9 Hz, 1H), 4.91 (d, J=11.0 Hz, 2H), 4.76 (d, J=14.9 Hz, 2H), 3.29 (d, J=8.3 Hz, 1H), 2.87 (dd, J=16.5, 8.6 Hz, 4H). MS m/z (ESI): 472.5 [M+H].

The compounds in following table 14 were prepared according to methods similar to that described in Example 45.

TABLE 14

| No. | Compound Structure | Compound Name | Starting material or regent different from that in Example 45 | Characterization Data |
|---|---|---|---|---|
| TDI01958 | 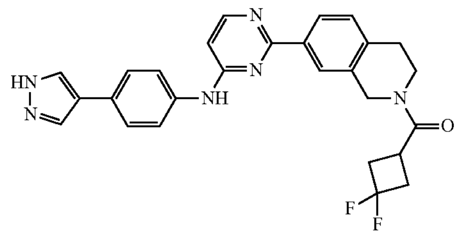 [SMILES: O=C(C1CC(F)(F)C1)N1CCc2ccc(-c3nccc(Nc4ccc(-c5cn[nH]c5)cc4)n3)cc2C1] | (7-(4-((4-(1H-pyrazol-4-yl)phenyl)amino)pyrimidin-2-yl)-3,4-dihydroisoquinolin-2(1H)-yl)(3,3-difluorocyclobutyl)methanone | The synthesis started from step 2 of Example 45; Br-indanamine·HCl in step 2 was replaced with Br-tetrahydroisoquinoline·HCl. | ¹H NMR (400 MHz, DMSO-d₆) δ 12.89 (s, 1H), 9.66 (s, 1H), 8.36 (d, J = 6.0 Hz, 1H), 8.26-8.11 (m, 3H), 7.91 (s, 1H), 7.81-7.71 (m, 2H), 7.63 (d, J = 8.0 Hz, 2H), 7.32 (dd, J = 8.0, 4 Hz, 1H), 6.71 (d, J = 6.0 Hz, 1H), 4.73 (d, J = 8.0 Hz, 2H), 3.71 (dt, J = 27.8, 5.8 Hz, 2H), 3.45-3.35 (m, 1H), 2.95-2.74 (m, 6H). MS m/z (ESI): 486.6 [M + H]. |
| TDI01962 | 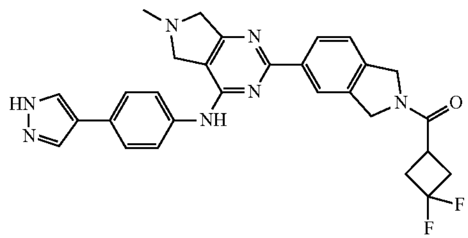 [SMILES: CN1Cc2nc(-c3ccc4c(c3)CN(C(=O)C3CC(F)(F)C3)C4)nc(Nc3ccc(-c4cn[nH]c4)cc3)c2C1] | (5-(4-((4-(1H-pyrazol-4-yl)phenyl)amino)-6-methyl-6,7-dihydro-5H-pyrrolo[3,4-d]pyrimidin-2-yl)isoindolin-2-yl)(3,3-difluorocyclobutyl)methanone | (Reg-1-16) and (Reg-1-57) in step 4 of Example 45 was replaced with | ¹H NMR (400 MHz, DMSO-d₆) δ 10.73 (s, 1H), 9.46 (s, 1H), 8.34-8.24 (m, 2H), 8.07 (s, 2H), 7.76 (s, 2H), 7.70 (s, 2H), 7.48 (s, 1H), 4.89 (s, 2H), 4.76 (d, J = 13.4 Hz, 4H), 4.46 (s, 2H), 3.29 (s, 1H), 3.12 (s, 3H), 2.92-2.76 (m, 4H). MS m/z (ESI): 527.6 [M + H]. |
| TDI01979 | 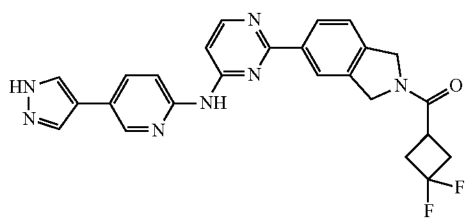 [SMILES: O=C(C1CC(F)(F)C1)N1Cc2ccc(-c3nccc(Nc4ccc(-c5cn[nH]c5)cn4)n3)cc2C1] | (5-(4-((5-(1H-pyrazol-4-yl)pyridin-2-yl)amino)pyrimidin-2-yl)isoindolin-2-yl)(3,3-difluorocyclobutyl)methanone | (Reg-1-16) and (Reg-1-52) in step 4 of Example 45 was replaced with | ¹H NMR (400 MHz, DMSO-d₆) δ 10.85 (s, 1H), 8.68 (s, 1H), 8.53 (d, J = 6.0 Hz, 1H), 8.31 (s, 1H), 8.27 (d, J = 2.0 Hz, 1H), 8.14-8.10 (m, 3H), 7.94-7.85 (m, 1H), 7.73-7.65 (m, 2H), 7.58-7.51 (m, 1H), 4.91 (s, 2H), 4.79 (s, 2H), 3.34-3.24 (m, 1H), 2.90-2.81 (m, 4H). MS m/z (ESI): 474.0 [M + H]. |

TABLE 14-continued

| No. | Compound Structure | Compound Name | Starting material or regent different from that in Example 45 | Characterization Data |
|---|---|---|---|---|
| TDI01990 | 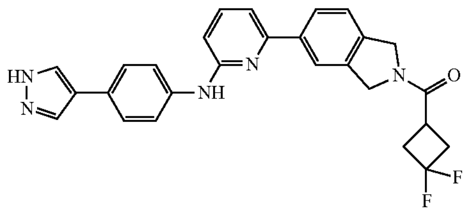 [SMILES: O=C(C1CC(F)(F)C1)N1Cc2ccc(-c3cccc(Nc4ccc(-c5cn[nH]c5)cc4)n3)cc2C1] | (5-(6-((4-(1H-pyrazol-4-yl)phenyl)amino)pyridin-2-yl)isoindolin-2-yl)(3,3-difluorocyclobutyl)methanone | (Reg-1-16)<br><br>in step 4 of Example 45 was replaced with<br><br>(Reg-1-60) | $^1$H NMR (400 MHz, DMSO-d$_6$) δ 9.16 (s, 1H), 8.04-7.98 (m, 4H), 7.77 (d, J = 8.0 Hz, 2H), 7.66 (t, J = 8.0 Hz, 1H), 7.56 (dd, J = 8.0, 4.0 Hz, 2H), 7.47 (dd, J = 16.0, 8.0 Hz, 1H), 7.31 (dd, J = 8.0, 4.0 Hz, 1H), 6.81 (d, J = 8.0 Hz, 1H), 4.89 (d, J = 12.0 Hz, 1H), 4.75 (d, J = 12.0 Hz, 1H), 3.36-3.23 (m, 1H), 2.96-2.74 (m, 4H). MS m/z (ESI): 472.0 [M + H]. |
| TDI01991 | 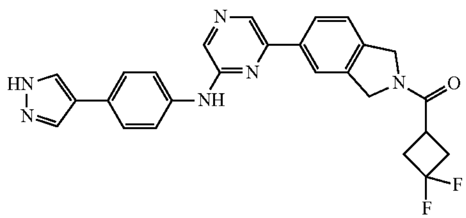 [SMILES: O=C(C1CC(F)(F)C1)N1Cc2ccc(-c3cncc(Nc4ccc(-c5cn[nH]c5)cc4)n3)cc2C1] | (5-(6-((4-(1H-pyrazol-4-yl)phenyl)amino)pyrazin-2-yl)isoindolin-2-yl)(3,3-difluorocyclobutyl)methanone | (Reg-1-16)<br><br>in step 4 of Example 45 was replaced with<br><br>(Reg-1-61) | $^1$H NMR (400 MHz, DMSO-d$_6$) δ 9.61 (s, 1H), 8.52 (d, J = 4.0 Hz, 1H), 8.18 (s, 1H), 8.13-7.98 (m, 4H), 7.79 (d, J = 8.0 Hz, 2H), 7.60 (dd, J = 8.0, 4.0 Hz, 2H), 7.51 (q, J = 8.0 Hz, 1H), 4.90 (d, J = 16.0 Hz, 2H), 4.76 (d, J = 16.0 Hz, 2H), 3.32-3.26 (m, 1H), 2.90-2.83 (m, 4H). MS m/z (ESI): 472.6 [M + H]. |

TABLE 14-continued

| No. | Compound Structure | Compound Name | Starting material or regent different from that in Example 45 | Characterization Data |
|---|---|---|---|---|
| TDI01999 | 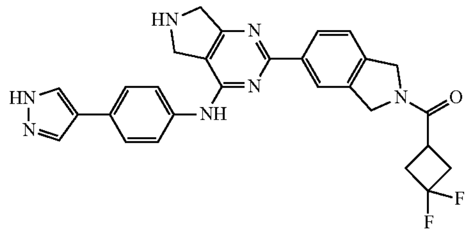 [SMILES: O=C(C1CC(F)(F)C1)N1Cc2ccc(-c3nc4c(c(Nc5ccc(-c6cn[nH]c6)cc5)n3)CNC4)cc2C1] | (5-(4-((4-(1H-pyrazol-4-yl)phenyl)amino)-6,7-dihydro-5H-pyrrolo[3,4-d]pyrimidin-2-yl)isoindolin-2-yl)(3,3-difluorocyclobutyl)methanone | (Reg-1-16); (Reg-1-56) in step 4 of Example 45 was replaced with and the final product was obtained by removing Boc in the intermediate obtained in the final step using a 4N hydrochloric acid/dioxane solution. | $^1$H NMR (300 MHz, DMSO-$d_6$) δ 9.48 (s, 2H), 9.37 (s, 1H), 8.30-8.22 (m, 2H), 8.05 (s, 2H), 7.75 (d, J = 3.4 Hz, 2H), 7.67 (d, J = 6.2 Hz, 2H), 7.54-7.41 (m, 1H), 4.88 (s, 2H), 4.75 (d, J = 10.2 Hz, 2H), 4.51 (d, J = 14.3 Hz, 4H), 3.27 (d, J = 9.6 Hz, 1H), 2.86 (dd, J = 16.3, 8.4 Hz, 4H). MS m/z (ESI): 513.6 [M + H]. |
| TDI01536 | 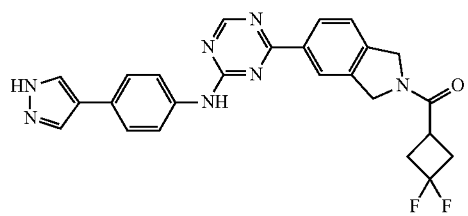 [SMILES: O=C(C1CC(F)(F)C1)N1Cc2ccc(-c3ncnc(Nc4ccc(-c5cn[nH]c5)cc4)n3)cc2C1] | (5-(4-((4-(1H-pyrazol-4-yl)phenyl)amino)-1,3,5-triazin-2-yl)isoindolin-2-yl)(3,3-difluorocyclobutyl)methanone | (Reg-1-16); (Reg-1-41) in step 4 of Example 45 was replaced with | $^1$H NMR (400 MHz, DMSO-$d_6$) δ 10.35 (s, 1H), 8.84 (s, 1H), 8.43-8.31 (m, 2H), 8.05 (s, 1H), 7.79 (s, 2H), 7.65 (s, 2H), 7.56 (d, J = 8.1 Hz, 1H), 4.92 (s, 2H), 4.78 (d, J = 9.8 Hz, 2H), 3.31 (s, 1H), 2.87 (dd, J = 16.3, 8.6 Hz, 4H). MS m/z (ESI): 473.8 [M + H]. |

| No. | Compound Structure | Compound Name | Starting material or regent different from that in Example 45 | Characterization Data |
|---|---|---|---|---|
| TDI01550 | 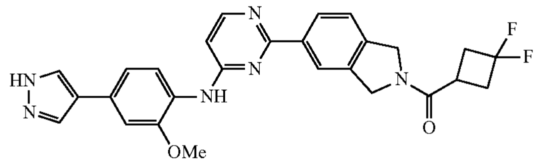 [SMILES: COc1cc(-c2cn[nH]c2)ccc1Nc1ccnc(-c2ccc3c(c2)CN(C(=O)C2CC(F)(F)C2)C3)n1] | (3,3-difluorocyclobutyl)(5-(4-((2-methoxy-4-(1H-pyrazol-4-yl)phenyl)amino)pyrimidin-2-yl)isoindolin-2-yl)methanone | (Reg-1-16) and (Reg-1-32) in step 4 of Example 45 was replaced with | $^1$H NMR (400 MHz, DMSO-d$_6$) δ 9.91 (dd, J = 34.5, 20.4 Hz, 2H), 8.33 (d, J = 6.2 Hz, 1H), 8.26-8.02 (m, 4H), 7.85 (s, 1H), 7.55 (dd, J = 14.8, 8.1 Hz, 1H), 7.38 (s, 1H), 7.33-7.27 (m, 1H), 6.86 (s, 1H), 4.90 (s, 2H), 4.76 (d, J = 7.8 Hz, 2H), 3.93 (s, 3H), 3.29 (dd, J = 10.0, 6.3 Hz, 1H), 2.86 (dd, J = 16.3, 8.4 Hz, 4H). MS m/z (ESI): 502.6 [M + H]. |
| TDI01564 | 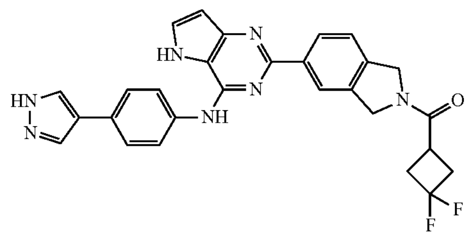 | (5-(4-((4-(1H-pyrazol-4-yl)phenyl)amino)-5H-pyrrolo[3,2-d]pyrimidin-2-yl)isoindolin-2-yl)(3,3-difluorocyclobutyl)methanone | (Reg-1-16) and (Reg-1-62) in step 4 of Example 45 was replaced with | $^1$H NMR (400 MHz, DMSO-d$_6$) δ 11.85 (s, 1H), 8.22 (dd, J = 16.1, 8.3 Hz, 2H), 8.10 (s, 2H), 7.93-7.86 (m, 2H), 7.78-7.70 (m, 2H), 7.61 (dd, J = 15.1, 7.8 Hz, 2H), 6.66 (s, 1H), 4.94 (d, J = 7.0 Hz, 2H), 4.80 (d, J = 15.9 Hz, 2H), 3.32 (d, J = 8.2 Hz, 1H), 2.88 (dd, J = 16.3, 8.2 Hz, 4H). MS m/z (ESI): 511.6 [M + H]. |

TABLE 14-continued

| No. | Compound Name | Compound Structure | Starting material or regent different from that in Example 45 | Characterization Data |
|---|---|---|---|---|
| TDI01565 | (5-(4-((4-(1H-pyrazol-4-yl)phenyl)amino)-7H-pyrrolo[2,3-d]pyrimidin-2-yl)isoindolin-2-yl)(3,3-difluorocyclobutyl)methanone | [structure] | (Reg-1-16) in step 4 of Example 45 was replaced with (Reg-1-63) | $^1$H NMR (400 MHz, DMSO-d$_6$) δ 11.81 (s, 1H), 9.43 (s, 1H), 8.33 (d, J = 18.2 Hz, 3H), 8.06 (s, 2H), 7.97 (d, J = 5.5 Hz, 2H), 7.66 (d, J = 4.3 Hz, 2H), 7.49-7.44 (m, 1H), 7.28 (s, 1H), 6.82 (s, 1H), 4.90 (d, J = 16.4 Hz, 2H), 4.76 (d, J = 21.9 Hz, 2H), 3.30 (s, 1H), 2.87 (dd, J = 16.3, 8.4 Hz, 4H). MS m/z (ESI): 512.1 [M + H]. |

TABLE 14-continued

| No. | Compound Structure | Compound Name | Starting material or regent different from that in Example 45 | Characterization Data |
|---|---|---|---|---|
| TDI01566 | 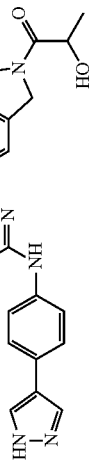 | 1-(5-(4-((1H-pyrazol-4-yl)phenyl)amino)-6,7-dihydro-5H-pyrrolo[3,4-d]pyrimidin-2-yl)isoindolin-2-yl)-2-hydroxypropan-1-one | 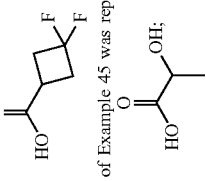 in step 2 of Example 45 was replaced with 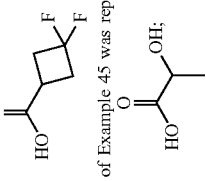; 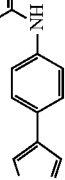 (Reg-1-16) in step 4 was replaced with  (Reg-1-56) and the final product was obtained by removing Boc in the intermediate obtained in the final step using a 4N hydrochloric acid/dioxane solution. | $^1$H NMR (400 MHz, DMSO-$d_6$) δ 9.50 (s, 2H), 9.39 (s, 1H), 8.35-8.22 (m, 2H), 8.07 (s, 2H), 7.78 (s, 2H), 7.69 (s, 2H), 7.49 (d, J = 8.8 Hz, 1H), 5.05 (s, 1H), 4.96 (s, 1H), 4.74 (d, J = 13.6 Hz, 2H), 4.52 (d, J = 19.2 Hz, 4H), 4.41 (s, 1H), 1.27 (d, J = 6.4 Hz, 3H). MS m/z (ESI): 467.7 [M + H]. |

| No. | Compound Structure | Compound Name | Starting material or regent different from that in Example 45 | Characterization Data |
|---|---|---|---|---|
| TDI01567B | 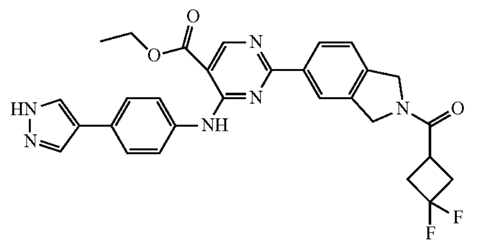 [SMILES: CCOC(=O)c1cnc(-c2ccc3c(c2)CN(C(=O)C2CC(F)(F)C2)C3)nc1Nc1ccc(-c2cn[nH]c2)cc1] | ethyl 4-((4-(1H-pyrazol-4-yl)phenyl)amino)-2-(2-(3,3-difluorocyclobutane-1-carbonyl)isoindolin-5-yl)pyrimidine-5-carboxylate | (Reg-1-16) in step 4 of Example 45 was replaced with (Reg-1-64) | $^1$H NMR (400 MHz, DMSO-d$_6$) δ 10.26 (s, 1H), 9.05 (s, 1H), 8.34 (dd, J = 16.4, 8.1 Hz, 3H), 8.10 (s, 2H), 7.80 (s, 3H), 7.73-7.70 (m, 2H), 7.53 (dd, J = 15.5,7.8 Hz, 1H), 4.92 (d, J = 5.9 Hz, 3H), 4.77 (d, J = 13.9 Hz, 3H), 4.42 (d, J = 7.2 Hz, 3H), 3.29 (s, 2H), 2.90-2.83 (m, 6H), 1.40 (t, J = 1.1 Hz, 4H). MS m/z (ESI): 545.0 [M + H]. |
| TDI01569 | 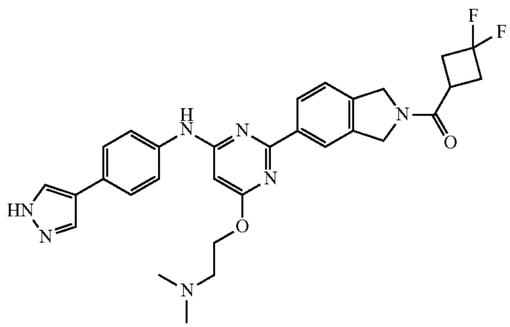 [SMILES: CN(C)CCOc1cc(Nc2ccc(-c3cn[nH]c3)cc2)nc(-c2ccc3c(c2)CN(C(=O)C2CC(F)(F)C2)C3)n1] | (5-(4-((4-(1H-pyrazol-4-yl)phenyl)amino)-6-(2-(dimethylamino)ethoxy)pyrimidin-2-yl)isoindolin-2-yl)(3,3-difluorocyclobutyl)methanone | (Reg-1-16) in step 4 of Example 45 was replaced with (Reg-1-51) | $^1$H NMR (400 MHz, DMSO-d$_6$) δ 9.83 (s, 1H), 9.65 (s, 1H), 8.02 (s, 2H), 7.96 (d, J = 6.6 Hz, 1H), 7.68 (d, J = 8.0 Hz, 2H), 7.59 (d, J = 8.3 Hz, 2H), 7.54-7.48 (m, 1H), 6.97 (s, 1H), 4.89 (s, 2H), 4.78-4.69 (m, 4H), 3.59 (s, 2H), 3.28 (d, J = 8.0 Hz, 1H), 2.94-2.77 (m, 10H). MS m/z (ESI): 559.5 [M + H]. |

TABLE 14-continued

| No. | Compound Structure | Compound Name | Starting material or regent different from that in Example 45 | Characterization Data |
|---|---|---|---|---|
| TDI01578 | 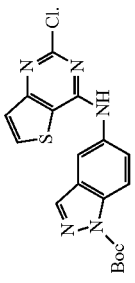 | (5-(4-((1H-indazol-5-yl)amino)thieno[3,2-d]pyrimidin-2-yl)isoindolin-2-yl)(3,3-difluorocyclobutyl)methanone | 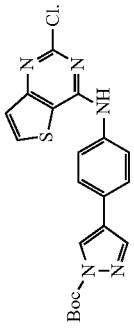<br>(Reg-1-16)<br>in step 4 of Example 45 was replaced with<br>(Reg-1-4) | $^1$H NMR (400 MHz, DMSO-d$_6$) δ 13.14 (d, J = 14.1 Hz, 1H), 10.07 (s, 1H), 8.36-8.30 (m, 2H), 8.22 (d, J = 4.9 Hz, 1H), 8.14 (s, 2H), 7.67 (s, 1H), 7.62 (d, J = 8.8 Hz, 1H), 7.48 (dd, J = 15.1, 6.7 Hz, 2H), 4.89 (d, J = 8.7 Hz, 2H), 4.75 (d, J = 13.4 Hz, 2H), 3.32-3.27 (m, 1H), 2.90-2.81 (m, 4H). MS m/z (ESI): 502.5 [M + H]. |
| TDI01584 | 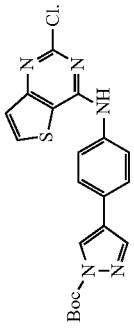 | (5-(4-(4-(1H-pyrazol-4-yl)phenyl)aminothieno[3,2-d]pyrimidin-2-yl)isoindolin-2-yl)(3,3-difluorocyclobutyl)methanone | (Reg-1-16)<br>in step 4 of Example 45 was replaced with<br>(Reg-1-33) | $^1$H NMR (400 MHz, DMSO-d$_6$) δ 10.06 (s, 1H), 8.46-8.21 (m, 4H), 8.10 (s, 2H), 7.85 (d, J = 5.7 Hz, 2H), 7.70 (dd, J = 8.3, 2.5 Hz, 2H), 7.55-7.48 (m, 2H), 4.91 (d, J = 9.8 Hz, 2H), 4.77 (d, J = 17.4 Hz, 2H), 3.32-3.26 (m, 1H), 2.87 (dd, J = 16.5, 8.5 Hz, 4H). MS m/z (ESI): 528.5 [M + H]. |

TABLE 14-continued

| No. | Compound Structure | Compound Name | Starting material or regent different from that in Example 45 | Characterization Data |
|---|---|---|---|---|
| TDI01585 | 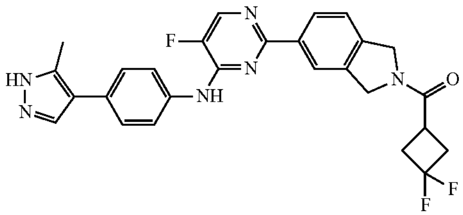 [SMILES: Cc1[nH]ncc1-c1ccc(Nc2nc(-c3ccc4c(c3)CN(C(=O)C3CC(F)(F)C3)C4)ncc2F)cc1] | (3,3-difluorocyclobutyl)(5-(5-fluoro-4-((4-(5-methyl-1H-pyrazol-4-yl)phenyl)amino)pyrimidin-2-yl)isoindolin-2-yl)methanone | (Reg-1-16) in step 4 of Example 45 was replaced with (Reg-1-65) | $^1$H NMR (400 MHz, DMSO-d$_6$) δ 9.73 (s, 1H), 8.48 (d, J = 3.2 Hz, 1H), 8.26-8.17 (m, 2H), 7.95-7.83 (m, 3H), 7.55-7.42 (m, 3H), 4.88 (d, J = 7.7 Hz, 2H), 4.74 (d, J = 14.1 Hz, 2H), 3.32-3.24 (m, 1H), 2.85 (dd, J = 16.4, 8.4 Hz, 4H), 2.41 (s, 3H). MS m/z (ESI): 504.5 [M + H]. |
| TDI01586 | | (5-(4-((4-(1H-pyrazol-4-yl)phenyl)amino)-5-fluoropyrimidin-2-yl)isoindolin-2-yl)(tetrahydro-2H-pyran-4-yl)methanone | step 2 of Example 45 was replaced with [tetrahydropyran-4-carboxylic acid]; (Reg-1-16) in step 4 was replaced with (Reg-1-40) | $^1$H NMR (400 MHz, DMSO-d$_6$) δ 9.68 (s, 1H), 8.47 (s, 1H), 8.27-8.17 (m, 2H), 8.06 (s, 2H), 7.87 (s, 2H), 7.67 (s, 2H), 7.47 (s, 1H), 5.01 (d, J = 7.4 Hz, 2H), 4.71 (d, J = 14.2 Hz, 2H), 3.90 (d, J = 10.9 Hz, 2H), 3.40 (s, 2H), 2.87-2.79 (m, 1H), 1.66 (s, 4H). MS m/z (ESI): 484.6 [M + H]. |

TABLE 14-continued

| No. | Compound Name | Starting material or regent different from that in Example 45 | Characterization Data |
|---|---|---|---|
| TDI01587 | 1-(4-((4-(1H-pyrazol-4-yl)phenyl)amino)-2-(2-(3,3-difluorocyclobutane-1-carbonyl)isoindolin-5-yl)-5,7-dihydro-6H-pyrrolo[3,4-d]pyrimidin-6-yl)ethan-1-one | (Reg-1-16) in step 4 of Example 45 was replaced with (Reg-1-58) | $^1$H NMR (400 MHz, DMSO-d$_6$) δ 9.23 (d, J = 6.8 Hz, 1H), 8.36-8.24 (m, 2H), 8.06 (s, 2H), 7.85 (d, J = 4.0 Hz, 2H), 7.66 (s, 2H), 7.48 (dd, J = 14.9, 7.9 Hz, 1H), 4.96-4.69 (m, 6H), 4.59 (d, J = 27.2 Hz, 2H), 3.29 (s, 1H), 2.86 (dd, J = 16.3, 8.3 Hz, 4H), 2.12 (d, J = 7.4 Hz, 3H). MS m/z (ESI): 556.2 [M + H]. |
| TDI01589 | (5-(4-((1H-indazol-5-yl)amino)-5-fluoropyrimidin-2-yl)isoindolin-2-yl)(3,3-difluorocyclobutyl)methnone | (Reg-1-16) in step 4 of Example 45 was replaced with (Reg-1-12) | $^1$H NMR (400 MHz, DMSO-d$_6$) δ 13.15-12.97 (m, 0H), 9.71 (s, 0H), 8.45 (d, J = 2.4 Hz, 0H), 8.34-8.07 (m, 1H), 7.73 (d, J = 8.9 Hz, 0H), 7.59 (d, J = 8.9 Hz, 0H), 7.45 (dd, J = 16.7, 8.0 Hz, 0H), 4.87 (d, J = 8.8 Hz, 1H), 4.72 (d, J = 11.9 Hz, 0H), 3.28 (d, J = 3.9 Hz, 1H), 2.85 (dd, J = 16.4, 8.4 Hz, 4H). MS m/z (ESI): 464.7 [M + H]. |

TABLE 14-continued

| No. | Compound Structure | Compound Name | Starting material or regent different from that in Example 45 | Characterization Data |
|---|---|---|---|---|
| TDI01596 | 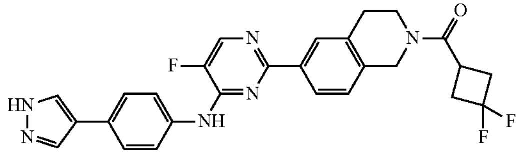 [SMILES: O=C(C1CC(F)(F)C1)N1CCc2cc(-c3ncc(F)c(Nc4ccc(-c5cn[nH]c5)cc4)n3)ccc2C1] | (6-(4-((4-((1H-pyrazol-4-yl)phenyl)amino)-5-fluoropyrimidin-2-yl)-3,4-dihydroisoquinolin-2(1H)-yl)(3,3-difluorocyclobutyl)methanone | The synthesis started from step 2 of Example 45; Br—[indoline]—NH·HCl in step 2 was replaced with Br—[tetrahydroisoquinoline]—NH·HCl; Boc—N[pyrazole]—[phenyl]—NH—[pyrimidine(Cl)] (Reg-1-16) in step 4 was replaced with Boc—N[pyrazole]—[phenyl]—NH—[pyrimidine(F)(Cl)] (Reg-1-40) | 1H NMR (400 MHz, DMSO-$d_6$) δ 9.68 (s, 1H), 8.46 (d, J = 2.6 Hz, 1H), 8.07 (d, J = 7.0 Hz, 5H), 7.87 (d, J = 7.9 Hz, 2H), 7.66 (d, J = 8.2 Hz, 2H), 7.33 (d, J = 7.2 Hz, 1H), 4.68 (d, J = 12.5 Hz, 2H), 3.70 (d, J = 31.3 Hz, 3H), 2.94 (s, 2H), 2.84 (dd, J = 15.9, 8.5 Hz, 4H). MS m/z (ESI): 504.7 [M + H]. |
| TDI01596B | 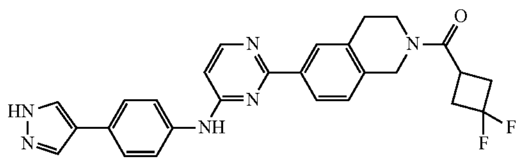 [SMILES: O=C(C1CC(F)(F)C1)N1CCc2cc(-c3nccc(Nc4ccc(-c5cn[nH]c5)cc4)n3)ccc2C1] | (6-(4-((4-((1H-pyrazol-4-yl)phenyl)amino)pyrimidin-2-yl)-3,4-dihydroisoquinolin-2(1H)-yl)(3,3-difluorocyclobutyl)methanone | The synthesis started from step 2 of Example 45; Br—[indoline]—NH·HCl in step 2 was replaced with Br—[tetrahydroisoquinoline]—NH·HCl. | 1H NMR (400 MHz, DMSO-$d_6$) δ 10.32 (s, 1H), 8.36 (d, J = 6.3 Hz, 1H), 8.08 (d, J = 12.4 Hz, 4H), 7.69 (t, J = 11.5 Hz, 4H), 7.42 (t, J = 8.1 Hz, 2H), 6.82 (d, J = 6.2 Hz, 1H), 4.72 (d, J = 12.8 Hz, 2H), 3.70 (dd, J = 21.5, 16.0 Hz, 3H), 3.41-3.36 (m, 1H), 2.91-2.80 (m, 4H). MS m/z (ESI): 486.6 [M + H]. |

TABLE 14-continued

| No. | Compound Structure | Compound Name | Starting material or regent different from that in Example 45 | Characterization Data |
|---|---|---|---|---|
| TDI01598 | 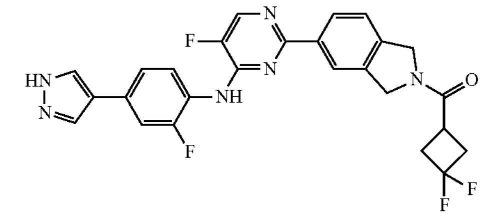 [SMILES: O=C(C1CC(F)(F)C1)N1Cc2ccc(-c3ncc(F)c(Nc4ccc(-c5cn[nH]c5)cc4F)n3)cc2C1] | (3,3-difluorocyclobutyl) (5-(5-fluoro-4-((2-fluoro-4-(1H-pyrazol-4-yl)phenyl)amino) pyrimidin-2-yl)isoindolin-2-yl)methanone | (Reg-1-16) in step 4 of Example 45 was replaced with (Reg-1-68) | $^1$H NMR (400 MHz, DMSO-d$_6$) δ 9.52 (s, 1H), 8.46 (s, 1H), 8.15 (d, J = 14.0 Hz, 3H), 8.09-8.02 (m, 2H), 7.65 (d, J = 12.1 Hz, 1H), 7.58 (d, J = 7.0 Hz, 1H), 7.52 (d, J = 8.0 Hz, 1H), 7.41-7.35 (m, 1H), 4.83 (s, 2H), 4.68 (d, J = 7.6 Hz, 2H), 3.26 (s, 1H), 2.83 (dd, J = 14.9, 7.5 Hz, 4H). MS m/z (ESI): 509.1 [M + H]. |
| TDI01611 | 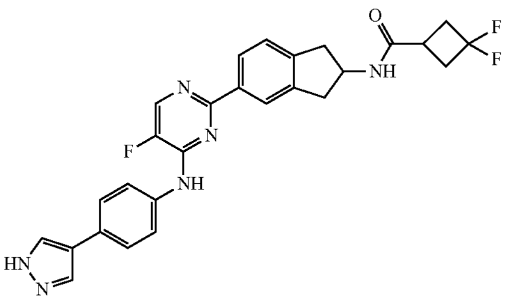 [SMILES: O=C(NC1Cc2ccc(-c3ncc(F)c(Nc4ccc(-c5cn[nH]c5)cc4)n3)cc2C1)C1CC(F)(F)C1] | N-(5-(4-((4-(1H-pyrazol-4-yl)phenyl)amino)-5-fluoropyrimidin-2-yl)-2,3-dihydro-1H-inden-2-yl)-3,3-difluorocyclobutane-1-carboxamide | The synthesis started from step 2 of Example 45; in step 2 was replaced with NH$_2$HBr; in step 4 was replaced with (Reg-1-16) (Reg-1-40) | $^1$H NMR (400 MHz, DMSO-d$_6$) δ 9.67 (s, 1H), 8.45 (d, J = 2.8 Hz, 1H), 8.38 (d, J = 6.6 Hz, 1H), 8.22-8.02 (m, 4H), 7.87 (d, J = 8.2 Hz, 2H), 7.65 (d, J = 8.3 Hz, 2H), 7.34 (d, J = 7.8 Hz, 1H), 4.52 (d, J = 6.0 Hz, 1H), 3.25 (td, J = 16.5, 7.2 Hz, 2H), 2.83 (d, J = 7.2 Hz, 3H), 2.67 (s, 4H). MS m/z (ESI): 504.6 [M + H]. |

TABLE 14-continued

| No. | Compound Structure | Compound Name | Starting material or regent different from that in Example 45 | Characterization Data |
|---|---|---|---|---|
| TDI01662 | 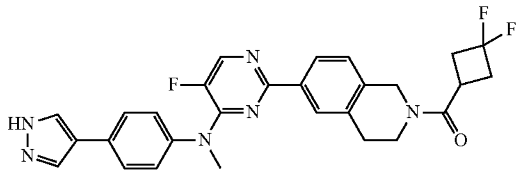 [SMILES: CN(c1ccc(-c2cn[nH]c2)cc1)c1nc(-c2ccc3c(c2)CCN(C(=O)C2CC(F)(F)C2)C3)ncc1F] | (6-(4-((4-((1H-pyrazol-4-yl)phenyl)(methyl)amino)-5-fluoropyrimidin-2-yl)-3,4-dihydroisoquinolin-2(1H)-yl)(3,3-difluorocyclobutyl)methanone | The synthesis started from step 2 of Example 45; in step 2 was replaced with (Reg-1-16); in step 4 was replaced with (Reg-1-67) | $^1$H NMR (400 MHz, DMSO-$d_6$) δ 8.31 (d, J = 8.0 Hz, 1H), 8.18-8.14 (m, 2H), 8.09 (s, 2H), 7.64 (d, J = 8.2 Hz, 2H), 7.33 (d, J = 8.2 Hz, 3H), 4.68 (s, 2H), 3.75-3.68 (m, 2H), 3.58 (s, 3H), 3.41-3.35 (m, 1H), 2.97-2.76 (m, 6H). MS m/z (ESI): 519.1 [M + H]. |

TABLE 14-continued

| No. | Compound Structure | Compound Name | Starting material or regent different from that in Example 45 | Characterization Data |
|---|---|---|---|---|
| TDI01682 | (structure) | (7-(4-((1H-indazol-5-yl)amino)pyrimidin-2-yl)-3,4-dihydroisoquinolin-2(1H)-yl)(3,3-difluorocyclobutyl)methanone | The synthesis started from step 2 of Example 45; (Reg-1-16) in step 2 was replaced with (Reg-1-27) in step 4 ws replaced with | $^1$H NMR (400 MHz, DMSO-d$_6$) δ 13.17 (s, 1H), 10.76 (s, 1H), 8.35 (d, J = 6.8 Hz, 1H), 8.13 (t, J = 6.5 Hz, 2H), 8.09-7.99 (m, 2H), 7.67-7.61 (m, 1H), 7.59-7.51 (m, 1H), 7.42 (t, J = 8.1 Hz, 1H), 6.88-6.78 (m, 1H), 4.77-4.70 (m, 2H), 3.78-3.72 (m, 1H), 3.70-3.65 (t, J = 5.6 Hz, 2H), 3.46-3.33 (s, 1H), 2.98-2.91 (m, 1H), 2.91-2.74 (m, 5H). MS m/z (ESI): 460.7 [M + H]. |

TABLE 14-continued

| No. | Compound Structure | Compound Name | Starting material or regent different from that in Example 45 | Characterization Data |
|---|---|---|---|---|
| TDI01683 | (structure) | (6-(4-((1H-indazol-5-yl)amino)pyrimidin-2-yl)-3,4-dihydroisoquinolin-2(1H)-yl)(3,3-difluorocyclobutyl)methanone | The synthesis started from step 2 of Example 45; (structure) in step 2 was replaced with (structure) (Reg-1-16) in step 4 was replaced with (structure) (Reg-1-1) | $^1$H NMR (400 MHz, DMSO-$d_6$) δ 13.15 (s, 1H), 10.65 (s, 1H), 8.35 (d, J = 6.6 Hz, 1H), 8.14 (s, 2H), 8.06 (d, J = 8.6 Hz, 2H), 7.64 (d, J = 8.6 Hz, 1H), 7.56 (s, 1H), 7.44 (t, J = 8.2 Hz, 1H), 6.82 (d, J = 5.7 Hz, 1H), 4.73 (d, J = 12.2 Hz, 2H), 3.76 (s, 1H), 3.69 (s, 1H), 3.41-3.36 (m, 1H), 2.96 (s, 1H), 2.91-2.78 (m, 5H). MS m/z (ESI): 460.7 [M + H]. |

Example 46: preparation of (6-(4-((4-(1H-pyrazol-4-yl) phenyl)amino)furo[3,2-d]pyrimidin-2-yl)-1-methyl-1H-indol-2-yl)(3,3-difluoroazetidin-1-yl)methanone (TDI01916)

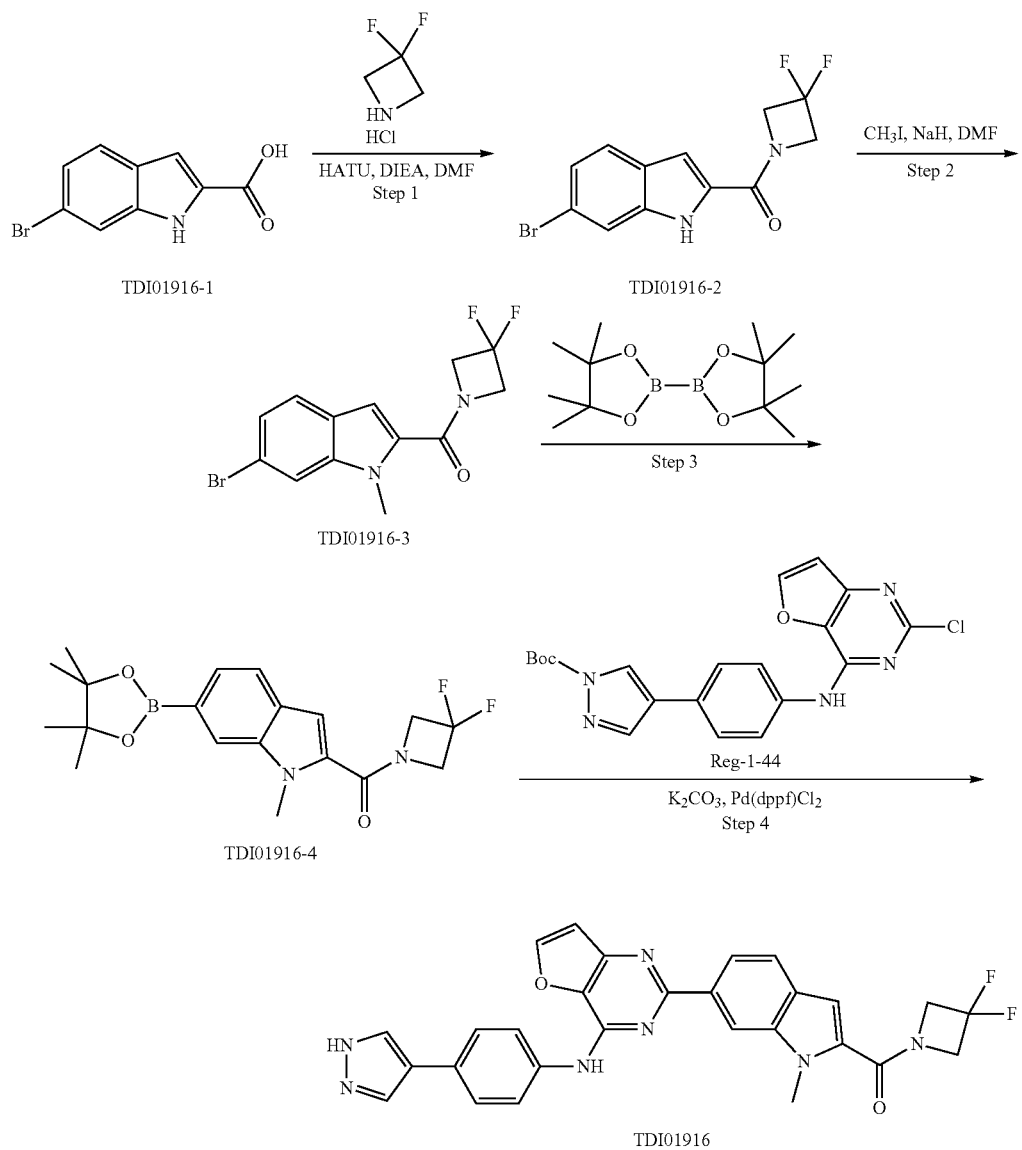

Step 1:
TDI1916-1 (31.3 g, 130 mmol), 3,3-difluoroazetidine hydrochloride (20 g, 140 mmol), HATU (60 g, 160 mmol) and DMF (330 mL) were added to a 1 L flask, DIEA (50 g, 390 mmol) was added, and the reaction was stirred at room temperature overnight. LC-MS indicated the reaction was complete. The reaction solution was concentrated to afford a crude product, which was added with water (200 mL), methanol(20 mL) and acetonitrile (20 mL), and the mixture was stirred at room temperature for 1 hour. The mixture was filtered, and the solid thus obtained was once again subjected to the above slurry process, and dried to afford TDI1916-2 (41 g, brown solid, yield: 100%).
$^1$H NMR (400 MHz, DMSO-d$_6$) δ 11.88 (s, 1H), 7.61 (s, 1H), 7.60 (d, J=8.6 Hz, 1H), 7.20 (d, J=8.6 Hz, 1H), 6.94 (s, 1H), 4.98 (s, 2H), 4.56 (s, 2H). MS m/z (ESI): 314.9, 316.9 [M+H, Br].

Step 2:
TDI1916-2 (30 g, 96 mmol) was dissolved in DMF (300 mL), and was cooled to 0° C. in an ice-water bath under protection of N$_2$. NaH (60%, 7.62 g, 191 mmol) was added portionwise, and the reaction was stirred for 1 hour before iodomethane (41 g, 288 mmol) was added. The reaction was stirred at 30° C. for 3 hours. LC-MS indicated the reaction was complete. The reaction solution was cooled to 0° C., and water (300 mL) was added. A large amount of solid precipitated, which was filtered, and the filter cake was washed with water (1 L) to neutral, and dried to afford TDI1916-3 (30.5 g, brown solid, yield: 96.5%).
$^1$H NMR (400 MHz, DMSO-d$_6$) δ 7.85 (s, 1H), 7.58 (d, J=8.4 Hz, 1H), 7.25 (d, J=8.4 Hz, 1H), 7.03 (s, 1H), 4.83 (s, 2H), 4.53 (s, 2H), 3.92 (s, 3H). MS m/z (ESI): 328.9, 330.9 [M+H, Br].

Step 3:
TDI1916-3 (30.5 g, 93 mmol), bis(pinacolato)diboron (26 g, 100 mmol) and potassium acetate (27.3 g, 280 mmol) were dissolved in 1,4-dioxane (500 mL), the flask was purged with N₂ 3 times, followed by addition o Pd(dppf)Cl₂ (10 g, 14 mmol). The flask was purged with N₂ 3 times again, and then the reaction was placed in an oil bath at 108° C. for 4 hours. LC-MS indicated the reaction was complete. The reaction solution was cooled to room temperature, concentrated under reduced pressure to afford a crude product, which was separated through column chromatography on silica gel (petroleum ether:ethyl acetate=1:1) to afford TDI1916-4 (27.5 g, brown solid, yield: 78.6%).

¹H NMR (400 MHz, DMSO-d₆) δ 7.82 (s, 1H), 7.62 (d, J=8.0 Hz, 1H), 7.41 (d, J=8.0 Hz, 1H), 7.02 (s, 1H), 4.85 (s, 2H), 4.54 (s, 2H), 3.97 (s, 3H), 1.32 (s, 12H). MS m/z (ESI): 377.0 [M+H].

Step 4:

Compound TDI01916-4 (3.0 g, 7.28 mmol) and compound Reg-1-44 (2.74 g, 7.28 mmol) were dissolved in a mixed solution of dioxane (80 mL) and water (8 mL), potassium carbonate (3 g, 21.8 mmol) was added, and the flask was purged with nitrogen three times. Pd(dppf)Cl₂ (1.6 g, 2.18 mmol) was added, the flask was purged with nitrogen three times again, and the reaction solution was stirred at 110° C. for 16 h. LC-MS indicated the reaction was complete. The reaction solution was cooled to room temperature, and the reaction solvent was removed through rotary evaporation under vacuum. The residue was purified by column chromatography (dichloromethane:methanol=60:1-40:1), to afford a crude product of compound TDI01916 (2 g), which was stirred in 10 mL dichloromethane for 0.5 h, filtered, and the filter cake was washed with dichloromethane (2 mL×3), and dried in vacuum to afford an off-white solid, TDI01916 (1.7 g, 44.4% yield).

¹H NMR (400 MHz, DMSO-d₆) δ 12.92 (s, 1H), 10.02 (s, 1H), 8.56 (s, 1H), 8.39 (s, 1H), 8.25-8.17 (m, 2H), 8.02-7.93 (m, 3H), 7.70 (dd, J=18.9, 8.4 Hz, 3H), 7.17 (s, 1H), 7.07 (s, 1H), 4.85 (s, 2H), 4.59 (s, 2H), 4.05 (s, 3H). MS m/z (ESI): 525.6 [M+H].

The compounds in following Table 15 were prepared according to methods similar to that described in Example 46.

TABLE 15

| No. | Compound Structure | Compound Name | Starting material or regent different from that in Example 46 | Characterization Data |
|---|---|---|---|---|
| TDI01851 | 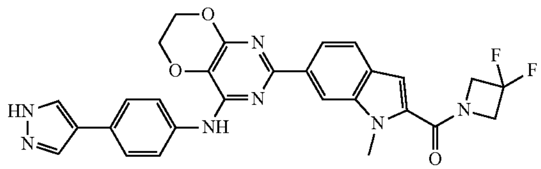 [SMILES: Cn1c(C(=O)N2CC(F)(F)C2)cc2ccc(-c3nc(Nc4ccc(-c5cn[nH]c5)cc4)c4c(n3)OCCO4)cc21] | (6-(4-((4-(1H-pyrazol-4-yl)phenyl)amino)-6,7-dihydro-[1,4]dioxino[2,3-d]pyrimidin-2-yl)-1-methyl-1H-indol-2-yl)(3,3-difluoroazetidin-1-yl)methanone | (Reg-1-44) was replaced with (Reg-1-69); and the final product was obtained by removing Boc in the intermediate obtained in the final step using a 4N hydrochloric acid/dioxane solution. | $^1$H NMR (400 MHz, DMSO-$d_6$) δ 8.93 (s, 1H), 8.36 (s, 1H), 8.05 (d, J = 5.6 Hz, 3H), 7.93 (d, J = 8.6 Hz, 2H), 7.69 (d, J = 8.5 Hz, 1H), 7.62 (d, J = 8.5 Hz, 2H), 7.05 (s, 1H), 4.90 (s, 4H), 4.56 (s, 2H), 4.43 (s, 4.02 (s, 3H). MS m/z (ESI): 543.9 [M + H]. |
| TDI01898B | 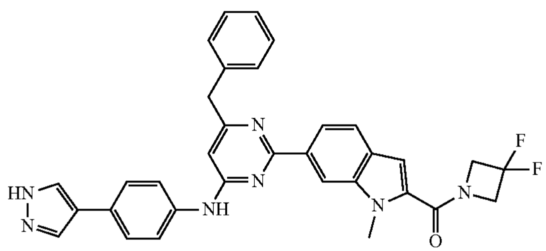 [SMILES: Cn1c(C(=O)N2CC(F)(F)C2)cc2ccc(-c3nc(Cc4ccccc4)cc(Nc4ccc(-c5cn[nH]c5)cc4)n3)cc21] | (6-(4-((4-(1H-pyrazol-4-yl)phenyl)amino)-6-benzylpyrimidin-2-yl)-1-methyl-1H-indol-2-yl)(3,3-difluoroazetidin-1-yl)methanone | (Reg-1-44) was replaced with 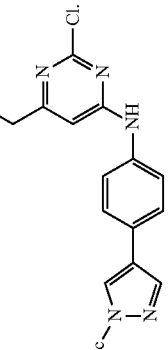 (Reg-1-84) | $^1$H NMR (400 MHz, CD$_3$OD) δ 8.48 (s, 1H), 8.01 (d, J = 9.9 Hz, 3H), 7.90 (d, J = 8.5 Hz, 1H), 7.69 (d, J = 7.8 Hz, 4H), 7.50-7.38 (m, 5H), 7.08 (s, 1H), 6.40 (s, 1H), 4.63 (s, 4H), 4.28 (s, 2H), 4.12 (s, 3H). MS m/z (ESI): 575.8 [M + H]. |

TABLE 15-continued

| No. | Compound Structure | Compound Name | Starting material or regent different from that in Example 46 | Characterization Data |
|---|---|---|---|---|
| TDI01903 | 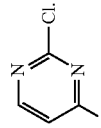 | (6-(4-((1H-pyrazol-4-yl)phenyl)amino)pyrimidin-2-yl)-1-ethyl-1H-indol-2-yl)(3,3-difluoroazetidin-1-yl)methanone | Iodomethane in step 2 of Example 46 was replaced with iodoethane; 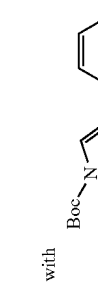 (Reg-1-44) with (Reg-1-16) | $^1$H NMR (400 MHz, DMSO-$d_6$) δ 8.54 (s, 1H), 8.41 (s, 1H), 8.08 (s, 3H), 7.90-7.73 (m, 3H), 7.69 (d, J = 8.1 Hz, 2H), 7.11 (s, 1H), 6.83 (s, 1H), 4.92 (s, 2H), 4.58 (d, J = 6.9 Hz, 4H), 1.41 (t, J = 6.9 Hz, 3H). MS m/z (ESI): 499.2 [M + H]. |
| TDI01905 | 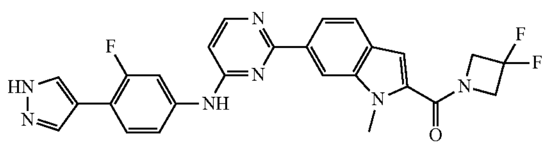 [SMILES: Cn1c(C(=O)N2CC(F)(F)C2)cc2ccc(-c3nccc(Nc4ccc(-c5cn[nH]c5)c(F)c4)n3)cc21] | (3,3-difluoroazetidin-1-yl)(6-(4-((3-fluoro-4-(1H-pyrazol-4-yl)phenyl)amino)pyrimidin-2-yl)-1-methyl-1H-indol-2-yl)methanone | (Reg-1-44) in step 4 of Example 46 was replaced with 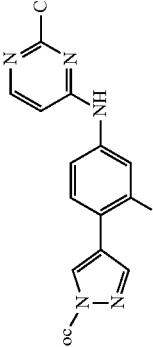 (Reg-1-39) | $^1$H NMR (400 MHz, DMSO-$d_6$) δ 13.09 (s, 1H), 9.95 (s, 1H), 8.56 (s, 1H), 8.45 (d, J = 5.7 Hz, 1H), 8.18 (d, J = 8.4 Hz, 1H), 8.15-7.96 (m, 3H), 7.75 (t, J = 8.6 Hz, 2H), 7.48 (d, J = 8.4 Hz, 1H), 7.08 (s, 1H), 6.76 (d, J = 5.7 Hz, 1H), 4.89 (s, 2H), 4.56 (s, 2H), 4.08-4.01 (m, 3H). MS m/z (ESI): 503.5 [M + H]. |

| No. | Compound Name | Starting material or regent different from that in Example 46 | Characterization Data |
|---|---|---|---|
| TDI01906 | (6-(4-((1H-indazol-5-yl)amino)pyrimidin-2-yl)-1-methyl-1H-indol-2-yl)(3,3-difluoroazetidin-1-yl)methanone | (Reg-1-44) in step 4 of Example 46 was replaced with (Reg-1-1) | ¹H NMR (400 MHz, DMSO-d₆) δ 10.71 (s, 1H), 8.52 (s, 1H), 8.37 (s, 1H), 8.19 (d, J = 32.9 Hz, 2H), 8.03 (s, 1H), 7.84 (s, 1H), 7.63 (d, J = 32.1 Hz, 2H), 7.12 (s, 1H), 6.84 (s, 1H), 5.76 (s, 1H), 4.55 (s, 4H), 4.04 (s, 3H). MS m/z (ESI): 460.0 [M + H]. |
| TDI01910 | (3,3-difluoroazetidin-1-yl)(6-(4-((3-methoxy-4-(1H-pyrazol-4-yl)phenyl)amino)pyrimidin-2-yl)-1-methyl-1H-indol-2-yl)methanone | (Reg-1-44) in step 4 of Example 46 was replaced with (Reg-1-43) Cl; and the final product was obtained by removing of Boc in the intermediate obtained in the final step using a 4N hydrochloric acid/dioxane solution. | ¹H NMR (400 MHz, CD₃OD) δ 8.43 (s, 1H), 8.28 (d, J = 7.2 Hz, 1H), 8.13 (s, 2H), 8.01 (d, J = 8.6 Hz, 1H), 7.92 (d, J = 8.5 Hz, 1H), 7.75 (d, J = 8.3 Hz, 2H), 7.36 (s, 1H), 7.10 (s, 1H), 6.97 (d, J = 7.2 Hz, 1H), 4.63 (s, 4H), 4.11 (s, 3H), 4.01 (s, 3H). MS m/z (ESI): 515.7 [M + H]. |

TABLE 15-continued

| No. | Compound Structure | Compound Name | Starting material or regent different from that in Example 46 | Characterization Data |
|---|---|---|---|---|
| TDI01915 | (structure) | (6-(4-((4-(1H-pyrazol-4-yl)phenyl)amino)-5-methoxypyrimidin-2-yl)-1-methyl-1H-indol-2-yl)(3,3-difluoroazetidin-1-yl)methanone | (Reg-1-44) was replaced with (Reg-1-36) | $^{1}$H NMR (400 MHz, DMSO-d$_6$) δ 9.02 (s, 1H), 8.44 (s, 1H), 8.19 (s, 1H), 8.10 (d, J = 8.6 Hz, 2H), 7.99 (d, J = 8.5 Hz, 3H), 7.71 (s, 1H), 7.64 (d, J = 8.5 Hz, 2H), 7.05 (s, 1H), 4.72 (d, J = 105.4 Hz, 4H), 4.03 (s, 6H). MS m/z (ESI): 516.0 [M + H]. |
| TDI01918 | (structure) | (6-(4-((4-(1H-pyrazol-4-yl)phenyl)amino)quinazolin-2-yl)-1-methyl-1H-indol-2-yl)(3,3-difluoroazetidin-1-yl)methanone | (Reg-1-44) was replaced with (Reg-1-45) | $^{1}$H NMR (400 MHz, DMSO-d$_6$) δ 8.70 (d, J = 7.8 Hz, 1H), 8.60 (s, 1H), 8.15 (s, 3H), 8.05 (s, 2H), 7.92 (d, J = 7.8 Hz, 2H), 7.83 (dd, J = 15.2, 8.6 Hz, 4H), 7.13 (s, 1H), 4.92 (s, 2H), 4.54 (d, J = 7.0 Hz, 2H), 4.05 (s, 3H). MS m/z (ESI): 535.9 [M + H]. |

TABLE 15-continued

| No. | Compound Structure | Compound Name | Starting material or regent different from that in Example 46 | Characterization Data |
|---|---|---|---|---|
| TDI01920 | 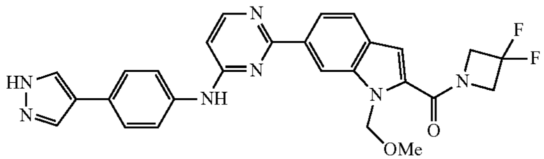 [SMILES: COCn1c(C(=O)N2CC(F)(F)C2)cc2ccc(-c3nccc(Nc4ccc(-c5cn[nH]c5)cc4)n3)cc21] | (6-(4-(4-((1H-pyrazol-4-yl)amino)pyrimidin-2-yl)phenyl)-1-(methoxymethyl)-1H-indol-2-yl)(3,3-difluoroazetidin-1-yl)methanone | Iodomethane in step 2 of Example 46 was replaced with MOMBr; (Reg-1-44) in step 4 was replaced with (Reg-1-16) | $^1$H NMR (400 MHz, DMSO-d$_6$) δ 10.43 (s, 1H), 8.62 (s, 1H), 8.40 (d, J = 6.4 Hz, 1H), 8.12 (s, 1H), 8.07 (s, 2H), 7.91-7.74 (m, 3H), 7.69 (d, J = 8.2 Hz, 2H), 7.22 (s, 1H), 6.83 (d, J = 6.0 Hz, 1H), 5.93 (s, 2H), 4.90 (s, 2H), 4.60 (s, 2H), 3.23 (s, 3H). MS m/z (ESI): 515.6 [M + H]. |
| TDI01921 | 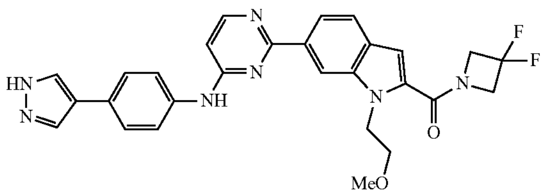 [SMILES: COCCn1c(C(=O)N2CC(F)(F)C2)cc2ccc(-c3nccc(Nc4ccc(-c5cn[nH]c5)cc4)n3)cc21] | (6-(4-(4-((1H-pyrazol-4-yl)amino)pyrimidin-2-yl)phenyl)-2-(2-methoxyethyl)-1H-indol-2-yl)(3,3-difluoroazetidin-1-yl)methanone | Iodomethane in step 2 of Example 46 was replaced with (Reg-1-44); step 4 was replaced with (Reg-1-16) | $^1$H NMR (400 MHz, DMSO-d$_6$) δ 10.50 (s, 1H), 8.57 (s, 1H), 8.40 (d, J = 6.4 Hz, 1H), 8.07 (s, 2H), 7.80 (s, 2H), 7.69 (d, J = 7.9 Hz, 2H), 7.21 (s, 1H), 7.09 (s, 1H), 6.96 (s, 1H), 6.83 (s, 1H), 4.79 (s, 2H), 4.72 (s, 2H), 4.56 (d, J = 12.9 Hz, 2H), 3.68-3.63 (m, 2H), 3.18 (s, 3H). MS m/z (ESI): 529.6 [M + H]. |

| No. | Compound Structure | Compound Name | Starting material or regent different from that in Example 46 | Characterization Data |
|---|---|---|---|---|
| TDI01932 | 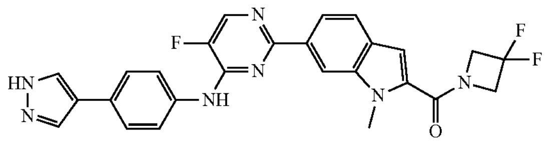 | (6-(4-((4-1H-pyrazol-4-yl)phenyl)amino)-5-fluoropyrimidin-2-yl)-1-methyl-1H-indol-2-yl)(3,3-difluoroazetidin-1-yl)methanone | (Reg-1-44) in step 4 of Example 46 was replaced with (Reg-1-40) | $^1$H NMR (400 MHz, DMSO-$d_6$) δ 9.76 (s, 1H), 8.51 (d, J = 3.6 Hz, 1H), 8.46 (s, 1H), 8.12-8.07 (m, 3H), 7.93 (d, J = 8.5 Hz, 2H), 7.71 (dd, J = 17.3, 8.5 Hz, 3H), 7.07 (s, 1H), 4.89 (s, 2H), 4.58 (s, 2H), 4.03 (s, 3H). MS m/z (ESI): 504.0 [M + H]. |
| TDI01936 | 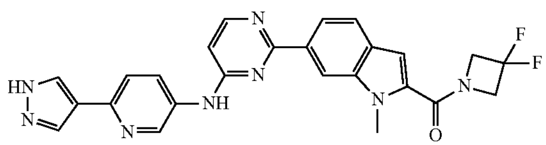 [SMILES: Cn1c(C(=O)N2CC(F)(F)C2)cc2ccc(-c3nccc(Nc4ccc(-c5cn[nH]c5)nc4)n3)cc21] | (6-(4-((6-(1H-pyrazol-4-yl)pyridin-3-yl)amino)pyrimidin-2-yl)-1-methyl-1H-indol-2-yl)(3,3-difluoroazetidin-1-yl)methanone | (Reg-1-44) in step 4 of Example 46 was replaced with (Reg-1-46) | $^1$H NMR (301 MHz, DMSO-$d_6$) δ 10.67 (s, 1H), 9.03 (s, 1H), 8.61-8.49 (m, 3H), 8.42-8.26 (m, 3H), 8.08 (d, J = 8.0 Hz, 1H), 7.97 (d, J = 8.0 Hz, 1H), 7.81 (d, J = 8.0 Hz, 1H), 7.11 (s, 1H), 6.89 (d, J = 6.2 Hz, 1H), 4.88 (s, 2H), 4.58 (s, 2H), 4.04 (s, 3H). MS m/z (ESI): 486.6 [M + H]. |

TABLE 15-continued

| No. | Compound Structure | Compound Name | Starting material or regent different from that in Example 46 | Characterization Data |
|---|---|---|---|---|
| TDI01937B | (structure) | (6-(4-((5-((1H-pyrazol-4-yl)pyridin-2-yl)amino)pyrimidin-2-yl)-1-methyl-1H-indol-2-yl)(3,3-difluoroazetidin-1-yl)methanone | (Reg-1-44) in step 4 of Example 46 was replaced with (Reg-1-52) | ¹H NMR (301 MHz, DMSO-d₆) δ 11.07 (s, 1H), 8.85 (s, 1H), 8.51-8.29 (m, 3H), 8.19 (s, 1H), 7.95 (s, 1H), 7.74 (d, J = 8.0 Hz, 1H), 7.52 (d, J = 8.0 Hz, 2H), 7.06 (s, 1H), 4.82-4.45 (m, 4H), 4.03 (s, 3H). MS m/z (ESI): 486.6 [M + H]. |
| TDI01943 | (structure) | (3,3-difluoroazetidin-1-yl)(6-(4-((2-hydroxy-4-(1H-pyrazol-4-yl)phenyl)amino)pyrimidin-2-yl)-1-methyl-1H-indol-2-yl)methanone | (Reg-1-44) in step 4 of Example 46 was replaced with (Reg-1-71); and the final product was obtained by removing MOM in the intermediate obtained in the final step using a 4N hydrochloric acid/dioxane solution. | ¹H NMR (400 MHz, DMSO-d₆) δ 10.15 (s, 1H), 8.48 (s, 1H), 8.36 (s, 1H), 8.01 (s, 4H), 7.88-7.77 (m, 2H), 7.20 (d, J = 4.6 Hz, 3H), 7.12 (s, 1H), 4.91 (s, 2H), 4.55 (s, 2H), 4.03 (s, 3H). MS m/z (ESI): 501.6 [M + H]. |

TABLE 15-continued

| No. | Compound Structure | Compound Name | Starting material or regent different from that in Example 46 | Characterization Data |
|---|---|---|---|---|
| TDI01945 | 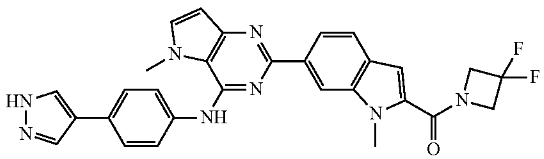 [SMILES: Cn1ccc2nc(-c3ccc4cc(C(=O)N5CC(F)(F)C5)n(C)c4c3)nc(Nc3ccc(-c4cn[nH]c4)cc3)c21] | (6-(4-((4-(1H-pyrazol-4-yl)phenyl)amino)-5-methyl-5H-pyrrolo[3,2-d]pyrimidin-2-yl)-1-methyl-1H-indol-2-yl)(3,3-difluoroazetidin-1-yl)methanone | (Reg-1-44) in step 4 of Example 46 was replaced with (Reg-1-72) | $^1$H NMR (400 MHz, DMSO-d$_6$) δ 8.40 (s, 2H), 8.14 (s, 2H), 7.97-7.67 (m, 7H), 7.09 (s, 2H), 6.63 (s, 1H), 4.87 (s, 3H), 4.55 (d, J = 11.6 Hz, 3H), 4.28 (s, 3H), 3.98 (s, 3H). MS m/z (ESI): 538.5 [M + H]. |
| TDI01947 | 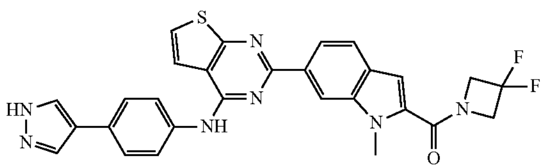 [SMILES: Cn1c(C(=O)N2CC(F)(F)C2)cc2ccc(-c3nc(Nc4ccc(-c5cn[nH]c5)cc4)c4ccsc4n3)cc21] | (6-(4-((4-(1H-pyrazol-4-yl)phenyl)amino)thieno[2,3-d]pyrimidin-2-yl)-1-methyl-1H-indol-2-yl)(3,3-difluoroazetidin-1-yl)methanone | the final product was obtained by removing Boc in the intermediate obtained in the final step using a 4N hydrochloric acid/dioxane solution. (Reg-1-44) in step 4 of Example 46 was replaced with (Reg-1-73) | $^1$H NMR (400 MHz, DMSO-d$_6$) δ 12.93 (s, 1H), 9.78 (s, 1H), 8.59 (s, 1H), 8.23 (d, J = 8.4 Hz, 1H), 7.96 (dd, J = 24.2, 7.1 Hz, 4H), 7.72 (dd, J = 13.3, 5.9 Hz, 4H), 7.56 (s, 1H), 7.08 (s, 1H), 4.89 (s, 2H), 4.56 (s, 2H), 4.06 (s, 3H). MS m/z (ESI): 541.9 [M + H]. |

TABLE 15-continued

| No. | Compound Name | Compound Structure | Starting material or regent different from that in Example 46 | Characterization Data |
|---|---|---|---|---|
| TDI01948 | (6-(4-((4-(1H-pyrazol-4-yl)phenyl)amino)pyrrolo[2,1-f][1,2,4]triazin-2-yl)-1-methyl-1H-indol-2-yl)(3,3-difluoroazetidin-1-yl)methanone | 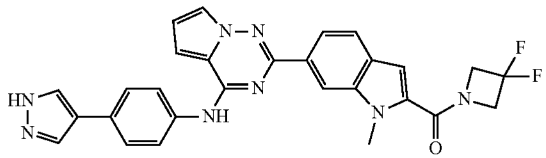 [SMILES: Cn1c(C(=O)N2CC(F)(F)C2)cc2ccc(-c3nc(Nc4ccc(-c5cn[nH]c5)cc4)c4cccn4n3)cc21] | (Reg-1-44) in step 4 of Example 46 was replaced with (Reg-1-70) | $^1$H NMR (400 MHz, DMSO-d$_6$) δ 12.91 (s, 1H), 9.97 (s, 1H), 8.43 (s, 1H), 8.06 (dd, J = 17.6, 8.4 Hz, 3H), 7.86 (s, 1H), 7.73 (dd, J = 8.2, 4.3 Hz, 2H), 7.50 (s, 1H), 7.22 (s, 1H), 7.08 (s, 1H), 6.78 (d, J = 3.0 Hz, 1H), 4.88 (s, 2H), 4.59 (s, 2H), 4.05 (s, 3H). MS m/z (ESI): 524.9 [M + H]. |
| TDI01949 | (6-(4-((4-(1H-pyrazol-4-yl)phenyl)amino)-5-chloropyrimidin-2-yl)-1-methyl-1H-indol-2-yl)(3,3-difluoroazetidin-1-yl)methanone | 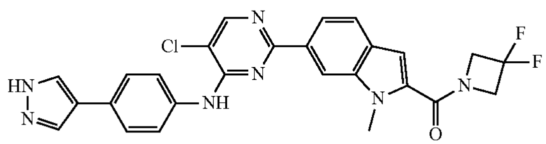 [SMILES: Cn1c(C(=O)N2CC(F)(F)C2)cc2ccc(-c3ncc(Cl)c(Nc4ccc(-c5cn[nH]c5)cc4)n3)cc21] | (Reg-1-44) in step 4 of Example 46 was replaced with (Reg-1-34) | $^1$H NMR (400 MHz, DMSO-d$_6$) δ 9.24 (s, 1H), 8.57 (s, 1H), 8.47 (s, 1H), 8.10 (s, 2H), 8.07 (dd, J = 8.5, 1.3 Hz, 1H), 7.82 (d, J = 8.7 Hz, 2H), 7.71 (dd, J = 8.4, 5.1 Hz, 3H), 7.07 (s, 1H), 4.88 (s, 2H), 4.57 (s, 2H), 4.01 (s, 3H). MS m/z (ESI): 519.9 [M + H]. |

TABLE 15-continued

| No. | Compound Structure | Compound Name | Starting material or regent different from that in Example 46 | Characterization Data |
|---|---|---|---|---|
| TDI01950 | 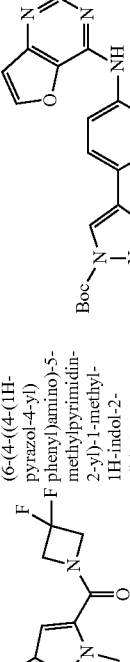 | (6-(4-((1H-pyrazol-4-yl)phenyl)amino)-5-methylpyrimidin-2-yl)-1-methyl-1H-indol-2-yl)(3,3-difluoroazetidin-1-yl)methanone | 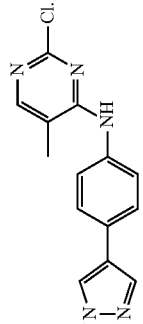 in step 4 of Example 46 (Reg-1-44) was replaced with 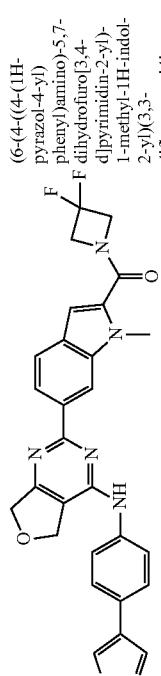 (Reg-1-74) | $^1$H NMR (400 MHz, DMSO-$d_6$) δ 9.63 (s, 1H), 8.45 (s, 1H), 8.36 (s, 1H), 8.11 (s, 2H), 7.95 (d, J = 8.4 Hz, 1H), 7.76 (dt, J = 16.5, 6.7 Hz, 6H), 7.10 (s, 1H), 4.88 (s, 2H), 4.56 (s, 2H), 4.01 (s, 3H), 2.33 (s, 3H). MS m/z (ESI): 499.2 [M + H]. |
| TDI01952 | 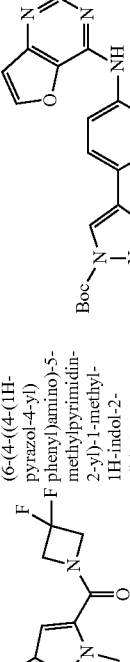 | (6-(4-((1H-pyrazol-4-yl)phenyl)amino)-5,7-dihydrofuro[3,4-d]pyrimidin-2-yl)-1-methyl-1H-indol-2-yl)(3,3-difluoroazetidin-1-yl)methanone | 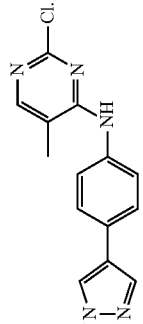 in step 4 of Example 46 (Reg-1-44) was replaced with 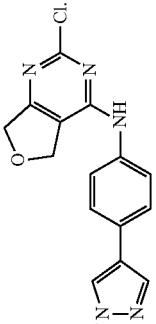 (Reg-1-75) | $^1$H NMR (400 MHz, DMSO-$d_6$) δ 9.29 (s, 1H), 8.52 (s, 1H), 8.28-8.01 (m, 3H), 7.85 (s, 2H), 7.78-7.65 (m, 2H), 7.07 (s, 1H), 5.03 (d, J = 40.1 Hz, 4H), 4.03 (s, 3H). MS m/z (ESI): 527.6 [M + H]. |

TABLE 15-continued

| No. | Compound Structure | Compound Name | Starting material or regent different from that in Example 46 | Characterization Data |
|---|---|---|---|---|
| TDI01953 | 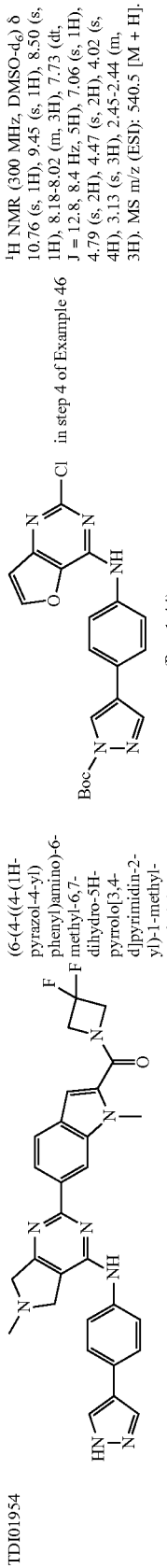 | (6-(4-((1H-pyrazol-4-yl)phenyl)amino)-6,7-dihydro-5H-pyrrolo[3,4-d]pyrimidin-2-yl)-1-methyl-1H-indol-2-yl)(3,3-difluoroazetidin-1-yl)methanone | 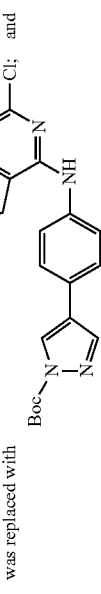 (Reg-1-44) in step 4 of Example 46 was replaced with 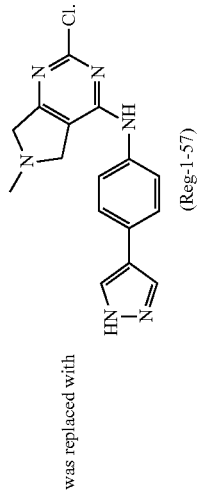 (Reg-1-56) the final product was obtained by removing Boc in the intermediate obtained in the final step using a 4N hydrochloric acid/dioxane solution. | $^1$H NMR (400 MHz, DMSO-d$_6$) δ 9.50 (s, 2H), 9.40 (s, 1H), 8.52 (s, 1H), 8.15 (d, J = 8.4 Hz, 1H), 8.08 (s, 2H), 7.83 (d, J = 8.3 Hz, 2H), 7.72 (dd, J = 16.5, 8.4 Hz, 3H), 7.08 (s, 1H), 4.92-4.77 (m, 4H), 4.53 (d, J = 5.1 Hz, 4H), 4.03 (s, 3H). MS m/z (ESI): 526.6 [M + H]. |
| TDI01954 | 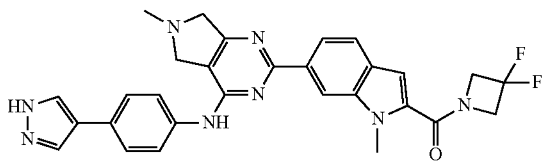 [SMILES: CN1Cc2nc(-c3ccc4cc(C(=O)N5CC(F)(F)C5)n(C)c4c3)nc(Nc3ccc(-c4cn[nH]c4)cc3)c2C1] | (6-(4-((1H-pyrazol-4-yl)phenyl)amino)-6-methyl-6,7-dihydro-5H-pyrrolo[3,4-d]pyrimidin-2-yl)-1-methyl-1H-indol-2-yl)(3,3-difluoroazetidin-1-yl)methanone | (Reg-1-44) in step 4 of Example 46 was replaced with (Reg-1-57) | $^1$H NMR (300 MHz, DMSO-d$_6$) δ 10.76 (s, 1H), 9.45 (s, 1H), 8.50 (s, 1H), 8.18-8.02 (m, 3H), 7.73 (dt, J = 12.8, 8.4 Hz, 5H), 7.06 (s, 1H), 4.79 (s, 2H), 4.47 (s, 2H), 4.02 (s, 4H), 3.13 (s, 3H), 2.45-2.44 (m, 3H). MS m/z (ESI): 540.5 [M + H]. |

TABLE 15-continued

| No. | Compound Structure | Compound Name | Starting material or regent different from that in Example 46 | Characterization Data |
|---|---|---|---|---|
| TDI01955 | 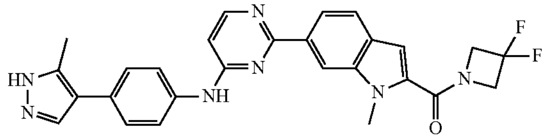 [SMILES: Cc1[nH]ncc1-c1ccc(Nc2ccnc(-c3ccc4cc(C(=O)N5CC(F)(F)C5)n(C)c4c3)n2)cc1] | (3,3-difluoroazetidin-1-yl)(1-methyl-6-(4-(4-(5-methyl-1H-pyrazol-4-yl)phenyl)amino)pyrimidin-2-yl)-1H-indol-2-yl)methanone | (Reg-1-44) in step 4 of Example 46 was replaced with (Reg-1-76) | ¹H NMR (400 MHz, DMSO-d₆) δ 10.57 (s, 1H), 8.53 (s, 1H), 8.41 (d, J = 6.5 Hz, 1H), 8.08 (d, J = 8.4 Hz, 1H), 7.82 (dd, J = 9.9, 7.0 Hz, 4H), 7.57 (d, J = 8.6 Hz, 2H), 7.13 (s, 1H), 6.86 (d, J = 6.6 Hz, 1H), 4.91 (s, 2H), 4.56 (s, 2H), 4.05 (s, 3H). MS m/z (ESI): 500.0 [M + H]. |
| TDI01960 | 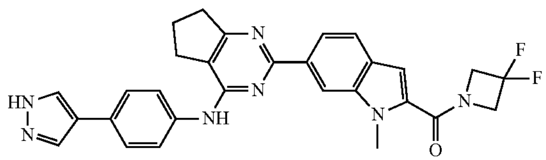 | (6-(4-((4-(1H-pyrazol-4-yl)phenyl)amino)-6,7-dihydro-5H-cyclopenta[d]pyrimidin-2-yl)-1-methyl-1H-indol-2-yl)(3,3-difluoroazetidin-1-yl)methanone | (Reg-1-44) in step 4 of Example 46 was replaced with (Reg-1-77) | ¹H NMR (400 MHz, DMSO-d₆) δ 12.90 (s, 1H), 8.80 (s, 1H), 8.51 (s, 1H), 8.17 (d, J = 8.1 Hz, 2H), 8.02-7.86 (m, 3H), 7.67 (dd, J = 21.6, 8.4 Hz, 3H), 7.05 (s, 1H), 4.87 (d, J = 10.1 Hz, 2H), 4.58 (s, 2H), 4.03 (s, 3H), 2.99-2.85 (m, 4H), 2.10 (dd, J = 14.9, 7.7 Hz, 2H). MS m/z (ESI): 526.0 [M + H]. |

TABLE 15-continued

| No. | Compound Structure | Compound Name | Starting material or regent different from that in Example 46 | Characterization Data |
|---|---|---|---|---|
| TD101537 | (structure) | (6-(4-((1H-pyrazol-4-yl)phenyl)amino)-5,6-dimethylpyrimidin-2-yl)-1-methyl-1H-indol-2-yl)(3,3-difluoroazetidin-1-yl)methanone | (Reg-1-44) in step 4 of Example 46 was replaced with (Reg-1-78) | $^1$H NMR (400 MHz, DMSO-$d_6$) δ 9.14 (s, 0H), 8.64 (s, 0H), 8.35 (d, J = 10.9 Hz, 1H), 7.75 (t, J = 9.0 Hz, 1H), 7.09 (s, 0H), 7.03 (d, J = 7.6 Hz, 1H), 4.87 (s, 1H), 4.63 (s, 1H), 4.08 (s, 1H), 2.69 (s, 3H), 2.58 (s, 3H). MS m/z (ESI): 514.0 [M + H]. |
| TD101617 | (structure) | (6-(4-((1H-pyrazol-4-yl)phenyl)amino)-5-fluoropyrimidin-2-yl)-1-(methoxymethyl)-1H-indol-2-yl)(3,3-difluoroazetidin-1-yl)methanone | Iodomethane in step 2 of Example 46 was replaced with MOMBr; the final product was obtained by removing Boc in the intermediate obtained in the final step using a 4N hydrochloric acid/dioxane solution. (Reg-1-44) in step 4 was replaced with (Reg-1-40) | $^1$H NMR (400 MHz, DMSO-$d_6$) δ 9.70 (s, 1H), 8.57 (s, 1H), 8.49 (d, J = 2.9 Hz, 1H), 8.14 (d, J = 8.4 Hz, 1H), 8.06 (s, 2H), 7.91 (d, J = 8.2 Hz, 2H), 7.75 (d, J = 8.3 Hz, 1H), 7.68 (s, 2H), 7.17 (s, 1H), 5.92 (s, 2H), 4.86 (d, J = 11.6 Hz, 2H), 4.63 (d, J = 25.1 Hz, 2H), 3.21 (s, 3H). MS m/z (ESI): 533.6 [M + H]. |

TABLE 15-continued

| No. | Compound Structure | Compound Name | Starting material or regent different from that in Example 46 | Characterization Data |
|---|---|---|---|---|
| TD101633 | | (6-(4-((1H-pyrazol-4-yl)phenyl)amino)-6,7-dihydro-5H-pyrrolo[3,4-d]pyrimidin-2-yl)-1-(methoxymethyl)-1H-indol-2-yl)(3,3-difluoroazetidin-1-yl)methanone | Iodomethane in step 2 of Example 46 was replaced with MOMBr; (Reg-1-44) with (Reg-1-56); and the final product was obtained by removing Boc in the intermediate obtained in the final step using a 4N hydrochloric acid/dioxane solution. | ¹H NMR (400 MHz, DMSO-d₆) δ 9.52 (s, 2H), 9.41 (s, 1H), 8.62 (s, 1H), 8.20 (d, J = 8.4 Hz, 1H), 8.06 (s, 2H), 7.92-7.76 (m, 3H), 7.69 (d, J = 8.1 Hz, 2H), 7.18 (s, 1H), 5.92 (s, 2H), 4.89 (dd, 28.9, 11.9 Hz, 2H), 4.55 (s, 4H), 4.12 (d, J = 14.8 Hz, 2H), 3.21 (s, 3H). MS m/z (ESI): 556.5 [M + H]. |
| TD101668 | | (6-(4-((1H-pyrazol-4-yl)phenyl)amino)-5-(methoxymethyl)pyrimidin-2-yl)-1-methyl-1H-indol-2-yl)(3,3-difluoroazetidin-1-yl)methanone | (Reg-1-44) in step 4 of Example 46 was replaced with (Reg-1-87) | ¹H NMR (400 MHz, DMSO-d₆) δ 12.94 (s, 1H), 8.58 (s, 1H), 8.53 (s, 1H), 8.40 (s, 1H), 8.15 (d, J = 8.5 Hz, 2H), 7.96 (s, 2H), 7.84 (d, J = 8.1 Hz, 2H), 7.70 (dd, J = 13.9, 8.5 Hz, 2H), 7.07 (s, 1H), 4.85 (dd, J = 43.7, 16.3 Hz, 4H), 4.59 (s, 2H), 4.03 (s, 3H), 3.40 (s, 3H). MS m/z (ESI): 530.1 [M + H]. |

TABLE 15-continued

| No. | Compound Structure | Compound Name | Starting material or regent different from that in Example 46 | Characterization Data |
|---|---|---|---|---|
| TDI01681 | 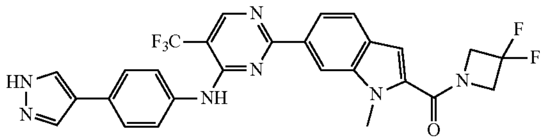 [SMILES: Cn1c(C(=O)N2CC(F)(F)C2)cc2ccc(-c3ncc(C(F)(F)F)c(Nc4ccc(-c5cn[nH]c5)cc4)n3)cc21] | (6-(4-((1H-pyrazol-4-yl) phenyl)amino)-5-(trifluoromethyl) pyrimidin-2-yl)-1-methyl-1H-indol-2-yl)(3,3-difluoroazetidin-1-yl)methanone | in step 4 of Example 46 (Reg-1-44) was replaced with (Reg-1-85) | $^1$H NMR (400 MHz, DMSO-d$_6$) δ 9.13 (s, 1H), 8.76 (s, 1H), 8.46 (s, 1H), 8.12 (s, 2H), 8.04 (d, J = 8.4 Hz, 1H), 7.70 (t, J = 8.7 Hz, 3H), 7.63 (d, J = 8.3 Hz, 2H), 7.05 (s, 1H), 4.87 (s, 2H), 4.55 (s, 2H), 3.95 (s, 3H). MS m/z (ESI): 553.7 [M + H]. |
| TDI01690 | 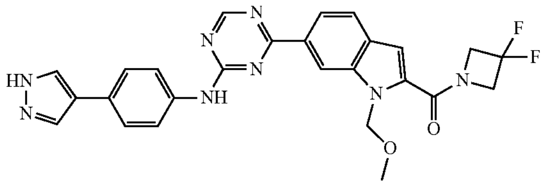 [SMILES: COCn1c(C(=O)N2CC(F)(F)C2)cc2ccc(-c3ncnc(Nc4ccc(-c5cn[nH]c5)cc4)n3)cc21] | (6-(4-((1H-pyrazol-4-yl) phenyl)amino)-1,3,5-triazin-2-yl)-1-(methoxymethyl)-1H-indol-2-yl)(3,3-difluoroazetidin-1-yl)methanone | Iodomethane in step 2 of Example 46 was replaced with MOMBr; in step 4 of Example 46 (Reg-1-44) was replaced with (Reg-1-41) | $^1$H NMR (400 MHz, DMSO-d$_6$) δ 10.33 (s, 1H), 8.84 (s, 1H), 8.73 (s, 1H), 8.26 (d, J = 7.8 Hz, 1H), 8.04 (s, 2H), 7.82 (d, J = 8.4 Hz, 3H), 7.64 (s, 2H), 7.21 (s, 1H), 5.94 (s, 2H), 4.90 (s, 2H), 4.60 (s, 2H), 3.22 (s, 3H). MS m/z (ESI): 516.6 [M + H]. |

Example 47: preparation of N-(4-(1H-pyrazol-4-yl)phenyl)-2-(2-(thiazol-2-yl)-1H-indol-6-yl)pyrimidin-4-amine (TDI01826)

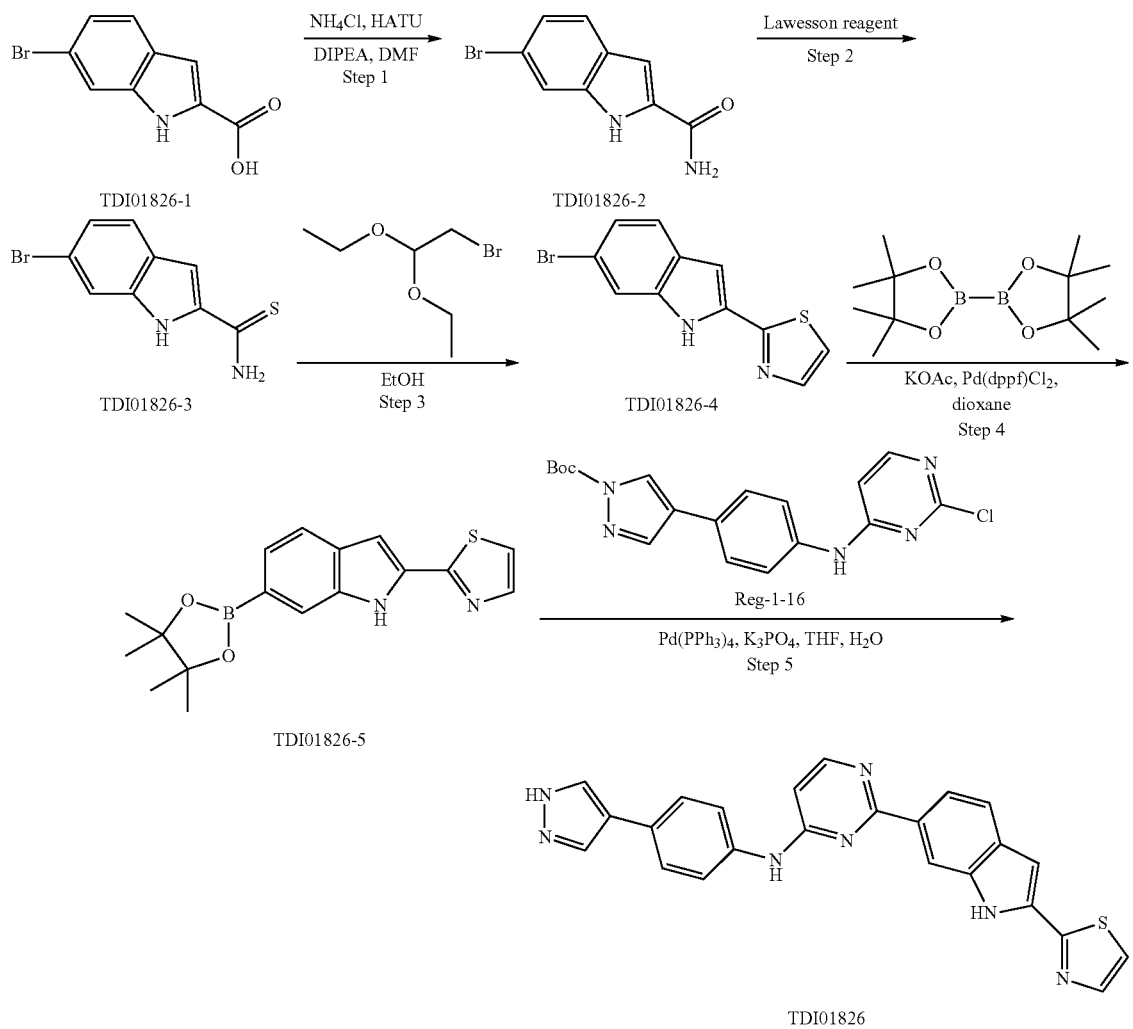

Step 1:

Compound TDI01826-1 (10.0 g, 41.6 mmol), NH₄Cl (2.67 g, 49.9 mmol), HATU (18.96 g, 49.9 mmol) and DIPEA (22 mL, 124.8 mmol) were dissolved in DMF (60 mL). The reaction solution was stirred at room temperature for 16 hours. LC-MS assay indicated the reaction was complete, and the reaction solvent was removed through rotary evaporation under vacuum. The residue was purified by column chromatography (petroleum ether:ethyl acetate=1:1) to afford compound TDI01826-2 (9.3 g, off-white solid, 93.5% yield).

$^1$H NMR (400 MHz, DMSO-$d_6$) δ 11.70 (s, 1H), 8.04 (s, 1H), 7.59 (d, J=8.0 Hz, 2H), 7.45 (s, 1H), 7.18-7.13 (m, 2H). MS m/z (ESI): 238.9 [M+H].

Step 2:

Compound TDI01826-2 (9.3 g, 38.9 mmol) and Lawesson reagent (18.9 g, 46.7 mmol) were dissolved in tetrahydrofuran (200 mL), and the reaction solution was stirred at 90° C. for 2 hours. LC-MS indicated the reaction was complete, and the reaction solvent was removed through rotary evaporation under vacuum. The residue was added with a saturated aqueous solution of sodium bicarbonate (150 mL) and ethyl acetate (150 mL), extracted and separated. The organic phase was dried and then rotary evaporated to remove the solvent, to afford compound TDI01826-3 (16 g, crude product). MS m/z (ESI): 254.9 [M+H].

Step 3:

Compound TDI01826-3 (16 g, crude product, 62.7 mmol) and bromoacetaldehyde diethylacetal (13.6 g, 69 mmol) were dissolved in ethanol (125 mL), concentrated hydrochloric acid (2.5 mL) was added, and the reaction solution was stirred at 90° C. for 16 hours. LC-MS indicated the reaction was complete. The reaction solution was cooled to room temperature, the reaction solvent was removed through rotary evaporation under vacuum, and the residue was purified by column chromatography (ethyl acetate; dichloromethane:methanol=10:1), to afford compound TDI01826-4 (4.9 g, 45% yield).

$^1$H NMR (300 MHz, DMSO-$d_6$) δ 12.04 (s, 1H), 7.92 (d, J=3.1 Hz, 1H), 7.79 (d, J=1.6 Hz, 1H), 7.54 (d, J=12.4 Hz, 2H), 7.15 (d, J=8.4 Hz, 1H), 7.06 (s, 1H). MS m/z (ESI): 278.7 [M+H].

Step 4:

Compound TDI01826-4 (4.9 g, 17.55 mmol) and bis(pinacolato)diboron (5.35 g, 21.06 mmol) were dissolved in 1,4-dioxane (60 mL), potassium acetate (5.16 g, 52.65 mmol) was added, and the flask was purged with nitrogen three times. Pd(dppf)Cl$_2$ (1.28 g, 1.755 mmol) was added, the flask was purged with nitrogen three times, and the reaction solution was stirred at 100° C. for 16 hours. LC-MS indicated the reaction was complete. The reaction solution was cooled to room temperature, and the reaction solvent was removed through rotary evaporation under vacuum. The residue was purified by column chromatography (petroleum ether:ethyl acetate=1:1), to afford compound TDI01826-5 (1.27 g, white solid, 22% yield).

$^1$H NMR (400 MHz, DMSO-d$_6$) δ 12.06 (s, 1H), 7.96 (d, J=3.2 Hz, 1H), 7.83-7.80 (m, 2H), 7.58 (d, J=8.0 Hz, 1H), 7.34 (dd, J=8.0, 0.8 Hz, 1H), 7.08 (d, J=1.4 Hz, 1H), 1.32 (s, 12H). MS m/z (ESI): 326.9 [M+H].

Step 5:

Compound TDI01826-5 (180 m g, 0.55 mmol) and Reg-1-16 (150 mg, 0.55 mmol) were dissolved in 1,4-dioxane:water (15:2 mL), potassium carbonate (229 mg, 1.66 mmol) was added, and the flask was purged with nitrogen three times. Pd(dppf)Cl$_2$ (80 mg, 0.11 mmol) was added, the flask was purged with nitrogen three times, and the reaction solution was stirred at 110° C. for 16 hours. LC-MS indicated the reaction was complete, the reaction solution was cooled to room temperature, and the reaction solvent was removed through rotary evaporation under vacuum. The residue was purified by column chromatography (dichloromethane:methanol=10:1), to afford compound TDI01826 (39 mg, 16% yield).

$^1$H NMR (400 MHz, DMSO-d$_6$) δ 12.20 (s, 1H), 9.63 (s, 1H), 8.54 (s, 1H), 8.37 (d, I=4.0 Hz, 1H), 8.13 (d, J=8.0 Hz, 2H), 8.04 (s, 2H), 7.96 (s, 1H), 7.85-7.81 (m, 3H), 7.67 (t, J=8.0 Hz, 3H), 7.11 (s, 1H), 6.68 (d, J=4.0 Hz, 1H). MS m/z (ESI): 436.2 [M+H].

The compounds in following table 16 were prepared according to methods similar to that described in Example 47.

TABLE 16

| No. | Compound Structure | Compound Name | Starting material or regent different from that in Example 47 | Characterization Data |
|---|---|---|---|---|
| TDI01871 | 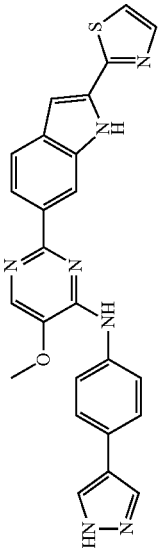 | N-(4-(1H-pyrazol-4-yl)phenyl)-5-methoxy-2-(2-(thiazol-2-yl)-1H-indol-6-yl)pyrimidin-4-amine | 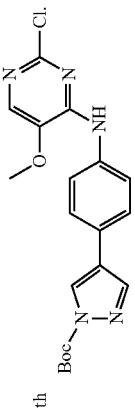 in step 5 of Example 47 was replaced with (Reg-1-36) | $^1$H NMR (400 MHz, DMSO-d$_6$) δ 12.36 (s, 1H), 8.37 (s, 1H), 8.11 (d, J = 10.9 Hz, 3H), 7.97 (dd, J = 15.2, 5.3 Hz, 4H), 7.85 (d, J = 2.8 Hz, 1H), 7.72 (t, J = 9.9 Hz, 3H), 7.15 (s, 1H), 4.07 (s, 3H). MS m/z (ESI): 466.0 [M + H]. |
| TDI01908 | 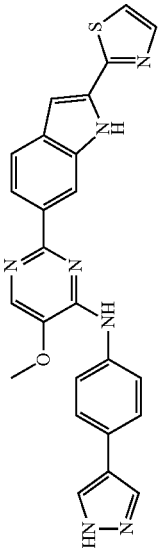 | N-(3-fluoro-4-(1H-pyrazol-4-yl)phenyl)-2-(2-(thiazol-2-yl)-1H-indol-6-yl)pyrimidin-4-amine | 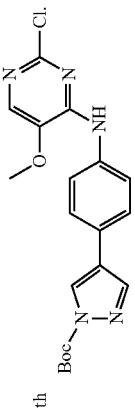 in step 5 of Example 47 was replaced with (Reg-1-39) | $^1$H NMR (400 MHz, DMSO-d$_6$) δ 12.44 (s, 1H), 8.47 (s, 1H), 8.41 (d, J = 6.3 Hz, 1H), 8.07 (s, 2H), 8.05-7.98 (m, 2H), 7.88 (d, J = 13.1 Hz, 2H), 7.80 (dd, J = 22.0, 8.4 Hz, 2H), 7.60 (d, J = 7.9 Hz, 1H), 7.17 (s, 1H), 6.83 (s, 1H). MS m/z (ESI): 453.9 [M + H]. |

TABLE 16-continued

| No. | Compound Structure | Compound Name | Starting material or regent different from that in Example 47 | Characterization Data |
|---|---|---|---|---|
| TDI01912 | 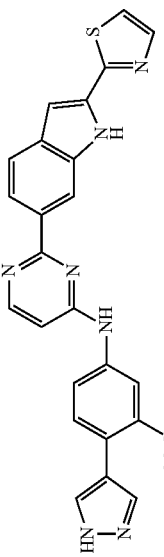 | N-(3-methoxy-4-(1H-pyrazol-4-yl)phenyl)-2-(2-(thiazol-2-yl)-1H-indol-6-yl)pyrimidin-4-amine |  in step 5 of Example 47 was replaced with 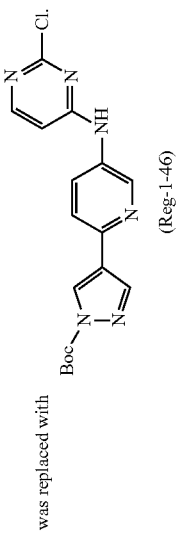 and the final product was obtained by removal of Boc using a 4N hydrochloric acid/dioxane solution in the final step. | ¹H NMR (400 MHz, DMSO-d₆) δ 12.72 (s, 1H), 11.84 (s, 1H), 8.48 (s, 1H), 8.34 (d, J = 6.9 Hz, 1H), 8.23 (d, J = 5.0 Hz, 2H), 8.06 (d, J = 8.2 Hz, 1H), 8.01 (d, J = 2.8 Hz, 1H), 7.89 (d, J = 2.9 Hz, 1H), 7.81 (dd, J = 22.7, 8.4 Hz, 3H), 7.46 (s, 1H), 7.22 (s, 1H), 7.17 (s, 1H), 3.95 (s, 3H). MS m/z (ESI): 465.6 [M + H]. |
| TDI01940 | 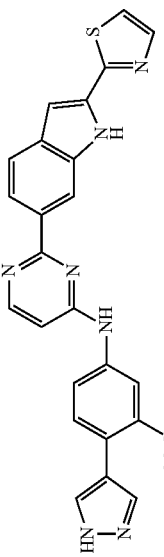 | N-(6-(1H-pyrazol-4-yl)pyridin-3-yl)-2-(2-(thiazol-2-yl)-1H-indol-6-yl)pyrimidin-4-amine |  in step 5 of Example 47 was replaced with  | ¹H NMR (400 MHz, DMSO-d₆) δ 12.41 (s, 1H), 10.63 (s, 1H), 8.97 (s, 1H), 8.50-8.40 (m, 2H), 8.36 (d, J = 8.0 Hz, 1H), 8.27 (s, 2H), 8.02-7.99 (m, 2H), 7.92 (d, J = 8.0 Hz, 1H), 7.86 (d, J = 4.0 Hz, 1H), 7.77 (d, J = 8.0 Hz, 1H), 7.17 (d, J = 2.0 Hz, 1H), 6.87 (d, J = 8.0 Hz, 1H). MS m/z (ESI): 437.0 [M + H]. |

TABLE 16-continued

| No. | Compound Name | Compound Structure | Starting material or regent different from that in Example 47 | Characterization Data |
|---|---|---|---|---|
| TDI01941 | N-(4-(1H-pyrazol-4-yl)phenyl)-2-(2-(thiazol-2-yl)-1H-indol-6-yl)furo[3,2-d]pyrimidin-4-amine | 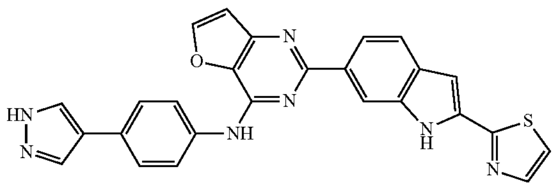 [SMILES: c1csc(-c2cc3ccc(-c4nc(Nc5ccc(-c6cn[nH]c6)cc5)c5occc5n4)cc3[nH]2)n1] | (Reg-1-16) in step 5 of Example 47 was replaced with (Reg-1-44) | ¹H NMR (400 MHz, DMSO-d₆) δ 12.92 (s, 1H), 12.18 (s, 1H), 9.98 (s, 1H), 8.55 (s, 1H), 8.38 (d, J = 1.9 Hz, 1H), 8.17 (d, J = 8.3 Hz, 2H), 8.03 (d, J = 8.5 Hz, 2H), 7.96 (d, J = 3.1 Hz, 2H), 7.81 (d, J = 3.1 Hz, 1H), 7.68 (m, J = 9.1 Hz, 3H), 7.18-7.09 (m, 2H), MS m/z (ESI): 475.6 [M + H]. |
| TDI01975 | 5-fluoro-N-(3-fluoro-4-(1H-pyrazol-4-yl)phenyl)-2-(2-(thiazol-2-yl)-1H-indol-6-yl)pyrimidin-4-amine | 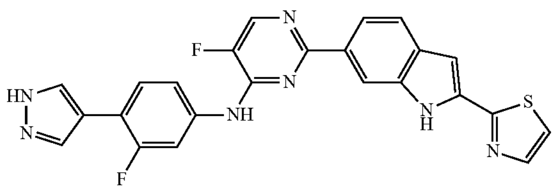 [SMILES: Fc1cc(Nc2nc(-c3ccc4cc(-c5nccs5)[nH]c4c3)ncc2F)ccc1-c1cn[nH]c1] | (Reg-1-16) in step 5 of Example 47 was replaced with (Reg-1-68) | ¹H NMR (400 MHz, DMSO-d₆) δ 12.23 (s, 1H), 9.82 (s, 1H), 8.52 (d, J = 3.3 Hz, 1H), 8.45 (s, 1H), 8.05 (d, J = 13.7 Hz, 3H), 7.99-7.92 (m, 2H), 7.85-7.80 (m, 2H), 7.69 (d, J = 8.4 Hz, 1H), 7.63-7.55 (m, 1H), 7.11 (s, 1H). MS m/z (ESI): 472.0 [M + H]. |

Example 48: preparation of N-(4-(1H-pyrazol-4-yl)phenyl)-2-(1-methyl-(2-(thiazol-2-yl)-1H-indol-6-yl)pyrimidin-4-amine (TDI01919)

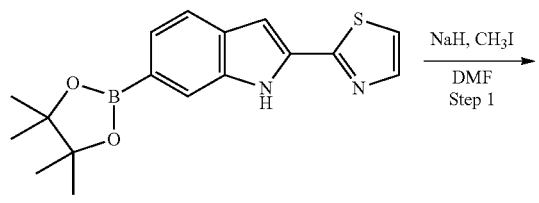

TDI01826-5

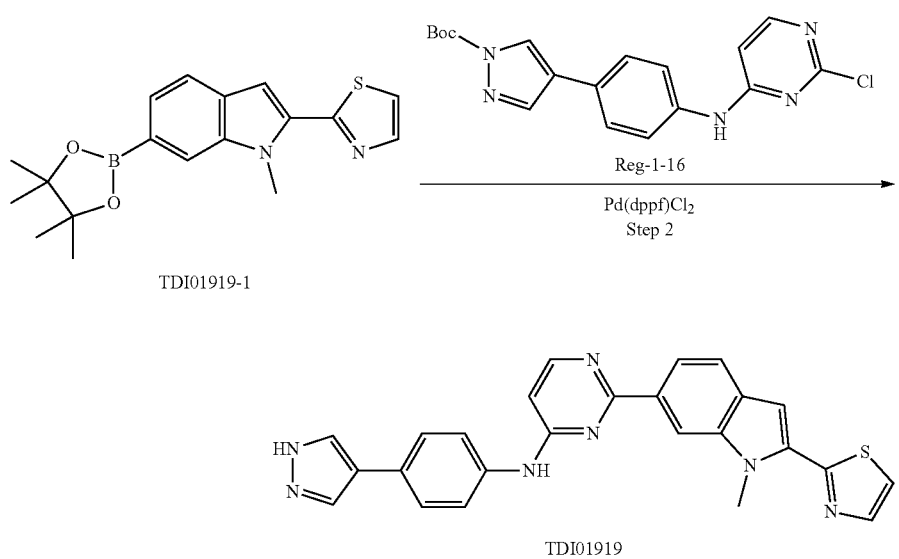

Step 1:

Compound TDI01826-5 (489 mg, 1.5 mmol) was dissolved in N,N-dimethylformamide (30 mL), sodium hydride (72 mg, 3 mmol) was added at 0° C., the reaction was stirred for 30 min before addition of iodomethane (638 mg, 4.5 mmol), and the reaction solution was stirred at room temperature for 16 hours. LC-MS indicated the reaction was complete. The reaction solution was rotary evaporated under vacuum to remove the reaction solvent, and the residue was purified by column chromatography (petroleum ether:ethyl acetate=4:1) to afford compound TDI01919-1 (420 mg, white solid, 82.3% yield).

$^1$H NMR (400 MHz, DMSO-$d_6$) δ 8.02 (d, J=3.3 Hz, 1H), 7.88-7.83 (m, 2H), 7.63 (d, J=8.0 Hz, 1H), 7.42 (d, J=7.9 Hz, 1H), 7.11 (s, 1H), 4.18 (s, 3H), 1.33 (s, 12H). MS m/z (ESI): 341.0 [M+H].

Step 2:

Compound TDI01919-1 (150 mg, 0.44 mmol) and Reg-1-16 (164 mg, 0.44 mmol) were dissolved in 1,4-dioxane:water (8:0.8 mL), potassium carbonate (182 mg, 1.32 mmol) was added, and the flask was purged with nitrogen three times. Pd(dppf)Cl$_2$ (129 mg, 0.176 mmol) was added, the flask was purged with nitrogen three times, and the reaction solution was stirred at 110° C. for 16 hours. LC-MS indicated the reaction was complete, the reaction solution was cooled to room temperature, and the reaction solvent was removed through rotary evaporation under vacuum. The residue was purified by preparative liquid chromatography to afford compound TDI01919 (40 mg, 20% yield).

$^1$H NMR (400 MHz, DMSO-$d_6$) δ 10.78 (s, 1H), 8.53 (s, 1H), 8.40 (d, J=6.6 Hz, 1H), 8.07 (dd, J=15.3, 12.2 Hz, 4H), 7.93 (d, J=3.0 Hz, 1H), 7.88-7.70 (m, 5H), 7.23 (s, 1H), 6.87 (s, 1H), 4.26 (s, 3H). MS m/z (ESI): 449.9 [M+H].

Example 49: preparation of 1-(5-(4-((1H-indazol-5-yl)amino)pyrimidin-2-yl)isoindolin-2-yl)-2-morpholinoethan-1-one (TDI01806)

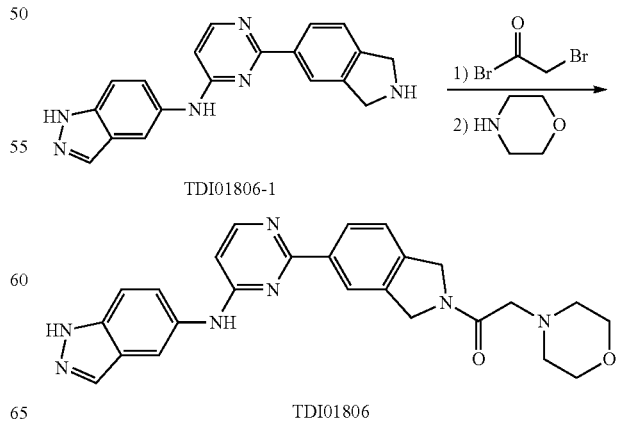

Compound TDI01806-1 was synthesized according to a method similar to that described in step 1 to step 3 of Example 35.

Under protection of nitrogen, TDI01806-1 (100 mg, 0.305 mmol) was added to dichloromethane (10 mL), the reaction was cooled to 0° C., 2-bromoacetyl bromide (38 mg, 0.336 mmol) and trifluoroacetic acid (31 mg, 0.305 mmol) were slowly dropwise added, and the reaction was stirred at room temperature for 2 hours. morpholine (200 mg, 2.30 mmol) was added in one portion, and the reaction was allowed to warmed to room temperature, and stirred for 2 hours. LC-MS indicated the reaction was complete. The solvent was evaporated to afford a crude product, which was separated to afford compound TDI01806 (12 mg, yellow solid, yield: 9%).

$^1$H NMR (400 MHz, DMSO-d$_6$) δ 8.32 (d, J=5.1 Hz, 1H), 8.19 (dd, J=24.1, 14.6 Hz, 4H), 7.59 (dt, J=14.1, 7.8 Hz, 3H), 6.82 (d, J=6.4 Hz, 1H), 4.91 (s, 2H), 4.83 (d, J=8.5 Hz, 2H), 4.34 (s, 2H), 3.75 (s, 4H), 3.08 (s, 4H). MS m/z (ESI): 456.0 [M+H].

Example 50: preparation of N-(2-(2-(benzo[d]oxazol-2-yl)-1H-indol-6-yl)pyrimidin-4-yl)-1H-indazol-5-amine (TDI01816)

Step 1:
Compound TDI01816-1 (5 g, 20.8 mmol) and thionyl chloride (25 mL) were mixed, and stirred at room temperature until TLC indicated no starting materials remained. The reaction mixture was concentrated to remove thionyl chloride, and dissolved in dry dichloromethane (50 mL), a solution of 2-aminophenol (2.15 g, 19.7 mmol) in dichloromethane (50 mL) was added dropwise at 0° C., and the reaction was stirred at room temperature for 16 hours. The reaction solution was filtered to remove the insolubles, and the filtrate was concentrated to afford compound TDI01816-2 (1.95 g, brown solid, crude product, 28% yield).

MS m/z (ESI): 330.9 [M+H].

Step 2:
Compound TDI01816-2 (500 mg, 1.51 mmol) was dissolved in toluene (50 mL), p-toluenesulfonic acid (321 mg, 1.86 mmol) was added, and the reaction solution was stirred at 120° C. for 48 hours. LC-MS assay indicated that the reaction was substantially complete. The reaction solution was cooled to room temperature, 100 mL ethyl acetate and 50 mL saturated aqueous solution of sodium bicarbonate were added, and the aqueous phase was extracted with ethyl

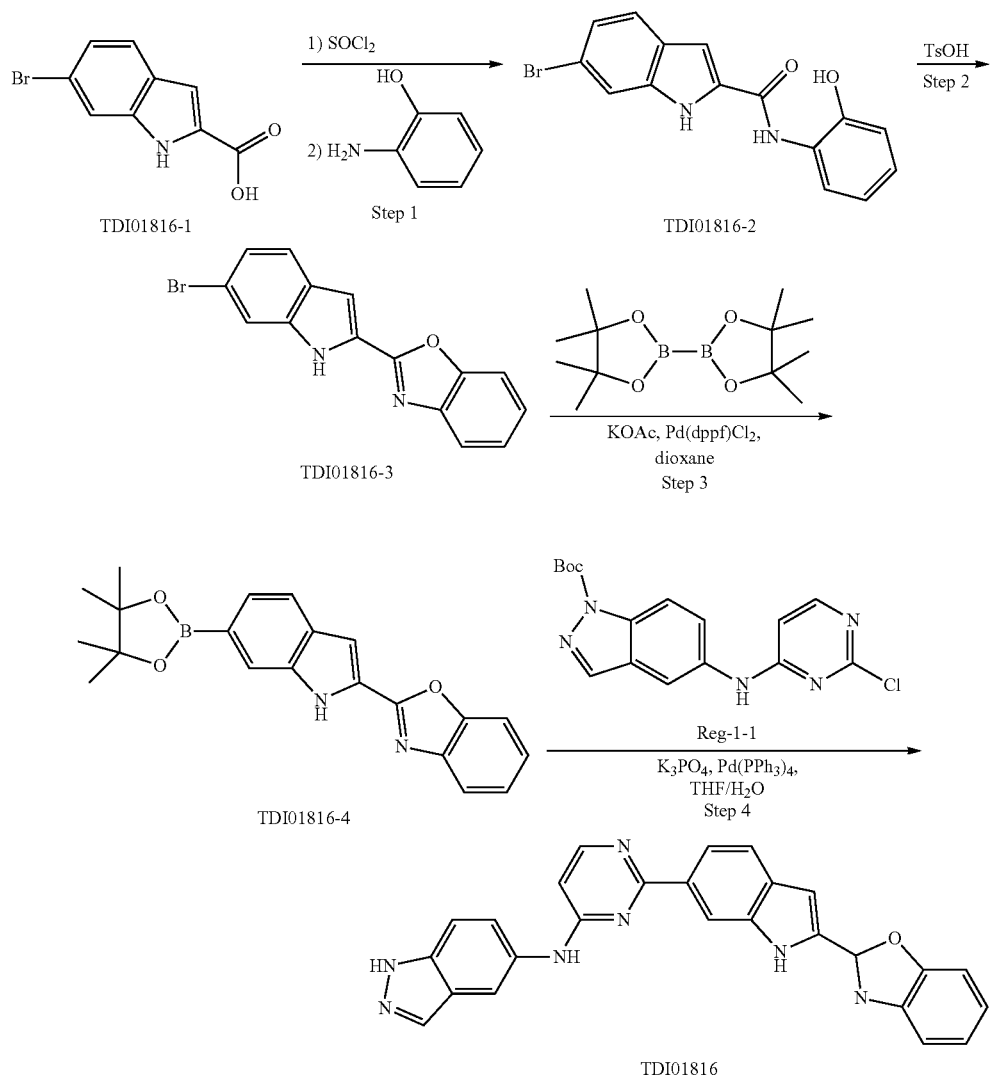

acetate (50 mL) after phase separation. The organic phases were combined and evaporated to dryness, and the reaction solvent was removed through rotary evaporation under vacuum. The residue was purified by column chromatography (petroleum ether:ethyl acetate=10:1 to 5:1) to afford compound TDI01816-3 (249 mg, white solid, 53% yield).

$^1$H NMR (400 MHz, DMSO-$d_6$) δ 12.48 (s, 1H), 7.83-7.80 (m, 2H), 7.68 (d, J=8.8 Hz, 1H), 7.66 (s, 1H), 7.49-7.42 (m, 2H), 7.38 (s, 1H), 7.25 (d, J=8.4 Hz, 1H). MS m/z (ESI): 312.9, 314.8 [M+H].

Step 3:

Compound TDI01816-3 (210 mg, 0.67 mmol) and bis(pinacolato)diboron (170 mg, 0.67 mol) were dissolved in 1,4-dioxane (20 mL), potassium acetate (197 mg, 2.01 mmol) and Pd (dppf)Cl$_2$ (49 mg, 0.067 mmol) were added, the flask was purged with nitrogen three times, and the reaction solution was stirred at 100° C. for 8 hours. LC-MS indicated the reaction was complete. The reaction solution was cooled to room temperature, filtered, the reaction solvent was removed through rotary evaporation under vacuum, and the residue was purified by column chromatography (petroleum ether:ethyl acetate=10:1 to 5:1) to afford compound TDI01816-4 (153 mg, 63% yield).

MS m/z (ESI): 361.0 [M+H].

Step 4:

Compound TDI01816-4 (100 mg, 0.28 mmol) and Reg-1-1 (96 mg, 0.28 mmol) were dissolved in tetrahydrofuran (20 mL) and water (2 mL), tripotassium phosphate (176 mg, 0.83 mmol) and Pd(PPh$_3$)$_4$ (32 mg, 0.028 mmol) were added, the flask was purged with nitrogen three times, and the reaction solution was stirred at 80° C. for 16 hours. LC-MS assay indicated the reaction was incomplete. The reaction solution was cooled to room temperature, and the reaction solvent was removed through rotary evaporation under vacuum. The residue was purified by preparative high pressure liquid chromatography to afford compound TDI01816 (1.8 mg, 1.5% yield).

$^1$H NMR (400 MHz, DMSO-$d_6$) δ 12.78 (s, 1H), 10.22 (s, 1H), 8.55 (s, 2H), 8.38 (s, 2H), 8.24 (d, J=29.3 Hz, 2H), 8.13 (s, 1H), 7.87 (s, 3H), 7.65 (s, 2H), 7.46 (t, J=14.8 Hz, 2H), 6.74 (s, 1H). MS m/z (ESI): 443.7 [M+H].

The compound in following table 18 was prepared according to a method similar to that described in Example 50.

TABLE 18

| No. | Compound Structure | Compound Name | Starting material or regent different from that in Example 50 | Characterization Data |
|---|---|---|---|---|
| TDI01816B | 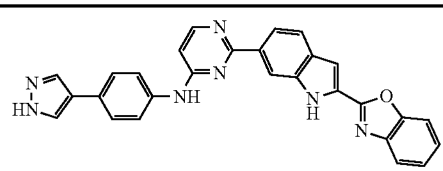 | N-(4-(1H-pyrazol-4-yl)phenyl)-2-(2-(benzo[d]oxazol-2-yl)-1H-indol-6-yl)pyrimidin-4-amine | (Reg-1-1) in step 4 of Example 50 was replaced with (Reg-1-16). | $^1$H NMR (400 MHz, DMSO-$d_6$) δ 12.81 (s, 1H), 8.55 (s, 1H), 8.38 (d, J = 6.4 Hz, 1H), 8.09 (s, 3H), 7.93-7.77 (m, 6H), 7.72 (d, J = 8.3 Hz, 2H), 7.47 (dd, J = 8.2, 4.4 Hz, 3H), 6.81 (s, 1H). MS m/z (ESI): 470.2 [M + H]. |

Example 51: preparation of 4-(04-(1H-pyrazol-4-yl)phenyl)amino)-2-(2-(3,3-difluorocyclobutane-1-carbonyl)isoindolin-5-yl)pyrimidin-5-carboxylic acid (TDI01567C) and 4-((4-(1H-pyrazol-4-yl)phenyl)amino)-2-(2-(3,3-difluorocyclobutane-1-carbonyl)isoindolin-5-yl)pyrimidin-5-carboxamide (TDI01567)

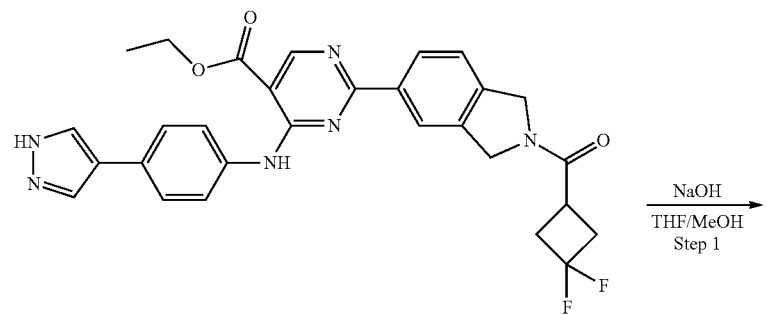

TDI01567B

-continued

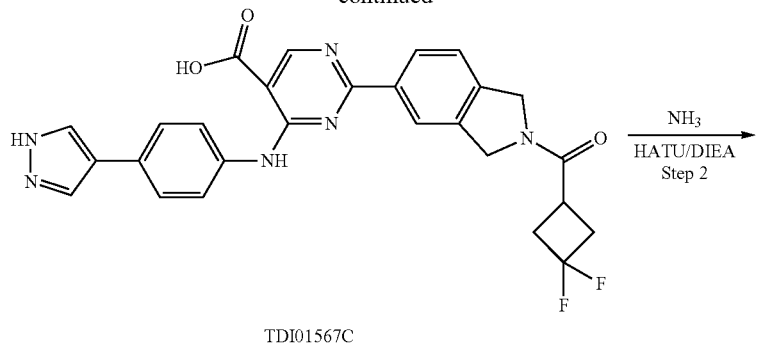

TDI01567C

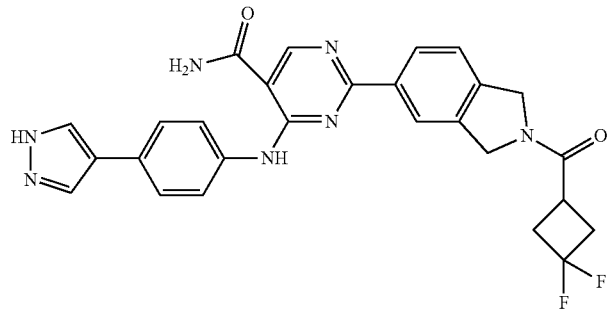

TDI01567

Step 1:

Compound TDI01567B (195 mg, 0.358 mmol) was dissolved in THF (6 mL) and MeOH (6 mL), and 1 M aqueous solution of sodium hydroxide (6 mL) was added. The reaction was performed at room temperature for 3 h. LC-MS indicated the reaction was complete. The reaction solvent was removed through rotary evaporation under vacuum, and the residue was purified by preparative high pressure liquid chromatography to afford compound TDI01567C (117 mg, yellow solid, yield 64%).

$^1$H NMR (400 MHz, DMSO-d$_6$) δ 10.56 (s, 1H), 9.02 (s, 1H), 8.35 (dd, J=16.6, 8.7 Hz, 2H), 8.10 (s, 2H), 7.83-7.78 (m, 2H), 7.71 (dd, J=8.4, 4.0 Hz, 2H), 7.53 (dd, J=15.5, 8.0 Hz, 2H), 4.92 (d, J=6.7 Hz, 2H), 4.77 (d, J=12.7 Hz, 2H), 3.28 (d, J=5.8 Hz, 1H), 2.87 (dd, J=16.4, 8.6 Hz, 4H). MS m/z (ESI): 516.7 [M+H].

Step 2:

Compound TDI01567C (100 mg, 0.194 mmol) and HATU (81 mg, 0.213 mmol) were dissolved in N,N-dimethylformamide, and diisopropylethylamine (125 mg, 0.968 mmol) was added. Ammonia gas was bubbled through the reaction solution, and the reaction solution was stirred at room temperature for 2 h. LC-MS indicated the reaction was complete, and the reaction solvent was removed through rotary evaporation under vacuum. The residue was purified by preparative high pressure liquid chromatography to afford compound TDI01567 (20.59 mg, yellow solid, yield 20%).

$^1$H NMR (400 MHz, DMSO-d$_6$) δ 11.49-11.46 (m, 1H), 9.01 (s, 1H), 8.44 (s, 1H), 8.32 (d, J=9.7 Hz, 2H), 8.08 (s, 2H), 7.89-7.83 (m, 1H), 7.80-7.77 (m, 2H), 7.70-7.67 (m, 2H), 7.56-7.49 (m, 1H), 4.91 (s, 2H), 4.76 (s, 2H), 2.87 (d, J=8.6 Hz, 4H). MS m/z (ESI): 515.8 [M+H].

Example 52: preparation of 6-(4-((4-(1H-pyrazol-4-yl)phenyl)amino)pyrimidin-2-yl)-N-(3-cyanopyridin-4-yl)-1H-indole-2-carboxamide (TDI01829B)

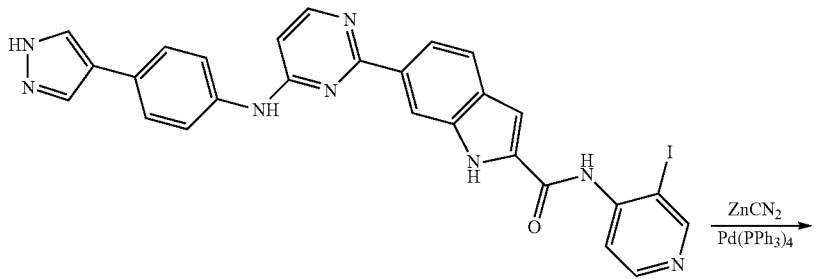

TDI01829C

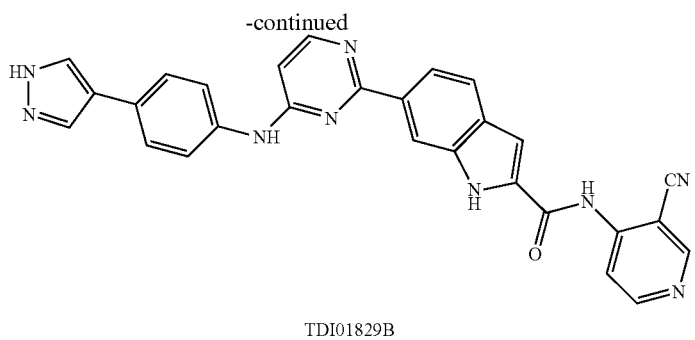

TDI01829B

Compound TDI01829C (30 mg, 0.05 mmol) and Zn(CN)$_2$ (17 mg, 0.15 mmol) were dissolved in N,N-dimethylformamide (3 mL), Pd(PPh$_3$)$_4$ (11 mg, 0.01 mmol) was added, the flask was purged with nitrogen three times, and the reaction solution was stirred at 110° C. for 16 hours. LC-MS indicated the reaction was complete. The reaction solution was cooled to room temperature, added with water (5 mL), extracted with ethyl acetate (10 mL×3), and the organic phase was rotary evaporated under vacuum to remove the solvent. The residue was purified by preparative high pressure liquid chromatography, to afford compound TDI01829B (2.37 mg, yellow solid, 10% yield).

$^1$H NMR (400 MHz, DMSO-d$_6$) δ 12.52 (s, 1H), 11.08 (s, 1H), 9.03 (s, 1H), 8.85 (s, 1H), 8.54 (s, 1H), 8.38 (d, J=5.6 Hz, 1H), 8.09 (s, 4H), 7.96 (s, 1H), 7.76 (dd, J=27.9, 10.9 Hz, 6H), 7.59 (s, 1H), 6.85 (s, 1H). MS m/z (ESI): 498.0 [M+H].

Example 53: preparation of (6-(4-((4-(1H-pyrazol-4-yl)phenyl)amino)pyrimidin-2-yl)-1H-indol-2-yl)dimethylphosphine oxide (TDI01846)

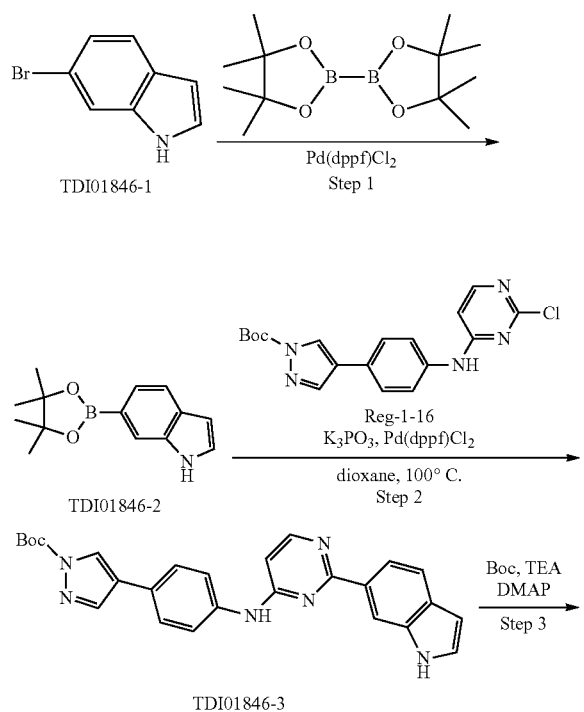

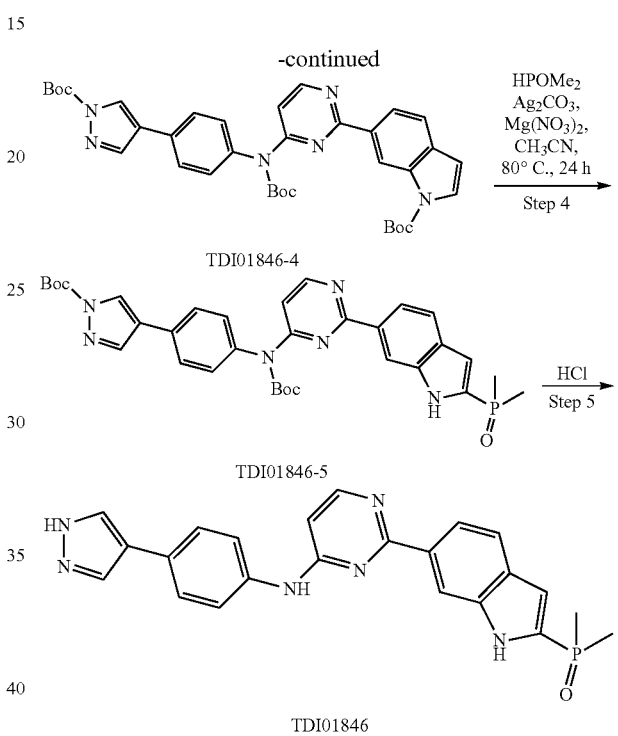

Step 1:

Compound TDI01846-1 (1.0 g, 5.1 mmol) and bis(pinacolato)diboron (1.3 g, 5.1 mmol) were dissolved in 1,4-dioxane (20 mL), potassium acetate (1.5 g, 15.3 mmol) and Pd(dppf)Cl$_2$ (373 mg, 0.51 mmol) were added, the flask was purged with nitrogen three times, and the reaction solution was stirred at 100° C. for 16 hours. LC-MS indicated the reaction was complete. The reaction solution was cooled to room temperature, filtered to remove the insolubles, and the filtrate was rotary evaporated under vacuum to remove solvents. The residue was purified by column chromatography (petroleum ether:ethyl acetate=4:1), to afford compound TDI01846-2 (670 mg, yellow solid, 54% yield).

$^1$H NMR (400 MHz, DMSO-d$_6$) δ 11.17 (s, 1H), 7.76 (s, 1H), 7.52 (d, J=7.9 Hz, 1H), 7.44 (t, J=2.7 Hz, 1H), 7.28 (d, J=7.9 Hz, 1H), 6.43 (s, 1H), 1.30 (s, 12H). MS m/z (ESI): 244.0 [M+H].

Step 2:

Compound TDI01846-2 (150 mg, 0.6 mmol) and compound Reg-1-16 (290 mg, 0.78 mmol) were dissolved in a mixed solution of dioxane (15 mL) and water (1.5 mL), tripotassium phosphate (382 mg, 1.8 mmol) and Pd(dppf)Cl$_2$ (42 mg, 0.06 mmol) were added, the flask was purged with nitrogen three times, and the reaction solution was stirred at 100° C. for 16 h. LC-MS indicated the reaction was complete. The reaction solution was cooled to room temperature, filtered to remove the insolubles, and the filtrate was rotary evaporated under vacuum to remove the reaction solvent. The residue was purified by column chromatography (dichloromethane:methanol=30:1) to afford compound TDI01846-3 (344 mg, crude product).

MS m/z (ESI): 453.0 [M+H].

Step 3:

Compound TDI01846-3 (344 mg, 0.76 mmol) was dissolved in dichloromethane (10 mL), triethylamine (232 mg, 23 mmol) and 4,4-dimethylaminopyridine 9 mg, 0.076 mmol) were added, Boc$_2$O (479 mg, 2.3 mmol) was then added, and the reaction was performed at room temperature overnight. The reaction solution was concentrated to afford a crude product. The residue was purified by column chromatography (petroleum ether:ethyl acetate=4:1) to afford compound TDI01846-4 (120 mg, off-white solid, 24% yield).

MS m/z (ESI): 652.8 [M+H].

Step 4:

A mixture of compound TDI01846-4 (70 mg, 0.11 mmol), Ag$_2$CO$_3$ (41 mg, 0.15 mmol) and Mg(NO$_3$)$_2$ (22 mg, 0.15 mmol) was added to acetonitrile (5 mL), HPOMe$_2$ (12 mg, 0.15 mmol) was then added in one portion, the flask was purged with nitrogen three times, and the reaction solution was stirred at 80° C. for 24 hours. LC-MS indicated the reaction was complete. The reaction solution was cooled to room temperature, the reaction solvent was removed through rotary evaporation under vacuum, and the residue was purified by preparative thin layer chromatography (developing agent:dichloromethane:methanol=15:1), to afford compound TDI01846-5 (100 mg, crude product).

MS m/z (ESI): 628.9 [M+H].

Step 5:

Compound TDI01846-5 (100 mg, crude product, theoretically 0.11 mmol) was dissolved in tetrahydrofuran (2 mL), 4M HCl/dioxane (1 mL) was added, and the reaction solution was stirred at room temperature for 16 hours. LC-MS indicated the reaction was complete. The reaction solution was cooled to room temperature, the reaction solvent was removed through rotary evaporation under vacuum, and the residue was purified by preparative liquid chromatography to afford compound TDI01846 (6.1 mg, yellow solid, yield 13%).

$^1$H NMR (400 MHz, DMSO-d$_6$) δ 12.20 (s, 1H), 8.46 (s, 1H), 8.36 (s, 1H), 8.08 (s, 1H), 8.03 (s, 1H), 7.92-7.76 (m, 3H), 7.71 (d, J=8.2 Hz, 2H), 7.66 (s, 1H), 7.02 (s, 1H), 6.89-6.75 (m, 2H), 1.77 (t, J=26.9 Hz, 6H). MS m/z (ESI): 428.9 [M+H].

Example 54: preparation of N-(2-(2-(benzo[d]thiazol-2-yl)-1H-indol-6-yl)pyrimidin-4-yl)-1H-indazol-5-amine (TDI01881)

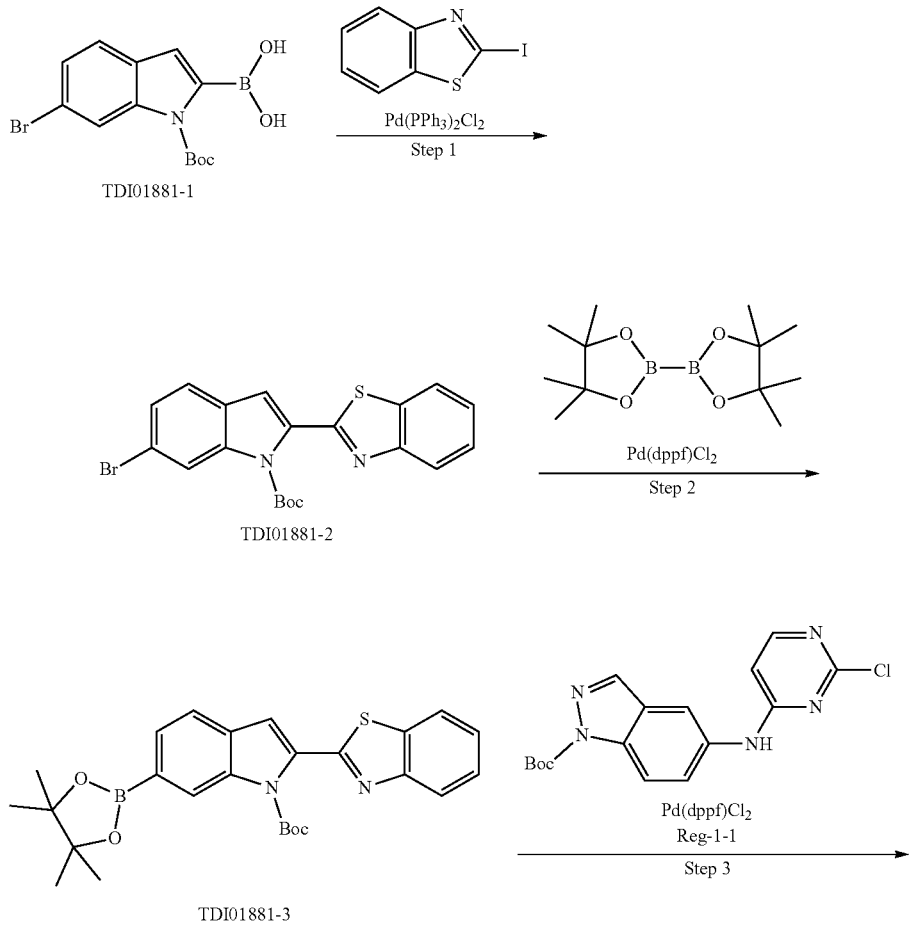

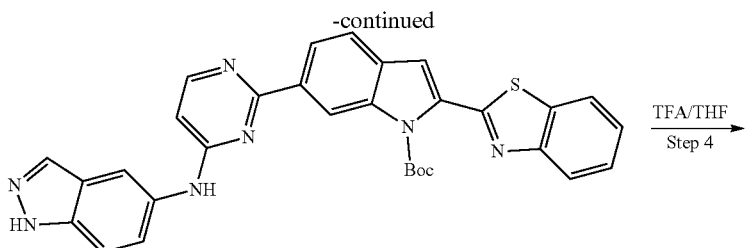

TDI01881-4

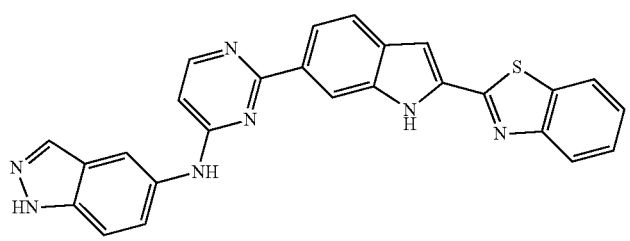

TDI01881

Step 1:

Compound TDI01881-1 (200 mg, 0.59 mmol), 2-iodobenzo[d]thiazole (170 mg, 0.65 mmol), sodium carbonate (191 mg, 1.77 mmol) and Pd(PPh$_3$)Cl$_2$ (42 mg, 0.059 mmol) were mixed in mixed solvents of acetonitrile (20 mL) and water (2 mL), the flask was purged with N$_2$ 3 times, and then the reaction solution was heated to reflux and reacted for 1 hour. LC-MS indicated the reaction was complete. The reaction solution was cooled to room temperature, filtered to remove salt impurities, the filtrate was concentrated under reduced pressure, and the crude product was separated through column chromatography on silica gel (petroleum ether:ethyl acetate=5:1) to afford compound TDI01881-2 (160 mg, brown viscous oil, yield: 63.5%).

$^1$H NMR (400 MHz, DMSO-d$_6$) δ 8.23 (d, J=12.7 Hz, 2H), 8.12 (d, J=8.0 Hz, 1H), 8.02 (d, J=8.3 Hz, 1H), 7.73 (d, J=8.4 Hz, 1H), 7.62 (d, J=7.5 Hz, 1H), 7.52 (m, 2H), 1.25 (s, 9H). MS m/z (ESI): 428.5, 430.5 [M+H, Br].

Step 2:

Compound TDI01881-2 (160 mg, 0.37 mmol), bis(pinacolato)diboron (150 mg, 0.49 mmol), potassium acetate (109 mg, 1.11 mmol) and Pd(dppf)Cl$_2$ (27 mg, 0.037 mmol) were dissolved in 1,4-dioxane (8 mL), the flask was purged with N$_2$ 3 times, and the reaction was refluxed in an oil bath at 108° C. for 10 hours. LC-MS indicated the reaction was complete. The reaction solution was cooled to room temperature, concentrated under reduced pressure to afford a crude product, which was separated through column chromatography on silica gel (petroleum ether:ethyl acetate=4:1) to afford compound TDI01881-3 (158 mg, orange solid, yield: 88.8%).

$^1$H NMR (400 MHz, DMSO-d$_6$) δ 8.46 (s, 1H), 8.23 (d, J=7.8 Hz, 1H), 8.11 (d, J=8.2 Hz, 1H), 7.75 (d, J=7.8 Hz, 1H), 7.61 (m, 2H), 7.53 (m, 1H), 7.36 (s, 1H), 1.34 (s, 12H), 1.24 (s, 9H).

Step 3:

Compound TDI01881-3 (50 mg, 0.24 mmol), compound Reg-1-1 (98 g, 0.28 mmol), potassium carbonate (116 mg, 0.84 mmol) and Pd(dppf)Cl$_2$ (82 mg, 0.112 mmol) were mixed in mixed solvents of 1,4-dioxane (5 mL) and water (0.5 mL), the flask was purged with N$_2$ 3 times, and then the reaction solution was heated to reflux overnight. LC-MS indicated the reaction was complete. The reaction solution was cooled to room temperature, filtered to remove salt impurities, and the filtrate was concentrated under reduced pressure to afford a crude product, which was separated to afford compound TDI01881-4 (16 mg, yellow solid, yield: 27.3%).

MS m/z (ESI): 559.5 [M+H].

Step 4:

Compound TDI01881-4 (16 mg, 0.029 mmol) was dissolved in trifluoroacetic acid (2 mL) and tetrahydrofuran (3 mL), and heated to reflux overnight. LC-MS indicated the reaction was complete. The reaction solution was cooled to room temperature, concentrated under reduced pressure to afford a crude product, which was separated to afford compound TDI01881 (1.45 mg, yellow solid, yield: 11.2%).

$^1$H NMR (400 MHz, DMSO-d$_6$) δ 13.12 (s, 1H), 12.68 (s, 1H), 8.52 (s, 1H), 8.35 (d, J=6.1 Hz, 1H), 8.28-8.16 (m, 3H), 8.09 (d, J=7.9 Hz, 1H), 7.81 (s, 1H), 7.68-7.56 (m, 3H), 7.52-7.48 (m, 1H), 7.36 (s, 1H), 7.20 (s, 1H), 6.74 (s, 1H), 6.66 (s, 1H). MS m/z (ESI): 460.0 [M+H].

The compound in following table 19 was prepared according to a method similar to that described in Example 54.

TABLE 19

| No. | Compound Structure | Compound Name | Starting material or regent different from that in Example 54 | Characterization Data |
|---|---|---|---|---|
| TDI01870 | 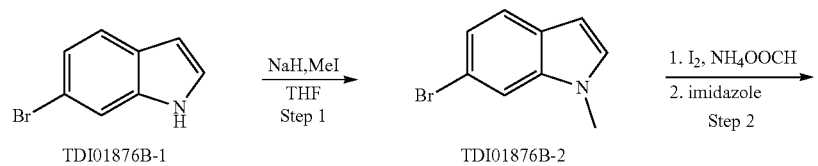 | N-(4-(1H-pyrazol-4-yl)phenyl)-2-(2-(pyrimidin-2-yl)-1H-indol-6-yl)pyrimidin-4-amine | 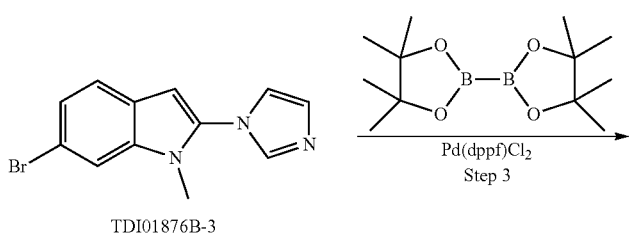 | ¹H NMR (400 MHz, DMSO-d₆) δ 12.48 (s, 1H), 10.77 (s, 1H), 8.95 (d, J = 4.8 Hz, 2H), 8.52 (s, 1H), 8.36 (d, J = 6.7 Hz, 1H), 8.11 (s, 2H), 7.96 (d, J = 8.2 Hz, 1H), 7.91-7.79 (m, 3H), 7.75 (d, J = 8.4 Hz, 2H), 7.49 (m, J = 4.9 Hz, 1H), 7.43 (s, 1H), 6.88 (d, J = 6.0 Hz, 1H). MS m/z (ESI): 430.7 [M + H]. |

Example 55: preparation of 2-(2-(1H-imidazol-1-yl)-1-methyl-1H-indol-6-yl)-N-(4-(1H-pyrazol-4-yl)phenyl)pyrimidin-4-amine (TDI01876B)

-continued

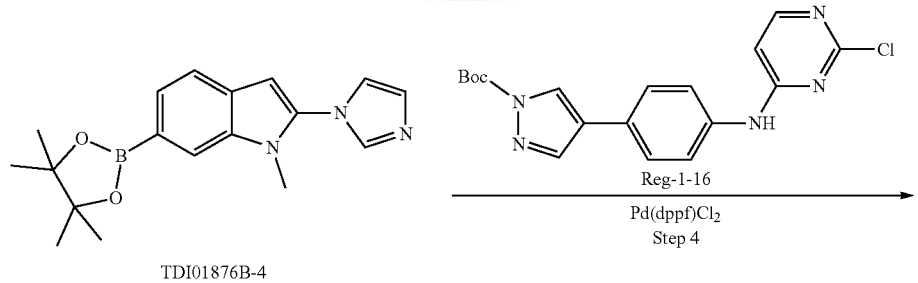
TDI01876B-4

Reg-1-16
Pd(dppf)Cl₂
Step 4

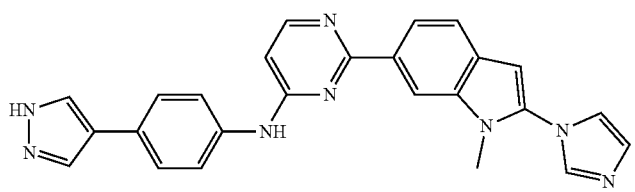
TDI01876B

Step 1:

Compound TDI01876B-1 (200 mg, 1.05 mmol) was dissolved in tetrahydrofuran (5 mL), and cooled to 0° C. under protection of nitrogen. Sodium hydride (63 mg, 60%, 1.53 mmol) was added portionwise, and the reaction was performed at 0° C. for 0.5 hour. Iodomethane (435 mg, 3.06 mmol) was added in one portion, and the reaction was stirred at room temperature overnight after the addition. LC-MS indicated the reaction was complete. 0.1 mL water was added dropwise, and the solvent was rotary evaporated to afford the crude product, which was separated through column chromatography on silica gel (petroleum ether:ethyl acetate=10:1) to afford compound TDI01876B-2 (180 mg, brown solid, yield: 84.5%).

¹H NMR (400 MHz, DMSO-d₆) δ 7.69 (s, 1H), 7.49 (d, J=8.4 Hz, 1H), 7.34 (d, J=3.0 Hz, 1H), 7.13 (m, 1H), 6.44 (d, J=3.0 Hz, 1H), 3.78 (s, 3H).

Step 2:

Compound TDI01876B-2 (180 mg, 0.86 mmol) and imidazole (146 mg, 2.15 mmol) were dissolved in mixed solvents of 1,4-dioxane (1 mL) and a saturated aqueous solution of ammonium formate, solid iodine (539 mg, 2.125 mmol) was added in one portion, and the reaction was stirred at room temperature overnight. LC-MS indicated the reaction was complete. Iodine was removed by washing with a saturated solution of sodium thiosulfate, the mixture was extracted with ethyl acetate (15 mL for three times), and the organic phases were combined and rotary evaporated to afford the crude product, which was purified by flash column chromatography to afford compound TDI01876B-3 (110 mg, brown solid, yield: 46.4%).

¹H NMR (400 MHz, DMSO-d₆) δ 8.03 (s, 1H), 7.86 (s, 1H), 7.58 (m, 2H), 7.26 (d, J=8.4 Hz, 1H), 7.19 (s, 1H), 6.66 (s, 1H), 3.56 (s, 3H). MS m/z (ESI): 275.9, 278.0 [M+H, Br].

Step 3:

Compound TDI01876B-3 (110 mg, 0.4 mmol), bis(pinacolato)diboron (112 mg, 0.44 mmol) and potassium acetate (118 g, 1.2 mmol) were dissolved in 1,4-dioxane (10 mL), the flask was purged with N₂ 3 times, followed by addition of Pd(dppf)Cl₂ (30 mg, 0.04 mmol), the flask was purged with N₂ 3 times again, and then the reaction was placed in an oil bath at 108° C. for 4 hours. LC-MS indicated the reaction was complete. The reaction solution was cooled to room temperature, concentrated under reduced pressure to afford the crude product, which was separated through column chromatography on silica gel (petroleum ether:ethyl acetate=8:1) to afford compound TDI01876B-4 (80 mg, yellow solid, yield: 62%).

¹H NMR (400 MHz, DMSO-d₆) δ 8.03 (s, 1H), 7.82 (s, 1H), 7.60 (d, J=7.4 Hz, 2H), 7.44 (d, J=7.9 Hz, 1H), 7.19 (s, 1H), 6.64 (s, 1H), 3.60 (s, 3H), 1.32 (s, 9H). MS m/z (ESI): 324.2 [M+H].

Step 4:

Compound TDI01876B-4 (80 mg, 0.25 mmol), Reg-1-16 (92 mg, 0.25 mmol) and potassium carbonate (104 mg, 0.75 mmol) were mixed in mixted solvents of 1,4-dioxane (5 mL) and water (0.5 mL), Pd(dppf)Cl₂ (37 mg, 0.05 mmol) was added, the flask was purged with N₂ 3 times, and then the reaction solution was heated to reflux and reacted for 20 hours. LC-MS indicated the reaction was complete. The reaction solution was cooled to room temperature, filtered to remove salt impurities, and the filtrate was concentrated under reduced pressure to afford the crude product, which was separated to afford TDI01876B (10 mg, yellow solid, yield: 9.3%).

¹H NMR (400 MHz, DMSO-d₆) δ 12.90 (s, 1H), 9.66 (s, 1H), 8.54 (s, 1H), 8.40 (d, J=5.4 Hz, 1H), 8.22 (d, J=8.3 Hz, 1H), 8.16 (s, 1H), 8.07 (s, 1H), 7.92 (s, 1H), 7.82 (d, J=7.6 Hz, 2H), 7.76-7.60 (m, 4H), 7.21 (s, 1H), 6.69 (s, 2H), 3.66 (s, 3H). MS m/z (ESI): 433.1 [M+H].

The compound in following table 20 was prepared according to a method similar to that described in Example 55.

TABLE 20

| No. | Compound Structure | Compound Name | Starting material or regent different from that in Example 55 | Characterization Data |
|---|---|---|---|---|
| TDI01684 | 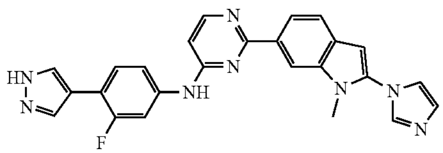 [SMILES: Cn1c(-n2ccnc2)cc2ccc(-c3nccc(Nc4ccc(-c5cn[nH]c5)c(F)c4)n3)cc21] | 2-(2-(1H-imidazol-1-yl)-1-methyl-1H-indol-6-yl)-N-(3-fluoro-4-(1H-pyrazol-4-yl)phenyl)pyrimidin-4-amine | (Reg-1-16) in step 4 of Example 55 was replaced with (Reg-1-39) | ¹H NMR (400 MHz, DMSO-d₆) δ 10.31 (s, 1H), 9.06 (s, 1H), 8.58 (s, 1H), 8.46 (d, J = 6.0 Hz, 1H), 8.18 (d, J = 8.2 Hz, 1H), 8.14-8.00 (m, 4H), 7.88-7.66 (m, 4H), 7.47 (d, J = 8.5 Hz, 1H), 6.91 (s, 1H), 6.82 (d, J = 5.8 Hz, 1H), 3.74 (s, 3H). MS m/z (ESI): 451.1 [M + H]. |

Example 56: preparation of (6-(4-((4-(1H-pyrazol-4-yl)phenyl)amino)pyrimidin-2-yl)-1-vinyl-1H-indol-2-yl)(3,3-difluoroazetidin-1-yl)methanone (TDI01923)

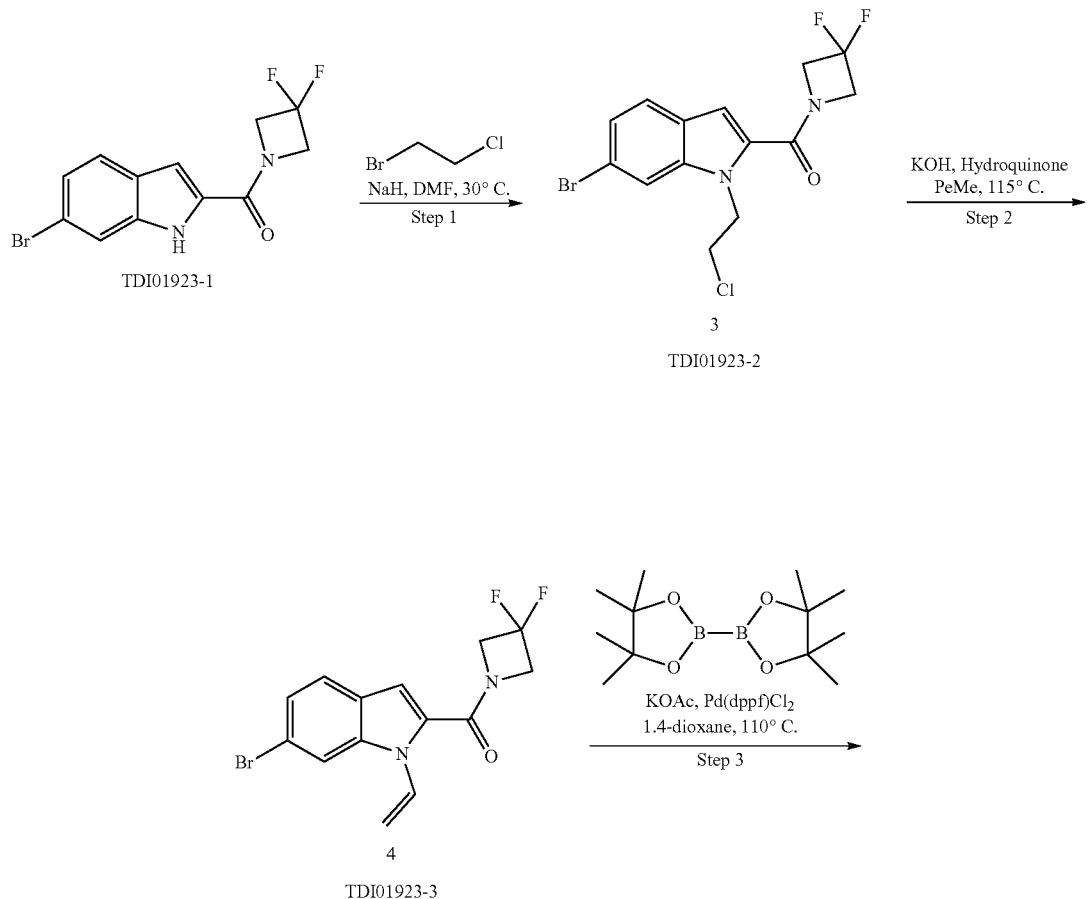

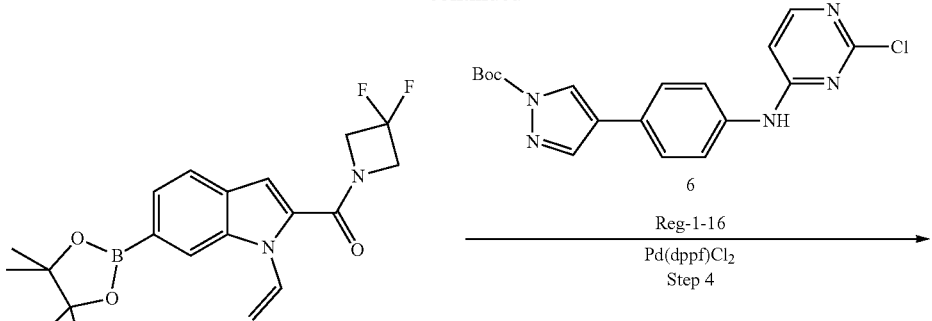

TDI01923-4

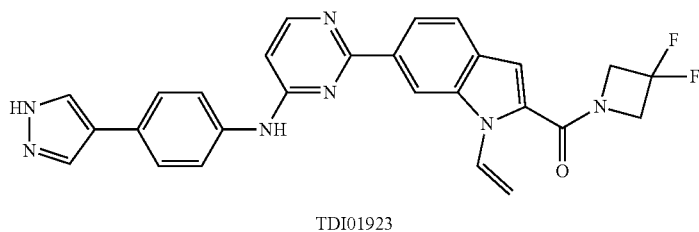

TDI01923

Starting compound TDI01923-1 was synthesized according to the method in step 1 of Example 46.

Step 1:

Compound TDI01923-1 (500 mg, 1.59 mmol) was dissolved in DMF (15 mL), and cooled to 0° C. in an ice-water bath under protection of $N_2$. NaH (60%, 96 mg, 2.39 mmol) was added portionwise, and 1-bromo-2-chloroethane (339 mg, 2.39 mmol) was added after the reaction was stirred for 15 minutes. The reaction was stirred at 30° C. for 16 hours. LC-MS indicated half completion of the reaction. The reaction solution was cooled to 0° C., added with water (45 mL), and then extracted with ethyl acetate (15 mL×3). The residue obtained after evaporation of the organic phase was purified by column chromatography (petroleum ether:ethyl acetate=5:1) to afford compound TDI01923-2 (280 mg, white solid, 47% yield).

$^1$H NMR (400 MHz, DMSO-$d_6$) δ 7.98 (s, 1H), 7.60 (d, J=8.5 Hz, 1H), 7.27 (dd, J=8.5, 1.1 Hz, 1H), 7.09 (s, 1H), 4.84 (t, J=6.0 Hz, 2H), 4.82 (s, 2H), 4.53 (s, 2H), 3.95 (t, J=6.0 Hz, 2H). MS m/z (ESI): 398.6, 400.4 [M+Na].

Step 2:

Compound TDI01923-2 (280 mg, 0.74 mmol), potassium hydroxide (376 mg, 6.7 mmol) and hydroquinone (2 mg, 0.0074 mmol) were dissolved in toluene (10 mL), the reaction was purged with nitrogen three times, and placed in an oil bath at 115° C. for 16 hours. LC-MS assay indicated the reaction was complete. The reaction solution was cooled to room temperature, concentrated, and the residue was purified by column chromatography (petroleum ether:ethyl acetate=10:1) to afford compound TDI01923-3 (70 mg, white solid, 28% yield).

MS m/z (ESI): 340.9, 342.9 [M+H].

Step 3:

Compound TDI01923-3 (70 mg, 0.21 mmol) and bis(pinacolato)diboron (63 mg, 0.25 mmol) were dissolved in 1,4-dioxane (10 mL), potassium acetate (62 mg, 0.63 mmol) and Pd(dppf)$Cl_2$ (31 mg, 0.042 mmol) were added, and the reaction was purged with nitrogen three times, and placed in an oil bath at 110° C. for 16 hours. LC-MS assay indicated the reaction was complete. The reaction solution was cooled to room temperature, filtered to remove the insolubles, and the filtrate was concentrated under reduced pressure. The residue was purified by column chromatography (petroleum ether:ethyl acetate=10:1 to 5:1), to afford compound TDI01923-4 (55 mg, white solid, 67% yield).

MS m/z (ESI): 389.0 [M+H].

Step 4:

Compound TDI01923-4 (55 mg, 0.14 mmol) and Reg-1-16 (58 mg, 0.16 mmol) were dissolved in 1,4-dioxane:water (5:0.5 mL), potassium carbonate (58 mg, 0.42 mmol) and Pd(dppf)$Cl_2$ (20 mg, 0.028 mmol) were added, the flask was purged with nitrogen three times, and the reaction solution was stirred at 110° C. for 16 hours. LC-MS indicated the reaction was complete, the reaction solution was cooled to room temperature, filtered to remove the insolubles, and the filtrate was rotary evaporated under vacuum to remove solvents. The residue was purified by preparative high pressure liquid chromatography to afford compound TDI01923 (5.7 mg, yellow solid, 8% yield).

$^1$H NMR (400 MHz, DMSO-$d_6$) δ 10.45 (s, 1H), 8.81 (s, 1H), 8.40 (d, J=6.4 Hz, 1H), 8.15 (d, J=8.4 Hz, 1H), 8.10 (s, 2H), 7.86 (d, J=8.4 Hz, 1H), 7.78 (d, J=7.8 Hz, 2H), 7.68 (d, J=8.4 Hz, 2H), 7.56 (d, J=7.0 Hz, 1H), 7.26 (s, 1H), 6.84 (d, J=6.4 Hz, 1H), 5.60 (d, J=16.0 Hz, 2H), 5.41 (d, J=8.8 Hz, 1H), 4.90 (s, 2H), 4.55 (s, 2H). MS m/z (ESI): 498.0 [M+H].

Example 57: preparation of (6-(4-(44-(1H-pyrazol-4-yl)phenyl)amino)pyrimidin-2-yl)-1-(2,2-difluoroethyl)-1H-indol-2-yl)(3,3-difluoroazetidin-1-yl)methanone (TDI01678)

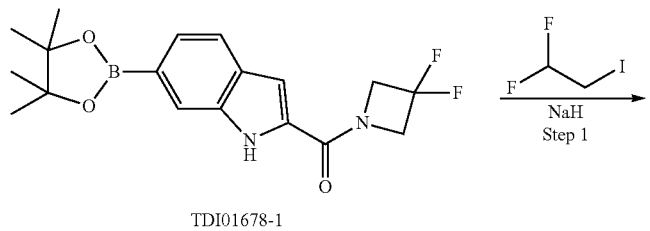

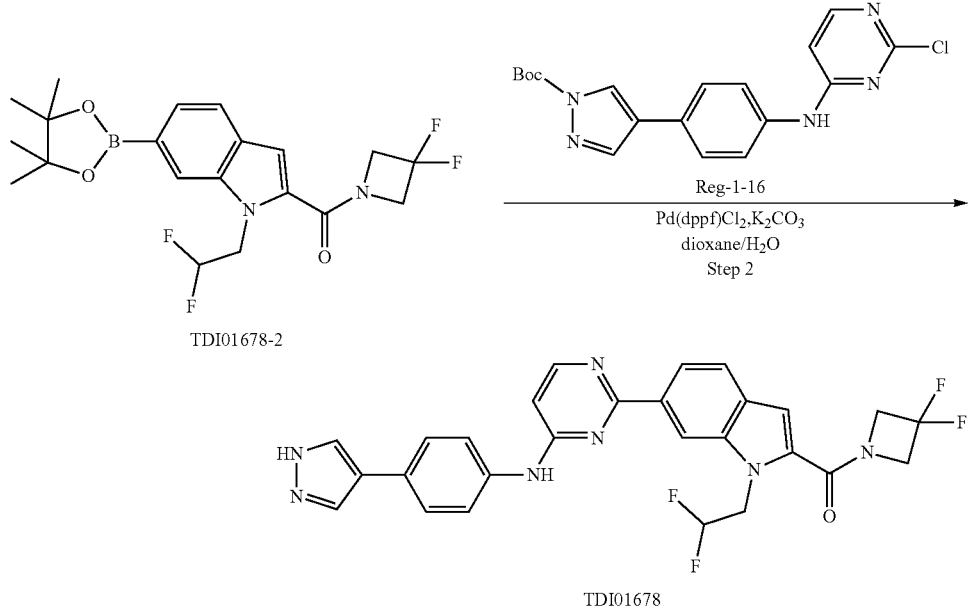

Compound TDI01678-1 in Example 57 was synthesized according to step 3 to step 4 of Example 2.

Step 1:

Compound TDI01678-1 (200 mg, 0.55 mmol) was dissolved in N,N-dimethylformamide (5 mL), sodium hydride (33 mg, 0.83 mmol) was added at 0° C., after being stirred for 30 min, 1,1-difluoro-2-iodoethane (159 mg, 0.83 mmol) was added, and the reaction solution was stirred at room temperature for 16 hours. LC-MS indicated there was product formation. The reaction solution was rotary evaporated under vacuum to remove the reaction solvent, and the residue was purified by column chromatography (petroleum ether:ethyl acetate=4:1) to afford compound TDI01678-2 (105 mg, 44.8% yield).

MS m/z (ESI): 426.9 [M+H].

Step 2:

Compound TDI01678-2 (105 mg, 0.246 mmol) and Reg-1-16 (92 mg, 0.246 mmol) were dissolved in 1,4-dioxane:water (10:1 mL), potassium carbonate (102 mg, 0.738 mmol) was added, and the flask was purged with nitrogen three times. Pd(dppf)Cl$_2$ (54 mg, 0.074 mmol) was added, the flask was purged with nitrogen three times, and the reaction solution was stirred at 110° C. for 16 hours. LC-MS indicated the reaction was complete. The reaction solution was cooled to room temperature, and the reaction solvent was removed through rotary evaporation under vacuum. The residue was purified by preparative liquid chromatography to afford compound TDI01678 (7 mg).

$^1$H NMR (400 MHz, DMSO-d$_6$) δ 10.37 (s, 1H), 8.64 (s, 1H), 8.41 (d, J=6.2 Hz, 1H), 8.13 (d, J=8.3 Hz, 1H), 8.04 (s, 2H), 7.89-7.79 (m, 3H), 7.68 (d, J=8.1 Hz, 2H), 7.25 (s, 1H), 6.83 (d, J=5.9 Hz, 1H), 6.66-6.38 (m, 1H), 5.01 (dd, J=36.5, 21.2 Hz, 4H), 4.57 (s, 2H). MS m/z (ESI): 535.5 [M+H].

Example 58: preparation of 5-(4-(44-(1H-pyrazol-4-yl)phenyl)amino)-5-fluoropyrimidin-2-yl)-2-((3,3-difluorocyclobutyl)methyl)isoindolin-1-one (TDI01593)

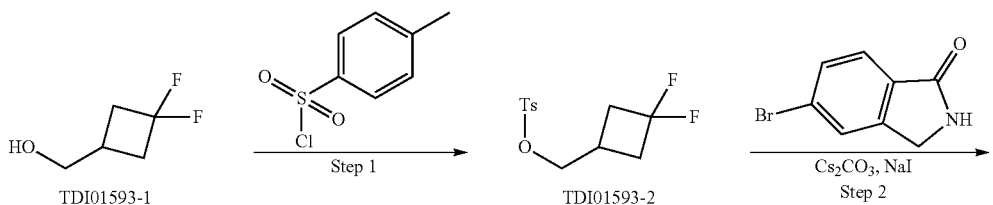

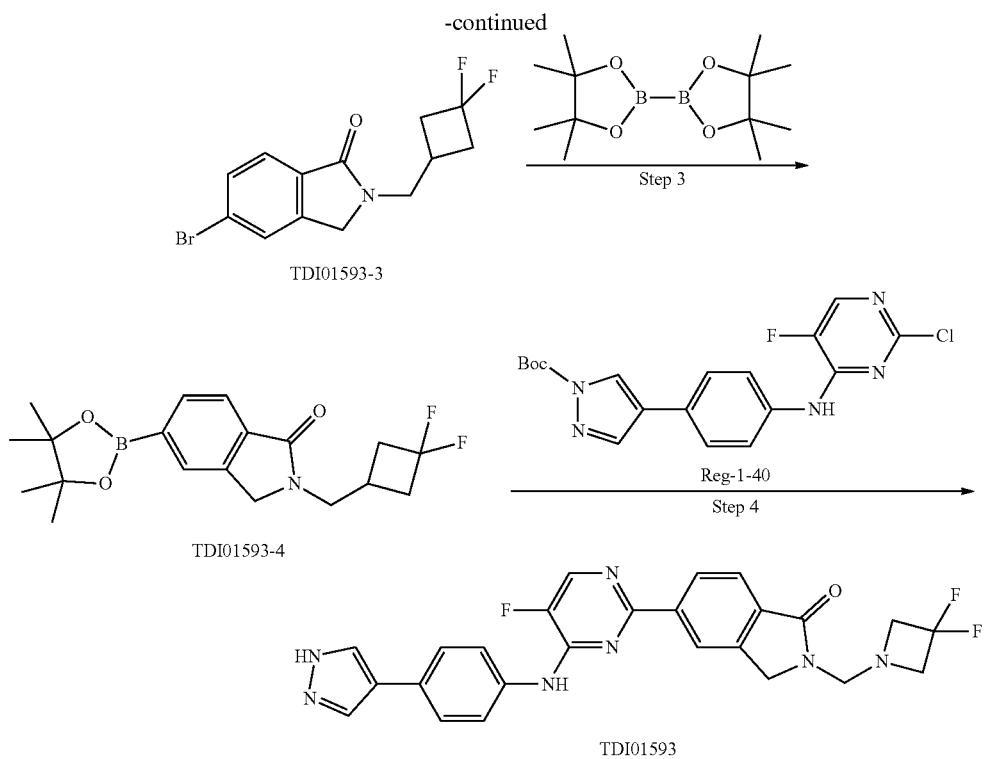

Step 1:

Compound TDI01593-1 (5 g, 40.95 mmol) and 4-toluene sulfonyl chloride (9.37 g, 49.14 mmol) were dissolved in dichloromethane (150 mL), 4-dimethylaminopyridine (500 mg, 4.095 mmol) and triethylamine (12.4 g, 123.0 mmol) were added, and the reaction solution was stirred at room temperature for 16 hours. LC-MS indicated the reaction was complete, the reaction solution was rotary evaporated under vacuum to remove the reaction solvent, and the residue was purified by column chromatography (petroleum ether:ethyl acetate=4:1) to afford compound TDI01593-2 (11.2 g, 99% yield).

$^1$H NMR (400 MHz, DMSO-d$_6$) δ 7.81 (d, J=7.9 Hz, 2H), 7.50 (d, J=7.9 Hz, 2H), 4.10 (d, J=6.6 Hz, 2H), 2.67-2.56 (m, 2H), 2.43 (s, 4H), 2.30 (dd, J=14.0, 6.3 Hz, 2H). MS m/z (ESI): 299.0 [M+Na].

Step 2:

Compound TDI01593-2 (6.5 g, 23.6 mmol) and 5-bromoisoindolin-1-one(2.0 g, 9.43 mmol) were dissolved in acetonitrile (100 mL), cesium carbonate (7.7 mg, 23.6 mmol) and sodium iodide (3.54 g, 23.6 mmol) were added, and the reaction solution was stirred at 100° C. for 16 hours. LC-MS assay indicated there was product formation. The reaction solution was subjected to vacuum filtration, the filtrate was rotary evaporated under vacuum to remove solvents, and the residue was purified by column chromatography (petroleum ether:ethyl acetate=4:1 to 1:1) to afford compound TDI01593-3 (800 mg, 26.8% yield).

$^1$H NMR (400 MHz, DMSO-d$_6$) δ7.87 (s, 1H), 7.69 (d, J=8.1 Hz, 1H), 7.62 (d, J=8.1 Hz, 1H), 4.50 (s, 2H), 3.65 (d, J=7.3 Hz, 2H), 2.74-2.64 (m, 2H), 2.48-2.30 (m, 3H). MS m/z (ESI): 315.7 [M+H].

Step 3:

Compound TDI01593-3 (600 mg, 1.9 mmol) and bis(pinacolato)diboron (579 mg, 2.28 mmol) were dissolved in 1,4-dioxane (20 mL), potassium acetate (559 mg, 5.7 mmol) was added, and the flask was purged with nitrogen three times. Pd(dppf)Cl$_2$ (278 mg, 0.38 mmol) was added, the flask was purged with nitrogen three times, and the reaction solution was stirred at 100° C. for 16 hours. LC-MS indicated the reaction was complete. The reaction solution was cooled to room temperature, and the reaction solvent was removed through rotary evaporation under vacuum. The residue was purified by column chromatography (petroleum ether:ethyl acetate=4:1) to afford compound TDI01593-4 (620 mg, 89.8% yield).

MS m/z (ESI): 364.1 [M+H].

Step 4:

Compound TDI01593-4 (200 mg, 0.55 mmol) and Reg-1-40 (215 mg, 0.55 mmol) were dissolved in 1,4-dioxane:water (10:1 mL), potassium carbonate (228 mg, 1.65 mmol) was added, and the flask was purged with nitrogen three times. Pd(dppf)Cl$_2$ (121 mg, 0.165 mmol) was added, the flask was purged with nitrogen three times, and the reaction solution was stirred at 110° C. for 16 hours. LC-MS indicated the reaction was complete. The reaction solution was cooled to room temperature, and the reaction solvent was removed through rotary evaporation under vacuum. The residue was purified by column chromatography and preparative liquid chromatography, to afford compound TDI01593 (52 mg).

$^1$H NMR (400 MHz, DMSO-d$_6$) δ 9.75 (s, 1H), 8.53 (d, J=3.1 Hz, 1H), 8.44 (s, 1H), 8.40 (d, J=7.7 Hz, 1H), 8.07 (s, 2H), 7.87 (d, J=8.2 Hz, 2H), 7.79 (d, J=8.0 Hz, 1H), 7.67 (d, J=8.2 Hz, 2H), 4.60 (s, 2H), 3.69 (d, J=6.9 Hz, 3H), 2.68 (s, 4H). MS m/z (ESI): 491.1 [M+H].

The compound in following table 21 was prepared according to a method similar to that described in Example 58.

TABLE 21

| No. | Compound Structure | Compound Name | Starting material or regent different from that in Example 58 | Characterization Data |
|---|---|---|---|---|
| TDI01590 | 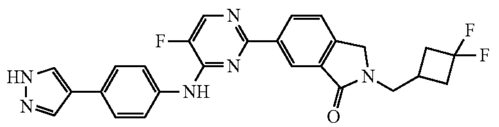 [SMILES: O=C1c2cc(-c3ncc(F)c(Nc4ccc(-c5cn[nH]c5)cc4)n3)ccc2CN1CC1CC(F)(F)C1] | 6-(4-((4-(1H-pyrazol-4-yl)phenyl)amino)-5-fluoro-pyrimidin-2-yl)-2-((3,3-difluoro-cyclobutyl)methyl)isoindolin-1-one | in step 2 of Example 58 was replaced with | $^1$H NMR (400 MHz, DMSO-$d_6$) δ 9.73 (s, 1H), 8.56-8.46 (m, 3H), 8.08 (s, 2H), 7.86 (d, J = 8.3 Hz, 2H), 7.72 (d, J = 7.8 Hz, 1H), 7.67 (d, J = 8.5 Hz, 2H), 4.58 (s, 2H), 3.69 (d, J = 6.8 Hz, 2H), 2.70 (d, J = 14.4 Hz, 3H), 2.42 (s, 2H). MS m/z (ESI): 491.1 [M + H]. |

Biological Assay

The kinase IC$_{50}$ was determined by a commercialized CISBIO kinase detection kit, HTRF KinEASE-STK S2 kit (62ST2PEC). ROCK2 (01-119) employed in the reaction was purchased from Carna Biosciences.

Before the assay, the following working solutions as needed were formulated with corresponding reagents according to the instruction of the kinase detection kit: 1×kinase buffer, 5×STK-S2 substrate working solution (1.5 µM) and 5×ATP working solution (1.5 µM), 5×ROCK2 kinase working solution, 4×Streptavidin-XL665 working solution, and 4×STK-Ab-Cryptate 2 detection solution. Then the assay was performed according to the following procedure.

A solution of a compound at a concentration of 10000 nM was prepared with the 1×kinase buffer containing 2.5% DMSO. Gradient dilution of the solution of the compound was performed with the kinase buffer containing DMSO, so as to obtain solutions of a test compound at 9 different concentrations. In addition to wells of test compounds, a positive well (containing all the reagents except the compound) and a negative well (containing all the reagents except the test compound and kinase) were set. Except for the control wells (positive and negative wells), a solution of a test compound (4 µL) was added to each of the reaction wells, and a solution of 2.5% DMSO was added to the control wells. Then the substrate (2 µM, i.e., 2 µL. 5×STK-S2 substrate working solution) was added to each of the reaction wells. The 5×ROCK2 kinase working solution (2 µL, containing 1.4 ng ROCK2 kinase) was added to each of the reaction wells except for the negative well, the volume of which was made up with the 1×kinase buffer (2 µL). The 5×ATP working solution (2 µL) was added to each of the reaction wells, and the mixtures were incubated at room temperature for 2 hours. After the kinase reaction was complete, the 4×Streptavidin-XL665 working solution was added to each of the reaction wells, the solutions were mixed, followed by immediate addition of the 4×STK-Ab-Cryptate 2 detection solution (5 µL), and the mixtures were incubated at room temperature for 1 hour. The fluorescence signal was read on ENVISION (Perkinelmer) (excitation wavelength: 320 nm, and emission wavelength: 665 nm and 615 nm). The inhibitory rate in each well was calculated based on the fluorescence intensity value: ER (Emission Ratio)=(fluorescence intensity at 665 nm/fluorescence intensity at 615 nm); inhibitory rate=(ER$_{positive}$−ER$_{test\ compound}$)/(ER$_{positive}$−ER$_{negative}$)*100%. Curves were plotted and fitted to obtain the median inhibitory concentration (IC$_{50}$) of each teat compound with the PRISM 5.0 software. IC$_{50}$ value of each compound is as shown in the following table.

| Compound No. | ROCK2 IC$_{50}$ (nM) |
|---|---|
| TDI01102 | 110 |
| TDI01103 | 167 |
| TDI01104 | 71 |
| TDI01106 | 112 |
| TDI01108 | 22 |
| TDI01109 | 447 |
| TDI01110 | 422 |
| TDI01111 | 100 |
| TDI01112 | 185 |
| TDI01113 | 42 |
| TDI01114 | 157 |
| TDI01116 | 236 |
| TDI01121 | 470 |
| TDI01122 | 219 |
| TDI01127 | 100 |
| TDI01128 | 145 |
| TDI01130 | 33 |
| TDI01131 | 101 |
| TDI01134 | 62 |
| TDI01135 | 123 |
| TDI01136 | 66 |
| TDI01140 | 109 |
| TDI01141 | 73 |
| TDI01142 | 225 |
| TDI01143 | 72 |
| TDI01149 | 100 |
| TDI01151 | 45 |
| TDI01152 | 88 |
| TDI01153 | 16 |
| TDI01156 | 25 |
| TDI01160 | 54 |
| TDI01161 | 210 |
| TDI01164 | 438 |
| TDI01167 | 223 |
| TDI01171 | 63 |
| TDI01175 | 197 |
| TDI01176 | 28 |
| TDI01177 | 71 |
| TDI01178 | 168 |
| TDI01180 | 37 |

| Compound No. | ROCK2 IC$_{50}$ (nM) |
|---|---|
| TDI01181 | 92 |
| TDI01182 | 46 |
| TDI01188 | 123 |
| TDI01191 | 225 |
| TDI01199 | 30 |
| TDI01200 | 23 |
| TDI01201 | 48 |
| TDI01213 | 255 |
| TDI01215 | 382 |
| TDI01221 | 91 |
| TDI01230 | 109 |
| TDI01232 | 295 |
| TDI01236 | 135 |
| TDI01237 | 171 |
| TDI01247 | 134 |
| TDI01248 | 500 |
| TDI01250 | 208 |
| TDI01251 | 101 |
| TDI01258 | 62 |
| TDI01276 | 113 |
| TDI01280 | 94 |
| TDI01285 | 116 |
| TDI01289 | 72 |
| TDI01290 | 46 |
| TDI01291 | 32 |
| TDI01292 | 242 |
| TDI01294 | 352 |
| TDI01296 | 211 |
| TDI01299 | 463 |
| TDI01311 | 465 |
| TDI01312 | 73 |
| TDI01315 | 126 |
| TDI01316 | 87 |
| TDI01317 | 112 |
| TDI01318 | 18 |
| TDI01319 | 258 |
| TDI01320 | 410 |
| TDI01324 | 101 |
| TDI01327 | 472 |
| TDI01330 | 474 |
| TDI01331 | 260 |
| TDI01332 | 257 |
| TDI01337 | 121 |
| TDI01338 | 115 |
| TDI01339 | 147 |
| TDI01343 | 436 |
| TDI01344 | 97 |
| TDI01344-2A | 107 |
| TDI01345 | 333 |
| TDI01347 | 356 |
| TDI01353 | 307 |
| TDI01354 | 254 |
| TDI01355 | 54 |
| TDI01360 | 26 |
| TDI01363 | 104 |
| TDI01366 | 260 |
| TDI01368 | 412 |
| TDI01369 | 266 |
| TDI01370 | 109 |
| TDI01372 | 123 |
| TDI01374 | 64 |
| TDI01379 | 411 |
| TDI01381 | 341 |
| TDI01385 | 107 |
| TDI01390 | 18 |
| TDI01392 | 172 |
| TDI01393 | 258 |
| TDI01394 | 28 |
| TDI01397 | 120 |
| TDI01398 | 16 |
| TDI01400 | 240 |
| TDI01403 | 110 |
| TDI01404 | 35 |
| TDI01405 | 160 |
| TDI01406 | 285 |
| TDI01408 | 400 |
| TDI01411 | 258 |
| TDI01415 | 262 |
| TDI01418 | 272 |
| TDI01419 | 385 |
| TDI01420 | 477 |
| TDI01421 | 289 |
| TDI01423 | 264 |
| TDI01424 | 138 |
| TDI01425 | 119 |
| TDI01426 | 365 |
| TDI01428 | 69 |
| TDI01429 | 99 |
| TDI01430 | 116 |
| TDI01431 | 203 |
| TDI01433 | 13 |
| TDI01434 | 34 |
| TDI01435 | 28 |
| TDI01437 | 247 |
| TDI01438 | 402 |
| TDI01439 | 203 |
| TDI01441 | 181 |
| TDI01442 | 305 |
| TDI01444 | 32 |
| TDI01445 | 64 |
| TDI01448 | 13 |
| TDI01450 | 453 |
| TDI01455 | 29 |
| TDI01456 | 15 |
| TDI01457 | 395 |
| TDI01461 | 140 |
| TDI01462 | 240 |
| TDI01463 | 11 |
| TDI01464 | 175 |
| TDI01465 | 398 |
| TDI01467 | 75 |
| TDI01470 | 33 |
| TDI01472 | 174 |
| TDI01473 | 18 |
| TDI01477 | 47 |
| TDI01485 | 276 |
| TDI01486 | 185 |
| TDI01487 | 193 |
| TDI01490 | 81 |
| TDI01497 | 319 |
| TDI01498 | 415 |
| TDI01500 | 13 |
| TDI01505 | 209 |
| TDI01506 | 295 |
| TDI01507 | 113 |
| TDI01508 | 159 |
| TDI01512 | 22 |
| TDI01513 | 269 |
| TDI01514 | 49 |
| TDI01515 | 110 |
| TDI01516 | 322 |
| TDI01517 | 92 |
| TDI01518 | 78 |
| TDI01519 | 102 |
| TDI01520 | 15 |
| TDI01523 | 86 |
| TDI01524 | 30 |
| TDI01525 | 335 |
| TDI01532 | 49 |
| TDI01534 | 114 |
| TDI01536 | 105 |
| TDI01538 | 198 |
| TDI01546 | 26 |
| TDI01550 | 21 |
| TDI01551 | 31 |
| TDI01552 | 51 |
| TDI01555 | 140 |
| TDI01557B | 49 |
| TDI01559 | 170 |
| TDI01560 | 83 |
| TDI01561 | 205 |
| TDI01562 | 23 |
| TDI01564 | 29 |
| TDI01565 | 57 |

| Compound No. | ROCK2 IC$_{50}$ (nM) |
|---|---|
| TDI01567 | 65 |
| TDI01567C | 29 |
| TDI01570 | 22 |
| TDI01575 | 169 |
| TDI01578 | 129 |
| TDI01580 | 19 |
| TDI01581 | 28 |
| TDI01582 | 24 |
| TDI01584 | 60 |
| TDI01585 | 93 |
| TDI01586 | 162 |
| TDI01587 | 25 |
| TDI01589 | 39 |
| TDI01590 | 266 |
| TDI01596 | 275 |
| TDI01596B | 130 |
| TDI01597B | 123 |
| TDI01598 | 216 |
| TDI01609 | 69 |
| TDI01613 | 27 |
| TDI01617 | 255 |
| TDI01618A | 129 |
| TDI01621 | 219 |
| TDI01628 | 28 |
| TDI01633 | 27 |
| TDI01634 | 16 |
| TDI01655 | 331 |
| TDI01656 | 442 |
| TDI01658 | 477 |
| TDI01668 | 42 |
| TDI01675 | 84 |
| TDI01676 | 242 |
| TDI01678 | 159 |
| TDI01681 | 238 |
| TDI01682 | 360 |
| TDI01683 | 360 |
| TDI01684 | 171 |
| TDI01690 | 427 |
| TDI01691 | 6 |
| TDI01801 | 68 |
| TDI01813 | 90 |
| TDI01814 | 18 |
| TDI01816 | 111 |
| TDI01823 | 336 |
| TDI01826 | 75 |
| TDI01829B | 82 |
| TDI01829C | 97 |
| TDI01832 | 167 |
| TDI01840 | 5 |
| TDI01841 | 11 |
| TDI01842 | 120 |
| TDI01842B | 61 |
| TDI01844 | 370 |
| TDI01847 | 14 |
| TDI01847B | 26 |
| TDI01848 | 90 |
| TDI01849 | 132 |
| TDI01849B | 210 |
| TDI01851 | 15 |
| TDI01852 | 482 |
| TDI01853 | 275 |
| TDI01855 | 147 |
| TDI01856 | 141 |
| TDI01861 | 41 |
| TDI01862 | 382 |
| TDI01864 | 30 |
| TDI01865 | 400 |
| TDI01868 | 32 |
| TDI01870 | 46 |
| TDI01876B | 240 |
| TDI01878 | 9 |
| TDI01881 | 161 |
| TDI01882 | 8 |
| TDI01884 | 26 |
| TDI01898 | 350 |
| TDI01901 | 387 |
| TDI01903 | 118 |
| TDI01905 | 9 |
| TDI01906 | 49 |
| TDI01908 | 27 |
| TDI01910 | 6 |
| TDI01912 | 44 |
| TDI01914 | 23 |
| TDI01915 | 18 |
| TDI01916 | 80 |
| TDI01918 | 165 |
| TDI01919 | 62 |
| TDI01920 | 200 |
| TDI01921 | 355 |
| TDI01923 | 50 |
| TDI01932 | 12 |
| TDI01936 | 27 |
| TDI01937B | 39 |
| TDI01940 | 147 |
| TDI01943 | 34 |
| TDI01944 | 44 |
| TDI01945 | 76 |
| TDI01947 | 88 |
| TDI01948 | 103 |
| TDI01949 | 59 |
| TDI01950 | 19 |
| TDI01951 | 27 |
| TDI01952 | 10 |
| TDI01953 | 4 |
| TDI01954 | 14 |
| TDI01955 | 33 |
| TDI01957 | 214 |
| TDI01958 | 214 |
| TDI01959 | 131 |
| TDI01960 | 50 |
| TDI01962 | 40 |
| TDI01965 | 393 |
| TDI01966 | 313 |
| TDI01967 | 45 |
| TDI01968A | 296 |
| TDI01973 | 52 |
| TDI01974 | 186 |
| TDI01976 | 18 |
| TDI01978 | 45 |
| TDI01979 | 137 |
| TDI01989 | 385 |
| TDI01991 | 39 |
| TDI01999 | 10 |

According to a biological test method similar to the above, the IC$_{50}$ values of the compounds on ROCK1 were tested. The results are shown in the following table.

| Compound No. | ROCK1 IC$_{50}$ (nM) |
|---|---|
| TDI01103 | 2055 |
| TDI01104 | 870 |
| TDI01109 | >10000 |
| TDI01110 | >10000 |
| TDI01111 | 1407 |
| TDI01113 | 554 |
| TDI01116 | >10000 |
| TDI01122 | 3267 |
| TDI01134 | 1372 |
| TDI01135 | 3000 |
| TDI01136 | 827 |
| TDI01141 | 839 |
| TDI01143 | 1484 |
| TDI01149 | 1323 |
| TDI01151 | 892 |
| TDI01152 | >10000 |
| TDI01153 | 2720 |
| TDI01156 | 1994 |
| TDI01160 | 2236 |
| TDI01161 | >10000 |
| TDI01164 | >10000 |
| TDI01167 | >10000 |

| Compound No. | ROCK1 IC$_{50}$ (nM) |
|---|---|
| TDI01175 | 5189 |
| TDI01176 | 521 |
| TDI01177 | 894 |
| TDI01180 | 2776 |
| TDI01181 | 947 |
| TDI01182 | 712 |
| TDI01188 | 1279 |
| TDI01191 | 2526 |
| TDI01199 | 1098 |
| TDI01200 | 559 |
| TDI01201 | 6916 |
| TDI01213 | >10000 |
| TDI01230 | 1503 |
| TDI01232 | >10000 |
| TDI01236 | >10000 |
| TDI01237 | >10000 |
| TDI01247 | >10000 |
| TDI01250 | >10000 |
| TDI01251 | >10000 |
| TDI01276 | >10000 |
| TDI01280 | 1023 |
| TDI01289 | 980 |
| TDI01290 | >10000 |
| TDI01291 | 573 |
| TDI01292 | 4839 |
| TDI01294 | >10000 |
| TDI01296 | 2868 |
| TDI01311 | >10000 |
| TDI01312 | 1843 |
| TDI01315 | 2150 |
| TDI01316 | 999 |
| TDI01318 | 274 |
| TDI01319 | >10000 |
| TDI01324 | 1741 |
| TDI01330 | 7934 |
| TDI01331 | >10000 |
| TDI01332 | 6272 |
| TDI01337 | 2760 |
| TDI01338 | 1802 |
| TDI01343 | 7107 |
| TDI01344-2A | 4208 |
| TDI01345 | 3909 |
| TDI01347 | 5584 |
| TDI01354 | >10000 |
| TDI01355 | >10000 |
| TDI01360 | 1470 |
| TDI01363 | >10000 |
| TDI01366 | >10000 |
| TDI01368 | >10000 |
| TDI01369 | 6792 |
| TDI01370 | 1491 |
| TDI01372 | >10000 |
| TDI01374 | >10000 |
| TDI01379 | >10000 |
| TDI01381 | 4114 |
| TDI01390 | 456 |
| TDI01392 | >10000 |
| TDI01393 | >10000 |
| TDI01394 | >10000 |
| TDI01397 | 5999 |
| TDI01398 | >10000 |
| TDI01403 | 3000 |
| TDI01404 | 1522 |
| TDI01405 | 4062 |
| TDI01408 | 5629 |
| TDI01411 | >10000 |
| TDI01415 | 3715 |
| TDI01418 | 5384 |
| TDI01419 | >10000 |
| TDI01420 | 9294 |
| TDI01421 | 5942 |
| TDI01423 | >10000 |
| TDI01424 | 4975 |
| TDI01425 | 2945 |
| TDI01426 | >10000 |
| TDI01428 | >10000 |
| TDI01429 | >10000 |
| TDI01430 | >10000 |
| TDI01431 | 4343 |
| TDI01433 | 1969 |
| TDI01434 | >10000 |
| TDI01435 | 1225 |
| TDI01437 | >10000 |
| TDI01438 | >10000 |
| TDI01439 | >10000 |
| TDI01441 | 6068 |
| TDI01442 | >10000 |
| TDI01444 | 8258 |
| TDI01445 | 3000 |
| TDI01448 | 3000 |
| TDI01450 | >10000 |
| TDI01455 | >10000 |
| TDI01456 | >10000 |
| TDI01457 | 4892 |
| TDI01461 | 4526 |
| TDI01462 | 3589 |
| TDI01463 | >10000 |
| TDI01464 | 2283 |
| TDI01465 | >10000 |
| TDI01467 | >10000 |
| TDI01470 | >10000 |
| TDI01472 | >10000 |
| TDI01473 | 592 |
| TDI01477 | 1132 |
| TDI01485 | 3993 |
| TDI01486 | 2997 |
| TDI01487 | 5044 |
| TDI01490 | 2254 |
| TDI01497 | >10000 |
| TDI01498 | >10000 |
| TDI01500 | >10000 |
| TDI01505 | 5672 |
| TDI01506 | 7296 |
| TDI01507 | 6837 |
| TDI01508 | >10000 |
| TDI01512 | 3629 |
| TDI01513 | 7418 |
| TDI01514 | 2734 |
| TDI01515 | 6855 |
| TDI01517 | >10000 |
| TDI01518 | 3033 |
| TDI01519 | 5239 |
| TDI01520 | >10000 |
| TDI01523 | 1889 |
| TDI01524 | 1416 |
| TDI01525 | >10000 |
| TDI01532 | >10000 |
| TDI01534 | >10000 |
| TDI01536 | >10000 |
| TDI01538 | 4926 |
| TDI01546 | 1550 |
| TDI01550 | >10000 |
| TDI01551 | 1728 |
| TDI01552 | 2946 |
| TDI01555 | >10000 |
| TDI01557B | >10000 |
| TDI01559 | >10000 |
| TDI01560 | >10000 |
| TDI01561 | >10000 |
| TDI01562 | >10000 |
| TDI01564 | >10000 |
| TDI01565 | >10000 |
| TDI01567 | >10000 |
| TDI01567C | >10000 |
| TDI01570 | >10000 |
| TDI01575 | >10000 |
| TDI01578 | >10000 |
| TDI01580 | 3292 |
| TDI01581 | >10000 |
| TDI01582 | >10000 |
| TDI01584 | >10000 |
| TDI01585 | >10000 |
| TDI01586 | >10000 |
| TDI01587 | >10000 |

-continued

| Compound No. | ROCK1 IC$_{50}$ (nM) |
|---|---|
| TDI01589 | >10000 |
| TDI01590 | >10000 |
| TDI01596 | >10000 |
| TDI01596B | >10000 |
| TDI01597B | >10000 |
| TDI01598 | >10000 |
| TDI01609 | >10000 |
| TDI01613 | >10000 |
| TDI01617 | >10000 |
| TDI01618A | >10000 |
| TDI01621 | >10000 |
| TDI01628 | >10000 |
| TDI01633 | >10000 |
| TDI01634 | 2038 |
| TDI01655 | >10000 |
| TDI01656 | >10000 |
| TDI01658 | >10000 |
| TDI01668 | >10000 |
| TDI01675 | >10000 |
| TDI01676 | >10000 |
| TDI01678 | >10000 |
| TDI01681 | >10000 |
| TDI01683 | >10000 |
| TDI01690 | >10000 |
| TDI01691 | 159 |
| TDI01813 | >10000 |
| TDI01816 | 6011 |
| TDI01823 | >10000 |
| TDI01826 | >10000 |
| TDI01829B | >10000 |
| TDI01829C | >10000 |
| TDI01832 | >10000 |
| TDI01840 | 89 |
| TDI01841 | 1000 |
| TDI01842 | 3000 |
| TDI01842B | 2771 |
| TDI01844 | >10000 |
| TDI01847B | 3380 |
| TDI01851 | >10000 |
| TDI01852 | >10000 |
| TDI01853 | 2826 |
| TDI01855 | 5424 |
| TDI01856 | 2036 |
| TDI01861 | >10000 |
| TDI01862 | >10000 |
| TDI01864 | 3000 |
| TDI01868 | >10000 |
| TDI01870 | >10000 |
| TDI01876B | >10000 |
| TDI01881 | >10000 |
| TDI01882 | 139 |
| TDI01884 | >10000 |
| TDI01898 | >10000 |
| TDI01903 | 5578 |
| TDI01905 | 2300 |
| TDI01906 | >10000 |
| TDI01908 | >10000 |
| TDI01910 | >10000 |
| TDI01912 | >10000 |
| TDI01915 | >10000 |
| TDI01916 | >10000 |
| TDI01918 | >10000 |
| TDI01919 | 4065 |
| TDI01920 | >10000 |
| TDI01921 | >10000 |
| TDI01923 | >10000 |
| TDI01932 | >10000 |
| TDI01936 | >10000 |
| TDI01937B | >10000 |
| TDI01940 | >10000 |
| TDI01943 | >10000 |
| TDI01944 | >10000 |
| TDI01945 | >10000 |
| TDI01947 | >10000 |
| TDI01948 | >10000 |
| TDI01949 | >10000 |
| TDI01950 | >10000 |
| TDI01951 | >10000 |
| TDI01952 | >10000 |
| TDI01953 | >10000 |
| TDI01954 | >10000 |
| TDI01955 | >10000 |
| TDI01957 | >10000 |
| TDI01958 | >10000 |
| TDI01959 | >10000 |
| TDI01960 | >10000 |
| TDI01962 | >10000 |
| TDI01965 | >10000 |
| TDI01966 | >10000 |
| TDI01967 | >10000 |
| TDI01968A | >10000 |
| TDI01973 | >10000 |
| TDI01974 | >10000 |
| TDI01976 | >10000 |
| TDI01978 | >10000 |
| TDI01979 | >10000 |
| TDI01989 | >10000 |
| TDI01991 | >10000 |
| TDI01999 | >10000 |

According to the above data, the IC$_{50}$ values of the tested compounds on ROCK2 are significantly lower than those on ROCK1, indicating the compound of the present invention has good selectivity towards ROCK2.

Various modifications of the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A compound or a pharmaceutically acceptable salt, ester, stereoisomer, polymorph, solvate, N-oxide, or isotopically labeled compound thereof, wherein the compound has the structure of formula (XVII):

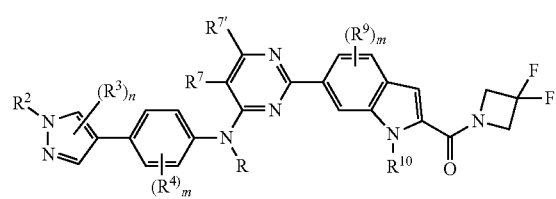

(XVII)

wherein:
R is selected from the group consisting of H and C$_{1-6}$ alkyl;
R$^2$ is selected from the group consisting of H and C$_{1-6}$ alkyl;
R$^3$, R$^4$, R$^7$, and R$^{7'}$, at each occurrence, are each independently selected from the group consisting of H, halogen, —NH$_2$, —OH, C$_{1-6}$ alkyl and —OR$^5$;
R$^9$, at each occurrence, is each independently selected from the group consisting of H, halogen, C$_{1-6}$ alkyl, C$_{2-6}$ alkenyl, C$_{3-10}$ cyclic hydrocarbyl, 3- to 10-membered heterocyclyl, C$_{6-10}$ aryl, 5- to 14-membered heteroaryl, C$_{6-12}$ aralkyl, —C(=O)R$^5$ and —C$_{1-6}$ alkylene-O(P=O)(OH)$_2$;
R$^{10}$ is selected from the group consisting of halogen, C$_{1-6}$ alkyl, C$_{2-6}$ alkenyl, C$_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)R⁵ and —$C_{1-6}$ alkylene-O(P=O) (OH)₂;

the above alkyl, alkenyl, cyclic hydrocarbyl, heterocyclyl, aryl, heteroaryl, heteroaromatic ring and aralkyl, at each occurrence, are each optionally substituted with one or more substituents independently selected from the group consisting of halogen, $C_{1-6}$ alkyl and —OR⁵;

R⁵, at each occurrence, is each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3; and n is an integer of 0, 1 or 2.

2. The compound according to claim 1, or a pharmaceutically acceptable salt, ester, stereoisomer, polymorph, solvate, N-oxide, or isotopically labeled compound thereof, wherein the compound is selected from the group consisting of:

| No. | Structural Formula |
|---|---|
| TDI01470 | |
| TDI01903 | |
| TDI01904 | |
| TDI01905 | |
| TDI01907 | |
| TDI01910 | |

| No. | Structural Formula |
|---|---|
| TDI01915 | 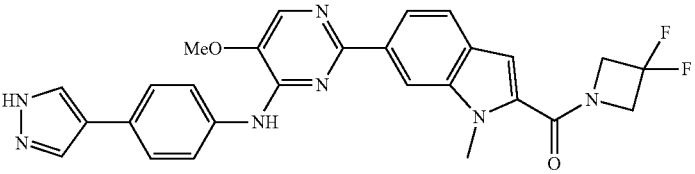 [SMILES: COc1cnc(-c2ccc3cc(C(=O)N4CC(F)(F)C4)n(C)c3c2)nc1Nc1ccc(-c2cn[nH]c2)cc1] |
| TDI01917 | 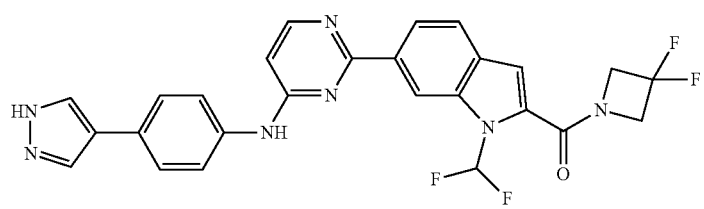 [SMILES: O=C(c1cc2ccc(-c3nccc(Nc4ccc(-c5cn[nH]c5)cc4)n3)cc2n1C(F)F)N1CC(F)(F)C1] |
| TDI01920 | 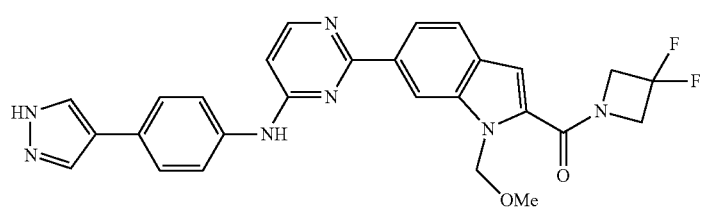 [SMILES: COCn1c(C(=O)N2CC(F)(F)C2)cc2ccc(-c3nccc(Nc4ccc(-c5cn[nH]c5)cc4)n3)cc21] |
| TDI01921 | 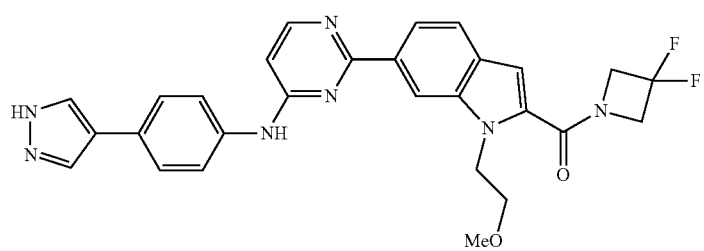 [SMILES: COCCn1c(C(=O)N2CC(F)(F)C2)cc2ccc(-c3nccc(Nc4ccc(-c5cn[nH]c5)cc4)n3)cc21] |
| TDI01923 | 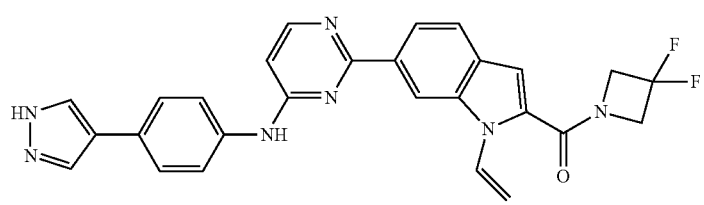 |
| TDI01924 | 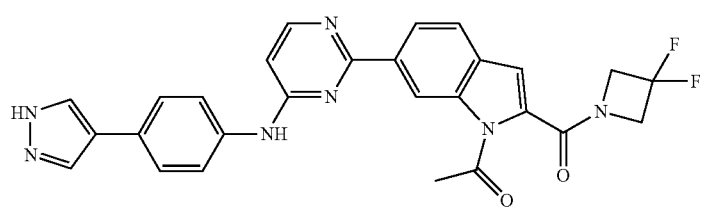 [SMILES: CC(=O)n1c(C(=O)N2CC(F)(F)C2)cc2ccc(-c3nccc(Nc4ccc(-c5cn[nH]c5)cc4)n3)cc21] |
| TDI01925 | 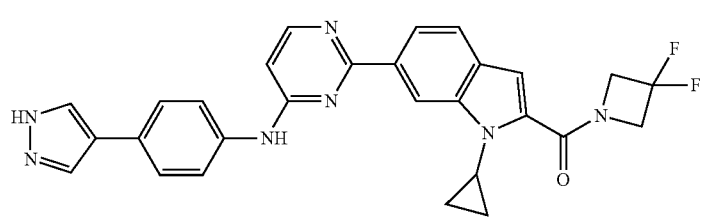 [SMILES: O=C(c1cc2ccc(-c3nccc(Nc4ccc(-c5cn[nH]c5)cc4)n3)cc2n1C1CC1)N1CC(F)(F)C1] |

-continued

| No. | Structural Formula |
|---|---|
| TDI01926 | |
| TDI01927 | |
| TDI01928 | |
| TDI01929 | |
| TDI01930 | |
| TDI01931 | |

| No. | Structural Formula |
|---|---|
| TDI01932 | ![structure] |

3. A method of inhibiting a Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof.

4. A method for the prevention or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof, to a subject in need thereof, wherein the disease is selected from the group consisting of an autoimmune disorder; a cardiovascular disorder; inflammation; a central nervous system disorder; an arterial thrombotic disorder; a fibrotic disorder; a metabolic syndrome; insulin resistance; hyperinsulinemia; type 2 diabetes; glucose intolerance; osteoporosis; and an ocular disorder.

5. A method for the prevention or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof, wherein the disease is selected from the group consisting of lupus nephritis, atherosclerosis, rheumatoid arthritis (RA), lung fibrosis, psoriasis, corneal graft rejection, insulin-dependent diabetes mellitus, multiple sclerosis, myasthenia gravis, Chron's disease, primary biliary cirrhosis, acute pancreatitis, contact dermatitis, delayed hypersensitivity, septic shock, osteoporosis, osteoarthritis, neuronal inflammation, Osier-Weber syndrome, restenosis, fungal infection, parasitic infection, and viral infection.

6. The compound or a pharmaceutically acceptable salt, ester, stereoisomer, polymorph, solvate, N-oxide, or isotopically labeled compound thereof, of claim 1 wherein the compound has the structure below:

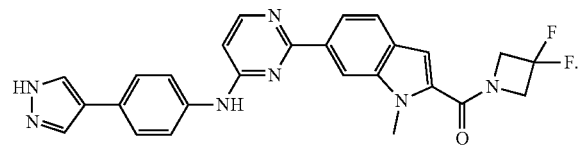 [SMILES: Cn1c(C(=O)N2CC(F)(F)C2)cc2ccc(-c3nccc(Nc4ccc(-c5cn[nH]c5)cc4)n3)cc21]

7. A pharmaceutical composition comprising a prophylactically or therapeutically effective amount of the compound of claim 6 and a pharmaceutically acceptable carrier.

8. The pharmaceutical composition of claim 7, wherein the pharmaceutical composition is in the form of a solid, semi-solid, liquid, or gas preparation.

9. The compound according to claim 1, or a pharmaceutically acceptable salt, ester, stereoisomer, polymorph, solvate, N-oxide, or isotopically labeled compound thereof, wherein R is H.

10. The compound according to claim 1, or a pharmaceutically acceptable salt, ester, stereoisomer, polymorph, solvate, N-oxide, or isotopically labeled compound thereof, wherein $R^2$ is H.

11. The compound according to claim 1, or a pharmaceutically acceptable salt, ester, stereoisomer, polymorph, solvate, N-oxide, or isotopically labeled compound thereof, wherein $R^3$ is H.

12. The compound according to claim 1, or a pharmaceutically acceptable salt, ester, stereoisomer, polymorph, solvate, N-oxide, or isotopically labeled compound thereof, wherein $R^4$, $R^7$, and $R^{7'}$, at each occurrence, are each independently selected from the group consisting of H, F and methoxy.

13. The compound according to claim 1, or a pharmaceutically acceptable salt, ester, stereoisomer, polymorph, solvate, N-oxide, or isotopically labeled compound thereof, wherein $R^9$ is H.

14. The compound according to claim 1, or a pharmaceutically acceptable salt, ester, stereoisomer, polymorph, solvate, N-oxide, or isotopically labeled compound thereof, wherein Rim is methyl, ethyl, isopropyl, vinyl, cyclopropyl, cyclobutyl, oxetanyl, monofluoromethyl, difluoromethyl, acetyl, —$CH_2OCH_3$, —$CH_2CH_2OCH_3$,

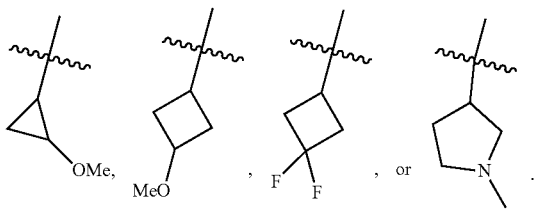

15. The compound according to claim 14, or a pharmaceutically acceptable salt, ester, stereoisomer, polymorph, solvate, N-oxide, or isotopically labeled compound thereof, wherein $R^{10}$ is methyl.

16. A method of inhibiting ROCK2, comprising administering an effective amount of the compound according to claim 1 or a pharmaceutically acceptable salt, ester, stereoisomer, polymorph, solvate, N-oxide, or isotopically labeled compound thereof to a subject in need thereof.

17. The method according to claim 4, wherein the autoimmune disorder is selected from the group consisting of rheumatoid arthritis, systemic lupus erythematosus (SLE), psoriasis, Crohn's disease, atopic dermatitis, eczema, and graft-versus-host disease (GVHD).

18. The method according to claim 4, wherein the cardiovascular disorder is selected from the group consisting of hypertension, atherosclerosis, restenosis, cardiac hypertrophy, cerebral ischemia, cerebral vasospasm, and erectile dysfunction.

19. The method according to claim 4, wherein the inflammation is selected from the group consisting of asthma, cardiovascular inflammation, ulcerative colitis, and renal inflammation.

20. The method according to claim 4, wherein the central nervous system disorder is selected from the group consisting of neuronal degeneration, spinal cord injury, Huntington's disease, Parkinson's disease, Alzheimer's disease, Amyotrophic lateral sclerosis (ALS), and multiple sclerosis.

21. The method according to claim 4, wherein the arterial thrombotic disorder is selected from the group consisting of platelet aggregation, and leukocyte aggregation.

22. The method according to claim 4, wherein the fibrotic disorder is selected from the group consisting of liver fibrosis, lung fibrosis, and kidney fibrosis.

23. The method according to claim 4, wherein the ocular disorder is selected from the group consisting of ocular hypertension, age related macular degeneration (AMD), choroidal neovascularization (CNV), diabetic macular edema (DME), iris neovascularization, uveitis, glaucoma and retinitis of prematurity (ROP).

24. The method according to claim 23, wherein the glaucoma is selected from the group consisting of primary open-angle glaucoma, acute angle-closure glaucoma, pigmentary glaucoma, congenital glaucoma, normal tension glaucoma, secondary glaucoma and neo vascular glaucoma.

25. A method for the prevention or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof, wherein the disease is selected from the group consisting of lupus, autoimmune nephritis, allograph rejection, allergic inflammation, and inflammatory bowel disease.

26. A method for slowing the progression of or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof, wherein the disease is a neoplastic disease selected from the group consisting of a lymphoma, leukemia, astrocytoma, sarcoma, and blastoma.

27. A method for slowing the progression of or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof, wherein the disease is carcinoma selected from the group consisting of squamous cell cancer, small-cell lung cancer, pituitary cancer, esophageal cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, bladder cancer, liver cancer, breast cancer, colon cancer, colorectal cancer, uterine carcinoma, salivary gland carcinoma, kidney cancer, prostate cancer, vulval cancer, thyroid cancer, brain cancer, endometrial cancer, testis cancer, cholangiocarcinoma, gallbladder carcinoma, gastric cancer, melanoma, and head and neck cancer.

28. A method for slowing the progression of or treatment of a disease mediated by the Rho-associated protein kinase (ROCK), comprising administering an effective amount of the compound according to claim 1 or a pharmaceutically acceptable salt, ester, stereoisomer, polymorph, solvate, N-oxide, or isotopically labeled compound thereof to a subject in need thereof, wherein the disease is selected from the group consisting of soft tissue sarcoma, hemangioma, and angiofibroma.

* * * * *